(12) United States Patent
Lopez

(10) Patent No.: US 9,303,007 B2
(45) Date of Patent: Apr. 5, 2016

(54) HEPATITIS C VIRUS INHIBITORS

(71) Applicant: BRISTOL-MYERS SQUIBB COMPANY, Princeton, NJ (US)

(72) Inventor: Omar D. Lopez, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/806,964

(22) Filed: Jul. 23, 2015

(65) Prior Publication Data

US 2015/0322031 A1   Nov. 12, 2015

Related U.S. Application Data

(63) Continuation of application No. 14/668,090, filed on Mar. 25, 2015, now abandoned, which is a continuation of application No. 13/672,266, filed on Nov. 8, 2012, now abandoned, which is a continuation of application No. 12/939,778, filed on Nov. 4, 2010, now abandoned.

(60) Provisional application No. 61/378,806, filed on Aug. 31, 2010.

(51) Int. Cl.
     *C07D 309/06*   (2006.01)

(52) U.S. Cl.
     CPC .................................. *C07D 309/06* (2013.01)

(58) Field of Classification Search
     USPC ........................................................ 549/426
     See application file for complete search history.

(56) References Cited

U.S. PATENT DOCUMENTS

| 8,362,020 | B2 | 1/2013 | Lopez et al. |
| 8,377,980 | B2 | 2/2013 | Belema et al. |
| 8,618,153 | B2 | 12/2013 | Bender et al. |
| 8,735,398 | B2 | 5/2014 | Lopez et al. |
| 9,006,455 | B2 | 4/2015 | Pack et al. |
| 2011/0269956 | A1 | 11/2011 | Pack et al. |
| 2011/0274648 | A1 | 11/2011 | Lavoie et al. |
| 2011/0281910 | A1 | 11/2011 | Lavoie et al. |
| 2012/0195857 | A1 | 8/2012 | Belema et al. |
| 2013/0115193 | A1 | 5/2013 | Lavoie et al. |
| 2014/0018389 | A1 | 1/2014 | Lavoie et al. |
| 2015/0197499 | A1 | 7/2015 | Lavoie et al. |

FOREIGN PATENT DOCUMENTS

WO   WO-2010/132601  A1  *  11/2010

* cited by examiner

*Primary Examiner* — Laura L. Stockton
(74) *Attorney, Agent, or Firm* — Pamela A. Mingo

(57) ABSTRACT

The present disclosure relates to compounds, compositions and methods for the treatment of Hepatitis C virus (HCV) infection. Also disclosed are pharmaceutical compositions containing such compounds and methods for using these compounds in the treatment of HCV infection.

1 Claim, No Drawings

HEPATITIS C VIRUS INHIBITORS

CROSS-REFERENCE TO RELATED APPLICATIONS

This Continuation application claims the benefit of U.S. Ser. No. 14/668,090, filed Mar. 25, 2015, now pending, which in turn is a Continuation application which claims the benefit of U.S. Ser. No. 13/672,266, filed Nov. 8, 2012, now abandoned, which in turn is a Continuation application which claims the benefit of U.S. Ser. No. 12/939,778 filed Nov. 4, 2010, now abandoned, which in turn is a Non-Provisional application which claims the benefit of U.S. Provisional Application Ser. No. 61/378,806 filed Aug. 31, 2010, all incorporated herein by reference in their entireties.

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

The current standard of care for HCV, which employs a combination of pegylated-interferon and ribavirin, has a non-optimal success rate in achieving sustained viral response and causes numerous side effects. Thus, there is a clear and long-felt need to develop effective therapies to address this undermet medical need.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS5B (also referred to herein as HCV polymerase) is a RNA-dependent RNA polymerase that is involved in the replication of HCV with other HCV proteins, including NS5A, in a replicase complex.

Compounds useful for treating HCV-infected patients are desired which selectively inhibit HCV viral replication. In particular, compounds which are effective to inhibit the function of the NS5A protein are desired. The HCV NS5A protein is described, for example, in the following references: Tan, S. L. et al., *Virology*, 284:1-12 (2001); Park, K.-J. et al., *J. Biol. Chem.*, 30711-30718 (2003); Tellinghuisen, T. L. et al., *Nature*, 435:374 (2005); Love, R. A. et al., *J. Virol.*, 83:4395 (2009); Appel, N. et al., *J. Biol. Chem.*, 281:9833 (2006); Huang, L., *J. Biol. Chem.*, 280:36417 (2005); Rice, C. et al., World Patent Application WO 2006/093867.

In its first aspect the present disclosure provides a compound of Formula (I)

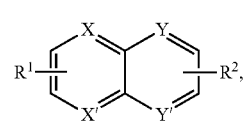

or a pharmaceutically acceptable salt thereof, wherein:

X and X' are each independently selected from CH, $CR^1$, and N;

Y and Y' are each independently selected from CH, $CR^2$, and N;

provided that no more than two of X, X', Y, and Y' are N;

$R^1$ and $R^2$ are independently selected from

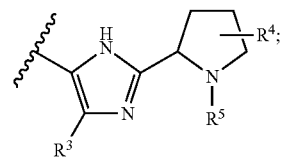

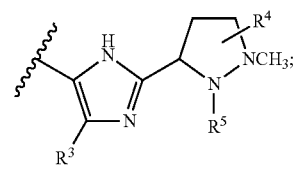

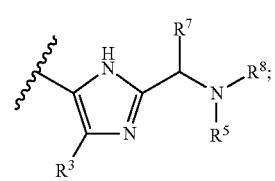

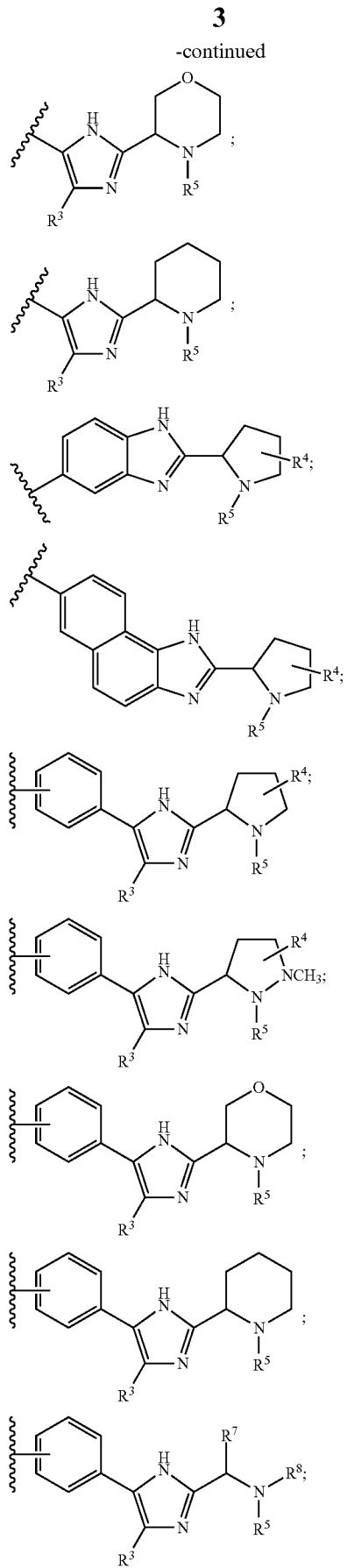
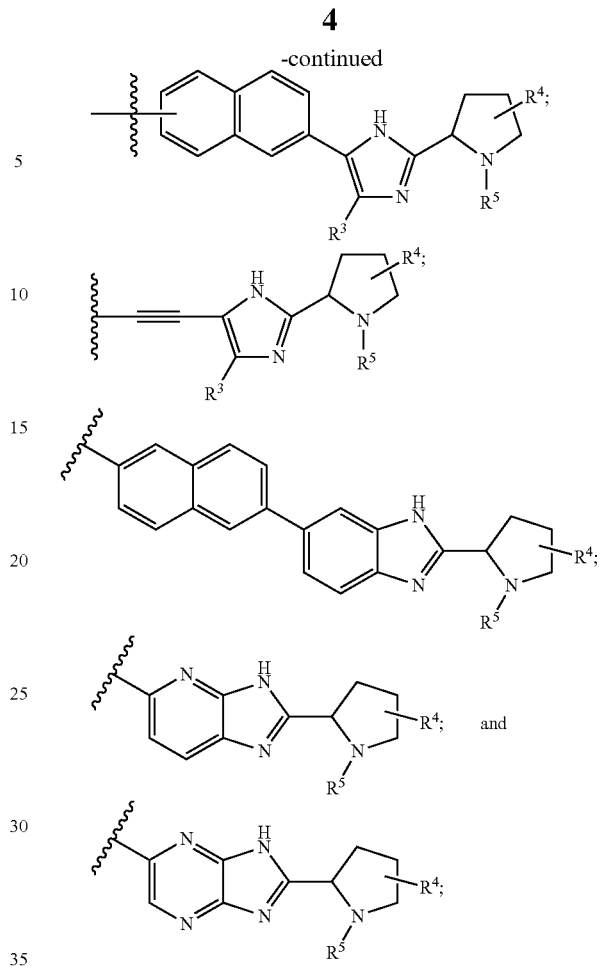

each R³ is independently selected from hydrogen, cyano, and halo;
each R⁴ is independently selected from hydrogen, and alkyl, wherein the alkyl can optionally form a fused three- to five-membered ring with an adjacent carbon atom wherein said ring is optionally substituted with one or two methyl groups; or, R⁴ and the carbon to which it is attached form an ethylene group;
each R⁵ is independently selected from hydrogen and —C(O)R⁶;
each R⁶ is independently selected from alkoxy, alkyl, arylalkoxy, arylalkyl, cycloalkyl, heterocyclyl, heterocyclylalkyl, (NR$^c$R$^d$)alkenyl, and (NR$^c$R$^d$)alkyl; and
each R⁷ and R⁸ is independently selected from hydrogen and alkyl.

In a first embodiment of the first aspect the present disclosure provides a compound of Formula (I), or a pharmaceutically acceptable salt thereof, wherein:
X and X' are independently selected from CH and CR¹; and
Y, and Y' are independently selected from CH and CR².

In a second embodiment of the first aspect the present disclosure provides a compound of Formula (I), or a pharmaceutically acceptable salt thereof, wherein:
X and X' are independently selected from CH and CR¹; and
Y and Y' are each N.

In a third embodiment of the first aspect the present disclosure provides a compound of Formula (I), or a pharmaceutically acceptable salt thereof, wherein:
Y and X' are each N;
X is selected from CH and CR¹; and
Y' is selected from CH and CR².

In a fourth embodiment of the first aspect the present disclosure provides a compound of Formula (I), or a pharmaceutically acceptable salt thereof, wherein:

X' is N; and
X is selected from CH and CR$^1$; and
Y and Y' are independently selected from CH and CR$^2$.

In a second aspect the present disclosure provides a composition comprising a compound of Formula (I), or a pharmaceutically acceptable salt thereof, and a pharmaceutically acceptable carrier. In a first embodiment of the second aspect the composition further comprises at least one additional compound having anti-HCV activity. In a second embodiment of the second aspect at least one of the additional compounds is an interferon or a ribavirin. In a third embodiment of the second aspect the interferon is selected from interferon alpha 2B, pegylated interferon alpha, consensus interferon, interferon alpha 2A, and lymphoblastoid interferon tau.

In a fourth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of Formula (I), or a pharmaceutically acceptable salt thereof. In a first embodiment of the third aspect the method further comprises administering at least one additional compound having anti-HCV activity prior to, after or simultaneously with the compound of Formula (I), or a pharmaceutically acceptable salt thereof. In a second embodiment of the third aspect at least one of the additional compounds is an interferon or a ribavirin. In a third embodiment of the third aspect the interferon is selected from interferon alpha 2B, pegylated interferon alpha, consensus interferon, interferon alpha 2A, and lymphoblastoid interferon tau.

In a fourth embodiment of the third aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the third aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when R$^1$ and R$^2$ both contain an R4 group, the two R$^4$ groups may be the same or different.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term "aryl".

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkylcarbonyloxy," as used herein, refers to an alkylcarbonyl group attached to the parent molecular moiety through an oxygen atom.

The term "alkyl," as used herein, refers to a group derived from a straight or branched chain saturated hydrocarbon containing from one to six carbon atoms. In the compounds of the present disclosure, when $R^4$ is alkyl, the alkyl can optionally form a fused three-membered ring with an adjacent carbon atom to provide the structure shown below.

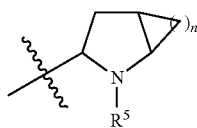

wherein n is selected from 1 and 2.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkenyl, alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^xR^y$, ($NR^xR^y$)alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkoxy," as used herein, refers to an aryl group attached to the parent molecular moiety through an alkoxy group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —$NR^cR^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, —$NR^xR^y$, and oxo.

The term "arylcarbonyl," as used herein, refers to an aryl group attached to the parent molecular moiety through a carbonyl group.

The term "cyano," as used herein, refers to —CN.

The term "cycloalkyl," as used herein, refers to a saturated monocyclic or bicyclic hydrocarbon ring system having three to fourteen carbon atoms and zero heteroatoms. Representative examples of cycloalkyl groups include, but are not limited to, cyclopropyl, cyclobutyl, cyclopentyl, cyclohexyl, bicyclo[3.1.1]heptyl, and adamantyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —$NR^xR^y$, wherein the aryl and the heterocyclyl are further optionally substituted with one, two, or three substituents independently selected from alkoxy, alkyl, cyano, halo, haloalkoxy, haloalkyl, hydroxy, nitro, and oxo.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "cycloalkylsulfonyl," as used herein, refers to a cycloalkyl group attached to the parent molecular moiety through a sulfonyl group.

The term "ethylene," as used herein, refers to =$CH_2$.

The term "formyl," as used herein, refers to —CHO.

The terms "halo" and "halogen," as used herein, refers to Cl, Br, F, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group or a three- to seven-membered aromatic or non-aromatic carbocyclic ring; bicyclic groups in which the heterocyclyl ring is substituted with a three- to seven-membered spirocyclic ring; as well as bridged bicyclic groups such as 7-azabicyclo[2.2.1]hept-7-yl, 2-azabicyclo[2.2.2]oct-2-yl, and 2-azabicyclo[2.2.2]oct-3-yl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isoquinolinyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, quinolinyl, tetrahydropyranyl, thiazolyl, thienyl, and thiomorpholinyl. The heterocyclyl groups of the present disclosure are optionally substituted with one, two, three, four, or five substituents independently selected from alkenyl, alkoxy, alkoxyalkyl, alkoxycarbonyl, alkyl, alkylcarbonyl, aryl, arylalkoxycarbonyl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^x$R$^y$, (NR$^x$R$^y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —NR$^c$R$^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^x$R$^y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —NO$_2$.

The term "—NR$^c$R$^d$," as used herein, refers to two groups, R$^c$ and R$^d$, which are attached to the parent molecular moiety through a nitrogen atom. R$^c$ and R$^d$ are independently selected from hydrogen, alkenyloxycarbonyl, alkoxyalkylcarbonyl, alkoxycarbonyl, alkyl, alkylcarbonyl, cycloalkyloxy, alkylsulfonyl, aryl, arylalkoxycarbonyl, arylalkyl, arylalkylcarbonyl, arylcarbonyl, aryloxycarbonyl, arylsulfonyl, cycloalkyl, cycloalkyloxycarbonyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^x$R$^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "(NR$^c$R$^d$)alkenyl," as used herein, refers to

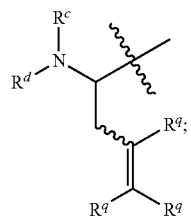

wherein R$^c$ and R$^d$ are as defined herein and each R$^q$ is independently hydrogen or C$_{1-3}$ alkyl.

The term "(NR$^c$R$^d$)alkyl," as used herein, refers to an alkyl group substituted with one, two, or three —NR$^c$R$^d$ groups. The alkyl part of the (NR$^c$R$^d$)alkyl is further optionally substituted with one or two additional groups selected from alkoxy, alkoxyalkylcarbonyl, alkoxycarbonyl, alkylsulfanyl, C$_2$ alkynyl, arylalkoxycarbonyl, carboxy, cyano, cycloalkyl, halo, heterocyclyl, heterocyclylcarbonyl, hydroxy, and (NR$^e$R$^f$)carbonyl; wherein the heterocyclyl is further optionally substituted with one, two, three, four, or five substituents independently selected from alkoxy, alkyl, cyano, halo, haloalkoxy, haloalkyl, and nitro.

The term "—NR$^e$R$^f$," as used herein, refers to two groups, R$^e$ and R$^f$, which are attached to the parent molecular moiety through a nitrogen atom. R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^x$R$^y$)alkyl, and (NR$^x$R$^y$)carbonyl.

The term "(NR$^e$R$^f$)alkyl," as used herein, refers to an alkyl group substituted with one, two, or three —NR$^e$R$^f$ groups.

The term "(NR$^e$R$^f$)alkylcarbonyl," as used herein, refers to an (NR$^e$R$^f$)alkyl group attached to the parent molecular moiety through a carbonyl group.

The term "(NR$^e$R$^f$)carbonyl," as used herein, refers to an —NR$^e$R$^f$ group attached to the parent molecular moiety through a carbonyl group.

The term "(NR$^e$R$^f$)sulfonyl," as used herein, refers to an —NR$^e$R$^f$ group attached to the parent molecular moiety through a sulfonyl group.

The term "—NR$^x$R$^y$," as used herein, refers to two groups, R$^x$ and R$^y$, which are attached to the parent molecular moiety through a nitrogen atom. R$^x$ and R$^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{x'}$R$^{y'}$)carbonyl, wherein R$^{x'}$ and R$^{y'}$ are independently selected from hydrogen and alkyl.

The term "(NR$^x$R$^y$)alkyl," as used herein, refers to an alkyl group substituted with one, two, or three —NR$^x$R$^y$ groups.

The term "(NR$^x$R$^y$)carbonyl," as used herein, refers to an —NR$^x$R$^y$ group attached to the parent molecular moiety through a carbonyl group.

The term "—NR$^x$R$^y$," as used herein, refers to two groups, R$^x$ and R$^y$, which are attached to the parent molecular moiety through a nitrogen atom. R$^x$ and R$^y$ are independently selected from hydrogen and alkyl.

The term "(NR$^x$R$^{y'}$)carbonyl," as used herein, refers to an —NR$^x$R$^{y'}$ group attached to the parent molecular moiety through a carbonyl group.

The term "oxo," as used herein, refers to =O.

The term "sulfonyl," as used herein, refers to —SO$_2$—.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of stereoisomeric products followed by separation such as conversion to a mixture of diastereomers followed by separation or recrystallization, chromatographic techniques, or direct separation of stereoisomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The compounds of the present disclosure also exist as tautomers; therefore the present disclosure also encompasses all tautomeric forms.

The term "compounds of the present disclosure", and equivalent expressions, are meant to embrace compounds of Formula (I), and pharmaceutically acceptable stereoisomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidyl-cholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology,* 38:1282 (2003); *Biochem. Biophys. Res. Commun.,* 313:42 (2004); *J. Gastroenterol.,* 38:567 (2003)).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin inhibitors | Novartis |
| Debio-025 | | | Debiopharm |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA / Elan Pharmaceuticals Inc., New York, NY |
| Summetrel | Antiviral | Antiviral | Endo Pharmaceuticals Holdings Inc., Chadds Ford, PA |
| GS-9132 (ACH-806) | Antiviral | HCV inhibitor | Achillion / Gilead |

TABLE 1-continued

| Brand Name | Physiological Class | Type of Inhibitor or Target | Source Company |
|---|---|---|---|
| Pyrazolopyrimidine compounds and salts From WO 2005/047288 26 May 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA / Eli Lilly and Co. Inc., Indianapolis, IN |
| HCV-796 | Antiviral | NS5B replicase inhibitor | Wyeth / Viropharma |
| NM-283 | Antiviral | NS5B replicase inhibitor | Idenix / Novartis |
| GL-59728 | Antiviral | NS5B replicase inhibitor | Gene Labs / Novartis |
| GL-60667 | Antiviral | NS5B replicase inhibitor | Gene Labs / Novartis |
| 2'C MeA | Antiviral | NS5B replicase inhibitor | Gilead |
| PSI 6130 | Antiviral | NS5B replicase inhibitor | Roche |
| R1626 | Antiviral | NS5B replicase inhibitor | Roche |
| 2'C Methyl adenosine | Antiviral | NS5B replicase inhibitor | Merck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |
| Ribavirin | Antiviral | Ribavirin | Schering-Plough Corporation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH 503034 | Antiviral | Serine protease inhibitor | Schering-Plough |
| Zadazim | Immune modulator | Immune modulator | SciClone Pharmaceuticals Inc., San Mateo, CA |
| Ceplene | Immuno-modulator | Immune modulator | Maxim Pharmaceuticals Inc., San Diego, CA |
| CELLCEPT ® | Immuno-suppressant | HCV IgG immuno-suppressant | F. Hoffmann-La Roche LTD, Basel, Switzerland |
| Civacir | Immuno-suppressant | HCV IgG immuno-suppressant | Nabi Biopharmaceuticals Inc., Boca Raton, FL |
| Albuferon - α | Interferon | Albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| REBIF ® | Interferon | IFN-β1a | Serono, Geneva, Switzerland |
| Roferon A | Interferon | IFN-α2a | F. Hoffmann-La Roche Ltd., Basel, Switzerland |

TABLE 1-continued

| Brand Name | Physiological Class | Type of Inhibitor or Target | Source Company |
|---|---|---|---|
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD / SciClone Pharmaceuticals Inc, San Mateo, CA |
| Rebetron | Interferon | IFN-α2b / ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen / Valentis |
| Wellferon | Interferon | Lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a / immune modulator | Maxim Pharmaceuticals Inc., San Diego, CA |
| Pegasys and Ribavirin | Interferon | PEGylated IFN-α2a / ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron / Ribavirin | Interferon | PEGylated IFN-α2b / ribavirin | Schering-Plough Corporation, Kenilworth, NJ |
| IP-501 | Liver protection | Antifibrotic | Indevus Pharmaceuticals Inc., Lexington, MA |
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering-Plough |
| TMS-435 | Antiviral | Serine protease inhibitor | Tibotec BVBA, Mechelen, Belgium |
| BI-201335 | Antiviral | Serine protease inhibitor | Boehringer Ingelheim Pharma KG, Ingelheim, Germany |
| MK-7009 | Antiviral | Serine protease inhibitor | Merck |
| PF-00868554 | Antiviral | Replicase inhibitor | Pfizer |
| ANA598 | Antiviral | Non-Nucleoside NS5B polymerase inhibitor | Anadys Pharmaceuticals, Inc., San Diego, CA, USA |
| IDX375 | Antiviral | Non-Nucleoside replicase inhibitor | Idenix Pharmaceuticals, Cambridge, MA, USA |
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |
| VCH-759 | Antiviral | NS5B polymerase inhibitor | Vir °Chem Pharma |
| VCH-916 | Antiviral | NS5B polymerase inhibitor | Vir °Chem Pharma |
| GS-9190 | Antiviral | NS5B polymerase inhibitor | Gilead |

TABLE 1-continued

| Brand Name | Physiological Class | Type of Inhibitor or Target | Source Company |
|---|---|---|---|
| Peg-interferon lamda | Antiviral | Interferon | ZymoGenetics / Bristol-Myers Squibb |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative examples which follow, are well-known to those skilled in the art. Some of the abbreviations used are as follows: Ph for phenyl; DME for 1,2-dimethoxyethane; TFA for trifluoroacetic acid; DCM for dichloromethane; HATU for O-(7-azabenzotriazol-1-yl)-N,N,N',N'-tetramethyluronium hexafluorophosphate; DMF for N,N-dimethylformamide; iPr$_2$EtN, DIEA, or DIPEA for diisopropylethylamine; h, hr, or hrs for hrs; MeOD for CD$_3$OD; MeOH for methanol; min or mins for minutes; EtOH for ethanol; Et for ethyl; DMSO for dimethylsulfoxide; rt or RT or Rt for room temperature or retention time (context will dictate); EDCI for 1-(3-dimethylaminopropyl)-3-ethyl-carbodiimide hydrochloride; Boc, boc, or BOC for tert-butoxycarbonyl; EtOAc or EtOAc for ethyl acetate; THF for tetrahydrofuran; TBDPS for t-butyldimethylsilyl; DMAP for 4-dimethylaminopyridine; TBAF for tetrabutylammonium fluoride; OAc for acetate; AcOH for acetic acid; SEMCl for 2-(trimethylsilyl)ethoxymethyl chloride; d for days; TEA or Et$_3$N for triethylamine; ACN or MeCN for acetonitrile; NCS for N-chlorosuccinimide; NBS for N-bromosuccinimide; Et$_2$O for diethyl ether; DCE for 1,2-dichloroethane; d for days; and DEA for diethylamine.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Starting materials can be obtained from commercial sources or prepared by well-established literature methods known to those of ordinary skill in the art.

SYNTHESIS OF COMMON CAPS

Compound Analysis Conditions

Purity assessment and low resolution mass analysis were conducted on a Shimadzu LC system coupled with Waters MICROMASS® ZQ MS system. It should be noted that retention times may vary slightly between machines. Additional LC conditions applicable to the current section, unless noted otherwise.
Cond.-MS-W1
Column=XTERRA® 3.0×50 mm S7
Start % B=0
Final % B=100
Gradient time=2 min
Stop time=3 min
Flow Rate=5 mL/min
Wavelength=220 nm
Solvent A=0.1% TFA in 10% methanol/90% H$_2$O
Solvent B=0.1% TFA in 90% methanol/10% H$_2$O
Cond.-MS-W2
Column=XTERRA® 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% H$_2$O
Solvent B=0.1% TFA in 90% methanol/10% H$_2$O
Cond.-MS-W5
Column=XTERRA® 3.0×50 mm S7
Start % B=0
Final % B=30
Gradient time=2 min
Stop time=3 min
Flow Rate=5 mL/min
Wavelength=220 nm
Solvent A=0.1% TFA in 10% methanol/90% H$_2$O
Solvent B=0.1% TFA in 90% methanol/10% H$_2$O
Cond.-D1
Column=XTERRA® C18 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% H$_2$O
Solvent B=0.1% TFA in 90% methanol/10% H$_2$O
Cond.-D2
Column=PHENOMENEX® Luna 4.6×50 mm S10
Start % B=0
Final % B=100
Gradient time=3 min
Stop time=4 min
Flow Rate=4 mL/min
Wavelength=220 nm Solvent A=0.1% TFA in 10% methanol/90% H₂O
Solvent B=0.1% TFA in 90% methanol/10% H₂O
Cond.-M3
Column=XTERRA® C18 3.0×50 mm S7
Start % B=0
Final % B=40
Gradient time=2 min
Stop time=3 min
Flow Rate=5 mL/min
Wavelength=220 nm
Solvent A=0.1% TFA in 10% methanol/90% H₂O
Solvent B=0.1% TFA in 90% methanol/10% H₂O
Condition I
Column=PHENOMENEX® Luna 3.0×50 mm S10
Start % B=0
Final % B=100
Gradient time=2 min
Stop time=3 min
Flow Rate=4 mL/min
Wavelength=220 nm
Solvent A=0.1% TFA in 10% methanol/90% H₂O
Solvent B=0.1% TFA in 90% methanol/10% H₂O
Condition II
Column=PHENOMENEX® Luna 4.6×50 mm S10
Start % B=0
Final % B=100
Gradient time=2 min
Stop time=3 min
Flow Rate=5 mL/min
Wavelength=220 nm
Solvent A=0.1% TFA in 10% methanol/90% H₂O
Solvent B=0.1% TFA in 90% methanol/10% H₂O
Condition III
Column=XTERRA® C18 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% H₂O
Solvent B=0.1% TFA in 90% methanol/10% H₂O Cap-1

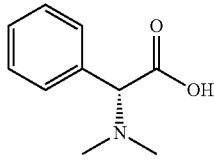

(R)-2-(Dimethylamino)-2-phenylacetic acid

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to H₂ (60 psi) for 3 hours. The reaction mixture was filtered through diatomaceous earth (CELITE®), and the filtrate was concentrated in vacuo. The resulting crude material was recrystallized from isopropanol to provide the HCl salt of Cap-1 as a white needle (4.0 g). Optical rotation: −117.1° [c=9.95 mg/mL in H₂O; λ=589 nm]. ¹H NMR (DMSO-d₆, δ=2.5 ppm, 500 MHz): δ 7.43-7.34 (m, 5H), 4.14 (s, 1H), 2.43 (s, 6H); LC (Condition I): RT=0.25; LC-MS: Anal. Calcd. for [M+H]⁺ C₁₀H₁₄NO₂ 180.10. found 180.17; HRMS: Anal. Calcd. for [M+H]⁺ C₁₀H₁₄NO₂ 180.1025. found 180.1017.

Cap-2

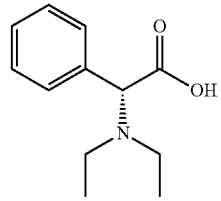

(R)-2-(Diethylamino)-2-phenylacetic acid

NaBH₃CN (6.22 g, 94 mmol) was added in portions over a few minutes to a cooled (ice/water) mixture of (R)-2-Phenylglycine (6.02 g, 39.8 mmol) and methanol (100 mL), and stirred for 5 minutes. Acetaldehyde (10 mL) was added dropwise over 10 minutes and stirring was continued at the same cooled temperature for 45 minutes and at ambient temperature for ~6.5 hours. The reaction mixture was cooled back with ice-water bath, treated with water (3 mL) and then quenched with a dropwise addition of concentrated HCl over ~45 minutes until the pH of the mixture was ~1.5-2.0. The cooling bath was removed and the stirring was continued while adding concentrated HCl in order to maintain the pH of the mixture around 1.5-2.0. The reaction mixture was stirred overnight, filtered to remove the white suspension, and the filtrate was concentrated in vacuo. The crude material was recrystallized from ethanol to afford the HCl salt of Cap-2 as a shining white solid in two crops (crop-1: 4.16 g; crop-2: 2.19 g). ¹H NMR (DMSO-d₆, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: [α]²⁵ −102.21° (c=0.357, H₂O); crop-2: [α]²⁵ −99.7° (c=0.357, H₂O). LC (Condition I): RT=0.43 min; LC-MS: Anal. Calcd. for [M+H]⁺ C₁₂H₁₈NO₂: 208.13. found 208.26.

Cap-3

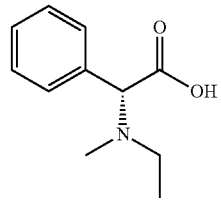

Acetaldehyde (5.0 mL, 89.1 mmol) and a suspension of 10% Pd/C (720 mg) in methanol/H₂O (4 mL/1 mL) was sequentially added to a cooled (~15° C.) mixture of (R)-2-phenylglycine (3.096 g, 20.48 mmol), 1N HCl (30 mL) and methanol (40 mL). The cooling bath was removed and the reaction mixture was stirred under a balloon of H₂ for 17 hours. An additional acetaldehyde (10 mL, 178.2 mmol) was added and stirring continued under H₂ atmosphere for 24 hours [Note: the supply of H₂ was replenished as needed throughout the reaction]. The reaction mixture was filtered through diatomaceous earth (CELITE®), and the filtrate was concentrated in vacuo. The resulting crude material was recrystallized from isopropanol to provide the HCl salt of (R)-2-(ethylamino)-2-phenylacetic acid as a shining white solid (2.846 g). $^1$H NMR (DMSO-d$_6$, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Condition I): RT=0.39 min; >95% homogeneity index; LC-MS: Anal. Calcd. for [M+H]$^+$ C$_{10}$H$_{14}$NO$_2$: 180.10. found 180.18.

A suspension of 10% Pd/C (536 mg) in methanol/H$_2$O (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL). The reaction mixture was stirred under a balloon of H$_2$ for ~72 hours, where the H$_2$ supply was replenished as needed. The reaction mixture was filtered through diatomaceous earth (CELITE®) and the filtrate was concentrated in vacuo. The resulting crude material was recrystallized from isopropanol (50 mL) to provide the HCl salt of Cap-3 as a white solid (985 mg). $^1$H NMR (DMSO-d$_6$, δ=2.5 ppm, 400 MHz): δ 10.48 (br s, 1H), 7.59-7.51 (m, 5H), 5.26 (s, 1H), 3.08 (app br s, 2H), 2.65 (br s, 3H), 1.24 (br m, 3H). LC (Condition I): RT=0.39 min; >95% homogeneity index; LC-MS: Anal. Calcd. for [M+H]$^+$ C$_{11}$H$_{16}$NO$_2$: 194.12. found 194.18; HRMS: Anal. Calcd. for [M+H]$^+$ C$_{11}$H$_{16}$NO$_2$: 194.1180. found 194.1181.

Cap-4

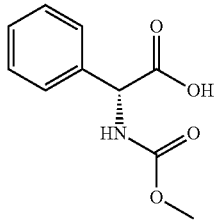

(R)-2-(Methoxycarbonylamino)-2-phenylacetic acid

ClCO$_2$Me (3.2 mL, 41.4 mmol) was added dropwise to a cooled (ice/water) THF (410 mL) semi-solution of (R)-tert-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated NaHCO$_3$ solution (30 mL), dried (MgSO$_4$), filtered, and concentrated in vacuo. The resultant colorless oil was triturated from hexanes, filtered and washed with hexanes (100 mL) to provide (R)-tert-butyl 2-(methoxycarbonylamino)-2-phenylacetate as a white solid (7.7 g). $^1$H NMR (DMSO-d$_6$, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Condition I): RT=1.53 min; ~90% homogeneity index; LC-MS: Anal. Calcd. for [M+Na]$^+$ C$_{14}$H$_{19}$NNaO$_4$: 288.12. found 288.15.

TFA (16 mL) was added dropwise to a cooled (ice/water) CH$_2$Cl$_2$ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: −176.9° [c=3.7 mg/mL in H$_2$O; λ=589 nm]. $^1$H NMR (DMSO-d$_6$, δ=2.5 ppm, 400 MHz): δ 12.84 (br s, 1H), 7.96 (d, J=8.3, 1H), 7.41-7.29 (m, 5H), 5.14 (d, J=8.3, 1H), 3.55 (s, 3H). LC (Condition I): RT=1.01 min; >95% homogeneity index; LC-MS: Anal. Calcd. for [M+H]$^+$ C$_{10}$H$_{12}$NO$_4$ 210.08. found 210.17; HRMS: Anal. Calcd. for [M+H]$^+$ C$_{10}$H$_{12}$NO$_4$ 210.0766. found 210.0756.

Cap-5

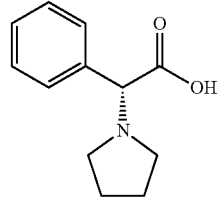

A mixture of (R)-2-phenylglycine (1.0 g, 6.62 mmol), 1,4-dibromobutane (1.57 g, 7.27 mmol) and Na$_2$CO$_3$ (2.10 g, 19.8 mmol) in ethanol (40 mL) was heated at 100° C. for 21 hours. The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). $^1$H NMR (DMSO-d$_6$, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H); RT=0.30 minutes (Condition I); >98% homogeneity index; LC-MS: Anal. Calcd. for [M+H]$^+$ C$_{12}$H$_{16}$NO$_2$: 206.12. found 206.25.

Cap-6

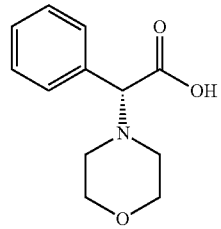

The TFA salt of Cap-6 was synthesized from (R)-2-phenylglycine and 1-bromo-2-(2-bromoethoxy)ethane by using the method of preparation of Cap-5. $^1$H NMR (DMSO-d$_6$, δ=2.5, 500 MHz) δ 12.20 (br s, 1H), 7.50 (m, 5H), 4.92 (s, 1H), 3.78 (app br s, 4H), 3.08 (app br s, 2H), 2.81 (app br s, 2H); RT=0.32 minutes (Condition I); >98%; LC-MS: Anal. Calcd. for [M+H]$^+$ C$_{12}$H$_{16}$NO$_3$: 222.11. found 222.20; HRMS: Anal. Calcd. for [M+H]$^+$ C$_{12}$H$_{16}$NO$_3$: 222.1130. found 222.1121.

Cap-7

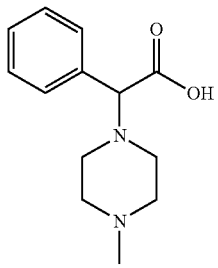

Cap-7a: enantiomer-1
Cap-7b: enantiomer-2

A CH$_2$Cl$_2$ (200 mL) solution of p-toluenesulfonyl chloride (8.65 g, 45.4 mmol) was added dropwise to a cooled (−5° C.) CH$_2$Cl$_2$ (200 mL) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried (MgSO$_4$), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. $^1$H NMR (DMSO-d$_6$, δ=2.5, 500 MHz) δ 7.78 (d, J=8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Condition III); >90% homogeneity index; LC-MS: Anal. Calcd. for [M+H]$^+$ C$_{22}$H$_{20}$NaO$_5$S: 419.09. found 419.04.

A THF (75 mL) solution of benzyl 2-phenyl-2-(tosyloxy) acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried (MgSO$_4$), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (CHIRALCEL® OD-H) indicated that the sample is a mixture of stereoisomers in a 38.2 to 58.7 ratio. The separation of the stereoisomers were effected as follow: the product was dissolved in 120 mL of ethanol/heptane (1:1) and injected (5 mL/injection) on chiral HPLC column (Chiracel OJ, 5 cm ID×50 cm L, 20 µm) eluting with 85:15 Heptane/ethanol at 75 mL/min, and monitored at 220 nm. Stereoisomer-1 (1.474 g) and stereoisomer-2 (2.2149 g) were retrieved as viscous oil. $^1$H NMR (CDCl$_3$, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Condition III); >98% homogeneity index; LC-MS: Anal. Calcd. for [M+H]$^+$ C$_{20}$H$_{25}$N$_2$O$_2$: 325.19. found 325.20.

A methanol (10 mL) solution of either stereoisomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 minutes. Immediately after the completion of the reaction, the catalyst was filtered through diatomaceous earth (CELITE®) and the filtrate was concentrated in vacuo to provide Cap-7, contaminated with phenylacetic acid as a tan foam (867.6 mg; mass is above the theoretical yield). The product was used for the next step without further purification. $^1$H NMR (DMSO-d$_6$, δ=2.5, 500 MHz) δ 7.44-7.37 (m, 2H), 7.37-7.24 (m, 3H), 3.92 (s, 1H), 2.63-2.48 (app. br s, 2H), 2.48-2.32 (m, 6H), 2.19 (s, 3H); RT=0.31 (Condition II); >90% homogeneity index; LC-MS: Anal. Calcd. for [M+H]$^+$ C$_{13}$H$_{19}$N$_2$O$_2$: 235.14. found 235.15; HRMS: Anal. Calcd. for [M+H]$^+$ C$_{13}$H$_{19}$N$_2$O$_2$: 235.1447. found 235.1440.

The synthesis of Cap-8 and Cap-9 was conducted according to the synthesis of Cap-7 by using appropriate amines for the SN$_2$ displacement step (i.e., 4-hydroxypiperidine for Cap-8 and (S)-3-fluoropyrrolidine for Cap-9) and modified conditions for the separation of the respective stereoisomeric intermediates, as described below.

Cap-8

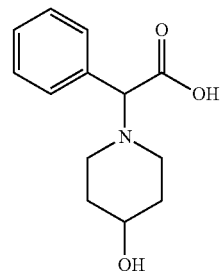

8a: enantiomer-1
8b: enantiomer-2

The stereoisomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 µm) eluting with 80:20 heptane/ethanol at 10 mL/min, monitored at 220 nm, to provide 186.3 mg of stereoisomer-1 and 209.1 mg of stereoisomer-2 as light-yellow viscous oils. These benzyl ester was hydrogenolysed according to the preparation of Cap-7 to provide Cap-8: $^1$H NMR (DMSO-d$_6$, δ=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 2H), 1.70 (m, 2H), 1.42 (m, 2H). RT=0.28 (Condition II); >98% homogeneity index; LC-MS: Anal. Calcd. for [M+H]$^+$ C$_{13}$H$_{18}$NO$_3$: 236.13. found 236.07; HRMS: Calcd. for [M+H]$^+$ C$_{13}$H$_{18}$NO$_3$: 236.1287. found 236.1283.

Cap-9

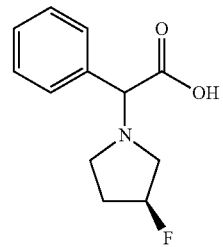

9a: diastereomer-1
8b: diastereomer-2

The diastereomeric separation of the intermediate benzyl 2-((S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 μm) eluting with 95% CO$_2$/5% methanol with 0.1% TFA, at 10 bar pressure, 70 mL/min flow rate, and a temperature of 35° C. The HPLC elute for the respective stereoisomers was concentrated, and the residue was dissolved in CH$_2$Cl$_2$ (20 mL) and washed with an aqueous medium (10 mL water+1 mL saturated NaHCO$_3$ solution). The organic phase was dried (MgSO$_4$), filtered, and concentrated in vacuo to provide 92.5 mg of fraction-1 and 59.6 mg of fraction-2. These benzyl esters were hydrogenolysed according to the preparation of Cap-7 to prepare Cap-9a and Cap-9b. Cap-9a (diastereomer-1; the sample is a TFA salt as a result of purification on a reverse phase HPLC using H$_2$O/methanol/TFA solvent): $^1$H NMR (DMSO-d$_6$, δ=2.5, 400 MHz) 7.55-7.48 (m, 5H), 5.38 (d of m, J=53.7, 1H), 5.09 (br s, 1H), 3.84-2.82 (br m, 4H), 2.31-2.09 (m, 2H). RT=0.42 (Condition I); >95% homogeneity index; LC-MS: Anal. Calcd. for [M+H]$^+$ C$_{12}$H$_{15}$FNO$_2$: 224.11. found 224.14; Cap-9b (diastereomer-2): $^1$H NMR (DMSO-d$_6$, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Condition I); LC-MS: Anal. Calcd. for [M+H]$^+$ C$_{12}$H$_{15}$FNO$_2$: 224.11. found 224.14.

Cap-10

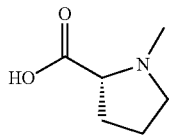

To a solution of D-proline (2.0 g, 17 mmol) and formaldehyde (2.0 mL of 37% wt. in H$_2$O) in methanol (15 mL) was added a suspension of 10% Pd/C (500 mg) in methanol (5 mL). The mixture was stirred under a balloon of hydrogen for 23 hours. The reaction mixture was filtered through diatomaceous earth (CELITE®) and concentrated in vacuo to provide Cap-10 as an off-white solid (2.15 g). $^1$H NMR (DMSO-d$_6$, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Condition II); >98% homogeneity index; LC-MS: Anal. Calcd. for [M+H]$^+$ C$_6$H$_{12}$NO$_2$: 130.09. found 129.96.

Cap-11

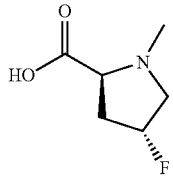

A mixture of (2S,4R)-4-fluoropyrrolidine-2-carboxylic acid (0.50 g, 3.8 mmol), formaldehyde (0.5 mL of 37% wt. in H$_2$O), 12 N HCl (0.25 mL) and 10% Pd/C (50 mg) in methanol (20 mL) was stirred under a balloon of hydrogen for 19 hours. The reaction mixture was filtered through diatomaceous earth (CELITE®) and the filtrate was concentrated in vacuo. The residue was recrystallized from isopropanol to provide the HCl salt of Cap-11 as a white solid (337.7 mg). $^1$H NMR (DMSO-d$_6$, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26

(m, 1H). RT=0.28 (Condition II); >98% homogeneity index; LC-MS: Anal. Calcd. for [M+H]$^+$ C$_6$H$_{11}$FNO$_2$: 148.08. found 148.06.

Cap-12 (same as Cap-52)

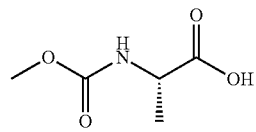

(S)-2-(Methoxycarbonylamino)propanoic acid

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH~2-3. The resulting solutions was extracted with ethyl acetate (3×100 mL), and the combined organic phase was dried (Na$_2$SO$_4$), filtered, and concentrated in vacuo to provide a colorless oil (2.58 g). 500 mg of this material was purified by a reverse phase HPLC (H$_2$O/methanol/TFA) to provide 150 mg of Cap-12 as a colorless oil. $^1$H NMR (DMSO-d$_6$, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

Cap-13

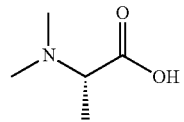

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (CELITE®) and the filtrate was concentrated in vacuo to provide the HCl salt of Cap-13 as an oil which solidified upon standing under vacuum (4.4 g; the mass is above theoretical yield). The product was used without further purification. $^1$H NMR (DMSO-d$_6$, δ=2.5, 500 MHz) δ 12.1 (br s, 1H), 4.06 (q, J=7.4, 1H), 2.76 (s, 6H), 1.46 (d, J=7.3, 3H).

Cap-14

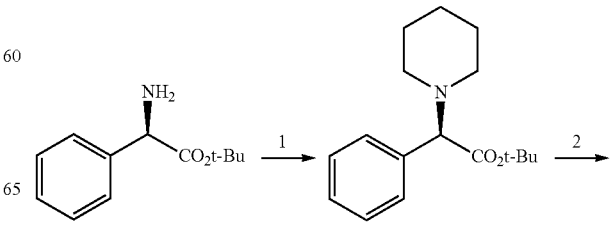

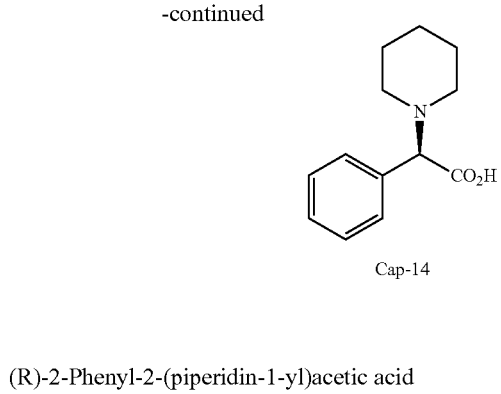

(R)-2-Phenyl-2-(piperidin-1-yl)acetic acid

Step 1

A mixture of (R)-(−)-D-phenylglycine tert-butyl ester (3.00 g, 12.3 mmol), NaBH$_3$CN (0.773 g, 12.3 mmol), KOH (0.690 g, 12.3 mmol) and acetic acid (0.352 mL, 6.15 mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried (MgSO$_4$), filtered and concentrated to dryness to provide a clear oil. This material was purified by reverse-phase preparative HPLC (Primesphere C-18, 30×100 mm; CH$_3$CN—H$_2$O-0.1% TFA) to give the intermediate ester (2.70 g, 56%) as a clear oil. $^1$H NMR (400 MHz, CDCl$_3$) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2 Hz, 1H), 2.59 (t, J=11.4 Hz, 1H), 2.07-2.02 (m, 2H), 1.82 (d, J=1.82 Hz, 3H), 1.40 (s, 9H). LC-MS: Anal. Calcd. for C$_{17}$H$_{25}$NO$_2$: 275. found: 276 (M+H)$^+$.

Step 2

To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; CH$_3$CN—H$_2$O-0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$H NMR (DMSO-d$_6$) δ 7.50 (s, 5H), 5.13 (s, 1H), 3.09 (br s, 2H), 2.92-2.89 (m, 2H), 1.74 (m, 4H), 1.48 (br s, 2H). LC-MS: Anal. Calcd. for C$_{13}$H$_{17}$NO$_2$: 219. found: 220 (M+H)$^+$.

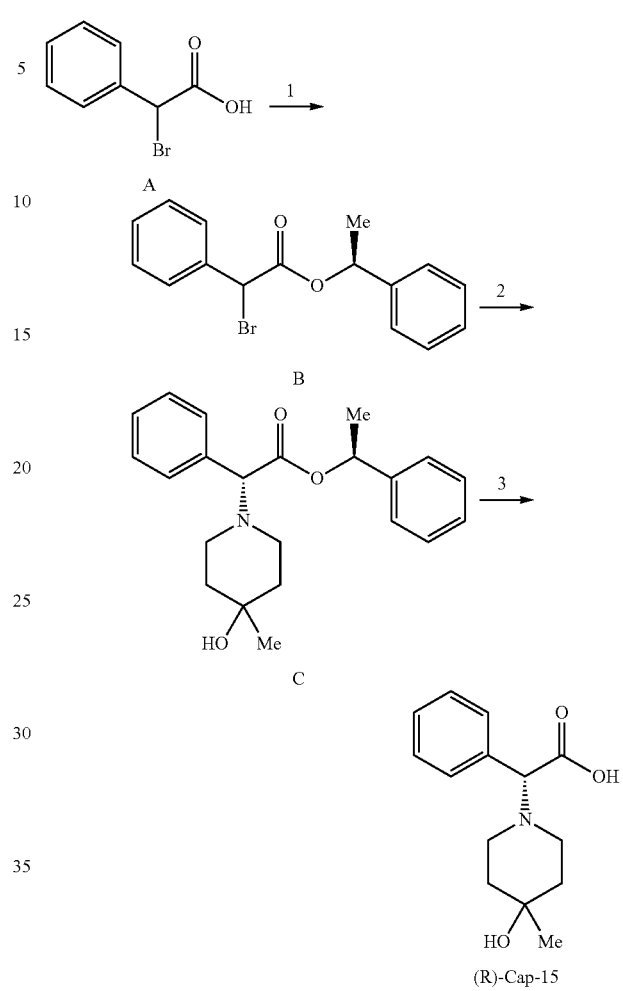

Step 1: (S)-1-Phenylethyl 2-bromo-2-phenylacetate

To a mixture of α-bromophenylacetic acid (10.75 g, 0.050 mol), (S)-(−)-1-phenylethanol (7.94 g, 0.065 mol) and DMAP (0.61 g, 5.0 mmol) in dry dichloromethane (100 mL) was added solid EDCI (12.46 g, 0.065 mol) all at once. The resulting solution was stirred at room temperature under Ar for 18 hours and then it was diluted with ethyl acetate, washed (H$_2$O×2, brine), dried (Na$_2$SO$_4$), filtered, and concentrated to give a pale yellow oil. Flash chromatography (SiO$_2$/hexane-ethyl acetate, 4:1) of this oil provided the title compound (11.64 g, 73%) as a white solid. $^1$H NMR (400 MHz, CDCl$_3$) δ 7.53-7.17 (m, 10H), 5.95 (q, J=6.6 Hz, 0.5H), 5.94 (q, J=6.6 Hz, 0.5H), 5.41 (s, 0.5H), 5.39 (s, 0.5H), 1.58 (d, J=6.6 Hz, 1.5H), 1.51 (d, J=6.6 Hz, 1.5H).

Step 2: (S)-1-Phenylethyl (R)-2-(4-hydroxy-4-methylpiperidin-1-yl)-2-phenylacetate To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 mL) was added. The mixture was stirred for 1 hour at room temperature and then it was heated at 55-60° C. (oil bath temperature) for 4 hours. The cooled reaction mixture was then diluted with ethyl acetate (30 mL), washed ($H_2O\times2$, brine), dried ($MgSO_4$), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid. (S,R)-isomer: $^1$H NMR (CD$_3$OD) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), 1.71-1.49 (m, 4H), 1.38 (d, J=6.6 Hz, 3H), 1.18 (s, 3H). LC-MS: Anal. Calcd. for $C_{22}H_{27}NO_3$: 353. found: 354 (M+H)$^+$. (S,S)-isomer: $^1$H NMR (CD$_3$OD) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LC-MS: Anal. Calcd. for $C_{22}H_{27}NO_3$: 353. found: 354 (M+H)$^+$.

Step 3: (R)-2-(4-Hydroxy-4-methylpiperidin-1-yl)-2-phenylacetic acid

To a solution of (S)-1-phenylethyl (R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; CH$_3$CN—H$_2$O-0.1% TFA) to give the title compound (as TFA salt) as a pale bluish solid (0,128 g, 98%). LC-MS: Anal. Calcd. for $C_{14}H_{19}NO_3$: 249. found: 250 (M+H)$^+$.

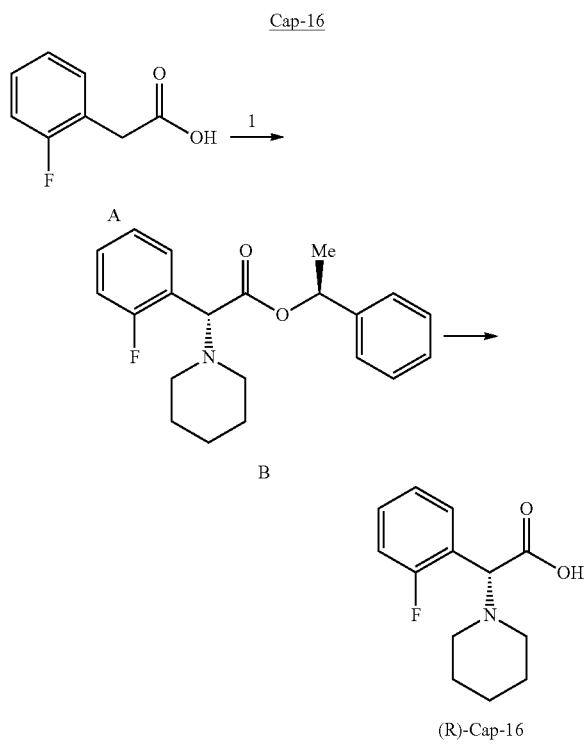

Cap-16

(R)-Cap-16

Step 1: (S)-1-Phenylethyl 2-(2-fluorophenyl)acetate

A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in CH$_2$Cl$_2$ (100 mL) was stirred at room temperature for 12 hours. The solvent was then concentrated and the residue partitioned with H$_2$O-ethyl acetate. The phases were separated and the aqueous layer back-extracted with ethyl acetate (2×). The combined organic phases were washed (H$_2$O, brine), dried (Na$_2$SO$_4$), filtered, and concentrated in vacuo. The residue was purified by silica gel chromatography (BIOTAGE®/0-20% ethyl acetate-hexane) to provide the title compound as a colorless oil (8.38 g, 92%). $^1$H NMR (400 MHz, CD$_3$OD) δ 7.32-7.23 (m, 7H), 7.10-7.04 (m, 2), 5.85 (q, J=6.5 Hz, 1H), 3.71 (s, 2H), 1.48 (d, J=6.5 Hz, 3H).

Step 2: (R)—((S)-1-Phenylethyl) 2-(2-fluorophenyl)-2-(piperidin-1-yl)acetate

To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of CBr$_4$ (13.5 g, 40.7 mmol) in THF (100 mL) was added and the mixture was allowed to warm to −10° C. and stirred at this temperature for 2 hours. The reaction mixture was quenched with saturated aq. NH$_4$Cl and the layers were separated. The aqueous layer was back-extracted with ethyl acetate (2×) and the combined organic phases were washed (H$_2$O, brine), dried (Na$_2$SO$_4$), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (BIOTAGE®/0-30% diethyl ether-hexane) to provide a pure mixture of diastereomers (2:1 ratio by $^1$H NMR) as a yellow oil (2.07 g, 31%), along with unreacted starting material (2.53 g, 51%). Further chromatography of the diastereomeric mixture (BIOTAGE®/0-10% diethyl ether-toluene) provided the title compound as a colorless oil (0.737 g, 11%). $^1$H NMR (400 MHz, CD$_3$OD) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LC-MS: Anal. Calcd. for $C_{21}H_{24}FNO_2$: 341. found: 342 (M+H)$^+$.

Step 3: (R)-2-(2-Fluorophenyl)-2-(piperidin-1-yl)acetic acid

A mixture of (R)—((S)-1-phenylethyl) 2-(2-fluorophenyl)-2-(piperidin-1-yl)acetate (0.737 g, 2.16 mmol) and 20% Pd(OH)$_2$/C (0.070 g) in ethanol (30 mL) was hydrogenated at room temperature and atmospheric pressure (H$_2$ balloon) for 2 hours. The solution was then purged with Ar, filtered through diatomaceous earth (CELITE®), and concentrated in vacuo. This provided the title compound as a colorless solid (0.503 g, 98%). $^1$H NMR (400 MHz, CD$_3$OD) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LC-MS: Anal. Calcd. for $C_{13}H_{16}FNO_2$: 237. found: 238 (M+H)$^+$.

Cap-17

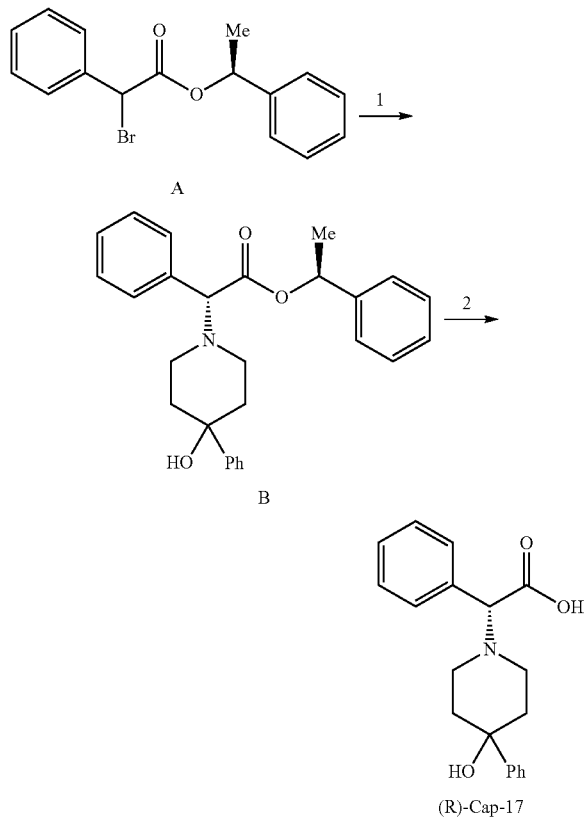

Step 1: (S)-1-Phenylethyl (R)-2-(4-hydroxy-4-phenylpiperidin-1-yl)-2-phenylacetate To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed ($H_2O \times 2$, brine), dried ($MgSO_4$), filtered and concentrated. The residue was purified on a silica gel column (0-60% ethyl acetate-hexane) to provide an approximately 2:1 mixture of diastereomers, as judged by $^1$H NMR. Separation of these isomers was performed using supercritical fluid chromatography (CHIRALCEL® OJ-H, 30×250 mm; 20% ethanol in $CO_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$H NMR (400 MHz, $CD_3OD$) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LC-MS: Anal. Calcd. for $C_{27}H_{29}NO_3$: 415. found: 416 $(M+H)^+$; (S,S)-isomer: $H^1$NMR (400 MHz, $CD_3OD$) δ 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=11.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LC-MS: Anal. Calcd. for $C_{27}H_{29}NO_3$: 415. found: 416 $(M+H)^+$.

The following esters were prepared in similar fashion:

Intermediate-17a

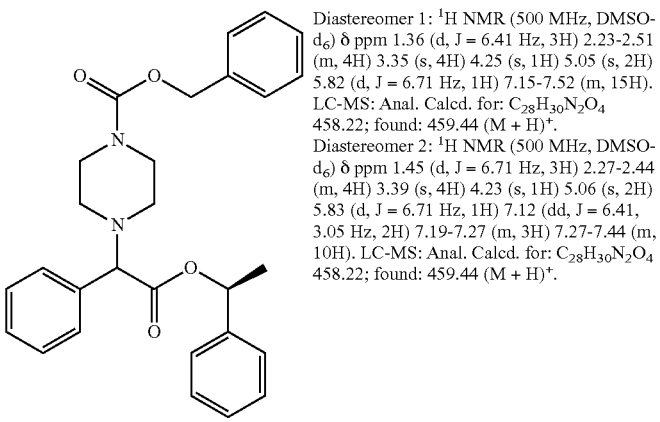

Diastereomer 1: $^1$H NMR (500 MHz, DMSO-$d_6$) δ ppm 1.36 (d, J = 6.41 Hz, 3H) 2.23-2.51 (m, 4H) 3.35 (s, 4H) 4.25 (s, 1H) 5.05 (s, 2H) 5.82 (d, J = 6.71 Hz, 1H) 7.15-7.52 (m, 15H). LC-MS: Anal. Calcd. for: $C_{28}H_{30}N_2O_4$ 458.22; found: 459.44 $(M + H)^+$.
Diastereomer 2: $^1$H NMR (500 MHz, DMSO-$d_6$) δ ppm 1.45 (d, J = 6.71 Hz, 3H) 2.27-2.44 (m, 4H) 3.39 (s, 4H) 4.23 (s, 1H) 5.06 (s, 2H) 5.83 (d, J = 6.71 Hz, 1H) 7.12 (dd, J = 6.41, 3.05 Hz, 2H) 7.19-7.27 (m, 3H) 7.27-7.44 (m, 10H). LC-MS: Anal. Calcd. for: $C_{28}H_{30}N_2O_4$ 458.22; found: 459.44 $(M + H)^+$.

Intermediate-17b

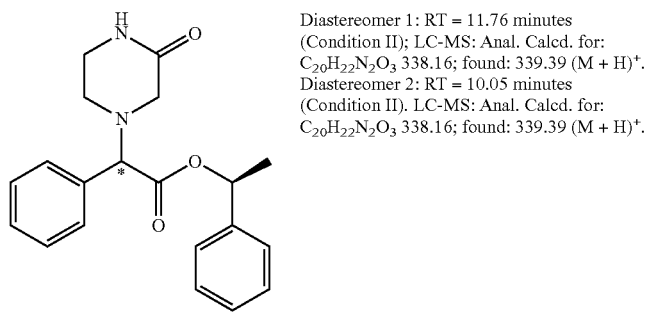

Diastereomer 1: RT = 11.76 minutes (Condition II); LC-MS: Anal. Calcd. for: $C_{20}H_{22}N_2O_3$ 338.16; found: 339.39 $(M + H)^+$.
Diastereomer 2: RT = 10.05 minutes (Condition II). LC-MS: Anal. Calcd. for: $C_{20}H_{22}N_2O_3$ 338.16; found: 339.39 $(M + H)^+$.

| | | |
|---|---|---|
| Intermediate-17c | 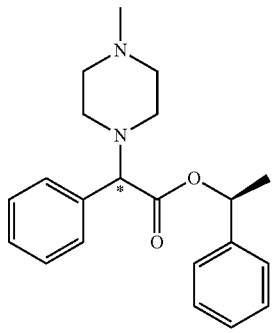 [SMILES: C[C@H](OC(=O)C(c1ccccc1)N1CCN(C)CC1)c1ccccc1] | Diastereomer 1: $T_R$ = 4.55 minutes (Condition I); LC-MS: Anal. Calcd. for: $C_{21}H_{26}N_2O_2$ 338.20; found: 339.45 $(M + H)^+$.<br>Diastereomer 2: $T_R$ = 6.00 minutes (Condition I). LC-MS: Anal. Calcd. for: $C_{21}H_{26}N_2O_2$ 338.20; found: 339.45 $(M + H)^+$. |
| Intermediate -17d | 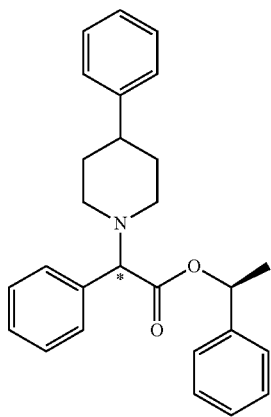 [SMILES: C[C@H](OC(=O)C(c1ccccc1)N1CCC(c2ccccc2)CC1)c1ccccc1] | Diastereomer 1: RT = 7.19 minutes (Condition I); LC-MS: Anal. Calcd. for: $C_{27}H_{29}NO_2$ 399.22; found: 400.48 $(M + H)^+$.<br>Diastereomer 2: RT = 9.76 minutes (Condition I); LC-MS: Anal. Calcd. for: $C_{27}H_{29}NO_2$ 399.22; found: 400.48 $(M + H)^+$. |

Chiral SFC Conditions for Determining Retention Time:
Condition I
Column: CHIRALPAK® AD-H Column, 4.62×50 mm, 5 μm
Solvents: 90% $CO_2$-10% methanol with 0.1% DEA
Temp: 35° C.
Pressure: 150 bar
Flow rate: 2.0 mL/min.
UV monitored at 220 nm
Injection: 1.0 mg/3 mL methanol
Condition II
Column: CHIRALCEL® OD-H Column, 4.62×50 mm, 5 μm
Solvents: 90% $CO_2$-10% methanol with 0.1% DEA
Temp: 35° C.
Pressure: 150 bar
Flow rate: 2.0 mL/min.
UV monitored at 220 nm
Injection: 1.0 mg/mL methanol Cap-17, Step 2: (R)-2-(4-Hydroxy-4-phenylpiperidin-1-yl)-2-phenylacetic acid. To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a white solid (0.230 g, 88%). LC-MS: Anal. Calcd. for $C_{19}H_{21}NO_3$: 311.15. found: 312 $(M+H)^+$.

The following carboxylic acids were prepared in optically pure form in a similar fashion:

| | | |
|---|---|---|
| Cap-17a | 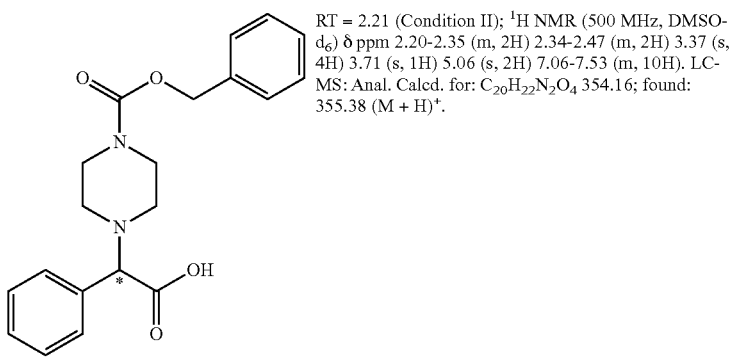 | RT = 2.21 (Condition II); $^1H$ NMR (500 MHz, DMSO-$d_6$) δ ppm 2.20-2.35 (m, 2H) 2.34-2.47 (m, 2H) 3.37 (s, 4H) 3.71 (s, 1H) 5.06 (s, 2H) 7.06-7.53 (m, 10H). LC-MS: Anal. Calcd. for: $C_{20}H_{22}N_2O_4$ 354.16; found: 355.38 $(M + H)^+$. |

| | | |
|---|---|---|
| Cap-17b | 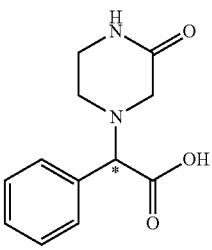 [SMILES: O=C1CN(C(C(=O)O)c2ccccc2)CCN1] | RT = 0.27 (Condition III); LC-MS: Anal. Calcd. for: $C_{12}H_{14}N_2O_3$ 234.10; found: 235.22 (M + H)$^+$. |
| Cap-17c | 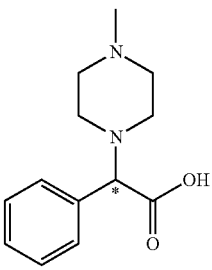 [SMILES: CN1CCN(C(C(=O)O)c2ccccc2)CC1] | RT = 0.48 (Condition II); LC-MS: Anal. Calcd. for: $C_{13}H_{18}N_2O_2$ 234.14; found: 235.31 (M + H)$^+$. |
| Cap-17d | 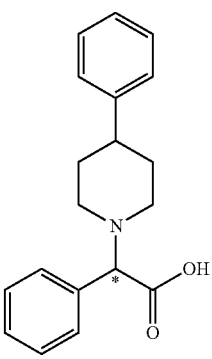 [SMILES: O=C(O)C(c1ccccc1)N1CCC(c2ccccc2)CC1] | RT = 2.21 (Condition I); LC-MS: Anal. Calcd. for: $C_{19}H_{21}NO_2$ 295.16; found: 296.33 (M + H)$^+$. |

LC-MS Conditions for Determining Retention Time:
Condition I
Column: PHENOMENEX® Luna 4.6×50 mm S10
Start % B=0
Final % B=100
Gradient Time=4 min
Flow Rate=4 mL/min
Wavelength=220
Solvent A=10% methanol-90% H$_2$O-0.1% TFA
Solvent B=90% methanol-10% H$_2$O-0.1% TFA
Condition II
Column: Waters-Sunfire 4.6×50 mm S5
Start % B=0
Final % B=100
Gradient Time=2 min
Flow Rate=4 mL/min
Wavelength=220
Solvent A=10% methanol-90% H$_2$O-0.1% TFA
Solvent B=90% methanol-10% H$_2$O-0.1% TFA
Condition III
Column: PHENOMENEX® 10μ 3.0×50 mm
Start % B=0
Final % B=100
Gradient Time=2 min
Flow Rate=4 mL/min
Wavelength=220
Solvent A=10% methanol-90% H$_2$O-0.1% TFA
Solvent B=90% methanol-10% H$_2$O-0.1% TFA

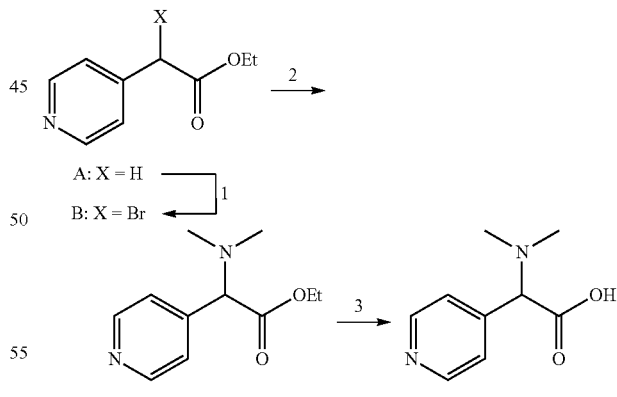

Cap-18

Step 1: (R,S)-Ethyl 2-(4-pyridyl)-2-bromoacetate

To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to −78° C. To this mixture was added CBr$_4$ (2.21 g, 6.66 mmol) and stirring was continued at −78° C. for 2 hours. The reaction mixture was then quenched with sat. aq. NH$_4$Cl and the phases were separated. The organic phase was washed (brine), dried (Na$_2$SO$_4$), filtered, and concentrated in vacuo. The resulting yellow oil was immediately purified by flash chromatography (SiO$_2$/hexane-ethyl acetate, 1:1) to provide the title compound (1.40 g, 95%) as a somewhat unstable yellow oil. $^1$H NMR (400 MHz, CDCl$_3$) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LC-MS: Anal. Calcd. for C$_9$H$_{10}$BrNO$_2$: 242, 244. found: 243, 245 (M+H)$^+$.

Step 2: (R,S)-Ethyl 2-(4-pyridyl)-2-(N,N-dimethylamino)acetate

To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by thin layer chromatography) the volatiles were removed in vacuo and the residue was purified by flash chromatography (BIOTAGE®, 40+M SiO$_2$ column; 50%-100% ethyl acetate-hexane) to provide the title compound (0.539 g, 31%) as a light yellow oil. $^1$H NMR (400 MHz, CDCl$_3$) δ 8.58 (d, J=6.0 Hz, 2H), 7.36 (d, J=6.0 Hz, 2H), 4.17 (m, 2H), 3.92 (s, 1H), 2.27 (s, 6H), 1.22 (t, J=7.0 Hz). LC-MS: Anal. Calcd. for C$_{11}$H$_{16}$N$_2$O$_2$: 208. found: 209 (M+H)$^+$.

Step 3: (R,S)-2-(4-Pyridyl)-2-(N,N-dimethylamino) acetic acid

To a solution of (R,S)-ethyl 2-(4-pyridyl)-2-(N,N-dimethylamino)acetate (0.200 g, 0.960 mmol) in a mixture of THF-methanol-H$_2$O (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. $^1$H NMR (400 MHz, DMSO-d$_6$) δ 8.49 (d, J=5.7 Hz, 2H), 7.34 (d, J=5.7 Hz, 2H), 3.56 (s, 1H), 2.21 (s, 6H).

The following examples were prepared in similar fashion using the method described above:

Cap-19 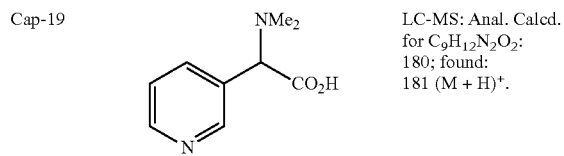 LC-MS: Anal. Calcd. for C$_9$H$_{12}$N$_2$O$_2$: 180; found: 181 (M + H)$^+$.

Cap-20 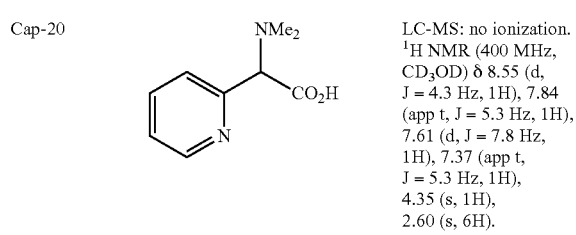 LC-MS: no ionization. $^1$H NMR (400 MHz, CD$_3$OD) δ 8.55 (d, J = 4.3 Hz, 1H), 7.84 (app t, J = 5.3 Hz, 1H), 7.61 (d, J = 7.8 Hz, 1H), 7.37 (app t, J = 5.3 Hz, 1H), 4.35 (s, 1H), 2.60 (s, 6H).

Cap-21 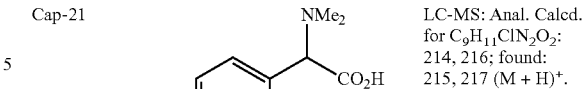 LC-MS: Anal. Calcd. for C$_9$H$_{11}$ClN$_2$O$_2$: 214, 216; found: 215, 217 (M + H)$^+$.

Cap-22 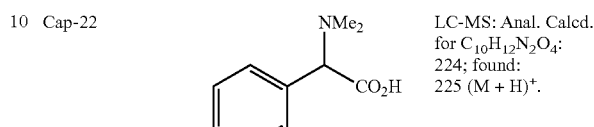 LC-MS: Anal. Calcd. for C$_{10}$H$_{12}$N$_2$O$_4$: 224; found: 225 (M + H)$^+$.

Cap-23 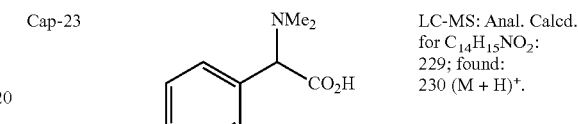 LC-MS: Anal. Calcd. for C$_{14}$H$_{15}$NO$_2$: 229; found: 230 (M + H)$^+$.

Cap-24 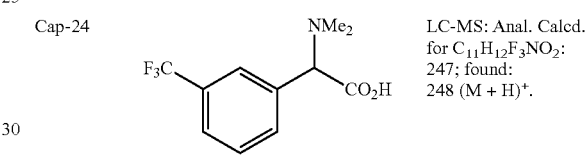 LC-MS: Anal. Calcd. for C$_{11}$H$_{12}$F$_3$NO$_2$: 247; found: 248 (M + H)$^+$.

Cap-25 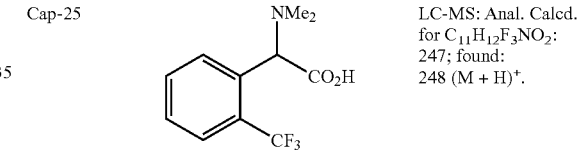 LC-MS: Anal. Calcd. for C$_{11}$H$_{12}$F$_3$NO$_2$: 247; found: 248 (M + H)$^+$.

Cap-26 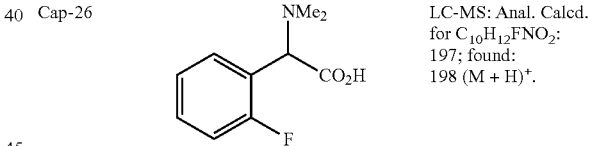 LC-MS: Anal. Calcd. for C$_{10}$H$_{12}$FNO$_2$: 197; found: 198 (M + H)$^+$.

Cap-27 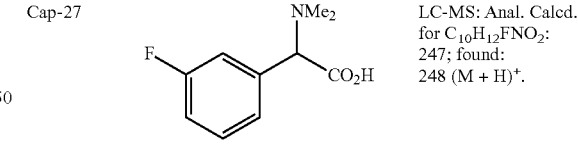 LC-MS: Anal. Calcd. for C$_{10}$H$_{12}$FNO$_2$: 247; found: 248 (M + H)$^+$.

Cap-28 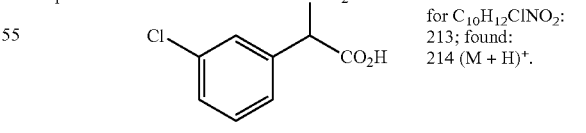 LC-MS: Anal. Calcd. for C$_{10}$H$_{12}$ClNO$_2$: 213; found: 214 (M + H)$^+$.

Cap-29 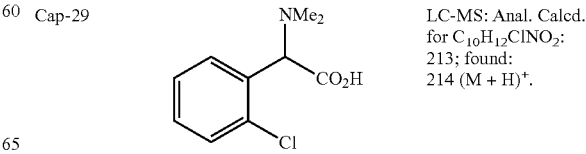 LC-MS: Anal. Calcd. for C$_{10}$H$_{12}$ClNO$_2$: 213; found: 214 (M + H)$^+$.

| | | |
|---|---|---|
| Cap-30 | ![Cap-30 structure: 4-chlorophenyl with NMe2 and CO2H] | LC-MS: Anal. Calcd. for $C_{10}H_{12}ClNO_2$: 213; found: 214 $(M + H)^+$. |
| Cap-31 | ![Cap-31 structure: 2-methylthiazol-4-yl with NMe2 and CO2H] | LC-MS: Anal. Calcd. for $C_8H_{12}N_2O_2S$: 200; found: 201 $(M + H)^+$. |
| Cap-32 | ![Cap-32 structure: thiophen-2-yl with NMe2 and CO2H] | LC-MS: Anal. Calcd. for $C_8H_{11}NO_2S$: 185; found: 186 $(M + H)^+$. |
| Cap-33 | ![Cap-33 structure: thiophen-3-yl with NMe2 and CO2H] | LC-MS: Anal. Calcd. for $C_8H_{11}NO_2S$: 185; found: 186 $(M + H)^+$. |
| Cap-34 | ![Cap-34 structure: benzisoxazol-3-yl with NMe2 and CO2H] | LC-MS: Anal. Calcd. for $C_{11}H_{12}N_2O_3$: 220; found: 221 $(M + H)^+$. |
| Cap-35 | ![Cap-35 structure: benzothiophen-3-yl with NMe2 and CO2H] | LC-MS: Anal. Calcd. for $C_{12}H_{13}NO_2S$: 235; found: 236 $(M + H)^+$. |
| Cap-36 | ![Cap-36 structure: 2-methylbenzothiazol-5-yl with NMe2 and CO2H] | LC-MS: Anal. Calcd. for $C_{12}H_{14}N_2O_2S$: 250; found: 251 $(M + H)^+$. |

Cap-37

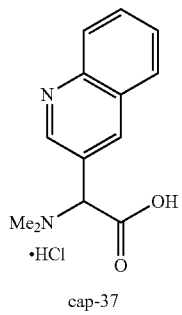

cap-37

Step 1: (R,S)-Ethyl 2-(quinolin-3-yl)-2-(N,N-dimethylamino)-acetate

A mixture of ethyl N,N-dimethylaminoacetate (0.462 g, 3.54 mmol), $K_3PO_4$ (1.90 g, 8.95 mmol), $Pd(t-Bu_3P)_2$ (0.090 g, 0.176 mmol), 3-bromoquinoline and toluene (10 mL) was degassed with a stream of Ar bubbles for 15 minutes. The reaction mixture was then heated at 100° C. for 12 hours, after which it was cooled to room temperature and poured into $H_2O$. The mixture was extracted with ethyl acetate (2×) and the combined organic phases were washed ($H_2O$, brine), dried ($Na_2SO_4$), filtered, and concentrated in vacuo. The residue was purified first by reverse-phase preparative HPLC (Primesphere C-18, 30×100 mm; $CH_3CN$—$H_2O$-5 mM $NH_4OAc$) and then by flash chromatography ($SiO_2$/hexane-ethyl acetate, 1:1) to provide the title compound (0.128 g, 17%) as an orange oil. $^1H$ NMR (400 MHz, $CDCl_3$) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LC-MS: Anal. Calcd. for $C_{15}H_{18}N_2O_2$: 258. found: 259 $(M+H)^+$.

Step 2: (R,S) 2-(Quinolin-3-yl)-2-(N,N-dimethylamino)acetic acid

A mixture of (R,S)-ethyl 2-(quinolin-3-yl)-2-(N,N-dimethylamino)acetate (0.122 g, 0.472 mmol) and 6M HCl (3 mL) was heated at 100° C. for 12 hours. The solvent was removed in vacuo to provide the dihydrochloride of the title compound (0.169 g, >100%) as a light yellow foam. The unpurified material was used in subsequent steps without further purification. LC-MS: Anal. Calcd. for $C_{13}H_{14}N_2O_2$: 230. found: 231 $(M+H)^+$.

Cap-37

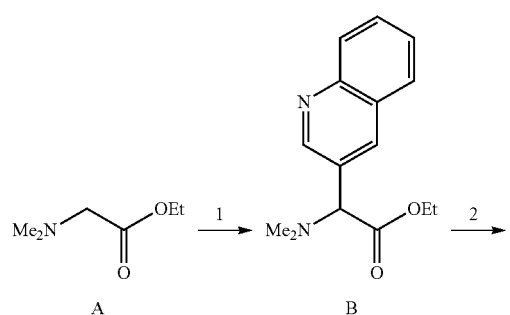

Cap-38

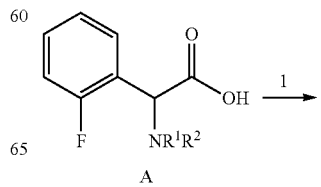

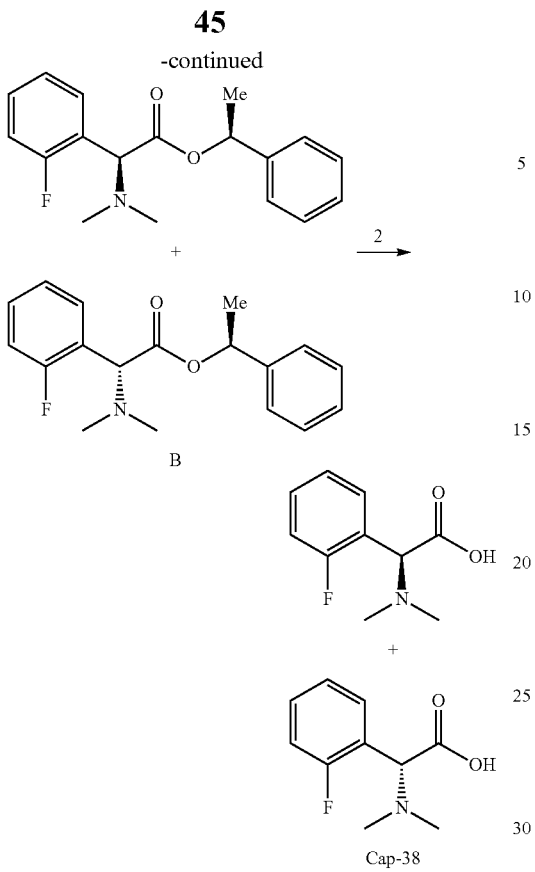

Step 1: (R)—((S)-1-Phenylethyl) 2-(dimethylamino)-2-(2-fluorophenyl)acetate and (S)—((S)-1-Phenylethyl) 2-(dimethylamino)-2-(2-fluorophenyl)acetate To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in $CH_2Cl_2$ (40 mL) was added EDCI (3.29 g, 17.15 mmol) and the mixture was allowed to stir at room temperature for 12 hours. The solvent was then removed in vacuo and the residue partitioned with ethyl acetate-$H_2O$. The layers were separated, the aqueous layer was back-extracted with ethyl acetate (2×) and the combined organic phases were washed ($H_2O$, brine), dried ($Na_2SO_4$), filtered, and concentrated in vacuo. The residue was purified by silica gel chromatography (BIOTAGE®/0-50% diethyl ether-hexane). The resulting pure diastereomeric mixture was then separated by reverse-phase preparative HPLC (Primesphere C-18, 30×100 mm; $CH_3CN$—$H_2O$-0.1% TFA) to give first (S)-1-phenethyl (R)-2-(dimethylamino)-2-(2-fluorophenyl)acetate (0.501 g, 13%) and then (S)-1-phenethyl (S)-2-(dimethylamino)-2-(2-fluorophenyl)-acetate (0.727 g. 18%), both as their TFA salts. (S,R)-isomer: $^1$H NMR (400 MHz, $CD_3OD$) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H). LC-MS: Anal. Calcd. for $C_{18}H_{20}FNO_2$: 301. found: 302 (M+H)$^+$; (S,S)-isomer: $^1$H NMR (400 MHz, $CD_3OD$) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LC-MS: Anal. Calcd. for $C_{18}H_{20}FNO_2$: 301. found: 302 (M+H)$^+$.

Step 2: (R)-2-(Dimethylamino)-2-(2-fluorophenyl)acetic acid

A mixture of (R)—((S)-1-phenylethyl) 2-(dimethylamino)-2-(2-fluorophenyl)acetate TFA salt (1.25 g, 3.01 mmol) and 20% $Pd(OH)_2/C$ (0.125 g) in ethanol (30 mL) was hydrogenated at room temperature and atmospheric pressure ($H_2$ balloon) for 4 hours. The solution was then purged with Ar, filtered through diatomaceous earth (CELITE®), and concentrated in vacuo. This gave the title compound as a colorless solid (0.503 g, 98%). $^1$H NMR (400 MHz, $CD_3OD$) δ 7.53-7.63 (m, 2H), 7.33-7.38 (m, 2H), 5.36 (s, 1H), 2.86 (s, 6H). LC-MS: Anal. Calcd. for $C_{10}H_{12}FNO_2$: 197. found: 198 (M+H)$^+$.

The S-isomer could be obtained from (S)—((S)-1-phenylethyl) 2-(dimethylamino)-2-(2-fluorophenyl)acetate TFA salt in similar fashion.

Cap-39

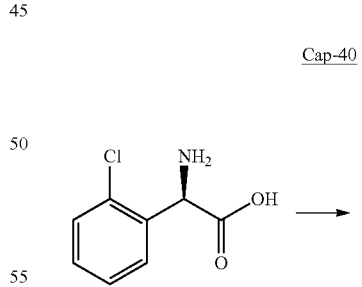

cap-39

A mixture of (R)-(2-chlorophenyl)glycine (0.300 g, 1.62 mmol), formaldehyde (35% aqueous solution, 0.80 mL, 3.23 mmol) and 20% $Pd(OH)_2/C$ (0.050 g) was hydrogenated at room temperature and atmospheric pressure ($H_2$ balloon) for 4 hours. The solution was then purged with Ar, filtered through diatomaceous earth (CELITE®) and concentrated in vacuo. The residue was purified by reverse-phase preparative HPLC (Primesphere C-18, 30×100 mm; $CH_3CN$—$H_2O$-0.1% TFA) to give the TFA salt of the title compound (R)-2-(dimethylamino)-2-(2-chlorophenyl)acetic acid as a colorless oil (0.290 g, 55%). $^1$H NMR (400 MHz, $CD_3OD$) δ 7.59-7.65 (m, 2H), 7.45-7.53 (m, 2H), 5.40 (s, 1H), 2.87 (s, 6H). LC-MS: Anal. Calcd. for $C_{10}H_{12}ClNO_2$: 213. found: 214 (M+H)$^+$.

Cap-40 cap-40

To an ice-cold solution of (R)-(2-chlorophenyl)glycine (1.00 g, 5.38 mmol) and NaOH (0.862 g, 21.6 mmol) in $H_2O$ (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed ($H_2O$, brine), dried ($Na_2SO_4$), and concentrated in vacuo to give the title compound (R)-2-(methoxycarbonylamino)-2-(2-chlorophenyl)acetic acid as a yellow-orange foam (1.31 g, 96%). $^1$H NMR (400 MHz, CD$_3$OD) δ 7.39-7.43 (m, 2H), 7.29-7.31 (m, 2H), 5.69 (s, 1H), 3.65 (s, 3H). LC-MS: Anal. Calcd. for C$_{10}$H$_{10}$ClNO$_4$: 243. found: 244 (M+H)$^+$.

Cap-41

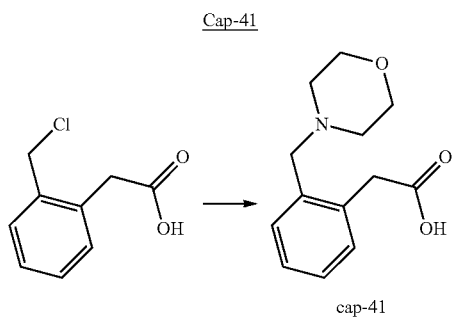 [SMILES: O=C(O)Cc1ccccc1CCl ; O=C(O)Cc1ccccc1CN1CCOCC1]

cap-41

To a suspension of 2-(2-(chloromethyl)phenyl)acetic acid (2.00 g, 10.8 mmol) in THF (20 mL) was added morpholine (1.89 g, 21.7 mmol) and the solution was stirred at room temperature for 3 hours. The reaction mixture was then diluted with ethyl acetate and extracted with H$_2$O (2×). The aqueous phase was lyophilized and the residue was purified by silica gel chromatography (BIOTAGE®/0-10% methanol-CH$_2$Cl$_2$) to give the title compound 2-(2-(Morpholinomethyl)phenyl)acetic acid as a colorless solid (2.22 g, 87%). $^1$H NMR (400 MHz, CD$_3$OD) δ 7.37-7.44 (m, 3H), 7.29-7.33 (m, 1H), 4.24 (s, 2H), 3.83 (br s, 4H), 3.68 (s, 2H), 3.14 (br s, 4H). LC-MS: Anal. Calcd. for C$_{13}$H$_{17}$NO$_3$: 235. found: 236 (M+H)$^+$.

The following examples were similarly prepared using the method described for Cap-41:

| Cap-42 | 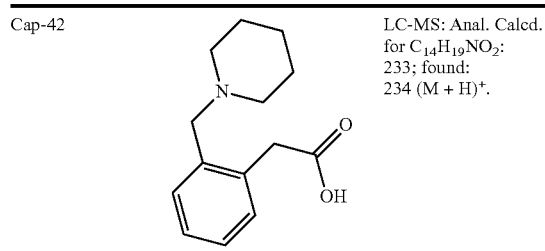 | LC-MS: Anal. Calcd. for C$_{14}$H$_{19}$NO$_2$: 233; found: 234 (M + H)$^+$. |
|---|---|---|
| Cap-43 | 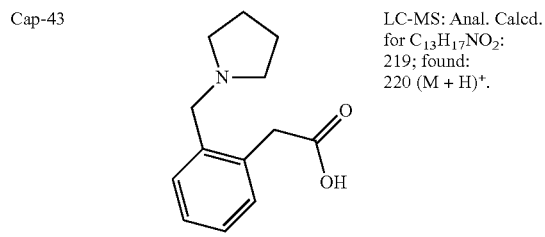 | LC-MS: Anal. Calcd. for C$_{13}$H$_{17}$NO$_2$: 219; found: 220 (M + H)$^+$. |
| Cap-44 | 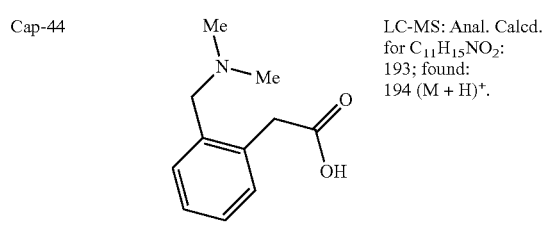 | LC-MS: Anal. Calcd. for C$_{11}$H$_{15}$NO$_2$: 193; found: 194 (M + H)$^+$. |
| Cap-45 | 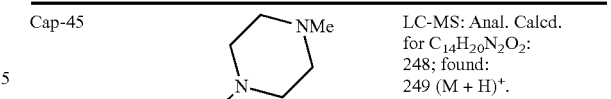 | LC-MS: Anal. Calcd. for C$_{14}$H$_{20}$N$_2$O$_2$: 248; found: 249 (M + H)$^+$. |

Cap-45a

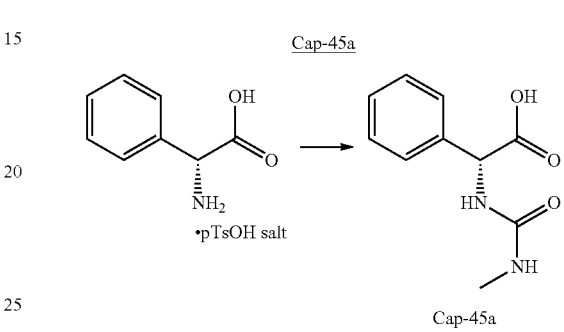

Cap-45a

HMDS (1.85 mL, 8.77 mmol) was added to a suspension of (R)-2-amino-2-phenylacetic acid p-toluenesulfonate (2.83 g, 8.77 mmol) in CH$_2$Cl$_2$ (10 mL) and the mixture was stirred at room temperature for 30 minutes. Methyl isocyanate (0.5 g, 8.77 mmol) was added in one portion stirring continued for 30 minutes. The reaction was quenched by addition of H$_2$O (5 mL) and the resulting precipitate was filtered, washed with H$_2$O and n-hexanes, and dried under vacuum. (R)-2-(3-methylureido)-2-phenylacetic acid (1.5 g; 82%) was recovered as a white solid and it was used without further purification. $^1$H NMR (500 MHz, DMSO-d$_6$) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LC-MS: Anal. Calcd. for C$_{10}$H$_{12}$N$_2$O$_3$ 208.08 found 209.121 (M+H)$^+$; HPLC PHENOMENEX® C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

Cap-46

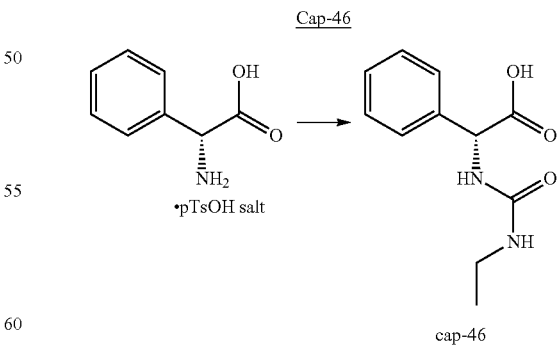

cap-46

The desired product was prepared according to the method described for Cap-45a. $^1$H NMR (500 MHz, DMSO-d$_6$) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LC-MS: Anal. Calcd. for $C_{11}H_{14}N_2O_3$ 222.10 found 223.15 (M+H)+. HPLC XTERRA® C-18 3.0×506 mm, 0 to 100% B over 2 minutes, 1 minute hold time, A=90% water, 10% methanol, 0.2% $H_3PO_4$, B=10% water, 90% methanol, 0.2% $H_3PO_4$, RT=0.87 min, 90% homogeneity index.

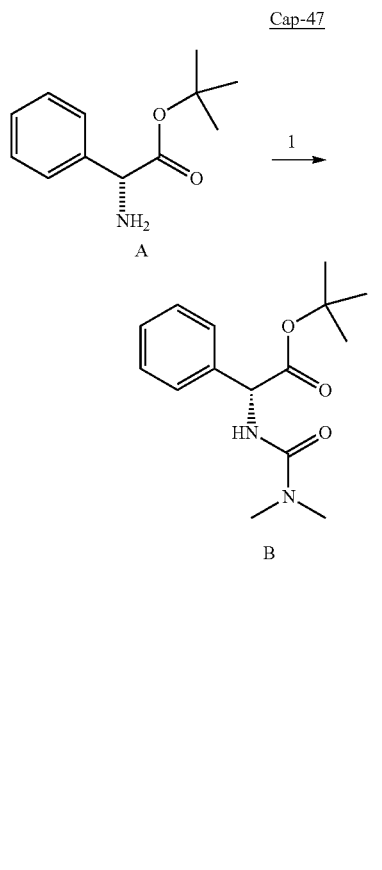

Step 1: (R)-tert-Butyl 2-(3,3-dimethylureido)-2-phenylacetate

To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with $H_2O$, 1N aq. HCl and brine, dried ($MgSO_4$), filtered and concentrated under reduced pressure. (R)-tert-butyl 2-(3,3-dimethylureido)-2-phenylacetate was obtained as a white solid (0.86 g; 75%) and used without further purification. $^1$H NMR (500 MHz, DMSO-$d_6$) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LC-MS: Anal. Calcd. for $C_{15}H_{22}N_2O_3$ 278.16 found 279.23 (M+H)+; HPLC PHENOMENEX® LUNA C-18 4.6× 50 mm, 0 to 100% B over 4 minutes, 1 minute hold time, A=90% water, 10% methanol, 0.1% TFA, B=10% water, 90% methanol, 0.1% TFA, RT=2.26 min, 97% homogeneity index.

Step 2: (R)-2-(3,3-Dimethylureido)-2-phenylacetic acid

To a stirred solution of ((R)-tert-butyl 2-(3,3-dimethylureido)-2-phenylacetate (0.86 g, 3.10 mmol) in $CH_2Cl_2$ (250 mL) was added TFA (15 mL) dropwise and the resulting solution was stirred at rt for 3 hours. The desired compound was then precipitated out of solution with a mixture of EtOAC:Hexanes (5:20), filtered off and dried under reduced pressure. (R)-2-(3,3-dimethylureido)-2-phenylacetic acid was isolated as a white solid (0.59 g, 86%) and used without further purification. $^1$H NMR (500 MHz, DMSO-$d_6$) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=7.32 Hz, 2H) 7.38-7.43 (m, 2H) 12.65 (s, 1H). LC-MS: Anal. Calcd. for $C_{11}H_{14}N_2O_3$: 222.24. found: 223.21 (M+H)+. HPLC XTERRA® C-18 3.0×50 mm, 0 to 100% B over 2 minutes, 1 minute hold time, A=90% water, 10% methanol, 0.2% $H_3PO_4$, B=10% water, 90% methanol, 0.2% $H_3PO_4$, RT=0.75 min, 93% homogeneity index.

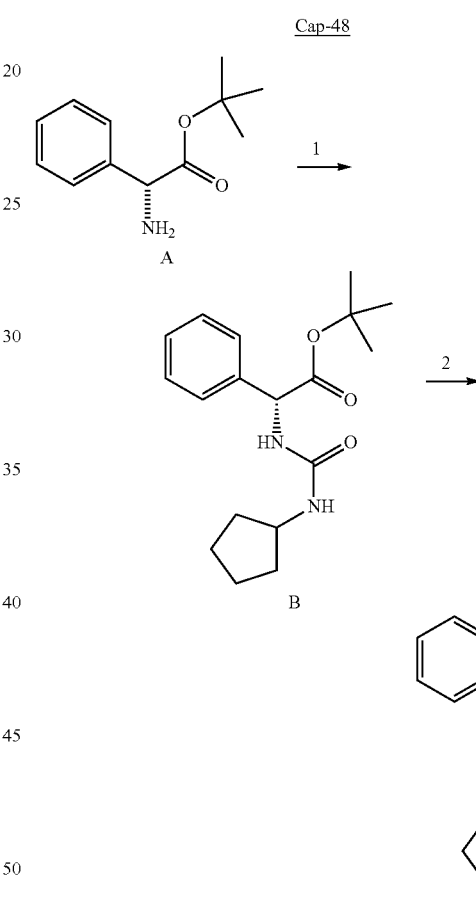

Step 1: (R)-tert-Butyl 2-(3-cyclopentylureido)-2-phenylacetate

To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes. After stirring at room temperature for 3 hours, the reaction was concentrated under reduced pressure and the resulting residue was taken up in ethyl acetate. The organic layer was washed with $H_2O$ and brine, dried ($MgSO_4$), filtered, and concentrated under reduced pressure. (R)-tert-butyl 2-(3-cyclopentylureido)-2-phenylacetate was obtained as an opaque oil (1.32 g; 100%) and used without further purification. ¹H NMR (500 MHz, CD₃Cl-D) δ ppm 1.50-1.57 (m, 2H) 1.58-1.66 (m, 2H) 1.87-1.97 (m, 2H) 3.89-3.98 (m, 1H) 5.37 (s, 1H) 7.26-7.38 (m, 5H). LC-MS: Anal. Calcd. for C₁₈H₂₆N₂O₃ 318.19 found 319.21 (M+H)⁺; HPLC XTERRA® C-18 3.0×50 mm, 0 to 100% B over 4 minutes, 1 minute hold time, A=90% water, 10% methanol, 0.1% TFA, B=10% water, 90% methanol, 0.1% TFA, RT=2.82 min, 96% homogeneity index.

Step 2: (R)-2-(3-Cyclopentylureido)-2-phenylacetic acid

To a stirred solution of (R)-tert-butyl 2-(3-cyclopentylureido)-2-phenylacetate (1.31 g, 4.10 mmol) in CH₂Cl₂ (25 mL) was added TFA (4 mL) and trietheylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). ¹H NMR (500 MHz, DMSO-d₆) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LC-MS: Anal. Calcd. for C₁₄H₁₈N₂O₃: 262.31. found: 263.15 (M+H)⁺. HPLC XTERRA® C-18 3.0×50 mm, 0 to 100% B over 2 minutes, 1 minute hold time, A=90% water, 10% methanol, 0.2% H₃PO₄, B=10% water, 90% methanol, 0.2% H₃PO₄, RT=1.24 min, 100% homogeneity index.

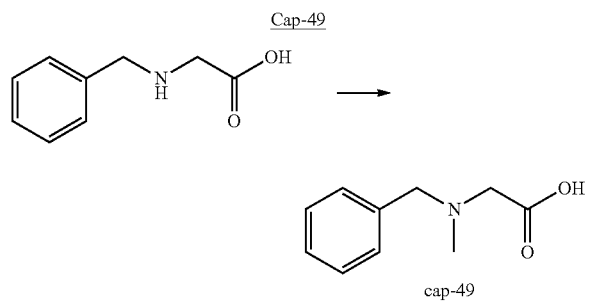

cap-49

To a stirred solution of 2-(benzylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC (XTERRA® 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl(methyl)-amino)acetic acid as its TFA salt (723 mg, 33%) as a colorless wax. ¹H NMR (300 MHz, DMSO-d₆) δ ppm 2.75 (s, 3H) 4.04 (s, 2H) 4.34 (s, 2H) 7.29-7.68 (m, 5H). LC-MS: Anal. Calcd. for: C₁₀H₁₃NO₂ 179.09. found: 180.20 (M+H)⁺.

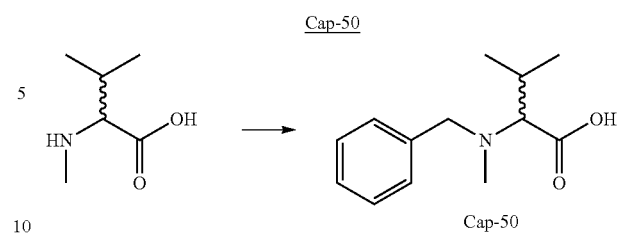

To a stirred solution of 3-methyl-2-(methylamino)butanoic acid (0.50 g, 3.81 mmol) in water (30 mL) was added K₂CO₃ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (XTERRA® 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. ¹H NMR (500 MHz, DMSO-d₆) δ ppm 0.98 (d, 3H) 1.07 (d, 3H) 2.33-2.48 (m, 1H) 2.54-2.78 (m, 3H) 3.69 (s, 1H) 4.24 (s, 2H) 7.29-7.65 (m, 5H). LC-MS: Anal. Calcd. for: C₁₃H₁₉NO₂ 221.14. found: 222.28 (M+H)⁺.

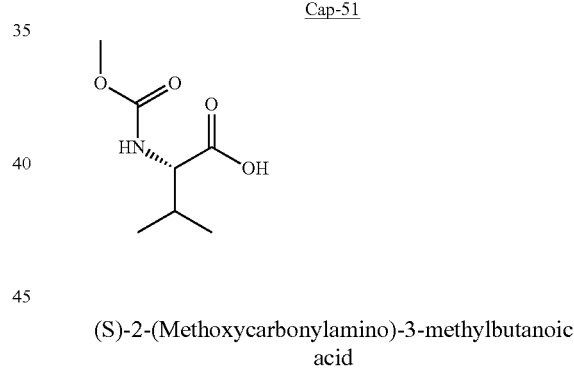

(S)-2-(Methoxycarbonylamino)-3-methylbutanoic acid

Na₂CO₃ (1.83 g, 17.2 mmol) was added to NaOH (33 mL of 1M/H₂O, 33 mmol) solution of L-valine (3.9 g, 33.29 mmol) and the resulting solution was cooled with ice-water bath. Methyl chloroformate (2.8 mL, 36.1 mmol) was added dropwise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with CH₂Cl₂ (50 mL, 3×). The organic phase was dried (MgSO₄) and evaporated in vacuo to afford Cap-51 as a white solid (6 g). ¹H NMR for the dominant rotamer (DMSO-d₆, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for [M+H]⁺ C₇H₁₄NO₄: 176.0923. found 176.0922.

Cap-51 (alternate route)

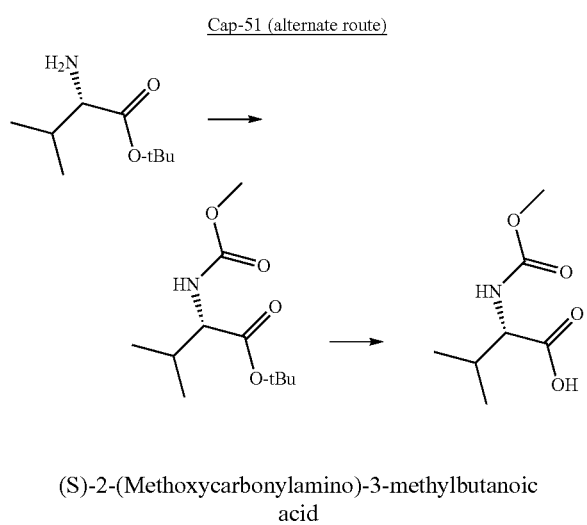

(S)-2-(Methoxycarbonylamino)-3-methylbutanoic acid

DIEA (137.5 mL, 0.766 mol) was added to a suspension of (S)-tert-butyl 2-amino-3-methylbutanoate hydrochloride (75.0 g, 0.357 mol) in THF (900 mL), and the mixture was cooled to 0° C. (ice/water bath). Methyl chloroformate (29.0 mL, 0.375 mol) was added dropwise over 45 min, the cooling bath was removed and the heterogeneous mixture was stirred at ambient temperature for 3 h. The solvent was removed under diminished pressure and the residue partitioned between EtOAc and water (1 L each). The organic layer was washed with $H_2O$ (1 L) and brine (1 L), dried ($MgSO_4$), filtered and concentrated under diminished pressure. The crude material was passed through a plug of silica gel (1 kg), eluting with hexanes (4 L) and 15:85 EtOAc/hexanes (4 L) to afford (S)-tert-butyl 2-(methoxycarbonylamino)-3-methylbutanoate as a clear oil (82.0 g, 99% yield). $^1$H NMR (500 MHz, DMSO-$d_6$, δ=2.5 ppm) 7.34 (d, J=8.6, 1 H), 3.77 (dd, J=8.6, 6.1, 1 H), 3.53 (s, 3H), 1.94-2.05 (m, 1H), 1.39 (s, 9H), 0.83-0.92 (m, 6H). $^{13}$C-NMR (126 MHz, DMSO-$d_6$, δ=39.2 ppm) 170.92, 156.84, 80.38, 60.00, 51.34, 29.76, 27.62, 18.92, 17.95. LC-MS: [M+Na]$^+$ 254.17.

Trifluoroacetic acid (343 mL, 4.62 mol) and Et$_3$SiH (142 mL, 0.887 mol) were added sequentially to a solution of (S)-tert-butyl 2-(methoxycarbonylamino)-3-methylbutanoate (82.0 g, 0.355 mol) in $CH_2Cl_2$ (675 mL), and the mixture was stirred at ambient temperature for 4 h. The volatile component was removed under diminished pressure and the resultant oil triturated with petroleum ether (600 mL) to afford a white solid, which was filtered and washed with hexanes (500 mL) and petroleum ether (500 mL). Recrystallization from EtOAc/petroleum ether afforded Cap-51 as white flaky crystals (54.8 g, 88% yield). MP=108.5-109.5° C. $^1$H NMR (500 MHz, DMSO-$d_6$, δ=2.5 ppm) 12.52 (s, 1H), 7.31 (d, J=8.6, 1 H), 3.83 (dd, J=8.6, 6.1, 1 H), 3.53 (s, 3H), 1.94-2.07 (m, 1H), 0.86 (dd, J=8.9, 7.0, 6 H). $^{13}$C NMR (126 MHz, DMSO-$d_6$, δ=39.2 ppm) 173.30, 156.94, 59.48, 51.37, 29.52, 19.15, 17.98. LC-MS: [M+H]$^+$=176.11. Anal. Calcd. for $C_7H_{13}NO_4$: C, 47.99; H, 7.48; N, 7.99. Found: C, 48.17; H, 7.55; N, 7.99. Optical Rotation: [α]$_D$=-4.16 (12.02 mg/mL; MeOH). Optical purity: >99.5% ee. Note: the optical purity assessment was made on the methyl ester derivative of Cap-51, which was prepared under a standard TMSCHN$_2$ (benzene/MeOH) esterification protocol. HPLC analytical conditions: column, CHIRALPAK® AD-H (4.6×250 mm, 5 μm); solvent, 95% heptane/5% IPA (isocratic); flow rate, 1 mL/min; temperature, 35° C.; UV monitored at 205 nm. [Note: Cap-51 could also be purchased from Flamm.]

Cap-52 (same as Cap-12)

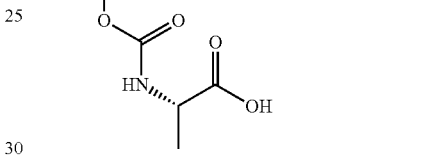

(S)-2-(Methoxycarbonylamino)propanoic acid

Cap-52 was synthesized from L-alanine according to the procedure described for the synthesis of Cap-51. For characterization purposes, a portion of the crude material was purified by a reverse phase HPLC ($H_2O$/methanol/TFA) to afford Cap-52 as a colorless viscous oil. $^1$H NMR (DMSO-$d_6$, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to Cap-64

Cap-53 to Cap-64 were prepared from appropriate starting materials according to the procedure described for the synthesis of Cap-51, with noted modifications if any.

| Cap | Structure | Data |
|---|---|---|
| Cap-53a: (R) Cap-53b: (S) ((S)-2-(methoxy-carbonyl-amino)butanoic acid) | 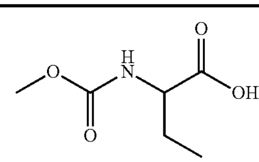 | $^1$H NMR (DMSO-$d_6$, δ = 2.5 ppm, 500 MHz): δ 12.51 (br s, 1H), 7.4 (d, J = 7.9, 0.9H), 7.06 (app s, 0.1H), 3.86-3.82 (m, 1H), 3.53 (s, 3H), 1.75-1.67 (m, 1H), 1.62-1.54 (m, 1H), 0.88 (d, J = 7.3, 3H). RT = 0.77 minutes (Cond. 2); LC-MS: Anal. Calcd. for [M + Na]$^+$ $C_6H_{11}NNaO_4$: 184.06; found 184.07. HRMS Calcd. for [M + Na]$^+$ $C_6H_{11}NNaO_4$: 184.0586; found 184.0592. |
| Cap-54a: (R) Cap-54b: (S) ((S)-2-cyclopropyl-2-(methoxy-carbonyl-amino)acetic acid) | 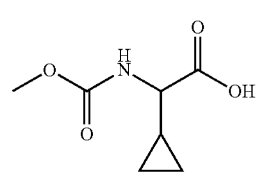 | $^1$H NMR (DMSO-$d_6$, δ = 2.5 ppm, 500 MHz): δ 12.48 (s, 1H), 7.58 (d, J = 7.6, 0.9H), 7.25 (app s, 0.1H), 3.52 (s, 3H), 3.36-3.33 (m, 1H), 1.10-1.01 (m, 1H), 0.54-0.49 (m, 1H), 0.46-0.40 (m, 1H), 0.39-0.35 (m, 1H), 0.31-0.21 (m, 1H). HRMS Calcd. for [M + H]$^+$ $C_7H_{12}NO_4$: 174.0766; found 174.0771 |

-continued

| Cap | Structure | Data |
|---|---|---|
| Cap-55 | 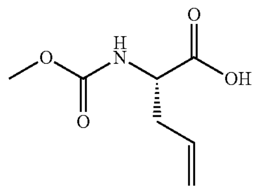 | ¹H NMR (DMSO-d₆, δ = 2.5 ppm, 500 MHz): δ 12.62 (s, 1H), 7.42 (d, J = 8.2, 0.9H), 7.07 (app s, 0.1H), 5.80-5.72 (m, 1H), 5.10 (d, J = 17.1, 1H), 5.04 (d, J = 10.4, 1H), 4.01-3.96 (m, 1H), 3.53 (s, 3H), 2.47-2.42 (m, 1H), 2.35-2.29 (m, 1H). |
| Cap-56 (S)-3-methoxy-2-(methoxy-carbonyl-amino)propanoic acid | 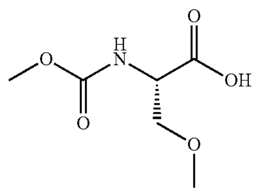 | ¹H NMR (DMSO-d₆, δ = 2.5 ppm, 500 MHz): δ 12.75 (s, 1H), 7.38 (d, J = 8.3, 0.9H), 6.96 (app s, 0.1H), 4.20-4.16 (m, 1H), 3.60-3.55 (m, 2H), 3.54 (s, 3H), 3.24 (s, 3H). |
| Cap-57 | 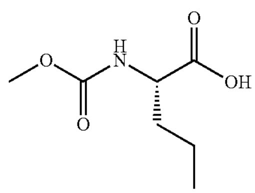 | ¹H NMR (DMSO-d₆, δ = 2.5 ppm, 500 MHz): δ 12.50 (s, 1H), 8.02 (d, J = 7.7, 0.08H), 7.40 (d, J = 7.9, 0.76H), 7.19 (d, J = 8.2, 0.07H), 7.07 (d, J = 6.7, 0.09H), 4.21-4.12 (m, 0.08H), 4.06-3.97 (m, 0.07H), 3.96-3.80 (m, 0.85H), 3.53 (s, 3H), 1.69-1.51 (m, 2H), 1.39-1.26 (m, 2H), 0.85 (t, J = 7.4, 3H). LC (Cond. 2): RT = 1.39 LC-MS: Anal. Calcd. for [M + H]⁺ C₇H₁₄NO₄: 176.09; found 176.06. |
| Cap-58 | 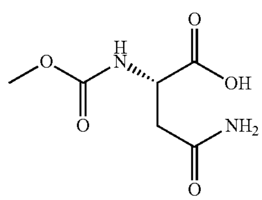 | ¹H NMR (DMSO-d₆, δ = 2.5 ppm, 500 MHz): δ 12.63 (br s, 1H), 7.35 (s, 1H), 7.31 (d, J = 8.2, 1H), 6.92 (s, 1H), 4.33-4.29 (m, 1H), 3.54 (s, 3H), 2.54 (dd, J = 15.5, 5.4, 1H), 2.43 (dd, J = 15.6, 8.0, 1H). RT = 0.16 min (Cond. 2); LC-MS: Anal. Calcd. for [M + H]⁺ C₆H₁₁N₂O₅: 191.07; found 191.14. |
| Cap-59a: (R) Cap-59b: (S) | 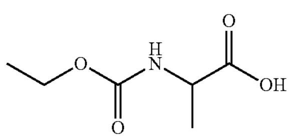 | ¹H NMR (DMSO-d₆, δ = 2.5 ppm, 400 MHz): δ 12.49 (br s, 1H), 7.40 (d, J = 7.3, 0.89H), 7.04 (br s, 0.11H), 4.00-3.95 (m, 3H), 1.24 (d, J = 7.3, 3H), 1.15 (t, J = 7.2, 3H). HRMS: Anal. Calcd. for [M + H]⁺ C₆H₁₂NO₄: 162.0766; found 162.0771. |
| Cap-60 | 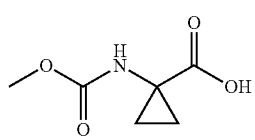 | The crude material was purified with a reverse phase HPLC (H₂O/MeOH/TFA) to afford a colorless viscous oil that crystallized to a white solid upon exposure to high vacuum. ¹H NMR (DMSO-d₆, δ = 2.5 ppm, 400 MHz): δ 12.38 (br s, 1H), 7.74 (s, 0.82H), 7.48 (s, 0.18H), 3.54/3.51 (two s, 3H), 1.30 (m, 2H), 0.98 (m, 2H). HRMS: Anal. Calcd. for [M + H]⁺ C₆H₁₀NO₄: 160.0610; found 160.0604. |
| Cap-61 | 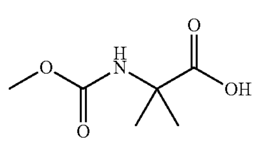 | ¹H NMR (DMSO-d₆, δ = 2.5 ppm, 400 MHz): δ 12.27 (br s, 1H), 7.40 (br s, 1H), 3.50 (s, 3H), 1.32 (s, 6H). HRMS: Anal. Calcd. for [M + H]⁺ C₆H₁₂NO₄: 162.0766; found 162.0765. |
| Cap-62 | 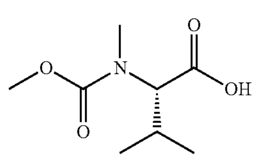 | ¹H NMR (DMSO-d₆, δ = 2.5 ppm, 400 MHz): δ 12.74 (br s, 1H), 4.21 (d, J = 10.3, 0.6H), 4.05 (d, J = 10.0, 0.4H), 3.62/3.60 (two singlets, 3H), 3.0 (s, 3H), 2.14-2.05 (m, 1H), 0.95 (d, J = 6.3, 3H), 0.81 (d, J = 6.6, 3H). LC-MS: Anal. Calcd. for [M − H]⁻ C₈H₁₄NO₄: 188.09; found 188.05. |

-continued

| Cap | Structure | Data |
|---|---|---|
| Cap-63 | 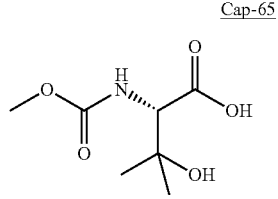 | [Note: the reaction was allowed to run for longer than what was noted for the general procedure.] $^1$H NMR (DMSO-d$_6$, δ = 2.5 ppm, 400 MHz): 12.21 (br s, 1H), 7.42 (br s, 1H), 3.50 (s, 3H), 2.02-1.85 (m, 4H), 1.66-1.58 (m, 4H). LC-MS: Anal. Calcd. for [M + H]$^+$ C$_8$H$_{14}$NO$_4$: 188.09; found 188.19. |
| Cap-64 | 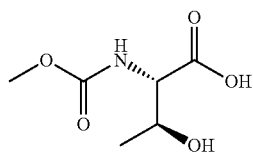 | [Note: the reaction was allowed to run for longer than what was noted for the general procedure.] $^1$H NMR (DMSO-d$_6$, δ = 2.5 ppm, 400 MHz): 12.35 (br s, 1H), 7.77 (s, 0.82H), 7.56/7.52 (overlapping br s, 0.18H), 3.50 (s, 3H), 2.47-2.40 (m, 2H), 2.14-2.07 (m, 2H), 1.93-1.82 (m, 2H). |

Cap-65

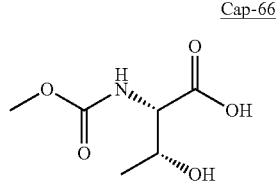

Cap-67

Methyl chloroformate (0.65 mL, 8.39 mmol) was added dropwise over 5 min to a cooled (ice-water) mixture of Na$_2$CO$_3$ (0.449 g, 4.23 mmol), NaOH (8.2 mL of 1M/H$_2$O, 8.2 mmol) and (S)-2-amino-3-hydroxy-3-methylbutanoic acid (1.04 g, 7.81 mmol). The reaction mixture was stirred for 45 min, and then the cooling bath was removed and stirring was continued for an additional 3.75 hr. The reaction mixture was washed with CH$_2$Cl$_2$, and the aqueous phase was cooled with ice-water bath and acidified with concentrated HCl to a pH region of 1-2. The volatile component was removed in vacuo and the residue was taken up in a 2:1 mixture of MeOH/CH$_2$Cl$_2$ (15 mL) and filtered, and the filtrate was rotervaped to afford Cap-65 as a white semi-viscous foam (1.236 g). $^1$H NMR (DMSO-d$_6$, δ=2.5 ppm, 400 MHz): δ 6.94 (d, J=8.5, 0.9H), 6.53 (br s, 0.1H), 3.89 (d, J=8.8, 1H), 2.94 (s, 3H), 1.15 (s, 3H), 1.13 (s, 3H).

Cap-66 and Cap-67 were prepared from appropriate commercially available starting materials by employing the procedure described for the synthesis of Cap-65.

Cap-66

$^1$H NMR (DMSO-d$_6$, δ=2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted].

$^1$H NMR (DMSO-d$_6$, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted].

Cap-68

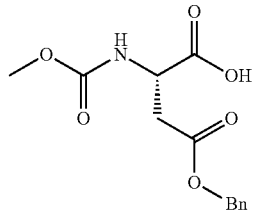

Methyl chloroformate (0.38 ml, 4.9 mmol) was added drop-wise to a mixture of 1N NaOH (aq) (9.0 ml, 9.0 mmol), 1M NaHCO$_3$ (aq) (9.0 ml, 9.0 mol), L-aspartic acid (3-benzyl ester (1.0 g, 4.5 mmol) and Dioxane (9 ml). The reaction mixture was stirred at ambient conditions for 3 hr, and then washed with Ethyl acetate (50 ml, 3×). The aqueous layer was acidified with 12N HCl to a pH~1-2, and extracted with ethyl acetate (3×50 ml). The combined organic layers were washed with brine, dried (Na$_2$SO$_4$), filtered, and concentrated in vacuo to afford Cap-68 as a light yellow oil (1.37 g; mass is above theoretical yield, and the product was used without further purification). $^1$H NMR (DMSO-d$_6$, δ=2.5 ppm, 500 MHz): δ 12.88 (br s, 1H), 7.55 (d, J=8.5, 1H), 7.40-7.32 (m, 5H), 5.13 (d, J=12.8, 1H), 5.10 (d, J=12.9, 1H), 4.42-4.38 (m, 1H), 3.55 (s, 3H), 2.87 (dd, J=16.2, 5.5, 1H), 2.71 (dd, J=16.2, 8.3, 1H). LC (Cond. 2): RT=1.90 min; LC-MS: Anal. Calcd. for [M+H]$^+$ C$_{13}$H$_{16}$NO$_6$: 282.10. found 282.12.

Cap-69a and Cap-69b

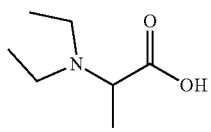

Cap-69a: (R)-enantiomer
Cap-69b: (S)-enantiomer

NaCNBH$_3$ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a DOWEX® 50WX8-100 ion-exchange resin (column was washed with water, and the compound was eluted with dilute NH$_4$OH, prepared by mixing 18 ml of NH$_4$OH and 282 ml of water) to afford Cap-69 (2.0 g) as an off-white soft hygroscopic solid. $^1$H NMR (DMSO-d$_6$, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to Cap-74x

Cap-70 to Cap-74x were prepared according to the procedure described for the synthesis of Cap-69 by employing appropriate starting materials.

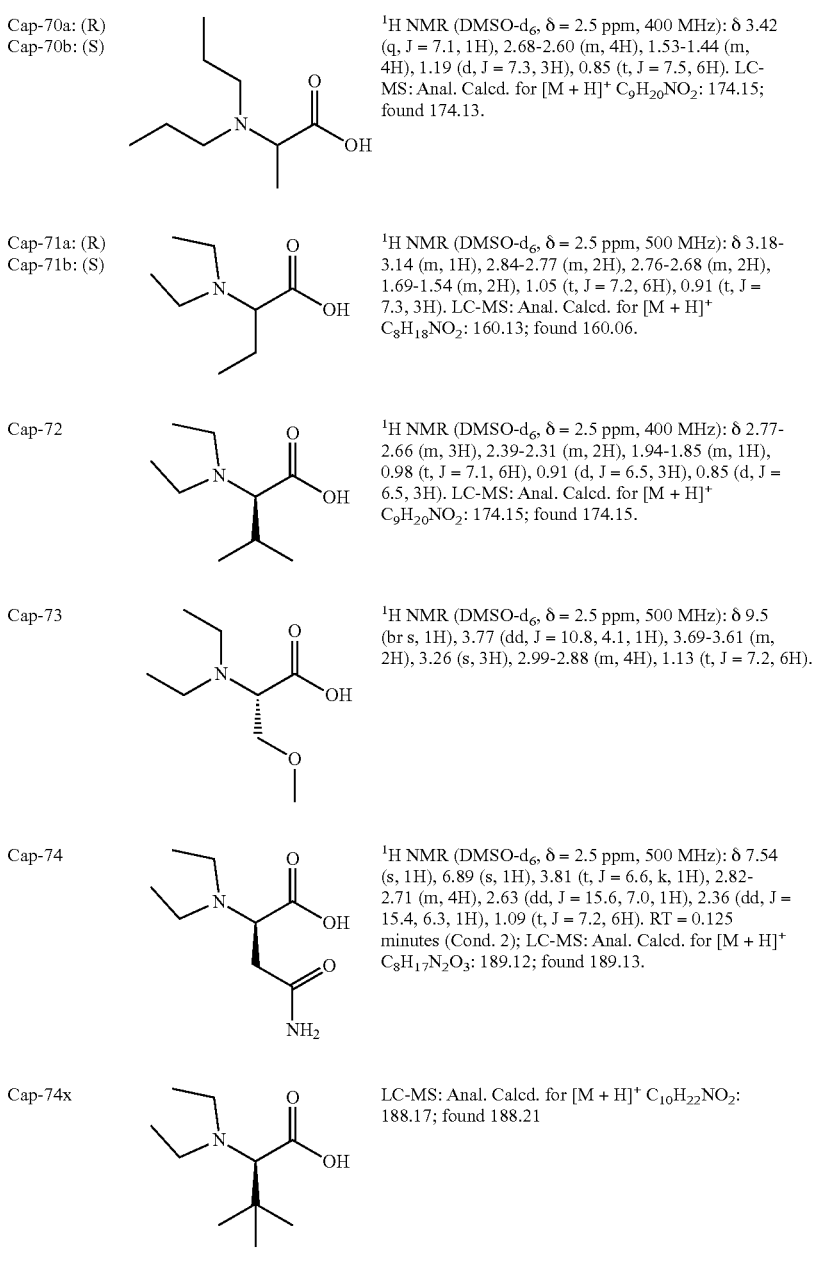

| | | |
|---|---|---|
| Cap-70a: (R)<br>Cap-70b: (S) | | $^1$H NMR (DMSO-d$_6$, δ = 2.5 ppm, 400 MHz): δ 3.42 (q, J = 7.1, 1H), 2.68-2.60 (m, 4H), 1.53-1.44 (m, 4H), 1.19 (d, J = 7.3, 3H), 0.85 (t, J = 7.5, 6H). LC-MS: Anal. Calcd. for [M + H]$^+$ C$_9$H$_{20}$NO$_2$: 174.15; found 174.13. |
| Cap-71a: (R)<br>Cap-71b: (S) | | $^1$H NMR (DMSO-d$_6$, δ = 2.5 ppm, 500 MHz): δ 3.18-3.14 (m, 1H), 2.84-2.77 (m, 2H), 2.76-2.68 (m, 2H), 1.69-1.54 (m, 2H), 1.05 (t, J = 7.2, 6H), 0.91 (t, J = 7.3, 3H). LC-MS: Anal. Calcd. for [M + H]$^+$ C$_8$H$_{18}$NO$_2$: 160.13; found 160.06. |
| Cap-72 | | $^1$H NMR (DMSO-d$_6$, δ = 2.5 ppm, 400 MHz): δ 2.77-2.66 (m, 3H), 2.39-2.31 (m, 2H), 1.94-1.85 (m, 1H), 0.98 (t, J = 7.1, 6H), 0.91 (d, J = 6.5, 3H), 0.85 (d, J = 6.5, 3H). LC-MS: Anal. Calcd. for [M + H]$^+$ C$_9$H$_{20}$NO$_2$: 174.15; found 174.15. |
| Cap-73 | | $^1$H NMR (DMSO-d$_6$, δ = 2.5 ppm, 500 MHz): δ 9.5 (br s, 1H), 3.77 (dd, J = 10.8, 4.1, 1H), 3.69-3.61 (m, 2H), 3.26 (s, 3H), 2.99-2.88 (m, 4H), 1.13 (t, J = 7.2, 6H). |
| Cap-74 | | $^1$H NMR (DMSO-d$_6$, δ = 2.5 ppm, 500 MHz): δ 7.54 (s, 1H), 6.89 (s, 1H), 3.81 (t, J = 6.6, k, 1H), 2.82-2.71 (m, 4H), 2.63 (dd, J = 15.6, 7.0, 1H), 2.36 (dd, J = 15.4, 6.3, 1H), 1.09 (t, J = 7.2, 6H). RT = 0.125 minutes (Cond. 2); LC-MS: Anal. Calcd. for [M + H]$^+$ C$_8$H$_{17}$N$_2$O$_3$: 189.12; found 189.13. |
| Cap-74x | | LC-MS: Anal. Calcd. for [M + H]$^+$ C$_{10}$H$_{22}$NO$_2$: 188.17; found 188.21 |

Cap-75

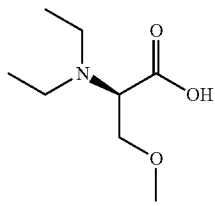

Cap-75, step a

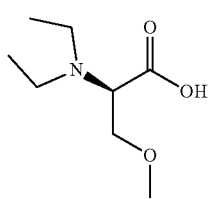

NaBH₃CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H₂O/TFA) to afford the TFA salt of (R)-benzyl 2-(diethylamino)-3-hydroxypropanoate as a colorless viscous oil (1.9 g). $^1$H NMR (DMSO-$d_6$, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21 (m, 4H), 1.23 (t, J=7.2, 6H). LC-MS (Cond. 2): RT=1.38 min; LC-MS: Anal. Calcd. for [M+H]⁺ $C_{14}H_{22}NO_3$: 252.16. found 252.19.

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 μL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by compound elution with 2N NH₃/Methanol. Removal of the volatile component in vacuo afforded Cap-75, contaminated with (R)-2-(diethylamino)-3-hydroxypropanoic acid, as a yellow semi-solid (100 mg). The product was used as is without further purification.

Cap-76

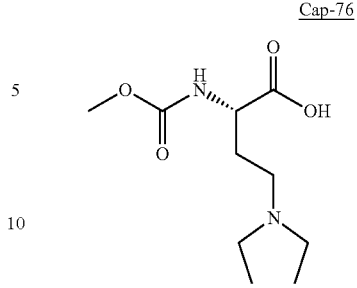

NaCNBH₃ (1.60 g, 24.2 mmol) was added in batches to a chilled (~15° C.) water/MeOH (12 mL each) solution of (S)-4-amino-2-(tert-butoxycarbonylamino) butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with DOWEX® 50WX8-100 ion-exchange resin (column was washed with water and the compound was eluted with dilute NH₄OH, prepared from 18 ml of NH₄OH and 282 ml of water) to afford intermediate (S)-2-amino-4-(diethylamino) butanoic acid as an off-white solid (1.73 g).

Methyl chloroformate (0.36 mL, 4.65 mmol) was added drop-wise over 11 min to a cooled (ice-water) mixture of Na₂CO₃ (0.243 g, 2.29 mmol), NaOH (4.6 mL of 1M/H₂O, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with CH₂Cl₂ (30 mL, 2×), and the aqueous phase was cooled with ice-water bath and acidified with concentrated HCl to a pH region of 2. The volatile component was then removed in vacuo and the crude material was free-based with MCX resin (6.0 g; column was washed with water, and sample was eluted with 2.0 M NH₃/MeOH) to afford impure Cap-76 as an off-white solid (704 mg). $^1$H NMR (MeOH-$d_4$, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC-MS: Anal. Calcd. for [M+H]⁺ $C_{10}H_{21}N_2O_4$: 233.15. found 233.24.

Cap-77a and Cap-77b

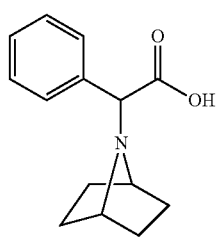

Cap-77a: enantiomer-1
Cap-77b: enantiomer-2

The synthesis of Cap-77 was conducted according to the procedure described for Cap-7 by using 7-azabicyclo[2.2.1]heptane for the SN₂ displacement step, and by effecting the stereoisomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% CO₂-10% EtOH at 70 mL/min, and a temperature of 35° C. to provide 124.5 mg of stereoisomer-1 and 133.8 mg of stereoisomer-2. These benzyl esters were hydrogenolysed according to the preparation of Cap-7 to provide Cap-77: $^1$H NMR (DMSO-d₆, δ=2.5 ppm, 400 MHz): δ 7.55 (m, 2H), 7.38-7.30 (m, 3H), 4.16 (s, 1H), 3.54 (app br s, 2H), 2.08-1.88 (m, 4H), 1.57-1.46 (m, 4H). LC (Cond. 1): RT=0.67 min; LC-MS: Anal. Calcd. for [M+H]⁺ $C_{14}H_{18}NO_2$: 232.13. found 232.18. HRMS: Anal. Calcd. for [M+H]⁺ $C_{14}H_{18}NO_2$: 232.1338. found 232.1340.

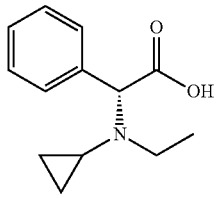

Cap-78

NaCNBH₃ (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and NaCNBH₃ (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC (H₂O/MeOH/TFA) to afford the TFA salt of Cap-78 as a colorless viscous oil (353 mg). $^1$H NMR (DMSO-d₆, δ=2.5 ppm, 400 MHz; after D₂O exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H). LC (Cond. 1): RT=0.64 min; LC-MS: Anal. Calcd. for [M+H]⁺ $C_{13}H_{18}NO_2$: 220.13. found 220.21. HRMS: Anal. Calcd. for [M+H]⁺ $C_{13}H_{18}NO_2$: 220.1338. found 220.1343.

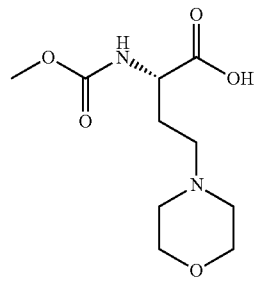

Cap-79

Ozone was bubbled through a cooled (−78° C.) CH₂Cl₂ (5.0 mL) solution Cap-55 (369 mg, 2.13 mmol) for about 50 min until the reaction mixture attained a tint of blue color. Me₂S (10 pipet drops) was added, and the reaction mixture was stirred for 35 min. The −78° C. bath was replaced with a −10° C. bath and stirring continued for an additional 30 min, and then the volatile component was removed in vacuo to afford a colorless viscous oil.

NaBH₃CN (149 mg, 2.25 mmol) was added to a MeOH (5.0 mL) solution of the above crude material and morpholine (500 μL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N NH₃/MeOH elution) and a reverse phase HPLC (H₂O/MeOH/TFA) to afford Cap-79 containing unknown amount of morpholine.

In order to consume the morpholine contaminant, the above material was dissolved in CH₂Cl₂ (1.5 mL) and treated with Et₃N (0.27 mL, 1.94 mmol) followed by acetic anhydride (0.10 mL, 1.06 mmol) and stirred at ambient condition for 18 hr. THF (1.0 mL) and H₂O (0.5 mL) were added and stirring continued for 1.5 hr. The volatile component was removed in vacuo, and the resultant residue was passed through MCX resin (MeOH wash; 2.0 N NH₃/MeOH elution) to afford impure Cap-79 as a brown viscous oil, which was used for the next step without further purification.

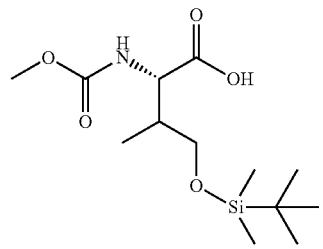

Cap-80a and Cap-80b

Cap-80a: S/S-diastereomer
Cap-80b: S/R-diastereomer

SOCl₂ (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO₃ solution. The aqueous phase was extracted with EtOAc (150 mL, 2×), and the combined organic phase was dried (MgSO$_4$), filtered, and concentrated in vacuo to afford (S)-1-benzyl 4-methyl 2-aminosuccinate as a colorless oil (9.706 g). $^1$H NMR (DMSO-d$_6$, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC-MS: Anal. Calcd. for [M+H]$^+$ C$_{12}$H$_{16}$NO$_4$: 238.11. found 238.22.

Pb(NO$_3$)$_2$ (6.06 g, 18.3 mmol) was added over 1 min to a CH$_2$Cl$_2$ (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et$_3$N (3.0 mL, 21.5 mmol), and the heterogeneous mixture was stirred at ambient condition for 48 hr. The mixture was filtered and the filtrate was treated with MgSO$_4$ and filtered again, and the final filtrate was concentrated. The resulting crude material was submitted to a BIOTAGE® purification (350 g silica gel, CH$_2$Cl$_2$ elution) to afford (S)-1-benzyl 4-methyl 2-(9-phenyl-9H-fluoren-9-ylamino)succinate as highly viscous colorless oil (7.93 g). $^1$H NMR (DMSO-d$_6$, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC-MS: Anal. Calcd. for [M+H]$^+$ C$_{31}$H$_{28}$NO$_4$: 478.20. found 478.19.

LiHMDS (9.2 mL of 1.0 M/THF, 9.2 mmol) was added drop-wise over 10 min to a cooled (−78° C.) THF (50 mL) solution of (S)-1-benzyl 4-methyl 2-(9-phenyl-9H-fluoren-9-ylamino)succinate (3.907 g, 8.18 mmol) and stirred for ~1 hr. MeI (0.57 mL, 9.2 mmol) was added drop-wise over 8 min to the mixture, and stirring was continued for 16.5 hr while allowing the cooling bath to thaw to room temperature. After quenching with saturated NH$_4$Cl solution (5 mL), most of the organic component was removed in vacuo and the residue was partitioned between CH$_2$Cl$_2$ (100 mL) and water (40 mL). The organic layer was dried (MgSO$_4$), filtered, and concentrated in vacuo, and the resulting crude material was purified with a BIOTAGE® (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in ~1.0:0.65 ratio ($^1$H NMR). The stereochemistry of the dominant isomer was not determined at this juncture, and the mixture was submitted to the next step without separation. Partial $^1$H NMR data (DMSO-d$_6$, δ=2.5 ppm, 400 MHz): major diastereomer, δ 4.39 (d, J=12.3, 1H of CH$_2$), 3.33 (s, 3H, overlapped with H$_2$O signal), 3.50 (d, J=10.9, NH), 1.13 (d, J=7.1, 3H); minor diastereomer, δ 4.27 (d, J=12.3, 1H of CH$_2$), 3.76 (d, J=10.9, NH), 3.64 (s, 3H), 0.77 (d, J=7.0, 3H). LC (Cond. 1): RT=2.19 min; LC-MS: Anal. Calcd. for [M+H]$^+$ C$_{32}$H$_{30}$NO$_4$: 492.22. found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M H$_3$PO$_4$/H$_2$O (250 mL) with stirring, and the mixture was extracted with ether (100 mL, 2×). The combined organic phase was washed with brine, dried (MgSO$_4$), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-ylamino)butanoate, contaminated with benzyl alcohol, as a colorless viscous oil and (2S,3R)-benzyl 4-hydroxy-3-methyl-2-(9-phenyl-9H-fluoren-9-ylamino)butanoate containing the (2S,3R) stereoisomer as an impurity. The later sample was resubmitted to the same column chromatography purification conditions to afford 750 mg of purified material as a white foam. [Note: the (2S,3S) isomer elutes before the (2S,3R) isomer under the above condition]. (2S,3S) isomer: $^1$H NMR (DMSO-d$_6$, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC-MS: Anal. Calcd. for [M+H]$^+$ C$_{31}$H$_{30}$NO$_3$: 464.45. found 464.22. (2S,3R) isomer: $^1$H NMR (DMSO-d$_6$, δ=2.5 ppm, 400 MHz): 7.81 (d, J=7.5, 2H), 7.39-7.10 (m, 16H), 4.63 (d, J=12.1, 1H), 4.50 (app t, J=4.9, 1H), 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H). LC (Cond. 1): RT=1.92 min; LC-MS: Anal. Calcd. for [M+H]$^+$ C$_{31}$H$_{30}$NO$_3$: 464.45. found 464.52.

The relative stereochemical assignments of the DIBAL-reduction products were made based on NOE studies conducted on lactone derivatives prepared from each isomer by employing the following protocol: LiHMDS (50 µL of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between CH$_2$Cl$_2$ (30 mL), water (20 mL) and saturated aqueous NH$_4$Cl solution (1 mL). The organic layer was dried (MgSO$_4$), filtered, and concentrated in vacuo, and the resulting crude material was submitted to a BIOTAGE® purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-d$_6$, δ=2.5 ppm, 400 MHz), 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC-MS: Anal. Calcd. for [M+Na]$^+$ C$_{24}$H$_{21}$NNaO$_2$: 378.15. found 378.42. (3S,4R)-lactone isomer: $^1$H NMR (DMSO-d$_6$, δ=2.5 ppm, 400 MHz), 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC-MS: Anal. Calcd. for [M+Na]$^+$ C$_{24}$H$_{21}$NNaO$_2$: 378.15. found 378.49.

TBDMS-Cl (48 mg, 0.312 mmol) followed by imidazole (28.8 mg, 0.423 mmol) were added to a CH$_2$Cl$_2$ (3 ml) solution of (2S,3S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with CH$_2$Cl$_2$ (30 mL) and washed with water (15 mL), and the organic layer was dried (MgSO$_4$), filtered, and concentrated in vacuo. The resultant crude material was purified with a BIOTAGE® (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer:

¹H NMR (DMSO-d₆, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC-MS: Anal. Calcd. for [M+H]⁺ C₃₇H₄₄NO₃Si: 578.31. found 578.40. (2S, 3R)-silyl ether isomer: ¹H NMR (DMSO-d₆, δ=2.5 ppm, 400 MHz), 7.82 (d, J=3.0, 1H), 7.80 (d, J=3.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S, 3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with H₂ as necessary. The reaction mixture was diluted with CH₂Cl₂ and filtered through a pad of diatomaceous earth (CELITE®-545), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/i-PrOH/H₂O) to afford (2S, 3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9-ylamino)butanoate was similarly elaborated to (2S, 3R)-2-amino-4-(tert-butyldimethylsilyloxy)-3-methylbutanoic acid. (2S,3S)-amino acid isomer: ¹H NMR (methanol-d₄, δ=3.29 ppm, 400 MHz), 3.76 (dd, J=10.5, 5.2, 1H), 3.73 (d, J=3.0, 1H), 3.67 (dd, J=10.5, 7.0, 1H), 2.37 (m, 1H), 0.97 (d, J=7.0, 3H), 0.92 (s, 9H), 0.10 (s, 6H). LC-MS: Anal. Calcd. for [M+H]⁺ C₁₁H₂₆NO₃Si: 248.17. found 248.44. (2S, 3R)-amino acid isomer: ¹H NMR (methanol-d₄, δ=3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal. Calcd. for [M+H]⁺ C₁₁H₂₆NO₃Si: 248.17. found 248.44.

Water (1 mL) and NaOH (0.18 mL of 1.0 M/H₂O, 0.18 mmol) were added to a mixture of (2S,3S)-2-amino-4-(tert-butyldimethylsilyloxy)-3-methylbutanoic acid (41.9 mg, 0.169 mmol) and Na₂CO₃ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with CH₂Cl₂ (15 mL, 2×). The combined organic phase was dried (MgSO₄), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: ¹H NMR (DMSO-d₆, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC-MS: Anal. Calcd. for [M+Na]⁺ C₁₃H₂₇NNaO₅Si: 328.16. found 328.46. Cap-80b: ¹H NMR (CDCl₃, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC-MS: Anal. Calcd. for [M+Na]⁺ C₁₃H₂₇NNaO₅Si: 328.16. found 328.53. The crude products were utilized without further purification.

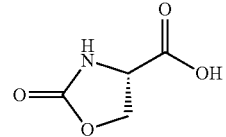

Cap-81

Prepared according to the protocol described by Falb et al., *Synthetic Communications*, 23:2839 (1993).

Cap-82 to Cap-85

Cap-82 to Cap-85 were synthesized from appropriate starting materials according to the procedure described for Cap-51 or Cap-13. The samples exhibited similar spectral profiles as that of their stereoisomers (i.e., Cap-4, Cap-13, Cap-51 and Cap-52, respectively).

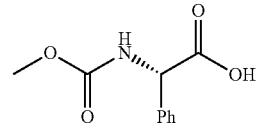

Cap-82

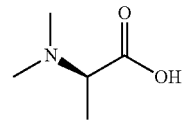

Cap-83

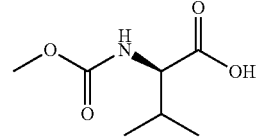

Cap-84

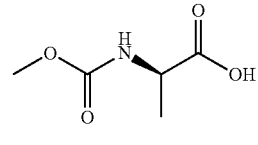

Cap-85

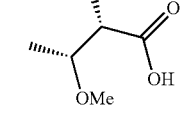

Cap-86

(2S,3R)-3-Methoxy-2-(methoxycarbonylamino)butanoic acid

To a mixture of O-methyl-L-threonine (3.0 g, 22.55 mmol), NaOH (0.902 g, 22.55 mmol) in H₂O (15 mL) was added ClCO₂Me (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in CH₂Cl₂ (250 mL) and the combined organic phases were concentrated under in vacuo to afford a colorless oil (4.18 g, 97%) which was of sufficient purity for use in subsequent steps. $^1$H NMR (400 MHz, CDCl$_3$) δ 4.19 (s, 1H), 3.92-3.97 (m, 1H), 3.66 (s, 3H), 1.17 (d, J=7.7 Hz, 3H). LC-MS: Anal. Calcd. for C$_7$H$_{13}$NO$_5$: 191. found: 190 (M−H)$^-$.

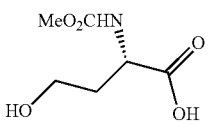

Cap-87

To a mixture of L-homoserine (2.0 g, 9.79 mmol), Na$_2$CO$_3$ (2.08 g, 19.59 mmol) in H$_2$O (15 mL) was added ClCO$_2$Me (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated in vacuo to afford a colorless solid (0.719 g, 28%) which was of sufficient purity for use in subsequent steps. $^1$H NMR (400 MHz, CDCl$_3$) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LC-MS: Anal. Calcd. for C$_7$H$_{13}$NO$_5$: 191. found: 192 (M+H)$^+$.

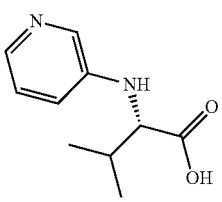

Cap-88

A mixture of L-valine (1.0 g, 8.54 mmol), 3-bromopyridine (1.8 mL, 18.7 mmol), K$_2$CO$_3$ (2.45 g, 17.7 mmol) and CuI (169 mg, 0.887 mmol) in DMSO (10 mL) was heated at 100° C. for 12 h. The reaction mixture was cooled to rt, poured into H$_2$O (ca. 150 mL) and washed with EtOAc (×2). The organic layers were extracted with a small amount of H$_2$O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H$_2$O (200 mL), MeOH (200 mL), and then NH$_3$ (3M in MeOH, 2×200 mL). The appropriate fractions was concentrated in vacuo and the residue (ca. 1.1 g) was dissolved in H$_2$O, frozen and lyophyllized. The title compound was obtained as a foam (1.02 g, 62%). $^1$H NMR (400 MHz, DMSO-d$_6$) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LC-MS: Anal. Calcd. for C$_{10}$H$_{14}$N$_2$O$_2$: 194. found: 195 (M+H)$^+$.

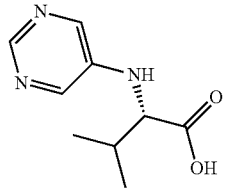

Cap-89

A mixture of L-valine (1.0 g, 8.54 mmol), 5-bromopyrimidine (4.03 g, 17.0 mmol), K$_2$CO$_3$ (2.40 g, 17.4 mmol) and CuI (179 mg, 0.94 mmol) in DMSO (10 mL) was heated at 100° C. for 12 h. The reaction mixture was cooled to RT, poured into H$_2$O (ca. 150 mL) and washed with EtOAc (×2). The organic layers were extracted with a small amount of H$_2$O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H$_2$O (200 mL), MeOH (200 mL), and then NH$_3$ (3M in MeOH, 2×200 mL). The appropriate fractions was concentrated in vacuo and the residue (ca. 1.1 g) was dissolved in H$_2$O, frozen and lyophyllized. The title compound was obtained as a foam (1.02 g, 62%). $^1$H NMR (400 MHz, CD$_3$OD) showed the mixture to contain valine and the purity could not be estimated. The material was used as is in subsequent reactions. LC-MS: Anal. Calcd. for C$_9$H$_{13}$N$_3$O$_2$: 195. found: 196 (M+H)$^+$.

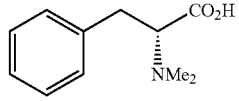

Cap-90

Cap-90 was prepared according to the method described for the preparation of Cap-1. The crude material was used as is in subsequent steps. LC-MS: Anal. Calcd. for C$_{11}$H$_{15}$NO$_2$: 193. found: 192 (M−H)$^-$.

Cap-91 to Cap-116

The following Caps were prepared according to the method used for preparation of Cap-51 unless noted otherwise:

| Cap | Structure | LC-MS |
| --- | --- | --- |
| Cap-91 | ![structure] | LC-MS: Anal. Calcd. for C$_{11}$H$_{13}$NO$_4$: 223; found: 222 (M − H)$^-$. |

-continued

| Cap | Structure | LC-MS |
|---|---|---|
| Cap-92 | (S)-3-phenyl-3-(NHCO₂Me)propanoic acid | LC-MS: Anal. Calcd. for C₁₁H₁₃NO₄: 223; found: 222 (M − H)⁻. |
| Cap-93 | N-(methoxycarbonyl)-3-(pyridin-2-yl)alanine | LC-MS: Anal. Calcd. for C₁₀H₁₂N₂O₄: 224; found: 225 (M + H)⁺. |
| Cap-94 | N-(methoxycarbonyl)-L-histidine | LC-MS: Anal. Calcd. for C₈H₁₁N₃O₄: 213; found: 214 (M + H)⁺. |
| Cap-95 | (3S)-3-(methoxycarbonylamino)-5-phenylpentanoic acid | LC-MS: Anal. Calcd. for C₁₃H₁₇NO₄: 251; found: 250 (M − H)⁻. |
| Cap-96 | (3S)-3-(methoxycarbonylamino)-4-phenylbutanoic acid | LC-MS: Anal. Calcd. for C₁₂H₁₅NO₄: 237; found: 236 (M − H)⁻. |
| Cap-97 | cis-2-(methoxycarbonylamino)cyclohexanecarboxylic acid | LC-MS: Anal. Calcd. for C₉H₁₅NO₄: 201; found: 200 (M − H)⁻. |
| Cap-98 | cis-2-(methoxycarbonylamino)cyclohexanecarboxylic acid (enantiomer) | LC-MS: Anal. Calcd. for C₉H₁₅NO₄: 201; found: 202 (M + H)⁺. |

| Cap | Structure | LC-MS |
|---|---|---|
| Cap-99 | 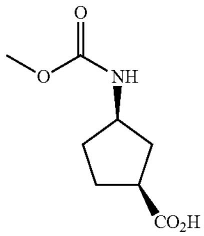 | ¹H NMR (400 MHz, CD₃OD) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-99a | 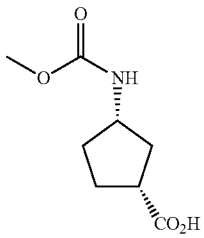 | ¹H NMR (400 MHz, CD₃OD) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-100 | 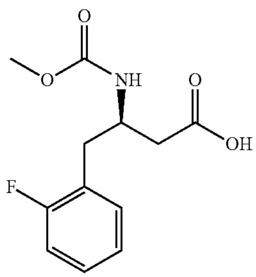 [SMILES: COC(=O)N[C@@H](CC(=O)O)Cc1ccccc1F] | LC-MS: Anal. Calcd. for $C_{12}H_{14}NO_4F$: 255; found: 256 $(M + H)^+$. |
| Cap-101 | 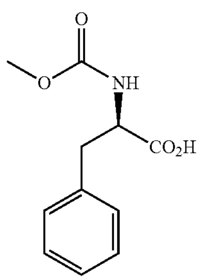 [SMILES: COC(=O)N[C@H](Cc1ccccc1)C(=O)O] | LC-MS: Anal. Calcd. for $C_{11}H_{13}NO_4$: 223; found: 222 $(M - H)^-$. |
| Cap-102 | 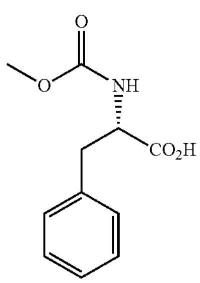 [SMILES: COC(=O)N[C@@H](Cc1ccccc1)C(=O)O] | LC-MS: Anal. Calcd. for $C_{11}H_{13}NO_4$: 223; found: 222 $(M - H)^-$ |
| Cap-103 | 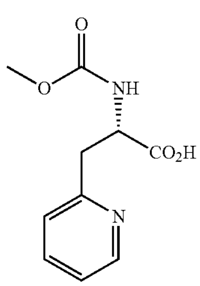 [SMILES: COC(=O)N[C@@H](Cc1ccccn1)C(=O)O] | LC-MS: Anal. Calcd. for $C_{10}H_{12}N_2O_4$: 224; found: 225 $(M + H)^+$. |

| Cap | Structure | LC-MS |
|---|---|---|
| Cap-104 | 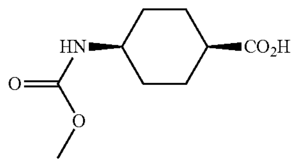 | ¹H NMR (400 MHz, CD₃OD) δ 3.60 (s, 3H), 3.50-3.53 (m, 1H), 2.66-2.69 and 2.44-2.49 (m, 1H), 1.91-2.01 (m, 2H), 1.62-1.74 (m, 4H), 1.51-1.62 (m, 2H). |
| Cap-105 | 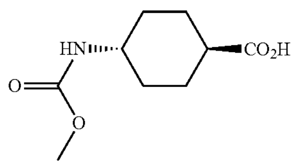 | ¹H NMR (400 MHz, CD₃OD) δ 3.60 (s, 3H), 3.33-3.35 (m, 1H, partially obscured by solvent), 2.37-2.41 and 2.16-2.23 (m, 1H), 1.94-2.01 (m, 4H), 1.43-1.53 (m, 2H), 1.17-1.29 (m, 2H). |
| Cap-106 | Prepared from cis-4-aminocyclohexane carboxylic acid and acetaldehyde by employing a similar procedure described for the synthesis of Cap-2. The crude HCl salt was passed through MCX (MeOH/H₂O/CH₂Cl₂ wash; 2N NH₃/MeOH elution) to afford an oil, which was dissolved in CH₃CN/H₂O and lyophilized to afford a tan solid. | ¹H NMR (400 MHz, CD₃OD) δ 3.16 (q, J = 7.3 Hz, 4H), 2.38-2.41 (m, 1H), 2.28-2.31 (m, 2H), 1.79-1.89 (m, 2H), 1.74 (app, ddd J = 3.5, 12.5, 15.9 Hz, 2H), 1.46 (app dt J = 4.0, 12.9 Hz, 2H), 1.26 (t, J = 7.3 Hz, 6H) |
| Cap-107 | 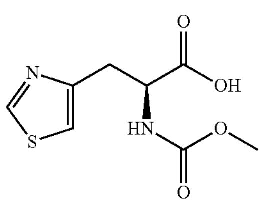 | LC-MS: Anal. Calcd. for C₈H₁₀N₂O₄S: 230; found: 231 (M + H)⁺. |
| Cap-108 | 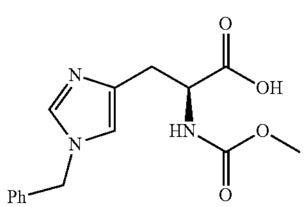 [SMILES: COC(=O)N[C@@H](Cc1cn(Cc2ccccc2)cn1)C(=O)O] | LC-MS: Anal. Calcd. for C₁₅H₁₇N₃O₄: 303; found: 304 (M + H)⁺. |
| Cap-109 | 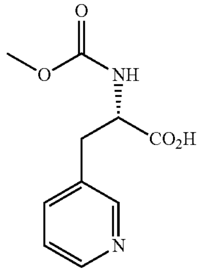 [SMILES: COC(=O)N[C@@H](Cc1cccnc1)C(=O)O] | LC-MS: Anal. Calcd. for C₁₀H₁₂N₂O₄: 224; found: 225 (M + H)⁺. |

-continued
| Cap | Structure | LC-MS |
|---|---|---|
| Cap-110 | 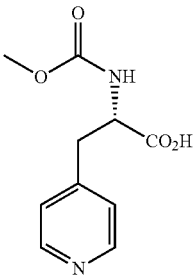 [SMILES: COC(=O)N[C@@H](Cc1ccncc1)C(=O)O] | LC-MS: Anal. Calcd. for $C_{10}H_{12}N_2O_4$: 224; found: 225 $(M + H)^+$. |
| Cap-111 | 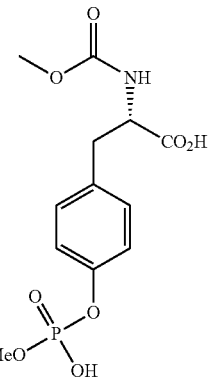 | LC-MS: Anal. Calcd. for $C_{12}H_{16}NO_8P$: 333; found: 334 $(M + H)^+$. |
| Cap-112 | 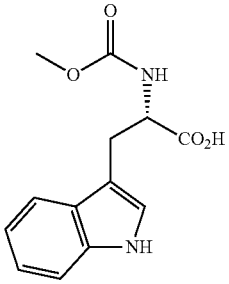 [SMILES: COC(=O)N[C@@H](Cc1c[nH]c2ccccc12)C(=O)O] | LC-MS: Anal. Calcd. for $C_{13}H_{14}N_2O_4$: 262; found: 263 $(M + H)^+$. |
| Cap-113 | 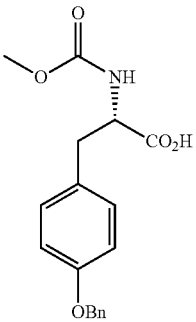 [SMILES: COC(=O)N[C@@H](Cc1ccc(OCc2ccccc2)cc1)C(=O)O] | LC-MS: Anal. Calcd. for $C_{18}H_{19}NO_5$: 329; found: 330 $(M + H)^+$. |
| Cap-114 | 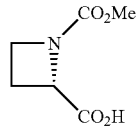 | $^1$H NMR (400 MHz, CDCl$_3$) δ 4.82-4.84 (m, 1H), 4.00-4.05 (m, 2H), 3.77 (s, 3H), 2.56 (s, br, 2H) |
| Cap-115 | 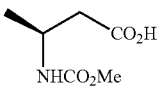 | $^1$H NMR (400 MHz, CDCl$_3$) δ 5.13 (s, br, 1H), 4.13 (s, br, 1H), 3.69 (s, 3H), 2.61 (d, J = 5.0 Hz, 2H), 1.28 (d, J = 9.1 Hz, 3H). |

| Cap | Structure | LC-MS |
|---|---|---|
| Cap-116 | (isopropyl-CH-CH2-CO2H with NHCO2Me) | ¹H NMR (400 MHz, CDCl₃) δ 5.10 (d, J = 8.6 Hz, 1H), 3.74-3.83 (m, 1H), 3.69 (s, 3H), 2.54-2.61 (m, 2H), 1.88 (sept, J = 7.0 Hz, 1H), 0.95 (d, J = 7.0 Hz, 6H). |

Cap-117 to Cap-123

For the preparation of Cap-117 to Cap-123 the Boc amino acids were obtained from commercially sources and were deprotected by treatment with 25% TFA in $CH_2Cl_2$. After complete reaction as judged by LC-MS the solvents were removed in vacuo and the corresponding TFA salt of the amino acid was carbamoylated with methyl chloroformate according to the procedure described for Cap-51.

| Cap | Structure | LC-MS |
|---|---|---|
| Cap-117 | (methyl carbamate, CH2-phenyl, CH2CO2H) | LC-MS: Anal. Calcd. for $C_{12}H_{15}NO_4$: 237; found: 238 (M + H)⁺. |
| Cap-118 | (methyl carbamate, CH2-(2-thienyl), CH2CO2H) | LC-MS: Anal. Calcd. for $C_{10}H_{13}NO_4S$: 243; found: 244 (M + H)⁺. |
| Cap-119 | (methyl carbamate, CH2-(2-thienyl), CH2CO2H) | LC-MS: Anal. Calcd. for $C_{10}H_{13}NO_4S$: 243; found: 244 (M + H)⁺. |
| Cap-120 | (methyl carbamate, CH2-(3-thienyl), CH2CO2H) | LC-MS: Anal. Calcd. for $C_{10}H_{13}NO_4S$: 243; found: 244 (M + H)⁺. |

| Cap | Structure | LC-MS |
|---|---|---|
| Cap-121 | ![structure] | $^{1}$H NMR (400 MHz, CDCl$_3$) δ 4.06-4.16 (m, 1H), 3.63 (s, 3H), 3.43 (s, 1H), 2.82 and 2.66 (s, br, 1H), 1.86-2.10 (m, 3H), 1.64-1.76 (m, 2H), 1.44-1.53 (m, 1H). |
| Cap-122 | ![structure] | $^{1}$H NMR profile is similar to that of its stereoisomer, Cap-121. |
| Cap-123 | ![structure] | LC-MS: Anal. Calcd. for C$_{27}$H$_{26}$N$_2$O$_6$: 474; found: 475 (M + H)$^+$. |

Cap-124

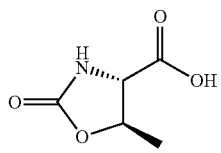

The hydrochloride salt of L-threonine tert-butyl ester was carbamoylated according to the procedure for Cap-51. The crude reaction mixture was acidified with 1N HCl to pH~1 and the mixture was extracted with EtOAc (2×50 mL). The combined organic phases were concentrated in vacuo to give a colorless oil which solidified on standing. The aqueous layer was concentrated in vacuo and the resulting mixture of product and inorganic salts was triturated with EtOAc—CH$_2$Cl$_2$-MeOH (1:1:0.1) and then the organic phase concentrated in vacuo to give a colorless oil which was shown by LC-MS to be the desired product. Both crops were combined to give 0.52 g of a solid. $^{1}$H NMR (400 MHz, CD$_3$OD) δ 4.60 (m, 1H), 4.04 (d, J=5.0 Hz, 1H), 1.49 (d, J=6.3 Hz, 3H). LC-MS: Anal. Calcd. for C$_5$H$_7$NO$_4$: 145. found: 146 (M+H)$^+$.

Cap-125

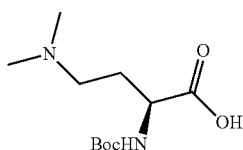

To a suspension of Pd(OH)$_2$, (20%, 100 mg), aqueous formaldehyde (37% wt, 4 ml), acetic acid, (0.5 mL) in methanol (15 mL) was added (S)-4-amino-2-(tert-butoxycarbonylamino)butanoic acid (1 g, 4.48 mmol). The reaction was purged several times with hydrogen and was stirred overnight with an hydrogen balloon room temperature. The reaction mixture was filtered through a pad of diatomaceous earth (CELITE®), and the volatile component was removed in vacuo. The resulting crude material was used as is for the next step. LC-MS: Anal. Calcd. for C$_{11}$H$_{22}$N$_2$O$_4$: 246. found: 247 (M+H)$^+$.

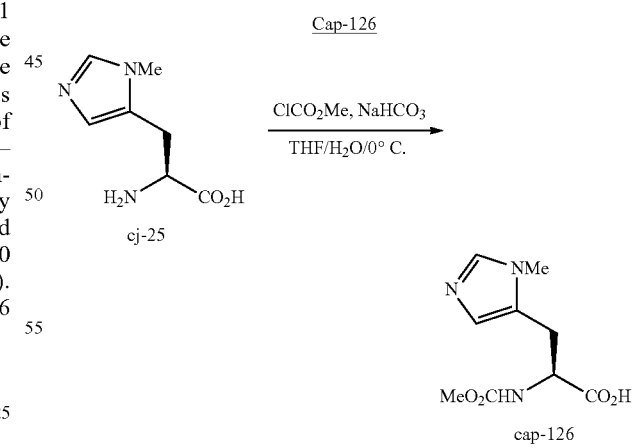

This procedure is a modification of that used to prepare Cap-51. To a suspension of 3-methyl-L-histidine (0.80 g, 4.70 mmol) in THF (10 mL) and H$_2$O (10 mL) at 0° C. was added NaHCO$_3$ (0.88 g, 10.5 mmol). The resulting mixture was treated with ClCO$_2$Me (0.40 mL, 5.20 mmol) and the mixture allowed to stir at 0° C. After stirring for ca. 2 h LC-MS showed no starting material remaining. The reaction was acidified to pH 2 with 6 N HCl.

The solvents were removed in vacuo and the residue was suspended in 20 mL of 20% MeOH in $CH_2Cl_2$. The mixture was filtered and concentrated to give a light yellow foam (1.21 g,). LC-MS and $^1$H NMR showed the material to be a 9:1 mixture of the methyl ester and the desired product. This material was taken up in THF (10 mL) and $H_2O$ (10 mL), cooled to 0° C. and LiOH (249.1 mg, 10.4 mmol) was added. After stirring ca. 1 h LC-MS showed no ester remaining Therefore the mixture was acidified with 6N HCl and the solvents removed in vacuo. LC-MS and $^1$H NMR confirm the absence of the ester. The title compound was obtained as its HCl salt contaminated with inorganic salts (1.91 g, >100%). The compound was used as is in subsequent steps without further purification. $^1$H NMR (400 MHz, $CD_3OD$) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H). LC-MS: Anal. Calcd. for $C_9H_{13}N_3O_4$: 227.09. found: 228.09 (M+H)$^+$.

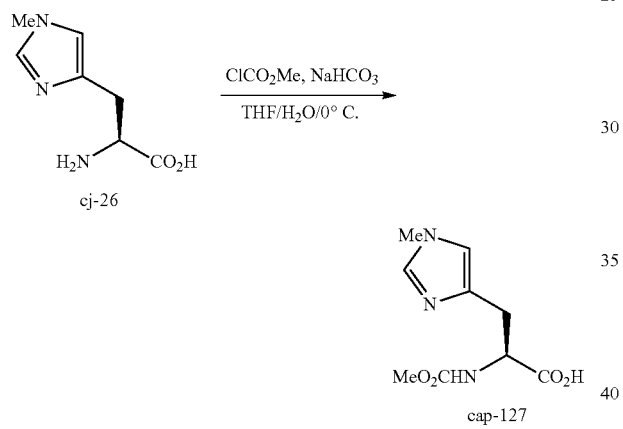

Cap-127

Cap-127 was prepared according to the method for Cap-126 above starting from (S)-2-amino-3-(1-methyl-1H-imidazol-4-yl)propanoic acid (1.11 g, 6.56 mmol), $NaHCO_3$ (1.21 g, 14.4 mmol) and $ClCO_2Me$ (0.56 mL, 7.28 mmol). The title compound was obtained as its HCl salt (1.79 g, >100%) contaminated with inorganic salts. LC-MS and $^1$H NMR showed the presence of ca. 5% of the methyl ester. The crude mixture was used as is without further purification. $^1$H NMR (400 MHz, $CD_3OD$) δ 8.90 (s, 1H), 7.35 (s, 1H), 4.48 (dd, J=5.0, 8.6 Hz, 1H), 3.89 (s, 3H), 3.62 (s, 3H), 3.35 (m, 1H), 3.08 (m, 1H); LC-MS: Anal. Calcd. for $C_9H_{13}N_3O_4$: 227.09. found: 228 (M+H)$^+$.

Preparation of Cap-128

Step 1. Preparation of (S)-benzyl 2-(tert-butoxycarbonylamino)pent-4-ynoate (cj-27b)

To a solution of cj-27a (1.01 g, 4.74 mmol), DMAP (58 mg, 0.475 mmol) and $iPr_2NEt$ (1.7 mL, 9.8 mmol) in $CH_2Cl_2$ (100 mL) at 0° C. was added Cbz-Cl (0.68 mL, 4.83 mmol). The solution was allowed to stir for 4 h at 0° C., washed (1N $KHSO_4$, brine), dried ($Na_2SO_4$), filtered, and concentrated in vacuo. The residue was purified by flash column chromatography (TLC 6:1 hex:EtOAc) to give the title compound (1.30 g, 91%) as a colorless oil. $^1$H NMR (400 MHz, $CDCl_3$) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, 2H), 2.00 (t, J=2.5 Hz, 1H), 1.44 (s, 9H). LC-MS: Anal. Calcd. for $C_{17}H_{21}NO_4$: 303. found: 304 (M+H)$^+$.

Step 2. Preparation of (S)-benzyl 3-(1-benzyl-1H-1,2,3-triazol-4-yl)-2-(tert-butoxycarbonylamino)propanoate (cj-28)

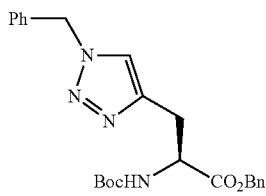

cj-28

To a mixture of (S)-benzyl 2-(tert-butoxycarbonylamino)pent-4-ynoate (0.50 g, 1.65 mmol), sodium ascorbate (0.036 g, 0.18 mmol), $CuSO_4$-$5H_2O$ (0.022 g, 0.09 mmol) and $NaN_3$ (0.13 g, 2.1 mmol) in $DMF$-$H_2O$ (5 mL, 4:1) at rt was added BnBr (0.24 mL, 2.02 mmol) and the mixture was warmed to 65° C. After 5 h LC-MS indicated low conversion. A further portion of $NaN_3$ (100 mg) was added and heating was continued for 12 h. The reaction was poured into EtOAc and $H_2O$ and shaken. The layers were separated and the aqueous layer extracted 3× with EtOAc and the combined organic phases washed ($H_2O$×3, brine), dried ($Na_2SO_4$), filtered, and concentrated. The residue was purified by flash (BIOTAGE®, 40+M 0-5% MeOH in $CH_2Cl_2$; TLC 3% MeOH in $CH_2Cl_2$) to afford a light yellow oil which solidified on standing (748.3 mg, 104%). The NMR was consistent with the desired product but suggests the presence of DMF. The material was used as is without further purification. $^1$H NMR (400 MHz, DMSO-$d_6$) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz), 2.96 (dd, J=9.1, 14.7 Hz, 1H), 1.31 (s, 9H). LC-MS: Anal. Calcd. for $C_{24}H_{28}N_4O_4$: 436. found: 437 $(M+H)^+$.

Step 3. Preparation of (S)-benzyl 3-(1-benzyl-1H-1,2,3-triazol-4-yl)-2-(methoxycarbonylamino)propanoate (cj-29)

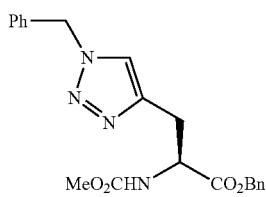

cj-29

A solution of (S)-benzyl 3-(1-benzyl-1H-1,2,3-triazol-4-yl)-2-(tert-butoxycarbonylamino)propanoate (0.52 g, 1.15 mmol) in $CH_2Cl_2$ was added TFA (4 mL). The mixture was allowed to stir at room temperature for 2 h. The mixture was concentrated in vacuo to give a colorless oil which solidified on standing. This material was dissolved in THF-$H_2O$ and cooled to 0° C. Solid $NaHCO_3$ (0.25 g, 3.00 mmol) was added followed by $ClCO_2Me$ (0.25 mL, 3.25 mmol). After stirring for 1.5 h the mixture was acidified to pH~2 with 6N HCl and then poured into $H_2O$-EtOAc. The layers were separated and the aq phase extracted 2× with EtOAc. The combined org layers were washed ($H_2O$, brine), dried ($Na_2SO_4$), filtered, and concentrated in vacuo to give a colorless oil (505.8 mg, 111%, NMR suggested the presence of an unidentified impurity) which solidified while standing on the pump. The material was used as is without further purification. $^1$H NMR (400 MHz, DMSO-$d_6$) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09 (dd, J=5.6, 14.7 Hz, 1H), 2.98 (dd, J=9.6, 14.7 Hz, 1H). LC-MS: Anal. Calcd. for $C_{21}H_{22}N_4O_4$: 394. found: 395 $(M+H)^+$.

Step 4. Preparation of (S)-2-(methoxycarbonylamino)-3-(1H-1,2,3-triazol-4-yl)propanoic acid (Cap-128)

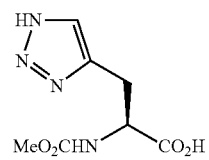

Cap-128

(S)-Benzyl 3-(1-benzyl-1H-1,2,3-triazol-4-yl)-2-(methoxycarbonylamino)propanoate (502 mg, 1.11 mmol) was hydrogenated in the presence of Pd—C (82 mg) in MeOH (5 mL) at atmospheric pressure for 12 h. The mixture was filtered through diatomaceous earth (CELITE®) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification. $^1$H NMR (400 MHz, DMSO-$d_6$) δ 12.78 (s, br, 1H), 7.59 (s, 1H), 7.50 (d, J=8.0 Hz, 1H), 4.19-4.24 (m, 1H), 3.49 (s, 3H), 3.12 (dd, J=4.8 Hz, 14.9 Hz, 1H), 2.96 (dd, J=9.9, 15.0 Hz, 1H). LC-MS: Anal. Calcd. for $C_7H_{10}N_4O_4$: 214. found: 215 $(M+H)^+$.

Preparation of Cap-129

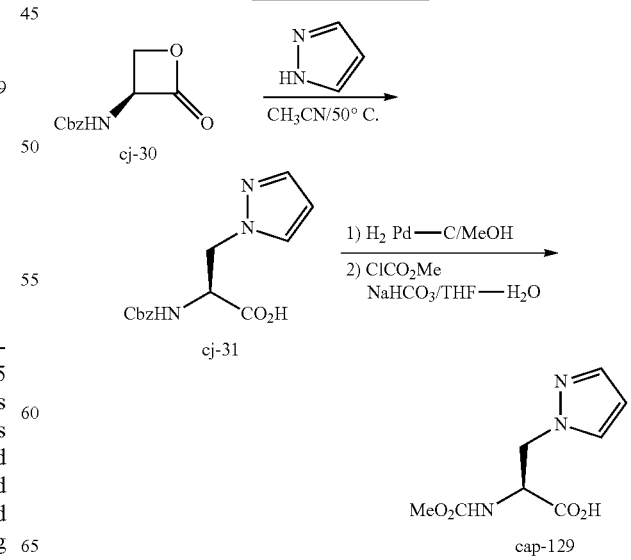

Step 1. Preparation of (S)-2-(benzyloxycarbonylamino)-3-(1H-pyrazol-1-yl)propanoic acid (cj-31)

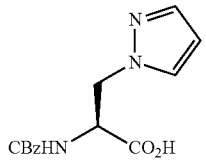

cj-31

A suspension of (S)-benzyl 2-oxooxetan-3-ylcarbamate (0.67 g, 3.03 mmol), and pyrazole (0.22 g, 3.29 mmol) in $CH_3CN$ (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of $CH_3CN$ (ca. 4 mL) to afford a second crop (43.5 mg). Total yield 370.4 mg (44%). m.p. 165.5-168° C. lit m.p. 168.5-169.5 [Vederas et al., *J. Am. Chem. Soc.*, 107:7105 (1985)]. $^1H$ NMR (400 MHz, $CD_3OD$) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LC-MS: Anal. Calcd. for $C_{14}H_{15}N_3O_4$: 289. found: 290 (M+H)$^+$.

Step 2. Preparation of (S)-2-(methoxycarbonylamino)-3-(1H-pyrazol-1-yl)propanoic acid (Cap-129)

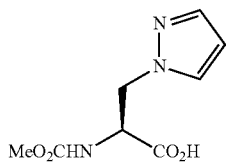

cap-129

(S)-2-(Benzyloxycarbonylamino)-3-(1H-pyrazol-1-yl) propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the reaction mixture was diluted with 5 mL $H_2O$ and a few drops of 6N HCl. The homogeneous solution was filtered through diatomaceous earth (CELITE®), and the MeOH removed in vacuo. The remaining solution was frozen and lyophyllized to give a yellow foam (188.9 mg). This material was suspended in THF-$H_2O$ (1:1, 10 mL) and then cooled to 0° C. To the cold mixture was added $NaHCO_3$ (146.0 mg, 1.74 mmol) carefully (evolution of $CO_2$). After gas evolution had ceased (ca. 15 min) $ClCO_2Me$ (0.06 mL, 0.78 mmol) was added dropwise. The mixture was allowed to stir for 2 h and was acidified to pH~2 with 6N HCl and poured into EtOAc. The layers were separated and the aqueous phase extracted with EtOAC (×5). The combined organic layers were washed (brine), dried ($Na_2SO_4$), filtered, and concentrated to give the title compound as a colorless solid (117.8 mg, 79%). $^1H$ NMR (400 MHz, DMSO-$d_6$) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LC-MS: Anal. Calcd. for $C_8H_{11}N_3O_4$: 213. found: 214 (M+H)$^+$.

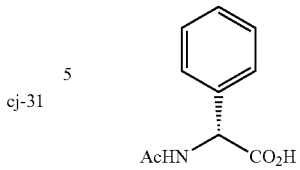

Cap-130

Cap-130 was prepared by acylation of commercially available (R)-phenylglycine analogous to the procedure given in: Calmes, M. et al., *Tetrahedron*, 43(10):2285 (1987).

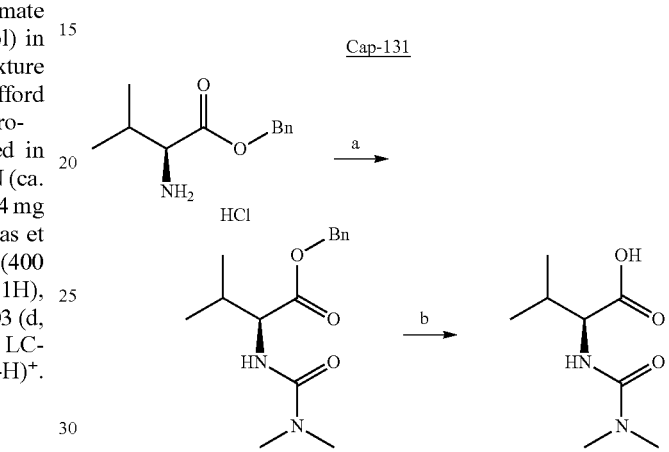

Step a

Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried ($MgSO_4$), filtered, and concentrated under reduced pressure. The resulting yellow oil was purified by flash chromatography, eluting with ethyl acetate:hexanes (1:1). Collected fractions were concentrated under vacuum providing 2.35 g (85%) of clear oil. $^1H$ NMR (300 MHz, DMSO-$d_6$) δ ppm 0.84 (d, J=6.95 Hz, 3H), 0.89 (d, J=6.59 Hz, 3H), 1.98-2.15 (m, 1H), 2.80 (s, 6H), 5.01-5.09 (m, J=12.44 Hz, 1H), 5.13 (d, J=12.44 Hz, 1H), 6.22 (d, J=8.05 Hz, 1H), 7.26-7.42 (m, 5H). LC (Cond. 1): RT=1.76 min; MS: Anal. Calcd. for [M+H]$^+$ $C_{16}H_{22}N_2O_3$: 279.17. found 279.03.

Step b

To an MeOH (50 mL) solution of the intermediate prepared above (2.35 g; 8.45 mmol) was added Pd/C (10%; 200 mg) and the resulting black suspension was flushed with $N_2$ (3×) and placed under 1 atm of $H_2$. The mixture was stirred at room temperature overnight and filtered though a microfiber filter to remove the catalyst. The resulting clear solution was then concentrated under reduced pressure to obtain 1.43 g (89%) of Cap-131 as a white foam, which was used without further purification. $^1H$ NMR (500 MHz, DMSO-$d_6$) δ ppm 0.87 (d, J=4.27 Hz, 3H), 0.88 (d, J=3.97 Hz, 3H), 1.93-2.11 (m, 1H), 2.80 (s, 6H), 3.90 (dd, J=8.39, 6.87 Hz, 1H), 5.93 (d, J=8.54

Hz, 1H), 12.36 (s, 1H). LC (Cond. 1): RT=0.33 min; MS: Anal. Calcd. for [M+H]+ C8H17N2O3: 189.12. found 189.04.

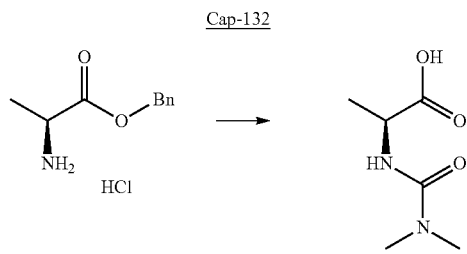

Cap-132

Cap-132 was prepared from (S)-benzyl 2-aminopropanoate hydrochloride according to the method described for Cap-131. ¹H NMR (500 MHz, DMSO-d6) δ ppm 1.27 (d, J=7.32 Hz, 3H), 2.80 (s, 6H), 4.06 (qt, 1H), 6.36 (d, J=7.32 Hz, 1H), 12.27 (s, 1H). LC (Cond. 1): RT=0.15 min; MS: Anal. Calcd. for [M+H]+ C6H13N2O3: 161.09. found 161.00.

Cap-133

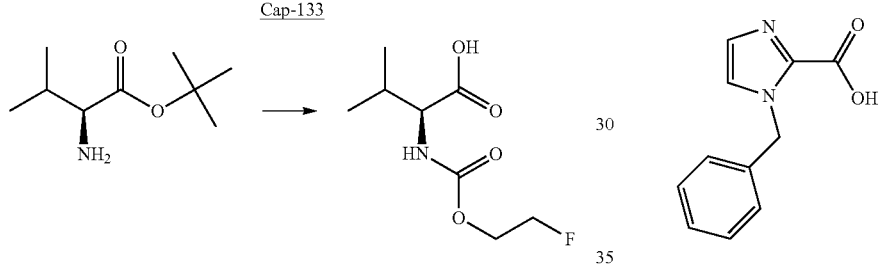

Cap-133 was prepared from (S)-tert-butyl 2-amino-3-methylbutanoate hydrochloride and 2-fluoroethyl chloroformate according to the method described for Cap-47. ¹H NMR (500 MHz, DMSO-d6) δ ppm 0.87 (t, J=6.71 Hz, 6H), 1.97-2.10 (m, 1H), 3.83 (dd, J=8.39, 5.95 Hz, 1H), 4.14-4.18 (m, 1H), 4.20-4.25 (m, 1H), 4.50-4.54 (m, 1H), 4.59-4.65 (m, 1H), 7.51 (d, J=8.54 Hz, 1H), 12.54 (s, 1H).

Cap-134

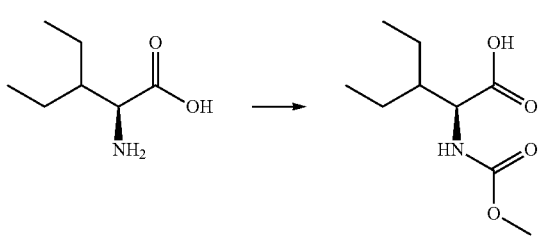

Cap-134 was prepared from (S)-diethyl alanine and methyl chloroformate according to the method described for Cap-51. ¹H NMR (500 MHz, DMSO-d6) δ ppm 0.72-0.89 (m, 6H), 1.15-1.38 (m, 4H), 1.54-1.66 (m, 1H), 3.46-3.63 (m, 3H), 4.09 (dd, J=8.85, 5.19 Hz, 1H), 7.24 (d, J=8.85 Hz, 1H), 12.55 (s, 1H). LC (Cond. 2): RT=0.66 min; LC-MS: Anal. Calcd. for [M+H]+ C9H18NO4: 204.12. found 204.02.

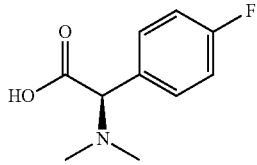

Cap-135

A solution of D-2-amino-(4-fluorophenyl)acetic acid (338 mg, 2.00 mmol), 1N HCl in diethylether (2.0 mL, 2.0 mmol) and formalin (37%, 1 mL) in methanol (5 mL) was subjected to balloon hydrogenation over 10% palladium on carbon (60 mg) for 16 h at 25° C. The mixture was then filtered through CELITE® to afford the HCl salt of Cap-135 as a white foam (316 mg, 80%). ¹H NMR (300 MHz, MeOH-d4) δ 7.59 (dd, J=8.80, 5.10 Hz, 2H), 7.29 (t, J=8.6 Hz, 2H), 5.17 (s, 1H), 3.05 (v br s, 3H), 2.63 (v br s, 3H); Rf=0.19 min (Cond.-MS-W5); 95% homogenity index; LRMS: Anal. Calcd. for [M+H]+ C10H13FNO2: 198.09. found: 198.10.

Cap-136

To a cooled (−50° C.) suspension of 1-benzyl-1H-imidazole (1.58 g, 10.0 mmol) in anhydrous diethyl ether (50 mL) under nitrogen was added n-butyl lithium (2.5 M in hexanes, 4.0 mL, 10.0 mmol) dropwise. After being stirred for 20 min at −50° C., dry carbon dioxide (passed through Drierite) was bubbled into the reaction mixture for 10 min before it was allowed to warm up to 25° C. The heavy precipitate which formed on addition of carbon dioxide to the reaction mixture was filtered to yield a hygroscopic, white solid which was taken up in water (7 mL), acidified to pH=3, cooled, and induced to crystallize with scratching. Filtration of this precipitate gave a white solid which was suspended in methanol, treated with 1N HCl/diethyl ether (4 mL) and concentrated in vacuo. Lyophilization of the residue from water (5 mL) afforded the HCl salt of Cap-136 as a white solid (817 mg, 40%). ¹H NMR (300 MHz, DMSO-d6) δ 7.94 (d, J=1.5 Hz, 1H), 7.71 (d, J=1.5 Hz, 1H), 7.50-7.31 (m, 5H), 5.77 (s, 2H); Rf=0.51 min (Cond.-MS-W5); 95% homogenity index; LRMS: Anal. Calc. for [M+H]+ C11H12N2O2: 203.08. found: 203.11.

Cap-137

-continued

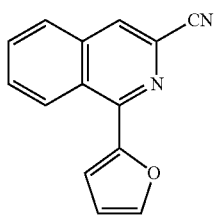

Cap-137, step a

A suspension of 1-chloro-3-cyanoisoquinoline (188 mg, 1.00 mmol; prepared according to the procedure in WO 2003/099274) (188 mg, 1.00 mmol), cesium fluoride (303.8 mg, 2.00 mmol), bis(tri-tert-butylphosphine)palladium dichloride (10 mg, 0.02 mmol) and 2-(tributylstannyl)furan (378 μL, 1.20 mmol) in anhydrous dioxane (10 mL) under nitrogen was heated at 80° C. for 16 h before it was cooled to 25° C. and treated with saturated, aqueous potassium fluoride solution with vigorous stirring for 1 h. The mixture was partitioned between ethyl acetate and water and the organic phase was separated, washed with brine, dried over Na$_2$SO$_4$, filtered and concentrated. Purification of the residue on silica gel (elution with 0% to 30% ethyl acetate/hexanes) afforded Cap-137, step a as a white solid which was used as is (230 mg, 105%). R$_t$=1.95 min (Cond.-MS-W2); 90% homogeneity index; LRMS: Anal. Calc. for [M+H]$^+$ C$_{14}$H$_8$N$_2$O: 221.07. found: 221.12.

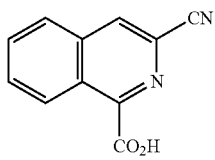

Cap-137

To a suspension of Cap-137, step a (110 mg, 0.50 mmol) and sodium periodate (438 mg, 2.05 mmol) in carbon tetrachloride (1 mL), acetonitrile (1 mL) and water (1.5 mL) was added ruthenium trichloride hydrate (2 mg, 0.011 mmol). The mixture was stirred at 25° C. for 2 h and then partitioned between dichloromethane and water. The aqueous layer was separated, extracted twice more with dichloromethane and the combined dichloromethane extracts were dried over Na$_2$SO$_4$, filtered and concentrated. Trituration of the residue with hexanes afforded Cap-137 (55 mg, 55%) as a grayish-colored solid. R$_t$=1.10 min (Cond.-MS-W2); 90% homogeneity index; LC-MS: Anal. Calc. for [M+H]$^+$ C$_{11}$H$_8$N$_2$O$_2$: 200.08. found: 200.08.

Synthetic Strategy. Method A.

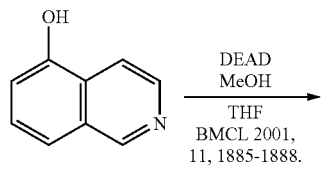

DEAD
MeOH
THF
BMCL 2001,
11, 1885-1888.

-continued

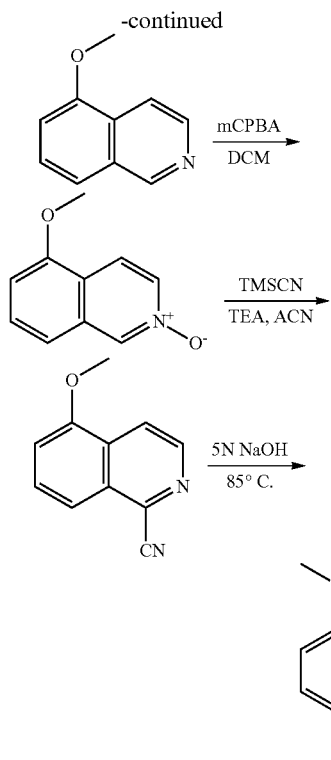

Cap-138

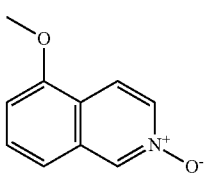

Cap-138, step b

To a stirred suspension of 5-hydroxisoquinoline (prepared according to the procedure in WO 2003/099274) (2.0 g, 13.8 mmol) and triphenylphosphine (4.3 g, 16.5 mmol) in dry tetrahydrofuran (20 mL) was added dry methanol (0.8 mL) and diethyl azodicarboxylate (3.0 mL, 16.5 mmol) portionwise. The mixture was stirred at room temperature for 20 h before it was diluted with ethyl acetate and washed with brine, dried over Na$_2$SO$_4$, filtered and concentrated. The residue was preabsorbed onto silica gel and purified (elution with 40% ethyl acetate/hexanes) to afford Cap-138, step a as a light yellow solid (1.00 g, 45%). $^1$H NMR (CDCl$_3$, 500 MHz) δ 9.19 (s, 1H), 8.51 (d, J=6.0 Hz, 1H), 7.99 (d, J=6.0 Hz, 1H), 7.52-7.50 (m, 2H), 7.00-6.99 (m, 1H), 4.01 (s, 3H); $R_f$=0.66 min (Cond. D2); 95% homogeneity index; LC-MS: Anal. Calc. for $[M+H]^+$ $C_{10}H_{10}NO$: 160.08. found 160.10.

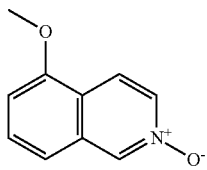

Cap-138, step b

To a stirred solution of Cap-138, step a (2.34 g, 14.7 mmol) in anhydrous dichloromethane (50 mL) at room temperature was added meta-chloroperbenzoic acid (77%, 3.42 g, 19.8 mmol) in one portion. After being stirred for 20 h, powdered potassium carbonate (2.0 g) was added and the mixture was stirred for 1 h at room temperature before it was filtered and concentrated to afford Cap-138, step b as a pale, yellow solid which was sufficiently pure to carry forward (2.15 g, 83.3%). $^1$H NMR (CDCl$_3$, 400 MHz) δ 8.73 (d, J=1.5 Hz, 1H), 8.11 (dd, J=7.3, 1.7 Hz, 1H), 8.04 (d, J=7.1 Hz, 1H), 7.52 (t, J=8.1 Hz, 1H), 7.28 (d, J=8.3 Hz, 1H), 6.91 (d, J=7.8 Hz, 1H), 4.00 (s, 3H); $R_f$=0.92 min, (Cond.-D1); 90% homogenity index; LC-MS: Anal. Calc. for $[M+H]^+$ $C_{10}H_{10}NO_2$: 176.07. found: 176.0.

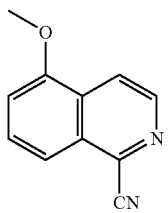

Cap-138, step c

To a stirred solution of Cap-138, step b (0.70 g, 4.00 mmol) and triethylamine (1.1 mL, 8.00 mmol) in dry acetonitrile (20 mL) at room temperature under nitrogen was added trimethylsilylcyanide (1.60 mL, 12.00 mmol). The mixture was heated at 75° C. for 20 h before it was cooled to room temperature, diluted with ethyl acetate and washed with saturated sodium bicarbonate solution and brine prior to drying over Na$_2$SO$_4$ and solvent concentration. The residue was flash chromatographed on silica gel (elution with 5% ethyl acetate/hexanes) to 25% ethyl acetate/hexanes to afford Cap-138, step c (498.7 mg) as a white, crystalline solid along with 223 mg of additional Cap-138, step c recovered from the filtrate. $^1$H NMR (CDCl$_3$, 500 MHz) δ 8.63 (d, J=5.5 Hz, 1H), 8.26 (d, J=5.5 Hz, 1H), 7.88 (d, J=8.5 Hz, 1H), 7.69 (t, J=8.0 Hz, 1H), 7.08 (d, J=7.5 Hz, 1H), 4.04 (s, 3H); $R_f$=1.75 min, (Cond.-D1); 90% homogeneity index; LC-MS: Anal. Calc. for $[M+H]^+$ $C_{11}H_9N_2O$: 185.07. found: 185.10.

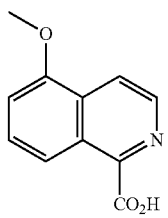

Cap-138

Cap-138, step c (0.45 g, 2.44 mmol) was treated with 5N sodium hydroxide solution (10 mL) and the resulting suspension was heated at 85° C. for 4 h, cooled to 25° C., diluted with dichloromethane and acidified with 1N hydrochloric acid. The organic phase was separated, washed with brine, dried over Na$_2$SO$_4$, concentrated to ¼ volume and filtered to afford Cap-138 as a yellow solid (0.44 g, 88.9%). $^1$H NMR (DMSO-d$_6$, 400 MHz) δ 13.6 (br s, 1H), 8.56 (d, J=6.0 Hz, 1H), 8.16 (d, J=6.0 Hz, 1H), 8.06 (d, J=8.8 Hz, 1H), 7.71-7.67 (m, 1H), 7.30 (d, J=8.0 Hz, 1H), 4.02 (s, 3H); $R_f$=0.70 min (Cond.-D1); 95% homogenity index; LC-MS: Anal. Calc. for $[M+H]^+$ $C_{11}H_{10}NO_3$: 204.07. found: 204.05.

Synthetic Strategy. Method B (Derived from *Tetrahedron Letters*, 42:6707 (2001)).

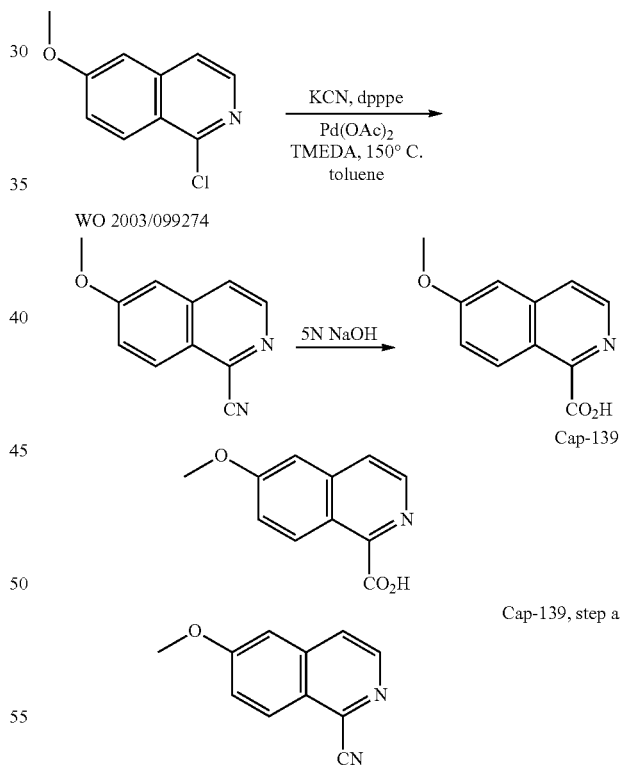

To a thick-walled, screw-top vial containing an argon-degassed suspension of 1-chloro-6-methoxyisoquinoline (1.2 g, 6.2 mmol; prepared according to the procedure in WO 2003/099274), potassium cyanide (0.40 g, 6.2 mmol), 1,5-bis(diphenylphosphino)pentane (0.27 g, 0.62 mmol) and palladium (II) acetate (70 mg, 0.31 mmol) in anhydrous toluene (6 mL) was added N,N,N',N'-tetramethylethylenediamine (0.29 mL, 2.48 mmol). The vial was sealed, heated at 150° C. for 22 h and then allowed to cool to 25° C. The reaction mixture was diluted with ethyl acetate, washed with water and brine, dried over Na$_2$SO$_4$, filtered and concentrated. The residue was purified on silica gel eluting with 5% ethyl acetate/hexanes to 25% ethyl acetate/hexanes to afford Cap-139, step a as a white solid (669.7 mg). $^1$H NMR (CDCl$_3$, 500 MHz) δ 8.54 (d, J=6.0 Hz, 1H), 8.22 (d, J=9.0 Hz, 1H), 7.76 (d, J=5.5 Hz, 1H), 7.41-7.39 (m, 1H), 7.13 (d, J=2.0 Hz, 1H), 3.98 (s, 3H); R$_t$=1.66 min (Cond.-D1); 90% homogenity index; LC-MS: Anal. Calc. for [M+H]$^+$ C$_{11}$H$_9$N$_2$O: 185.07. found: 185.20.

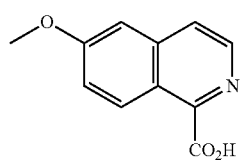
Cap-139

Cap-139 was prepared from the basic hydrolysis of Cap-139, step a with 5N NaOH according to the procedure described for Cap-138. $^1$H NMR (400 MHz, DMSO-d$_6$) δ 13.63 (v br s, 1H), 8.60 (d, J=9.3 Hz, 1H), 8.45 (d, J=5.6 Hz, 1H), 7.95 (d, J=5.9 Hz, 1H), 7.49 (d, J=2.2 Hz, 1H), 7.44 (dd, J=9.3, 2.5 Hz, 1H), 3.95 (s, 3H); R$_t$=0.64 min (Cond.-D1); 90% homogenity index; LC-MS: Anal. Calc. for [M+H]$^+$ C$_{11}$H$_{10}$NO$_3$: 204.07. found: 204.05.

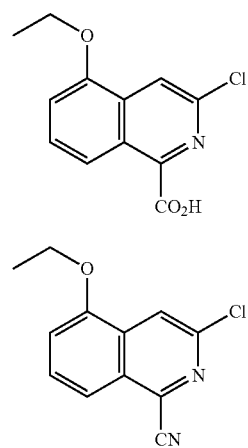
Cap-140

Cap-140, step a

To a vigorously-stirred mixture of 1,3-dichloro-5-ethoxy-isoquinoline (482 mg, 2.00 mmol; prepared according to the procedure in WO 2005/051410), palladium (II) acetate (9 mg, 0.04 mmol), sodium carbonate (223 mg, 2.10 mmol) and 1,5-bis(diphenylphosphino)pentane (35 mg, 0.08 mmol) in dry dimethylacetamide (2 mL) at 25° C. under nitrogen was added N,N,N',N'-tetramethylethylenediamine (60 mL, 0.40 mmol). After 10 min, the mixture was heated to 150° C., and then a stock solution of acetone cyanohydrin (prepared from 457 µL of acetone cyanohydrin in 4.34 mL DMA) was added in 1 mL portions over 18 h using a syringe pump. The mixture was then partitioned between ethyl acetate and water and the organic layer was separated, washed with brine, dried over Na$_2$SO$_4$, filtered and concentrated. The residue was purified on silica gel eluting with 10% ethyl acetate/hexanes to 40% ethyl acetate/hexanes to afford Cap-140, step a as a yellow solid (160 mg, 34%). R$_t$=2.46 min (Cond.-MS-W2); 90% homogenity index; LC-MS: Anal. Calc. for [M+H]$^+$ C$_{12}$H$_9$ClN$_2$O: 233.05. found: 233.08.

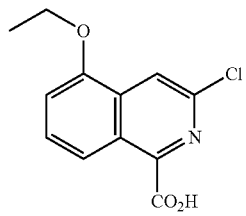
Cap-140

Cap-140 was prepared by the acid hydrolysis of Cap-140, step a with 12N HCl as described in the procedure for the preparation of Cap-141, described below. R$_t$=2.24 min (Cond.-MS-W2); 90% homogenity index; LC-MS: Anal. Calc. for [M+H]$^+$ C$_{12}$H$_{11}$ClNO$_3$: 252.04. found: 252.02.

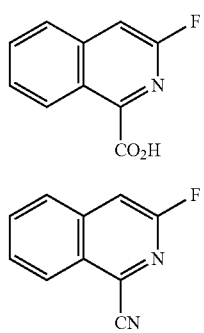
Cap-141

Cap-141, step a

Cap-141, step a was prepared from 1-bromo-3-fluoroiso-quinoline (prepared from 3-amino-1-bromoisoquinoline using the procedure outlined in J. Med. Chem., 13:613 (1970)) as described in the procedure for the preparation of Cap-140, step a (vide supra). $^1$H NMR (500 MHz, CDCl$_3$) δ 8.35 (d, J=8.5 Hz, 1H), 7.93 (d, J=8.5 Hz, 1H), 7.83 (t, J=7.63 Hz, 1H), 7.77-7.73 (m, 1H), 7.55 (s, 1H); R$_t$=1.60 min (Cond.-D1); 90% homogenity index; LC-MS: Anal. Calc. for [M+H]$^+$ C$_{10}$H$_6$FN$_2$: 173.05. found: 172.99.

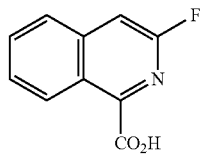
Cap-141

Cap-141, step a (83 mg, 0.48 mmol) was treated with 12N HCl (3 mL) and the resulting slurry was heated at 80° C. for 16 h before it was cooled to room temperature and diluted with water (3 mL). The mixture was stirred for 10 min and then filtered to afford Cap-141 as an off-white solid (44.1 mg, 47.8%). The filtrate was diluted with dichloromethane and washed with brine, dried over Na$_2$SO$_4$, and concentrated to afford additional Cap-141 which was sufficiently pure to be carried forward directly (29.30 mg, 31.8%). $^1$H NMR (DMSO-d$_6$, 500 MHz) δ 14.0 (br s, 1H), 8.59-8.57 (m, 1H), 8.10 (d, J=8.5 Hz, 1H), 7.88-7.85 (m, 2H), 7.74-7.71 (m, 1H); R$_t$=1.33 min (Cond.-D1); 90% homogenity index; LC-MS: Anal. Calc. for [M+H]$^+$ C$_{10}$H$_7$FNO$_2$: 192.05. found: 191.97.

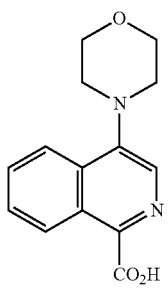

Cap-142

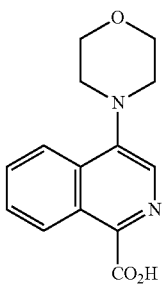

Cap-142

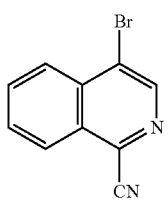

Cap-142, step a

Cap-142 was prepared from Cap-142, step b with 5N sodium hydroxide as described in the procedure for Cap-138. $R_f$=0.72 min (Cond.-MS-W1); 90% homogenity index; LC-MS: Anal. Calc. for [M+H]$^+$ $C_{14}H_{15}N_2O_3$: 259.11. found: 259.08.

Cap-142, step a was prepared from 4-bromoisoquinoline N-oxide as described in the two-step procedure for the preparation of Cap-138, steps b and c. $R_f$=1.45 min (Cond.-MS-W1); 90% homogenity index; LC-MS: Anal. Calc. for [M+H]$^+$ $C_{10}H_6BrN_2$: 232.97. found: 233.00.

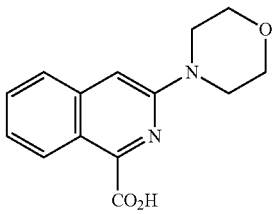

Cap-143

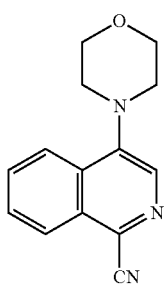

Cap-142, step b

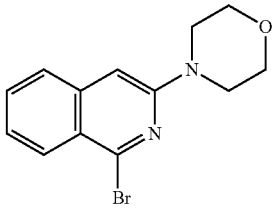

Cap-143, step a

To an argon-degassed suspension of Cap-142, step a (116 mg, 0.50 mmol), potassium phosphate tribasic (170 mg, 0.80 mmol), palladium (II) acetate (3.4 mg, 0.015 mmol) and 2-(dicyclohexylphosphino)biphenyl (11 mg, 0.03 mmol) in anhydrous toluene (1 mL) was added morpholine (61 μL, 0.70 mmol). The mixture was heated at 100° C. for 16 h, cooled to 25° C. and filtered through diatomaceous earth (CELITE®). Purification of the residue on silica gel, eluting with 10% to 70% ethyl acetate/hexanes afforded Cap-142, step b (38 mg, 32%) as a yellow solid, which was carried forward directly. $R_f$=1.26 min (Cond.-MS-W1); 90% homogenity index; LC-MS: Anal. Calc. for [M+H]$^+$ $C_{14}H_{14}N_3O$: 240.11. found: 240.13.

To a stirred solution of 3-amino-1-bromoisoquinoline (444 mg, 2.00 mmol) in anhydrous dimethylformamide (10 mL) was added sodium hydride (60%, unwashed, 96 mg, 2.4 mmol) in one portion. The mixture was stirred at 25° C. for 5 min before 2-bromoethyl ether (90%, 250 μL, 2.00 mmol) was added. The mixture was stirred further at 25° C. for 5 h and at 75° C. for 72 h before it was cooled to 25° C., quenched with saturated ammonium chloride solution and diluted with ethyl acetate. The organic layer was separated, washed with water and brine, dried over $Na_2SO_4$, filtered and concentrated. Purification of the residue on silica gel eluting with 0% to 70% ethyl acetate/hexanes afforded Cap-143, step a as a yellow solid (180 mg, 31%). $R_f$=1.75 min (Cond.-MS-W1); 90% homogenity index; LC-MS: Anal. Calc. for [M+H]$^+$ $C_{13}H_{14}BrN_2O$: 293.03. found: 293.04.

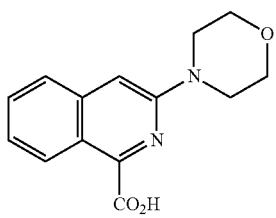

Cap-143

To a cold (−60° C.) solution of Cap-143, step a (154 mg, 0.527 mmol) in anhydrous tetrahydrofuran (5 mL) was added a solution of n-butyllithium in hexanes (2.5 M, 0.25 mL, 0.633 mmol). After 10 min, dry carbon dioxide was bubbled into the reaction mixture for 10 min before it was quenched with 1N HCl and allowed to warm to 25° C. The mixture was then extracted with dichloromethane (3×30 mL) and the combined organic extracts were concentrated in vacuo. Purification of the residue by a reverse phase HPLC (MeOH/water/TFA) afforded Cap-143 (16 mg, 12%). $R_f$=1.10 min (Cond.-MS-W1); 90% homogenity index; LC-MS: Anal. Calc. for [M+H]$^+$ $C_{14}H_{15}N_2O_3$: 259.11. found: 259.08.

Cap-144

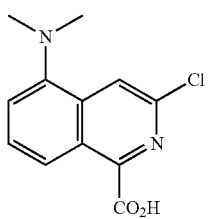

Cap-144, step a 1,3-Dichloroisoquinoline (2.75 g, 13.89 mmol) was added in small portions to a cold (0° C.) solution of fuming nitric acid (10 mL) and concentrated sulfuric acid (10 mL). The mixture was stirred at 0° C. for 0.5 h before it was gradually warmed to 25° C. where it stirred for 16 h. The mixture was then poured into a beaker containing chopped ice and water and the resulting suspension was stirred for 1 h at 0° C. before it was filtered to afford Cap-144, step a (2.73 g, 81%) as a yellow solid which was used directly. $R_f$=2.01 min. (Cond.-D1); 95% homogenity index; LC-MS: Anal. Calc. for [M+H]$^+$ $C_9H_5Cl_2N_2O_2$: 242.97. found: 242.92.

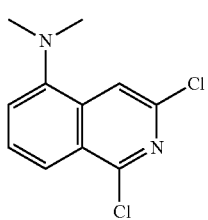

Cap-144, step b

Cap-144, step a (0.30 g, 1.23 mmol) was taken up in methanol (60 mL) and treated with platinum oxide (30 mg), and the suspension was subjected to Parr hydrogenation at 7 psi $H_2$ for 1.5 h. Then formalin (5 mL) and additional platinum oxide (30 mg) were added, and the suspension was resubjected to Parr hydrogenation at 45 psi $H_2$ for 13 h. It was then suction-filtered through diatomaceous earth (CELITE®) and concentrated down to ¼ volume. Suction-filtration of the ensuing precipitate afforded the title compound as a yellow solid which was flash chromatographed on silica gel eluting with 5% ethyl acetate in hexanes to 25% ethyl acetate in hexanes to afford Cap-144, step b (231 mg, 78%) as a pale yellow solid. $R_f$=2.36 min (Cond.-D1); 95% homogenity index; $^1$H NMR (400 MHz, CDCl$_3$) δ 8.02 (s, 1H), 7.95 (d, J=8.6 Hz, 1H), 7.57-7.53 (m, 1H), 7.30 (d, J=7.3 Hz, 1H), 2.88 (s, 6H); LC-MS: Anal. Calc. for [M+H]$^+$ $C_{11}H_{11}Cl_2N_2$: 241.03. found: 241.02. HRMS: Anal. Calc. for [M+H]$^+$ $C_{11}H_{11}Cl_2N_2$: 241.0299. found: 241.0296.

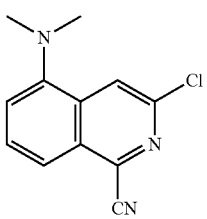

Cap-144, step c

Cap-144, step c was prepared from Cap-144, step b according to the procedure described for the preparation of Cap-139, step a. $R_f$=2.19 min (Cond.-D1); 95% homogenity index; LC-MS: Anal. Calc. for [M+H]$^+$ $C_{12}H_{11}ClN_3$: 232.06. found: 232.03. HRMS: Anal. Calc. for [M+H]$^+$ $C_{12}H_{11}ClN_3$: 232.0642. found: 232.0631.

Cap-144

Cap-144 was prepared according to the procedure described for Cap-141. $R_f$=2.36 min (Cond.-D1); 90%; LC-MS: Anal. Calc. for [M+H]$^+$ $C_{12}H_{12}ClN_2O_2$: 238.01. found: 238.09.

Cap-145 to Cap-162

Cap-145 to Cap-162 were prepared from the appropriate 1-chloroisoquinolines according to the procedure described for the preparation of Cap-138 (Method A) or Cap-139 (Method B) unless noted otherwise as outlined below.

| Cap # | Cap | Method | Hydrolysis | $R_f$ (LC-Cond.); % homogeneity index; MS data |
|---|---|---|---|---|
| Cap-145 | Prepared from commercially available 1,3-dichloroisoquinoline | B | 12N HCl | 1.14 min (Cond.-MS-W1); 90%; LC-MS: Anal. Calc. for [M + H]$^+$ $C_{10}H_7ClNO_2$: 208.02; found: 208.00. |
| Cap-146 | Prepared from commercially available 3-hydroxyisoquinoline | A | 5N NaOH | 1.40 min (Cond.-D1); 95%; LC-MS: Anal. Calc. for [M + H]$^+$ $C_{11}H_{10}NO_3$: 204.07; found: 204.06. |
| Cap-147 | Prepared from commercially available 1-chloro-4-hydroxyisoquinoline | B | 5N NaOH | 0.87 min (Cond.-D1); 95%; LC-MS: Anal. Calc. for [M + H]$^+$ $C_{11}H_{10}NO_3$: 204.07; found: 204.05. |
| Cap-148 | Prepared from commercially available 7-hydroxyisoquinoline | A | 5N NaOH | 0.70 min (Cond.-D1); 95%; LC-MS: Anal. Calc. for [M + H]$^+$ $C_{11}H_{10}NO_3$: 204.07; found: 204.05. |
| Cap-149 | Prepared from commercially available 5-hydroxyisoquinoline | A | 5N NaOH | 0.70 min (Cond.-D1); 95%; LC-MS: Anal. Calc. for [M + H]$^+$ $C_{11}H_{10}NO_3$: 204.07; found: 204.05. |
| Cap-150 | Prepared from 8-methoxy-1-chloroisoquinoline, which can be synthesized following the procedure in WO 2003/099274 | A | 12N HCl | 0.26 min (Cond.-D1); 95%; LC-MS: Anal. Calc. for [M + H]$^+$ $C_{11}H_{10}NO_3$: 204.07; found: 204.04. |

| Cap # | Cap | Method | Hydrolysis | $R_f$ (LC-Cond.); % homogeneity index; MS data |
|---|---|---|---|---|
| Cap-151 3-chloro-5-methoxyisoquinoline-1-carboxylic acid | [Structure: 5-methoxy-3-chloroisoquinoline-1-carboxylic acid] Prepared from 5-methoxy-1,3-dichloroisoquinoline, which can be synthesized following the procedure in WO 2005/051410 | B | 12N HCl | 1.78 min (Cond.-D1); 90%; LC-MS: Anal. Calc. for [M + H]$^+$ $C_{11}H_9ClNO_3$: 238.03; found: 238.09. |
| Cap-152 | [Structure: 6-methoxy-3-chloroisoquinoline-1-carboxylic acid] Prepared from commercially available 6-methoxy-1,3-dichloroisoquinoline | B | 12N HCl | 1.65 min (Cond.-D1); 95%; LC-MS: Anal. Calc. for [M + H]$^+$ $C_{11}H_9ClNO_3$: 238.00; found: 238.09. |
| Cap-153 | [Structure: 4-bromoisoquinoline-1-carboxylic acid] Prepared from 4-bromoisoquinoline, which can be synthesized following the procedure in WO 2003/062241 | A | 6N HCl | 1.18 min (Cond.-MS-W1); 95%; LC-MS: Anal. Calc. for [M + H]$^+$ $C_{10}H_7BrNO_2$: 251.97; found: 251.95. |
| Cap-154 | [Structure: 7-fluoroisoquinoline-1-carboxylic acid] Prepared from 7-fluoro-1-chloroisoquinoline, which can be synthesized following the procedure in WO 2003/099274 | B | 5N NaOH | 0.28 min (Cond.-MS-W1); 90%; LC-MS: Anal. Calc. for [M + H]$^+$ $C_{10}H_7FNO_2$: 192.05; found: 192.03. |
| Cap-155 | [Structure: 7-chloroisoquinoline-1-carboxylic acid] Prepared from 1,7-dichloroisoquinoline, which can be synthesized following the procedure in WO 2003/099274 | B | 5N NaOH | 0.59 min (Cond.-MS-W1); 90%; LC-MS: Anal. Calc. for [M + H]$^+$ $C_{10}H_7ClNO_2$: 208.02; found: 208.00. |

-continued

| Cap # | Cap | Method | Hydrolysis | $R_t$ (LC-Cond.); % homogeneity index; MS data |
|---|---|---|---|---|
| Cap-156 | 6-chloroisoquinoline-1-carboxylic acid<br>Prepared from 1,6-dichloroisoquinoline, which can be synthesized following the procedure in WO 2003/099274 | B | 5N NaOH | 0.60 min (Cond.-MS-W1); 90%; LC-MS: Anal. Calc. for $[M + H]^+$ $C_{10}H_7ClNO_2$: 208.02; found: 208.03. |
| Cap-157 | 4-chloroisoquinoline-1-carboxylic acid<br>Prepared from 1,4-dichloroisoquinoline, which can be synthesized following the procedure in WO 2003/062241 | B | 12N HCl | 1.49 min (Cond.-D1); 95%; LC-MS: Anal. Calc. for $[M + H]^+$ $C_{10}H_{17}ClNO$: 208.02; found: 208.00. |
| Cap-158 | 5-chloroisoquinoline-1-carboxylic acid<br>Prepared from 1,5-dichloroisoquinoline, which can be synthesized following the procedure in WO 2003/099274 | B | 5N NaOH | 0.69 min (Cond.-MS-W1); 90%; LC-MS: Anal. Calc. for $[M + H]^+$ $C_{10}H_7ClNO_2$: 208.02; found: 208.01. |
| Cap-159 | 5-fluoroisoquinoline-1-carboxylic acid<br>Prepared from 5-fluoro-1-chloroisoquinoline, which can be synthesized following the procedure in WO 2003/099274 | B | 5N NaOH | 0.41 min (Cond.-MS-W1); 90%; LC-MS: Anal. Calc. for $[M + H]^+$ $C_{10}H_7FNO_2$: 192.05; found: 192.03. |
| Cap-160 | 6-fluoroisoquinoline-1-carboxylic acid<br>Prepared from 6-fluoro-1-chloroisoquinoline, which can be synthesized following the procedure in WO 2003/099274 | B | 5N NaOH | 0.30 min (Cond.-MS-W1); 90%; LC-MS: Anal. Calc. for $[M + H]^+$ $C_{10}H_7FNO_2$: 192.05; found: 192.03. |

| Cap # | Cap | Method | Hydrolysis | $R_f$ (LC-Cond.); % homogeneity index; MS data |
|---|---|---|---|---|
| Cap-161 | ![structure] Prepared from 4-bromoquinoline-2-carboxylic acid and dimethylamine (DMSO, 100° C.) | — | — | 0.70 min (Cond. D1); 95%; LC-MS: Anal. Calc. for $[M + H]^+$ $C_{12}H_{13}N_2O_2$: 217.10; found: 217.06. |
| Cap-162 | ![structure] Prepared from m-anisidine following the procedure described in *J. Hetero. Chem.*, 17 (1993) and *Heterocycles*, 60:953 (2003). | — | — | 0.65 min (Cond.-M3); 95%; LC-MS: Anal. Calc. for $[M + H]^+$ $C_{11}H_{10}NO_3$: 204.07; found: 203.94. |

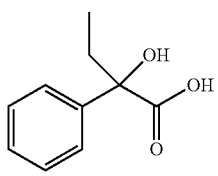

Cap-163

To a solution of 2-ketobutyric acid (1.0 g, 9.8 mmol) in diethylether (25 ml) was added phenylmagnesium bromide (22 ml, 1M in THF) dropwise. The reaction was stirred at ~25° C. under nitrogen for 17.5 h. The reaction was acidified with 1N HCl and the product was extracted with ethyl acetate (3×100 ml). The combined organic layer was washed with water followed by brine and dried over $MgSO_4$. After concentration in vacuo, a white solid was obtained. The solid was recrystallized from hexanes/ethyl acetate to afford Cap-163 as white needles (883.5 mg). $^1$H NMR (DMSO-$d_6$, δ=2.5 ppm, 500 MHz): 12.71 (br s, 1H), 7.54-7.52 (m, 2H), 7.34-7.31 (m, 2H), 7.26-7.23 (m, 1H), 5.52-5.39 (br s, 1H), 2.11 (m, 1H), 1.88 (m, 1H), 0.79 (app t, J=7.4 Hz, 3H).

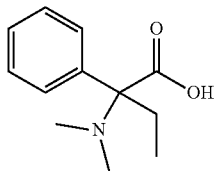

Cap-164

A mixture of 2-amino-2-phenylbutyric acid (1.5 g, 8.4 mmol), formaldehyde (14 mL, 37% in water), 1N HCl (10 mL) and 10% Pd/C (0.5 mg) in MeOH (40 mL) was exposed to $H_2$ at 50 psi in a Parr bottle for 42 h. The reaction was filtered over CELITE® and concentrated in vacuo, the residue was taken up in MeOH (36 mL) and the product was purified with a reverse phase HPLC (MeOH/$H_2$O/TFA) to afford the TFA salt of Cap-164 as a white solid (1.7 g). $^1$H NMR (DMSO-$d_6$, δ=2.5 ppm, 500 MHz) 7.54-7.47 (m, 5H), 2.63 (m, 1H), 2.55 (s, 6H), 2.31 (m, 1H), 0.95 (app t, J=7.3 Hz, 3H).

Cap-165

To a mixture of 2-amino-2-indanecarboxylic acid (258.6 mg, 1.46 mmol) and formic acid (0.6 ml, 15.9 mmol) in 1,2-dichloroethane (7 ml) was added formaldehyde (0.6 ml, 37% in water). The mixture was stirred at ~25° C. for 15 min then heated at 70° C. for 8 h. The volatile component was removed in vacuo, and the residue was dissolved in DMF (14 mL) and purified by a reverse phase HPLC (MeOH/$H_2$O/TFA) to afford the TFA salt of Cap-165 as a viscous oil (120.2 mg). $^1$H NMR (DMSO-$d_6$, δ=2.5 ppm, 500 MHz): 7.29-7.21 (m, 4H), 3.61 (d, J=17.4 Hz, 2H), 3.50 (d, J=17.4 Hz, 2H), 2.75 (s, 6H). LC-MS: Anal. Calcd. for $[M+H]^+$ $C_{12}H_{16}NO_2$: 206.12. found: 206.07.

Cap-166a and Cap-166b

Cap-166a: Diastereomer-1
Cap-166b: Diastereomer-2

Cap-166a and Cap-166b were prepared from (1S,4S)-(+)-2-methyl-2,5-diazabicyclo[2.2.1]heptane (2HBr) according to the method described for the synthesis of Cap-7a and Cap-7b, with the exception that the benzyl ester intermediate was separated using a semi-prep Chrialcel OJ column, 20×250 mm, 10 µm eluting with 85:15 heptane/ethanol mixture at 10 mL/min elution rate for 25 min. Cap-166b: $^1$H NMR (DMSO-$d_6$, δ=2.5 ppm, 500 MHz): 7.45 (d, J=7.3 Hz, 2H), 7.27-7.19 (m, 3H), 4.09 (s, 1H), 3.34 (app br s, 1H), 3.16 (app br s, 1H), 2.83 (d, J=10.1 Hz, 1H), 2.71 (m, 2H), 2.46 (m, 1H), 2.27 (s, 3H), 1.77 (d, J=9.8 Hz, 1H), 1.63 (d, J=9.8 Hz, 1H). LC-MS: Anal. Calcd. for [M+H]$^+$ $C_{14}H_{19}N_2O_2$: 247.14. found: 247.11.

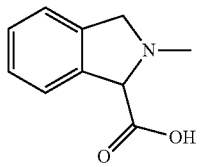

Cap-167

A solution of racemic Boc-1,3-dihydro-2H-isoindole carboxylic acid (1.0 g, 3.8 mmol) in 20% TFA/$CH_2Cl_2$ was stirred at ~25° C. for 4 h. All the volatile component was removed in vacuo. A mixture of the resultant crude material, formaldehyde (15 mL, 37% in water), 1N HCl (10 mL) and 10% Pd/C (10 mg) in MeOH was exposed to $H_2$ (40 PSI) in a Parr bottle for 23 h. The reaction mixture was filtered over CELITE® and concentrated in vacuo to afford Cap-167 as a yellow foam (873.5 mg). $^1$H NMR (DMSO-$d_6$, δ=2.5 ppm, 500 MHz) 7.59-7.38 (m, 4H), 5.59 (s, 1H), 4.84 (d, J=14 Hz, 1H), 4.50 (d, J=14.1 Hz, 1H), 3.07 (s, 3H). LC-MS: Anal. Calcd. for [M+H]$^+$ $C_{10}H_{12}NO_2$: 178.09. found: 178.65.

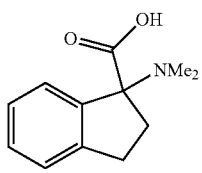

Cap-168

Racemic Cap-168 was prepared from racemic Boc-aminoindane-1-carboxylic acid according to the procedure described for the preparation of Cap-167. The crude material was employed as such.

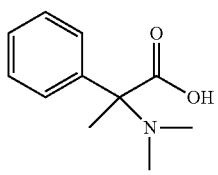

Cap-169

A mixture of 2-amino-2-phenylpropanoic acid hydrochloride (5.0 g, 2.5 mmol), formaldehyde (15 ml, 37% in water), 1N HCl (15 ml), and 10% Pd/C (1.32 g) in MeOH (60 mL) was placed in a Parr bottle and shaken under hydrogen (55 PSI) for 4 days. The reaction mixture was filtered over CELITE® and concentrated in vacuo. The residue was taken up in MeOH and purified by reverse phase prep-HPLC (MeOH/water/TFA) to afford the TFA salt of Cap-169 as a viscous semi-solid (2.1 g). $^1$H NMR (CDCl$_3$, δ=7.26 ppm, 500 MHz): 7.58-7.52 (m, 2H), 7.39-7.33 (m, 3H), 2.86 (br s, 3H), 2.47 (br s, 3H), 1.93 (s, 3H). LC-MS: Anal. Calcd. for [M+H]$^+$ $C_{11}H_{16}NO_2$: 194.12. found: 194.12.

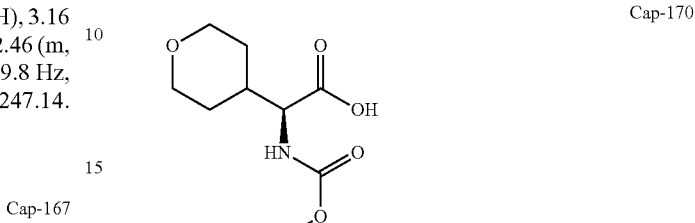

Cap-170

(S)-2-(Methoxycarbonylamino)-2-(tetrahydro-2H-pyran-4-yl)acetic acid

To (S)-2-amino-2-(tetrahydro-2H-pyran-4-yl)acetic acid (505 mg; 3.18 mmol; obtained from Astatech) in water (15 ml) was added sodium carbonate (673 mg; 6.35 mmol), and the resultant mixture was cooled to 0° C. and then methyl chloroformate (0.26 ml; 3.33 mmol) was added dropwise over 5 minutes. The reaction was allowed to stir for 18 hours while allowing the bath to thaw to ambient temperature. The reaction mixture was then partitioned between 1N HCl and ethyl acetate. The organic layer was removed and the aqueous layer was further extracted with 2 additional portions of ethyl acetate. The combined organic layers were washed with brine, dried over magnesium sulfate, filtered and concentrated in vacuo to afford Cap-170 a colorless residue. $^1$H NMR (500 MHz, DMSO-$d_6$) δ ppm 12.65 (1H, br s), 7.44 (1H, d, J=8.24 Hz), 3.77-3.95 (3H, m), 3.54 (3H, s), 3.11-3.26 (2H, m), 1.82-1.95 (1H, m), 1.41-1.55 (2H, m), 1.21-1.39 (2H, m); LC-MS: Anal. Calcd. for [M+H]$^+$ $C_9H_{16}NO_5$: 218.1. found 218.1.

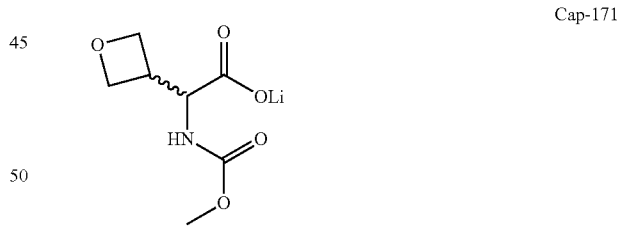

Cap-171

A solution of methyl 2-(benzyloxycarbonylamino)-2-(oxetan-3-ylidene)acetate (200 mg, 0.721 mmol; Il Farmaco (2001), 56, 609-613) in ethyl acetate (7 ml) and $CH_2Cl_2$ (4.00 ml) was degassed by bubbling nitrogen for 10 min. Dimethyl dicarbonate (0.116 ml, 1.082 mmol) and Pd/C (20 mg, 0.019 mmol) were then added, the reaction mixture was fitted with a hydrogen balloon and allowed to stir at ambient temperature overnight at which time TLC (95:5 $CH_2Cl_2$/MeOH: visualized with stain made from 1 g Ce(NH$_4$)$_2$SO$_4$, 6 g ammonium molybdate, 6 ml sulfuric acid, and 100 ml water) indicated complete conversion. The reaction was filtered through CELITE® and concentrated. The residue was purified via BIOTAGE® (load with dichloromethane on 25 samplet; elute on 25S column with dichloromethane for 3CV then 0 to 5%

MeOH/dichloromethane over 250 ml then hold at 5% MeOH/dichloromethane for 250 ml; 9 ml fractions). Collected fractions containing desired material and concentrated to 120 mg (81%) of methyl 2-(methoxycarbonylamino)-2-(oxetan-3-yl)acetate as a colorless oil. $^1$H NMR (500 MHz, chloroform-d) δ ppm 3.29-3.40 (m, J=6.71 Hz, 1H) 3.70 (s, 3H) 3.74 (s, 3H) 4.55 (t, J=6.41 Hz, 1H) 4.58-4.68 (m, 2H) 4.67-4.78 (m, 2H) 5.31 (br s, 1H). LC-MS: Anal. Calcd. for [M+H]$^+$ C$_8$H$_{14}$NO$_5$: 204.2. found 204.0.

To methyl 2-(methoxycarbonylamino)-2-(oxetan-3-yl)acetate (50 mg, 0.246 mmol) in THF (2 mL) and water (0.5 mL) was added lithium hydroxide monohydrate (10.33 mg, 0.246 mmol). The resultant solution was allowed to stir overnight at ambient temperature. TLC (1:1 EA/Hex; Hanessian stain [1 g Ce(NH$_4$)$_2$SO$_4$, 6 g ammonium molybdate, 6 ml sulfuric acid, and 100 ml water]) indicated ~10% starting material remaining Added an additional 3 mg LiOH and allowed to stir overnight at which time TLC showed no starting material remaining Concentrated in vacuo and placed on high vac overnight providing 55 mg lithium 2-(methoxycarbonylamino)-2-(oxetan-3-yl)acetate as a colorless solid. $^1$H NMR (500 MHz, MeOD) δ ppm 3.39-3.47 (m, 1H) 3.67 (s, 3H) 4.28 (d, J=7.93 Hz, 1H) 4.64 (t, J=6.26 Hz, 1H) 4.68 (t, J=7.02 Hz, 1H) 4.73 (d, J=7.63 Hz, 2H).

Cap-172

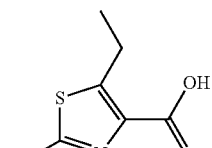

Cap-172, step a

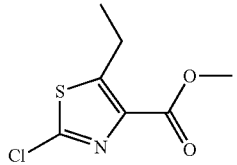

The following diazotization step was adapted from Barton, A. et al., *J. C. S. Perkin Trans I*, 159-164 (1982): A solution of NaNO$_2$ (166 mg, 2.4 mmol) in water (0.6 mL) was added slowly to a stirred, cold (0° C.) solution of methyl 2-amino-5-ethyl-1,3-thiazole-4-carboxylate (186 mg, 1.0 mmol), CuSO$_4$.5H$_2$O (330 mg, 1.32 mmol), NaCl (260 mg, 4.45 mmol) and H$_2$SO$_4$ (5.5 mL) in water (7.5 mL). The mixture was stirred at 0° C. for 45 min and allowed to warm up to room temperature where it stirred further for 1 h before CuCl (118 mg) was added. This mixture was stirred further at room temperature for 16 h before it was diluted with brine and extracted with ether twice. The organic layers were combined, dried over MgSO$_4$ and concentrated to give methyl 2-chloro-5-ethylthiazole-4-carboxylate (i.e., Cap-172, step a) (175 mg, 85%) as an orange oil (80% pure) which was used directly in the next reaction. R$_f$=1.99 min (Cond.-MD1); LC-MS: Anal. Calcd. for [M+H]$^+$ C$_7$H$_9$ClNO$_2$S: 206.01. found: 206.05.

Cap-172

To a solution of methyl 2-chloro-5-ethylthiazole-4-carboxylate (175 mg) in THF/H$_2$O/MeOH (20 mL/3 mL/12 mL) was added LiOH (305 mg, 12.76 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-172 (60 mg, 74%) as a red solid which was used without further purification. $^1$H NMR (300 MHz, DMSO-d$_6$) δ ppm 13.03-13.42 (1H, m), 3.16 (2H, q, J=7.4 Hz), 1.23 (3H, t, J=7.5 Hz). R$_f$=1.78 min (Cond.-MD1); LC-MS: Anal. Calcd. for [M+H]$^+$ C$_6$H$_7$ClNO$_2$S: 191.99. found: 191.99.

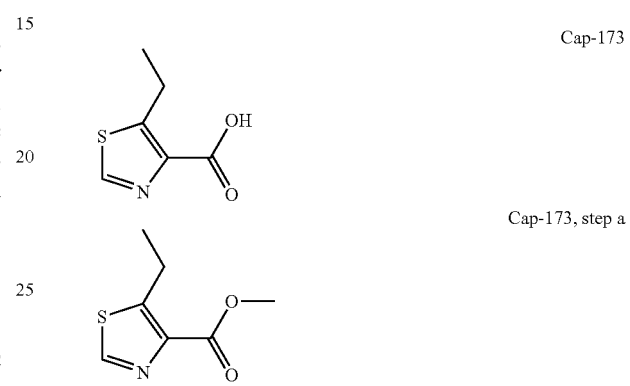

The following diazotization step was adapted from Barton, A. et al., *J.C.S. Perkin Trans I*, 159-164 (1982): A solution of NaNO$_2$ (150 mg, 2.17 mmol) in water (1.0 mL) was added dropwise to a stirred, cold (0° C.) solution of methyl 2-amino-5-ethyl-1,3-thiazole-4-carboxylate (186 mg, 1.0 mmol) in 50% H$_3$PO$_2$ (3.2 mL). The mixture was stirred at 0° C. for 1 h and allowed to warm up to room temperature where it stirred further for 2 h. After recooling to 0° C., the mixture was treated slowly with a solution of NaOH (85 mg) in water (10 mL). The mixture was then diluted with saturated NaHCO$_3$ solution and extracted twice with ether. The organic layers were combined, dried over MgSO$_4$ and concentrated to give methyl 5-ethylthiazole-4-carboxylate (i.e., Cap-173, step a) (134 mg, 78%) as an orange oil (85% pure) which was used directly in the next reaction. R$_f$=1.58 min (Cond.-MD1); LC-MS: Anal. Calcd. for [M+H]$^+$ C$_7$H$_{10}$NO$_2$S: 172.05. found: 172.05.

Cap-173

To a solution of methyl 5-ethylthiazole-4-carboxylate (134 mg) in THF/H$_2$O/MeOH (18 mL/2.7 mL/11 mL) was added LiOH (281 mg, 11.74 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-173 (90 mg, 73%) as an orange solid which was used without further purification. $^1$H NMR (300 MHz, DMSO-d$_6$) δ ppm 12.74-13.04 (1H, m), 3.20 (2H, q, J=7.3 Hz), 1.25 (3H, t, J=7.5 Hz). R$_f$=1.27 min (Cond.-MD1); LC-MS: Anal. Calcd. for [M+H]$^+$ C$_6$H$_8$NO$_2$S: 158.03. found: 158.04.

Cap-174

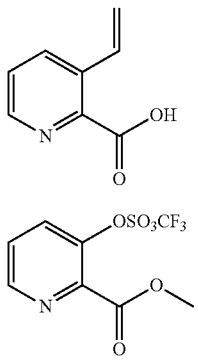

Cap-174, step a

Triflic anhydride (5.0 g, 18.0 mmol) was added dropwise to a cold (0° C.) solution of methyl 3-hydroxypicolinate (2.5 g, 16.3 mmol) and TEA (2.5 mL, 18.0 mmol) in CH$_2$Cl$_2$ (80 mL). The mixture was stirred at 0° C. for 1 h before it was allowed to warm up to room temperature where it stirred for an additional 1 h. The mixture was then quenched with saturated NaHCO$_3$ solution (40 mL) and the organic layer was separated, washed with brine, dried over MgSO$_4$ and concentrated to give methyl 3-(trifluoromethylsulfonyloxy)picolinate (i.e., Cap-174, step a) (3.38 g, 73%) as a dark brown oil (>95% pure) which was used directly without further purification. $^1$H NMR (300 MHz, CDCl$_3$) δ ppm 8.72-8.79 (1H, m), 7.71 (1H, d, J=1.5 Hz), 7.58-7.65 (1H, m), 4.04 (3H, s). R$_t$=1.93 min (Cond.-MD1); LC-MS: Anal. Calcd. for [M+H]$^+$ C$_8$H$_7$F$_3$NO$_5$S: 286.00. found: 286.08.

Cap-174

To a solution of methyl 3-(trifluoromethylsulfonyloxy)picolinate (570 mg, 2.0 mmol) in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. overnight before a saturated solution of KF (20 mL) was added to the reaction mixture at room temperature. This mixture was stirred for 4 h before it was filtered through CELITE® and the pad of CELITE® was washed with ethyl acetate. The aqueous phase of the filtrate was then separated and concentrated down in vacuo. The residue was treated with 4N HCl in dioxanes (5 mL) and the resulting mixture was extracted with methanol, filtered and evaporated to afford Cap-174 (260 mg) as a green solid which was slightly contaminated with inorganic salts but was used without further purification. $^1$H NMR (300 MHz, DMSO-d$_6$) δ ppm 8.21 (1H, d, J=3.7 Hz), 7.81-7.90 (1H, m), 7.09 (1H, dd, J=7.7, 4.8 Hz), 6.98 (1H, dd, J=17.9, 11.3 Hz), 5.74 (1H, dd, J=17.9, 1.5 Hz), 5.20 (1H, d, J=11.0 Hz). R$_t$=0.39 min (Cond.-MD1); LC-MS: Anal. Calcd. for [M+H]$^+$ C$_8$H$_8$NO$_2$: 150.06. found: 150.07.

Cap-175

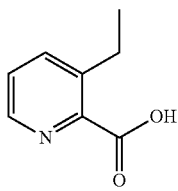

Cap-175, step a

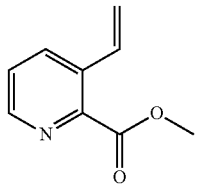

To a solution of methyl 3-(trifluoromethylsulfonyloxy)picolinate (i.e., Cap-174, step a) (570 mg, 2.0 mmol), an intermediate in the preparation of Cap-174, in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. for 4 h before the solvent was removed in vacuo. The residue was taken up in acetonitrile (50 mL) and hexanes (50 mL) and the resulting mixture was washed twice with hexanes. The acetonitrile layer was then separated, filtered through CELITE®, and evaporated. Purification of the residue by flash chromatography on a Horizon instrument (gradient elution with 25% ethyl acetate in hexanes to 65% ethyl acetate in hexanes) afforded methyl 3-vinylpicolinate (i.e., Cap-175, step a) (130 mg, 40%) as a yellow oil. $^1$H NMR (300 MHz, CDCl$_3$) δ ppm 8.60 (1H, dd, J=4.6, 1.7 Hz), 7.94 (1H, d, J=7.7 Hz), 7.33-7.51 (2H, m), 5.72 (1H, d, J=17.2 Hz), 5.47 (1H, d, J=11.0 Hz), 3.99 (3H, s). R$_t$=1.29 min (Cond.-MD1); LC-MS: Anal. Calcd. for [M+H]$^+$ C$_9$H$_{10}$NO$_2$: 164.07. found: 164.06.

Cap-175, step b

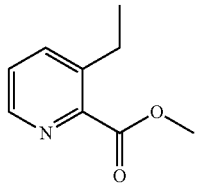

Palladium on carbon (10%, 25 mg) was added to a solution of methyl 3-vinylpicolinate (120 mg, 0.74 mmol) in ethanol (10 mL). The suspension was stirred at room temperature under an atmosphere of hydrogen for 1 h before it was filtered through CELITE® and the pad of CELITE® was washed with methanol. The filtrate was concentrated down to dryness to yield methyl 3-ethylpicolinate (i.e., Cap-175, step b) which was taken directly into the next reaction. R$_t$=1.15 min (Cond.-MD1); LC-MS: Anal. Calcd. for [M+H]$^+$ C$_9$H$_{12}$NO$_2$: 166.09. found: 166.09.

Cap-175

To a solution of methyl 3-ethylpicolinate in THF/H$_2$O/MeOH (5 mL/0.75 mL/3 mL) was added LiOH (35 mg, 1.47 mmol). The mixture was stirred at room temperature for 2 d before additional LiOH (80 mg) was added. After an additional 24 h at room temperature, the mixture was filtered and the solvent was removed in vacuo. The residue was then treated with 4N HCl in dioxanes (5 mL) and the resulting suspension was concentrated down to dryness to yield Cap-175 as a yellow solid which was used without further purification. $^1$H NMR (300 MHz, DMSO-d$_6$) δ ppm 8.47 (1H, dd, J=4.8, 1.5 Hz), 7.82-7.89 (1H, m), 7.53 (1H, dd, J=7.7, 4.8 Hz), 2.82 (2H, q, J=7.3 Hz), 1.17 (3H, t, J=7.5 Hz). R$_t$=0.36 min (Cond.-MD1); LC-MS: Anal. Calcd. for [M+H]$^+$ $C_8H_{10}NO_2$: 152.07. found: 152.10.

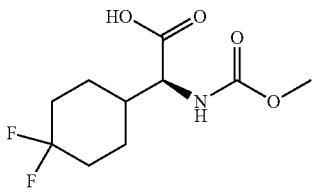

Cap-176

(S)-2-(4,4-Difluorocyclohexyl)-2-(methoxycarbonylamino)acetic acid

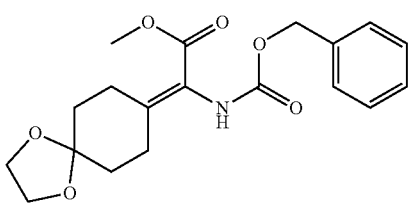

Cap-176, step a

A solution of 1,4-dioxaspiro[4.5]decan-8-one (15 g, 96 mmol) in EtOAc (150 mL) was added to a solution of methyl 2-(benzyloxycarbonylamino)-2-(dimethoxyphosphoryl)acetate (21.21 g, 64.0 mmol) in 1,1,3,3-tetramethylguanidine (10.45 mL, 83 mmol) and EtOAc (150 mL). The resulting solution was the stirred at ambient temperature for 72 h and then it was diluted with EtOAc (25 mL). The organic layer was washed with 1N HCl (75 mL), H$_2$O (100 mL) and brine (100 mL), dried (MgSO$_4$), filtered and concentrated. The residue was purified via BIOTAGE® (5% to 25% EtOAc/Hexanes; 300 g column). The combined fractions containing the product were then concentrated under vacuum and the residue was re-crystallized from hexanes/EtOAc to give white crystals that corresponded to methyl 2-(benzyloxycarbonylamino)-2-(1,4-dioxaspiro[4.5]decan-8-ylidene)acetate (6.2 g) $^1$H NMR (400 MHz, CDCl$_3$-d) δ ppm 7.30-7.44 (5H, m), 6.02 (1H, br. s.), 5.15 (2H, s), 3.97 (4H, s), 3.76 (3H, br. s.), 2.84-2.92 (2H, m), 2.47 (2H, t, J=6.40 Hz), 1.74-1.83 (4H, m). LC (Cond. OL1): R$_t$=2.89 min. LC-MS: Anal. Calcd. for [M+Na]$^+$ $C_{19}H_{23}NNaO_6$: 745.21. found: 745.47.

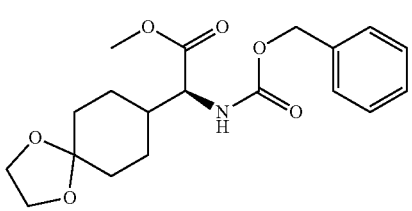

Cap-176, step b

Ester Cap-176, step b was prepared from alkene Cap-176, step a according to the method of Burk, M. J. et al. (J. Am. Chem. Soc., 117:9375-9376 (1995)) and references therein): A 500 mL high-pressure bottle was charged with alkene Cap-176, step a (3.5 g, 9.68 mmol) in degassed MeOH (200 mL) under a blanket of N$_2$. The solution was then charged with (−)-1,2-Bis((2S,5S)-2,5-dimethylphospholano)ethane(cyclooctadiene) rhodium (I) tetrafluoroborate (0.108 g, 0.194 mmol) and the resulting mixture was flushed with N$_2$ (3×) and charged with H$_2$ (3×). The solution was shaken vigorously under 70 psi of H$_2$ at ambient temperature for 72 h. The solvent was removed under reduced pressure and the remaining residue was taken up in EtOAc. The brownish solution was then filtered through a plug of Silica Gel and eluted with EtOAc. The solvent was concentrated under vacuum to afford a clear oil corresponding to ester Cap-176, step b (3.4 g). $^1$H NMR (500 MHz, CDCl$_3$-d) δ ppm 7.28-7.43 (5H, m), 5.32 (1H, d, J=9.16 Hz), 5.06-5.16 (2H, m), 4.37 (1H, dd, J=9.00, 5.04 Hz), 3.92 (4H, t, J=3.05 Hz), 3.75 (3H, s), 1.64-1.92 (4H, m), 1.37-1.60 (5H, m). LC (Cond. OL1): R$_t$=1.95 min. LC-MS: Anal. Calcd. for [M+H]$^+$ $C_{19}H_{26}NO_6$: 364.18. found: 364.27.

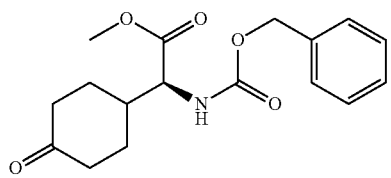

Cap-176, step c

Ester Cap-176, step b (4.78 g, 13.15 mmol) was dissolved in THF (15 mL) followed by sequential addition of water (10 mL), glacial acetic acid (26.4 mL, 460 mmol) and dichloroacetic acid (5.44 mL, 65.8 mmol). The resulting mixture was stirred for 72 h at ambient temperature, and the reaction was quenched by slow addition of solid Na$_2$CO$_3$ with vigorous stirring until the release of gas was no longer visible. Crude product was extracted into 10% ethyl acetate-dichloromethane and the organic layers were combined, dried (MgSO$_4$) filtered and concentrated. The resulting residue was purified via BIOTAGE® (0 to 30% EtOAc/Hex; 25 g column) to afford ketone Cap-176, step c (3.86 g) as a clear oil. $^1$H NMR (400 MHz, CDCl$_3$-d) δ ppm 7.28-7.41 (5H, m), 5.55 (1H, d, J=8.28 Hz), 5.09 (2H, s), 4.46 (1H, dd, J=8.16, 5.14 Hz), 3.74 (3H, s), 2.18-2.46 (5H, m), 1.96-2.06 (1H, m), 1.90 (1H, ddd, J=12.99, 5.96, 2.89 Hz), 1.44-1.68 (2H, m, J=12.36, 12.36, 12.36, 12.36, 4.77 Hz). LC (Cond. OL1): R$_t$=1.66 min. LC-MS: Anal. Calcd. for [M+Na]$^+$ $C_{17}H_{21}NNaO_5$: 342.13. found: 342.10.

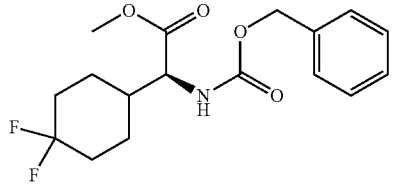

Cap-176, step d

DEOXO-FLUOR® (3.13 mL, 16.97 mmol) was added to a solution of ketone Cap-176, step c (2.71 g, 8.49 mmol) in CH$_2$Cl$_2$ (50 mL) followed by addition of a catalytic amount of EtOH (0.149 mL, 2.55 mmol). The resulting yellowish solution was stirred at rt overnight. The reaction was quenched by addition of sat. aq. NaHCO$_3$ (25 mL) and the mixture was extracted with EtOAc (3×75 mL)). The combined organic layers were dried (MgSO$_4$), filtered and dried to give a yellowish oil. The residue was purified via BIOTAGE® chromatography (2% to 15% EtOAc/Hex; 90 g column) and a white solid corresponding to the difluoro amino acid difluoride Cap-176, step d (1.5 g) was recovered. $^1$H NMR (400 MHz, CDCl$_3$-d) δ ppm 7.29-7.46 (5H, m), 5.34 (1H, d, J=8.28 Hz), 5.12 (2H, s), 4.41 (1H, dd, J=8.66, 4.89 Hz), 3.77 (3H, s), 2.06-2.20 (2H, m), 1.83-1.98 (1H, m), 1.60-1.81 (4H, m), 1.38-1.55 (2H, m). $^{19}$F NMR (376 MHz, CDCl$_3$-d) δ ppm −92.15 (1F, d, J=237.55 Hz), −102.44 (1F, d, J=235.82 Hz). LC (Cond. OL1): R$_t$=1.66 min. LC-MS: Anal. Calcd. for [2M+Na]$^+$ C$_{34}$H$_{42}$F$_4$N$_2$NaO$_8$: 705.28. found: 705.18.

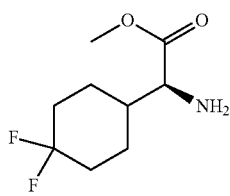

Cap-176, step e

Difluoride Cap-176, step d (4 g, 11.72 mmol) was dissolved in MeOH (120 mL) and charged with Pd/C (1.247 g, 1.172 mmol). The suspension was flushed with N$_2$ (3×) and the reaction mixture was placed under 1 atm of H$_2$ (balloon). The mixture was stirred at ambient temperature for 48 h. The suspension was then filtered though a plug of CELITE® and concentrated under vacuum to give an oil that corresponded to amino acid Cap-176, step e (2.04 g) and that was used without further purification. $^1$H NMR (400 MHz, DMSO-d$_6$) δ ppm 3.62 (3H, s), 3.20 (1H, d, J=5.77 Hz), 1.91-2.09 (2H, m), 1.50-1.88 (7H, m), 1.20-1.45 (2H, m). $^{19}$F NMR (376 MHz, DMSO-d$_6$) δ ppm −89.39 (1F, d, J=232.35 Hz), −100.07 (1F, d, J=232.35 Hz). $^{13}$C NMR (101 MHz, DMSO-d$_6$) δ ppm 175.51 (1C, s), 124.10 (1C, t, J=241.21, 238.90 Hz), 57.74 (1C, s), 51.39 (1C, s), 39.23 (1C, br. s.), 32.02-33.83 (2C, m), 25.36 (1C, d, J=10.02 Hz), 23.74 (1C, d, J=9.25 Hz). LC (Cond. OL2): R$_t$=0.95 min. LC-MS: Anal. Calcd. for [2M+H]$^+$ C$_{18}$H$_{31}$F$_4$N$_2$O$_2$: 415.22. found: 415.40.

Cap-176. step f

Methyl chloroformate (1.495 mL, 19.30 mmol) was added to a solution of amino acid Cap-176, step e (2 g, 9.65 mmol) and DIEA (6.74 mL, 38.6 mmol) in CH$_2$Cl$_2$ (100 mL). The resulting solution was stirred at rt for 3 h and volatiles were removed under reduced pressure. The residue was purified via BIOTAGE® (0% to 20% EtOAc/Hex; 90 g column). A clear oil that solidified upon standing under vacuum and corresponding to carbamate Cap-176, step f (2.22 g) was recovered. $^1$H NMR (500 MHz, CDCl$_3$-d) δ ppm 5.27 (1H, d, J=8.55 Hz), 4.39 (1H, dd, J=8.85, 4.88 Hz), 3.77 (3H, s), 3.70 (3H, s), 2.07-2.20 (2H, m), 1.84-1.96 (1H, m), 1.64-1.82 (4H, m), 1.39-1.51 (2H, m). $^{19}$F NMR (471 MHz, CDCl$_3$-d) δ ppm −92.55 (1F, d, J=237.13 Hz), −102.93 (1F, d, J=237.12 Hz). $^{13}$C NMR (126 MHz, CDCl$_3$-d) δ ppm 171.97 (1C, s), 156.69 (1C, s), 119.77-125.59 (1C, m), 57.24 (1C, br. s.), 52.48 (1C, br. s.), 52.43 (1C, s), 39.15 (1C, s), 32.50-33.48 (2C, m), 25.30 (1C, d, J=9.60 Hz), 24.03 (1C, d, J=9.60 Hz). LC (Cond. OL1): R$_t$=1.49 min. LC-MS: Anal. Calcd. for [M+Na]$^+$ C$_{11}$H$_{17}$F$_2$NNaO$_4$: 288.10. found: 288.03.

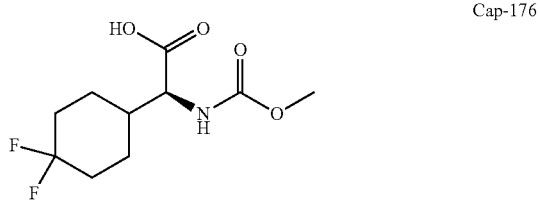 [SMILES: COC(=O)N[C@H](C(=O)O)C1CCC(F)(F)CC1]

Cap-176

(S)-2-(4,4-Difluorocyclohexyl)-2-(methoxycarbonylamino)acetic acid

A solution of LiOH (0.379 g, 15.83 mmol) in water (25 mL) was added to a solution of carbamate Cap-176, step f (2.1 g, 7.92 mmol) in THF (75 mL) and the resulting mixture was stirred at ambient temperature for 4 h. THF was removed under vacuum and the remaining aqueous phase was acidified with 1N HCl solution (2 mL) and then extracted with EtOAc (2×50 mL). The combined organic layers were dried (MgSO$_4$), filtered and concentrated to give a white foam corresponding to Cap-176 (1.92 g). $^1$H NMR (400 MHz, DMSO-d$_6$) δ ppm 12.73 (1H, s), 7.50 (1H, d, J=8.78 Hz), 3.97 (1H, dd, J=8.53, 6.02 Hz), 3.54 (3H, s), 1.92-2.08 (2H, m), 1.57-1.90 (5H, m), 1.34-1.48 (1H, m), 1.27 (1H, qd, J=12.72, 3.26 Hz). $^{19}$F NMR (376 MHz, DMSO-d$_6$) δ ppm −89.62 (1F, d, J=232.35 Hz), −99.93 (1F, d, J=232.35 Hz). LC (Cond. OL2): R$_t$=0.76 min. LC-MS: Anal. Calcd. for [M−H]$^+$ C$_{10}$H$_{14}$F$_2$NO$_4$: 250.09. found: 250.10.

Cap-177a and Cap-177b

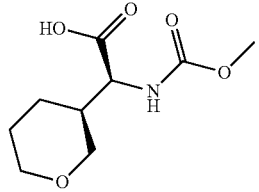

Cap 177a

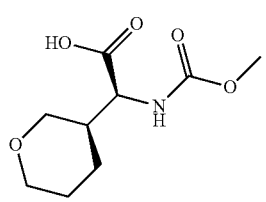

Cap 177b

Cap-177a and Cap-177b, step a

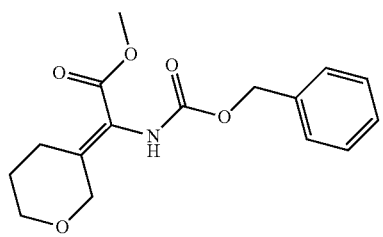

119

-continued

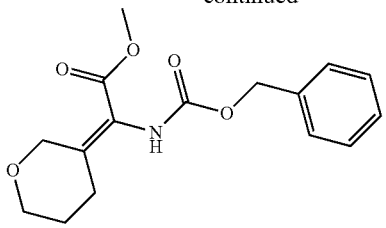

1,1,3,3-Tetramethylguanidine (0.985 mL, 7.85 mmol) was added to a stirred solution of methyl 2-(benzyloxycarbonylamino)-2-(dimethoxyphosphoryl)acetate (2.0 g, 6.0 mmol) in EtOAc (40 mL) and the mixture was stirred at rt under $N_2$ for 10 min. Then dihydro-2H-pyran-3(4H)-one [23462-75-1] (0.604 g, 6.04 mmol) was added and the mixture was stirred at rt for 16 h. The reaction mixture was then cooled in freezer for 10 min and neutralized with aq. citric acid (1.5 g in 20 mL water). The two phases were partitioned and the organic layer was washed with 0.25 N aq.HCl and brine, and then dried ($MgSO_4$) and concentrated to a colorless oil. The crude material was purified by flash silica chromatography (loading solvent: DCM, eluted with EtOAc/Hexanes, gradient from 20% to 30% EtOAc) to yield two isomeric products: The first eluted product was (Z)-methyl 2-(benzyloxycarbonylamino)-2-(2H-pyran-3(4H,5H,6H)-ylidene)acetate (490 mg) (white solid), and the second was (E)-methyl 2-(benzyloxycarbonylamino)-2-(2H-pyran-3(4H,5H,6H)-ylidene)acetate (433 mg) (white solid). LC-MS retention time 1.398 min (for Z-isomer) and 1.378 min (for E-isomer); m/z 304.08 (for Z-isomer) and 304.16 (for E-isomer) (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) (for Z-isomer) δ ppm 7.30-7.44 (m, 5H), 6.18 (br. s., 1H), 5.10-5.17 (m, 2H), 4.22 (s, 2H), 3.78 (br. s., 3H), 2.93-3.02 (m, 2H), 1.80 (dt, J=11.7, 5.8 Hz, 2H), 1.62 (s, 2H). $^1$H NMR (400 MHz, chloroform-d) (for E-isomer) δ ppm 7.31-7.44 (m, 5H), 6.12 (br. s., 1H), 5.13-5.17 (m, 2H), 4.64 (br. s., 2H), 3.70-3.82 (m, 5H), 2.49 (t, J=6.5 Hz, 2H), 1.80 (br. s., 2H). (Note: the absolute regiochemistry was determined by $^1$H NMR shifts and coupling constants).

Cap-177a and Cap-177b, step b

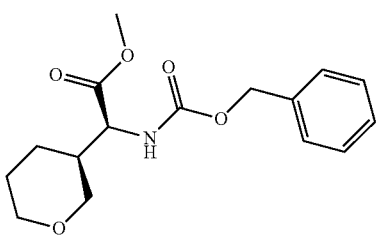

120

-continued

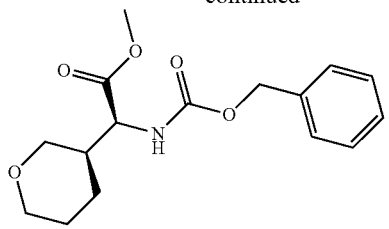

(−)-1,2-Bis((2S,5S)-2,5-dimethylpholano)ethane(cyclooctadiene)-rhodium(I)tetrafluoroborate (28.2 mg, 0.051 mmol) was added to a stirred solution of (Z)-methyl 2-(benzyloxycarbonylamino)-2-(2H-pyran-3(4H,5H,6H)-ylidene)acetate (310 mg, 1.015 mmol) in MeOH (10 mL) and the mixture was vacuum flushed with $N_2$, followed by $H_2$, and then the reaction was stirred under $H_2$ (60 psi) at rt for 2 d. The reaction mixture was concentrated and the residue was purified by flash silica chromatography (loading solvent: DCM, eluted with 20% EtOAc in hexanes) to yield (S)-methyl 2-(benzyloxycarbonylamino)-2-((S)-tetrahydro-2H-pyran-3-yl)acetate (204 mg) as clear colorless oil. LC-MS retention time 1.437 min; m/z 307.89 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) δ ppm 7.30-7.46 (m, 5H), 5.32 (d, J=8.8 Hz, 1H), 5.12 (s, 2H), 4.36 (dd, J=8.9, 5.6 Hz, 1H), 3.84-3.98 (m, 2H), 3.77 (s, 3H), 3.28-3.37 (m, 1H), 3.23 (dd, J=11.3, 10.5 Hz, 1H), 2.04-2.16 (m, 1H), 1.61-1.75 (m, 3H), 1.31-1.43 (m, 1H).

The other stereoisomer ((E)-methyl 2-(benzyloxycarbonylamino)-2-(2H-pyran-3(4H,5H,6H)-ylidene)acetate) (360 mg, 1.18 mmol) was reduced in a similar manner to yield (S)-methyl 2-(benzyloxycarbonylamino)-2-((R)-tetrahydro-2H-pyran-3-yl)acetate (214 mg) as clear colorless oil. LC-MS retention time 1.437 min; m/z 308.03 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) δ ppm 7.30-7.44 (m, 5H), 5.31 (d, J=9.0 Hz, 1H), 5.12 (s, 2H), 4.31 (dd, J=8.7, 6.9 Hz, 1H), 3.80-3.90 (m, 2H), 3.77 (s, 3H), 3.37 (td, J=10.8, 3.5 Hz, 1H), 3.28 (dd, J=11.3, 9.8 Hz, 1H), 1.97-2.10 (m, 1H), 1.81 (d, J=11.5 Hz, 1H), 1.61-1.72 (m, 2H), 1.33-1.46 (m, 1H).

Cap-177a and Cap-177b, step c

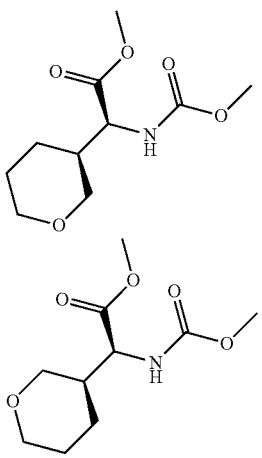

10% Pd/C (69.3 mg, 0.065 mmol) was added to a solution of (S)-methyl 2-(benzyloxycarbonylamino)-2-((S)-tetrahydro-2H-pyran-3-yl)acetate (200 mg, 0.651 mmol) and dimethyl dicarbonate [4525-33-1] (0.104 mL, 0.976 mmol) in MeOH (10 mL). The reaction mixture was vacuum flushed with $N_2$, followed by $H_2$, and then the reaction was stirred under $H_2$ (55 psi) at rt for 5 h. The reaction mixture was filtered through CELITE®/silica pad and the filtrate was concentrated to a colorless oil. The crude oil was purified by flash silica chromatography (loading solvent: DCM, eluted with 30% EtOAc in hexanes) to yield product (S)-methyl 2-(methoxycarbonylamino)-2-((S)-tetrahydro-2H-pyran-3-yl)acetate (132 mg) as colorless oil. LC-MS retention time 0.92 min; m/z 231.97 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) δ ppm 5.24 (d, J=8.5 Hz, 1H), 4.34 (dd, J=8.9, 5.6 Hz, 1H), 3.84-3.97 (m, 2H), 3.77 (s, 3H), 3.70 (s, 3H), 3.29-3.38 (m, 1H), 3.23 (dd, J=11.2, 10.4 Hz, 1H), 2.03-2.14 (m, 1H), 1.56-1.75 (m, 3H), 1.32-1.43 (m, 1H).

Another diastereomer ((S)-methyl 2-(benzyloxycarbonylamino)-2-((R)-tetrahydro-2H-pyran-3-yl)acetate) was transformed in a similar manner to yield (S)-methyl 2-(methoxycarbonylamino)-2-((R)-tetrahydro-2H-pyran-3-yl)acetate as clear colorless oil. LC-MS retention time 0.99 min; m/z 231.90 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) δ ppm 5.25 (d, J=8.0 Hz, 1H), 4.29 (dd, J=8.4, 7.2 Hz, 1H), 3.82-3.90 (m, 2H), 3.77 (s, 3H), 3.70 (s, 3H), 3.37 (td, J=10.8, 3.3 Hz, 1H), 3.28 (t, J=10.5 Hz, 1H), 1.96-2.08 (m, 1H), 1.81 (dd, J=12.9, 1.6 Hz, 1H), 1.56-1.72 (m, 2H), 1.33-1.46 (m, 1H).

Cap-177a and Cap-177b, step d

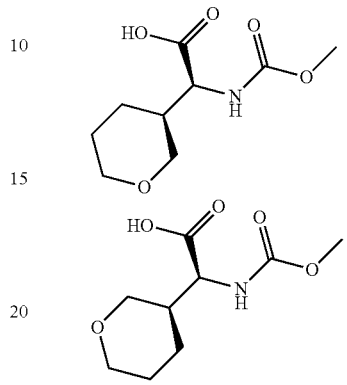

To a solution of (S)-methyl 2-(methoxycarbonylamino)-2-((S)-tetrahydro-2H-pyran-3-yl)acetate (126 mg, 0.545 mmol) in THF (4 mL) stirring at rt was added a solution of 1M LiOH (1.090 mL, 1.090 mmol) in water. The reaction was stirred at rt for 3 h, neutralized with 1M HCl (1.1 mL) and extracted with EtOAc (3×10 mL). The organics were dried, filtered and concentrated to yield (S)-2-(methoxycarbonylamino)-2-((S)-tetrahydro-2H-pyran-3-yl)acetic acid (Cap-177a) (125 mg) as a clear colorless oil. LC-MS retention time 0.44 min; m/z 218.00 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) δ ppm 5.28 (d, J=8.8 Hz, 1H), 4.38 (dd, J=8.7, 5.6 Hz, 1H), 3.96-4.04 (m, 1H), 3.91 (d, J=11.0 Hz, 1H), 3.71 (s, 3H), 3.33-3.41 (m, 1H), 3.24-3.32 (m, 1H), 2.10-2.24 (m, 1H), 1.74-1.83 (m, 1H), 1.63-1.71 (m, 2H), 1.35-1.49 (m, 1H).

Another diastereomer ((S)-methyl 2-(methoxycarbonylamino)-2-((R)-tetrahydro-2H-pyran-3-yl)acetate) was transformed in a similar manner to yield (S)-2-(methoxycarbonylamino)-2-((R)-tetrahydro-2H-pyran-3-yl)acetic acid (Cap-177b) as clear colorless oil. LC-MS retention time 0.41 min; m/z 217.93 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) δ ppm 6.18 (br. s., 1H), 5.39 (d, J=8.5 Hz, 1H), 4.27-4.37 (m, 1H), 3.82-3.96 (m, 2H), 3.72 (s, 3H), 3.42 (td, J=10.8, 3.3 Hz, 1H), 3.35 (t, J=10.4 Hz, 1H), 2.01-2.18 (m, 1H), 1.90 (d, J=11.8 Hz, 1H), 1.59-1.76 (m, 2H), 1.40-1.54 (m, 1H).

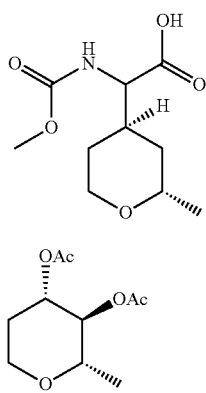

Cap-178

Cap-178, step a

To a solution of (2S,3S,4S)-2-methyl-3,4-dihydro-2H-pyran-3,4-diyl diacetate (5 g, 23.34 mmol) in 20 mL of MeOH in a hydrogenation tank was added Pd/C (150 mg, 0.141 mmol). The resulting mixture was hydrogenated at 40 psi on Parr Shaker for 1 hour. The mixture was then filtered and the filtrate was concentrated to afford Cap-178, step a (5.0 g) as a clear oil, which solidified while standing. ¹H NMR (500 MHz, CDCl₃) δ ppm 4.85-4.94 (1H, m), 4.69 (1H, t, J=9.46 Hz), 3.88-3.94 (1H, m), 3.44 (1H, td, J=12.21, 1.83 Hz), 3.36 (1H, dq, J=9.42, 6.12 Hz), 2.03-2.08 (1H, m), 2.02 (3H, s), 2.00 (3H, s), 1.70-1.80 (1H, m), 1.16 (3H, d, J=6.10 Hz).

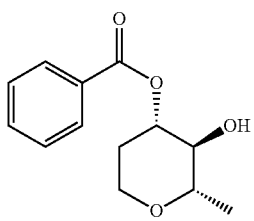

Cap-178, step b

To a solution of Cap-178, step a (5.0 g, 23 mmol) in 50 mL of MeOH was added several drops of sodium methoxide. After stirring at room temperature for 30 min, sodium methoxide (0.1 mL, 23.12 mmol) was added and the solution was stirred at room temperature overnight. The solvent was then removed under vacuum. The residue was diluted with benzene and concentrated to afford the corresponding diol as a yellow solid. The solid was dissolved in 50 mL of pyridine and to this solution at −35° C. was added benzoyl chloride (2.95 mL, 25.4 mmol) dropwise. The resulting mixture was stirred at −35° C. for 1 hour then at room temperature overnight. The mixture was diluted with Et₂O and washed with water. The aqueous layer was extracted with EtOAc (2×). The combined organic layers were dried with MgSO₄ and concentrated. The crude product was purified by flash chromatography (silica gel, 5%-15% EtOAc/Hex) to afford Cap-178, step b (4.5 g) as clear oil which slowly crystallized upon prolonged standing. LC-MS: Anal. Calcd. for [M+Na]⁺ C₁₃H₁₆NaO₄ 259.09. found 259.0; ¹H NMR (500 MHz, CDCl₃) δ ppm 8.02-8.07 (2H, m), 7.55-7.61 (1H, m), 7.45 (2H, t, J=7.78 Hz), 5.01 (1H, ddd, J=11.44, 8.70, 5.49 Hz), 3.98 (1H, ddd, J=11.90, 4.88, 1.53 Hz), 3.54 (1H, td, J=12.36, 2.14 Hz), 3.41 (1H, t, J=9.00 Hz), 3.31-3.38 (1H, m), 2.13-2.19 (1H, m), 1.83-1.94 (1H, m), 1.36 (3H, d, J=5.80 Hz).

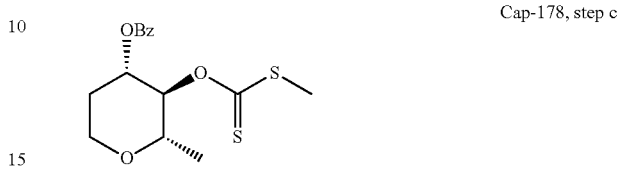

Cap-178, step c

To a mixture of NaH (1.143 g, 28.6 mmol) (60% in mineral oil) in 6 mL of CS₂ was added Cap-178, step b (4.5 g, 19 mmol) in 40 mL of CS₂ dropwise over 15 min. The resulting mixture was stirred at room temperature for 30 min. The mixture turned light orange with some solid. MeI (14.29 mL, 229 mmol) was then added dropwise over 20 min. The mixture was then stirred at room temperature overnight. The reaction was carefully quenched with saturated NH₄Cl solution. The mixture was extracted with EtOAc (3×). The combined organic layers were dried with MgSO₄ and concentrated. The crude product was purified by flash chromatography (silica gel, 6% EtOAc/Hex) to afford Cap-178, step c (3.13 g) as clear oil. LC-MS: Anal. Calcd. for [M+Na]⁺ C₁₅H₁₈NaO₄S₂ 349.05. found 349.11; ¹H NMR (500 MHz, CDCl₃) δ ppm 7.94-8.00 (2H, m), 7.50-7.58 (1H, m), 7.41 (2H, t, J=7.78 Hz), 5.96 (1H, t, J=9.46 Hz), 5.28 (1H, ddd, J=11.37, 9.38, 5.49 Hz), 4.02 (1H, ddd, J=11.98, 4.96, 1.68 Hz), 3.54-3.68 (2H, m), 2.48 (3H, s), 2.31 (1H, dd), 1.88-1.99 (1H, m), 1.28 (3H, d).

Cap-178, step d

To a mixture of Cap-178, step c (3.13 g, 9.59 mmol) and AIBN (120 mg, 0.731 mmol) in 40 mL of benzene at 80° C. was added tri-n-butyltin hydride (10.24 mL, 38.4 mmol). The resulting mixture was stirred at reflux temperature for 20 min then cooled to room temperature. The mixture was diluted with diethyl ether and 100 mL of KF (10 g) aqueous solution was added and the mixture was stirred vigorously for 30 min. The two layers were then separated and the aqueous phase was extracted with EtOAc (2×). The organic layer was dried with MgSO₄ and concentrated. The crude product was purified by flash chromatography (silica gel, deactivated with 3% Et₃N in Hexanes and flushed with 3% Et₃N in Hexanes to remove tributyltin derivative and then eluted with 15% EtOAc/Hex) to afford Cap-178, step d (1.9 g) as clear oil. ¹H NMR (500 MHz, CDCl₃) δ ppm 7.98-8.07 (2H, m), 7.52-7.58 (1H, m), 7.43 (2H, t, J=7.63 Hz), 5.08-5.17 (1H, m), 4.06 (1H, ddd, J=11.90, 4.88, 1.53 Hz), 3.50-3.59 (2H, m), 2.08-2.14 (1H, m), 1.99-2.06 (1H, m), 1.69-1.80 (1H, m), 1.41-1.49 (1H, m), 1.24 (3H, d, J=6.10 Hz).

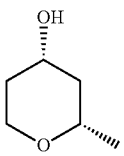

Cap-178, step e

To a mixture of Cap-178, step d (1.9 g, 8.63 mmol) in 10 mL of MeOH was added sodium methoxide (2 mL, 4.00 mmol) (2 M in methanol). The resulting mixture was stirred at room temperature for 5 hours. The solvent was removed under vacuum. The mixture was neutralized with saturated NH₄Cl solution and extracted with EtOAc (3×). The organic layers were dried with MgSO₄ and concentrated to afford Cap-178, step e (0.8 g) as clear oil. The product was used in the next step without further purification. $^1$H NMR (400 MHz, CDCl₃) δ ppm 4.01 (1H, ddd, J=11.80, 5.02, 1.76 Hz), 3.73-3.83 (1H, m), 3.36-3.46 (2H, m), 1.92-2.00 (1H, m), 1.88 (1H, m), 1.43-1.56 (1H, m), 1.23 (3H, d), 1.15-1.29 (1H, m).

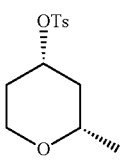

Cap-178, step f

Tosyl-Cl (2.63 g, 13.77 mmol) was added to a solution of Cap-178, step e (0.8 g, 6.89 mmol) and pyridine (2.23 mL, 27.5 mmol) in 100 mL of CH₂Cl₂. The resulting mixture was stirred at room temperature for 3 days. 10 mL of water was then added into the reaction mixture and the mixture was stirred at room temperature for an hour. The two layers were separated and the organic phase was washed with water and 1 N HCl aq. solution. The organic phase was dried with MgSO₄ and concentrated to afford Cap-178, step f (1.75 g) as a light yellow solid. The product was used in the next step without further purification. Anal. Calcd. for [M+H]⁺ C₁₃H₁₉O₄S 271.10. found 270.90; $^1$H NMR (500 MHz, CDCl₃) δ ppm 7.79 (2H, d, J=8.24 Hz), 7.34 (2H, d, J=7.93 Hz), 4.53-4.62 (1H, m), 3.94 (1H, ddd, J=12.13, 4.96, 1.83 Hz), 3.29-3.41 (2H, m), 2.45 (3H, s), 1.90-1.97 (1H, m), 1.79-1.85 (1H, m), 1.64-1.75 (1H, m), 1.38-1.48 (1H, m), 1.17 (3H, d, J=6.10 Hz).

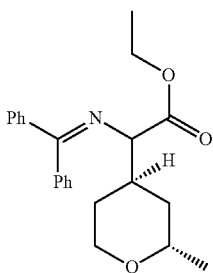

Cap-178, step g

To a microwave tube was placed ethyl 2-(diphenylmethyleneamino)acetate (1.6 g, 5.92 mmol) and Cap-178, step f (1.6 g, 5.92 mmol). 10 mL of toluene was added. The tube was sealed and LiHMDS (7.1 mL, 7.10 mmol) (1 N in toluene) was added dropwise under N₂. The resulting dark brown solution was heated at 100° C. under microwave radiation for 6 hours. To the mixture was then added water and the mixture was extracted with EtOAc (3×). The combined organic layers were washed with brine, dried with MgSO₄ and concentrated to afford a diastereomeric mixture of Cap-3, step g (3.1 g) as an orange oil. The crude mixture was submitted to the next step without separation. LC-MS: Anal. Calcd. for [M+H]⁺ C₂₃H₂₈NO₃ 366.21. found 366.3.

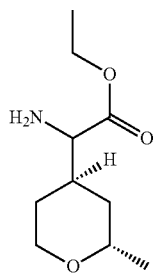

Cap-178, step h

To a solution of the diastereomeric mixture of ethyl Cap-178, step g in 20 mL of THF was added HCl (30 ml, 60.0 mmol) (2 N aqueous). The resulting mixture was stirred at room temperature for 1 hour. The mixture was extracted with EtOAc and the aqueous layer was concentrated to afford an HCl salt of Cap-178, step h (1.9 g) as an orange oil. The salt was used in the next step without further purification. LC-MS: Anal. Calcd. for [M+H]⁺ C₁₀H₂₀NO₃ 202.14. found 202.1.

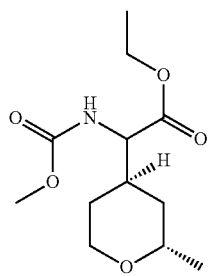

Cap-178, step i

A solution of 1.9 g Cap-178, step h (HCl salt), DiPEA (4.19 mL, 24.0 mmol) and methyl chloroformate (1.24 mL, 16.0 mmol) in 20 mL of CH₂Cl₂ was stirred at room temperature for 1 hour. The mixture was diluted with CH₂Cl₂ and washed with water. The organic layer was dried with Na₂SO₄ and concentrated. The crude product was purified by flash chromatography (silica gel, 0-20% EtOAc/Hex) to afford Cap-178, step i (1.1 g) as a yellow oil. Anal. Calcd. for [M+Na]⁺ C₁₂H₂₁NNaO₅ 282.13. found 282.14; $^1$H NMR (400 MHz, CDCl₃) δ ppm 5.16 (1H, br. s.), 4.43-4.58 (1H, m), 4.17-4.28 (2H, m), 3.89-4.03 (1H, m), 3.72-3.78 (2H, m), 3.67-3.72 (3H, m), 2.07-2.19 (1H, m), 1.35-1.77 (4H, m), 1.30 (3H, td, J=7.09, 2.89 Hz), 1.19 (3H, d, J=6.53 Hz).

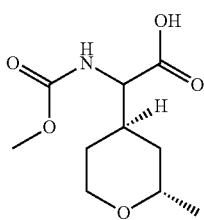

Cap-178, step j

To a mixture of Cap-178, step i (1.1 g, 4.2 mmol) in 5 mL of THF and 2 mL of water was added LiOH (6.36 mL, 12.7 mmol) (2 N aq.). The resulting mixture was stirred at room temperature overnight. The mixture was then neutralized with 1 N HCl aq. and extracted with EtOAc (3×). The combined organic layers were dried with $MgSO_4$ and concentrated to afford Cap-178, step j (0.8 g) as a clear oil. LC-MS: Anal. Calcd. for $[M+H]^+$ $C_{10}H_{18}NO_5$ 232.12. found 232.1; $^1H$ NMR (400 MHz, $CDCl_3$)$_6$ ppm 5.20 (1H, d, J=8.28 Hz), 4.54 (1H, t, J=8.16 Hz), 3.95-4.10 (1H, m), 3.66-3.85 (5H, m), 2.15-2.29 (1H, m), 1.41-1.85 (4H, m), 1.23 (3H, dd, J=6.53, 1.76 Hz).

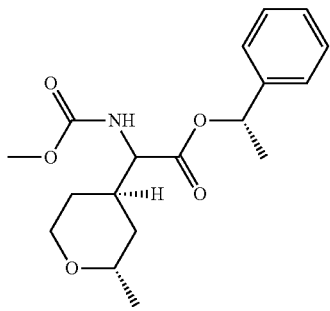

Cap-178, step k

To a solution of Cap-178, step j (240 mg, 1.04 mmol), (S)-1-phenylethanol (0.141 mL, 1.142 mmol) and EDC (219 mg, 1.14 mmol) in 10 mL of $CH_2Cl_2$ was added DMAP (13.95 mg, 0.114 mmol). The resulting solution was stirred at room temperature overnight and the solvent was removed under vacuum. The residue was taken up into EtOAc, washed with water, dried with $MgSO_4$ and concentrated. The crude product was purified by chromatography (silica gel, 0-15% EtOAc/Hexanes) to afford Cap-178, step k as a mixture of two diastereomers. The mixture was separated by chiral HPLC (CHIRALPAK® AS column, 21×250 mm, 10 um) eluting with 90% 0.1% diethylamine/Heptane-10% EtOH at 15 mL/min to afford Cap-178, step k stereoisomer 1 (eluted first) and Cap-178, step k stereoisomer 2 (eluted second) as white solids. The stereochemistry of the isomers was not assigned.

Cap-178, step k stereoisomer 1 (130 mg): LC-MS: Anal. Calcd. for $[M+Na]^+$ $C_{18}H_{25}NNaO_5$ 358.16. found 358.16; $^1H$ NMR (500 MHz, $CDCl_3$) δ ppm 7.28-7.38 (5H, m), 5.94 (1H, q, J=6.71 Hz), 5.12 (1H, d, J=9.16 Hz), 4.55 (1H, t, J=9.00 Hz), 3.72-3.81 (1H, m), 3.67 (3H, s), 3.60-3.70 (2H, m), 1.98-2.08 (1H, m), 1.59 (3H, d, J=6.71 Hz), 1.38-1.47 (2H, m), 1.30 (2H, t, J=5.34 Hz), 0.93 (3H, d, J=6.41 Hz).

Cap-178, Stereoisomer 1

To a solution of Cap-178, step k stereoisomer 1 ((S)-2-(methoxycarbonylamino)-2-((2S,4R)-2-methyltetrahydro-2H-pyran-4-yl)acetic acid) (150 mg, 0.447 mmol) in 10 mL of EtOH was added Pd/C (20 mg, 0.188 mmol) and the mixture was hydrogenated on Parr shaker at 40 psi overnight. The mixture was then filtered and the filtrate was concentrated to afford Cap-178, stereoisomer 1 (100 mg) as a sticky white solid. LC-MS: Anal. Calcd. for $[M+H]^+$ $C_{10}H_{18}NO_5$ 232.12. found 232.1; $^1H$ NMR (500 MHz, $CDCl_3$) δ ppm 5.14-5.27 (1H, m), 4.51 (1H, t, J=8.39 Hz), 3.90-4.07 (1H, m), 3.60-3.83 (5H, m), 2.06-2.27 (1H, m), 1.45-1.77 (4H, m), 1.21 (3H, d, J=6.41 Hz).

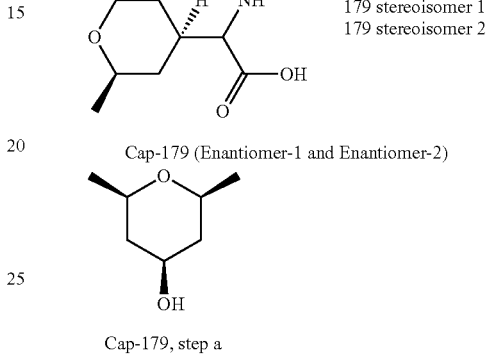

179 stereoisomer 1
179 stereoisomer 2

Cap-179 (Enantiomer-1 and Enantiomer-2)

Cap-179, step a 2,6-Dimethyl-4H-pyran-4-one (10 g, 81 mmol) was dissolved in ethanol (125 mL) and Pd/C (1 g, 0.94 mmol) was added. The mixture was hydrogenated in a Parr shaker under $H_2$ (0.325 g, 161 mmol) (70 psi) at room temperature for 12 hrs. The catalyst was filtered through a pad of CELITE® and washed with ethanol. The filtrate was concentrated in vacuum and he residue was purified via BIOTAGE® (2% to 25% EtOAc/Hex; 160 g column). Two fractions of clear oils were isolated. The first eluting one corresponded to (2R,6S)-2,6-dimethyldihydro-2H-pyran-4(3H)-one (1.8 g) while the second one corresponded to Cap-179, step a (1.8 g).

(2R,6S)-2,6-Dimethyldihydro-2H-pyran-4(3H)-one data: $^1H$ NMR (500 MHz, $CDCl_3$) δ ppm 3.69 (2H, ddd, J=11.29, 5.95, 2.29 Hz), 2.24-2.36 (2H, m), 2.08-2.23 (2H, m), 1.18-1.34 (6H, m); $^{13}C$ NMR (126 MHz, $CDCl_3$) δ ppm 206.96 (1C, br. s.), 72.69 (2C, s), 48.70 (2C, s), 21.72 (2C, s).

Cap-179, step a data: $^1H$ NMR (500 MHz, $CDCl_3$) δ ppm 3.69-3.78 (1H, m), 3.36-3.47 (2H, m), 2.10 (1H, br. s.), 1.88 (2H, dd, J=12.05, 4.73 Hz), 1.19 (6H, d, J=6.10 Hz), 1.10 (2H, q, J=10.70 Hz); $^{13}C$ NMR (126 MHz, $CDCl_3$) δ ppm 71.44 (2C, s), 67.92 (1C, s), 42.59 (2C, s), 21.71 (2C, s).

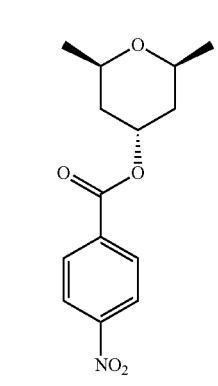

Cap-179, step b

DEAD (2.311 mL, 14.59 mmol) was added drop wise to a solution of Cap-179, step a (0.38 g, 2.92 mmol), 4-nitrobenzoic acid (2.195 g, 13.14 mmol) and Ph$_3$P (3.83 g, 14.59 mmol) in benzene (25 mL). Heat evolution was detected and the resulting amber solution was stirred at ambient temperature for 6 h. Solvent was removed under reduced pressure and the residue was purified via BIOTAGE® (0 to 15% EtOAc/Hex; 80 g column). A white solid corresponding to Cap-179, step b (0.77 g) was isolated. LC-MS: Anal. Calcd. for [M]$^+$ C$_{14}$H$_{17}$NO$_5$: 279.11. found 279.12. $^1$H NMR (500 MHz, CDCl$_3$) δ ppm 8.27-8.32 (2H, m), 8.20-8.24 (2H, m), 5.45 (1H, quin, J=2.82 Hz), 3.92 (2H, dqd, J=11.90, 6.10, 6.10, 6.10, 1.53 Hz), 1.91 (2H, dd, J=14.80, 2.29 Hz), 1.57 (3H, dt, J=14.65, 3.05 Hz), 1.22 (6H, d, J=6.10 Hz).

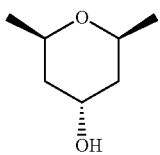

Cap-179, step c

A solution LiOH (0.330 g, 13.8 mmol) in water (8 mL) was added to a solution of Cap-179, step b (0.77 g, 2.76 mmol) in THF (30 mL) and the resulting mixture was stirred at ambient temperature for 16 h. THF was removed under reduced pressure and the aqueous layer was diluted with more water (20 mL) and extracted with EtOAc (3×15 mL). The combined organic layers were dried (MgSO$_4$), filtered and concentrated under vacuum. An oily residue with a white solid was recovered. The mixture was triturated with hexanes and the solid was filtered off to yield a clear oil corresponding to Cap-179, step c (0.34 g). $^1$H NMR (500 MHz, CDCl$_3$) δ ppm 4.21 (1H, quin, J=2.82 Hz), 3.87-3.95 (2H, m), 1.72 (1H, br. s.), 1.63 (2H, dd, J=14.34, 2.14 Hz), 1.39-1.47 (2H, m), 1.17 (6H, d, J=6.41 Hz).

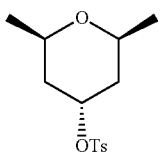

Cap-179, step d p-Tosyl chloride (3.98 g, 20.89 mmol) was added to a solution of Cap-179, step c (1.36 g, 10.5 mmol) and Pyridine (3.38 mL, 41.8 mmol) in CH$_2$Cl$_2$ (150 mL) at room temperature and stirred for 24 h and then concentrated to a yellow oil. The remaining residue was added to pyridine (20 mL) and water (30 mL) and the resulting mixture was stirred at ambient temperature for 1½ h. The mixture was extracted with Et$_2$O (75 mL) and the separated organic layer was the washed thoroughly with 1 N aq. HCl (4×50 mL). The organic layer was then dried (MgSO$_4$), filtered and concentrated. A white solid corresponding to Cap-179, step d (2.2 g) was isolated. LC-MS: Anal. Calcd. for [2M+H]$^+$ C$_{28}$H$_{41}$O$_8$S$_2$: 569.22. found 569.3. $^1$H NMR (400 MHz, CDCl$_3$) δ ppm 7.80 (2H, d, J=8.28 Hz), 7.35 (2H, d, J=8.03 Hz), 4.89 (1H, quin, J=2.82 Hz), 3.77-3.88 (2H, m), 2.46 (3H, s), 1.77 (2H, dd, J=14.93, 2.89 Hz), 1.36 (2H, ddd, J=14.31, 11.54, 2.76 Hz), 1.13 (6H, d, J=6.27 Hz).

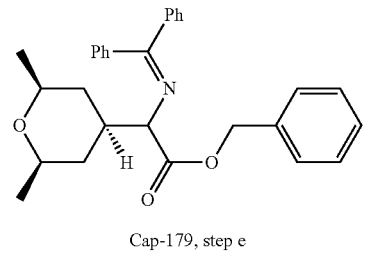 [SMILES: C[C@@H]1C[C@H](C(N=C(c2ccccc2)c2ccccc2)C(=O)OCc2ccccc2)C[C@H](C)O1]

Cap-179, step e

LiHMDS (4.30 mL, 4.30 mmol) was added to a solution of Cap-179, step d (1.02 g, 3.59 mmol) and benzyl 2-(diphenylmethyleneamino)acetate (1.181 g, 3.59 mmol) in toluene (25 mL) at room temperature in a sealed microwave vial and the resulting mixture was then stirred for 5 h at 100° C. under microwave radiation. The reaction was quenched with water (10 mL), extracted with EtOAc, washed with water, dried over MgSO$_4$, filtrated, and concentrated in vacuum. The residue was purified via BIOTAGE® (0% to 6% EtOAc/Hex; 80 g column) and a yellow oil corresponding to Cap-179, step e (1.2 g) was isolated. Anal. Calcd. for [2M+Na]$^+$ C$_{58}$H$_{62}$N$_2$NaO$_6$: 905.45. found 905.42. $^1$H NMR (400 MHz, CDCl$_3$) δ ppm 7.64-7.70 (4H, m), 7.29-7.44 (29H, m), 7.06 (4H, dd, J=7.65, 1.63 Hz), 5.18 (2H, d, J=2.01 Hz), 3.89 (2H, d, J=6.53 Hz), 3.79-3.87 (1H, m), 3.46 (5H, dquind, J=11.26, 5.87, 5.87, 5.87, 5.87, 1.88 Hz), 2.47 (2H, s), 2.35-2.46 (2H, m), 1.78 (1H, dd, J=14.81, 3.01 Hz), 1.62-1.65 (1H, m), 1.61 (2H, s), 1.36-1.43 (3H, m), 1.19 (7H, d, J=6.27 Hz), 1.14 (11H, dd, J=6.15, 2.89 Hz), 0.86-0.96 (3H, m).

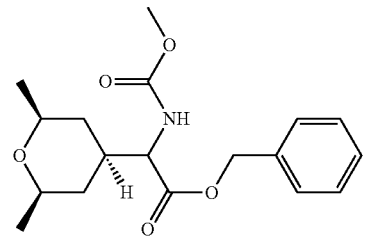

Cap-179, step f
(Enantiomer-1 and Enantiomer-2)

Cap-179, step e (2.08 g, 4.71 mmol) was dissolved in THF (100 mL) and treated with 2 N HCl (9.42 mL, 18.84 mmol). The resulting clear solution was stirred at ambient temperature for 4 h and then THF was removed under reduced pressure. The remaining aqueous layer was extracted with hexanes (3×20 ml) and after diluting with H$_2$O (20 mL), the aqueous phase was basified with 1 N NaOH to pH=10 and extracted with EtOAc (3×10 mL). The combined organic layers were dried (MgSO$_4$), filtered and concentrated under vacuum. The resulting residue was taken up in CH$_2$Cl$_2$ (100 mL) and charged with DIEA (2.468 mL, 14.13 mmol) and methyl chloroformate (0.401 mL, 5.18 mmol). The resulting solution was stirred at ambient temperature for 2 h. The reaction mixture was quenched with water (10 mL) and the organic layer was removed under reduced pressure. The aqueous layer was then extracted with EtOAc (3×10 mL) and the combined organic layers were dried (MgSO$_4$), filtered and concentrated. The residue was purified via BIOTAGE® (10% EtOAc/Hex; 25 g column). A clear colorless oil corresponding to Cap-179, step f (1.05 g) was recovered. LC-MS: Anal. Calcd. for [M+H]$^+$ C$_{15}$H$_{26}$NO$_5$: 336.18. found 336.3. $^1$H NMR (500 MHz, CDCl$_3$) δ ppm 7.32-7.40 (5H, m), 5.26 (1H, d, J=8.24 Hz), 5.13-5.24 (2H, m), 4.36 (1H, dd, J=8.85, 4.88 Hz), 3.68 (3H, s), 3.32-3.46 (2H, m), 2.02-2.14 (1H, m), 1.52 (1H, d, J=12.82 Hz), 1.32 (1H, d, J=12.51 Hz), 1.11-1.18 (6H, m), 0.89-1.07 (2H, m).

A chiral SFC method was developed to separate the racemic mixture by using 12% methanol as the modifier on a CHIRALPAK® AD-H column (30×250 mm, 5 µm) (Temp=35° C., Pressure=150 bar, Wavelength=210 nm, Flow rate=70 mL/min for 8 min, Solvent A=CO$_2$, Solvent B=MeOH). The two separated isomers, Cap-179 step f (Enantiomer-1) (first eluting) and Cap-179 step f (Enantiomer-2) (second eluting) exhibited the same analytical data as the corresponding mixture (see above).

Cap-179 (Enantiomer-1 and Enantiomer-2)

Cap-179 step f (Enantiomer-1) (0.35 g, 1.044 mmol) was dissolved in MeOH (50 mL) in a Parr bottle and charged with Pd/C (0.111 g, 1.044 mmol). The suspension was then placed in a Parr shaker and the mixture was flushed with N$_2$ (3×), placed under 40 psi of H$_2$ (2.104 mg, 1.044 mmol) and shaken at room temperature for 2 h. The catalyst was filtered off through a pad of CELITE® and the solvent was removed under reduced pressure, to yield an amber solid corresponding to Cap-179 Enantiomer-1 (0.25 g). $^1$H NMR (500 MHz, DMSO-d$_6$) δ ppm 12.74 (4H, br. s.), 7.35 (4H, d, J=6.10 Hz), 3.85 (4H, br. s.), 3.53 (3H, s), 3.35 (2H, ddd, J=15.95, 9.99, 6.10 Hz), 1.97 (1H, br. s.), 1.48 (2H, t, J=13.28 Hz), 1.06 (6H, d, J=6.10 Hz), 0.82-1.00 (2H, m).

Cap-179 Enantiomer-2 was prepared similarly: $^1$H NMR (500 MHz, DMSO-d$_6$) δ ppm 12.50 (1H, br. s.), 7.31 (1H, br. s.), 3.84 (1H, t, J=7.32 Hz), 3.53 (3H, s), 3.29-3.41 (2H, m), 1.99 (1H, s), 1.48 (2H, t, J=14.34 Hz), 1.06 (6H, d, J=6.10 Hz), 0.95 (1H, q, J=12.21 Hz), 0.87 (1H, q, J=11.80 Hz). [Note: the minor variation in the $^1$H NMR profile of the enantiomers is likely a result of a difference in sample concentration.]

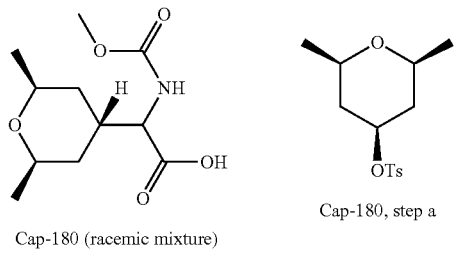

Cap-180 (racemic mixture)

Cap-180, step a p-Tosyl-Cl (4.39 g, 23.0 mmol) was added to a solution of Cap-179, step a (1.50 g, 11.5 mmol) and pyridine (3.73 mL, 46.1 mmol) in CH$_2$Cl$_2$ (50 mL) at room temperature and stirred for 2 days. The reaction was diluted with CH$_2$Cl$_2$, washed with water, then 1 N HCl. The organic layer was dried (MgSO$_4$) and concentrated to a yellow oil which was purified via BIOTAGE® (5% to 20% EtOAc/Hex; 40 g column). A clear oil that solidified under vacuum and corresponding to Cap-180, step a (2.89 g) was isolated. LC-MS: Anal. Calcd. for [2M+Na]$^+$ C$_{28}$H$_{40}$NaO$_8$S$_2$: 591.21. found 591.3. $^1$H NMR (500 MHz, CDCl$_3$) δ ppm 7.80 (2H, d, J=8.24 Hz), 7.35 (2H, d, J=7.93 Hz), 4.59 (1H, tt, J=11.37, 4.96 Hz), 3.36-3.46 (2H, m), 2.46 (3H, s), 1.91 (2H, dd, J=12.05, 5.04 Hz), 1.37 (2H, dt, J=12.67, 11.52 Hz), 1.19 (6H, d, J=6.10 Hz).

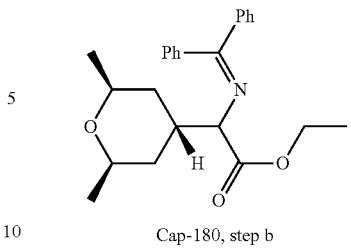

Cap-180, step b

LiHMDS 1 N (7.09 mL, 7.09 mmol) was added to a solution of Cap-180, step a (1.68 g, 5.91 mmol) and ethyl 2-(diphenylmethyleneamino)acetate (1.579 g, 5.91 mmol) in toluene (30 mL) at room temperature and the resulting mixture was then stirred for 16 h at 85° C. The reaction was quenched with water (50 mL), extracted with EtOAc, washed with water, dried over MgSO$_4$, filtrated, and concentrated in vacuo. The residue was purified via BIOTAGE® (0% to 15% EtOAc/Hex; 40 g column). A clear yellowish oil corresponding to Cap-180, step b (racemic mixture; 0.64 g) was isolated. LC-MS: Anal. Calcd. for [M+H]$^+$ C$_{24}$H$_{30}$NO$_3$: 380.22. found 380.03. $^1$H NMR (400 MHz, CDCl$_3$) δ ppm 7.64-7.70 (2H, m), 7.45-7.51 (3H, m), 7.38-7.44 (1H, m), 7.31-7.37 (2H, m), 7.13-7.19 (2H, m), 4.39 (1H, d, J=10.54 Hz), 4.16-4.26 (2H, m), 3.29-3.39 (1H, m), 2.93-3.03 (1H, m), 2.70 (1H, m, J=9.41, 4.14 Hz), 1.42-1.49 (2H, m), 1.31-1.37 (1H, m), 1.29 (4H, t, J=7.15 Hz), 1.04 (6H, dd, J=7.78, 6.27 Hz).

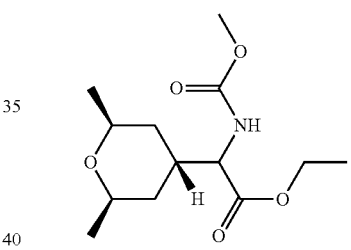

Cap-180, step c

Cap-180, step b (0.36 g, 0.949 mmol) was dissolved in THF (10 mL) and treated with 2 N HCl (1.897 mL, 3.79 mmol). The resulting clear solution was stirred at ambient temperature for 20 h and THF was removed under reduced pressure. The remaining aqueous layer was extracted with hexanes (3×20 mL) and after diluting with H$_2$O (20 mL), the aqueous phase was basified with 1 N NaOH to pH=10 and extracted with EtOAc (3×10 mL). The combined organic layers were dried (MgSO$_4$), filtered and concentrated under vacuum. The resulting residue was taken up in CH$_2$Cl$_2$ (10.00 mL) and charged with DIEA (0.497 mL, 2.85 mmol) and methyl chloroformate (0.081 mL, 1.044 mmol). The resulting solution was stirred at ambient temperature for 2 h and the reaction mixture was quenched with water (10 mL) and the organic layer was removed under reduced pressure. Aqueous layer was extracted with EtOAc (3×10 mL) and the combined organic layers were dried (MgSO$_4$), filtered and concentrated. An amber oil corresponding to Cap-180, step c (0.21 g) was recovered and it was used without further purification. LC-MS: Anal. Calcd. for [M+H]$^+$ C$_{13}$H$_{24}$NO$_5$: 273.17. found 274.06. $^1$H NMR (400 MHz, CDCl$_3$) δ ppm 5.20 (1H, d, J=8.03 Hz), 4.59 (1H, t, J=10.16 Hz), 4.11-4.27 (3H, m), 3.69-3.82 (2H, m), 3.64 (3H, s), 1.95-2.07 (1H, m), 1.63 (1H, d, J=13.80 Hz), 1.41 (2H, dd, J=8.03, 4.02 Hz), 1.31-1.37

(1H, m), 1.26 (3H, t, J=7.15 Hz), 1.16 (1H, d, J=6.27 Hz), 1.12 (6H, dd, J=6.15, 3.89 Hz).

Cap-180 (Racemic Mixture)

Cap-180, step c (0.32 g, 1.2 mmol) was dissolved in THF (10 mL) and charged with LiOH (0.056 g, 2.342 mmol) in water (3.33 mL) at 0° C. The resulting solution was stirred at rt for 2 h. THF was removed under reduced pressure and the remaining residue was diluted with water (15 mL) and washed with Et$_2$O (2×10 mL). The aqueous layer was then acidified with 1N HCl to pH~2 and extracted with EtOAc (3×15 mL). The combined organic layers were dried (MgSO$_4$), filtered and concentrated under vacuum to yield Cap-180 (racemic mixture) (0.2 g) as a white foam. LC-MS: Anal. Calcd. for [M+H]$^+$ C$_{11}$H$_{20}$NO$_5$: 246.13. found 246.00. $^1$H NMR (400 MHz, CDCl$_3$) δ ppm 5.14 (1H, d, J=9.03 Hz), 4.65 (1H, t, J=9.91 Hz), 3.63-3.89 (5H, m), 1.99-2.13 (1H, m), 1.56-1.73 (2H, m), 1.48-1.55 (1H, m), 1.35-1.48 (1H, m), 1.27 (1H, br. s.), 1.17 (6H, d, J=6.02 Hz).

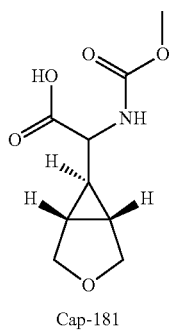

Cap-181

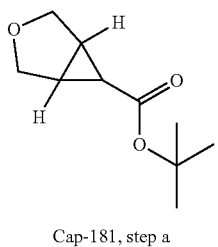

Cap-181, step a

A solution of tert-butyl diazoacetate (1.832 mL, 13.22 mmol) in 50 mL of CH$_2$Cl$_2$ was added into a mixture of 2,5-dihydrofuran (9.76 mL, 132 mmol), Rhodium(II) acetate dimer (0.058 g, 0.132 mmol) in 40 mL of CH$_2$Cl$_2$ dropwise by a syringe pump over 5 hours. The resulting mixture was then stirred at room temperature overnight. The solvent was removed under vacuum. The residue was purified by chromatography (silica gel, 0%-15% EtOAc/Hex) to afford Cap-181 step a (trans-isomer) (720 mg) and Cap-181, step a (cis-isomer) (360 mg) as clear oil. Cap-181 step a (trans-isomer): $^1$H NMR (500 MHz, CDCl$_3$) δ ppm 3.88 (2H, d, J=8.55 Hz), 3.70 (2H, d, J=8.55 Hz), 2.03-2.07 (2H, m), 1.47 (1H, t, J=3.20 Hz), 1.41 (9H, s); Cap-1, step a (cis-isomer): $^1$H NMR (400 MHz, CDCl$_3$) δ ppm 4.06 (2H, d, J=8.53 Hz), 3.73 (2H, d, J=8.03 Hz), 1.81-1.86 (2H, m), 1.65-1.71 (1H, m), 1.43-1.47 (9H, m).

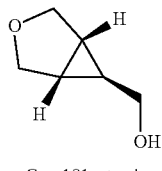

Cap-181, step b

To a solution of (Cap-181, step a (trans-isomer)) (700 mg, 3.80 mmol) in 15 mL of diethyl ether at −10° C. was added LiAlH4 (7.60 mL, 7.60 mmol) (1 M in THF) dropwise over 1 hour. The resulting mixture was stirred at −10° C. for 1 hour then at room temperature for 1 hour. The mixture was then cooled to −5° C. 10 mL of Rochelle's salt (potassium sodium tartrate) aqueous solution was added dropwise to quench the reaction. The mixture was stirred at room temperature for 30 min and then extracted with EtOAc (3×). The combined organic layers were dried with MgSO$_4$ and concentrated to afford Cap-181, step b (380 mg) as light yellow oil. The product was used in the next step without purification. $^1$H NMR (400 MHz, CDCl$_3$) δ ppm 3.85 (2H, d, J=8.28 Hz), 3.68 (2H, d, J=8.53 Hz), 3.45-3.55 (2H, m), 1.50-1.56 (2H, m), 1.02-1.11 (1H, m).

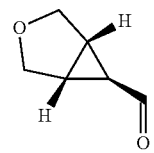

Cap-181, step c

To a solution of DMSO (4.82 mL, 67.9 mmol) in CH$_2$Cl$_2$ (70 mL) was added dropwise oxalyl chloride (3.14 mL, 35.8 mmol) at −78° C. The resulting mixture was stirred at −78° C. for 15 min. A solution of Cap-181, step b (3.10 g, 27.2 mmol) in 35 mL of CH$_2$Cl$_2$ was added and the mixture was stirred at −78° C. for 1 hour. Et$_3$N (18.93 mL, 136 mmol) was then added dropwise. After 30 min, the cooling bath was removed and the reaction was quenched with cold 20% K$_2$HPO$_4$ aq. solution (10 mL) and water. The mixture was stirred at room temperature for 15 min and then diluted with Et$_2$O. The layers were separated. The aqueous layer was extracted with Et$_2$O (2×). The combined organic layers were washed with brine, dried with MgSO$_4$ and concentrated. The residue was purified by flash chromatography (silica gel, 100% CH$_2$Cl$_2$) to afford Cap-181, step c (2.71 g) as light yellow oil. $^1$H NMR (500 MHz, CDCl$_3$) δ ppm 9.41 (1H, d, J=4.27 Hz), 3.96 (2H, d, J=8.85 Hz), 3.80 (2H, d, J=8.55 Hz), 2.27-2.33 (2H, m), 1.93 (1H, m).

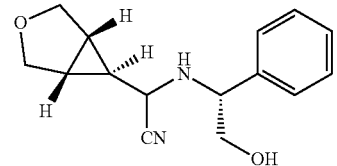

Cap-181, step d

To a mixture of Cap-181, step c (2.7 g, 24.08 mmol) in 50 mL of water at 0° C. was added sodium bisulfite (2.506 g, 24.08 mmol) and KCN (1.631 g, 25.04 mmol), followed by a solution of (R)-2-amino-2-phenylethanol (3.30 g, 24.08 mmol) in 18 mL of MeOH. The resulting mixture was stirred at room temperature for 2 hours and then heated to reflux overnight. The mixture was cooled to room temperature. 100 mL of EtOAc was added. After mixing for 15 min, the layers were separated. The aqueous layer was extracted with EtOAc (2×). The combined organic layers were washed with brine, dried with MgSO$_4$ and concentrated. The crude diastereomeric mixture was purified by reverse phase HPLC (Column: Water Sunfire 30×150 mm, acetonitrile/water/NH$_4$OAc) to afford a two diastereomers of Cap-181, step d. The absolute stereochemistry of each isomer was not determined. Diastereomer 1 (later eluting fraction) (570 mg): LC-MS: Anal. Calcd. for [M+H]$^+$ C$_{15}$H$_{19}$N$_2$O$_2$ 259.14. found 259.2.

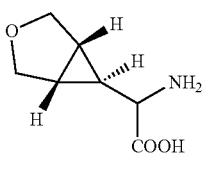

Cap-181, step e

To a solution of Cap-181, step d (diastereomer 1) (570 mg, 2.207 mmol) in 20 mL of CH₂Cl₂ and 20 mL of MeOH at 0° C. was added lead tetraacetate (1174 mg, 2.65 mmol). The resulting orange mixture was stirred at 0° C. for 10 min. Water (20 mL) was then added into the mixture and the mixture was filtered off (CELITE®). The filtrate was concentrated and diluted with 25 mL of 6 N HCl aq. solution. The resulting mixture was refluxed for 4 hours. The mixture was filtered off and washed with CH₂Cl₂. The aqueous layer was concentrated to afford Cap-181, step e (HCl salt). The crude product was used in the next step without further purification. ¹H NMR (500 MHz, MeOD) δ ppm 3.87-3.91 (2H, m), 3.73 (2H, dd, J=8.70, 2.90 Hz), 3.55 (1H, d, J=10.07 Hz), 2.02-2.07 (1H, m), 1.94-1.99 (1H, m), 1.03-1.10 (1H, m).

Cap-181

To a mixture of the above crude Cap-181, step e in 1 N NaOH aq. solution (10 mL) was added sodium bicarbonate (371 mg, 4.42 mmol). Methyl chloroformate (0.342 mL, 4.42 mmol) was then added dropwise, and the resulting mixture was stirred at room temperature for 3 hours. The mixture was neutralized with 1 N HCl aq. Solution and extracted with EtOAc (3×). The combined organic layers were dried with MgSO₄ and concentrated to afford Cap-181 (100 mg, 21% over two steps) as light yellow oil. LC-MS: Anal. Calcd. for [M+H]⁺ C₉H₁₄NO₅ 216.09. found 216.1. ¹H NMR (500 MHz, CDCl₃) δ ppm 5.29 (1H, br. s.), 3.53-4.02 (8H, m), 1.66-1.92 (2H, m), 1.08 (1H, br. s.).

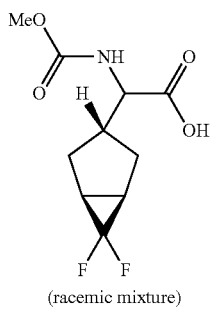

Cap-182
(racemic mixture)

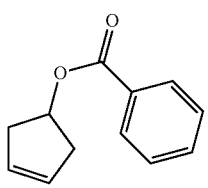

Cap-182 step a

A solution of cyclopent-3-enol (5 g, 59.4 mmol) and Et₃N (9.94 mL, 71.3 mmol) in 50 mL of CH₂Cl₂ was stirred at room temperature for 15 min. Benzoyl chloride (8.28 mL, 71.3 mmol) was then added dropwise and the mixture was stirred at room temperature overnight. The mixture was then washed with water, and the organic layer was dried with MgSO₄ and concentrated. The residue was purified by flash chromatography (silica gel, EtOAc/Hex 0-10%) to afford Cap-182, step a (9.25 g) as clear oil. ¹H NMR (400 MHz, CDCl₃) δ ppm 8.01-8.07 (2H, m), 7.55 (1H, t, J=7.40 Hz), 7.43 (2H, t, J=7.65 Hz), 5.79 (2H, s), 5.64 (1H, tt, J=6.93, 2.60 Hz), 2.87 (2H, dd, J=16.56, 6.78 Hz), 2.52-2.63 (2H, m).

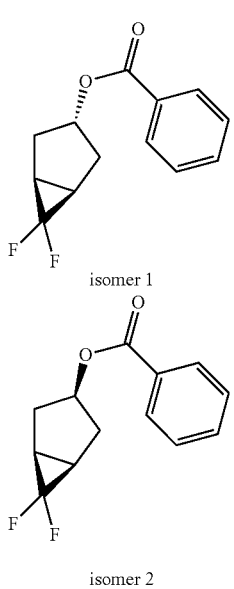

Cap-182, step b isomer 1 isomer 2

To a round bottom flask with a magnetic stirring bar was added sodium fluoride (5.02 mg, 0.120 mmol) and Cap-182, step a (2.25 g, 11.95 mmol). The flask was heated up to 100° C. and neat trimethylsilyl 2,2-difluoro-2-(fluorosulfonyl)acetate (5.89 mL, 29.9 mmol) was added slowly by syringe pump over 5 hours, and heated at 100° C. overnight. The mixture was then diluted with CH₂Cl₂, washed with water, sat. NaHCO₃ aq. solution and brine, dried with MgSO₄ and concentrated. The crude product was purified by flash chromatography (silica gel, 0-5% EtOAc/Hex) to afford Cap-182, step b (isomer 1) (750 mg) and Cap-182, step b (isomer 2) (480 mg) as clear oils. Relative stereochemical assignment was made by NOE study. Cap-182, step b (isomer 1): LC-MS: Anal. Calcd. for [M+H]⁺ C₁₃H₁₃F₂O₂ 239.09. found 239.2. ¹H NMR (500 MHz, CDCl₃) δ ppm 7.99-8.04 (2H, m), 7.56 (1H, t, J=7.32 Hz), 7.43 (2H, t, J=7.63 Hz), 5.25-5.33 (1H, m), 2.50 (2H, dd, J=14.04, 6.71 Hz), 2.14-2.22 (2H, m), 2.08-2.14 (2H, m). Cap-182, step b (isomer 2): LC-MS: Anal. Calcd. for [M+H]⁺ C₁₃H₁₃F₂O₂ 239.09. found 239.2. ¹H NMR (400 MHz, CDCl₃) δ ppm 7.98-8.08 (2H, m), 7.53-7.59 (1H, m), 7.41-7.48 (2H, m), 5.53-5.62 (1H, m), 2.59-2.70 (2H, m), 2.01-2.11 (4H, m).

Cap-182, step c

To a solution of Cap-182, step b (isomer 2) (480 mg, 2.015 mmol) in 4 mL of MeOH was added KOH (4 mL, 2.015 mmol) (10% aq.). The resulting mixture was stirred at room temperature overnight. The mixture was then extracted with CH$_2$Cl$_2$ (3×). The combined organic layers were dried with MgSO$_4$ and concentrated to afford Cap-182, step c (220 mg) as a light yellow solid. $^1$H NMR (500 MHz, CDCl$_3$) δ ppm 4.41-4.54 (1H, m), 2.38-2.50 (2H, m), 1.89-1.99 (2H, m), 1.81 (2H, dd, J=14.50, 5.04 Hz).

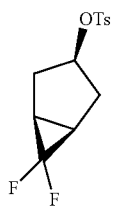

Cap-182, step d p-Tosyl-Cl (625 mg, 3.28 mmol) was added to a solution of Cap-182, step c (220 mg, 1.640 mmol) and pyridine (0.531 mL, 6.56 mmol) in 7 mL of CH$_2$Cl$_2$. The mixture was stirred at room temperature overnight and then diluted with CH$_2$Cl$_2$, washed with water and 1 N HCl aq. solution. The organic layer was dried (MgSO$_4$) and concentrated. The residue was purified by flash chromatography (silica gel, 0-15% EtOAc/Hexane) to afford Cap-182, step d (325 mg) as a clear oil. LC-MS: Anal. Calcd. For [M+Na]$^+$ C$_{13}$H$_{14}$F$_2$NaO$_3$S 311.05. found 311.2. $^1$H NMR (500 MHz, CDCl$_3$) δ ppm 7.76 (2H, d, J=8.24 Hz), 7.34 (2H, d, J=8.24 Hz), 4.99-5.08 (1H, m), 2.45 (3H, s), 2.31-2.41 (2H, m), 1.84-1.94 (4H, m).

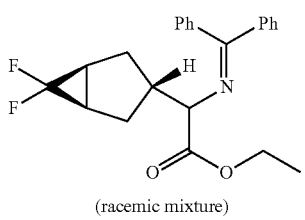

Cap-182, step e (racemic mixture)

To a microwave tube was added N-(diphenylmethylene) glycine ethyl ester (241 mg, 0.902 mmol) and Cap-182, step d (260 mg, 0.902 mmol) in 2 mL of toluene. The tube was sealed and LiHMDS (1.082 mL of 1 N in THF, 1.082 mmol) was added dropwise under N$_2$. The resulting dark brown solution was heated at 100° C. in microwave for 5 hours. The mixture was then quenched with water, and extracted with EtOAc (3×). The combined organic layers were washed with water, dried with MgSO$_4$ and concentrated. The crude product was purified by flash chromatography (silica gel, 0-5% EtOAc/Hex) to afford a racemic mixture of Cap-182, step e (240 mg) as light yellow oil. The mixture was submitted to the next step without separation. LC-MS: Anal. Calcd. for [M+H]$^+$ C$_{23}$H$_{24}$F$_2$NO$_2$ 384.18. found 384.35. $^1$H NMR (500 MHz, CDCl$_3$) δ ppm 7.63-7.70 (2H, m), 7.43-7.51 (3H, m), 7.38-7.43 (1H, m), 7.31-7.38 (2H, m), 7.13-7.22 (2H, m), 4.13-4.22 (2H, m), 3.95 (1H, d, J=6.41 Hz), 2.67-2.79 (1H, m), 2.07-2.16 (1H, m), 1.97-2.07 (2H, m), 1.90 (2H, m), 1.65-1.76 (1H, m), 1.25 (3H, t, J=7.17 Hz).

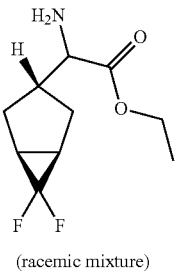

Cap-182, step f (racemic mixture)

To a solution of Cap-182, step e (240 mg, 0.626 mmol) in 4 mL of THF was added HCl (1 mL, 2.0 mmol) (2 N aq.). The resulting mixture was stirred at room temperature for 2 hours. The mixture was then washed with EtOAc, neutralized with sat. NaHCO$_3$ aq. solution and then extracted with EtOAc (3×). The combined organic layers were dried with MgSO$_4$ and concentrated to afford Cap-182, step f (120 mg) as clear oil. LC-MS: Anal. Calcd. for [M+H]$^+$ C$_{10}$H$_{16}$F$_2$NO$_2$ 220.11. found 220.26. $^1$H NMR (500 MHz, CDCl$_3$) δ ppm 4.14-4.25 (2H, m), 3.26 (1H, d, J=6.71 Hz), 2.22-2.35 (1H, m), 1.90-2.11 (5H, m), 1.79-1.90 (1H, m), 1.22-1.34 (3H, m).

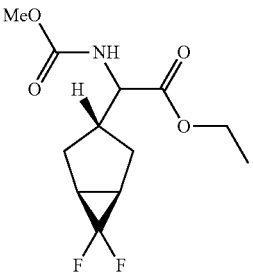

Cap-182, step g (racemic mixture)

To a solution of Cap-182, step f (120 mg, 0.547 mmol) in 2 mL of CH$_2$Cl$_2$ was added methyl chloroformate (0.085 mL, 1.095 mmol). The resulting mixture was stirred at room temperature for 1 hour. The mixture was diluted with CH$_2$Cl$_2$ and washed with water. The organic layer was dried with Na$_2$SO$_4$ and concentrated to afford Cap-182, step g (150 mg) as a white solid. LC-MS: Anal. Calcd. for [M+H]$^+$ C$_{12}$H$_{18}$F$_2$NO$_4$ 278.12. found 278.2. $^1$H NMR (500 MHz, CDCl$_3$) δ ppm 5.23 (1H, d, J=8.24 Hz), 4.29 (1H, t, J=7.48 Hz), 4.15-4.23 (2H, m), 3.68 (3H, s), 2.37 (1H, br. s.), 2.02-2.10 (1H, m), 1.85-2.00 (4H, m), 1.75-1.84 (1H, m), 1.27 (3H, t, J=7.02 Hz).

Cap-182 (Racemic Mixture)

To a mixture of Cap-182, step g (150 mg, 0.541 mmol) in 2 mL of THF and 1 mL of water was added LiOH (0.811 mL, 1.623 mmol) (2 N aq.). The resulting mixture was stirred at room temperature overnight. The mixture was neutralized with 1 N HCl aq. solution and extracted with EtOAc (3×). The combined organic layers were dried with MgSO$_4$ and concentrated to afford Cap-182 (133 mg) as a white solid. LC-MS: Anal. Calcd. for [M+H]$^+$ C$_{10}$H$_{14}$F$_2$NO$_4$ 250.09. found 250.13. $^1$H NMR (500 MHz, CDCl$_3$) δ ppm 5.18-5.36 (1H, m), 4.28-4.44 (1H, m), 3.70 (3H, s), 2.37-2.56 (1H, m), 1.74-2.31 (6H, m).

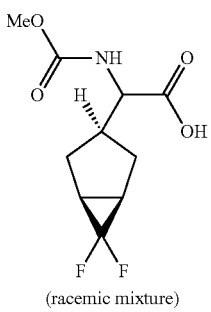

Cap-183

(racemic mixture)

Cap-183 was synthesized from Cap-182, step b (isomer 1) according to the procedure described for the preparation of Cap-182. Anal. Calcd. for [M+H]$^+$ $C_{10}H_{14}F_2NO_4$ 250.09. found 249.86. $^1$H NMR (500 MHz, CDCl$_3$) δ ppm 5.15 (1H, d, J=8.24 Hz), 4.32 (1H, t, J=7.48 Hz), 3.69 (3H, s), 2.83-2.99 (1H, m), 1.96-2.26 (4H, m), 1.70 (1H, t, J=11.75 Hz), 1.59 (1H, t, J=12.05 Hz).

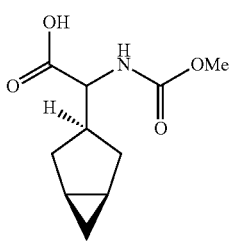

Cap-184

(racemic mixture)

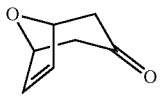

Cap-184, step a

A mixture of ethyl 2-amino-2-((1R,3r,5S)-bicyclo[3.1.0]hexan-3-yl)acetate (prepared from commercially available (1R,3r,5S)-bicyclo[3.1.0]hexan-3-ol by employing the same procedures described for the preparation of Cap-182; 350 mg, 1.910 mmol), DiPEA (0.667 mL, 3.82 mmol), methyl chloroformate (0.296 mL, 3.82 mmol) in 5 mL of CH$_2$Cl$_2$ was stirred at room temperature for 1 hour. The mixture was then diluted with CH$_2$Cl$_2$ and washed with water. The organic layer was dried with MgSO$_4$ and concentrated to afford Cap-184 step a (461 mg) as yellow oil. LC-MS: Anal. Calcd. for [M+H]$^+$ $C_{12}H_{20}NO_4$ 242.14. found 242.2. $^1$H NMR (500 MHz, CDCl$_3$) δ ppm 5.04 (1H, d, J=7.63 Hz), 4.09-4.20 (2H, m), 4.05 (1H, t, J=8.39 Hz), 3.63 (3H, s), 2.55-2.70 (1H, m), 1.96-2.09 (2H, m), 1.37-1.60 (4H, m), 1.24 (3H, t, J=7.17 Hz), 0.66-0.76 (1H, m), −0.03-0.06 (1H, m).

Cap-184 (Racemic Mixture)

To a mixture of ethyl ester Cap-184, step a (461 mg, 1.911 mmol) in 5 mL of THF and 2 mL of water was added LiOH (2.87 mL, 5.73 mmol) (2 N aq.). The resulting mixture was stirred at room temperature overnight. The mixture was then neutralized with 1 N HCl aqueous solution, and extracted with EtOAc (3×). The combined organic layers were dried with MgSO$_4$ and concentrated to afford Cap-184 (350 mg) as clear oil. LC-MS: Anal. Calcd. for [2M+Na]$^+$ $C_{20}H_{30}N_2NaO_8$ 449.19. found 449.3. $^1$H NMR (500 MHz, CDCl$_3$) δ ppm 5.07 (1H, d, J=8.85 Hz), 4.13 (1H, t, J=8.24 Hz), 3.68 (3H, s), 2.64-2.79 (1H, m), 2.04-2.21 (2H, m), 1.23-1.49 (4H, m), 0.71-0.81 (1H, m), 0.03-0.12 (1H, m).

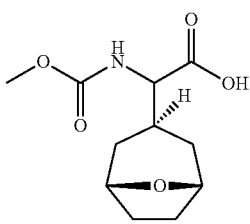

Cap-185 (Enantiomer-1 and Enantiomer-2)

Cap-185, step a

To a mixture of furan (1.075 mL, 14.69 mmol) and zinc (1.585 g, 24.24 mmol) in 1 ml of THF was added 1,1,3,3-tetrabromopropan-2-one (8.23 g, 22.03 mmol) and triethyl borate (5.25 mL, 30.8 mmol) in 4 mL of THF dropwise during 1 hour in dark. The resulting mixture was stirred at room temperature in dark for 17 hours. The resulting dark brown mixture was cooled to −15° C., and 6 mL of water was added. The mixture was warmed to 0° C. and stirred at this temperature for 30 min. The mixture was then filtered and washed with ether. The filtrate was diluted with water and extracted with ether (3×). The combined organic layers were dried with MgSO$_4$ and concentrated to afford dark brown oil. The dark brown oil was dissolved in 6 mL of MeOH and the solution was added dropwise to a mixture of zinc (4.99 g, 76 mmol), copper (I) chloride (0.756 g, 7.64 mmol) and ammonium chloride (5.4 g, 101 mmol) in 20 mL of MeOH. The reaction temperature was maintained below 15° C. during addition. The mixture was then stirred at room temperature for 20 hours, filtered, and the filtrate was diluted with water and extracted with CH$_2$Cl$_2$ (3×). The combined organic layers were dried with MgSO$_4$ and concentrated. The crude product was purified by flash chromatography (silica gel, 0-14% EtOAc/Hex) to afford Cap-185, step a as a white solid (1.0 g) as a white solid, which turned yellow soon. $^1$H NMR (500 MHz, CDCl$_3$) δ ppm 6.24 (2H, s), 5.01 (2H, d, J=4.88 Hz), 2.73 (2H, dd, J=16.94, 5.04 Hz), 2.31 (2H, d, J=16.79 Hz).

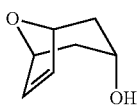

Cap-185, step b

To a solution of Cap-185, step a (240 mg, 1.933 mmol) in 2 mL of THF at −78° C. was added L-selectride (3.87 mL, 3.87 mmol) (1 M in THF) dropwise over 100 min. The resulting mixture was stirred at −78° C. for 1 hour and then at room temperature overnight. The mixture was then cooled to 0° C., 4 mL of 20% NaOH aqueous solution was added, followed by 2 mL of H₂O₂ (30% water solution) dropwise. The resulting mixture was stirred for 1 hour and then neutralized with 6N HCl (~5 mL). The aqueous layer was saturated with NaCl and extracted with CH₂Cl₂ (3×). The combined organic layers were dried with MgSO₄ and concentrated. The crude product was purified by flash chromatography (silica gel, 0-40% EtOAc/Hex) to afford Cap-185, step b (180 mg) as clear oil. ¹H NMR (400 MHz, CDCl₃) δ ppm 6.49 (2H, s), 4.76 (2H, d, J=4.27 Hz), 3.99 (1H, t, J=5.77 Hz), 2.29 (2H, ddd, J=15.18, 5.65, 4.02 Hz), 1.70-1.78 (2H, m).

Cap-185, step c

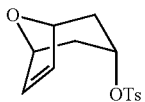

p-Tosyl-Cl (544 mg, 2.85 mmol) was added to a solution of Cap-185, step b (180 mg, 1.427 mmol) and pyridine (0.462 mL, 5.71 mmol) in 5 mL of CH₂Cl₂ (5 mL) and the mixture was stirred at room temperature for 2 days. The reaction was diluted with CH₂Cl₂ and washed with 1 N aq. HCl. The aqueous layer was extracted with CH₂Cl₂ (2×). The combined organic layers were dried with MgSO₄ and concentrated. The crude product was purified by flash chromatography (silica gel, 0-15% EtOAc/Hex) to afford Cap-185, step c (210 mg) as a white solid. ¹H NMR (500 MHz, CDCl₃) δ ppm 7.73 (2H, d, J=8.24 Hz), 7.32 (2H, d, J=8.24 Hz), 6.25 (2H, s), 4.76 (1H, t, J=5.65 Hz), 4.64 (2H, d, J=3.66 Hz), 2.44 (3H, s), 2.18 (2H, td, J=10.07, 5.49 Hz), 1.71 (2H, d, J=15.56 Hz).

Cap-185, step d

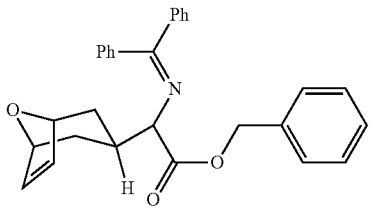

A microwave tube was charged with benzyl 2-(diphenylmethyleneamino)acetate (1.5 g, 4.57 mmol) and Cap-185, step c (1.28 g, 4.57 mmol) in 5 mL of toluene. The tube was sealed and LiHMDS (5.5 mL, 5.5 mmol) (1 N in toluene) was added dropwise under N₂. The resulting dark brown solution was heated at 100° C. in microwave for 5 hours. To the mixture was then added water and EtOAc. The layers were separated and the water phase was extracted with EtOAc (2×). The combined organic layers were concentrated to afford Cap-185, step d as a racemic mixture of. The crude mixture was submitted to the next step without purification or separation. LC-MS: Anal. Calcd. for [M+H]⁺ C₂₉H₂₈NO₃ 438.21. found 438.4.

Cap-185, step e

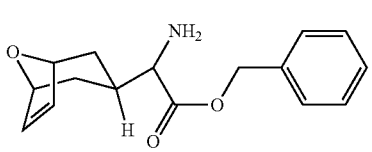

To a solution of the racemic mixture of Cap-185, step d in 30 mL of THF was added HCl (20 mL) (2 N aq.). The resulting mixture was stirred at room temperature for 2 hours. After the reaction was done as judged by TLC, the two layers were separated. The aqueous layer was washed with EtOAc, neutralized with sat. NaHCO₃ aq. solution and then extracted with EtOAc (3×). The combined organic layers were dried with MgSO₄ and concentrated to afford Cap-185, step e. LC-MS: Anal. Calcd. for [M+H]⁺ C₁₆H₂₀NO₃ 274.14. found 274.12.

Cap-185, step f

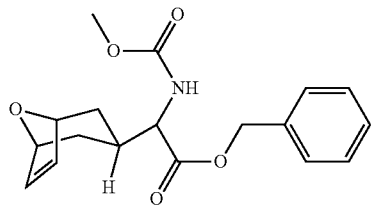

A solution of the crude Cap-185, step e, DiPEA (1.24 mL, 7.1 mmol) and methyl chloroformate (0.55 mL, 7.1 mmol) in 5 mL of CH₂Cl₂ was stirred at room temperature for 1 hour. The mixture was then diluted with CH₂Cl₂ and washed with water. The organic layer was dried with Na₂SO₄ and concentrated. The crude product was purified by flash chromatography (silica gel, 0-40% EtOAc/Hex) to afford 700 mg of the racemic mixture. The mixture was then separated by chiral HPLC (CHIRALPAK® AD-H column, 30×250 mm, 5 um) eluting with 88% CO₂-12% EtOH at 70 mL/min to afford 240 mg of Enantiomer-1 and 310 mg of Enantiomer-2 of Cap-1, step f as white solids. Enantiomer-1: LC-MS: Anal. Calcd. for [M+H]⁺ C₁₈H₂₂NO₅ 332.15. found 332.3. ¹H NMR (500 MHz, CDCl₃) δ ppm 7.30-7.40 (5H, m), 6.03-6.16 (2H, m), 5.09-5.26 (3H, m), 4.65-4.74 (2H, m), 4.33 (1H, dd, J=9.16, 4.88 Hz), 3.67 (3H, s), 2.27-2.38 (1H, m), 1.61-1.69 (1H, m), 1.45-1.56 (1H, m), 1.34 (1H, dd, J=13.43, 5.19 Hz), 1.07 (1H, dd, J=13.12, 5.19 Hz). Enantiomer-2: LC-MS: Anal. Calcd. for [M+H]⁺ C₁₈H₂₂NO₅ 332.15. found 332.06.

Cap-185 (Enantiomer-1 and Enantiomer-2)

To a hydrogenation bottle containing a solution Cap-185, step f (Enantiomer-2) (300 mg, 0.905 mmol) in 10 mL of MeOH was added Pd/C (15 mg, 0.141 mmol) under a cover of nitrogen. The mixture was hydrogenated on a Parr shaker at 40 psi for 3 hours. The mixture was then filtered and the filtrate was concentrated to afford Cap-185 (Enantiomer-2) (200 mg) as a white solid. LC-MS: Anal. Calcd. for [M+H]⁺ C₁₁H₁₈NO₅ 244.12. found 244.2. ¹H NMR (500 MHz, CDCl₃) δ ppm 5.33 (1H, br. s.), 4.46 (2H, d), 4.28 (1H, br. s.), 3.68 (3H, s), 2.35 (1H, br. s.), 1.91-2.03 (2H, m), 1.56-1.80 (4H, m), 1.36-1.55 (2H, m). [Note: Cap-185 (Enantiomer-1) can be obtained in a similar fashion.]

Cap-186

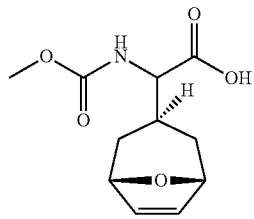

To a solution of the ester Cap-185, step f (Enantiomer-2) (150 mg, 0.453 mmol) in 4 mL of MeOH was added NaOH (4 mL of 1 N in water, 4.00 mmol). The resulting mixture was stirred at room temperature for 3 hours. The methanol was then removed under vacuum, and the residue was neutralized with 1 N HCl solution and extracted with EtOAc (3×). The combined organic layers were dried with $MgSO_4$ and concentrated to afford Cap-186 that was contaminated with some benzyl alcohol (sticky white solid; 115 mg). LC-MS: Anal. Calcd. for $[M+H]^+$ $C_{11}H_{16}NO_5$ 242.10. found 242.1. $^1H$ NMR (500 MHz, $CDCl_3$) δ ppm 6.10-6.19 (2H, m), 5.36 (1H, d, J=8.85 Hz), 4.75-4.84 (2H, m), 4.28 (1H, dd, J=8.55, 4.58 Hz), 3.68 (3H, s), 2.33-2.45 (1H, m), 1.60-1.72 (2H, m), 1.30-1.48 (2H, m).

Cap-187

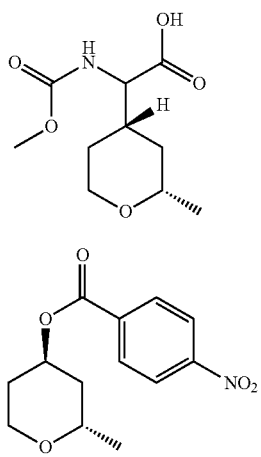

Cap-187

Cap-187, step a

To a solution of Cap-178, step e (2.2 g, 18.94 mmol), $PPh_3$ (24.84 g, 95 mmol) and 4-nitrobenzoic acid (14.24 g, 85 mmol) in 30 mL of benzene was added DEAD (42.9 mL, 95 mmol) dropwise. The resulting light orange solution was stirred at room temperature overnight. The solvent was then removed under vacuum and the residue was purified by flash chromatography (silica gel, 0-15% EtOAc/Hex) to afford Cap-187, step a (2.3 g) as a white solid. $^1H$ NMR (500 MHz, $CDCl_3$) δ ppm 8.27-8.34 (2H, m), 8.20-8.26 (2H, m), 5.45 (1H, t, J=2.90 Hz), 3.83-3.96 (3H, m), 1.90-2.03 (2H, m), 1.80-1.88 (1H, m), 1.61-1.70 (1H, m), 1.21 (3H, d, J=6.10 Hz).

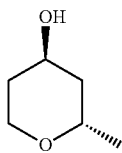

Cap-187, step b

To a solution of Cap-187, step a (2.3 g, 8.67 mmol) in 10 mL of MeOH was added sodium methoxide (2.372 mL, 8.67 mmol) (25% in Methanol). The resulting mixture was stirred at room temperature for 3 hours. Water was added, and the mixture was extracted with EtOAc (5×). The combined organic layers were dried with $MgSO_4$ and concentrated. The crude product was purified by flash chromatography (silica gel, 0-15% EtOAc/Hex, then 15-50% EtOAc/Hex) to afford Cap-187, step b (0.85 g) as clear oil. $^1H$ NMR (500 MHz, $CDCl_3$) δ ppm 4.19-4.23 (1H, m), 3.82-3.91 (2H, m), 3.73-3.79 (1H, m), 1.79-1.88 (1H, m), 1.62-1.68 (1H, m), 1.46-1.58 (2H, m), 1.14 (3H, d, J=6.10 Hz).

Cap-187

The individual enantiomers of Cap-187 were synthesized from Cap-187, step b according to the procedure described for Cap-178. LC-MS: Anal. Calcd. for $[M+H]^+$ $C_{10}H_{18}NO_5$ 232.12. found 232.1. $^1H$ NMR (400 MHz, $CDCl_3$) δ ppm 5.26 (1H, d, J=7.78 Hz), 4.32-4.43 (1H, m), 4.07 (1H, dd, J=11.54, 3.51 Hz), 3.72 (3H, s), 3.39-3.50 (2H, m), 2.08-2.23 (1H, m), 1.54-1.68 (1H, m), 1.38-1.52 (1H, m), 1.11-1.32 (5H, m).

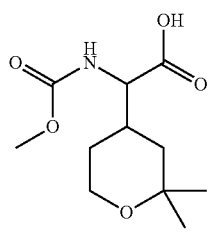

Cap-188 (four stereoisomers)

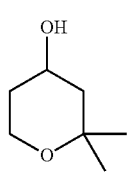

Cap-188, step a

To a solution of 2,2-dimethyldihydro-2H-pyran-4(3H)-one (2 g, 15.60 mmol) in 50 mL of MeOH was slowly added sodium borohydride (0.649 g, 17.16 mmol). The resulting mixture was stirred at room temperature for 3 hours. To the mixture was then added 1 N HCl aqueous solution until it crosses into acidic pH range and then extracted with EtOAc (3×). The combined organic layers were dried with $MgSO_4$ and concentrated to afford Cap-188, step a (1.9 g) as clear oil. The product was used in the next step without purification. $^1H$ NMR (400 MHz, $CDCl_3$) δ ppm 3.91-4.02 (1H, m), 3.79-3.86 (1H, m), 3.63 (1H, td, J=12.05, 2.51 Hz), 1.82-1.93 (2H, m), 1.40-1.53 (1H, m), 1.29-1.38 (1H, m), 1.27 (3H, s), 1.20 (3H, s).

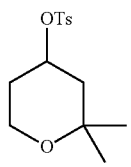

Cap-188.1 and Cap-188.2, step b p-Tosyl-Cl (5.56 g, 29.2 mmol) was added to a solution of Cap-188, step a (1.9 g, 14.59 mmol) and pyridine (4.72 mL, 58.4 mmol) in 100 mL of $CH_2Cl_2$. The resulting mixture was stirred at room temperature for 3 days. To the reaction was added 10 mL of water, and the mixture was stirred at room temperature for an additional hour. The two layers were separated and the organic phase was washed with water and 1 N HCl aqueous solution. The organic phase was dried with $MgSO_4$ and concentrated to afford the mixture of two enantiomers as a light yellow solid. The mixture was then separated by chiral HPLC (CHIRALPAK® AD column, 21×250 mm, 10 um) eluting with 92% 0.1% diethylamine/Heptane- 8% EtOH at 15 mL/min to afford Cap-188.1, step b (1.0 g) and Cap-188.2, step b (1.0 g). The absolute stereochemistry of the two enantiomers was not assigned. Cap-188.1, step b: LC-MS: Anal. Calcd. for [2M+Na]$^+$ $C_{28}H_{40}NaO_8S_2$ 591.21. found 591.3. $^1$H NMR (500 MHz, CDCl$_3$) δ ppm 7.79 (2H, d, J=8.24 Hz), 7.34 (2H, d, J=8.24 Hz), 4.72-4.81 (1H, m), 3.78 (1H, dt, J=12.44, 4.16 Hz), 3.53-3.61 (1H, m), 2.45 (3H, s), 1.75-1.86 (2H, m), 1.61-1.71 (1H, m), 1.52-1.60 (1H, m), 1.22 (3H, s), 1.14 (3H, s). Cap-188.2, step b: LC-MS: Anal. Calcd. for [2M+Na]$^+$ $C_{28}H_{40}NaO_8S_2$ 591.21. found 591.3.

Cap-188

The four stereoisomers of Cap-188 could be synthesized from Cap-188.1, step b and Cap-188.2, step b, according to the procedure described for the preparation of Cap-178. Cap-188 (Steroisomer-1): LC-MS: Anal. Calcd. for [M+Na]$^+$ $C_{11}H_{19}NNaO_5$ 268.12. found 268.23. $^1$H NMR (500 MHz, CDCl$_3$) δ ppm 5.32 (1H, d, J=8.55 Hz), 4.26-4.35 (1H, m), 3.57-3.82 (5H, m), 2.11-2.34 (1H, m), 1.25-1.58 (4H, m), 1.21 (6H, d, J=6.10 Hz). Cap-188 (Stereoisomer-2): LC-MS: Anal. Calcd. for [M+H]$^+$ $C_{11}H_{20}NO_5$ 246.13. found 246.1. $^1$H NMR (500 MHz, CDCl$_3$) δ ppm 5.25 (1H, d, J=8.55 Hz), 4.33 (1H, dd, J=8.39, 5.04 Hz), 3.80 (1H, dd, J=11.90, 3.97 Hz), 3.62-3.76 (4H, m), 2.20-2.32 (1H, m), 1.52-1.63 (1H, m), 1.27-1.49 (3H, m), 1.22 (6H, d, J=14.04 Hz).

Cap-189

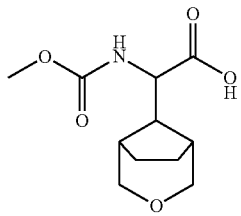

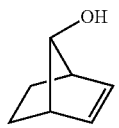

Cap-189, step a

To a solution of phenylmagnesium bromide (113 mL, 340 mmol) (3 M in ether) in 100 mL of ether was added dropwise exo-2,3-epoxynorbornane (25 g, 227 mmol) in 50 mL of ether. After the initial exotherm, the mixture was heated to reflux overnight. The reaction was then cooled to room temperature and quenched carefully with water (~10 mL). The mixture was diluted with ether and washed with a 3 N HCl aqueous solution (~160 mL). The aqueous layer was extracted with ether (2×) and the combined organic layers were dried with MgSO$_4$ and concentrated. The crude product was purified by flash chromatography (silica gel, 0-18% EtOAc/Hex) to afford Cap-189, step a (11 g). $^1$H NMR (400 MHz, CDCl$_3$) δ ppm 6.03-6.11 (2H, m), 3.76 (1H, d, J=11.29 Hz), 2.72-2.81 (2H, m), 1.98 (1H, d, J=11.29 Hz), 1.67-1.76 (2H, m), 0.90-0.97 (2H, m).

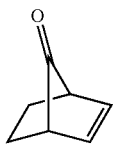

Cap-189, step b

To a solution of oxalyl chloride (59.9 mL, 120 mmol) in 200 mL of CH$_2$Cl$_2$ at −78° C. was added DMSO (17.01 mL, 240 mmol) in 100 mL of CH$_2$Cl$_2$. The mixture was stirred for 10 min, and Cap-189, step a (11 g, 100 mmol) in 150 mL of CH$_2$Cl$_2$ was added followed by Et$_3$N (72.4 mL, 519 mmol) in 30 mL of CH$_2$Cl$_2$. The mixture was stirred at −78° C. for 30 min and then warmed to room temperature. Water (150 mL) was added and the mixture was stirred at room temperature for 30 mins. The two layers were then separated, and the aqueous layer was extracted with CH$_2$Cl$_2$ (2×). The organic layers were combined, dried with MgSO$_4$ and concentrated. The crude product was purified by flash chromatography (silica gel, 0-5% EtOAc/Hex) to afford Cap-189, step b (5.3 g) as a light yellow oil. $^1$H NMR (500 MHz, CDCl$_3$) δ ppm 6.50-6.55 (2H, m), 2.78-2.84 (2H, m), 1.92-1.99 (2H, m), 1.17-1.23 (2H, m).

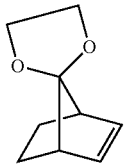

Cap-189, step c

A mixture of Cap-189, step b (5.3 g, 49.0 mmol), p-toluenesulfonic acid monohydrate (1.492 g, 7.84 mmol) and ethylene glycol (4.10 mL, 73.5 mmol) in 100 mL of benzene was refluxed for 4 hours and then stirred at room temperature overnight. The reaction was partitioned between Et$_2$O and aqueous sat. NaHCO$_3$ solution and the two layers were separated. The organic layer was washed with brine, dried with MgSO$_4$ and concentrated. The crude product was purified by flash chromatography (silica gel, 0-6% EtOAc/Hex) to afford Cap-189, step c (5.2 g) as a clear oil. $^1$H NMR (400 MHz, CDCl$_3$) δ ppm 6.20 (2H, t, J=2.13 Hz), 3.90-3.97 (2H, m), 3.81-3.89 (2H, m), 2.54 (2H, m), 1.89-1.99 (2H, m), 0.95-1.03 (2H, m).

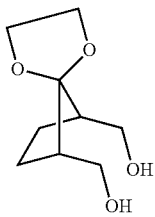

Cap-189, step d

A solution of Cap-189, step c (5.2 g, 34.2 mmol) in 60 mL of MeOH and 50 mL of CH$_2$Cl$_2$ was cooled to −78° C. and treated with ozone gas until a light blue color was apparent. The reaction was then bubbled with N$_2$ to remove the excess ozone gas (blue color disappeared) and sodium borohydride (1.939 g, 51.3 mmol) was added into the reaction. The reaction was then warmed to 0° C. Acetone was added into the mixture to quench the excess sodium borohydride. The mixture was concentrated and the residue was purified by flash chromatography (silica gel, 100% EtOAc) to afford Cap-189, step d (5.0 g) as a clear oil. $^1$H NMR (400 MHz, CDCl$_3$) δ ppm 3.99-4.09 (4H, m), 3.68 (4H, m), 2.17-2.29 (2H, m), 1.92-2.10 (2H, m), 1.77-1.88 (2H, m), 1.57-1.70 (2H, m).

Cap-189, step e

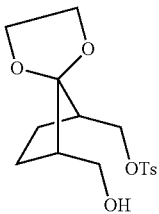

To a solution of Cap-189, step d (1 g, 5.31 mmol) in 20 mL of CH$_2$Cl$_2$ was added silver oxide (3.8 g), p-Ts-Cl (1.215 g, 6.38 mmol) and KI (0.176 g, 1.063 mmol). The resulting solution was stirred at room temperature for 3 days. The mixture was then filtered and the filtrate was concentrated. The crude product was purified by flash chromatography (silica gel, 60% EtOAc/Hex) to afford Cap-189, step e (0.79 g) as clear oil. LC-MS: Anal. Calcd. for [M+Na]$^+$ C$_{16}$H$_{22}$NaO$_6$S 365.10. found 365.22. $^1$H NMR (400 MHz, CDCl$_3$) δ ppm 7.80 (2H, d, J=8.28 Hz), 7.36 (2H, d, J=8.03 Hz), 4.11-4.17 (1H, m), 3.85-4.06 (5H, m), 3.64-3.71 (1H, m), 3.55-3.63 (1H, m), 2.47 (3H, s), 2.32-2.43 (1H, m), 2.15-2.27 (1H, m), 1.70-1.89 (2H, m), 1.52-1.66 (1H, m), 1.35-1.47 (1H, m).

Cap-189, step f

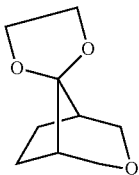

To a solution of Cap-189, step e (2.2 g, 6.43 mmol) in 40 mL of MeOH was added potassium carbonate (1.776 g, 12.85 mmol). The resulting mixture was stirred at room temperature overnight. The mixture was then diluted with water and EtOAc. The two layers were separated. The aqueous layer was extracted with EtOAc (2×). The combined organic layers were washed with brine, dried with MgSO$_4$ and concentrated. The crude product was purified by flash chromatography (silica gel, 0-15% EtOAc/Hex) to afford Cap-189, step f (0.89 g, 5.23 mmol, 81%) as clear oil. $^1$H NMR (400 MHz, CDCl$_3$) δ ppm 3.89-4.02 (6H, m), 3.58 (2H, dd, J=10.79, 2.51 Hz), 1.69-1.89 (6H, m).

Cap-189, step g

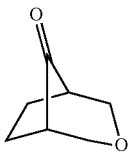

To the solution of Cap-189, step f (890 mg, 5.23 mmol) in 15 mL of THF was added HCl (15 mL, 45.0 mmol) (3 M aqueous). The resulting mixture was stirred at room temperature overnight. The mixture was then diluted with ether and the two layers were separated. The aqueous phase was extracted with ether (2×) and the combined organic layers were dried with MgSO$_4$ and concentrated to afford Cap-189, step g (0.95 g, containing some residual solvents). The product was used in the next step without purification. $^1$H NMR (500 MHz, CDCl$_3$) δ ppm 3.95-4.00 (2H, m), 3.85 (2H, d, J=10.68 Hz), 2.21-2.28 (2H, m), 1.99-2.04 (2H, m), 1.90-1.96 (2H, m).

Cap-189, step h

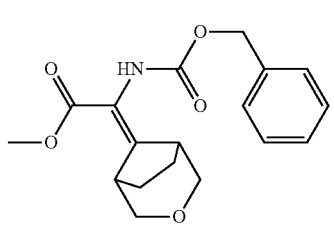

(Enantiomer-1 and Enantiomer-2)

To a solution of (+/−)-benzyloxycarbonyl-α-phosphonoglycine trimethyl ester (1733 mg, 5.23 mmol) in 6 mL of THF at −20° C. was added 1,1,3,3-tetramethylguanidine (0.723 mL, 5.75 mmol). The resultant light yellow mixture was stirred at −20° C. for 1 hour, and Cap-189, step g (660 mg, 5.23 mmol) in 3 mL of THF was added and mixture was then stirred at room temperature for 3 days. The reaction mixture was then diluted with EtOAc, washed with a 0.1 N HCl aq. solution. The aqueous layer was extracted with EtOAc (2×) and the combined organic layers were dried with MgSO$_4$ and concentrated. The crude product was purified by flash chromatography (silica gel, 0-4% EtOAc/CH$_2$Cl$_2$) to afford 960 mg of the racemic mixture. The mixture was separated by chiral HPLC (CHIRALPAK® AD column, 21×250 mm, 10 um) eluting with 90% 0.1% diethylamine/Heptane-10% EtOH at 15 mL/min to afford Cap-189, step h (Enantiomer-1; 300 mg) and Cap-189, step h (Enantiomer-2; 310 mg) as white solids. Cap-189, step h (Enantiomer-1): LC-MS: Anal. Calcd. for [M+H]$^+$ C$_{18}$H$_{22}$NO$_5$ 332.15. found 332.2. $^1$H NMR (500 MHz, CDCl$_3$) δ ppm 7.29-7.41 (5H, m), 6.00 (1H, br. s.), 5.13 (2H, s), 3.63-3.87 (8H, m), 2.84 (1H, br. s.), 1.84-2.02 (2H, m), 1.63-1.84 (2H, m). Cap-189, step h (Enantiomer-2): LC-MS: Anal. Calcd. for [M+H]$^+$ C$_{18}$H$_{22}$NO$_5$ 332.15. found 332.2.

Cap-189, step i

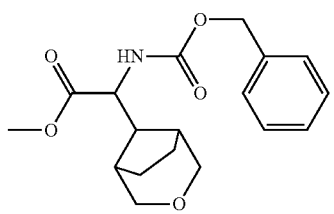

N$_2$ was bubbled through a solution of Cap-189, step h (Enantiomer-2; 290 mg, 0.875 mmol) in 10 mL of MeOH in a 500 mL hydrogenation bottle for 30 mins. To the solution was added (S,S)-Me-BPE-Rh (9.74 mg, 0.018 mmol), and the mixture was then hydrogenated at 60 psi for 6 days. The mixture was concentrated, and chiral analytical HPLC (CHIRALPAK® OJ column) indicated that there were a small amount of remaining starting material and one major product. The residue was then separated by chiral HPLC (CHIRALPAK® OJ column, 21×250 mm, 10 um) eluting with 70% 0.1% diethylamine/Heptane-30% EtOH at 15 mL/min to afford Cap-189, step i, (150 mg) as clear oil. LC-MS: Anal. Calcd. for [M+H]+ C18H24NO5 334.17. found 334.39. 1H NMR (500 MHz, CDCl3) δ ppm 7.28-7.41 (5H, m), 5.12-5.18 (1H, m), 5.09 (2H, s), 4.05 (1H, t, J=10.07 Hz), 3.75 (3H, s), 3.60-3.72 (2H, m), 3.41-3.50 (2H, m), 2.10 (1H, br. s.), 1.72-1.99 (6H, m).

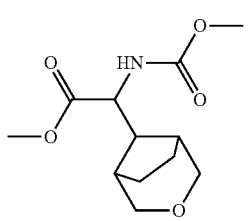

Cap-189, step j

To a solution of Cap-189, step i (150 mg, 0.450 mmol) in 10 mL of MeOH in a hydrogenation bottle were added dimethyl dicarbonate (0.072 mL, 0.675 mmol) and 10% Pd/C (23.94 mg, 0.022 mmol) under a cover of nitrogen cover. The mixture was then hydrogenated on Parr-shaker at 45 psi overnight. The mixture was filtered and the filtrate was concentrated to afford Cap-189, step j (110 mg) as a clear oil. LC-MS: Anal. Calcd. for [M+H]+ C12H20NO5 258.13. found 258.19. 1H NMR (500 MHz, CDCl3) δ ppm 5.08 (1H, d, J=9.16 Hz), 4.03 (1H, t, J=10.07 Hz), 3.75 (3H, s), 3.60-3.72 (5H, m), 3.46 (2H, t, J=10.38 Hz), 2.11 (1H, br. s.), 1.72-1.99 (6H, m).

Cap-189

To a mixture of Cap-189, step j (110 mg, 0.428 mmol) in 2 mL of THF and 1 mL of water was added LiOH (0.641 mL, 1.283 mmol) (2 N aq.). The resulting mixture was stirred at room temperature overnight. The mixture was neutralized with a 1 N HCl aq. solution and extracted with EtOAc (3×). The combined organic layers were dried with MgSO4 and concentrated to afford Cap-189 (100 mg) as a white solid. LC-MS: Anal. Calcd. for [M+Na]+ C11H17NNaO5 266.10. found 266.21. 1H NMR (500 MHz, CDCl3) δ ppm 5.10 (1H, d, J=9.16 Hz), 4.02 (1H, t, J=10.07 Hz), 3.62-3.78 (5H, m), 3.49 (2H, d, J=10.68 Hz), 2.07-2.22 (2H, m), 1.72-1.98 (6H, m).

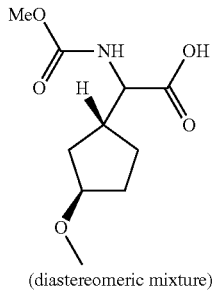

Cap-190

(diastereomeric mixture)

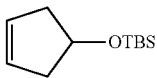

Cap-190, step a

To a mixture of cyclopent-3-enol (2.93 g, 34.8 mmol) and imidazole (5.22 g, 77 mmol) in 30 mL of DMF at 0° C. was added t-butyldimethylchlorosilane (6.30 g, 41.8 mmol). The resulting colorless mixture was stirred at room temperature overnight. Hexanes and water were then added to the mixture and the two layers were separated. The aqueous layer was extracted with EtOAc (2×) and the combined organic layers were washed with brine, dried with MgSO4 and concentrated. The crude product was purified by flash chromatography (silica gel, 2% EtOAc/Hex) to afford Cap-190, step a (6.3 g) as a clear oil. 1H NMR (500 MHz, CDCl3) δ ppm 5.65 (2H, s), 4.49-4.56 (1H, m), 2.56 (2H, dd, J=15.26, 7.02 Hz), 2.27 (2H, dd, J=15.26, 3.36 Hz), 0.88 (9H, s), 0.06 (6H, s).

Cap-190, step b

To a solution of Cap-190, step a (2.3 g, 11.59 mmol) in 40 mL of CH2Cl2 at 0° C. was added m-CPBA (5.60 g, 16.23 mmol) in 5 portions. The reaction mixture was stirred at room temperature overnight. Hexanes and water were then added to the mixture and the two layers were separated. The organic layer was washed with 50 mL aq. 10% NaHSO3 and brine, dried with MgSO4 and concentrated. The crude product was purified by flash chromatography (silica gel, 3%-6% EtOAc/Hex) to afford Cap-190, step b (1.42 g) and its trans diastereomer (0.53 g) as clear oils. Cap-190, step b (cis): 1H NMR (400 MHz, CDCl3) δ ppm 4.39-4.47 (1H, m), 3.47 (2H, s), 2.01-2.10 (2H, m), 1.93-2.00 (2H, m), 0.88 (9H, s), 0.04 (6H, s). Cap-190, step b (trans): 1H NMR (400 MHz, CDCl3) δ ppm 4.04-4.14 (1H, m), 3.47 (2H, s), 2.41 (2H, dd, J=14.05, 7.28 Hz), 1.61 (2H, dd, J=14.18, 6.90 Hz), 0.87 (9H, s), 0.03 (6H, s).

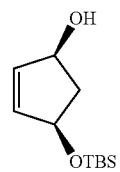

Cap-190, step c

To a solution of (S)-1,2'-methylenedipyrrolidine (0.831 g, 5.39 mmol) in 15 mL of benzene at 0° C. was added dropwise n-butyllithium (4.90 mL, 4.90 mmol) (1 M in hexane). The solution turned bright yellow. The mixture was stirred at 0° C. for 30 min. Cap-190, step b (cis-isomer; 0.7 g, 3.27 mmol) in 10 mL of benzene was then added and the resulting mixture was stirred at 0° C. for 3 hours. EtOAc and sat. NH4Cl aq. solution were added into the mixture, and the two layers were separated. The organic layer was washed with water and brine, dried with MgSO₄ and concentrated. The crude product was purified by flash chromatography (silica gel, 15% EtOAc/Hex) to afford Cap-190, step c (400 mg) as a light yellow oil. ¹H NMR (500 MHz, CDCl₃) δ ppm 5.84-5.98 (2H, m), 4.53-4.69 (2H, m), 2.63-2.73 (1H, m), 1.51 (1H, dt, J=13.73, 4.43 Hz), 0.89 (9H, s), 0.08 (6H, s).

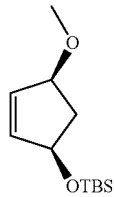

Cap-190, step d

To a solution of Cap-190, step c (400 mg, 1.866 mmol), MeI (1.866 mL, 3.73 mmol) (2 M in t-butyl methyl ether) in 5 mL of THF at 0° C. was added NaH (112 mg, 2.80 mmol) (60% in mineral oil). The resulting mixture was allowed to warm up to room temperature and stirred at room temperature overnight. The reaction was then quenched with water and extracted with EtOAc (3×). The combined organic layers were washed with brine, dried with MgSO₄ and concentrated. The crude product was purified by flash chromatography (silica gel, 5% EtOAc/Hex) to afford Cap-190, step d (370 mg) as light yellow oil. ¹H NMR (500 MHz, CDCl₃) δ ppm 5.92-5.96 (1H, m), 5.87-5.91 (1H, m), 4.64-4.69 (1H, m), 4.23-4.28 (1H, m), 3.32 (3H, s), 2.62-2.69 (1H, m), 1.54 (1H, dt, J=13.12, 5.49 Hz), 0.89 (9H, s), 0.07 (5H, d, J=1.83 Hz).

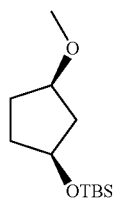

Cap-190, step e

To a solution of Cap-190, step d (400 mg, 1.751 mmol) in 10 mL of EtOAc in a hydrogenation bottle was added platinum(IV) oxide (50 mg, 0.220 mmol). The resulting mixture was hydrogenated at 50 psi on Parr shaker for 2 hours. The mixture was then filtered through CELITE®, and the filtrate was concentrated to afford Cap-190, step e (400 mg) as a clear oil. LC-MS: Anal. Calcd. for [M+H]⁺ C₁₂H₂₇O₂Si 231.18. found 231.3. ¹H NMR (500 MHz, CDCl₃) δ ppm 4.10-4.17 (1H, m), 3.65-3.74 (1H, m), 3.27 (3H, s), 1.43-1.80 (6H, m), 0.90 (9H, s), 0.09 (6H, s).

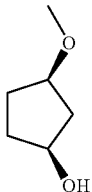

Cap-190, step f

To a solution of Cap-190, step e (400 mg, 1.736 mmol) in 5 mL of THF was added TBAF (3.65 mL, 3.65 mmol) (1 N in THF). The color of the mixture turned brown after several min., and it was stirred at room temperature overnight. The volatile component was removed under vacuum, and the residue was purified by flash chromatography (silica gel, 0-25% EtOAc/Hex) to afford Cap-190, step f (105 mg) as light yellow oil. ¹H NMR (500 MHz, CDCl₃) δ ppm 4.25 (1H, br. s.), 3.84-3.92 (1H, m), 3.29 (3H, s), 1.67-2.02 (6H, m).

Cap-190

Cap-190 was then synthesized from Cap-190, step f according to the procedure described for Cap-182. LC-MS: Anal. Calcd. for [M+Na]⁺ C₁₀H₁₇NNaO₅ 254.10. found 254.3. ¹H NMR (500 MHz, CDCl₃) δ ppm 5.25 (1H, d, J=8.55 Hz), 4.27-4.41 (1H, m), 3.81-3.90 (1H, m), 3.69 (3H, s), 3.26 (3H, s), 2.46-2.58 (1H, m), 1.76-1.99 (3H, m), 1.64-1.73 (1H, m), 1.40-1.58 (1H, m), 1.22-1.38 (1H, m).

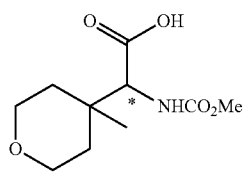

Cap-191 (Enantiomer-1)

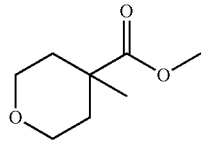

Cap-191, step a

To a solution of diisopropylamine (3 ml, 21.05 mmol) in THF (3 ml) at −78° C. under nitrogen was added n-butyl lithium (2.5 M in hexanes; 8.5 ml, 21.25 mmol). The reaction was stirred at −78° C. for 10 min then brought up to 0° C. for 25 min. The reaction was cooled down again to −78° C., methyl tetrahydro-2H-pyran-4-carboxylate (3 g, 20.81 mmol) in THF (3 ml) was added. The reaction was stirred at −78° C. for 15 min then brought up to 0° C. for 30 min. The reaction was cooled down to −78° C., methyl iodide (1.301 ml, 20.81 mmol) was added. After the addition, the cold bath was removed and the reaction was allowed to slowly warm up to ~25° C. and stirred for 22 h. Ethyl acetate and aqueous HCl (0.1N) were added, and the organic layer was separated and washed with brine and dried (MgSO₄), filtered, and concentrated in vacuo. The residue was loaded on a Thomson's silica gel cartridge eluting with 10% ethyl acetate/hexanes to afford a light yellow oil (2.83 g). ¹H NMR (400 MHz, DMSO-d₆) δ ppm 3.73-3.66 (m, 2H), 3.66 (s, 3H), 3.40-3.30 (m, 2H), 1.95-1.93 (dm, 1H), 1.92-1.90 (dm, 1H), 1.43 (ddd, J=13.74, 9.72, 3.89, 2H), 1.18 (s, 3H).

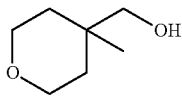

Cap-191, step b

To a solution of Cap-191, step a (3 g, 18.96 mmol) in toluene (190 ml) at −78° C. under nitrogen was added diisobutylaluminum hydride (1.5M in toluene; 26.5 ml, 39.8 mmol) dropwise. The reaction was continued to stir at −78° C. for 1.5 h., and the bath was removed and was stirred for 18 h. The reaction was quenched with MeOH (20 mL). HCl (1M, 150 mL) was added and the mixture was extracted with EtOAc (4×40 mL). The combined organic phases were washed with brine, dried (MgSO$_4$), filtered, and concentrated in vacuo. The residue was purified with flash chromatography (silica gel; 40% ethyl acetate/hexanes) to afford a colorless oil (1.36 g). $^1$H NMR (400 MHz, CDCl$_3$) δ ppm 3.77 (dt, J=11.73, 4.55, 2H), 3.69-3.60 (m, 2H), 3.42 (s, 2H), 1.71-1.40 (bs, 1H) 1.59 (ddd, J=13.74, 9.72, 4.39, 2H), 1.35-1.31 (m, 1H), 1.31-1.27 (m, 1H), 1.06 (s, 3H).

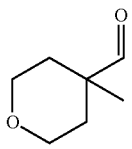

Cap-191, step c

To a solution of DMSO (5.9 ml, 83 mmol) in CH$_2$Cl$_2$ (85 ml) at −78° C. under nitrogen was added oxalyl chloride (3.8 ml, 43.4 mmol) and stirred for 40 min. A solution of Cap-191, step b (4.25 g, 32.6 mmol) in CH$_2$Cl$_2$ (42.5 ml) was then added. The reaction was continued to be stirred at −78° C. under nitrogen for 2 h. The reaction was quenched with cold 20% K$_2$HPO$_4$ (aq) (10 mL) and water. The mixture was stirred at ~25° C. for 15 min, diluted with diethyl ether (50 mL) and the layers were separated. The aqueous layer was extracted with diethyl ether (2×50 mL). The combined organic layers were washed with brine, dried (MgSO$_4$), filtered, and concentrated in vacuo. The residue was taken up in CH$_2$Cl$_2$ (4 mL) and purified with flash chromatography (silica gel, eluting with CH$_2$Cl$_2$) to afford a colorless oil (2.1 g). $^1$H NMR (400 MHz, CDCl$_3$) δ ppm 9.49 (s. 1H), 3.80 (dt, J=11.98, 4.67, 2H), 3.53 (ddd, J=12.05, 9.41, 2.89, 2H), 1.98 (ddd, J=4.71, 3.20, 1.38, 1H), 1.94 (ddd, J=4.71, 3.20, 1.38, 1H), 1.53 (ddd, J=13.87, 9.60, 4.14, 2H), 1.12 (s, 3H).

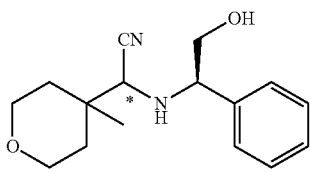

Cap-191, step d

To a solution of Cap 191c (2.5 g, 19.51 mmol) in CHCl$_3$ (20 ml) under nitrogen at ~25° C. was added (R)-2-amino-2-phenylethanol (2.94 g, 21.46 mmol) and stirred for 5 h. The reaction was cooled to 0° C., trimethylsilyl cyanide (3.8 ml, 30.4 mmol) was added dropwise. The cold bath was removed and the reaction was allowed to stir at ~25° C. under nitrogen for 15.5 h. The reaction was treated with 3N HCl (20 mL) and water (20 mL), and the product was extracted with CHCl$_3$ (3×50 mL). The combined organic layers were dried (NaSO$_4$), filtered, and concentrated in vacuo. The residue was purified with flash chromatography (silica gel; 40% ethyl acetate/hexanes) to afford two diastereomers: Cap-191, step d1 (diastereomer 1) as a colorless oil which solidified into a white solid upon standing (3 g). $^1$H NMR (400 MHz, DMSO-d$_6$) δ ppm 7.42-7.26 (m, 5H), 5.21 (t, J=5.77, 1H), 3.87 (dd, J=8.53, 4.52, 1H), 3.61-3.53 (m, 1H), 3.53-3.37 (m, 5H), 3.10 (d, J=13.05, 1H), 2.65 (d, J=13.05, 1H), 1.64-1.55 (m, 1H), 1.55-1.46 (m, 1H), 1.46-1.39 (m, 1H), 1.31-1.23 (m, 1H), 1.11 (s, 3H). LC-MS: Anal. Calcd. for [M+H]$^+$ C$_{16}$H$_{23}$N$_2$O$_2$: 275.18. found 275.20. Cap-191, step d2 (diastereomer 2) as a light yellow oil (0.5 g). $^1$H NMR (400 MHz, DMSO-d$_6$) δ ppm 7.44-7.21 (m, 5H), 4.82 (t, J=5.40, 1H), 3.82-3.73 (m, 1H), 3.73-3.61 (m, 3H), 3.61-3.37 (m, 5H), 2.71 (dd, J=9.29, 4.77, 1H), 1.72-1.55 (m, 2H), 1.48-1.37 (m, 1H), 1.35-1.25 (m, 1H), 1.10 (s, 3H). LC-MS: Anal. Calcd. for [M+H]$^+$ C$_{16}$H$_{23}$N$_2$O$_2$: 275.18. found 275.20.

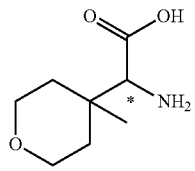

Cap-191, step e

To a solution of Cap-191, step d2 (diastereomer 2) (0.4472 g, 1.630 mmol) in CH$_2$Cl$_2$ (11 ml) and MeOH (5.50 ml) at 0° C. under nitrogen was added lead tetraacetate (1.445 g, 3.26 mmol). The reaction was stirred for 1.5 h, the cold bath was removed and stirring was continued for 20 h. The reaction was treated with a phosphate buffer (pH=7; 6 mL) and stirred for 45 min. The reaction was filtered over CELITE®, washed with CH$_2$Cl$_2$ and the layers were separated. The aqueous layer was extracted with CH$_2$Cl$_2$ (3×25 mL), and the combined organic layers was washed with brine, dried (MgSO$_4$), filtered and concentrated in vacuo. The residue was purified with flash chromatography (silica gel; 15% ethyl acetate/hexanes) to afford the imine intermediate as a colorless oil (181.2 mg). $^1$H NMR (400 MHz, DMSO-d$_6$) δ ppm 8.55 (d, J=1.00, 1H), 7.89-7.81 (m, 2H), 7.61-7.46 (m, 3H), 4.80 (d, J=1.00, 1H), 3.74 (tt, J=11.80, 4.02, 2H), 3.62-3.46 (m, 2H), 1.79-1.62 (m, 2H), 1.46-1.30 (m, 2H), 1.15 (s, 3H).

The imine intermediate was taken up in 6N HCl (10 mL) and heated at 90° C. for 10 days. The reaction was removed from the heat, allowed to cool to room temperature and extracted with ethyl acetate (3×25 mL). The aqueous layer was concentrated in vacuo to afford an off-white solid. The solid was taken up in MeOH and loaded on a pre-conditioned MCX (6 g) cartridge, washed with MeOH followed by elution with 2N $NH_3$/MeOH solution and concentrated in vacuo to afford an off-white solid (79.8 mg). $^1$H NMR (400 MHz, DMSO-$d_6$) δ ppm 14.33-13.51 (bs, 1H), 8.30 (bs, 3H), 3.82-3.75 (m, 1H), 3.70 (dt, J=11.80, 4.02, 2H), 3.58-3.43 (m, 2H), 1.76-1.60 (m, 2H), 1.47-1.36 (m, 1H), 1.36-1.27 (m, 1H), 1.08 (s, 3H). LC-MS: Anal. Calcd. for [M+H]$^+$ $C_8H_{16}NO_3$: 174.11. found 174.19.

Cap-191 (Enantiomer-1)

To a solution of Cap-191, step e (0.0669 g, 0.386 mmol) and sodium carbonate (0.020 g, 0.193 mmol) in sodium hydroxide (1M aq.; 0.4 ml, 0.40 mmol) at 0° C. was added methyl chloroformate (0.035 ml, 0.453 mmol) dropwise. The reaction was removed from the cold bath and allowed to stir at ~25° C. for 3 h. The reaction was washed with diethyl ether (3×20 mL). The aqueous layer was acidified with 12 N HCl (pH~1-2), and extracted with ethyl acetate (2×20 mL). The combined organic layers were dried ($MgSO_4$), filtered, and concentrated in vacuo to afford Cap-191 as a colorless film (66.8 mg). $^1$H NMR (400 MHz, DMSO-$d_6$) δ ppm 13.10-12.37 (bs, 1H), 7.37 (d, J=9.04, 1H), 4.02 (d, J=9.29, 1H), 3.72-3.57 (m, 2H), 3.56 (s, 3H), 3.54-3.44 (m, 2H), 1.65 (ddd, J=13.61, 9.72, 4.27, 1H), 1.53 (ddd, J=13.68, 9.66, 4.27, 1H), 1.41-1.31 (m, 1H), 1.31-1.22 (m, 1H), 1.00 (s, 3H). LC-MS: Anal. Calcd. for [M+Na]$^+$ $C_{10}H_{17}NO_5Na$: 254.10. found 254.11.

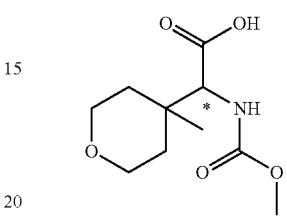

Cap-192 (Enantiomer-2)

Cap-192 (Enantiomer-2) was prepared from Cap-191, step d1 according to the procedure described for the preparation of its enantiomer Cap-191.

INTERMEDIATES
Scheme 1

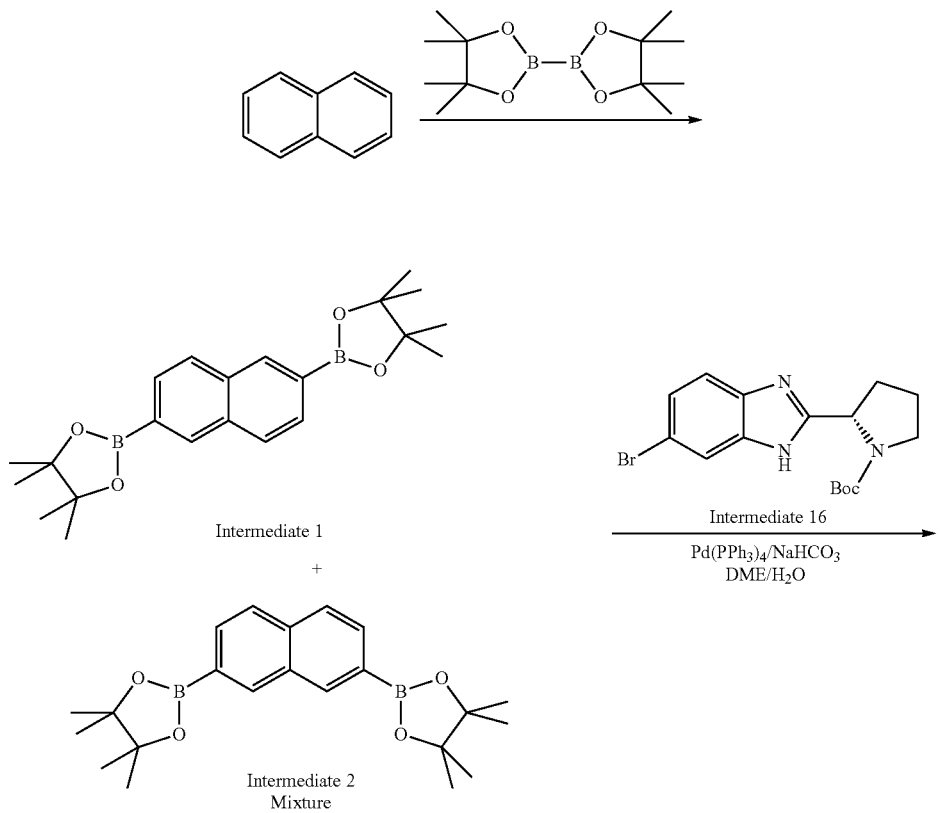

-continued
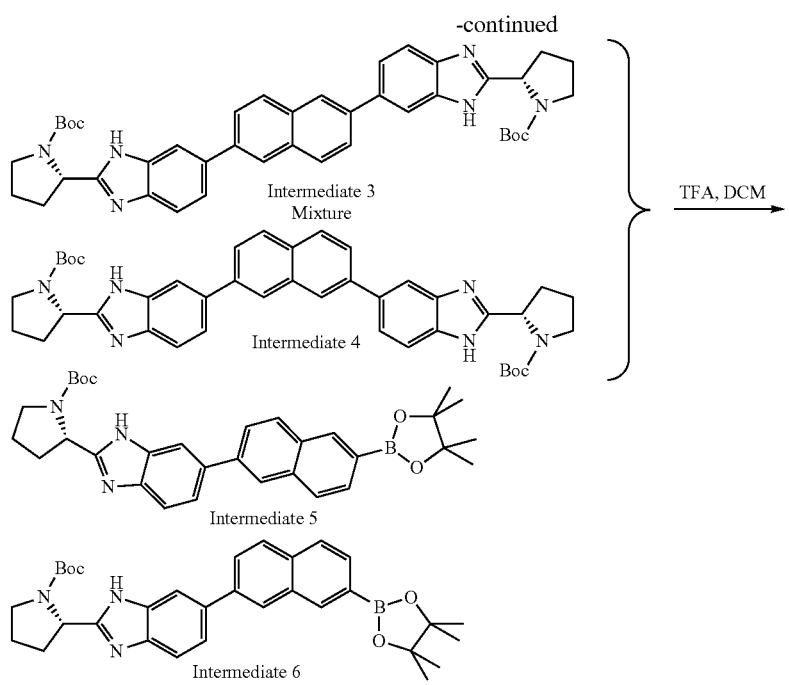
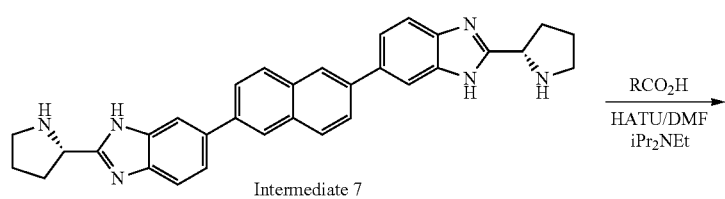
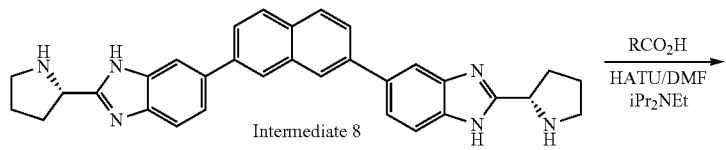
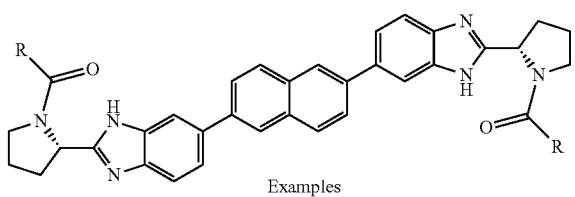
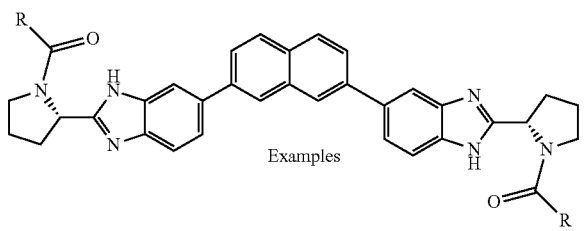

Mixture of Intermediate 1

2,6-Bis(4,4,5,5-tetramethyl-1,3,2-dioxaborolan-2-yl)naphthalene and

Intermediate 2

2,7-Bis(4,4,5,5-tetramethyl-1,3,2-dioxaborolan-2-yl)naphthalene

To a degassed solution of naphthalene (19.34 g, 151 mmol) and bis(pinacolato)diboron (84 g, 330 mmol) in cyclohexane (500 mL) was added 4,4'-di-tert-buthyl-2,2'-dipyridyl (4.05 g, 15.1 mmol) and di-μ-methoxybis(1,5-cyclooctadiene)diirridium (I) (5.0 g, 7.5 mmol). The flask was sealed and heated at 80° C. for 16 h then allowed to cool to room temperature. The reaction color turned dark red upon heating. The volatile component was removed in vacuo and the resulting material was purified with flash chromatography (sample was dry loaded on silica gel and eluted with 0-100% ethyl acetate/toluene) to afford a mixture of 2,6-bis(4,4,5,5-tetramethyl-1,3,2-dioxaborolan-2-yl)naphthalene and 2,7-bis(4,4,5,5-tetramethyl-1,3,2-dioxaborolan-2-yl)naphthalene (54.57 g, 95% yield, 1.5:1 ratio) as white solid.

Intermediate 1: $^1$H NMR (500 MHz, benzene-$d_6$) δ ppm 8.70 (s, 2H), 8.16 (d, J=8.2 Hz, 2H), 7.75 (d, J=8.2 Hz, 2H), 1.15 (s, 24H).

Intermediate 2: $^1$H NMR (500 MHz, benzene-$d_6$) δ ppm 8.77 (s, 2H), 8.22 (d, J=8.2 Hz, 2H), 7.66 (d, J=8.2 Hz, 2H). 1.15 (s, 24H).

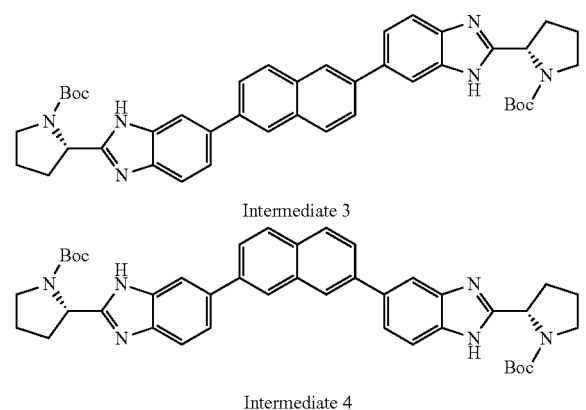

Intermediate 3

Intermediate 4

Mixture of Intermediate 3

(2S,2'S)-tert-Butyl 2,2'-(6,6'-(naphthalene-2,6-diyl)bis(1H-benzo[d]imidazole-6,2-diyl))dipyrrolidine-1-carboxylate and

Intermediate 4

(2S,2'S)-tert-Butyl 2,2'-(5,5'-(naphthalene-2,7-diyl)bis(1H-benzo[d]imidazole-5,2-diyl))dipyrrolidine-1-carboxylate To a mixture of 2,6-bis(4,4,5,5-tetramethyl-1,3,2-dioxaborolan-2-yl)naphthalene and 2,7-bis(4,4,5,5-tetramethyl-1,3,2-dioxaborolan-2-yl)naphthalene (1.5:1) (1.25 g, 3.29 mmol) and (S)-tert-butyl 2-(6-bromo-1H-benzo[d]imidazol-2-yl)pyrrolidine-1-carboxylate (3.01 g, 8.22 mmol) in 1,2-dimethoxyethane (50 mL) and water (12.5 mL) was added NaHCO$_3$ (1.38 g, 16.4 mmol). The reaction mixture was degassed in vacuo and flushed with nitrogen. Pd(Ph$_3$P)$_4$ (190 mg, 0.164 mmol) was added and the pressure flask was capped and heated with an oil bath at 85° C. for 16 hours. The volatile component was removed in vacuo. The residue was partitioned between ethyl acetate and water. The layers were separated and the aqueous phase was extracted several times with ethyl acetate. The combined organic phases were filtered through a pad of diatomaceous earth (CELITE®) and the filtrate was dried (Na$_2$SO$_4$), filtered and concentrated in vacuo. The resulting material was purified with flash chromatography (sample was dry loaded on silica gel and eluted with 10-100% ethyl acetate/CH$_2$Cl$_2$) then flushed with (10% methanol/CH$_2$Cl$_2$) to afford a mixture of (2S,2'S)-tert-butyl 2,2'-(6,6'-(naphthalene-2,6-diyl)bis(1H-benzo[d]imidazole-6,2-diyl))dipyrrolidine-1-carboxylate and (2S,2'S)-tert-butyl 2,2'-(5,5'-(naphthalene-2,7-diyl)bis(1H-benzo[d]imidazole-5,2-diyl))dipyrrolidine-1-carboxylate (622 mg, 27.1% yield) as orange solid which was used without further purification. An aliquot was purified by a reverse phase HPLC (water/acetonitrile/TFA) to provide an analytical sample of each intermediate as a TFA salt.

Analytical data for Intermediate 3: LC-MS retention time 1.46 min; calcd. for C$_{42}$H$_{46}$N$_6$O$_4$: 698.36. found m/z 699.26 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.28 (br s, 2H), 8.13 (t, J=8.7 Hz, 4H), 8.05 (t, J=8.4 Hz, 2H), 7.92 (dd, J=14.8, 8.7 Hz, 3H), 5.20-5.36 (m, 2H), 3.70-3.84 (m, 2H), 3.57-3.70 (m, 2H), 2.54-2.70 (m, 2H), 2.18-2.28 (m, 2H), 2.14 (quin, J=6.9 Hz, 4H), 1.50 (s, 9H), 1.23 (s, 9H).

Analytical data for Intermediate 4: LC-MS retention time 1.52 min; calcd. for C$_{42}$H$_{46}$N$_6$O$_4$: 698.36. found m/z 699.24 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.33 (br s, 2H), 7.98-8.17 (m, 6H), 7.83-7.98 (m, 4H), 5.18-5.35 (m, 2H), 3.71-3.83 (m, 2H), 3.57-3.70 (m, 2H), 2.63 (br s, 2H), 2.19-2.28 (m, 2H), 2.07-2.18 (m, 4H), 1.50 (s, 9H), 1.22 (s, 9H).

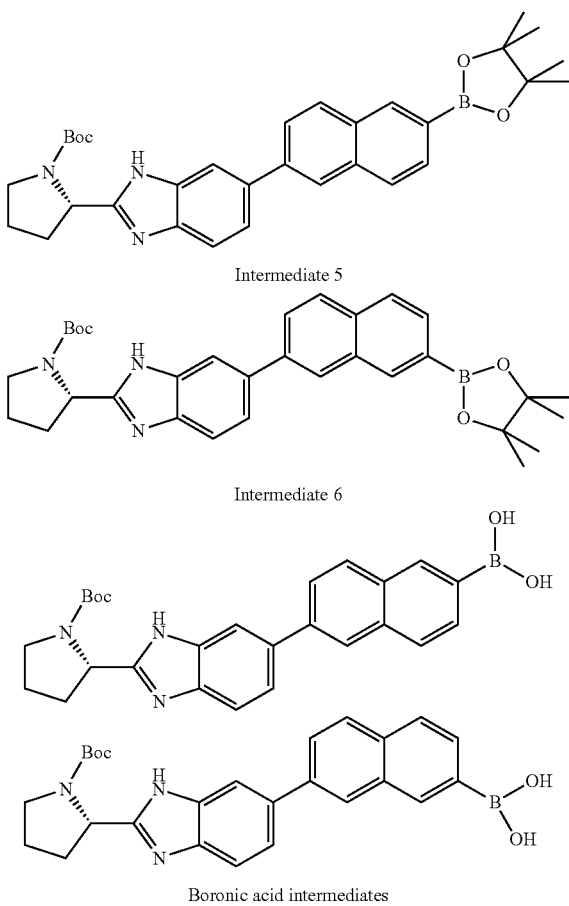

Intermediate 5

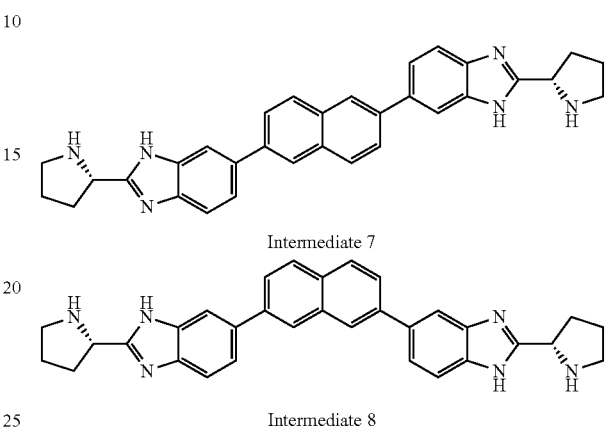

Intermediate 7

Intermediate 8

Mixture of Intermediate 5

(S)-tert-Butyl 2-(6-(6-(4,4,5,5-tetramethyl-1,3,2-dioxaborolan-2-yl)naphthalen-2-yl)-1H-benzo[d]imidazol-2-yl)pyrrolidine-1-carboxylate trifluoroacetate and

Intermediate 6

(S)-tert-Butyl 2-(6-(7-(4,4,5,5-tetramethyl-1,3,2-dioxaborolan-2-yl)naphthalen-2-yl)-1H-benzo[d]imidazol-2-yl)pyrrolidine-1-carboxylate trifluoroacetate After flash chromatography purification, the above reaction also provided a mixture of (S)-tert-butyl 2-(6-(6-(4,4,5,5-tetramethyl-1,3,2-dioxaborolan-2-yl)naphthalen-2-yl)-1H-benzo[d]imidazol-2-yl)pyrrolidine-1-carboxylate trifluoroacetate and (S)-tert-butyl 2-(6-(7-(4,4,5,5-tetramethyl-1,3,2-dioxaborolan-2-yl)naphthalen-2-yl)-1H-benzo[d]imidazol-2-yl)pyrrolidine-1-carboxylate (658 mg). During the HPLC separation (TFA buffer) the boronic esters partially hydrolyzed to afford the same mixture as boronic acid intermediates. LC-MS retention time 1.34 min (boronic acids) and 2.05 (boronic esters); calcd. for (boronic acids) $C_{26}H_{28}BN_3O_4$: 457.22. Found m/z 458.14 $[M+H]^+$. For (boronic esters) $[M+H]^+$ $C_{32}H_{38}BN_3O_4$: 539.3. found m/z 490.16 $[M]^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA.

Intermediate 7

2,6-Bis(2-((S)-pyrrolidin-2-yl)-1H-benzo[d]imidazol-6-yl)naphthalene and

Intermediate 8

2,7-Bis(2-((S)-pyrrolidin-2-yl)-1H-benzo[d]imidazol-6-yl)naphthalene

A mixture of (2S,2'S)-tert-butyl 2,2'-(6,6'-(naphthalene-2,6-diyl)bis(1H-benzo[d]imidazole-6,2-diyl))dipyrrolidine-1-carboxylate and (2S,2'S)-tert-butyl 2,2'-(5,5'-(naphthalene-2,7-diyl)bis(1H-benzo[d]imidazole-5,2-diyl))dipyrrolidine-1-carboxylate (594 mg, 0.162 mmol) and TFA (2 mL) in $CH_2Cl_2$ (10 mL) was stirred at ambient conditions for 3 hours. The volatile component was removed in vacuo and the crude material was purified by a reverse phase HPLC (water/acetonitrile/TFA) to provide a TFA salt of 2,6-bis(2-((S)-pyrrolidin-2-yl)-1H-benzo[d]imidazol-6-yl)naphthalene (434 mg) as yellow solid and a TFA salt of 2,7-bis(2-((S)-pyrrolidin-2-yl)-1H-benzo[d]imidazol-6-yl)naphthalene (204.8 mg) as yellow solid.

Analytical data for Intermediate 7: LC-MS retention time 1.05 min; calcd. for $C_{32}H_{30}N_6$ 498.25. found m/z 499.21 $[M+H]^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.18 (s, 1H), 8.06 (d, J=8.6 Hz, 1H), 8.00 (s, 1H), 7.84-7.92 (m, 1H), 7.73-7.81 (m, 2H), 5.08 (t, J=7.6 Hz, 1H), 3.56-3.66 (m, 1H), 3.48-3.56 (m, 1H), 2.62-2.71 (m, 1H), 2.36-2.47 (m, 1H), 2.19-2.36 (m, 2H).

Analytical data for Intermediate 8: LC-MS retention time 1.11 min; calcd. for $C_{32}H_{30}N_6$ 498.25. Found m/z 499.20 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.23 (s, 2H), 8.01 (m, 4H), 7.82-7.89 (m, 2H), 7.69-7.82 (m, 4H), 5.08 (t, J=7.6 Hz, 2H), 3.57-3.66 (m, 2H), 3.48-3.57 (m, 2H), 2.60-2.73 (m, 2H), 2.37-2.48 (m, 2H), 2.19-2.36 (m, 4H).

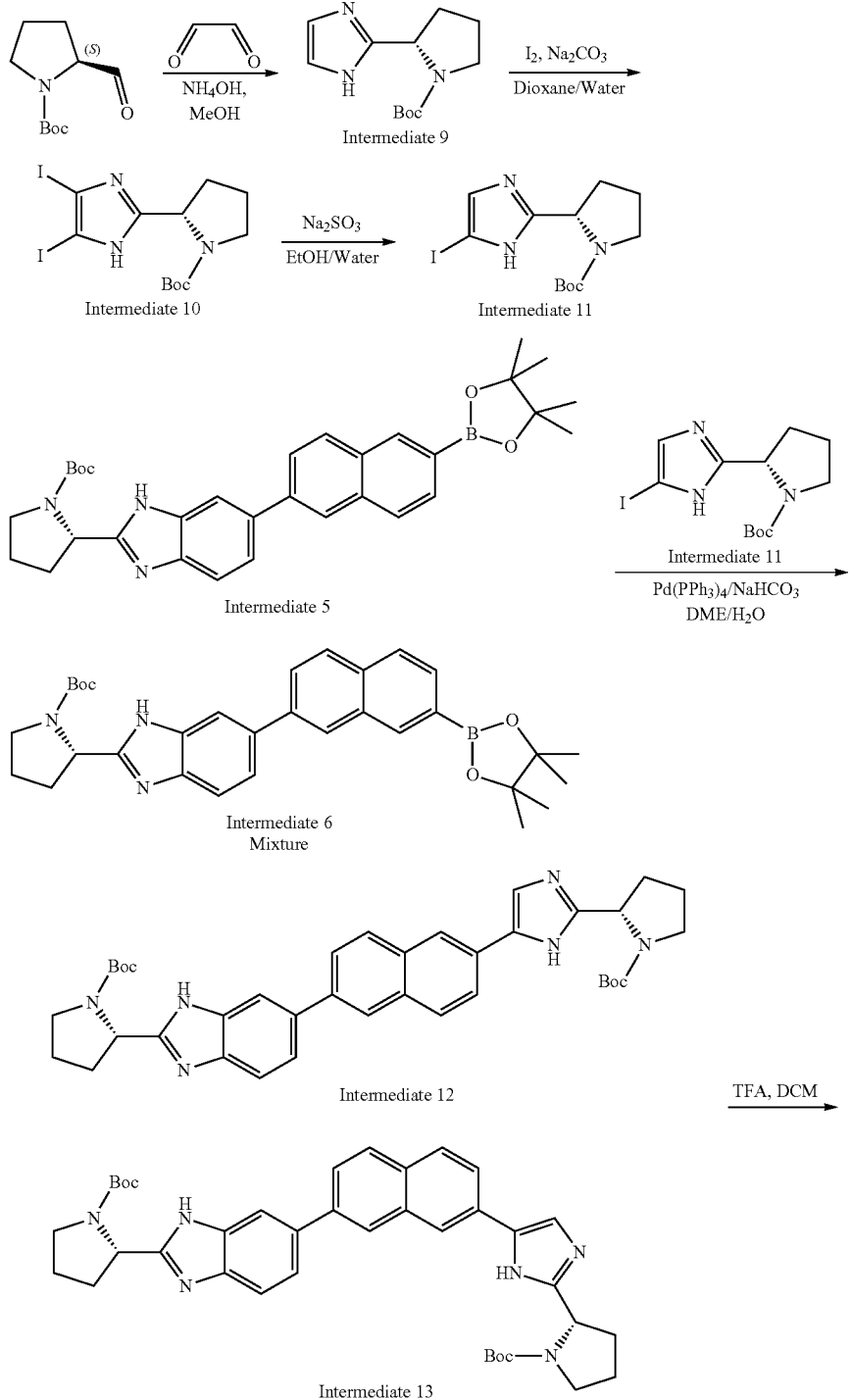

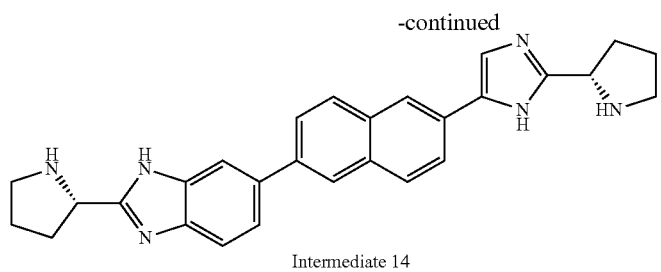

Intermediate 14

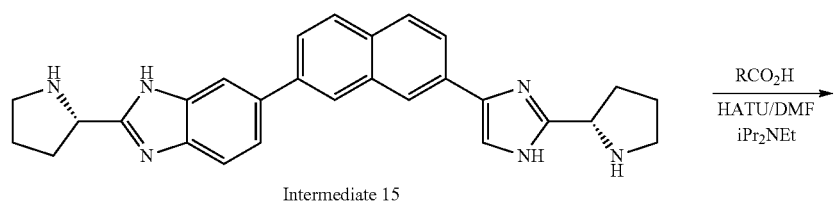

Intermediate 15

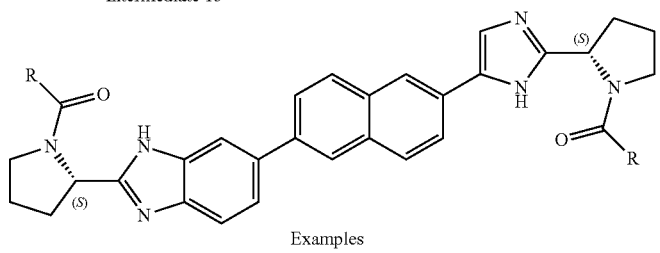

Examples

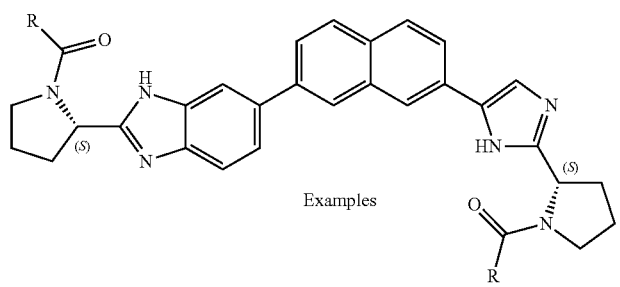

Examples

Intermediate 9

(S)-tert-Butyl 2-(1H-imidazol-2-yl)pyrrolidine-1-carboxylate

Glyoxal (2.0 mL of 40% in water) was added dropwise over 11 minutes to a methanol solution of NH$_4$OH (32 mL) and (S)-Boc-prolinal (8.56 g, 43.0 mmol) and the reaction was stirred at ambient temperature for 19 hours. The volatile component was removed in vacuo and the residue was purified by a flash chromatography (silica gel, ethyl acetate) followed by a recrystallization (ethyl acetate, room temperature) to provide (S)-tert-butyl 2-(1H-imidazol-2-yl)pyrrolidine-1-carboxylate as a white fluffy solid (4.43 g, 18.6 mmol, 43% yield). $^1$H NMR (DMSO-d$_6$, 400 MHz) δ ppm 11.68/11.59 (br s, 1H), 6.94 (s, 1H), 6.76 (s, 1H), 4.76 (m, 1H), 3.48 (m, 1H), 3.35-3.29 (m, 1H), 2.23-1.73 (m, 4H), 1.39/1.15 (s, 9H). LC-MS. RT=0.87 min; >95% homogeneity index; LC-MS: Anal. Calcd. for [M+H]$^+$ C$_{12}$H$_{20}$N$_3$O$_2$ 238.16. found 238.22. The compound shown to have a 98.9 ee % when analyzed under the chiral HPLC conditions noted below.
Column: CHIRALPAK® AD, 10 um, 4.6×50 mm
Solvent: 1.7% ethanol/heptane (isocratic)
Flow rate: 1 mL/min
Wavelength: either 220 or 256 nm
Relative retention time: 3.25 min (R), 5.78 minutes (S)

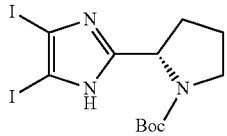 [SMILES: CC(C)(C)OC(=O)N1CCC[C@H]1c1nc(I)c(I)[nH]1]

Intermediate 10

(S)-tert-Butyl 2-(4,5-diiodo-1H-imidazol-2-yl)pyrrolidine-1-carboxylate

Iodine (16.17 g, 63.7 mmol) was added to a solution of (S)-tert-butyl 2-(1H-imidazol-2-yl)pyrrolidine-1-carboxylate (6.87 g, 29.0 mmol) and sodium carbonate (9.21 g, 87 mmol) in dioxane (72 mL) and water (72 mL) at ambient temperature. The flask was covered with aluminum foil and stirrer for 16 hours. The reaction mixture was diluted with ethyl acetate and a saturated aqueous solution of sodium thiosulfate. The mixture was stirred for 15 minutes and the phases were separated. The aqueous phase was extracted several times with ethyl acetate. The combined organic phases were dried (Na$_2$SO$_4$), filtered and concentrated in vacuo to afford (S)-tert-butyl 2-(4,5-diiodo-1H-imidazol-2-yl)pyrrolidine-1-carboxylate (12.5 g 88%) as a tan solid. LC-MS retention time 1.40 min; calcd. for C$_{12}$H$_{17}$I$_2$N$_3$O$_2$ 488.94. found m/z 489.96 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 4.72-4.84 (m, 1H), 3.58-3.70 (m, 1H), 3.43-3.54 (m, 1H), 2.36 (br s, 1H), 1.88-2.08 (m, 3H), 1.47 (br s, 3H), 1.27 (br s, 6H).

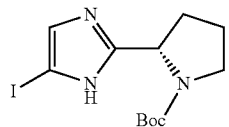 [SMILES: CC(C)(C)OC(=O)N1CCC[C@H]1c1ncc(I)[nH]1]

Intermediate 11

(S)-tert-Butyl 2-(5-iodo-1H-imidazol-2-yl)pyrrolidine-1-carboxylate

Sodium sulfite (10.31 g, 82 mmol) was added to a solution of (S)-tert-butyl 2-(4,5-diiodo-1H-imidazol-2-yl)pyrrolidine-1-carboxylate (4.0 g, 8.2 mmol) in ethanol (75 mL) and water (75 mL). The suspension was heated with an oil bath at 100° C. for 4 hours and at 90° C. for 16 h. The reaction was diluted with ethyl acetate and water. The layers were separated and the aqueous layer was extracted several times with ethyl acetate. The combined organic phases were dried (brine, Na$_2$SO$_4$), filtered and concentrated in vacuo. The residue was purified by a flash chromatography (sample was dry loaded on silica gel and eluted with, 0 to 40% ethyl acetate/CH$_2$Cl$_2$) to afford (S)-tert-butyl 2-(5-iodo-1H-imidazol-2-yl)pyrrolidine-1-carboxylate (2.17 g, 73.1%) as a white solid. LC-MS retention time 0.930 min; calcd. for C$_{12}$H$_{18}$I N$_3$O$_2$ 363.04. found m/z 364.06 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 7.52-7.64 (m, 1H), 4.95-5.10 (m, 1H), 3.57-3.70 (m, 1H), 3.47-3.57 (m, 1H), 2.37-2.55 (m, 1H), 1.94-2.10 (m, 3H), 1.46 (s, 4H), 1.27 (s, 5H).

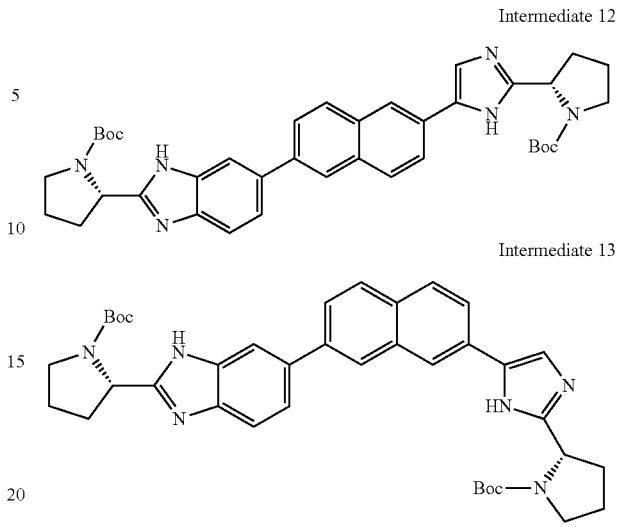

Mixture of Intermediate 12

(S)-tert-Butyl 2-(5-(6-(2-((S)-1-(tert-butoxycarbonyl)pyrrolidin-2-yl)-1H-benzo[d]imidazol-6-yl)naphthalen-2-yl)-1H-imidazol-2-yl)pyrrolidine-1-carboxylate and Intermediate 13

(S)-tert-Butyl 2-(5-(7-(2-((S)-1-(tert-butoxycarbonyl)pyrrolidin-2-yl)-1H-benzo[d]imidazol-6-yl)naphthalen-2-yl)-1H-imidazol-2-yl)pyrrolidine-1-carboxylate To a mixture of (S)-tert-butyl 2-(6-(6-(4,4,5,5-tetramethyl-1,3,2-dioxaborolan-2-yl)naphthalen-2-yl)-1H-benzo[d]imidazol-2-yl)pyrrolidine-1-carboxylate trifluoroacetate and (S)-tert-butyl 2-(6-(7-(4,4,5,5-tetramethyl-1,3,2-dioxaborolan-2-yl)naphthalen-2-yl)-1H-benzo[d]imidazol-2-yl)pyrrolidine-1-carboxylate trifluoroacetate (560 mg, 0.980 mmol) and (S)-tert-butyl 2-(5-iodo-1H-imidazol-2-yl)pyrrolidine-1-carboxylate (463 mg, 1.27 mmol) in 1,2-dimethoxyethane (11.2 mL) and water (2.8 mL) was added NaHCO$_3$ (412 mg, 4.90 mmol). The reaction mixture was degassed in vacuo for 5 minutes and was flushed with nitrogen. Pd(Ph$_3$P)$_4$ (57 mg, 0.049 mmol) was added and the pressure flask was capped and heated with an oil bath at 100° C. for 16 hours. The volatile component was removed in vacuo. The residue was partitioned between ethyl acetate and water and the aqueous phase was extracted several times with ethyl acetate. The combined organic phases were dried (Na$_2$SO$_4$), filtered and concentrated in vacuo. The resulting material was purified with flash chromatography (sample was dry loaded on silica gel and eluted with 50-100% ethyl acetate/hexanes) to afford a partially purified mixture of products which was further purified by a reverse phase HPLC (water/acetonitrile/TFA) to provide a mixture of a TFA salt of (S)-tert-butyl 2-(5-(6-(2-((S)-1-(tert-butoxycarbonyl)pyrrolidin-2-yl)-1H-benzo[d]imidazol-6-yl)naphthalen-2-yl)-1H-imidazol-2-yl)pyrrolidine-1-carboxylate and a TFA salt of (S)-tert-butyl 2-(5-(7-(2-((S)-1-(tert-butoxycarbonyl)pyrrolidin-2-yl)-1H-benzo[d]imidazol-6-yl)naphthalen-2-yl)-1H-imidazol-2-yl)pyrrolidine-1-carboxylate (74 mg). LC-MS retention time 1.32 min; calcd. for [M+H]+ $C_{38}H_{44}N_6O_4$ 648.34. found m/z 649.20 [M+H]+. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/ 90% water/0.1% TFA and Solvent B was 90% acetonitrile/ 10% water/0.1% TFA. The mixture was used without further purification.

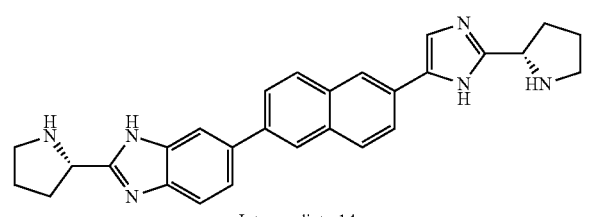

Intermediate 14

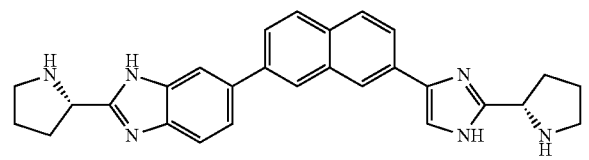

Intermediate 15

Intermediate 14

2-((S)-Pyrrolidin-2-yl)-6-(6-(2-((S)-pyrrolidin-2-yl)-1H-imidazol-5-yl)naphthalen-2-yl)-1H-benzo[d]imidazole and Intermediate 15

2-((S)-Pyrrolidin-2-yl)-6-(7-(2-((S)-pyrrolidin-2-yl)-1H-imidazol-4-yl)naphthalen-2-yl)-1H-benzo[d]imidazole A mixture of (S)-tert-butyl 2-(5-(6-(2-((S)-1-(tert-butoxycarbonyl)pyrrolidin-2-yl)-1H-benzo[d]imidazol-6-yl)naphthalen-2-yl)-1H-imidazol-2-yl)pyrrolidine-1-carboxylate and (S)-tert-butyl 2-(5-(7-(2-((S)-1-(tert-butoxycarbonyl) pyrrolidin-2-yl)-1H-benzo[d]imidazol-6-yl)naphthalen-2-yl)-1H-imidazol-2-yl)pyrrolidine-1-carboxylate as TFA salts (74 mg) and TFA (2 mL) in $CH_2Cl_2$ (10 mL) was stirred at ambient conditions for 4 hours. The volatile component was removed in vacuo. The crude material was purified by a reverse phase HPLC (0 to 50% water/acetonitrile/TFA) to provide a TFA salt of 2-((S)-pyrrolidin-2-yl)-6-(6-(2-((S)-pyrrolidin-2-yl)-1H-imidazol-5-yl)naphthalen-2-yl)-1H-benzo[d]imidazole (32 mg, 31%) as yellow oil and a TFA salt of 2-((S)-pyrrolidin-2-yl)-6-(7-(2-((S)-pyrrolidin-2-yl)-1H-imidazol-4-yl)naphthalen-2-yl)-1H-benzo[d]imidazole (16 mg) as yellow oil.

Analytical data for Intermediate 14: LC-MS retention time 0.081 min; calcd. for $C_{38}H_{28}N_6$ 448.24. found m/z 449.20 [M+H]+. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.33 (s, 1H), 8.17 (s, 1H), 8.03 (d, J=3.7 Hz, 1H), 8.01 (s, 2H), 7.92-7.97 (m, 1H), 7.87-7.92 (m, 1H), 7.75-7.80 (m, 3H), 5.11 (t, J=7.8 Hz, 1H), 4.99 (t, J=7.9 Hz, 1H), 3.49-3.69 (m, 4H), 2.56-2.76 (m, 2H), 2.41-2.52 (m, 2H), 2.21-2.41 (m, 4H).

Analytical data for Intermediate 15: LC-MS retention time 0.87 min; calcd. for $C_{38}H_{28}N_6$ 448.24. found m/z 449.21 [M+H]+. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.39 (s, 1H), 8.19 (s, 1H), 7.97-8.04 (m, 3H), 7.91 (d, J=8.6 Hz, 1H), 7.87 (d, J=8.6 Hz, 1H), 7.85 (s, 1H), 7.78 (s, 2H), 5.12 (t, J=7.6 Hz, 1H), 5.04 (t, J=8.1 Hz, 1H), 3.50-3.68 (m, 4H), 2.60-2.74 (m, 2H), 2.41-2.55 (m, 2H), 2.21-2.41 (m, 4H).

Scheme 3

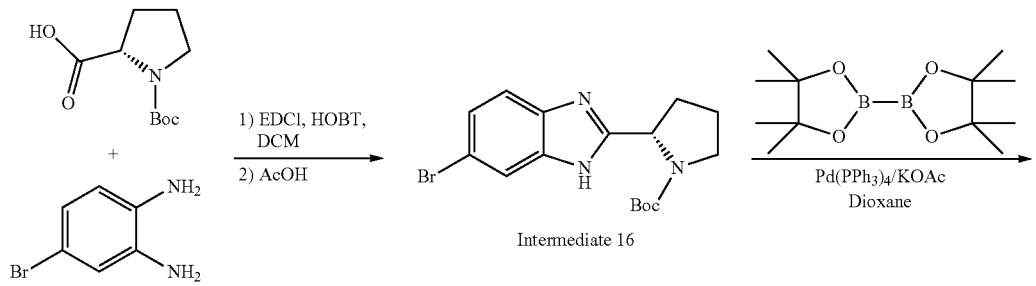

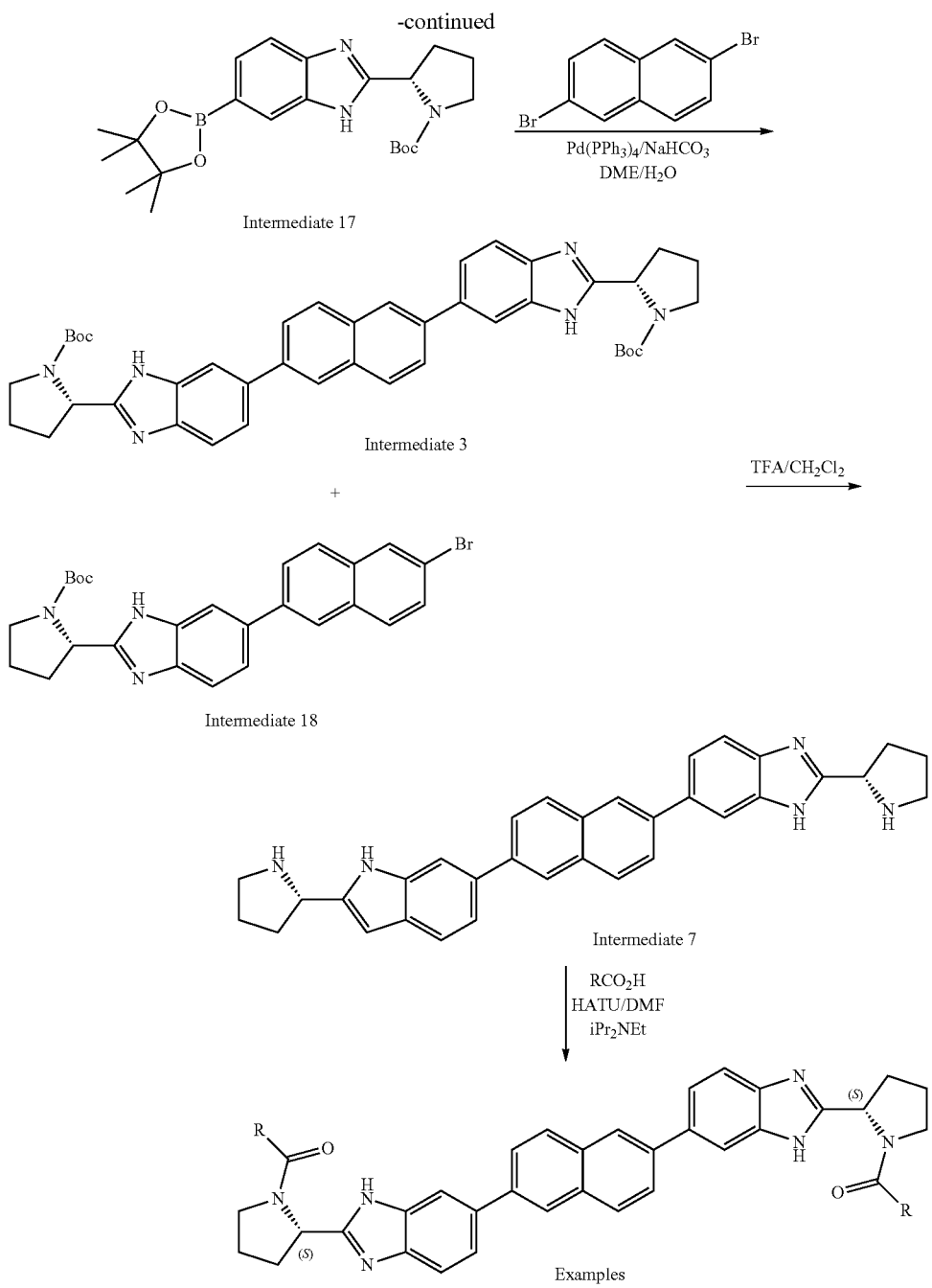

Intermediate 16

(S)-tert-Butyl 2-(6-bromo-1H-benzo[d]imidazol-2-yl)pyrrolidine-1-carboxylate EDCI.HCl (16.9 g, 88.0 mmol) was added to a mixture of 4-bromobenzene-1,2-diamine (15.0 g, 80.0 mmol), N-Boc-L-proline (18.13 g, 84.0 mmol) and 1-hydroxybenzotriazole (12.28 g, 80.0 mmol) in $CH_2Cl_2$ (500 mL) and stirred at ambient conditions for 16 h. The mixture was then diluted with water. The resulting white precipitate was filtered away and the layers were separated. The organic layer was washed with water, dried (brine; $Na_2SO_4$), filtered and concentrated in vacuo to provide a brown foam. Acetic acid (300 mL) was added to the foam and the mixture was heated at 85° C. (bath temperature) for 5 h. The volatile component was removed in vacuo and the residue was dissolved in EtOAc, washed with water and the organic phase was dried ($Na_2SO_4$), filtered and concentrated in vacuo. The resultant crude material was submitted to flash chromatography (silica gel; 0-37% EtOAc/$CH_2Cl_2$). The partially pure material was re-submitted to flash chromatography (silica gel; 20-35% EtOAc/$CH_2Cl_2$) to provide (S)-tert-butyl 2-(6-bromo-1H-benzo[d]imidazol-2-yl)pyrrolidine-1-carboxylate (17.98 g, 61.2% yield) as yellow foam. LC-MS retention time 1.23 min; calcd. for $C_{16}H_{20}BrN_3O_2$: 365.07. found m/z 368.07 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD) δ ppm 7.59-7.75 (m., 1H), 7.38-7.53 (m, 1H), 7.31-7.38 (m, 1H), 5.04-5.09 (m, 0.3H), 4.94-5.00 (m, 0.7H), 3.68-3.76 (m, 1H), 3.50-3.59 (m, 1H), 2.34-2.51 (m., 1H), 1.95-2.12 (m., 3H), 1.47 (br s, 3H), 1.15 (s, 6H).

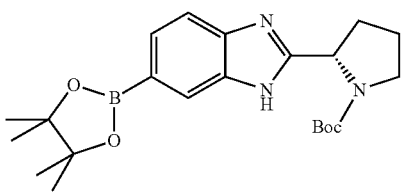 [SMILES: CC(C)(C)OC(=O)N1CCC[C@H]1c1nc2ccc(B3OC(C)(C)C(C)(C)O3)cc2[nH]1]

Intermediate 17

(S)-tert-Butyl 2-(6-(4,4,5,5-tetramethyl-1,3,2-dioxaborolan-2-yl)-1H-benzo[d]imidazol-2-yl)pyrrolidine-1-carboxylate To a flask containing a mixture of (S)-tert-butyl 2-(6-bromo-1H-benzo[d]imidazol-2-yl)pyrrolidine-1-carboxylate (4.5 g, 12 mmol) and bis(pinacolato)diboron (6.55 g, 25.8 mmol) in 1,4-dioxane (50 mL) was added potassium acetate (3.01 g, 30.7 mmol). The reaction flask was degassed in vacuo for 5 minutes and then purged with nitrogen. The catalyst Pd(Ph$_3$P)$_4$ (710 mg, 0.614 mmol) was added and the flask was capped and heated with an oil bath at 85° C. (bath temperature) for 16 h. The reaction mixture was concentrated in vacuo. The crude material was partitioned between CH$_2$Cl$_2$ and a saturated NaHCO$_3$ solution and the aqueous layer was extracted with CH$_2$Cl$_2$. The combined organic phase was dried (brine, Na$_2$SO$_4$), filtered and concentrated in vacuo. The resulting material was purified with flash chromatography (sample was dry loaded on silica gel and eluted with 10-50% ethyl acetate/CH$_2$Cl$_2$) to provide (S)-tert-butyl 2-(6-(4,4,5,5-tetramethyl-1,3,2-dioxaborolan-2-yl)-1H-benzo[d]imidazol-2-yl)pyrrolidine-1-carboxylate (2.80 g, 55% yield) as white solid. LC-MS retention time 1.493 min; calcd. for C$_{22}$H$_{32}$BN$_3$O$_4$: 413.25. found m/z 414.23 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (400 MHz, MeOD) δ ppm 7.81-8.08 (m, 1H), 7.40-7.68 (m., 2H), 4.95-5.13 (m, 1H), 3.68-0.3.79 (br s, 1H), 3.48-3.60 (br s, 1H), 2.35-2.52 (br s, 1H), 1.95-2.15 (m, 3H), 1.46 (s, 3H), 1.37 (s, 12H), 1.13 (s, 6H).

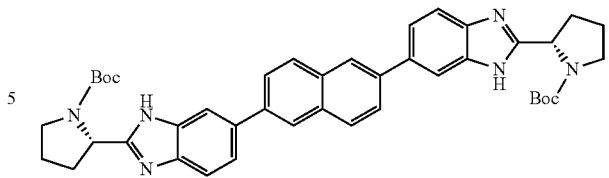

Intermediate 3 tert-Butyl 2-(5-(6-(2-(1-(tert-butoxycarbonyl)-2-pyrrolidinyl)-1H-benzimidazol-6-yl)-2-naphthyl)-1H-benzimidazol-2-yl)-1-pyrrolidinecarboxylate To a mixture of (S)-tert-butyl 2-(6-(4,4,5,5-tetramethyl-1,3,2-dioxaborolan-2-yl)-1H-benzo[d]imidazol-2-yl)pyrrolidine-1-carboxylate (1.29 g, 33.1 mmol) and 2,6-dibromonaphthalene (446 mg, 1.56 mmol) in 1,2-dimethoxyethane (20 mL) and water (6 mL) was added NaHCO$_3$ (787 mg, 9.36 mmol). The reaction mixture was degassed in vacuo for 10 minutes and was flushed with nitrogen. The catalyst Pd(Ph$_3$P)$_4$ (90 mg, 0.078 mmol) was added and the flask was capped and heated with an oil bath at 100° C. for 16 hours. The volatile component was removed in vacuo. The residue was partitioned between CH$_2$Cl$_2$ and water and the layers were separated. The aqueous phase was extracted several times with CH$_2$Cl$_2$ and the combined organic phases were dried (brine, Na$_2$SO$_4$), filtered and concentrated in vacuo. The resulting material was purified with flash chromatography (sample was dry loaded on silica gel and eluted with 0-70% ethyl acetate/CH$_2$Cl$_2$) to afford tert-butyl 2-(5-(6-(2-(1-(tert-butoxycarbonyl)-2-pyrrolidinyl)-1H-benzimidazol-6-yl)-2-naphthyl)-1H-benzimidazol-2-yl)-1-pyrrolidinecarboxylate (605 mg) as yellow solid. LC-MS retention time 1.46 min; calcd. for C$_{42}$H$_{46}$N$_6$O$_4$: 698.36. found m/z 699.26 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA $^1$H NMR (500 MHz, MeOD) δ ppm 8.28 (br s, 2H), 8.13 (t, J=8.7 Hz, 4H), 8.05 (t, J=8.4 Hz, 2H), 7.92 (dd, J=14.8, 8.7 Hz, 4H), 5.20-5.36 (m, 2H), 3.70-3.84 (m, 2H), 3.57-3.70 (m, 2H), 2.54-2.70 (m, 2H), 2.18-2.28 (m, 2H), 2.14 (quin, J=6.9 Hz, 4H), 1.50 (s, 9H), 1.23 (s, 9H).

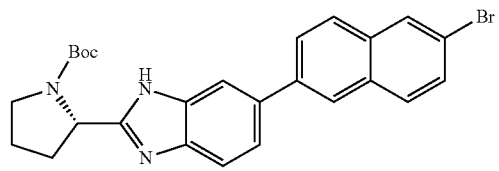 [SMILES: CC(C)(C)OC(=O)N1CCC[C@H]1c1nc2ccc(-c3ccc4cc(Br)ccc4c3)cc2[nH]1]

Intermediate 18 tert-Butyl (2S)-2-(5-(6-bromo-2-naphthyl)-1H-benzimidazol-2-yl)-1-pyrrolidinecarboxylate The above reaction also provided tert-butyl (2S)-2-(5-(6-bromo-2-naphthyl)-1H-benzimidazol-2-yl)-1-pyrrolidinecarboxylate (519 mg) as yellow solid. LC-MS retention time 1.88 min; calcd. for [M+H]+ $C_{26}H_{26}BrN_3O_2$: 491.12. found m/z 494.04 [M+H]+. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.21 (d, J=8.6 Hz, 1H), 8.05-8.14 (m, 2H), 7.93-8.05 (m, 2H), 7.82-7.93 (m, 3H), 7.57-7.67 (m, 1H), 5.28 (br s, 1H), 3.98 (s, 1H), 3.70-3.80 (m, 1H), 3.57-3.70 (m, 1H), 2.54-2.71 (m, 1H), 2.17-2.29 (m, 1H), 2.09-2.17 (m, 2H), 1.49 (s, 4H), 1.22 (s, 5H).

Intermediate 7

5,5'-(2,6-Naphthalenediyl)bis(2-(2-pyrrolidinyl)-1H-benzimidazole)

A mixture of tert-butyl 2-(5-(6-(2-(1-(tert-butoxycarbonyl)-2-pyrrolidinyl)-1H-benzimidazol-6-yl)-2-naphthyl)-1H-benzimidazol-2-yl)-1-pyrrolidinecarboxylate (591 mg. 0.844 mmol) and TFA (2 mL) in $CH_2Cl_2$ (10 mL) was stirred at ambient conditions for 2 hours. The volatile component was removed in vacuo and the resulting material was loaded onto a MCX column, flushed with methanol, released with 2.0 M $NH_3$/methanol elution) and concentrated to provide 5,5'-(2,6-naphthalenediyl)bis(2-(2-pyrrolidinyl)-1H-benzimidazole) (419 mg) as tan solid. LC-MS retention time 1.02 min; calcd. for $C_{33}H_{31}N_5$: 498.25. found m/z 499.25 [M+H]+. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.18 (s, 1H), 8.06 (d, J=8.6 Hz, 1H), 8.00 (s, 1H), 7.84-7.92 (m, 1H), 7.73-7.81 (m, 2H), 5.08 (t, J=7.6 Hz, 1H), 3.56-3.66 (m, 1H), 3.48-3.56 (m, 1H), 2.62-2.71 (m, 1H), 2.36-2.47 (m, 1H), 2.19-2.36 (m, 2H).

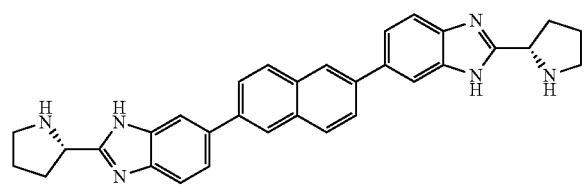

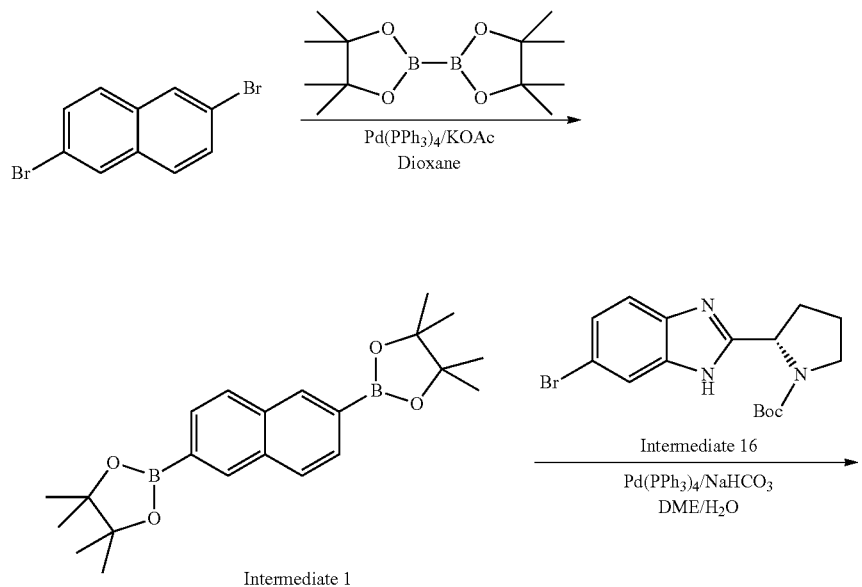

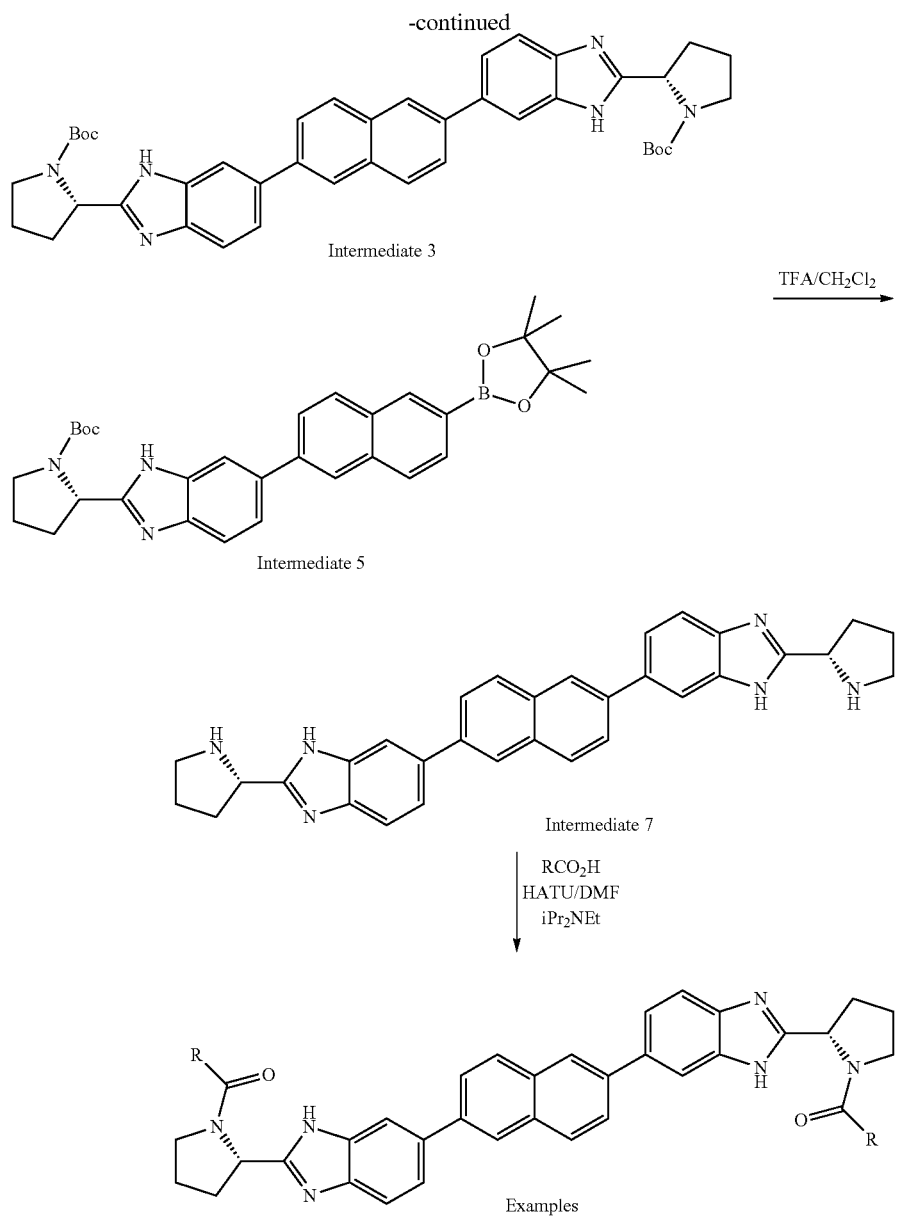

Intermediate 3

Intermediate 5

Intermediate 7

Examples

Intermediate 1

2,6-Bis(4,4,5,5-tetramethyl-1,3,2-dioxaborolan-2-yl) naphthalene

A pressure flask containing a mixture of 2,6-dibromonaphthalene (8.0 g, 28 mmol), bis(pinacolato)diboron (21.3 g, 84.0 mmol), potassium acetate (3.01 g, 30.7 mmol) and 1,4-dioxane (50 mL) was degassed in vacuo for 5 minutes and purged with nitrogen. The catalyst $Pd(Ph_3P)_4$ (710 mg, 0.614 mmol) was added. The flask was capped and heated with an oil bath at 85° C. (bath temperature) for 16 hours. The reaction mixture was concentrated in vacuo and the crude material was partitioned between $CH_2Cl_2$ and a saturated $NaHCO_3$ solution. The aqueous layer was extracted with $CH_2Cl_2$ and the combined organic phases was dried ($Na_2SO_4$), filtered and concentrated in vacuo. The resulting material was purified with flash chromatography (sample was dry loaded on silica gel and eluted with 50-100% $CH_2Cl_2$/Hexanes) to provide 2,6-bis(4,4,5,5-tetramethyl-1,3,2-dioxaborolan-2-yl) naphthalene contaminated with bis(pinacolato)diboron. The solid was dissolved into $CH_2Cl_2$ and methanol was added until precipitation was observed. The precipitate was collected by filtration to afford 2,6-bis(4,4,5,5-tetramethyl-1,3,2-dioxaborolan-2-yl)naphthalene (5.1 g, 48% yield) as white solid. $^1H$ NMR (500 MHz, benzene-$d_6$) δ ppm 8.70 (s, 2H), 8.16 (d, J=8.2 Hz, 2H), 7.75 (d, J=8.2 Hz, 2H), 1.15 (s, 24H).

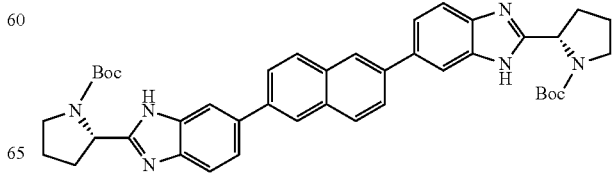

Intermediate 3

(2S,2'S)-tert-Butyl 2,2'-(6,6'-(naphthalene-2,6-diyl) bis(1H-benzo[d]imidazole-6,2-diyl))dipyrrolidine-1-carboxylate To a mixture of 2,6-bis(4,4,5,5-tetramethyl-1,3,2-dioxaborolan-2-yl)naphthalene (2.0 g, 5.3 mmol) and (S)-tert-butyl 2-(6-bromo-1H-benzo[d]imidazol-2-yl)pyrrolidine-1-carboxylate (2.89 g, 7.89 mmol) in 1,2-dimethoxyethane (42.1 mL) and water (10.5 mL) was added NaHCO$_3$ (2.21 g, 26.3 mmol). The reaction mixture was degassed in vacuo and was flushed with nitrogen. The catalyst Pd(Ph$_3$P)$_4$ (90 mg, 0.078 mmol) was added. The flask was capped and heated with an oil bath at 100° C. for 16 hours. The volatile component was removed in vacuo and the residue was partitioned between ethyl acetate and water. The layers were separated and the aqueous phase was extracted several times with ethyl acetate. The combined organic phases were filtered through a pad of diatomaceous earth (CELITE®) and the filtrate was dried (Na$_2$SO$_4$), filtered and concentrated in vacuo. The resulting material was purified with flash chromatography (sample was dry loaded on silica gel and eluted with 0-100% ethyl acetate/hexanes) to afford (2S,2'S)-tert-butyl 2,2'-(6,6'-(naphthalene-2,6-diyl)bis(1H-benzo[d]imidazole-6,2-diyl)) dipyrrolidine-1-carboxylate (761 mg, 21% yield) as orange solid. LC-MS retention time 1.46 min; calcd. for C$_{42}$H$_{46}$N$_6$O$_4$: 698.36. found m/z 699.26 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA $^1$H NMR (500 MHz, MeOD) δ ppm 8.28 (br s, 2H), 8.13 (t, J=8.7 Hz, 4H), 8.05 (t, J=8.4 Hz, 2H), 7.92 (dd, J=14.8, 8.7 Hz, 4H), 5.20-5.36 (m, 2H), 3.70-3.84 (m, 2H), 3.57-3.70 (m, 2H), 2.54-2.70 (m, 2H), 2.18-2.28 (m, 2H), 2.09-2.19 (m, 4H), 1.50 (s, 9H), 1.23 (s, 9H).

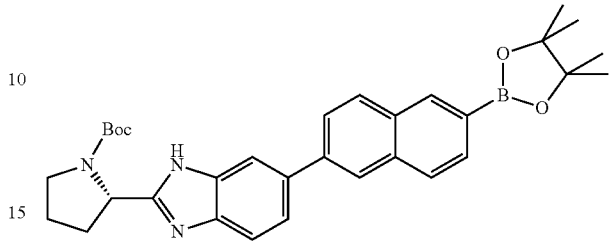

Intermediate 5

(S)-tert-Butyl 2-(6-(6-(4,4,5,5-tetramethyl-1,3,2-dioxaborolan-2-yl)naphthalen-2-yl)-1H-benzo[d] imidazol-2-yl)pyrrolidine-1-carboxylate The above reaction also provided (S)-tert-butyl 2-(6-(6-(4,4,5,5-tetramethyl-1,3,2-dioxaborolan-2-yl)naphthalen-2-yl)-1H-benzo[d]imidazol-2-yl)pyrrolidine-1-carboxylate (1.58 g, 56% yield) as tan solid. LC-MS retention time 1.46 min; calcd. for C$_{32}$H$_{38}$BN$_3$O$_4$: 539.3. found m/z 540.24 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA.

Scheme 5

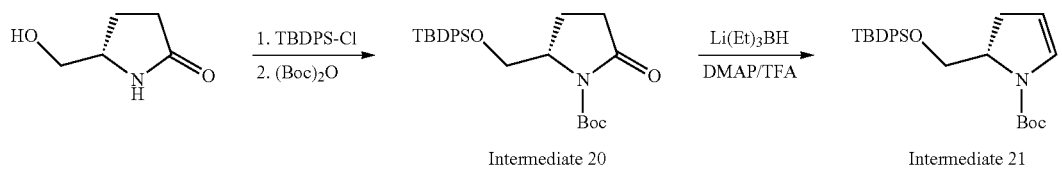

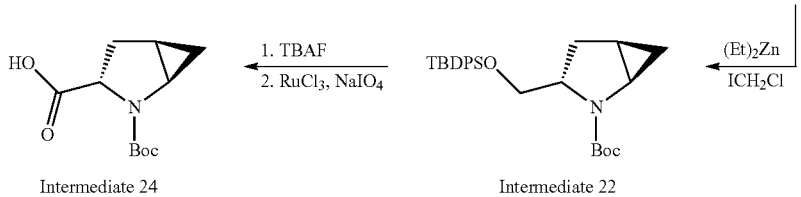

Intermediate 19

(S)-5-((tert-Butyldiphenylsilyloxy)methyl)pyrrolidin-2-one

To a solution of (S)-5-(hydroxymethyl)pyrrolidin-2-one (10 g, 87 mmol) in $CH_2Cl_2$ (50 mL) was added tert-butylchlorodiphenylsilane (25.6 g, 93 mmol), $Et_3N$ (12.1 mL, 87 mmol) and DMAP (1.06 g, 8.7 mmol). The mixture was stirred at room temperature until the starting pyrrolidinone was completely consumed and then diluted with $CH_2Cl_2$ (50 mL) and washed with water (50 mL). The organic layer was dried ($Na_2SO_4$), filtered, evaporated in vacuo and the crude material was submitted to flash chromatography (silica gel; 30 to 100% of EtOAc/hexanes) to afford (S)-5-((tert-butyldiphenylsilyloxy)methyl)pyrrolidin-2-one (22.7 g, 74% yield) as a colorless oil. LC-MS $(M+H)^+=354.58$. $^1H$ NMR (400 MHz, DMSO-$d_6$) δ ppm 7.69 (br s, 1H), 7.64-7.61 (m, 4H), 7.50-7.42 (m, 6H), 3.67-3.62 (m, 1H), 3.58-3.51 (m, 2H), 2.24-2.04 (m, 3H), 1.87-1.81 (m, 1H), 1.00 (s, 9H).

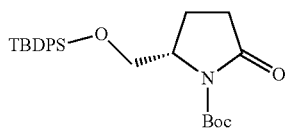

Intermediate 20

(S)-tert-Butyl 2-((tert-butyldiphenylsilyloxy)methyl)-5-oxopyrrolidine-1-carboxylate Di-tert-butyl dicarbonate (38.5 g, 177 mmol) was added in portions as a solid over 10 min to a solution of (S)-5-((tert-butyldiphenylsilyloxy)methyl)pyrrolidin-2-one (31.2 g, 88.3 mmol), $Et_3N$ (8.93 g, 88 mmol) and DMAP (1.08 g, 8.83 mmol) in $CH_2Cl_2$ (200 mL) and the reaction mixture was stirred for 18 h at 24° C. Most of the volatile material was removed in vacuo and the crude material was purified by silica gel chromatography (20% EtOAc/hexanes to 50% EtOAc/hexanes) to afford (S)-tert-butyl 2-((tert-butyldiphenylsilyloxy)methyl)-5-oxopyrrolidine-1-carboxylate (32.65 g, 82% yield) as a white solid. LC-MS $(M-Boc+H)^+=354.58$. $^1H$ NMR (400 MHz, DMSO-$d_6$) δ ppm 7.61-7.59 (m, 2H), 7.56-7.54 (m, 2H), 7.50-7.38 (m, 6H), 4.18 (m, 1H), 3.90 (dd, J=10.4, 3.6, 1H), 3.68 (dd, J=10.4, 2.1, 1H), 2.68-2.58 (m, 1H), 2.40-2.33 (m, 1H), 2.22-2.12 (m, 1H), 2.01-1.96 (m, 1H), 1.35 (s, 9H), 0.97 (s, 9H).

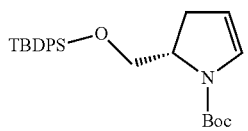

Intermediate 21

(S)-tert-Butyl 2-((tert-butyldiphenylsilyloxy)methyl)-2,3-dihydro-1H-pyrrole-1-carboxylate A three-necked flask equipped with a thermometer and a nitrogen inlet was charged with (S)-tert-butyl 2-((tert-butyldiphenylsilyloxy)methyl)-5-oxopyrrolidine-1-carboxylate (10.05 g, 22.16 mmol) and toluene (36 mL) and lowered into −55° C. cooling bath. When the internal temperature of the mixture reached −50° C., lithium triethylborohydride (23 mL of 1.0 M/THF, 23 mmol) was added dropwise over 30 min and the mixture stirred for 35 min while maintaining the internal temperature between −50° C. and −45° C. Hunig's base (16.5 mL, 94 mmol) was added dropwise over 10 min. Then, DMAP (34 mg, 0.278 mmol) was added in one batch, followed by the addition of trifluoroacetic anhydride (3.6 mL, 25.5 mmol) over 15 min, while maintaining the internal temperature between −50° C. and −45° C. The bath was removed 10 min later and the reaction mixture was stirred for 14 h while allowing it to rise to ambient temperature. The reaction mixture was diluted with toluene (15 mL), cooled with an ice-water bath and treated slowly with water (55 mL) over 5 min. The phases were separated and the organic layer washed with water (50 mL, 2×) and concentrated in vacuo. The crude material was purified by flash chromatography (silica gel; 5% EtOAc/hexanes) to afford (S)-tert-butyl 2-((tert-butyldiphenylsilyloxy)methyl)-2,3-dihydro-1H-pyrrole-1-carboxylate (7.947 g, 82% yield) as a colorless viscous oil. LC-MS: $[M+Na]^+=460.19$. Rt=2.41 min under the following HPLC conditions: Solvent gradient from 100% A: 0% B to 0% A: 100% B (A=0.1% TFA in 1:9 MeOH/water; B=0.1% TFA in 9:1 MeOH/water) over 2 min and hold for 1 min; detection at 220 nm; PHENOMENEX® Luna 3.0×50 mm S10 column. $^1H$ NMR (400 MHz, DMSO-$d_6$) δ ppm 7.62-7.58 (m, 4H), 7.49-7.40 (m, 6H), 6.47 (br s, 1H), 5.07/5.01 (overlapping br d, 1H), 4.18 (br s, 1H), 3.89 (br s, 0.5H), 3.69 (br s, 1.5H), 2.90-2.58 (br m, 2H), 1.40/1.26 (overlapping br s, 9H), 0.98 (s, 9H).

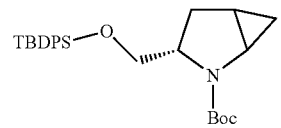

Intermediate 22

(3S)-tert-Butyl 3-((tert-butyldiphenylsilyloxy)methyl)-2-azabicyclo[3.1.0]hexane-2-carboxylate Diethylzinc (19 mL of ~1.1 M in toluene, 21 mmol) was added dropwise over 15 min to a cooled (−30° C.) toluene (27 mL) solution of (S)-tert-butyl 2-((tert-butyldiphenylsilyloxy)methyl)-2,3-dihydro-1H-pyrrole-1-carboxylate (3.94 g, 9.0 mmol). Chloroiodomethane (stabilized over copper; 3.0 mL, 41 mmol) was added dropwise over 10 min and stirred while maintaining the bath temperature at −25° C. for 1 h and between −25° C. and −21° C. for 18.5 h. The reaction mixture was opened to the air and quenched by the slow addition of 50% saturated $NaHCO_3$ solution (40 mL) and then removed from the cooling bath and stirred at ambient temperature for 20 min. The reaction mixture was filtered through a filter paper and the white cake was washed with 50 mL of toluene. The organic phase of the filtrate was separated and washed with water (40 mL, 2×), dried ($MgSO_4$) and concentrated in vacuo. The crude material was purified using by silica gel chromatography (350 g silica gel; sample was loaded with 7% EtOAc/hexanes; eluted with 7-20% EtOAc/hexanes) to afford (3S)-tert-butyl 3-((tert-butyldiphenylsilyloxy)methyl)-2-azabicyclo[3.1.0]hexane-2-carboxylate (3.69 g, 90.7%) as a mixture of cis/trans-isomers. [Note: the exact cis/trans-isomer ratio was not determined at this stage]. LC- MS: [M+Na]⁺=474.14. Rt=2.39 min under the following HPLC conditions: Solvent gradient from 100% A: 0% B to 0% A: 100% B (A=0.1% TFA in 1:9 MeOH/water; B=0.1% TFA in 9:1 MeOH/water) over 2 min and hold for 1 min; detection at 220 nm; PHENOMENEX® Luna 3.0×50 mm S10 column. ¹H NMR (400 MHz, DMSO-$d_6$) δ ppm 7.62-7.60 (m, 4H), 7.49-7.40 (m, 6H), 3.77/3.67 (overlapping br s, 3H), 3.11-3.07 (m, 1H), 2.23 (app br s, 1H), 2.05-2.00 (m, 1H), 1.56-1.50 (m, 1H), 1.33 (very broad s, 9H), 1.00 (s, 9H), 0.80 (m, 1H), 0.30 (m, 1H).

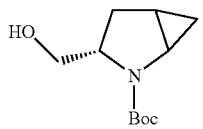

Intermediate 23

(3S)-tert-Butyl 3-(hydroxymethyl)-2-azabicyclo[3.1.0]hexane-2-carboxylate

TBAF (7.27 mL of 1.0 M in THF, 7.27 mmol) was added dropwise over 5 min to a THF (30 mL) solution of (3S)-tert-butyl 3-((tert-butyldiphenylsilyloxy)methyl)-2-azabicyclo[3.1.0]hexane-2-carboxylate (mixture of cis/trans-isomers) (3.13 g, 6.93 mmol) and the mixture was stirred at ambient temperature for 4.75 h. After the addition of saturated NH₄Cl solution (5 mL), most of the volatile material was removed in vacuo and the residue partitioned between CH₂Cl₂ (70 mL) and 50% saturated NH₄Cl solution (30 mL). The aqueous phase was extracted with CH₂Cl₂ (30 mL) and the combined organic phase was dried (MgSO₄), filtered, concentrated in vacuo and then exposed to high vacuum overnight. The crude material was purified using a flash chromatography (silica gel; 40-50% EtOAc/hexanes) to afford (3S)-tert-butyl 3-(hydroxymethyl)-2-azabicyclo[3.1.0]hexane-2-carboxylate (1.39 g, 94% yield) as a mixture of cis/trans-isomers and a colorless oil. [Note: the exact cis/trans-isomer ratio was not determined at this stage.] LC-MS (M+Na)⁺=236.20. ¹H NMR (400 MHz, DMSO-$d_6$, δ=2.5 ppm) δ ppm 4.70 (t, J=5.7, 1H), 3.62-3.56 (m, 1H), 3.49-3.44 (m, 1H), 3.33-3.27 (m, 1H), 3.08-3.04 (m, 1H), 2.07 (br m, 1H), 1.93-1.87 (m, 1H), 1.51-1.44 (m, 1H), 1.40 (s, 9H), 0.76-0.71 (m, 1H), 0.26 (m, 1H).

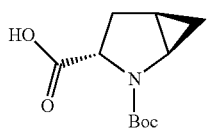 [SMILES: CC(C)(C)OC(=O)N1[C@@H]2C[C@@H]2C[C@H]1C(=O)O]

Intermediate 24

(1R,3S,5R)-2-(tert-Butoxycarbonyl)-2-azabicyclo[3.1.0]hexane-3-carboxylic acid

A semi-solution of NaIO₄ (6.46 g, 30.2 mmol) in water (31 mL) was added to a solution of (3S)-tert-butyl 3-(hydroxymethyl)-2-azabicyclo[3.1.0]hexane-2-carboxylate (mixture of cis/trans-isomers) (2.15 g, 10.08 mmol) in CH₃CN (20 mL) and CCl₄ (20 mL). RuCl₃ (0.044 g, 0.212 mmol) was added immediately and the heterogeneous reaction mixture was stirred vigorously for 75 min. The reaction mixture was diluted with water (60 mL) and extracted with CH₂Cl₂ (50 mL, 3×). The combined organic phases was treated with 1 mL MeOH, allowed to stand for about 5 min and then filtered through a pad of diatomaceous earth (CELITE®). The pad was washed with CH₂Cl₂ (50 mL) and the filtrate was concentrated in vacuo to afford a light charcoal-colored solid. The crude material was dissolved in EtOAc (~10 mL) with heating and allowed to stand at ambient temperature with seeding. About 15 min into the cooling phase, a rapid crystal formation was observed. About 1 h later, hexanes (~6 mL) was added and the mixture refrigerated overnight (it did not appear that additional material precipitated out). The mixture was filtered and washed with ice/water-cooled hexanes/EtOAc (2:1 ratio; 20 mL) and dried under high vacuum to afford the first crop of (1R,3S,5R)-2-(tert-butoxycarbonyl)-2-azabicyclo[3.1.0]hexane-3-carboxylic acid (off-white crystals, 1.222 g). The mother liquor was concentrated in vacuo and the residue dissolved in ~3 mL of EtOAc with heating, allowed to stand at ambient temperature for 1 h and then 3 mL hexanes was added and stored in a refrigerator for ~15 h. A second crop of (1R,3S,5R)-2-(tert-butoxycarbonyl)-2-azabicyclo[3.1.0]hexane-3-carboxylic acid was retrieved similarly (grey crystals, 0.133 g), for a combined yield of 59%. LC-MS [M+Na]⁺=250.22. Rt=1.48 min under the following HPLC conditions: Solvent gradient from 100% A: 0% B to 0% A: 100% B (A=0.1% TFA in 1:9 methanol/water; B=0.1% TFA in 9:1 methanol/water) over 3 min; detection at 220 nm; PHENOMENEX® Luna 3.0×50 mm S10 column. MP (dec.) for the first crop=147.5-149.5° C. ¹H NMR (400 MHz, DMSO-$d_6$) δ ppm 12.46 (s, 1H), 3.88 (app br s, 1H), 3.27 (app br s, 1H; overlapped with water signal), 2.28 (br m, 1H), 2.07 (app br s, 1H), 1.56 (app s, 1H), 1.40/1.34 (two overlapped s, 9H), 0.71 (m, 1H), 0.45 (m, 1H). 13C-NMR (100.6 MHz, DMSO-$d_6$) 172.96, 172.60, 154.45, 153.68, 78.74, 59.88, 59.58, 36.91, 31.97, 31.17, 27.77, 27.52, 14.86, 14.53, 13.69. Anal. Calcd. for $C_{11}H_7NO_4$: C, 58.13; H, 7.54; N, 6.16. Found (for first crop): C, 58.24; H, 7.84; N, 6.07. Optical rotation (10 mg/mL in CHCl₃): [α]D=−216 and −212 for the first and second crop, respectively.

An Alternative Synthesis for Intermediate 24:

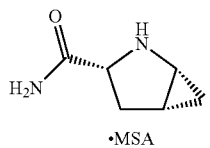

·MSA (1R,3R,5R)-2-Azabicyclo[3.1.0]hexane-3-carboxamide (·CH₃SO₃H) was prepared according to the procedure described for the synthesis of its stereoisomer in patent WO 2004/052850.

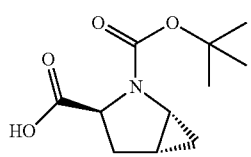 [SMILES: CC(C)(C)OC(=O)N1[C@@H]2C[C@@H]2C[C@H]1C(=O)O]

Intermediate 24

(1R,3S,5R)-2-(tert-Butoxycarbonyl)-2-azabicyclo[3.1.0]hexane-3-carboxylic acid A 1 L round bottom flask equipped with a nitrogen inlet, overhead agitator, thermocouple and heating mantle was charged with 50 g (225 mmol) (1R,3R,5R)-2-Azabicyclo[3.1.0]hexane-3-carboxamide (.CH$_3$SO$_3$H) and 250 mL isopropanol. The resulting slurry was then charged with 252 mL of 23 wt % NaOEt in EtOH (2.68 M, 675 mmol, 3.0 equiv) and stirred at 50° C. for ca. 1 h. The mixture was charged with 12.2 mL (675 mmol, 3 equiv) of water and heated to 60° C. The resulting slurry was allowed to stir at 60° C. for ca. 18 h. The slurry was cooled to rt and charged with 250 mL water and 98.2 g (450 mmol, 2.0 equiv) di-t-butyldicarbonate. Ethanol and isopropanol were removed via vacuum distillation and the aqueous mixture cooled to 0° C. The mixture was neutralized with 76 ml (456 mmol) 6M aqueous HCl while maintaining an internal temperature <5° C. The product was extracted with 500 mL MTBE and the rich organic layer was washed with 100 mL water. The clear solution was concentrated down to 150 mL via vacuum distillation and the resulting slurry was charged with 600 mL heptane while maintaining an internal temperature >45° C. The slurry was cooled to rt over ca. 30 min and allowed to stir at rt for ca. 2 h. The product was filtered, washed with 250 mL 4:1 heptane:MTBE and dried under vacuum at 70° C. to give 40.5 g (178 mmol, 79% yield, 99.8 AP at 205 nm) of (1R,3S,5R)-2-(tert-butoxycarbonyl)-2-azabicyclo[3.1.0]hexane-3-carboxylic acid: $^1$H NMR (400 MHz, DMSO-d$_6$) δ 12.48 (s, 1H), 4.02-3.80 (m, 1H), 3.45-3.15 (m, 1H), 2.40-2.19 (m, 1H), 2.19-2.0 (m, 1H), 1.70-1.50 (m, 1H), 1.50-1.20 (m, 9H), 0.83-0.60 (m, 1H), 0.33-0.55 (m, 1H); $^{13}$C NMR (100 MHz, DMSO-d$_6$) δ 173.7, 173.2, 155.0, 154.3, 79.4, 60.5, 60.2, 37.6, 32.6, 31.8, 28.4, 28.2, 15.6, 15.2, 14.4; HRMS calcd for C$_{11}$H$_{18}$NO$_4$ (M+H; ESI$^+$): 228.1236. Found: 228.1234.

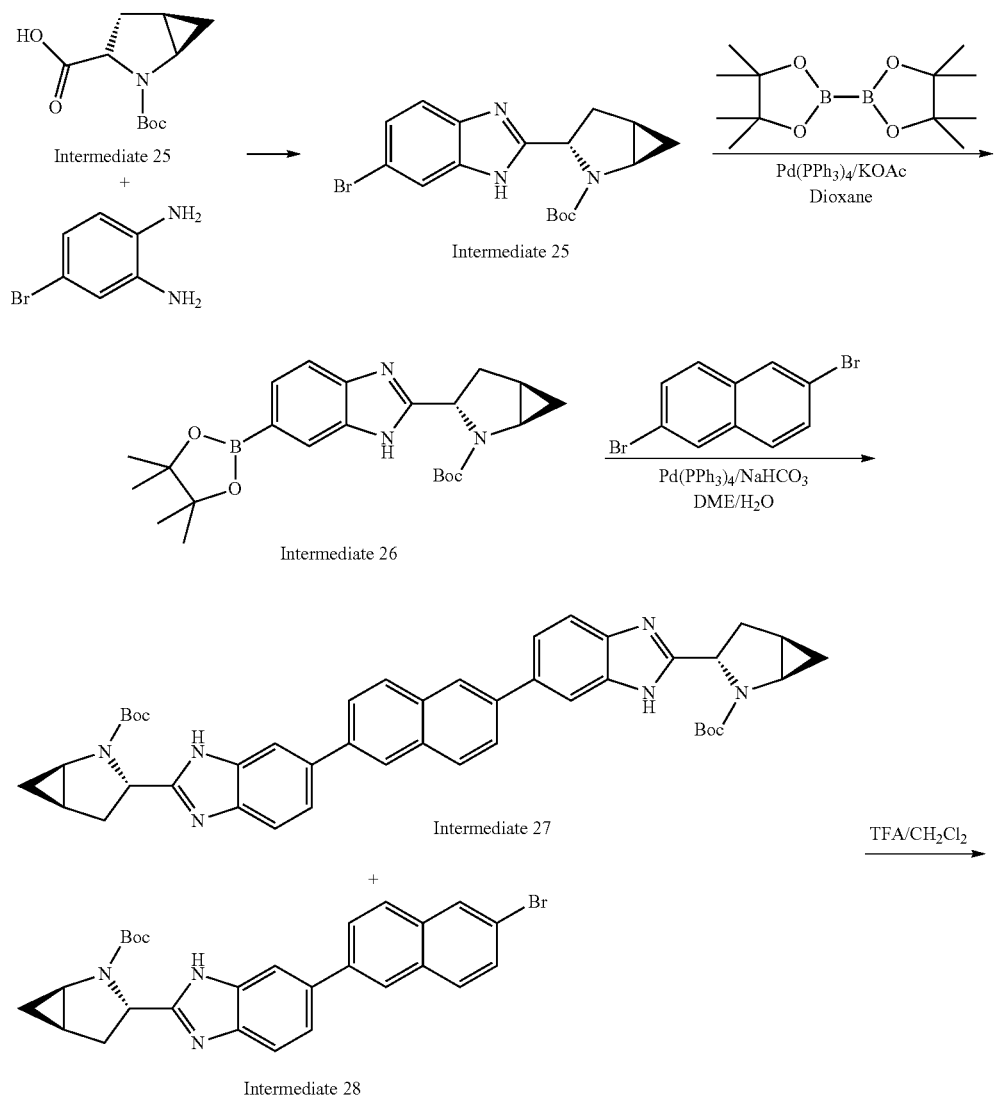

Scheme 6

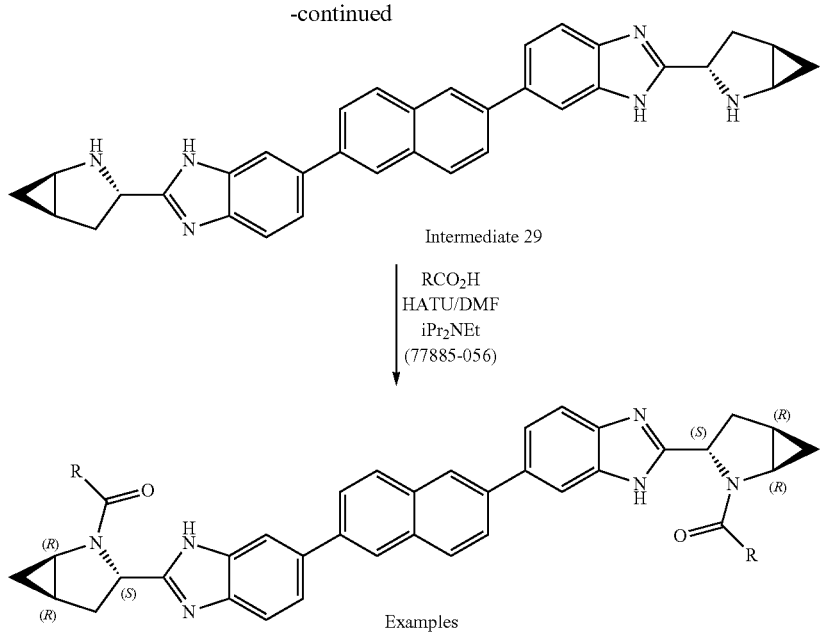

Intermediate 29

RCO₂H
HATU/DMF
iPr₂NEt
(77885-056)

Examples

Intermediate 25

(1R,3S,5R)-tert-Butyl 3-(6-bromo-1H-benzo[d]imidazol-2-yl)-2-azabicyclo[3.1.0]hexane-2-carboxylate EDCI.HCl (2.65 g, 13.8 mmol) was added to a mixture of 4-bromobenzene-1,2-diamine 2.35 g, 12.6 mmol), (1R,3S,5R)-2-(tert-butoxycarbonyl)-2-azabicyclo[3.1.0]hexane-3-carboxylic acid (3.00 g, 13.2 mmol) and 1-hydroxybenzotriazole (1.93 g, 12.6 mmol) in CH₂Cl₂ (80 mL) and stirred at ambient conditions for 16 h. The mixture was then diluted with CH₂Cl₂, washed with water, dried (brine; MgSO₄), filtered and concentrated in vacuo to provide a brown foam. Acetic acid (80 mL) was added to the foam and the mixture was heated at 75° C. (bath temperature) for 5 h. The volatile component was removed in vacuo and the residue was dissolved in EtOAc, washed with saturated NaHCO₃ solution and the organic phase was dried (brine; MgSO₄), filtered and concentrated in vacuo. The resultant crude material was submitted to flash chromatography (silica gel; 50-100% EtOAc/hexanes) to provide (1R,3S,5R)-tert-butyl 3-(6-bromo-1H-benzo[d]imidazol-2-yl)-2-azabicyclo[3.1.0]hexane-2-carboxylate (3.01 g, 7.96 mmol, 63.3% yield) as a light orange foam, which was used without further purification. The reaction also yielded 847 mg of same product with lower purity. An aliquot of the collected material was purified further by preparative HPLC (C-18/30-100% CH₃CN-water+0.1% NH₄OAc) to achieve an analytical sample. LC-MS retention time 1.248 min; calcd. for C₁₇H₂₁BrN₃O₂: 378.08. found m/z 380.05 [M+H]⁺. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. ¹H NMR (500 MHz, MeOD) δ ppm 7.67 (br s, 1H), 7.43 (br s, 1H), 7.34 (d, J=8.6 Hz, 1H), 4.75 (br s, 1H), 3.62 (br s, 1H), 2.50-2.57-2.31 (m, 1H), 2.31 (dt, J=13.2, 6.7 Hz, 1H), 1.66-1.85 (m, 1H), 1.45 (br s, 3H), 1.11 (br s, 6H), 0.87 (dt, J=8.6, 5.8 Hz, 1H), 0.66 (br s, 1H).

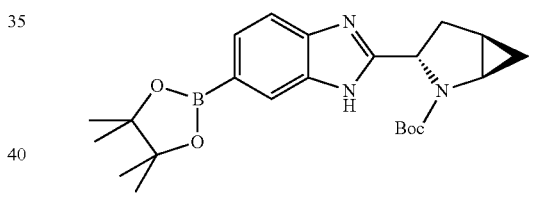

Intermediate 26

(1R,3S,5R)-tert-Butyl 3-(6-(4,4,5,5-tetramethyl-1,3,2-dioxaborolan-2-yl)-1H-benzo[d]imidazol-2-yl)-2-azabicyclo[3.1.0]hexane-2-carboxylate To a pressure flask containing a mixture of (1R,3S,5R)-tert-butyl 3-(6-bromo-1H-benzo[d]imidazol-2-yl)-2-azabicyclo[3.1.0]hexane-2-carboxylate (2.0 g, 5.3 mmol) and bis(pinacolato)diboron (2.69 g, 10.6 mmol) in 1,4-dioxane (50 mL) was added potassium acetate (0.78 g, 7.9 mmol). The reaction flask was degassed in vacuo for 10 min and purged with nitrogen. Pd(Ph₃P)₄ (305 mg, 0.264 mmol) was added to the reaction mixture and the flask was capped and heated with an oil bath at 85° C. (bath temperature) for 16 hours. The reaction mixture was concentrated in vacuo and the crude material was partitioned between CH₂Cl₂ (150 mL) and an aqueous medium (50 mL water+10 mL saturated NaHCO₃ solution). The aqueous layer was extracted with CH₂Cl₂ and the combined organic phase was dried (Na₂SO₄), filtered and concentrated in vacuo. The resulting material was purified with flash chromatography (sample was dry loaded on silica gel and eluted with 20-100% ethyl acetate/hexanes) to provide (1R,3S,5R)-tert-butyl 3-(6-(4,4,5,5-tetramethyl-1,3,2-dioxaborolan-2-yl)-1H-benzo[d]imidazol-2-yl)-2-azabicyclo[3.1.0]hexane-2-carboxylate (1.74 g, 77% yield) as white foam. An aliquot of the collected material was further purified by preparative HPLC (C-18/30-100% CH$_3$CN-water+0.1% NH$_4$OAc). LC-MS retention time 1.78 min; calcd. for C$_{23}$H$_{32}$BN$_{32}$ 425.25. found m/z 426.21 [M+H]$^+$. LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 5% acetonitrile/95% water/10 mmol ammonium acetate and Solvent B was 95% acetonitrile/5% water/10 mmol ammonium acetate. MS data was determined using a MICROMASS® Platform for LC in electrospray mode $^1$H NMR (500 MHz, MeOD) δ ppm 7.94 (s, 1H), 7.61 (d, J=7.9 Hz, 1H), 7.41-7.56 (m, 1H), 4.83 (br s, 1H), 3.64 (d, J=1.2 Hz, 1H), 2.51-2.70 (m, 1H), 2.33 (dt, J=13.4, 6.6 Hz, 1H), 1.67-1.84 (m, J=8.5, 6.10, 5.8, 5.8 Hz, 1H), 1.39-1.59 (br s, 3H), 1.37 (s, 12H), 1.10 (br s, 6H), 0.88 (dt, J=8.2, 5.8 Hz, 1H), 0.66 (br s, 1H).

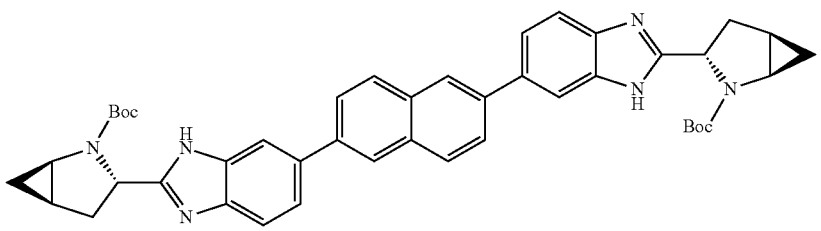

Intermediate 27

(1R,1'R,3S,3'S,5R,5'R)-tert-Butyl 3,3'-(6,6'-(naphthalene-2,6-diyl)bis(1H-benzo[d]imidazole-6,2-diyl))bis(2-azabicyclo[3.1.0]hexane-2-carboxylate)

To a mixture of (1R,3S,5R)-tert-butyl 3-(6-(4,4,5,5-tetramethyl-1,3,2-dioxaborolan-2-yl)-1H-benzo[d]imidazol-2-yl)-2-azabicyclo[3.1.0]hexane-2-carboxylate (1.50 g, 3.53 mmol) and 2,6-dibromonaphthalene (403 mg, 1.41 mmol) in 1,2-dimethoxyethane (21.7 mL) and water (6.50 mL) was added NaHCO$_3$ (356 mg, 4.23 mmol). The reaction mixture was degassed in vacuo for 10 minutes and flushed with nitrogen. Pd(Ph$_3$P)$_4$ (82 mg, 0.071 mmol) was added and the reaction mixture was heated with an oil bath at 100° C. for 16 hours and then the volatile component was removed in vacuo. The residue was partitioned between CH$_2$Cl$_2$ and water (30 mL) and the aqueous phase was extracted several times with CH$_2$Cl$_2$. The combined organic phases were washed with brine, dried (Na$_2$SO$_4$), filtered and concentrated in vacuo. The resulting material was purified with flash chromatography (sample was dry loaded on silica gel and eluted with 0-70% ethyl acetate/CH$_2$Cl$_2$) to afford (1R,1'R,3S,3'S,5R,5'R)-tert-butyl 3,3'-(6,6'-(naphthalene-2,6-diyl)bis(1H-benzo[d]imidazole-6,2-diyl))bis(2-azabicyclo[3.1.0]hexane-2-carboxylate) (377 mg) as yellow solid. LC-MS retention time 1.49 min; calcd. for C$_{44}$H$_{46}$N$_6$O$_4$: 722.36. found m/z 723.26 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD) δ ppm 8.26 (s, 2H), 8.12 (d, J=8.5 Hz, 2H), 8.09 (s, 2H), 8.00 (m, J=8.6 Hz, 2H), 7.93 (m, J=8.6 Hz, 2H), 7.86 (d, J=8.6 Hz, 2H), 5.01 (br s, 2H), 3.68 (br s, 2H), 2.76 (dd, J=13.3, 9.3 Hz, 2H), 2.42-2.54 (m, 2H), 1.87 (br s, 2H), 1.49 (br s, 9H), 1.19 (br s, 9H), 0.94 (dt, J=8.3, 6.1 Hz, 2H), 0.79 (br s, 2H).

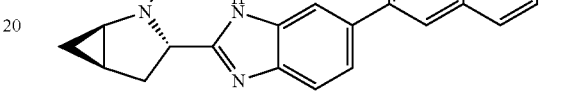

Intermediate 28

(1R,3S,5R)-tert-Butyl 3-(6-(6-bromonaphthalen-2-yl)-1H-benzo[d]imidazol-2-yl)-2-azabicyclo[3.1.0]hexane-2-carboxylate The above reaction also provided (1R,3S,5R)-tert-butyl 3-(6-(6-bromonaphthalen-2-yl)-1H-benzo[d]imidazol-2-yl)-2-azabicyclo[3.1.0]hexane-2-carboxylate (418 mg) as yellow solid. LC-MS retention time 1.90 min; calcd. for C$_{27}$H$_{26}$BrN$_3$O$_2$: 503.12. found m/z 506.05 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD) δ ppm 8.20 (s, 1H), 8.12 (s, 1H), 8.05 (s, 1H), 7.93-8.00 (m, 2H), 7.86-7.93 (m, 2H), 7.84 (d, J=8.6 Hz, 1H), 7.63 (dd, J=8.6, 1.8 Hz, 1H), 5.00 (br s, 1H), 3.68 (br s, 1H), 2.75 (dd, J=13.4, 9.2 Hz, 1H), 2.41-2.54 (m, 1H), 1.87 (br s, 1H), 1.49 (br s, 5H), 1.17 (br s, 4H), 0.87-0.98 (m, 1H), 0.79 (br s, 1H).

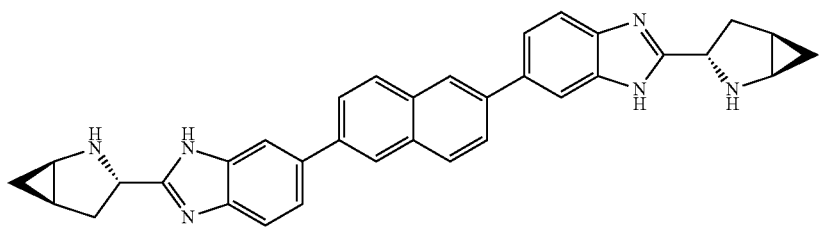

Intermediate 29

2,6-Bis(2-(((1R,3S,5R)-2-azabicyclo[3.1.0]hexan-3-yl)-1H-benzo[d]imidazol-6-yl)naphthalene

A mixture of (1R,1'R,3S,3'S,5R,5'R)-tert-butyl 3,3'-(6,6'-(naphthalene-2,6-diyl)bis(1H-benzo[d]imidazole-6,2-diyl))bis(2-azabicyclo[3.1.0]hexane-2-carboxylate) (360 mg, 0.498 mmol) and TFA (2 mL) in CH$_2$Cl$_2$ (10 mL) was stirred at ambient conditions for 3 hours. The volatile component was removed in vacuo and the resulting material was loaded onto an MCX column, flushed with methanol, eluted with 2.0 M NH$_3$/methanol and concentrated to provide 2,6-bis(2-((1R,3S,5R)-2-azabicyclo[3.1.0]hexan-3-yl)-1H-benzo[d]imidazol-6-yl)naphthalene as yellow solid (253 mg). LC-MS retention time 1.07 min; calcd. for C$_{34}$H$_{30}$N$_6$: 522.25. found m/z 523.19 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD) δ ppm 8.17 (s, 2H), 8.06 (d, J=8.2 Hz, 2H), 8.00 (s, 2H), 7.88 (d, J=8.6 Hz, 2H), 7.71-7.81 (m, 4H), 4.84 (dd, J=10.8, 7.5 Hz, 2H), 3.47-3.53 (m, 2H), 2.80 (dd, J=12.8, 7.6 Hz, 2H), 2.54-2.63 (m, 2H), 2.04-2.11 (m, 2H), 1.20-1.27 (m, 2H), 1.02 (q, J=7.7 Hz, 2H).

Scheme 7

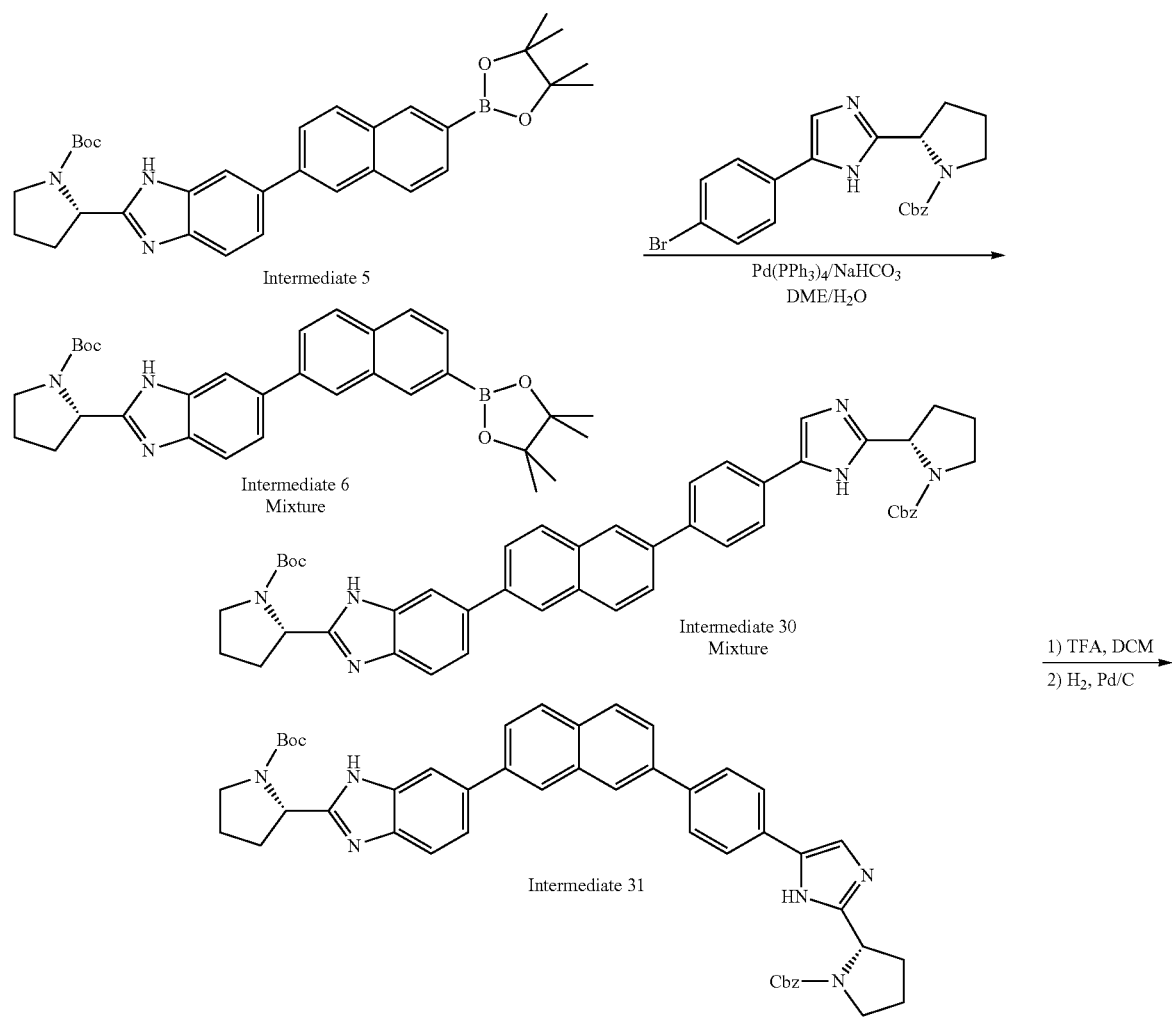

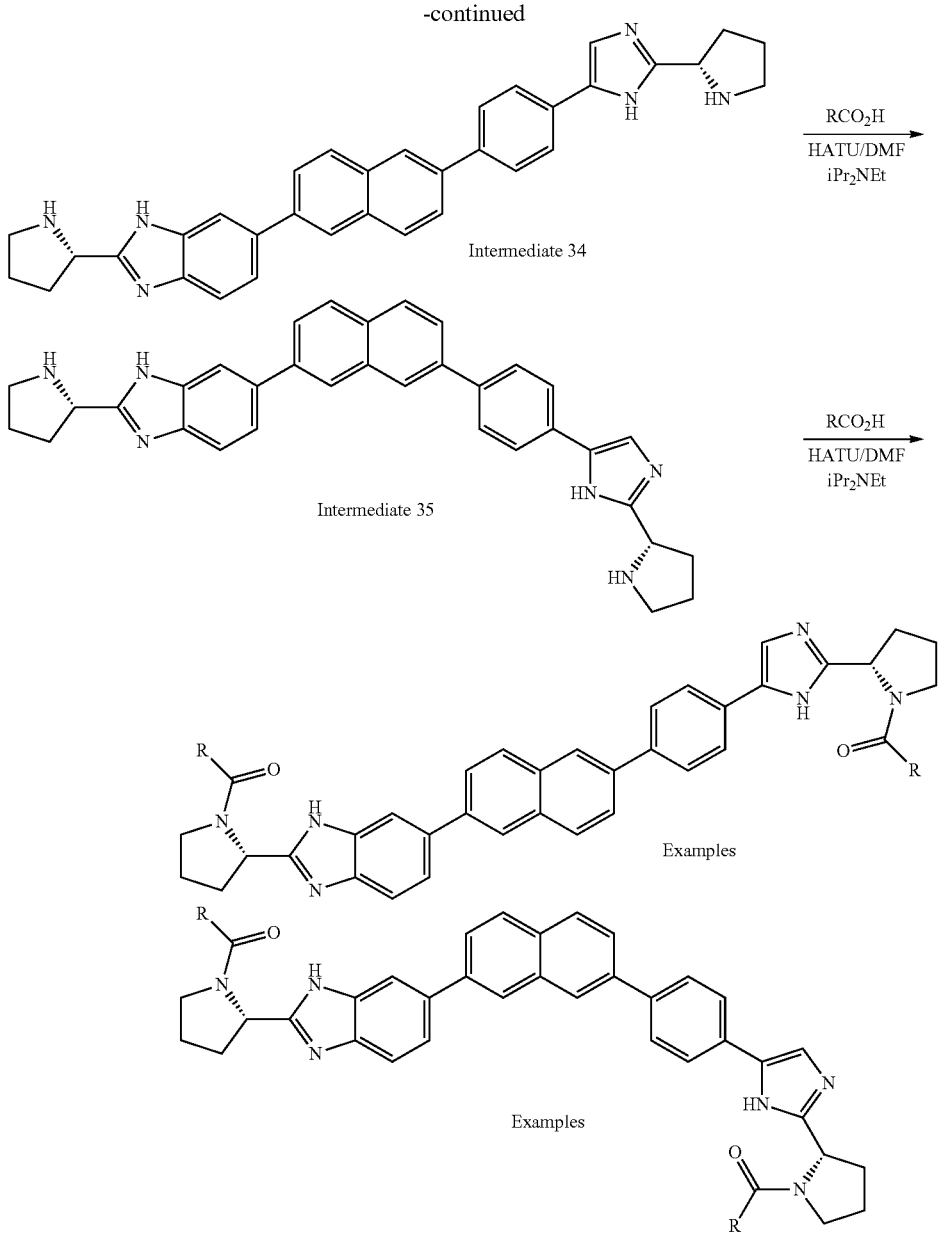

Mixture of Intermediate 30

(S)-Benzyl 2-(5-(4-(6-(2-((S)-1-(tert-butoxycarbonyl)pyrrolidin-2-yl)-1H-benzo[d]imidazol-6-yl)naphthalen-2-yl)phenyl)-1H-imidazol-2-yl)pyrrolidine-1-carboxylate bistrifluoroacetate and Intermediate 31

(S)-Benzyl 2-(5-(4-(7-(2-((S)-1-(tert-butoxycarbonyl)pyrrolidin-2-yl)-1H-benzo[d]imidazol-6-yl)naphthalen-2-yl)phenyl)-1H-imidazol-2-yl)pyrrolidine-1-carboxylate bistrifluoroacetate To a mixture of a TFA salt of (S)-tert-butyl 2-(6-(6-(4,4,5,5-tetramethyl-1,3,2-dioxaborolan-2-yl)naphthalen-2-yl)-1H-benzo[d]imidazol-2-yl)pyrrolidine-1-carboxylate and a TFA salt of (S)-tert-butyl 2-(6-(7-(4,4,5,5-tetramethyl-1,3,2-dioxaborolan-2-yl)naphthalen-2-yl)-1H-benzo[d]imidazol-2-yl)pyrrolidine-1-carboxylate (190 mg), (S)-benzyl 2-(5-(4-bromophenyl)-1H-imidazol-2-yl)pyrrolidine-1-carboxylate (Patent applications: WO 2008/021928, WO 2008/021936 and WO 2008/021927) (213 mg, 0.499 mmol), in 1,2-dimethoxyethane (10.0 mL) and water (2.0 mL) was added NaHCO$_3$ (140 mg, 1.663 mmol). The reaction mixture was degassed in vacuo for 5 minutes and was flushed with nitrogen. Pd(Ph$_3$P)$_4$ (19 mg, 0.017 mmol) was added and the pressure flask was capped and heated with an oil bath at 85° C. for 16 hours. The volatile component was removed in vacuo and the residue was partitioned between ethyl acetate and water. The layers were separated and the aqueous phase was extracted several times with ethyl acetate. The combined organic phases were dried (Na$_2$SO$_4$), filtered and concentrated in vacuo. The resulting material was purified with flash chromatography (sample was dry loaded on silica gel and eluted with 0-5% methanol/CH$_2$Cl$_2$) to afford partially purified products. The residue was further purified by a reverse phase HPLC (water/acetonitrile/TFA) to provide a mixture of a TFA salt of (S)-benzyl 2-(5-(4-(6-(2-((S)-1-(tert-butoxycarbonyl)pyrrolidin-2-yl)-1H-benzo[d]imidazol-6-yl)naphthalen-2-yl)phenyl)-1H-imidazol-2-yl)pyrrolidine-1-carboxylate and a TFA salt of (S)-benzyl 2-(5-(4-(7-(2-((S)-1-(tert-butoxycarbonyl)pyrrolidin-2-yl)-1H-benzo[d]imidazol-6-yl)naphthalen-2-yl)phenyl)-1H-imidazol-2-yl)pyrrolidine-1-carboxylate (381 mg) which was used without further purification. LC-MS retention time 1.54 min; calcd. for $C_{47}H_{46}N_6O_4$ 758.36. found m/z 759.37 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA.

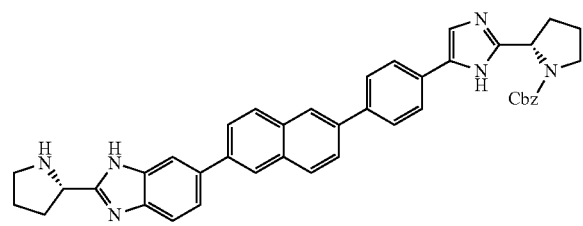

Intermediate 32

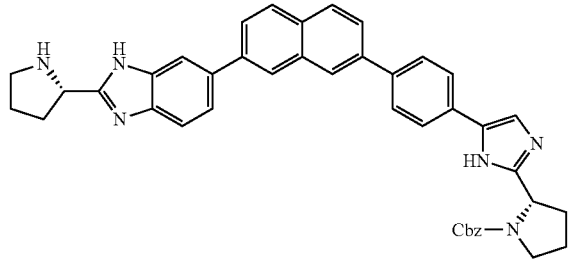

Intermediate 33

Mixture of Intermediate 32

(S)-Benzyl 2-(5-(4-(6-(2-((S)-pyrrolidin-2-yl)-1H-benzo[d]imidazol-6-yl)naphthalen-2-yl)phenyl)-1H-imidazol-2-yl)pyrrolidine-1-carboxylate and Intermediate 33

(S)-Benzyl 2-(5-(4-(7-(2-((S)-pyrrolidin-2-yl)-1H-benzo[d]imidazol-6-yl)naphthalen-2-yl)phenyl)-1H-imidazol-2-yl)pyrrolidine-1-carboxylate A mixture of a TFA salt of (S)-benzyl 2-(5-(4-(6-(2-((S)-1-(tert-butoxycarbonyl)pyrrolidin-2-yl)-1H-benzo[d]imidazol-6-yl)naphthalen-2-yl)phenyl)-1H-imidazol-2-yl)pyrrolidine-1-carboxylate and a TFA salt of (S)-benzyl 2-(5-(4-(7-(2-((S)-1-(tert-butoxycarbonyl)pyrrolidin-2-yl)-1H-benzo[d]imidazol-6-yl)naphthalen-2-yl)phenyl)-1H-imidazol-2-yl)pyrrolidine-1-carboxylate (381 mg) and TFA (2 mL) in $CH_2Cl_2$ (10 mL) was stirred at ambient conditions for 4 hours. The volatile component was removed in vacuo and the crude material was purified by a reverse phase HPLC (0 to 50% water/acetonitrile/NH$_4$OAc) to provide a mixture of (S)-benzyl 2-(5-(4-(6-(2-((S)-pyrrolidin-2-yl)-1H-benzo[d]imidazol-6-yl)naphthalen-2-yl)phenyl)-1H-imidazol-2-yl)pyrrolidine-1-carboxylate and (S)-benzyl 2-(5-(4-(7-(2-((S)-pyrrolidin-2-yl)-1H-benzo[d]imidazol-6-yl)naphthalen-2-yl)phenyl)-1H-imidazol-2-yl)pyrrolidine-1-carboxylate (70 mg, 21% yield) as yellow oil. LC-MS retention time 2.87 min; calcd. for $C_{42}H_{38}N_6O_2$ 658.31. found m/z 659.47 [M+H]$^+$. LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 80% Solvent A/20% Solvent B to 0% Solvent A/100% Solvent B, a gradient time of 4 min, a hold time of 1 min and an analysis time of 5 min where Solvent A was 5% acetonitrile/95% water/10 mmol NH$_4$OAc and Solvent B was 95% acetonitrile/5% water/10 mmol NH$_4$OAc. $^1$H NMR (Mixture of compounds, 500 MHz, MeOD) δ ppm 8.07-8.24 (m, 4H), 7.91-8.03 (m, 6H), 7.73-7.89 (m, 12H), 7.66-7.73 (m, 4H), 7.27-7.46 (m, 6H), 7.09-7.18 (m, 4H), 6.97-7.04 (m, 2H), 5.01-5.21 (m, 5H), 4.83-5.01 (m, 2H), 3.72-3.82 (m, 2H), 3.53-3.65 (m, 2H), 3.42-3.52 (m, 2H), 3.35-3.42 (m, 4H), 2.48-2.62 (m, 2H), 2.28-2.47 (m, 4H), 2.04-2.24 (m, 8H).

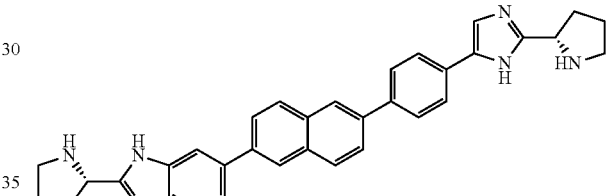

Intermediate 34

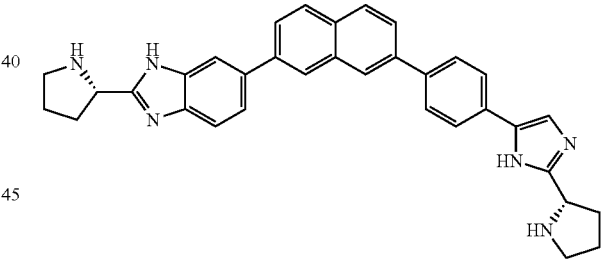

Intermediate 35

Intermediate 34

2-((S)-Pyrrolidin-2-yl)-6-(6-(4-(2-((S)-pyrrolidin-2-yl)-1H-imidazol-5-yl)phenyl)naphthalen-2-yl)-1H-benzo[d]imidazole tetratrifluoroacetate and Intermediate 35

2-((S)-Pyrrolidin-2-yl)-6-(7-(4-(2-((S)-pyrrolidin-2-yl)-1H-imidazol-5-yl)phenyl)naphthalen-2-yl)-1H-benzo[d]imidazole tetratrifluoroacetate To a solution of a mixture of (S)-benzyl 2-(5-(4-(6-(2-((S)-pyrrolidin-2-yl)-1H-benzo[d]imidazol-6-yl)naphthalen-2-yl)phenyl)-1H-imidazol-2-yl)pyrrolidine-1-carboxylate and (S)-benzyl 2-(5-(4-(7-(2-((S)-pyrrolidin-2-yl)-1H-benzo[d]

imidazol-6-yl)naphthalen-2-yl)phenyl)-1H-imidazol-2-yl) pyrrolidine-1-carboxylate (70 mg. 0.057 mmol) and potassium carbonate ($K_2CO_3$) in methanol (5 mL) was added a slurry of palladium on carbon (10%, 11 mg) in methanol (2 mL) at ambient temperature. The reactor was vacuum purged and backfilled with hydrogen. The reaction was stirred for 16 h under a balloon of hydrogen. The mixture was filtered through a pad of diatomaceous earth (CELITE®) under vacuum and the filtrate was evaporated in vacuo. The crude material was purified by a reverse phase HPLC (0 to 50% water/acetonitrile/TFA) to provide a TFA salt of 2-((S)-pyrrolidin-2-yl)-6-(6-(4-(2-((S)-pyrrolidin-2-yl)-1H-imidazol-5-yl)phenyl)naphthalen-2-yl)-1H-benzo[d]imidazole (50 mg) as white solid and a TFA salt of 2-((S)-pyrrolidin-2-yl)-6-(7-(4-(2-((S)-pyrrolidin-2-yl)-1H-imidazol-5-yl)phenyl) naphthalen-2-yl)-1H-benzo[d]imidazole (24 mg) as white solid.

Analytical data for Intermediate 34: LC-MS retention time 1.06 min; calcd. for $C_{34}H_{32}N_6$ 524.27. found m/z 525.26 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 80% Solvent A/20% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.19 (d, J=10.4 Hz, 2H), 8.02-8.10 (m, 3H), 7.84-7.96 (m, 7H), 7.77-7.83 (m, 2H), 5.14 (t, J=7.8 Hz, 1H), 5.06-5.11 (m, 1H), 3.52-3.67 (m, 4H), 2.61-2.74 (m, 2H), 2.43-2.56 (m, 2H), 2.30-2.42 (m, 2H), 2.18-2.30 (m, 2H).

Analytical data for Intermediate 35: LC-MS retention time 1.13 min; calcd. for $C_{34}H_{32}N_6$ 524.27. found m/z 525.24 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 80% Solvent A/20% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.27 (d, J=7.0 Hz, 2H), 7.99-8.06 (m, 3H), 7.90-7.96 (m, 4H), 7.87 (td, J=8.2, 1.7 Hz, 2H), 7.76-7.85 (m, 3H), 5.13 (t, J=7.8 Hz, 1H), 5.03-5.08 (m, 1H), 3.51-3.67 (m, 4H), 2.61-2.74 (m, 2H), 2.42-2.54 (m, 2H), 2.20-2.40 (m, 4H).

Scheme 8

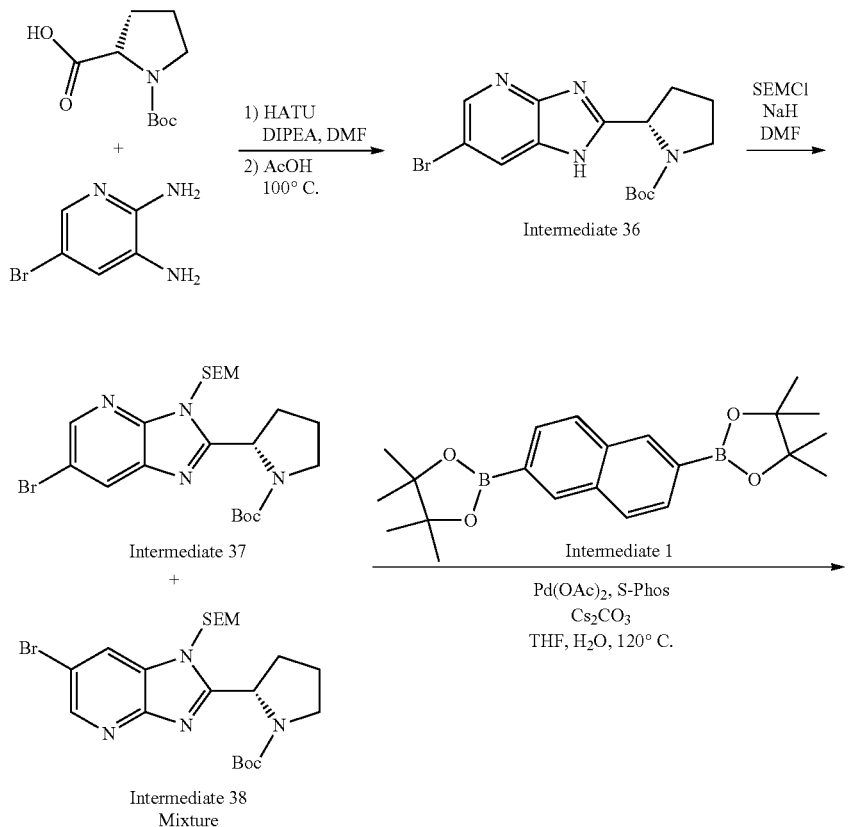

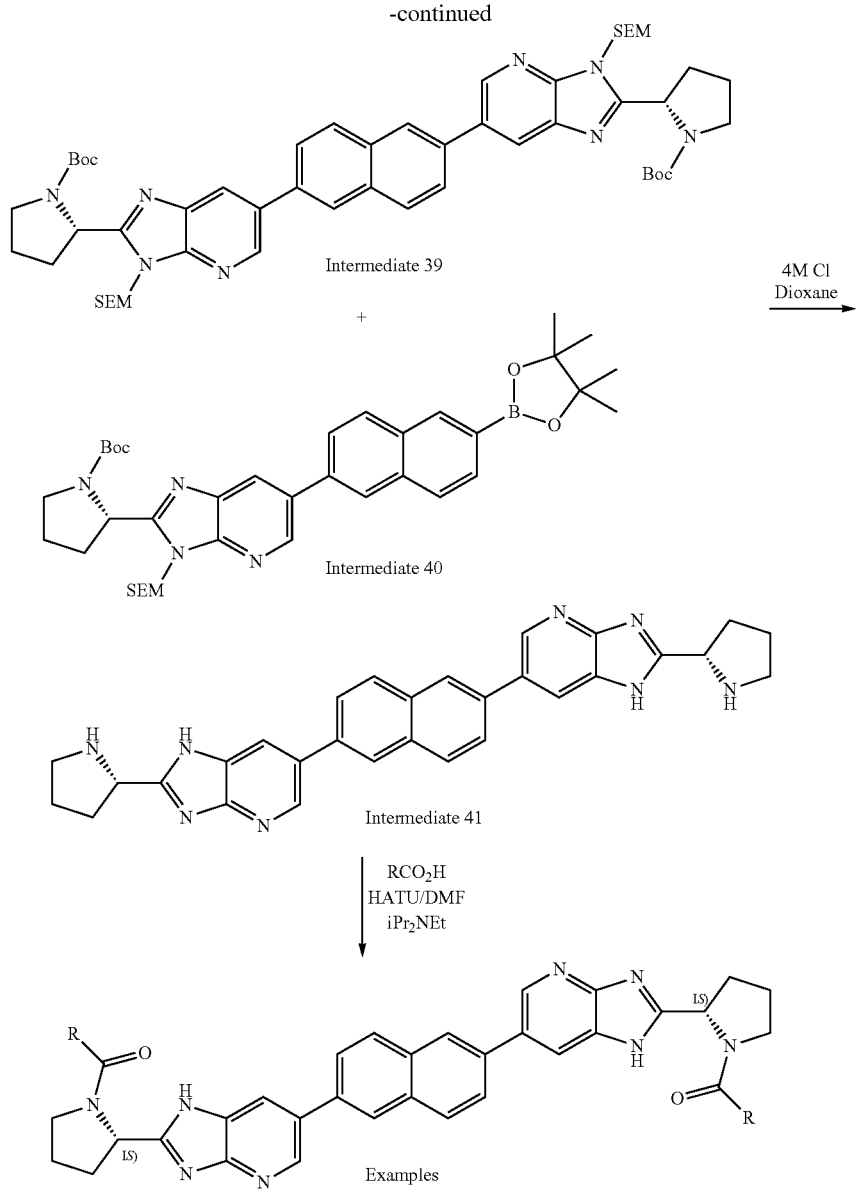

Intermediate 36

(S)-tert-Butyl 2-(6-bromo-1H-imidazo[4,5-b]pyridin-2-yl)pyrrolidine-1-carboxylate HATU (3.64 g, 9.57 mmol) was added to a stirred solution of 5-bromopyridine-2,3-diamine (1.64 g, 8.70 mmol) and (S)-1-(tert-butoxycarbonyl)pyrrolidine-2-carboxylic acid (1.87 g, 8.70 mmol) in DMF (50 mL) and DIPEA (3.19 mL, 18.3 mmol). The reaction mixture was stirred at room temperature for 3 d, diluted with water (400 mL) and extracted with EtOAc (150 mL). The organic layer was washed with brine (50 mL), dried ($MgSO_4$), filtered and concentrated. The crude material was partially purified by flash chromatography (110 g $SiO_2$, 1-4% MeOH/DCM) to yield 3.36 g of solidified foam. The material was dissolved into AcOH (35.0 mL) and heated at 100° C. for 8 h. The reaction was cooled to room temperature, concentrated and purified by flash chromatography (loaded with DCM, 80 g $SiO_2$, 20-40% EtOAc/Hexanes) to yield (S)-tert-butyl 2-(6-bromo-1H-imidazo[4,5-b]pyridin-2-yl)pyrrolidine-1-carboxylate (1.73 g) as yellow solid. LC-MS retention time 1.33 min; m/z 365, 367 (1:1) (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. $^1$H NMR (400 MHz, MeOD) δ ppm 8.40 (br s, 1H), 8.09 (br s, 1H), 5.12-4.96 (m, 1H), 3.77-3.67 (m, 1H), 3.62-3.51 (m, 1H), 2.56-2.38 (m, 1H), 2.15-1.90 (m, 3H), 1.46 (s, 3.5H), 1.16 (s, 5.5H).

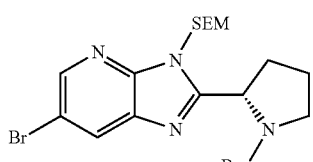

Intermediate 37

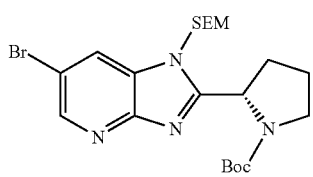

Intermediate 38

Mixture of Intermediate 37

(S)-tert-Butyl 2-(6-bromo-3-((2-(trimethylsilyl)ethoxy)methyl)-3H-imidazo[4,5-b]pyridin-2-yl)pyrrolidine-1-carboxylate and Intermediate 38

(S)-tert-Butyl 2-(6-bromo-1-((2-(trimethylsilyl)ethoxy)methyl)-1H-imidazo[4,5-b]pyridin-2-yl)pyrrolidine-1-carboxylate A 60% dispersion of NaH (0.120 g, 3.00 mmol) was added to a stirred solution of (S)-tert-butyl 2-(6-bromo-1H-imidazo[4,5-b]pyridin-2-yl)pyrrolidine-1-carboxylate (1.0 g, 2.7 mmol) in DMF (25 mL) and the reaction was stirred for 1.5 h at room temperature. Then SEM-Cl (0.483 mL, 2.72 mmol) was added and the reaction was stirred 16 h. The reaction was diluted with water (~30 mL) and EtOAc (~35 mL), the layers were separated and the organic layer was washed with brine (30 mL), dried (MgSO$_4$), filtered and concentrated. The residual crude yellow oil was purified by flash chromatography (80 g SiO$_2$, 20-30% EtOAc/hexanes) to yield a mixture of (S)-tert-butyl 2-(6-bromo-3-((2-(trimethylsilyl)ethoxy)methyl)-3H-imidazo[4,5-b]pyridin-2-yl)pyrrolidine-1-carboxylate and (S)-tert-butyl 2-(6-bromo-1-((2-(trimethylsilyl)ethoxy)methyl)-1H-imidazo[4,5-b]pyridin-2-yl)pyrrolidine-1-carboxylate (838 mg) as a yellow oil. The mixture was used w/o further purification. LC-MS retention time 2.54 min; m/z 497,499 (1:1) (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode.

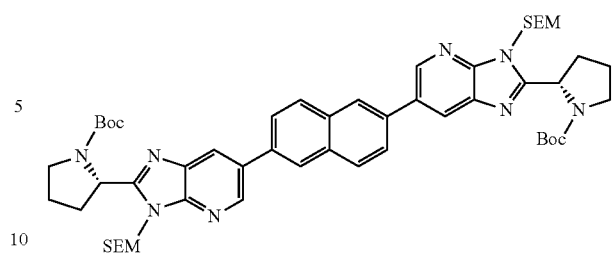

Intermediate 39

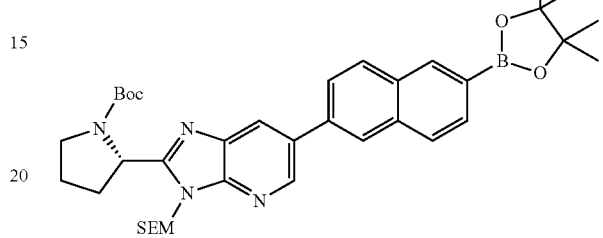

Intermediate 40

Intermediate 39

(2S,2'S)-tert-Butyl 2,2'-(6,6'-(naphthalene-2,6-diyl)bis(3-((2-(trimethylsilyl)ethoxy)methyl)-3H-imidazo[4,5-b]pyridine-6,2-diyl))dipyrrolidine-1-carboxylate and Intermediate 40

(S)-tert-Butyl 2-(6-(6-(4,4,5,5-tetramethyl-1,3,2-dioxaborolan-2-yl)naphthalen-2-yl)-3-((2-(trimethylsilyl)ethoxy)methyl)-3H-imidazo[4,5-b]pyridin-2-yl)pyrrolidine-1-carboxylate In a microwave vial, 2,6-bis(4,4,5,5-tetramethyl-1,3,2-dioxaborolan-2-yl)naphthalene (57 mg, 0.150 mmol), a mixture of (S)-tert-butyl 2-(6-bromo-3-((2-(trimethylsilyl)ethoxy)methyl)-3H-imidazo[4,5-b]pyridin-2-yl)pyrrolidine-1-carboxylate and (S)-tert-butyl 2-(6-bromo-1-((2-(trimethylsilyl)ethoxy)methyl)-1H-imidazo[4,5-b]pyridin-2-yl)pyrrolidine-1-carboxylate (112 mg), cesium carbonate (147 mg, 0.450 mmol) and dicyclohexyl(2',6'-dimethoxybiphenyl-2-yl)phosphine (12.3 mg, 0.030 mmol) were dissolved into THF (3 mL) and water (0.3 mL). An additional 1.5 mL of THF was added and the reaction was sparged with bubbling nitrogen until ~2 mL had evaporated away. To the clear solution was added palladium (II) acetate (3.37 mg, 0.015 mmol). The vial was flushed with nitrogen, sealed and then heated with microwave irradiation at 120° C. for 30 min. The reaction was diluted with EtOAc (~3 mL) and washed with water (2 mL) and brine (2 mL). The reaction was dried (MgSO$_4$), filtered and concentrated to a yellow oil which was purified by flash chromatography (12 g SiO$_2$, 25-75% EtOAc/hexanes) to yield (2S,2'S)-tert-butyl 2,2'-(6,6'-(naphthalene-2,6-diyl)bis(3-((2-(trimethylsilyl)ethoxy)methyl)-3H-imidazo[4,5-b]pyridine-6,2-diyl))dipyrrolidine-1-carboxylate (74 mg) as a clear colorless oil (mixture of SEM regioisomers) and (S)-tert-butyl 2-(6-(6-(4,4,5,5-tetramethyl-1,3,2-dioxaborolan-2-yl)naphthalen-2-yl)-3-((2-(trimethylsilyl)ethoxy)methyl)-3H-imidazo[4,5-b]pyridin-2-yl)pyrrolidine-1-carboxylate (32 mg) as a colorless oil (mixture of SEM regioisomers). Each was used without further purification.

Analytical data for Intermediate 39: LC-MS retention time 3.42 min; m/z 961.9 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. $^1$H NMR (400 MHz, MeOD) (mixture of SEM regioisomers) δ ppm 8.84-8.75 (m, 2H), 8.39-8.31 (m, 2H), 8.26-8.18 (m, 2H), 8.11 (br s, 2H), 7.92-7.84 (m, 2H), 5.94-5.83 (m, 3H), 5.79 (d, J=11.0 Hz, 1H), 5.34-5.25 (m, 2H), 3.86-3.57 (m, 8H), 2.61-2.39 (m, 2H), 2.34-1.99 (m, 6H), 1.45 (s, 8H), 1.17 (s, 10H), 1.10-0.87 (m, 4H), −0.02 (s, 18H).

Analytical data for Intermediate 40: LC-MS retention time 3.15 min; m/z 671.5 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. (mixture of SEM regioisomers) δ ppm 8.82-8.75 (m, 1H), 8.39-8.29 (m, 2H), 8.21-8.15 (m, 1H), 8.07-8.01 (m, 1H), 8.11 (br s, 2H), 7.98-7.93 (m, 1H), 7.89-7.80 (m, 2H), 5.94-5.85 (m, 1.5H), 5.79 (d, J=11.3 Hz, 0.5H), 5.33-5.24 (m, 1H), 3.85-3.56 (m, 4H), 2.62-2.39 (m, 1H), 2.33-1.99 (m, 1H), 1.49-0.87 (m, 23H), −0.02 (s, 9H).

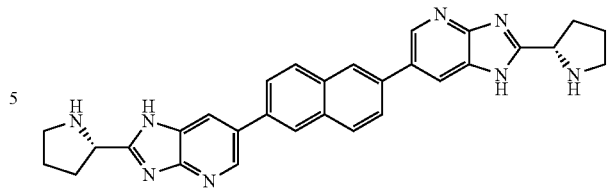

Intermediate 41

2,6-Bis(2-((S)-pyrrolidin-2-yl)-3H-imidazo[4,5-b]pyridin-6-yl)naphthalene

4M Hydrogen chloride (2.0 mL, 8.0 mmol) in dioxane was added to a stirred solution of (2S,2'S)-tert-butyl 2,2'-(6,6'-(naphthalene-2,6-diyl)bis(3-((2-(trimethylsilyl)ethoxy)methyl)-3H-imidazo[4,5-b]pyridine-6,2-diyl))dipyrrolidine-1-carboxylate (74 mg, 0.077 mmol) (mixture of SEM regioisomers) in methanol (1 mL). The reaction was stirred at room temperature for 16 h and then concentrated to dryness to yield a hydrochloride salt of 2,6-bis(2-((S)-pyrrolidin-2-yl)-3H-imidazo[4,5-b]pyridin-6-yl)naphthalene (51.1 mg) as yellow solid which was used without further purification. LC-MS retention time 0.83 min; m/z 501.13 (MH+). LC data was recorded on a Shimadzu LC-10AS liquid chromatograph equipped with a Sunfire 5u C18 4.6×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% trifluoroacetic acid and Solvent B was 10% water/90% acetonitrile/0.1% trifluoroacetic acid. MS data was determined using a MICROMASS® Platform for LC in electrospray mode. $^1$H NMR (400 MHz, D$_2$O) δ ppm 8.76 (s, 2H), 8.54 (s, 2H), 8.07-7.97 (m, 4H), 7.86-7.78 (m, 2H), 5.26-5.16 (m, 2H), 3.98-3.65 (m, 8H), 2.79-2.63 (m, 2H), 2.46-2.25 (m, 6H).

Scheme 9

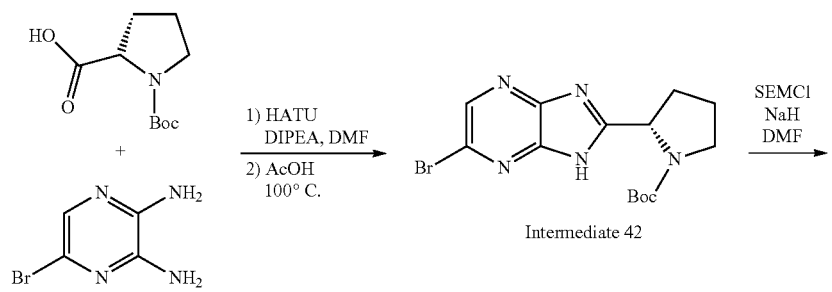

Intermediate 42

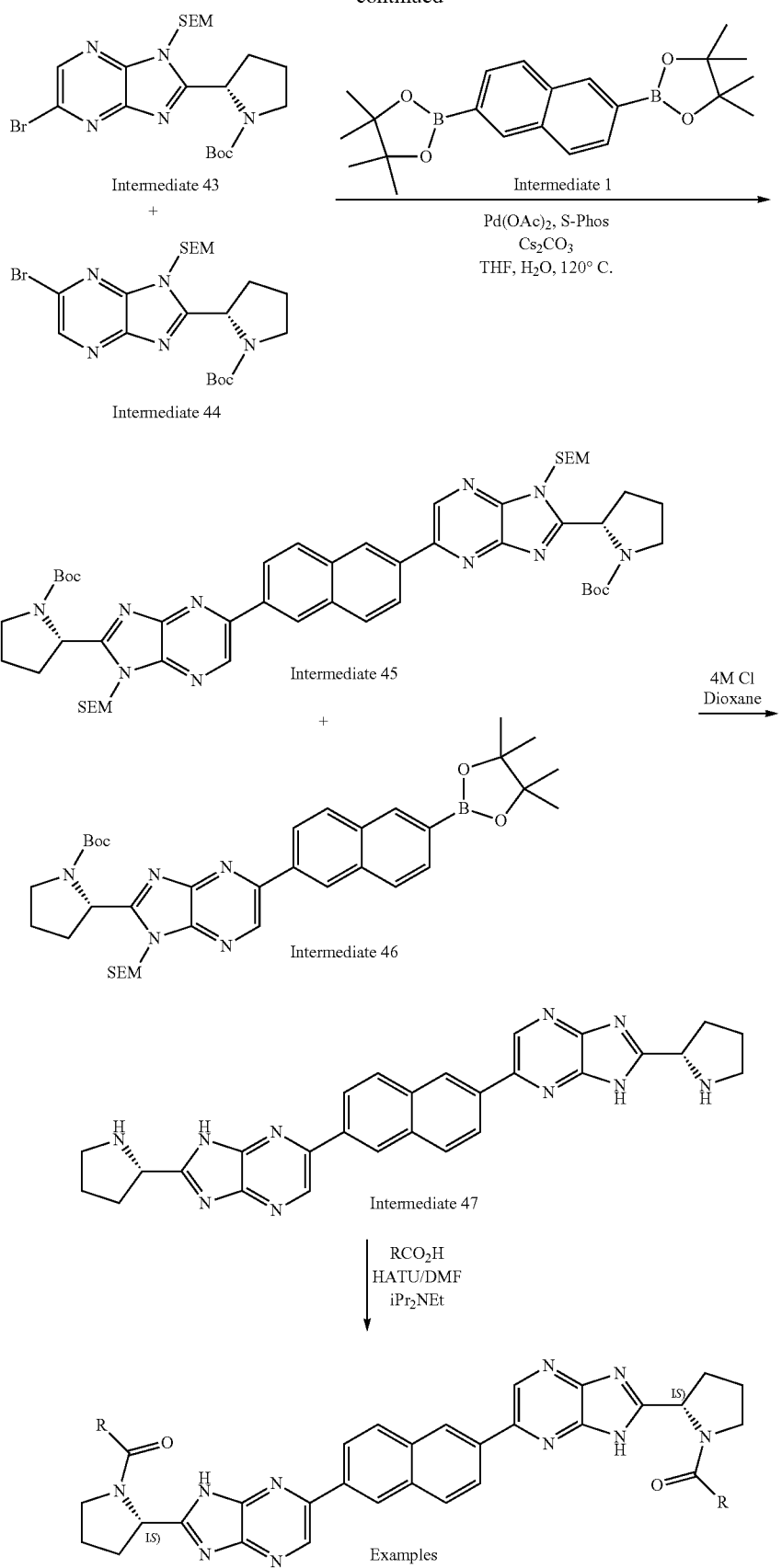

Intermediate 42

(S)-tert-Butyl 2-(6-bromo-1H-imidazo[4,5-b]pyrazin-2-yl)pyrrolidine-1-carboxylate HATU (5.05 g, 13.3 mmol) was added to a stirred solution of 5-bromopyrazine-2,3-diamine (2.28 g, 12.1 mmol) and (S)-1-(tert-butoxy carbonyl)pyrrolidine-2-carboxylic acid (2.60 g, 12.0 mmol) in DMF (50 mL) and DIPEA (4.42 mL, 25.3 mmol). The reaction mixture was stirred at room temperature for 3 d and then at 90° C. for 1 d. The reaction mixture was diluted with water (350 mL) and extracted with EtOAc (200 mL). The organic layer was washed with brine (100 mL), dried (MgSO$_4$), filtered and concentrated. The crude material was partially purified by flash chromatography (110 g SiO$_2$, 1-4% MeOH/DCM) to yield 1.9 g of solidified foam. The material was dissolved into AcOH (35.0 mL) and heated at 95° C. for 8 h. The reaction was cooled to room temperature, concentrated and purified by flash chromatography (loaded with DCM, 80 g SiO$_2$, 20-30% EtOAc/Hexanes) to yield (S)-tert-butyl 2-(6-bromo-1H-imidazo[4,5-b]pyrazin-2-yl)pyrrolidine-1-carboxylate (760 mg, 2.06 mmol, 17% yield) as yellow solidified foam. LC-MS retention time 1.28 min; m/z 366, 368 (1:1) (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. $^1$H NMR (400 MHz, MeOD) δ ppm 8.50-8.43 (m, 1H), 5.11-4.99 (m, 1H), 3.77-3.68 (m, 1H), 3.62-3.51 (m, 1H), 2.57-2.40 (m, 1H), 2.19-1.95 (m, 3H), 1.46 (s, 3.5H), 1.17 (s, 5.5H).

Intermediate 43

(S)-tert-Butyl 2-(5-bromo-1-((2-(trimethylsilyl)ethoxy)methyl)-1H-imidazo[4,5-b]pyrazin-2-yl)pyrrolidine-1-carboxylate and

Intermediate 44

(S)-tert-Butyl 2-(6-bromo-1-((2-(trimethylsilyl)ethoxy)methyl)-1H-imidazo[4,5-b]pyrazin-2-yl)pyrrolidine-1-carboxylate A 60% dispersion of NaH (75 mg, 1.9 mmol) was added to a stirred solution of (S)-tert-butyl 2-(6-bromo-1H-imidazo[4,5-b]pyrazin-2-yl)pyrrolidine-1-carboxylate (627 mg, 1.70 mmol) in DMF (15 mL) and the reaction was stirred for 1.5 h at room temperature. Then SEM-Cl (0.30 mL, 1.7 mmol) was added and the reaction was stirred overnight. The reaction was diluted with water (~30 mL) and EtOAc (~35 mL), the layers were separated and the organic layer was washed with brine (30 mL), dried (MgSO$_4$), filtered and concentrated. The crude yellow oil was purified by flash chromatography (40 g SiO$_2$, 20-30% EtOAc/hexanes) to yield (S)-tert-butyl 2-(5-bromo-1-((2-(trimethylsilyl)ethoxy)methyl)-1H-imidazo[4,5-b]pyrazin-2-yl)pyrrolidine-1-carboxylate (421 mg) as a clear colorless oil and (S)-tert-butyl 2-(6-bromo-1-((2-(trimethylsilyl)ethoxy)methyl)-1H-imidazo[4,5-b]pyrazin-2-yl)pyrrolidine-1-carboxylate (345 mg) as a clear colorless oil. The absolute regiochemistry of the SEM group was not established unambiguously, the names (and structures) may be exchanged in these intermediates.

Analytical data for Intermediate 43: LC-MS retention time 2.43 min; m/z 496, 498 (1:1) (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. $^1$H NMR (400 MHz, MeOD) δ ppm 8.52 (s, 0.5H), 8.49 (s, 0.5H), 5.90-5.72 (m, 2H), 5.32-5.25 (m, 1H), 3.82-3.54 (m 4H), 2.59-2.41 (m, 1H), 2.32-1.98 (m, 3H), 1.43 (s, 4.5H), 1.15 (s, 4.5H), 1.07-0.85 (m, 2H), −0.02 (s, 9H).

Analytical data for Intermediate 44: LC-MS retention time 2.41 min; m/z 496, 498 (1:1) (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. $^1$H NMR (400 MHz, MeOD) δ ppm 8.61 (s, 0.5H), 8.58 (s, 0.5H), 5.88-5.71 (m, 2H), 5.28 (dd, J=8.5, 4.5 Hz, 1H), 3.82-3.54 (m 4H), 2.59-2.41 (m, 1H), 2.32-1.98 (m, 3H), 1.43 (s, 4.5H), 1.15 (s, 4.5H), 1.09-0.85 (m, 2H), −0.02 (s, 9H).

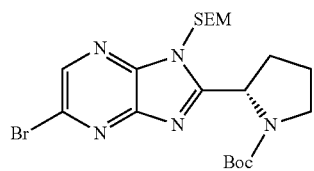

Intermediate 43

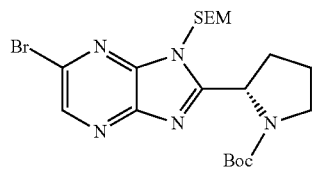

Intermediate 44

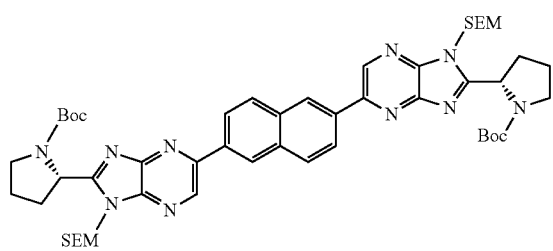

Intermediate 39

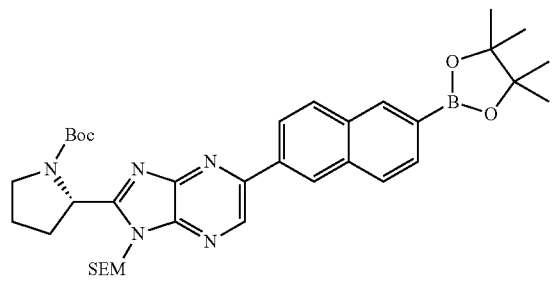

Intermediate 40

Intermediate 45

(2S,2'S)-tert-Butyl 2,2'-(5,5'-(naphthalene-2,6-diyl) bis(1-((2-(trimethylsilyl)ethoxy)methyl)-1H-imidazo [4,5-b]pyrazine-5,2-diyl))dipyrrolidine-1-carboxylate and Intermediate 46

(S)-tert-Butyl 2-(5-(6-(4,4,5,5-tetramethyl-1,3,2-dioxaborolan-2-yl)naphthalen-2-yl)-1-((2-(trimethylsilyl)ethoxy)methyl)-1H-imidazo[4,5-b]pyrazin-2-yl)pyrrolidine-1-carboxylate In a microwave vial, 2,6-bis(4,4,5,5-tetramethyl-1,3,2-dioxaborolan-2-yl)naphthalene (149 mg, 0.393 mmol), (S)-tert-butyl 2-(5-bromo-1-((2-(trimethylsilyl)ethoxy)methyl)-1H-imidazo[4,5-b]pyrazin-2-yl)pyrrolidine-1-carboxylate (294 mg, 0.590 mmol) (or a SEM regioisomer), cesium carbonate (384 mg, 1.18 mmol) and dicyclohexyl(2',6'-dimethoxybiphenyl-2-yl)phosphine (32.3 mg, 0.079 mmol) were dissolved into THF (4 mL) and water (0.4 mL). An additional 1.5 mL of THF was added and the reaction was sparged with bubbling nitrogen until the 1.5 mL had evaporated away. To the clear solution was added palladium(II) acetate (8.83 mg, 0.039 mmol). The vial was flushed with nitrogen, sealed and then heated with microwave irradiation at 120° C. for 30 min. The reaction was diluted with EtOAc (~3 mL) and washed with water (2 mL) and brine (2 mL). The reaction was dried (MgSO$_4$), filtered and concentrated to a yellow oil which was purified by flash chromatography (12 g SiO$_2$, 25-75% EtOAc/hexanes) to yield (2S,2'S)-tert-butyl 2,2'-(5,5'-(naphthalene-2,6-diyl)bis(1-((2-(trimethylsilyl) ethoxy)methyl)-1H-imidazo[4,5-b]pyrazine-5,2-diyl))dipyrrolidine-1-carboxylate (or a SEM regioisomer) (210 mg) as a yellow solidified foam and (S)-tert-butyl 2-(5-(6-(4,4,5,5-tetramethyl-1,3,2-dioxaborolan-2-yl)naphthalen-2-yl)-1-((2-(trimethylsilyl)ethoxy)methyl)-1H-imidazo[4,5-b]pyrazin-2-yl)pyrrolidine-1-carboxylate (or a SEM regioisomer) (53.5 mg) as a colorless oil.

Analytical date for Intermediate 45: LC-MS retention time 3.27 min; m/z 963.89 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. $^1$H NMR (400 MHz, MeOD) (mixture of SEM regioisomers) δ ppm 9.29-9.15 (m 2H), 8.79-8.66 (m, 2H), 8.43-8.29 (m, 2H), 8.20-7.98 (m, 2H), 6.03-5.84 (m, 4H), 5.34 (dd, J=8.3, 4.3 Hz, 2H), 3.87-3.70 (m, 6H), 3.68-3.58 (m, 2H), 2.63-2.43 (m, 2H), 2.36-1.14 (m, 4H), 2.14-1.99 (m, 2H), 1.46 (s, 8H), 1.17 (s, 10H), 1.35-0.85 (m, 4H), −0.02 (s, 18H).

Analytical date for Intermediate 45: LC-MS retention time 3.07 min; m/z 672.52 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode.

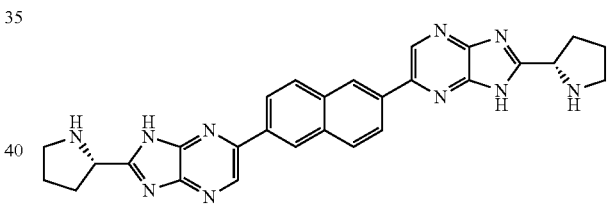

Intermediate 47

2,6-Bis(2-((S)-pyrrolidin-2-yl)-1H-imidazo[4,5-b] pyrazin-5-yl)naphthalene

4M Hydrogen chloride (6.0 mL, 24 mmol) in dioxane was added to a stirred solution of (2S,2'S)-tert-butyl 2,2'-(5,5'-(naphthalene-2,6-diyl)bis(1-((2-(trimethylsilyl)ethoxy)methyl)-1H-imidazo[4,5-b]pyrazine-5,2-diyl))dipyrrolidine-1-carboxylate (210 mg, 0.218 mmol) (absolute regiochemistry of the SEM was not established) in methanol (3 mL). The reaction was stirred at room temperature for 16 h and concentrated to dryness to yield a hydrochloride salt of 2,6-bis (2-((S)-pyrrolidin-2-yl)-1H-imidazo[4,5-b]pyrazin-5-yl) naphthalene (143 mg) as orange solid which was used without further purification. LC-MS retention time 0.90 min; m/z 503.21 (MH+). LC data was recorded on a Shimadzu LC-10AS liquid chromatograph equipped with a Sunfire 5u C18 4.6×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% trifluoroacetic acid and Solvent B was 10% water/90% acetonitrile/0.1% trifluoroacetic acid. MS data was determined using a MICROMASS® Platform for LC in electrospray mode. $^1$H NMR (400 MHz, D$_2$O) δ ppm 8.59 (s, 2H), 7.94 (s, 2H), 7.85 (d, J=8.5 Hz, 2H), 7.76 (d, J=8.5 Hz, 2H), 5.23-5.16 (m, 2H), 3.98-3.66 (m, 8H), 2.78-2.64 (m, 2H), 2.47-2.28 (m, 6H).

in DMF (30 mL) at room temp was added in one portion di-tert-butyl dicarbonate (387 mg, 1.78 mmol). The reaction mixture was stirred overnight at room temperature and purified on a BIOTAGE® (dry loaded to a 80 g silica gel cartridge and eluted with a gradient of 0 to 50% DCM in MeOH), to yield tert-butyl (2S)-2-(5-(6-(2-((2S)-2-pyrrolidinyl)-1H-benzimidazol-5-yl)-2-naphthyl)-1H-benzimidazol-2-yl)-1-pyrrolidinecarboxylate (500 mg, 0.835 mmol, 47.1% yield)

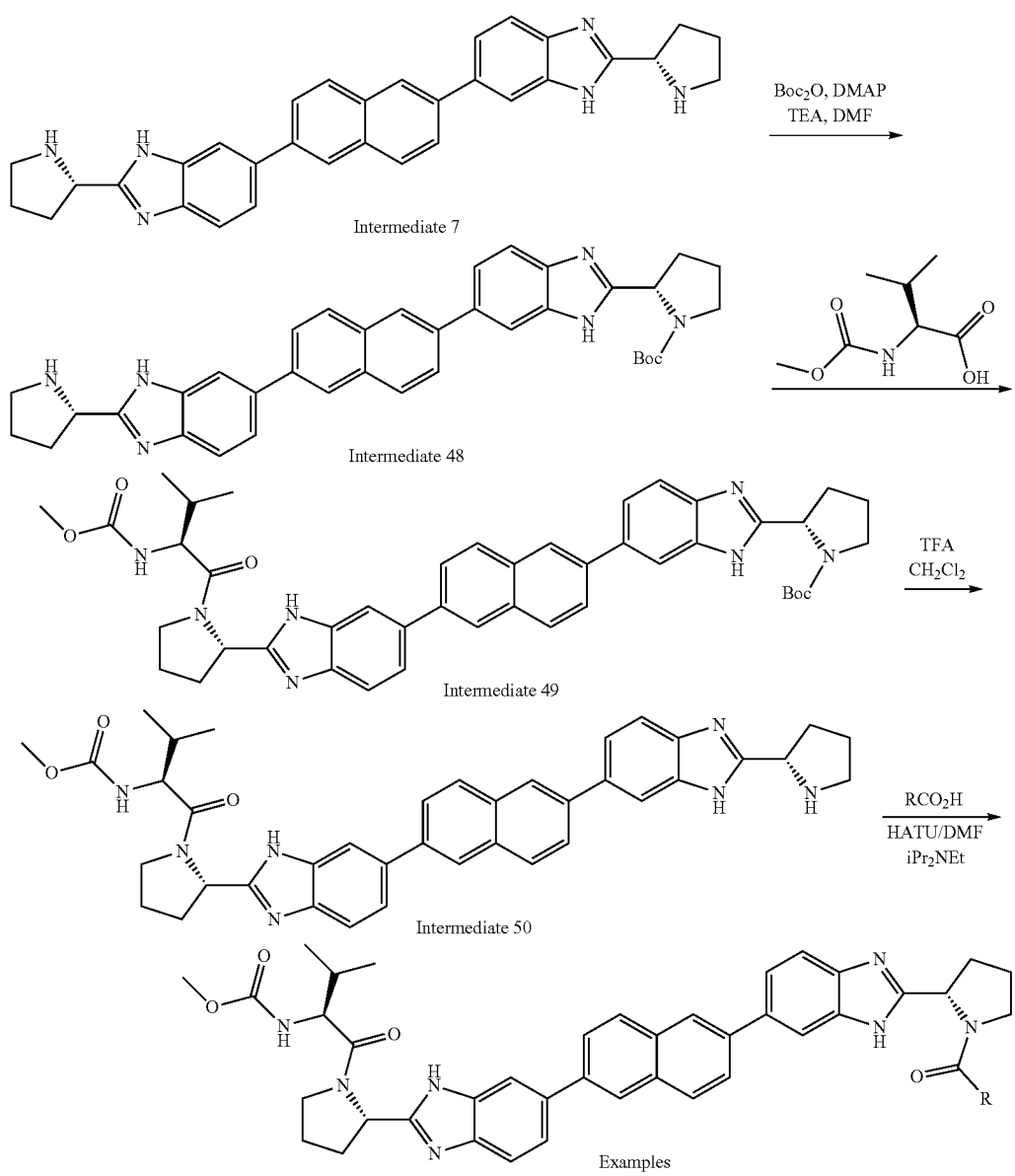

Scheme 10

Intermediate 48 tert-Butyl (2S)-2-(5-(6-(2-((2S)-2-pyrrolidinyl)-1H-benzimidazol-5-yl)-2-naphthyl)-1H-benzimidazol-2-yl)-1-pyrrolidinecarboxylate To a solution of 2,6-bis(2-((S)-pyrrolidin-2-yl)-1H-benzo[d]imidazol-6-yl)naphthalene (885 mg, 1.78 mmol), DMAP (10.8 mg, 0.089 mmol) and triethylamine (1.2 mL, 8.9 mmol)

as orange solid. LC-MS retention time 1.207 min; m/z 599.25 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD) δ ppm 8.27 (d, J=3.1 Hz, 1H), 8.23 (s, 1H), 8.04-8.17 (m, 4H), 8.03 (s, 1H), 7.88-7.97 (m, 3H), 7.75-7.83 (m, 2H), 5.28-5.35 (m, 1H), 5.11 (t, J=7.8 Hz, 1H), 3.75-3.83 (m, 1H), 3.60-3.72 (m, 2H), 3.51-3.59 (m, 1H), 2.60-2.74 (m, 2H), 2.40-2.50 (m, 1H), 2.21-2.38 (m, 3H), 2.10-2.20 (m, 2H), 1.52 (s, 4H), 1.25 (s, 4H).

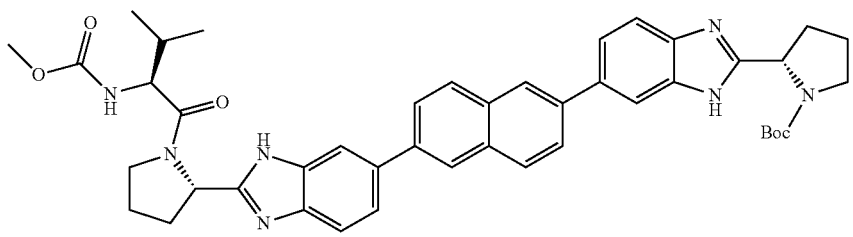 [SMILES: COC(=O)N[C@H](C(=O)N1CCC[C@H]1c1nc2ccc(-c3ccc4cc(-c5ccc6nc([C@@H]7CCCN7C(=O)OC(C)(C)C)[nH]c6c5)ccc4c3)cc2[nH]1)C(C)C]

Intermediate 49 tert-Butyl (2S)-2-(5-(6-(2-((2S)-1-(N-(methoxycarbonyl)-L-valyl)-2-pyrrolidinyl)-1H-benzimidazol-5-yl)-2-naphthyl)-1H-benzimidazol-2-yl)-1-pyrrolidinecarboxylate To a solution of tert-butyl (2S)-2-(5-(6-(2-((2S)-2-pyrrolidinyl)-1H-benzimidazol-5-yl)-2-naphthyl)-1H-benzimidazol-2-yl)-1-pyrrolidinecarboxylate (400 mg, 0.668 mmol), (S)-2-(methoxycarbonylamino)-3-methylbutanoic acid (176 mg, 1.00 mmol) and DIEA (0.583 mL, 3.34 mmol) in DMF (10 mL) was added HATU (381 mg, 1.00 mmol). The reaction mixture was stirred 2 h at room temperature and then purified by prep HPLC (using a Waters Sunfire C18 column 30×150 mm 5u eluted with a gradient of 0 to 50% ACN-Water+0.1% TFA) to yield a TFA salt of tert-butyl (2S)-2-(5-(6-(2-((2S)-1-(N-(methoxycarbonyl)-L-valyl)-2-pyrrolidinyl)-1H-benzimidazol-5-yl)-2-naphthyl)-1H-benzimidazol-2-yl)-1-pyrrolidinecarboxylate (445 mg) as yellow solid. LC-MS retention time 1.317 min; m/z 756.28 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode.

Intermediate 50

Methyl ((1S)-2-methyl-1-(((2S)-2-(5-(6-(2-((2S)-2-pyrrolidinyl)-1H-benzimidazol-5-yl)-2-naphthyl)-1H-benzimidazol-2-yl)-1-pyrrolidinyl)carbonyl)propyl)carbamate To a solution of a TFA salt of tert-butyl (2S)-2-(5-(6-(2-((2S)-1-(N-(methoxycarbonyl)-L-valyl)-2-pyrrolidinyl)-1H-benzimidazol-5-yl)-2-naphthyl)-1H-benzimidazol-2-yl)-1-pyrrolidinecarboxylate (445 mg) in DCM (10 mL) at room temp was added TFA (1 mL, 13 mmol). The mixture was stirred at rt for 3 h, concentrated, and the residue was diluted in MeOH, loaded onto a Strata XC MCX cartridge and washed with methanol. The compound was release from the cartridge by eluting with a solution of 2M ammonia in methanol and then evaporated under reduced pressure to give methyl ((1S)-2-methyl-1-(((2S)-2-(5-(6-(2-((2S)-2-pyrrolidinyl)-1H-benzimidazol-5-yl)-2-naphthyl)-1H-benzimidazol-2-yl)-1-pyrrolidinyl)carbonyl)propyl)carbamate (275 mg) as orange solid LC-MS retention time 1.120 min; m/z 656.27 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD) δ ppm 8.26 (br s, 1H), 8.22 (br s, 1H), 8.08-8.16 (m, 3H), 8.04-8.08 (m, 1H), 8.03 (s, 1H), 7.86-7.96 (m, 3H), 7.73-7.82 (m, 2H), 5.88-5.93 (m, 0.1H), 5.37-5.44 (m, 0.9H), 5.07-5.15 (m, 1H), 4.28-4.33 (m, 1H), 4.12-4.19 (m, 0.8H), 4.06-4.10 (m, 0.2H), 3.94-4.02 (m, 1H), 3.59-3.75 (m, 4H), 3.50-3.59 (m, 1H), 2.63-2.74 (m, 2H), 2.41-2.47 (m, 1H), 2.23-2.40 (m, 5H), 2.06-2.16 (m, 1H), 1.00-1.04 (m, 0.4H), 0.94-1.00 (m, 3H), 0.88-0.93 (m, 2.6H).

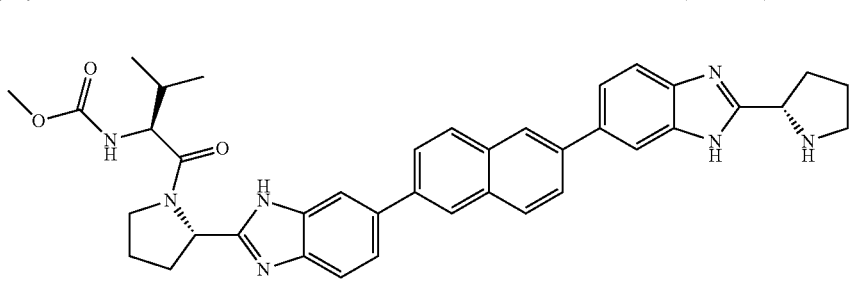 [SMILES: COC(=O)N[C@H](C(=O)N1CCC[C@H]1c1nc2ccc(-c3ccc4cc(-c5ccc6nc([C@@H]7CCCN7)[nH]c6c5)ccc4c3)cc2[nH]1)C(C)C]

Scheme 11
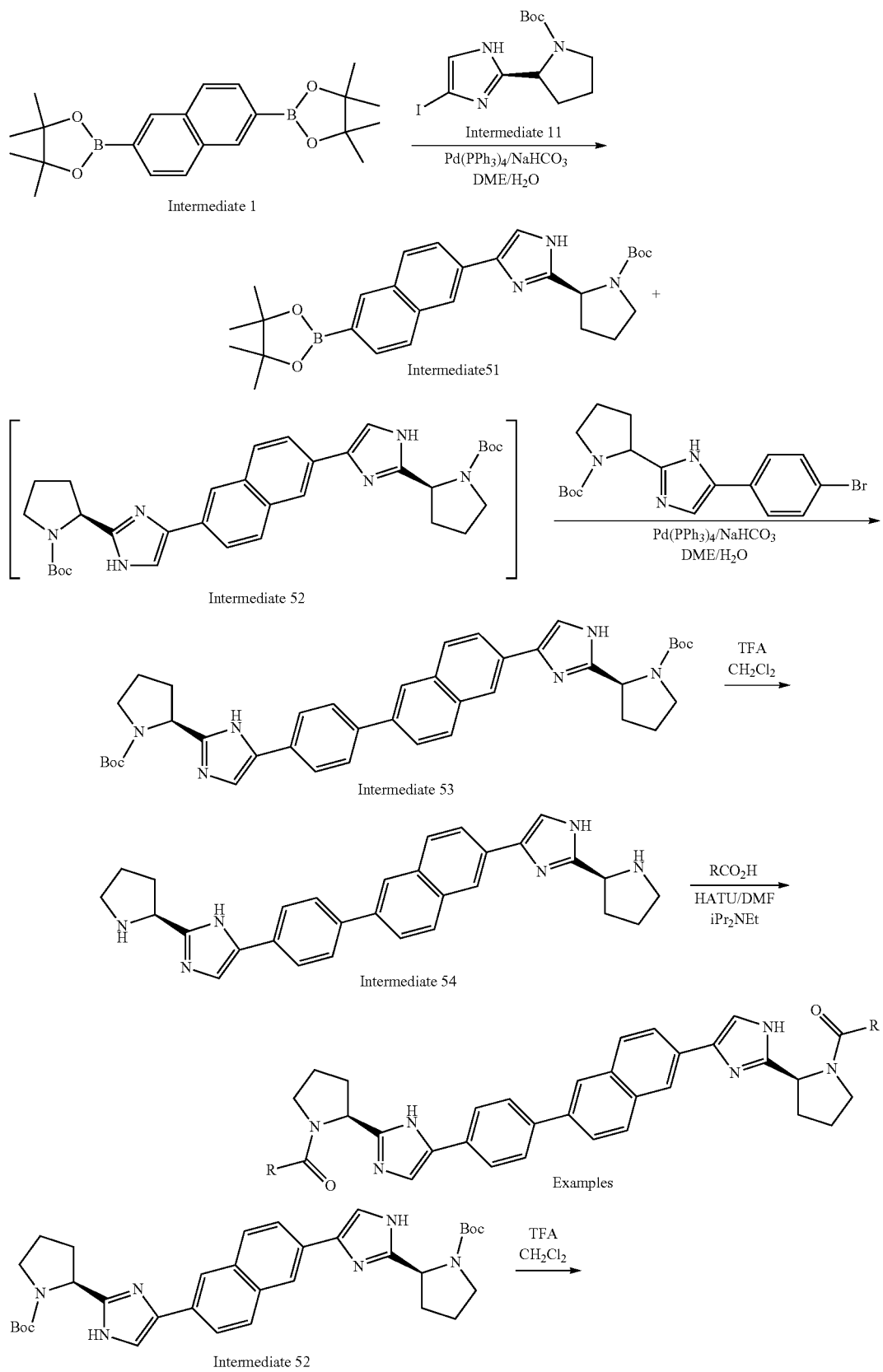

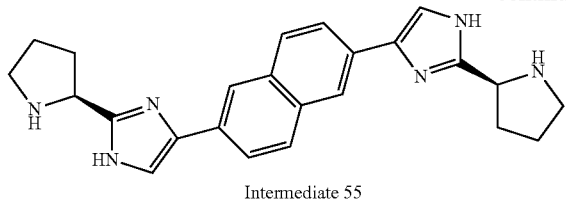 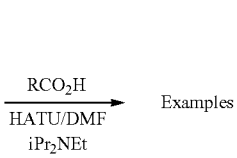

Intermediate 55

Intermediate 51

(S)-tert-Butyl 2-(4-(6-(4,4,5,5-tetramethyl-1,3,2-dioxaborolan-2-yl)naphthalen-2-yl)-1H-imidazol-2-yl)pyrrolidine-1-carboxylate and

Intermediate 52

(2S,2'S)-tert-Butyl 2,2'-(4,4'-(naphthalene-2,6-diyl)bis(1H-imidazole-4,2-diyl))dipyrrolidine-1-carboxylate A 100 mL pressure vessel equipped with a magnetic stir bar was charged with 2,6-bis(4,4,5,5-tetramethyl-1,3,2-dioxaborolan-2-yl)naphthalene (2.00 g, 5.26 mmol), (S)-tert-butyl 2-(5-iodo-1H-imidazol-2-yl)pyrrolidine-1-carboxylate (2.10 g, 5.79 mmol) and Pd(Ph$_3$P)$_4$ (0.058 g, 0.05 mmol) in DME (47.8 mL) and water (4.8 mL). The solution was degassed under vacuum for 5 min and the reactor was back filled with nitrogen. The vessel was sealed and the reaction mixture was heated overnight at 120° C. The reaction was cooled to room temperature and the volatiles were removed under. The residue was partitioned between water and EtOAc and the water layer was extracted with additional EtOAc. The combined organic layers were dried (Na$_2$SO$_4$), filtered, and concentrated. The crude product was purified with a BIOTAGE® (dry loaded onto a 90 g silica gel cartridge and eluted with a gradient of 0 to 30% EtOAc in DCM) and repurified with a BIOTAGE® (dry loaded onto a 80 g silica gel cartridge and eluted with a gradient of 0 to 50% EtOAc in DCM) to yield (S)-tert-butyl 2-(4-(6-(4,4,5,5-tetramethyl-1,3,2-dioxaborolan-2-yl)naphthalen-2-yl)-1H-imidazol-2-yl)pyrrolidine-1-carboxylate (949 mg) as a yellow solid. The material (contaminated with (2S,2'S)-tert-butyl 2,2'-(4,4'-(naphthalene-2,6-diyl)bis(1H-imidazole-4,2-diyl))dipyrrolidine-1-carboxylate) was used in the next step without further purification. LC-MS retention time 1.760 min; m/z 490.21 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode.

The preparative HPLC from the next reaction yielded (2S,2'S)-tert-butyl 2,2'-(4,4'-(naphthalene-2,6-diyl)bis(1H-imidazole-4,2-diyl))dipyrrolidine-1-carboxylate (92 mg, 0.111 mmol, 11% yield) as yellow solid LC-MS retention time 1.113 min; m/z 599.24 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD) δ ppm 8.35 (br s, 2H), 8.13 (br s, 2H), 8.08 (br s, 1H), 8.00 (br s, 1H), 7.95 (m, 2H), 5.18 (br s, 2H), 3.68-3.78 (m, 2H), 3.62 (br s, 2H), 2.51-2.68 (m, 2H), 2.21 (br s, 2H), 2.06-2.15 (m, 4H), 1.50 (br s, 9H), 1.31 (br s, 9H).

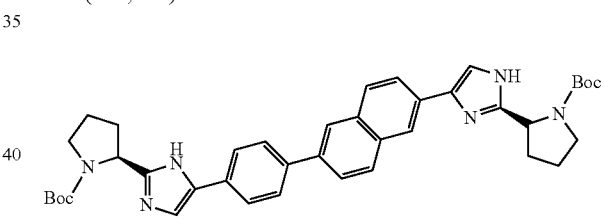

Intermediate 53

(S)-tert-Butyl 2-(5-(4-(6-(2-((S)-1-(tert-butoxycarbonyl)pyrrolidin-2-yl)-1H-imidazol-4-yl)naphthalen-2-yl)phenyl)-1H-imidazol-2-yl)pyrrolidine-1-carboxylate A 100 mL pressure vessel equipped with a magnetic stir bar was charged with (S)-tert-butyl 2-(4-(6-(4,4,5,5-tetramethyl-1,3,2-dioxaborolan-2-yl)naphthalen-2-yl)-1H-imidazol-2-yl)pyrrolidine-1-carboxylate (500 mg, 1.02 mmol), (S)-tert-butyl 2-(5-(4-bromophenyl)-1H-imidazol-2-yl)pyrrolidine-1-carboxylate (601 mg, 1.53 mmol) and Pd(Ph$_3$P)$_4$ (58 mg, 0.05 mmol) in DME (10 mL) and water (1.0 mL). The solution was degassed under vacuum for 5 min and the reactor was back filled with nitrogen. The mixture was heated for 8 h at 120° C., additional Pd(Ph$_3$P)$_4$ (57.8 mg, 0.05 mmol) was added and the mixture was degassed and stirred overnight at 130° C. The reaction was cooled to room temperature and the volatiles were removed under vacuum. The residue was partitioned between water and EtOAc and the water layer was extracted with additional EtOAc. The combined organic layers were dried (Na₂SO₄), filtered, and concentrated. The crude product was purified on a BIOTAGE® (dry loaded onto a 90 g silica gel cartridge and eluted with a gradient of 5 to 100% EtOAc in DCM) and then repurified by prep HPLC (using a Waters Sunfire C18 column 30×100 mm 5u eluted MeOH-Water+0.1% TFA) to yield a TFA salt of (S)-tert-butyl 2-(5-(4-(6-(2-((S)-1-(tert-butoxycarbonyl)pyrrolidin-2-yl)-1H-imidazol-4-yl)naphthalen-2-yl)phenyl)-1H-imidazol-2-yl)pyrrolidine-1-carboxylate (50 mg). LC-MS retention time 1.278 min; m/z 675.70 [M+H]⁺. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. ¹H NMR (500 MHz, MeOD) δ ppm 8.31 (d, J=15.9 Hz, 2H), 8.14-8.18 (m, 1H), 8.10 (d, J=8.85 Hz, 1H), 8.05 (s, 0.6H), 7.96-8.03 (m, 4H), 7.85-7.94 (m, 3.4H), 5.11-5.23 (m, 2H), 3.69-3.77 (m, 2H), 3.62 (br s, 2H), 2.51-2.67 (m, 2H), 2.16-2.26 (m, 2H), 2.05-2.16 (m, 4H), 1.51 (s, 9H), 1.32 (s, 9H).

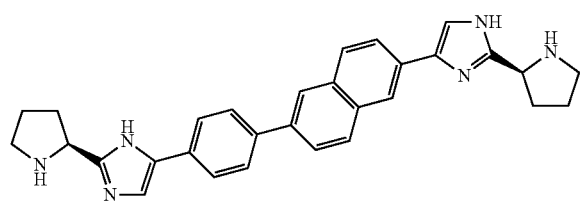 [SMILES: c1cc(-c2cnc([C@@H]3CCCN3)[nH]2)ccc1-c1ccc2cc(-c3c[nH]c([C@@H]4CCCN4)n3)ccc2c1]

Intermediate 54

2-((2S)-2-Pyrrolidinyl)-4-(4-(6-(2-((2S)-2-pyrrolidinyl)-1H-imidazol-4-yl)-2-naphthyl)phenyl)-1H-imidazole To a solution of a TFA salt of (S)-tert-butyl 2-(5-(4-(6-(2-((S)-1-(tert-butoxycarbonyl)pyrrolidin-2-yl)-1H-imidazol-4-yl)naphthalen-2-yl)phenyl)-1H-imidazol-2-yl)pyrrolidine-1-carboxylate (50 mg) in DCM (10 mL) was added TFA (2.0 mL, 26 mmol) in one portion. The mixture was agitated at room temperature for 2 h. The reaction was concentrated under vacuum to yield a TFA salt of 2-((S)-pyrrolidin-2-yl)-5-(4-(6-(2-((S)-pyrrolidin-2-yl)-1H-imidazol-5-yl)naphthalen-2-yl)phenyl)-1H-imidazole (51.5 mg) as orange solid, which was used without further purification. LC-MS retention time 0.978 min; m/z 475.19 [M+H]⁺. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. HPLC-MS (TFA) 78457-087 using a Waters Sunfire C18 column 4.6×50 mm 5u showed the reaction was complete peak found at RT=0.978 min. MH+=475.19. ¹H NMR (500 MHz, MeOD) δ ppm 8.34 (s, 1H), 8.20 (s, 1H), 8.03 (dd, J=14.2, 8.7 Hz, 2H), 7.84-7.96 (m, 7H), 7.79-7.84 (m, 1H,) 4.99-5.11 (m, 2H), 3.48-3.63 (m, 4H), 2.57-2.70 (m, 2H), 2.41-2.55 (m, 2H), 2.29-2.41 (m, 2H), 2.15-2.29 (m, 2H).

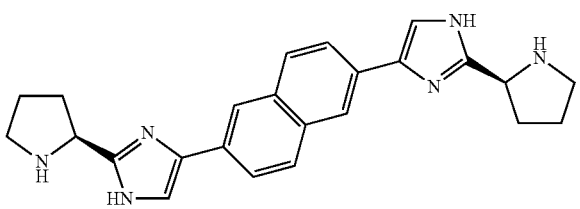 [SMILES: c1cc2cc(-c3c[nH]c([C@@H]4CCCN4)n3)ccc2cc1-c1c[nH]c([C@@H]2CCCN2)n1]

Intermediate 55

4,4'-(2,6-Naphthalenediyl)bis(2-((2S)-2-pyrrolidinyl)-1H-imidazole)

To a solution of a TFA salt of (2S,2'S)-tert-butyl 2,2'-(4,4'-(naphthalene-2,6-diyl)bis(1H-imidazole-4,2-diyl))dipyrrolidine-1-carboxylate (82 mg) in DCM (2 mL) at room temperature was added TFA (2.0 mL, 26 mmol) in one portion. The mixture was stirred for 3 h at room temperature, purified by prep HPLC (Waters Sunfire C18 column 30×100 mm 5u eluted with a gradient of 5 to 90% MeOH-Water+0.1% TFA) and repurified by prep HPLC (PHENOMENEX® Luna C18 column 30×100 mm 10u eluted with a gradient of 10 to 90% methanol-Water+0.1% TFA) to yield a TFA salt of 4,4'-(2,6-naphthalenediyl)bis(2-((2S)-2-pyrrolidinyl)-1H-imidazole) (68 mg) as tan solid. LC-MS retention time 0.978 min; m/z 399.18 [M+H]⁺. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. ¹H NMR (500 MHz, MeOD) δ ppm 8.31 (s, 2H), 7.95-8.00 (m, 2H), 7.91-7.95 (m, 2H), 7.85 (s, 2H), 5.03 (t, J=8.2 Hz, 2H), 3.49-3.62 (m, 4H), 2.59-2.67 (m, 2H), 2.42-2.52 (m, 2H), 2.31-2.40 (m, 2H), 2.17-2.28 (m, 2H).

Scheme 12

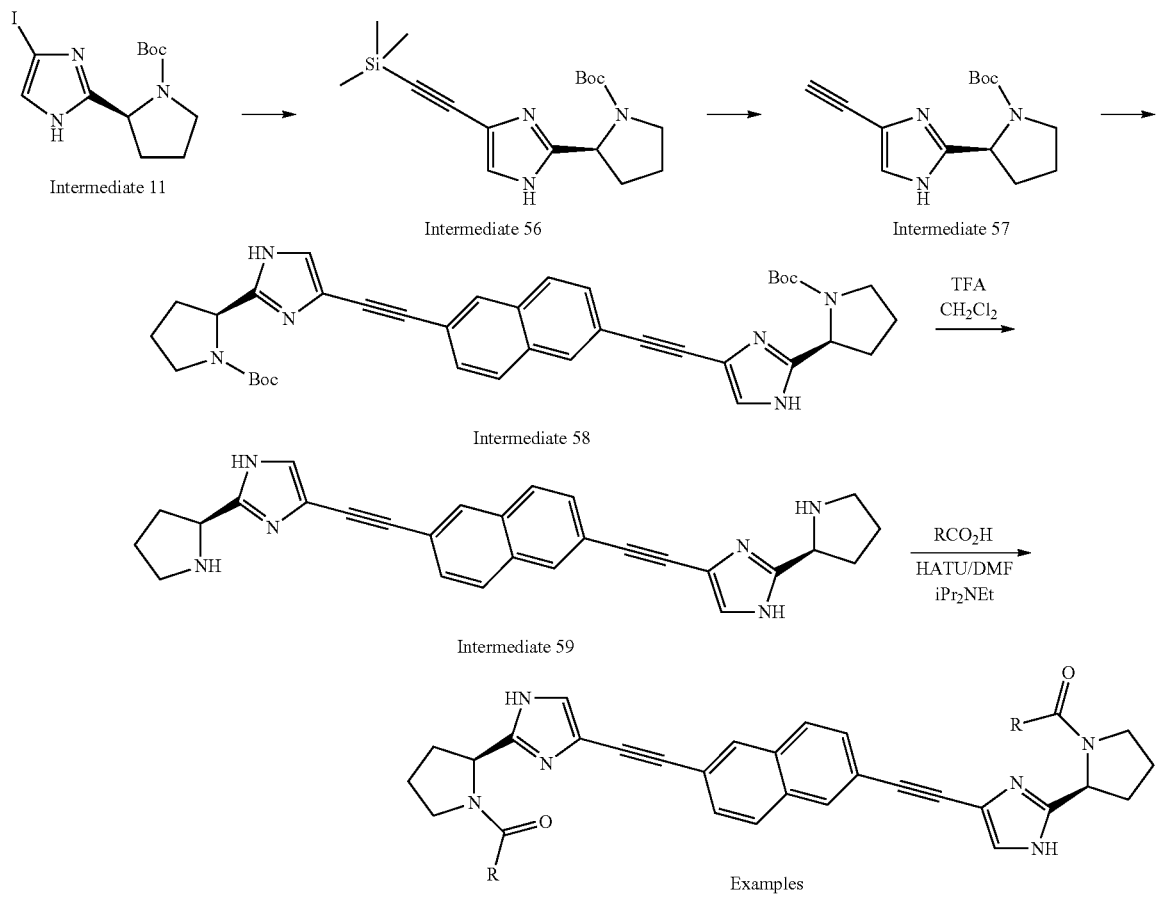

Intermediate 56

(S)-tert-Butyl 2-(5-((trimethylsilyl)ethynyl)-1H-imidazol-2-yl)pyrrolidine-1-carboxylate (S)-tert-Butyl 2-(5-iodo-1H-imidazol-2-yl)pyrrolidine-1-carboxylate (750 mg, 2.07 mmol) and copper(I) iodide (79 mg, 0.41 mmol) were dissolved into DMF (20 mL) and triethylamine (1.439 mL, 10.33 mmol). The reaction solution was vacuum flushed for 10 minutes (aspirator vacuum, flushed with nitrogen) and then ethynyltrimethylsilane (1.2 mL, 8.3 mmol) and finally Pd(PPh₃)₄ (119 mg, 0.103 mmol) were added. The flask was flushed with nitrogen, seal and heated at 50° C. overnight. The reaction was concentrated to a crude black tar, dissolved into DCM and purified via BIOTAGE® Horizon (80 g SiO₂, 20-40% EtOAc/hexanes) to yield (S)-tert-butyl 2-(5-((trimethylsilyl)ethynyl)-1H-imidazol-2-yl)pyrrolidine-1-carboxylate (546 mg, 1.64 mmol, 79% yield) as a yellow solid. This material was used without further purification. LC-MS retention time 1.393 min; m/z 332.33 (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 2 min, a hold time of 1 min, and an analysis time of 3 min where Solvent A was 5% acetonitrile/95% H₂O/10 mM ammonium acetate and Solvent B was 5% H₂O/95% acetonitrile/10 mM ammonium acetate. MS data was determined using a MICROMASS® Platform for LC in electrospray mode. $^1$H NMR (400 MHz, CDCl₃) δ ppm 7.19-7.13 (m, 1H), 4.92-4.85 (m, 1H), 3.43-3.31 (m, 2H), 3.04-2.83 (m, 1H), 2.20-1.88 (m, 3H), 1.51 (s, 3H), 1.49 (s, 6H), 0.25 (s, 3H), 0.23 (s, 6H).

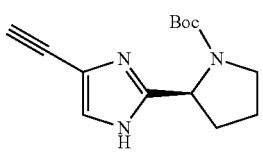 [SMILES: C#Cc1c[nH]c([C@@H]2CCCN2C(=O)OC(C)(C)C)n1]

Intermediate 57

(S)-tert-Butyl 2-(5-ethynyl-1H-imidazol-2-yl)pyrrolidine-1-carboxylate (S)-tert-Butyl 2-(5-((trimethylsilyl)ethynyl)-1H-imidazol-2-yl)pyrrolidine-1-carboxylate (537 mg, 1.61 mmol) was dissolved into MeOH (20 mL) and then potassium carbonate (22 mg, 0.16 mmol) was added and the reaction was stirred at rt for 3 h. The reaction was concentrated, dissolved into dichloromethane, loaded onto a SiO₂ column and purified by BIOTAGE® Horizon (30-50% EtOAc/hexanes) to yield (S)- tert-butyl 2-(5-ethynyl-1H-imidazol-2-yl)pyrrolidine-1-carboxylate (346 mg, 1.32 mmol, 82% yield) as an off-white solid. LC-MS retention time 0.878 min; m/z 260.35 (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 2 min, a hold time of 1 min, and an analysis time of 3 min where Solvent A was 5% acetonitrile/95% $H_2O$/10 mM ammonium acetate and Solvent B was 5% $H_2O$/95% acetonitrile/10 mM ammonium acetate. MS data was determined using a MICROMASS® Platform for LC in electrospray mode. $^1$H NMR (400 MHz, $CDCl_3$) δ ppm 7.21-7.17 (m, 1H), 4.92-4.87 (m, 1H), 3.43-3.30 (m, 2H), 3.05 (s, 1H), 3.03-2.85 (m, 1H), 2.20-1.88 (m, 3H), 1.60-1.45 (m, 9H).

recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 2 min, a hold time of 1 min, and an analysis time of 3 min where Solvent A was 5% acetonitrile/95% $H_2O$/10 mM ammonium acetate and Solvent B was 5% $H_2O$/95% acetonitrile/10 mM ammonium acetate. MS data was determined using a MICROMASS® Platform for LC in electrospray mode. $^1$H NMR (400 MHz, $CDCl_3$) δ ppm 10.70 (br s, 2H), 7.98 (s, 2H), 7.74 (d, J=8.3 Hz, 2H), 7.57 (d, J=8.3 Hz, 2H), 7.30-7.25 (m, 2H, under solvent peak), 4.95 (dd, J=7.3, 3.3 Hz, 2H), 3.46-3.37 (m, 4H), 3.08-2.91 (m, 2H), 2.24-2.08 (m, 4H), 2.03-1.92 (m, 2H), 1.51 (s, 18H).

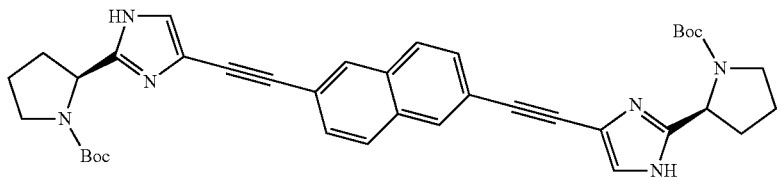 [SMILES: CC(C)(C)OC(=O)N1CCC[C@H]1c1nc(C#Cc2ccc3cc(C#Cc4c[nH]c([C@@H]5CCCN5C(=O)OC(C)(C)C)n4)ccc3c2)c[nH]1]

Intermediate 58 tert-Butyl (2S)-2-(4-((6-((2-((2S)-1-(tert-butoxycarbonyl)-2-pyrrolidinyl)-1H-imidazol-5-yl)ethynyl)-2-naphthyl)ethynyl)-1H-imidazol-2-yl)-1-pyrrolidinecarboxylate (S)-tert-Butyl 2-(5-ethynyl-1H-imidazol-2-yl)pyrrolidine-1-carboxylate (340 mg, 1.30 mmol), 2,6-dibromonaphthalene (744 mg, 2.60 mmol) and copper(I) iodide (12.39 mg, 0.065 mmol) were slurried into DMF (10 mL) and triethylamine (0.54 mL, 3.9 mmol). The solution was vacuum flushed with nitrogen (5×), treated with $Pd(PPh_3)_4$ (75 mg, 0.065 mmol) and then vacuum flushed with nitrogen (2×). The cloudy yellow solution was stirred under nitrogen at rt for 3 h. The reaction was concentrated to a yellow-orange semisolid, slurried into DMF/MeOH (~1:1), filtered and purified in five injections by prep HPLC (acetonitrile/water with 10 mM ammonium acetate, 15-100%). The fractions containing the desired product were combined and concentrated to yield tert-butyl (2S)-2-(4-((6-((2-((2S)-1-(tert-butoxycarbonyl)-2-pyrrolidinyl)-1H-imidazol-5-yl)ethynyl)-2-naphthyl)ethynyl)-1H-imidazol-2-yl)-1-pyrrolidinecarboxylate (70 mg, 0.11 mmol, 18% yield) as a light yellow solid. LC-MS retention time 1.448 min; m/z 647.45 (MH+). LC data was

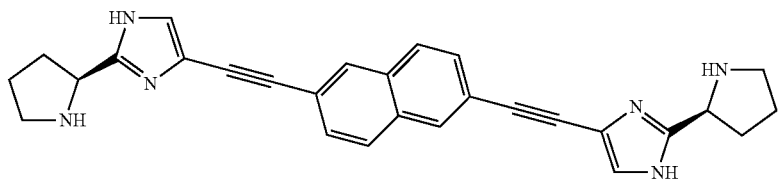 [SMILES: C(#Cc1c[nH]c([C@@H]2CCCN2)n1)c1ccc2cc(C#Cc3c[nH]c([C@@H]4CCCN4)n3)ccc2c1]

Intermediate 59

4,4'-(2,6-Naphthalenediyldi-2,1-ethynediyl)bis(2-((2S)-2-pyrrolidinyl)-1H-imidazole)

(2S,2'S)-tert-Butyl 2,2'-(5,5'-(naphthalene-2,6-diylbis(ethyne-2,1-diyl))bis(1H-imidazole-5,2-diyl))dipyrrolidine-1-carboxylate (32 mg, 0.049 mmol) was dissolved into dichloroethane (2 mL) and then TFA (1 mL, 13 mmol) was added. The solution was stirred at rt for 1 h. The reaction was concentrated to dryness to yield a TFA salt of 4,4'-(2,6-naphthalenediyldi-2,1-ethynediyl)bis(2-((2S)-2-pyrrolidinyl)-1H-imidazole) (41.6 mg) as tan solid. $^1$H NMR (500 MHz, $CD_3OD$) δ ppm 8.05 (s, 2H), 7.89 (d, J=8.3 Hz, 2H), 7.59 (d, J=8.6 Hz, 2H), 7.52 (s, 2H), 4.89-4.84 (m, 2H), 3.56-3.44 (m, 4H), 2.59-2.50 (m, 2H), 2.42-2.24 (m, 4H), 2.26-2.14 (m, 2H).

Scheme 13

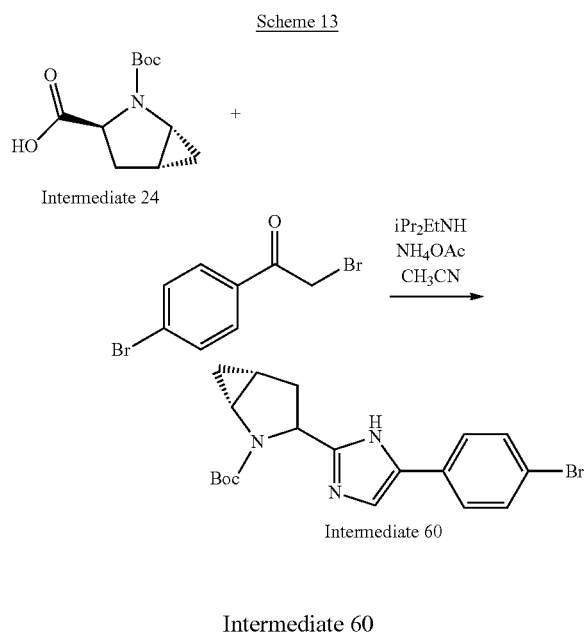

Intermediate 60

(1R,5R)-tert-Butyl 3-(5-(4-bromophenyl)-1H-imidazol-2-yl)-2-azabicyclo[3.1.0]hexane-2-carboxylate Hunig's Base (7.69 mL, 44.0 mmol) was added to a stirred solution of 2-bromo-1-(4-bromophenyl)ethanone (12.23 g, 44.0 mmol) and (1R,3S,5R)-2-(tert-butoxycarbonyl)-2-azabicyclo[3.1.0]hexane-3-carboxylic acid (10 g, 44 mmol) in dry MeCN (400 mL). The mixture was stirred for 16 h at RT. The solvent was removed in vacuo and the residue was taken up in ethyl acetate and washed with saturated sodium bicarbonate solution and brine, dried (sodium sulfate), filtered and concentrated. In a pressure vessel the residue was taken up in xylene (400 mL) and ammonium acetate (33.9 g, 440 mmol) was added. The vessel was sealed and heated at 140° C. for 2 h. The solvent was removed in vacuo and the residue was taken up in ethyl acetate and washed with saturated sodium bicarbonate solution (pH=9), brine, dried over sodium sulfate and concentrated. The crude product, as a reddish orange foam, was dissolved in methylene chloride and placed onto a 300 g Thompson silica gel cartridge (eluted with 20% B to 100% B for 4000 mL where Solvent B=ethyl acetate and Solvent A=hexanes) to yield (1R,3S,5R)-tert-butyl 3-(5-(4-bromophenyl)-1H-imidazol-2-yl)-2-azabicyclo[3.1.0]hexane-2-carboxylate (16.67 g, 39.1 mmol, 88.8% yield) as a golden-brown foam. LC-MS retention time 1.762 min; m/z 403.94 [M+H]⁺. LC data was recorded on a Shimadzu LC-10AS liquid chromatograph equipped with a PHENOMENEX® Luna S10 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. ¹H NMR (500 MHz, MeOD) δ ppm 7.62 (br d, J=8.6 Hz, 2H), 7.50 (br d, J=8.6 Hz, 2H), 7.37 (s, 1H), 4.66 (br s, 1H), 3.58 (br s, 1H), 2.56-2.47 (m, 1H), 2.36-2.27 (m, 1H), 1.75-1.67 (m, 1H), 0.97 (br s, 9H), 0.88-0.81 (m, 1H), 0.64-0.57 (m, 1H).

Scheme 14

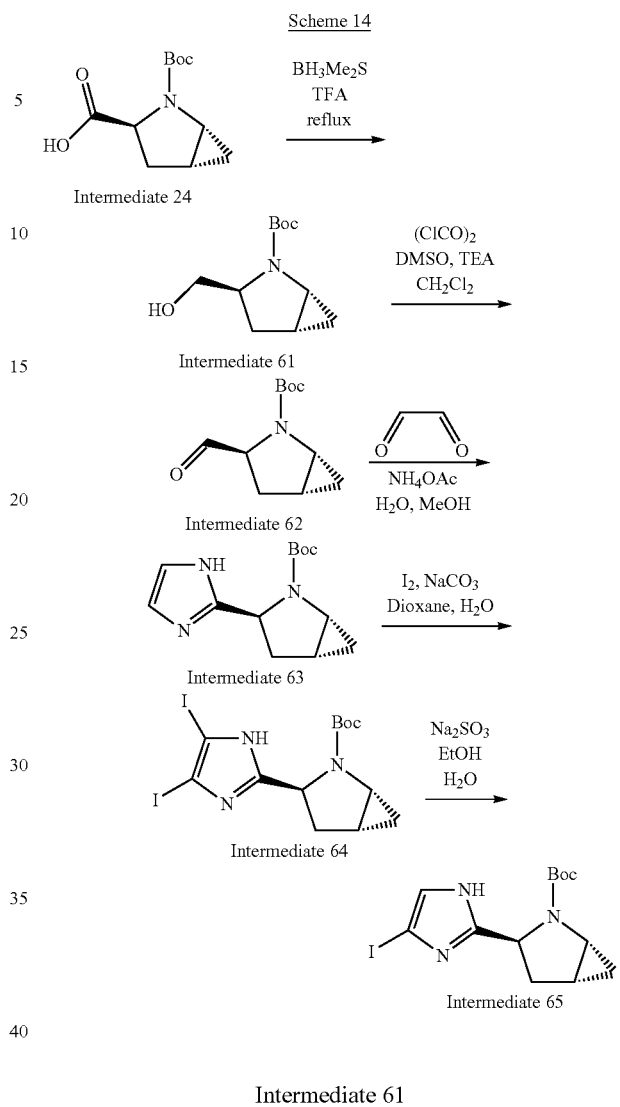

Intermediate 61

(1R,3S,5R)-tert-Butyl 3-(hydroxymethyl)-2-azabicyclo[3.1.0]hexane-2-carboxylate To a solution of (1R,3S,5R)-2-(tert-butoxycarbonyl)-2-azabicyclo[3.1.0]hexane-3-carboxylic acid (9.85 g, 43.3 mmol) in THF (200 mL) at 0° C. was added dropwise borane-methyl sulfide complex (282 mL, 563 mmol) over 30 min. The ice bath was removed, the mixture was stirred for 1 h and then heated at reflux for 2 h. The mixture was cooled to 0° C., slowly quenched with methanol (~200 mL) and concentrated under vacuum. The residue was dissolved in DCM and washed with water (emulsion), 1N HCl, sat NaHCO₃ aq, and brine. The organic layer was dried over Na₂SO₄, filtered and concentrated to yield (1R,3S,5R)-tert-butyl 3-(hydroxymethyl)-2-azabicyclo[3.1.0]hexane-2-carboxylate (8.43 g, 39.5 mmol, 91% yield) as colorless oil. LC-MS retention time 1.398 min; m/z 236.20 [M+Na]⁺. LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min and an analysis time of 4 min where Solvent A was 10% methanol/90% water/0.1% TFA and Solvent B was 90% methanol/10% water/0.1% TFA. MS data was determined using a MICROMASS® Platform for LC in electrospray mode. ¹H NMR (500 MHz, MeOD) δ ppm 3.72-3.79 (m, 1H), 3.52-3.64 (m, 3H), 3.15-3.24 (m, 1H), 2.00-2.08 (m, 1H), 1.62-1.72 (m, 1H), 1.54-1.62 (m, 1H), 1.45-1.51 (m, 9H), 0.84 (br s, 1H), 0.36 (td, J=5.0, 2.4 Hz, 1H).

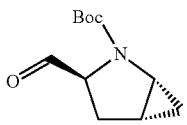 [SMILES: CC(C)(C)OC(=O)N1[C@H](C=O)C[C@H]2C[C@H]21]

Intermediate 62

(1R,3S,5R)-tert-Butyl 3-formyl-2-azabicyclo[3.1.0]hexane-2-carboxylate

To a solution of (1R,3S,5R)-tert-butyl 3-(hydroxymethyl)-2-azabicyclo[3.1.0]hexane-2-carboxylate (4.85 g, 22.74 mmol) in DCM (125 mL) at 0° C. was added Dess-Martin periodinane (11.57 g, 27.3 mmol). The reaction was warmed up to RT and stirred for 3 h. The reaction was poured into a saturated aq solution of NaHCO₃ then ca ~20 g of Na₂S₂O₃ was added and stirred for 1 h. The layers were separated and the aqueous layer was extracted several times with DCM. The combined organic extracts were dried over Na₂SO₄ and evaporated in vacuo. The residue was purified by flash column chromatography (BIOTAGE®), eluting with a gradient of 0 to 40% EtOAc/hexanes to afford (1R,3S,5R)-tert-butyl 3-formyl-2-azabicyclo[3.1.0]hexane-2-carboxylate (4.47 g, 21.2 mmol, 93% yield) as colorless oil. LC-MS retention time 0.813 min; m/z no ionization (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H₂O/0.1% TFA and Solvent B was 10% H₂O/90% MeOH/0.1% TFA. MS data was determined using a MICROMASS® Platform for LC in electrospray mode. ¹H NMR (400 MHz, chloroform-d) δ ppm 9.48 (br s, 1H), 3.67-3.97 (m, 1H), 3.33-3.59 (m, 1H), 2.10-2.31 (m, 2H), 1.56-1.67 (m, 1H), 1.47 (br s, 9H), 0.80 (br s, 1H), 0.55 (br s, 1H).

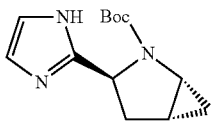 [SMILES: CC(C)(C)OC(=O)N1[C@@H]2C[C@@H]2C[C@H]1c1ncc[nH]1]

Intermediate 63

(1R,3S,5R)-tert-Butyl 3-(1H-imidazol-2-yl)-2-azabicyclo[3.1.0]hexane-2-carboxylate Ammonium hydroxide (16.40 mL, 421 mmol) was added dropwise to a stirred solution of (1R,3S,5R)-tert-butyl 3-formyl-2-azabicyclo[3.1.0]hexane-2-carboxylate (4.4 g) in methanol (15 mL) at 0° C. The reaction was allowed to warm to room temp and stirred for 45 min. Then, oxalaldehyde 40% H₂O (5.32 mL, 46.3 mmol) was added dropwise and the reaction mixture was stirred overnight. The reaction color turned brown over time. The reaction was diluted with brine and concentrated to remove the volatile solvent. The remaining aqueous layer was then extracted several times with ethyl acetate. The combined organic layers were dried over Na₂SO₄ evaporated under vacuum. The residue was purified by flash column chromatography (BIOTAGE®), eluting with a gradient of 0 to 70% EtOAc/hexanes to afford (1R,3S,5R)-tert-butyl 3-(1H-imidazol-2-yl)-2-azabicyclo[3.1.0]hexane-2-carboxylate (3.71 g, 14.9 mmol, 71% yield) as white solid. LC-MS retention time 0.772 min; m/z 250.20 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H₂O/0.1% TFA and Solvent B was 10% H₂O/90% MeOH/0.1% TFA. MS data was determined using a MICROMASS® Platform for LC in electrospray mode. ¹H NMR (400 MHz, chloroform-d) δ ppm 10.43 (br s, 1H), 6.99 (s, 2H), 4.86 (dd, J=9.0, 5.0 Hz, 1H), 3.35 (br s, 1H), 3.20 (br s, 1H), 2.28-2.38 (m, 1H), 1.71-1.80 (m, 1H), 1.49 (s, 9H), 0.83-0.90 (m, 1H), 0.45 (br s, 1H).

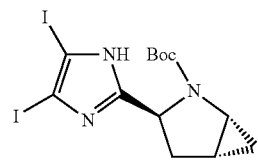 [SMILES: CC(C)(C)OC(=O)N1[C@@H]2C[C@@H]2C[C@H]1c1nc(I)c(I)[nH]1]

Intermediate 64

(1R,3S,5R)-tert-Butyl 3-(4,5-diiodo-1H-imidazol-2-yl)-2-azabicyclo[3.1.0]hexane-2-carboxylate Iodine (I₂, 12.43 g, 49.0 mmol) was added to a solution of 3-(1H-imidazol-2-yl)-2-azabicyclo[3.1.0]hexane-2-carboxylate (5.55 g, 22.3 mmol) and sodium carbonate (7.08 g, 66.8 mmol) in dioxane (56 mL) and water (56 mL) and the reaction mixture was stirred in the dark for 16 h at room temperature. The reaction mixture was diluted with EtOAc and washed an aqueous saturated solution of sodium thiosulfate. The layers were separated and the aqueous layer was extracted with EtOAc. The combined organic layers were dried over Na₂SO₄ and evaporated under vacuum. The residue was purified by flash column chromatography (BIOTAGE®), eluting with a gradient of 0 to 100% EtOAc/hexanes to afford (1R,3S,5R)-tert-butyl 3-(4,5-diiodo-1H-imidazol-2-yl)-2-azabicyclo[3.1.0]hexane-2-carboxylate (8.3 g, 16 mmol, 71% yield) as white solid. LC-MS retention time 1.455 min; m/z 502.07 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (400 MHz, MeOD) δ ppm 4.51 (br s, 1H), 3.56 (br s, 1H), 2.40-2.54 (m, 1H), 2.18-2.27 (m, 1H), 1.65-1.73 (m, 1H), 1.20-1.40 (br s, 9H), 0.82 (dt, J=8.6, 5.8 Hz, 1H), 0.58 (br s, 1H).

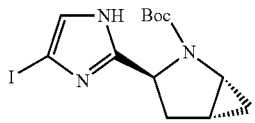

Intermediate 65

(1R,3S,5R)-tert-Butyl 3-(4-iodo-1H-imidazol-2-yl)-2-azabicyclo[3.1.0]hexane-2-carboxylate A 250 mL pressure flask equipped with a stir bar was charge with a solution of (1R,3S,5R)-tert-butyl 3-(4,5-di-iodo-1H-imidazol-2-yl)-2-azabicyclo[3.1.0]hexane-2-carboxylate (8.3 g, 17 mmol) in EtOH (83 mL) and water (83 mL). Then, sodium sulfite (20.88 g, 166 mmol) was added and the mixture was heated at 90° C. for 16 h. The reaction mixture was extracted with EtOAc and the combined organic layers were dried over Na$_2$SO$_4$ and evaporated under vacuum. The residue was purified by flash column chromatography (BIOTAGE®), eluting with a gradient of 0 to 15% EtOAc/DCM to afford (1R,3S,5R)-tert-butyl 3-(4-iodo-1H-imidazol-2-yl)-2-azabicyclo[3.1.0]hexane-2-carboxylate (3.84 g, 10.2 mmol, 62% yield) as yellow solid along with the fully reduced product (1R,3S,5R)-tert-butyl 3-(1H-imidazol-2-yl)-2-azabicyclo[3.1.0]hexane-2-carboxylate (550 mg, 2.21 mmol, 13% yield). LC-MS retention time 0.932 min; m/z 376.22 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (500 MHz, MeOD) δ ppm 7.12 (br s, 1H), 4.59 (br s, 1H), 3.44-3.64 (br s, 1H), 2.40-2.52 (m, 1H), 2.17-2.30 (m, 1H), 1.65-1.73 (m, 1H), 1.27 (br s, 9H), 0.84 (dt, J=8.5, 5.7 Hz, 1H), 0.58 (br s, 1H).

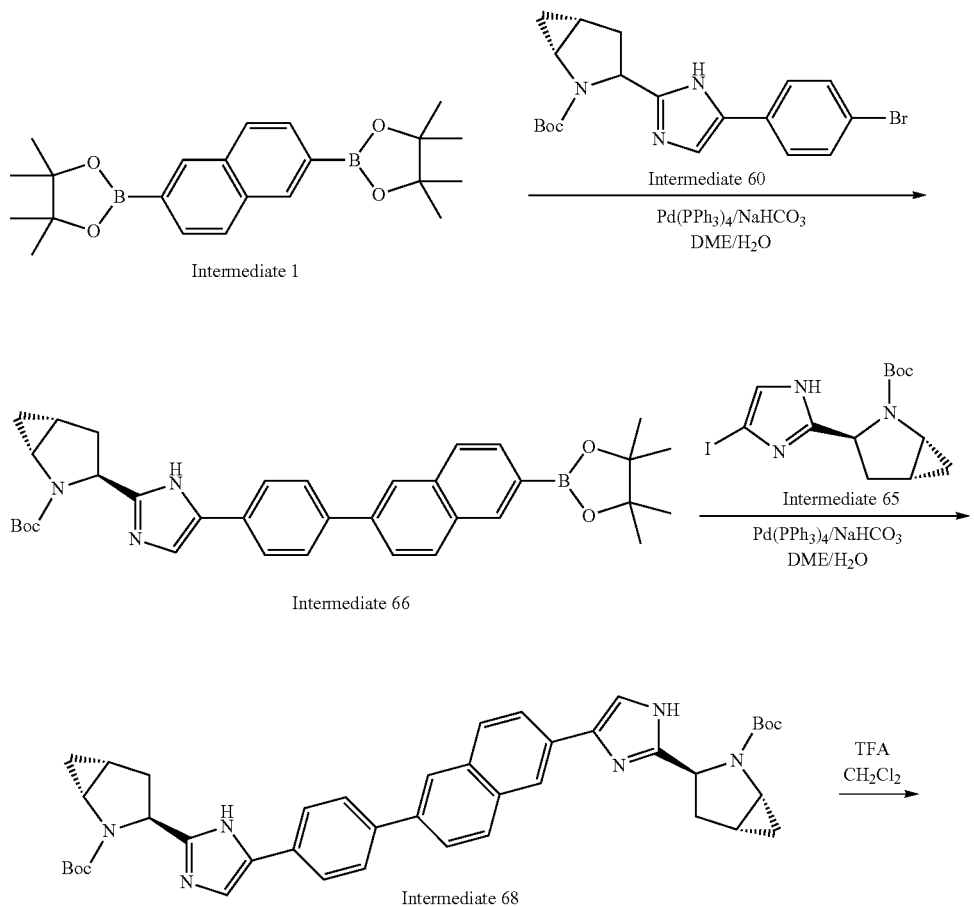

Scheme 15

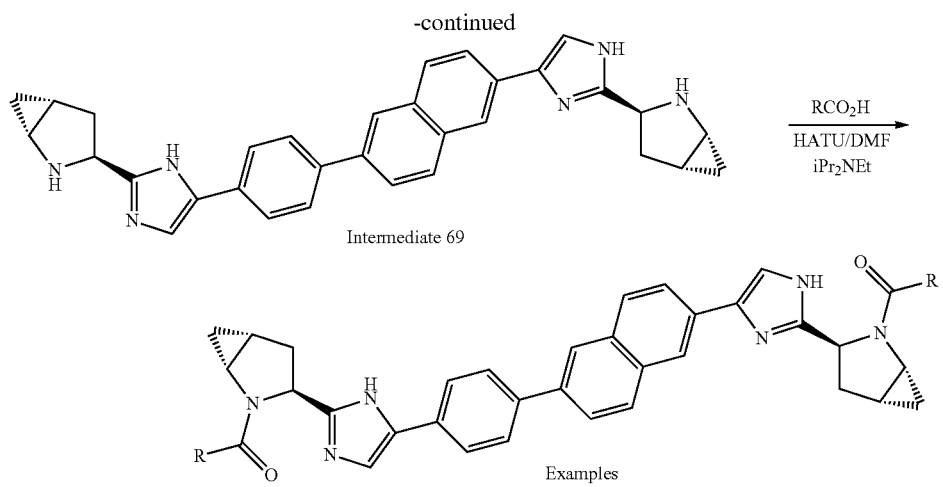

Intermediate 69

Examples

Intermediate 66

(1R,3S,5R)-tert-Butyl 3-(5-(4-(6-(4,4,5,5-tetramethyl-1,3,2-dioxaborolan-2-yl)naphthalen-2-yl)phenyl)-1H-imidazol-2-yl)-2-azabicyclo[3.1.0]hexane-2-carboxylate and

Intermediate 67

(1R,1'R,3S,3'S,5R,5'R)-tert-Butyl 3,3'-(5,5'-(4,4'-(naphthalene-2,6-diyl)bis(4,1-phenylene))bis(1H-imidazole-5,2-diyl))bis(2-azabicyclo[3.1.0]hexane-2-carboxylate)

A solution of 2,6-bis(4,4,5,5-tetramethyl-1,3,2-dioxaborolan-2-yl)naphthalene (1.0 g, 2.6 mmol), (1R,3S,5R)-tert-butyl 3-(5-(4-bromophenyl)-1H-imidazol-2-yl)-2-azabicyclo[3.1.0]hexane-2-carboxylate (1.06 g, 2.63 mmol), Na$_2$CO$_3$ (0.837 g, 7.89 mmol) in DME (20 mL) and water (2 mL) was degassed under vacuum for 10 min. The mixture was heated at 80° C. and then Pd(Ph$_3$P)$_4$ (0.152 g, 0.132 mmol) was added under a stream of nitrogen. The reactor was sealed and the heating was pursued further at 120° C. for 16 h. The DME was removed in vacuo and the crude material was partitioned between EtOAc/H$_2$O. The layers were separated and the aqueous layer was extracted several times with EtOAc. The combined organic extracts were dried over Na$_2$SO$_4$ and evaporated in vacuo. The residue was purified by flash column chromatography (BIOTAGE®), eluting with a gradient of 0 to 5% MeOH/DCM to afford the partially pure target product contaminated with reaction side products. The impure product was purified again by flash column chromatography (BIOTAGE®), eluting with a gradient of 50 to 100% EtOAc/hexanes, then the column was flushed with 10% MeOH/DCM to afford (1R,3S,5R)-tert-butyl 3-(5-(4-(6-(4,4,5,5-tetramethyl-1,3,2-dioxaborolan-2-yl)naphthalen-2-yl)phenyl)-1H-imidazol-2-yl)-2-azabicyclo[3.1.0]hexane-2-carboxylate (606 mg) as yellow foam. LC-MS retention time 1.608 min; m/z 578.4 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (500 MHz, chloroform-d, Partial NMR) δ ppm 4.89 (br s, 1H), 3.20-3.66 (m, 1H), 2.33-2.50 (m, 1H), 1.76-1.86 (m, 1H), 1.52 (br s, 9H), 1.24-1.32 (m, 12H), 0.87-0.93 (m, 1H), 0.51 (br s, 1H).

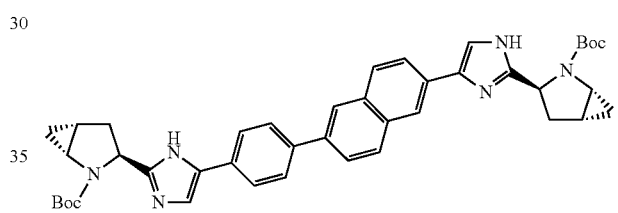

Intermediate 68

(1R,3S,5R)-tert-Butyl 3-(5-(4-(6-(2-((1R,3S,5R)-2-(tert-butoxycarbonyl)-2-azabicyclo[3.1.0]hexan-3-yl)-1H-imidazol-4-yl)naphthalen-2-yl)phenyl)-1H-imidazol-2-yl)-2-azabicyclo[3.1.0]hexane-2-carboxylate

A solution of (1R,3S,5R)-tert-butyl 3-(5-(4-(6-(4,4,5,5-tetramethyl-1,3,2-dioxaborolan-2-yl)naphthalen-2-yl)phenyl)-1H-imidazol-2-yl)-2-azabicyclo[3.1.0]hexane-2-carboxylate (568 mg), (1R,3S,5R)-tert-butyl 3-(5-iodo-1H-imidazol-2-yl)-2-azabicyclo[3.1.0]hexane-2-carboxylate (369 mg, 0.983 mmol), Na$_2$CO$_3$ (313 mg, 2.95 mmol) in DME (10 mL) and water (2 mL) was degassed under vacuum for 10 min. The mixture was heated at 80° C. and then Pd(Ph$_3$P)$_4$ (114 mg, 0.098 mmol) was added under a stream of nitrogen. The reactor was sealed and the heating was pursued further at 130° C. overnight. The DME was removed in vacuo and the crude material was partitioned between EtOAc/H$_2$O. The layers were separated and the aqueous layer was extracted several times with EtOAc. The combined organic extracts were dried over Na$_2$SO$_4$ and evaporated in vacuo. The residue was purified by flash column chromatography (BIOTAGE®), eluting with a gradient of 20 to 100% EtOAc/hexanes, then 5% MeOH/DCM to afford the partially pure (1R,3S,5R)-tert-butyl 3-(5-(4-(6-(2-((1R,3S,5R)-2-(tert-butoxycarbonyl)-2-azabicyclo[3.1.0]hexan-3-yl)-1H-imidazol-4-yl)naphthalen-2-yl)phenyl)-1H-imidazol-2-yl)-2-azabicyclo[3.1.0]hexane-2-carboxylate (277 mg). LC-MS retention time 1.578 min; m/z 699.56 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% TFA and Solvent B was 10% $H_2O$/90% MeOH/0.1% TFA. MS data was determined using a MICROMASS® Platform for LC in electrospray mode. $^1$H NMR (500 MHz, MeOD) δ ppm 7.62-7.69 (m, 6H), 7.53-7.59 (m, 4H), 6.95 (s, 2H), 4.67 (br s, 2H), 3.46-3.56 (m, 2H), 2.50-2.59 (m, 0.5H), 2.32-2.49 (m, 2H), 2.27 (br s, 1.5H), 1.65-1.78 (m, 2H), 1.28 (br. s, 18H), 0.80-0.88 (m, 2H), 0.53-0.66 (m, 2H).

Intermediate 69

(1R,3S,5R)-3-(4-(4-(6-(2-((1R,3S,5R)-2-Azabicyclo[3.1.0]hex-3-yl)-1H-imidazol-4-yl)-2-naphthyl)phenyl)-1H-imidazol-2-yl)-2-azabicyclo[3.1.0]hexane To a solution of (1R,3S,5R)-tert-butyl 3-(5-(4-(6-(2-((1R,3S,5R)-2-(tert-butoxycarbonyl)-2-azabicyclo[3.1.0]hexan-3-yl)-1H-imidazol-5-yl)naphthalen-2-yl)phenyl)-1H-imidazol-2-yl)-2-azabicyclo[3.1.0]hexane-2-carboxylate (275 mg) in DCM (10 mL) was added TFA (2 mL, 26.0 mmol). The mixture was stirred for 2 h at room temperature. The volatiles were removed under vacuum and the crude residue was purified by a reverse phase HPLC (water/MeOH/TFA) to afford a TFA salt of (1R,3S,5R)-3-(4-(4-(6-(2-((1R,3S,5R)-2-azabicyclo[3.1.0]hex-3-yl)-1H-imidazol-4-yl)-2-naphthyl)phenyl)-1H-imidazol-2-yl)-2-azabicyclo[3.1.0]hexane (106 mg) as tan solid. LC-MS retention time 1.153 min; m/z 499.36 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% TFA and Solvent B was 10% $H_2O$/90% MeOH/0.1% TFA. MS data was determined using a MICROMASS® Platform for LC in electrospray mode. $^1$H NMR (500 MHz, MeOD) δ ppm 8.33 (s, 1H), 8.19 (s, 1H), 7.99-8.05 (m, 2H), 7.85-7.95 (m, 6H), 7.83 (s, 1H), 7.76 (s, 1H), 4.78 (q, J=9.4 Hz, 2H), 3.47-3.54 (m, 2H), 2.65-2.74 (m, 4H), 2.02-2.12 (m, 2H), 1.18-1.25 (m, 2H), 0.97-1.05 (m, 2H).

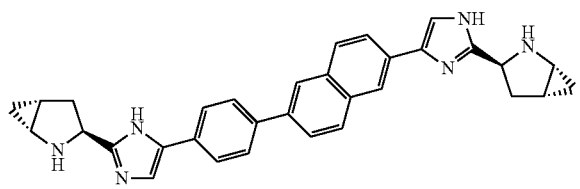 [SMILES: c1cc(-c2cnc([C@@H]3C[C@H]4C[C@H]4N3)[nH]2)ccc1-c1ccc2cc(-c3c[nH]c([C@@H]4C[C@H]5C[C@H]5N4)n3)ccc2c1]

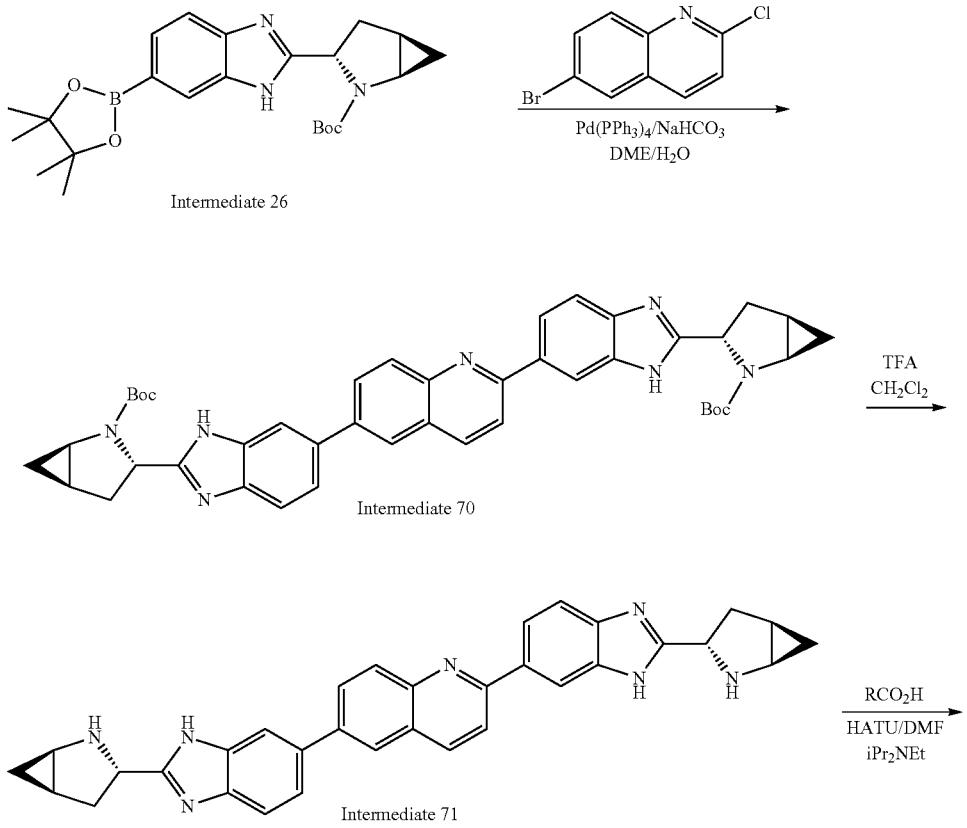

Scheme 16

-continued

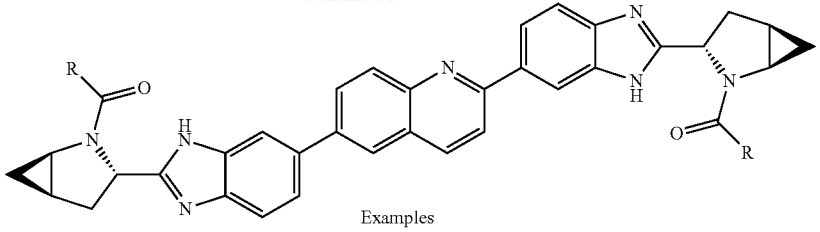

Examples

Intermediate 70 tert-Butyl (1R,3S,5R)-3-(5-(2-(2-((1R,3S,5R)-2-(tert-butoxycarbonyl)-2-azabicyclo[3.1.0]hex-3-yl)-1H-benzimidazol-6-yl)-6-quinolinyl)-1H-benzimidazol-2-yl)-2-azabicyclo[3.1.0]hexane-2-carboxylate To a degassed solution of 6-bromo-2-chloroquinoline (30 mg, 0.12 mmol), Na$_2$CO$_3$ (39.3 mg, 0.371 mmol) and (1R,3S,5R)-tert-butyl 3-(6-(4,4,5,5-tetramethyl-1,3,2-dioxaborolan-2-yl)-1H-benzo[d]imidazol-2-yl)-2-azabicyclo[3.1.0]hexane-2-carboxylate (116 mg, 0.272 mmol) in dioxane (1 mL) and H$_2$O (0.2 mL) was added Pd(Ph$_3$P)$_4$ (14.3 mg, 0.012 mmol) and the mixture was stirred at 110° C. for 2 h. The reaction mixture was diluted with MeOH, and purified by prep HPLC (H$_2$O-MeOH with 0.1% TFA buffer) to yield a TFA salt of tert-butyl (1R,3S,5R)-3-(5-(2-(2-((1R,3S,5R)-2-(tert-butoxycarbonyl)-2-azabicyclo[3.1.0]hex-3-yl)-1H-benzimidazol-6-yl)-6-quinolinyl)-1H-benzimidazol-2-yl)-2-azabicyclo[3.1.0]hexane-2-carboxylate (60.6 mg, 0.057 mmol, 46.3% yield) as a yellow solid. LC-MS retention time 2.05 min; m/z 724 [M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 8.68 (1H, d, J=8.5 Hz), 8.60 (1H, s), 8.44 (1H, dd, J=8.5, 1.5 Hz), 8.39 (1H, d, J=1.3 Hz), 8.33 (1H, d, J=8.8 Hz), 8.23-8.29 (1H, m), 8.25 (1H, d, J=8.5 Hz), 8.19 (1H, s), 8.08 (1H, d, J=9.0 Hz), 7.96 (1H, d, J=9.0 Hz), 7.93 (1H, d, J=9.5 Hz), 5.02-5.12 (2H, m), 3.70 (2H, br s), 2.74-2.85 (2H, m), 2.45-2.57 (2H, m), 1.84-1.96 (2H, m), 1.05-1.68 (18H, m), 0.89-1.01 (2H, m), 0.77-0.86 (2H, m).

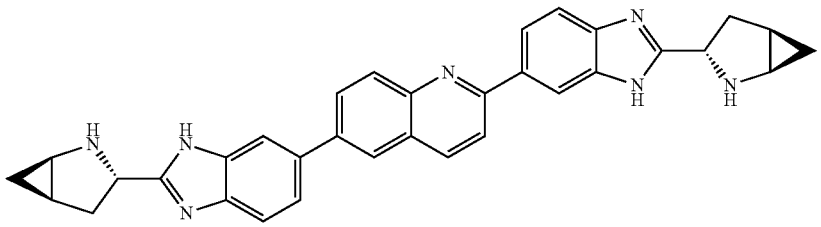

Intermediate 71

2,6-Bis(2-((1R,3S,5R)-2-azabicyclo[3.1.0]hexan-3-yl)-1H-benzo[d]imidazol-6-yl)quinoline A TFA salt of tert-butyl (1R,3S,5R)-3-(5-(2-(2-((1R,3S,5R)-2-(tert-butoxycarbonyl)-2-azabicyclo[3.1.0]hex-3-yl)-1H-benzimidazol-6-yl)-6-quinolinyl)-1H-benzimidazol-2-yl)-2-azabicyclo[3.1.0]hexane-2-carboxylate (51 mg, 0.054 mmol) was mixed with a dioxane solution of HCl (0.5 mL, 2.00 mmol), and stirred at rt for 2 h. The volatiles were removed to yield an HCl salt of 2,6-bis(2-((1R,3S,5R)-2-azabicyclo[3.1.0]hexan-3-yl)-1H-benzo[d]imidazol-6-yl)quinoline (53 mg) as yellow solid. LC-MS retention time 1.20 min; m/z 524 [M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220).

Scheme 17

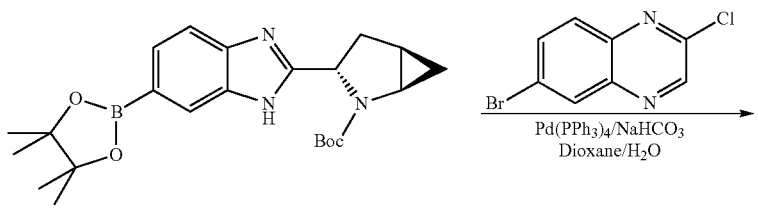

Intermediate 26

-continued

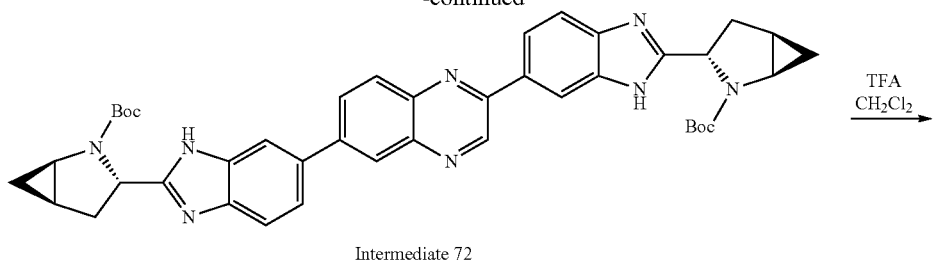
Intermediate 72

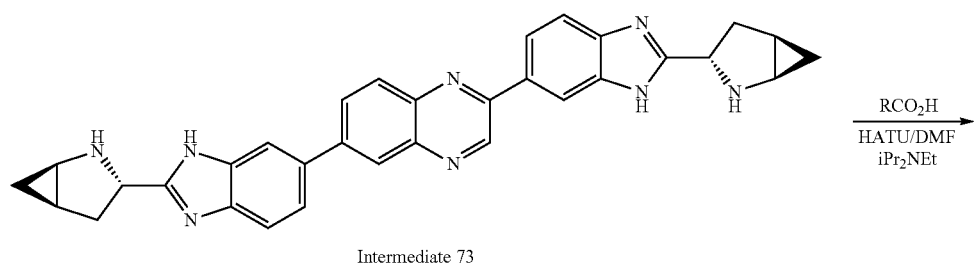
Intermediate 73

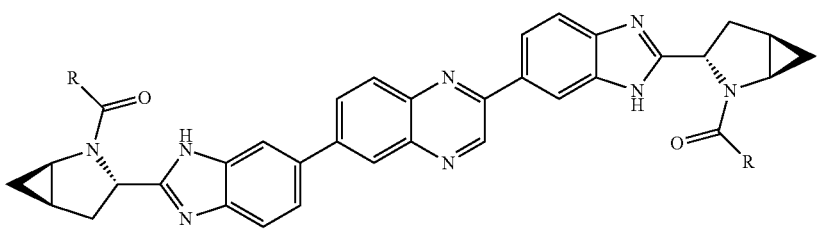
Examples

Intermediate 72 tert-Butyl (1R,3S,5R)-3-(5-(2-(2-((1R,3S,5R)-2-(tert-butoxycarbonyl)-2-azabicyclo[3.1.0]hex-3-yl)-1H-benzimidazol-6-yl)-6-quinoxalinyl)-1H-benzimidazol-2-yl)-2-azabicyclo[3.1.0]hexane-2-carboxylate Pd(Ph$_3$P)$_4$ (14.24 mg, 0.012 mmol) was added to a degassed solution of 6-bromo-2-chloroquinoxaline (30 mg, 0.123 mmol), NaHCO$_3$ (31.1 mg, 0.370 mmol) and (1R,3S,5R)-tert-butyl 3-(6-(4,4,5,5-tetramethyl-1,3,2-dioxaborolan-2-yl)-1H-benzo[d]imidazol-2-yl)-2-azabicyclo[3.1.0]hexane-2-carboxylate (131 mg, 0.308 mmol) in dioxane (1.0 mL) and H$_2$O (0.2 mL) and the mixture was stirred at 100° C. for 2 h, then at 110° C. for 2 h. The reaction was diluted with MeOH, filtered and the filtrate was purified by prep HPLC (H$_2$O-MeOH with 0.1% TFA buffer) to yield a TFA salt of tert-butyl (1R,3S,5R)-3-(5-(2-(2-((1R,3S,5R)-2-(tert-butoxycarbonyl)-2-azabicyclo[3.1.0]hex-3-yl)-1H-benzimidazol-6-yl)-6-quinoxalinyl)-1H-benzimidazol-2-yl)-2-azabicyclo[3.1.0]hexane-2-carboxylate (67.6 mg) as a yellow solid. LC-MS retention time 2.13 min; m/z 725 [M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 9.60 (1H, s), 8.71 (1H, s), 8.56 (1H, dd, J=8.8, 1.5 Hz), 8.45 (1H, d, J=1.5 Hz), 8.26-8.35 (2H, m), 8.21 (1H, s), 8.06-8.11 (1H, m), 7.91-7.99 (2H, m), 5.02-5.13 (2H, m), 3.70 (2H, br s), 2.79 (2H, dd, J=13.4, 9.2 Hz), 2.43-2.57 (2H, m), 1.83-1.96 (2H, m), 1.07-1.65 (18H, m), 0.95 (2H, m), 0.77-0.85 (2H, m).

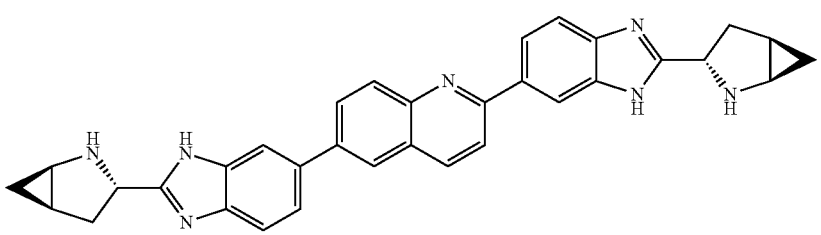 [SMILES: c1cc2nc(-c3ccc4nc([C@@H]5C[C@H]6C[C@H]6N5)[nH]c4c3)ccc2cc1-c1ccc2nc([C@@H]3C[C@H]4C[C@H]4N3)[nH]c2c1]

Intermediate 73

2,6-Bis(2-((1R,3S,5R)-2-azabicyclo[3.1.0]hexan-3-yl)-1H-benzo[d]imidazol-6-yl)quinoxaline TFA (0.25 mL, 3.24 mmol) was added to a solution of a TFA salt of tert-butyl (1R,3S,5R)-3-(5-(2-(2-((1R,3S,5R)-2-(tert-butoxycarbonyl)-2-azabicyclo[3.1.0]hex-3-yl)-1H-benzimidazol-6-yl)-6-quinoxalinyl)-1H-benzimidazol-2-yl)-2-azabicyclo[3.1.0]hexane-2-carboxylate (65 mg) in DCM (0.5 mL) and the mixture was stirred at rt for 16 h. The volatiles were removed and the residue was triturated with Et$_2$O. The resulting solid was collected via filtration funnel and rinsed with Et$_2$O to yield a TFA salt of 2,6-bis(2-((1R,3S,5R)-2-azabicyclo[3.1.0]hexan-3-yl)-1H-benzo[d]imidazol-6-yl)quinoxaline (60 mg) as yellow solid. LC-MS retention time 1.51 min; m/z 525 [M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 9.52 (1H, s), 8.58 (1H, s), 8.36 (1H, s), 8.22-8.33 (2H, m), 8.30 (1H, d, J=9.5 Hz), 8.08 (1H, s), 7.76-7.94 (2H, m), 7.83 (1H, d, J=9.5 Hz), 4.80-5.05 (2H, m), 3.45-3.61 (2H, m), 2.70-2.92 (2H, m), 2.50-2.67 (2H, m), 2.00-2.18 (2H, m), 1.26 (2H, br s), 1.04 (2H, br s).

Scheme 18

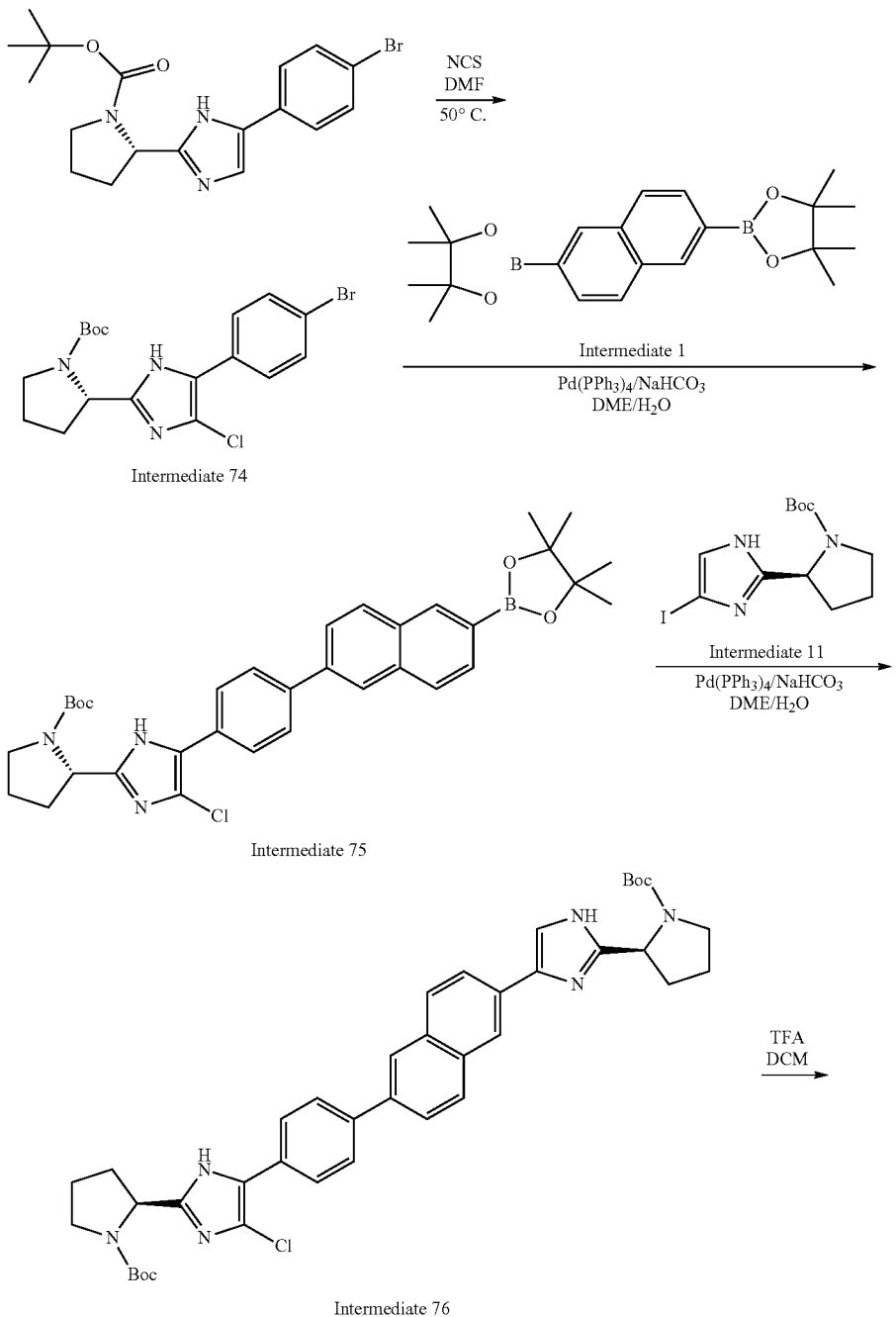

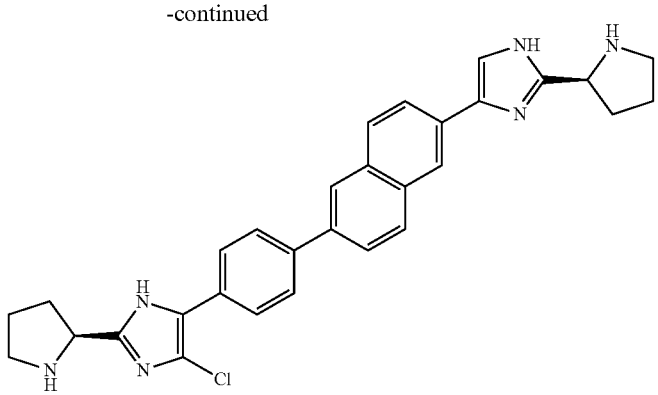

Intermediate 77

Intermediate 74

(S)-tert-Butyl 2-(5-(4-bromophenyl)-4-chloro-1H-imidazol-2-yl)pyrrolidine-1-carboxylate NCS (0.51 g, 3.82 mmol) was added to a solution of tert-butyl 2-(5-(4-bromophenyl)-1H-imidazol-2-yl)pyrrolidine-1-carboxylate (1.0 g, 2.55 mmol) in DMF (25 mL) and the mixture was heated at 50° C. overnight. The volatiles were removed under vacuum. The residue was purified by flash column chromatography (BIOTAGE®), eluting with a gradient of 0 to 10% EtOAc/DCM to afford the partially pure (S)-tert-butyl 2-(5-(4-bromophenyl)-4-chloro-1H-imidazol-2-yl)pyrrolidine-1-carboxylate (1.04 g) as yellow foam. LC-MS retention time 1.99 min; m/z 427.12 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (500 MHz, MeOD) δ ppm 7.63 (s, 4H), 4.74-4.81 (m, 1H), 3.64-3.72 (m, 1H), 3.45-3.55 (m, 1H), 2.27-2.42 (m, 1H), 2.00-2.15 (m, 2H), 1.90-2.00 (m, 1H), 1.48 (m, 3H), 1.27 (m, 6H).

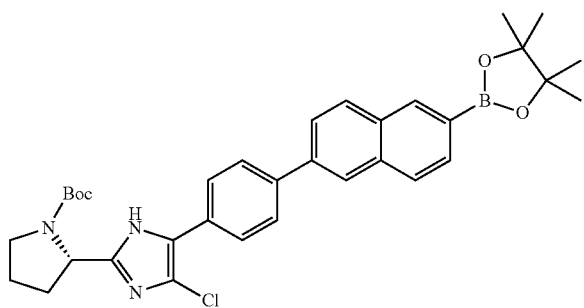 [SMILES: CC(C)(C)OC(=O)N1CCC[C@H]1c1nc(Cl)c(-c2ccc(-c3ccc4cc(B5OC(C)(C)C(C)(C)O5)ccc4c3)cc2)[nH]1]

Intermediate 75

(S)-tert-Butyl 2-(4-chloro-5-(4-(6-(4,4,5,5-tetramethyl-1,3,2-dioxaborolan-2-yl)naphthalen-2-yl)phenyl)-1H-imidazol-2-yl)pyrrolidine-1-carboxylate A solution of (S)-tert-butyl 2-(5-(4-bromophenyl)-4-chloro-1H-imidazol-2-yl)pyrrolidine-1-carboxylate (1.04 g, 2.44 mmol) and 2,6-bis(4,4,5,5-tetramethyl-1,3,2-dioxaborolan-2-yl)naphthalene (0.926 g, 2.44 mmol) in DME (10 mL) and water (2 mL) was degassed under vacuum for 10 min. The mixture was heated at ca ~80° C., Pd(Ph$_3$P)$_4$ (0.282 g, 0.244 mmol) was added under a stream of nitrogen and the reactor was sealed. The heating was pursued further to 130° C. for 8 h. Additional Pd(PPh$_3$)$_4$ (100 mg) was added and the heating was pursued overnight. The DME was removed in vacuo and the crude material was partitioned between EtOAc/H$_2$O. The layers were separated and the aqueous layer was extracted several times with EtOAc. The combined organic extracts were dried over Na$_2$SO$_4$ and evaporated in vacuo. The residue was purified by flash column chromatography (BIOTAGE®), eluting with a gradient of 0 to 100% EtOAc/hexanes to afford the partially pure (S)-tert-butyl 2-(4-chloro-5-(4-(6-(4,4,5,5-tetramethyl-1,3,2-dioxaborolan-2-yl)naphthalen-2-yl)phenyl)-1H-imidazol-2-yl)pyrrolidine-1-carboxylate contaminated with triphenylphosphine (292 mg). A small aliquot was purified further by a reverse phase HPLC (water/acetonitrile/TFA) to afford the pure title material. The remaining material was used in subsequent step without further purification. LC-MS retention time 2.227 min; m/z 598.46 (MH–) LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/10 mM ammonium acetate and Solvent B was 10% H$_2$O/90% MeOH/10 mM ammonium acetate. MS data was determined using a MICROMASS® Platform for LC in electrospray mode. $^1$H NMR (500 MHz, MeOD, TFA salt, partial NMR) δ ppm 3.71 (br s, 2H), 3.55 (br s, 2H), 2.45 (br s, 1H), 2.07-2.17 (m, 2H), 1.97-2.06 (m, 1H), 1.50 (s, 3H), 1.43 (m, 6H), 1.31 (br s, 6H).

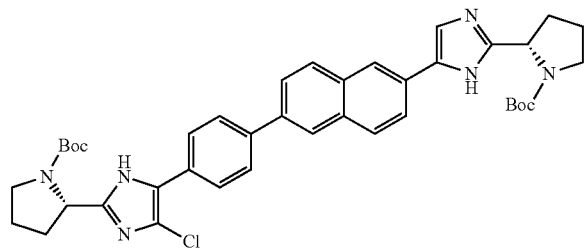 [SMILES: CC(C)(C)OC(=O)N1CCC[C@H]1c1ncc(-c2ccc3cc(-c4ccc(-c5[nH]c([C@@H]6CCCN6C(=O)OC(C)(C)C)nc5Cl)cc4)ccc3c2)[nH]1]

Intermediate 76

(S)-tert-Butyl 2-(5-(4-(6-(2-((S)-1-(tert-butoxycarbo-nyl)pyrrolidin-2-yl)-1H-imidazol-5-yl)naphthalen-2-yl)phenyl)-4-chloro-1H-imidazol-2-yl)pyrrolidine-1-carboxylate A solution of (S)-tert-butyl 2-(5-iodo-1H-imidazol-2-yl)pyrrolidine-1-carboxylate (163 mg, 0.450 mmol), (S)-tert-butyl 2-(5-iodo-1H-imidazol-2-yl)pyrrolidine-1-carboxylate (163 mg, 0.450 mmol), sodium bicarbonate (113 mg, 1.350 mmol) in a solvent mixture of DME (10 mL) and water (2 mL) was degassed under vacuum for 10 min. The mixture was heated at 80° C. then Pd(Ph₃P)₄ (52.0 mg, 0.045 mmol) was added and the reactor was flushed with nitrogen and sealed. The heating was pursued further to 120° C. for 16 h. The flask was cooled to room temperature, the DME was removed in vacuo and the crude material was partitioned between DCM/H₂O. The layers were separated and the aqueous layer was extracted several times with DCM. The combined organic extracts were dried over Na₂SO₄ and evaporated in vacuo. The residue was purified by flash column chromatography (BIOTAGE®), eluting with a gradient of 0 to 100% EtOAc/hexanes to afford the partially pure (S)-tert-butyl 2-(5-(4-(6-(2-((S)-1-(tert-butoxycarbonyl)pyrrolidin-2-yl)-1H-imidazol-5-yl)naphthalen-2-yl)phenyl)-4-chloro-1H-imidazol-2-yl)pyrrolidine-1-carboxylate contaminated with triphenylphosphine (77 mg). LC-MS retention time 1.830 min; m/z 709.43 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H₂O/0.1% TFA and Solvent B was 10% H₂O/90% MeOH/0.1% TFA. MS data was determined using a MICROMASS® Platform for LC in electrospray mode. ¹H NMR (400 MHz, chloroform-d Partial NMR) δ ppm 5.00 (d, J=4.5 Hz, 2H), 3.38-3.52 (m, 4H), 3.10 (br. s, 1H), 2.91 (br s, 1H), 2.09-2.33 (m, 4H), 1.93-2.05 (m, 2H), 1.54 (s, 18H).

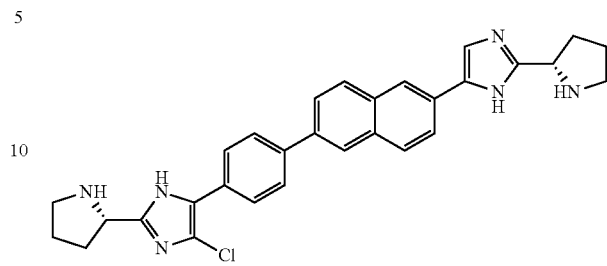

Intermediate 77

4-Chloro-2-((S)-pyrrolidin-2-yl)-5-(4-(6-(2-((S)-pyrrolidin-2-yl)-1H-imidazol-5-yl)naphthalen-2-yl)phenyl)-1H-imidazole TFA (2 mL) was added to a solution of (S)-tert-butyl 2-(5-(4-(6-(2-((S)-1-(tert-butoxycarbonyl)pyrrolidin-2-yl)-1H-imidazol-5-yl)naphthalen-2-yl)phenyl)-4-chloro-1H-imidazol-2-yl)pyrrolidine-1-carboxylate (75 mg) in DCM (10 mL) and the mixture was stirred for 2 h at room temperature. The solvents were removed in vacuo and the residue was taken up in a solvent mixture of 1:1 methanol/CH₂Cl₂ and filtered through an MCX cartridge (Strata XC). The cartridge was washed with methanol and the compound was eluted with a solution of NH₃ in methanol (2M). The appropriate fractions were concentrated in vacuo to afford 4-chloro-2-((S)-pyrrolidin-2-yl)-5-(4-(6-(2-((S)-pyrrolidin-2-yl)-1H-imidazol-5-yl)naphthalen-2-yl)phenyl)-1H-imidazole (40 mg, 0.079 mmol) as yellow solid. LC-MS retention time 1.353 min; m/z 509.32 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H₂O/0.1% TFA and Solvent B was 10% H₂O/90% MeOH/0.1% TFA. MS data was determined using a MICROMASS® Platform for LC in electrospray mode. ¹H NMR (500 MHz, MeOD, partially soluble only) δ ppm 8.20 (s, 1H), 8.09 (s, 1H), 7.88-7.96 (m, 2H), 7.76-7.88 (m, 6H), 7.51 (s, 1H), 4.50 (t, J=7.28 Hz, 1H), 4.35 (t, J=7.15 Hz, 1H), 3.03-3.31 (partially masked by methanol, m, 4H), 2.24-2.42 (m, 2H), 1.88-2.21 (m, 6H).

Scheme 19

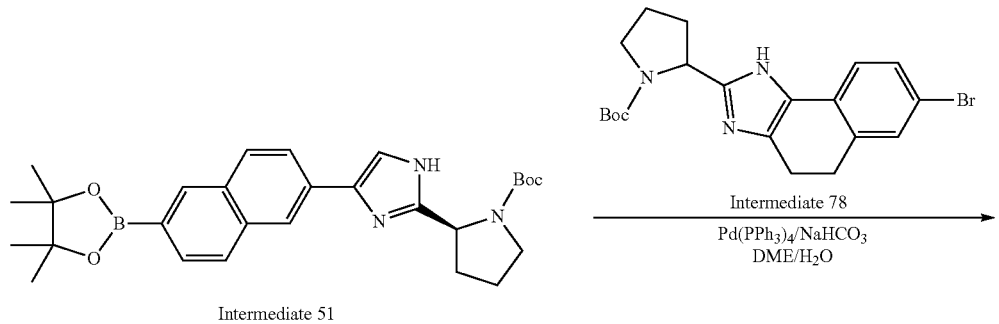

Intermediate 51 → Intermediate 78

Pd(PPh₃)₄/NaHCO₃
DME/H₂O

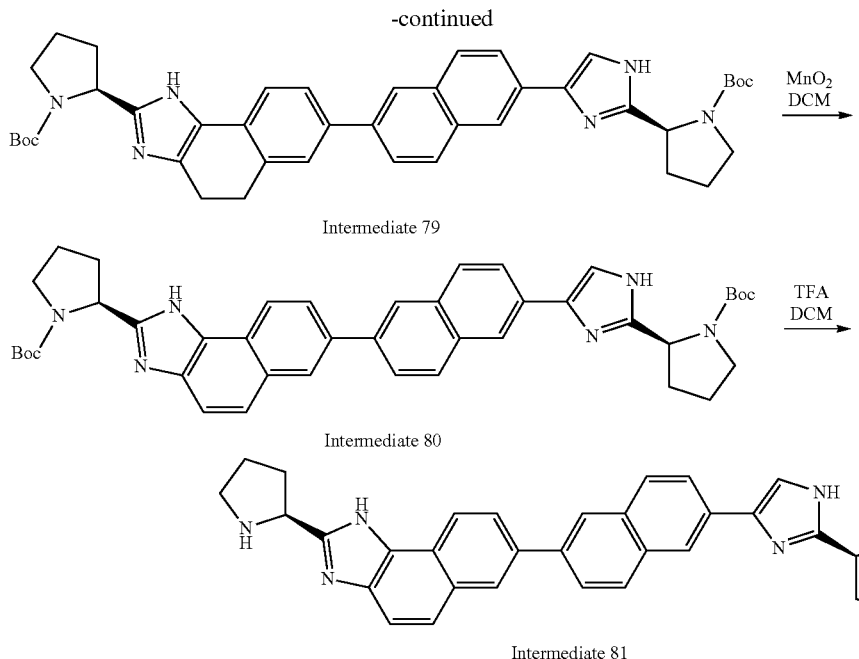

Intermediate 79

Intermediate 80

Intermediate 81

Intermediate 79

(S)-tert-Butyl 2-(7-(6-(2-((S)-1-(tert-butoxycarbonyl)pyrrolidin-2-yl)-1H-imidazol-5-yl)naphthalen-2-yl)-4,5-dihydro-1H-naphtho[1,2-d]imidazol-2-yl)pyrrolidine-1-carboxylate A solution of (S)-tert-butyl 2-(5-(6-(4,4,5,5-tetramethyl-1,3,2-dioxaborolan-2-yl)naphthalen-2-yl)-1H-imidazol-2-yl)pyrrolidine-1-carboxylate (402 mg, 0.821 mmol), (S)-tert-butyl 2-(7-bromo-4,5-dihydro-1H-naphtho[1,2-d]imidazol-2-yl)pyrrolidine-1-carboxylate (344 mg, 0.821 mmol) and sodium bicarbonate (207 mg, 2.46 mmol) in DME (14 mL) and water (1.8 mL) was degassed under vacuum for 10 min. The mixture was heated at 80° C. at which time the flask was opened and Pd(Ph$_3$P)$_4$ (76 mg, 0.066 mmol) was added. The flask was flushed with nitrogen, sealed and heated at 120° C. for 16 h. The flask was cooled to room temp., the DME was removed in vacuo and the crude material was partitioned between DCM and H$_2$O. The layers were separated and the aqueous layer was extracted several times with DCM. The combined organic extracts were dried over Na$_2$SO$_4$ and evaporated in vacuo. The residue was purified by flash column chromatography (BIOTAGE®), eluting with a gradient of 20 to 100% EtOAc/Hexanes and then 0 to 10% methanol/DCM to afford (S)-tert-butyl 2-(7-(6-(2-((S)-1-(tert-butoxycarbonyl)pyrrolidin-2-yl)-1H-imidazol-5-yl)naphthalen-2-yl)-4,5-dihydro-1H-naphtho[1,2-d]imidazol-2-yl)pyrrolidine-1-carboxylate (183 mg). LC-MS retention time 1.543 min; m/z 701.47 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode.

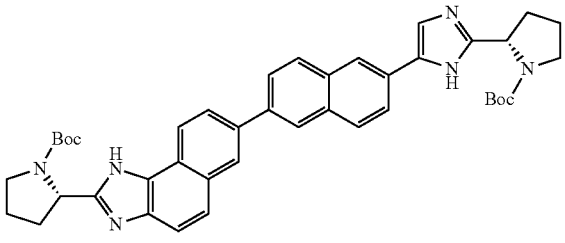 [SMILES: CC(C)(C)OC(=O)N1CCC[C@H]1c1ncc(-c2ccc3cc(-c4ccc5c(ccc6nc([C@@H]7CCCN7C(=O)OC(C)(C)C)[nH]c65)c4)ccc3c2)[nH]1]

Intermediate 80

(S)-tert-Butyl 2-(7-(6-(2-((S)-1-(tert-butoxycarbonyl)pyrrolidin-2-yl)-1H-imidazol-5-yl)naphthalen-2-yl)-1H-naphtho[1,2-d]imidazol-2-yl)pyrrolidine-1-carboxylate Manganese(IV) oxide (1.53 g, 17.6 mmol) was added to a solution of (S)-tert-butyl 2-(7-(6-(2-((S)-1-(tert-butoxycarbonyl)pyrrolidin-2-yl)-1H-imidazol-5-yl)naphthalen-2-yl)-4,5-dihydro-1H-naphtho[1,2-d]imidazol-2-yl)pyrrolidine-1-carboxylate (183 mg, 0.196 mmol) in DCM (5 mL) and the mixture was stirred overnight at room temperature. The reaction mixture was filtered through a pad of diatomaceous earth (CELITE®) and washed with a solution of methanol/DCM 1:1. The volatiles were removed under vacuum using a rotavap to afford (S)-tert-butyl 2-(7-(6-(2-((S)-1-(tert-butoxycarbonyl)pyrrolidin-2-yl)-1H-imidazol-5-yl)naphthalen-2-yl)-1H-naphtho[1,2-d]imidazol-2-yl)pyrrolidine-1-carboxylate (163 mg) as tan solid. LC-MS retention time 1.523 min; m/z 699.53 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode.

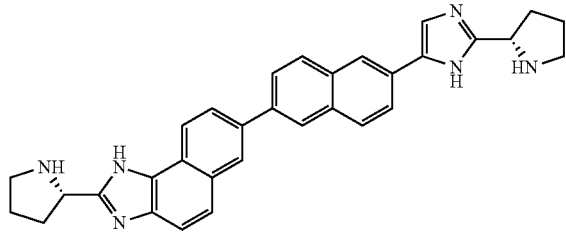 [SMILES: c1cc2cc(-c3cnc([C@@H]4CCCN4)[nH]3)ccc2cc1-c1ccc2c(ccc3nc([C@@H]4CCCN4)[nH]c32)c1]

Intermediate 81

2-((S)-Pyrrolidin-2-yl)-7-(6-(2-((S)-pyrrolidin-2-yl)-1H-imidazol-5-yl)naphthalen-2-yl)-1H-naphtho[1,2-d]imidazole TFA (2 mL, 26.0 mmol) was added in one portion to a stirred solution of (S)-tert-butyl 2-(7-(6-(2-((S)-1-(tert-butoxycarbonyl)pyrrolidin-2-yl)-1H-imidazol-5-yl)naphthalen-2-yl)-1H-naphtho[1,2-d]imidazol-2-yl)pyrrolidine-1-carboxylate (137 mg) in CH$_2$Cl$_2$ (10 mL) at room temperature. The mixture was stirred for 2 h at room temp. and then the solvents were removed in vacuo. The residue was taken up in 50% methanol/CH$_2$Cl$_2$ and filtered through an MCX cartridge (Strata XC). The cartridge was washed with methanol and the compound was eluted with a solution of NH$_3$ in methanol (2M). The appropriate fractions were concentrated in vacuo to afford 2-((S)-pyrrolidin-2-yl)-7-(6-(2-((S)-pyrrolidin-2-yl)-1H-imidazol-5-yl)naphthalen-2-yl)-1H-naphtho[1,2-d]imidazole (98 mg, 0.20 mmol) as orange solid. LC-MS retention time 1.245 min; m/z 499.30 (MH+).

LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (TFA salt, 500 MHz, MeOD) δ ppm 8.59 (d, J=8.5 Hz, 1H), 8.43 (d, J=1.5 Hz, 1H), 8.36 (s, 1H), 8.31 (s, 1H), 8.13 (dd, J=8.6, 1.8 Hz, 1H), 8.01-8.10 (m, 3H), 7.90-7.98 (m, 2H), 7.87 (s, 1H), 7.80 (d, J=8.6 Hz, 1H), 5.18 (t, J=7.9 Hz, 1H), 5.05 (t, J=8.1 Hz, 1H), 3.63-3.72 (m, 1H), 3.52-3.63 (m, 3H), 2.61-2.77 (m, 2H), 2.45-2.58 (m, 2H), 2.33-2.43 (m, 2H), 2.20-2.33 (m, 2H).

Scheme 20

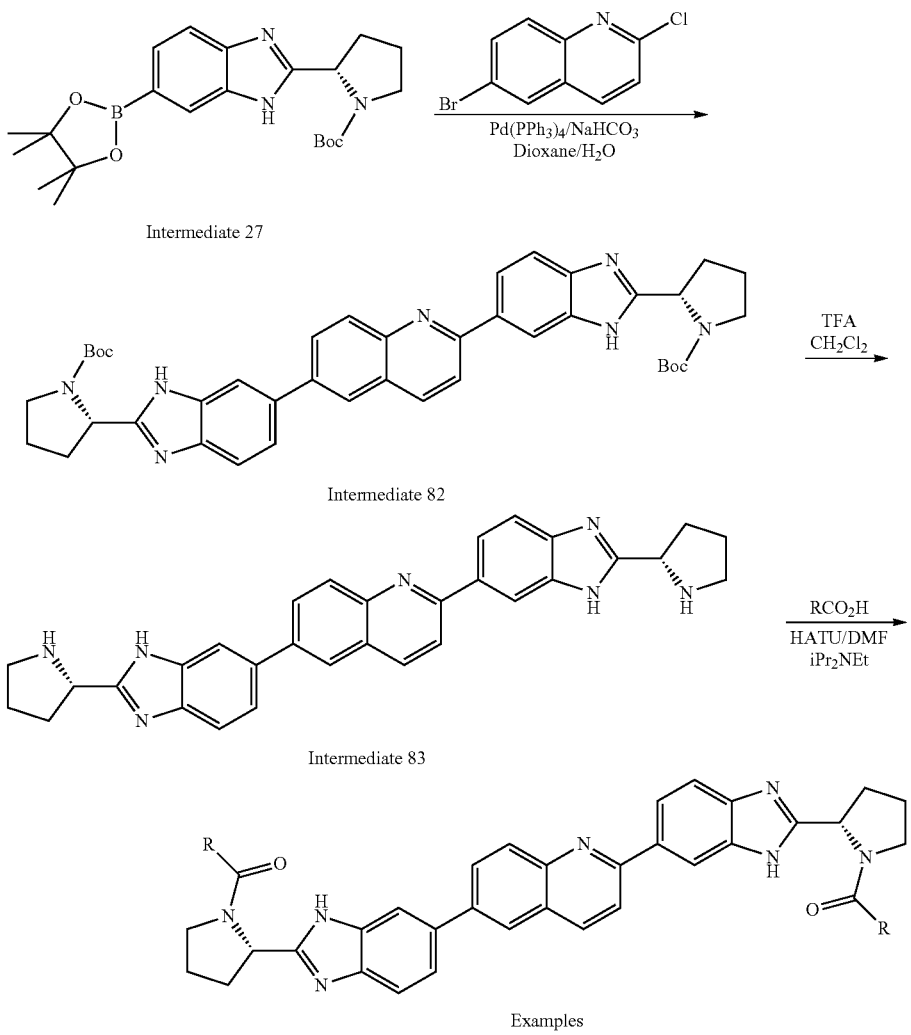

Intermediate 82

(2S,2'S)-tert-Butyl 2,2'-(6,6'-(quinoline-2,6-diyl)bis(1H-benzo[d]imidazole-6,2-diyl))dipyrrolidine-1-carboxylate Pd(Ph$_3$P)$_4$ (19.06 mg, 0.016 mmol) was added to a stirred and degassed solution of 6-bromo-2-chloroquinoline (40 mg, 0.165 mmol), (S)-tert-butyl 2-(6-(4,4,5,5-tetramethyl-1,3,2-dioxaborolan-2-yl)-1H-benzo[d]imidazol-2-yl)pyrrolidine-1-carboxylate (150 mg, 0.363 mmol) and NaHCO$_3$ (41.6 mg, 0.495 mmol) in dioxane (1 mL) and H$_2$O (0.2 mL). The reaction mixture was then heated at 110° C. for 2 h., cooled to rt, diluted with MeOH and purified by prep HPLC (H$_2$O-MeOH with 0.1% TFA buffer) to yield a TFA salt of (2S,2'S)-tert-butyl 2,2'-(6,6'-(quinoline-2,6-diyl)bis(1H-benzo[d]imidazole-6,2-diyl))dipyrrolidine-1-carboxylate (73 mg) as a yellow solid. LC-MS retention time 2.02 min; m/z 700 [M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 8.63-8.74 (1H, m), 8.60 (1H, s), 8.44 (1H, dd, J=8.7, 1.6 Hz), 8.38 (1H, br s), 8.32 (1H, d, J=8.8 Hz), 8.25 (2H, d, J=8.8 Hz), 8.14-8.21 (1H, m), 8.04-8.12 (1H, m), 7.90-8.00 (2H, m), 5.24-5.36 (2H, m), 3.73-3.83 (2H, m), 3.59-3.72 (2H, m), 2.57-2.74 (2H, m), 2.20-2.33 (2H, m), 2.09-2.20 (4H, m), 1.50 (9H, br s), 1.23 (9H, br s).

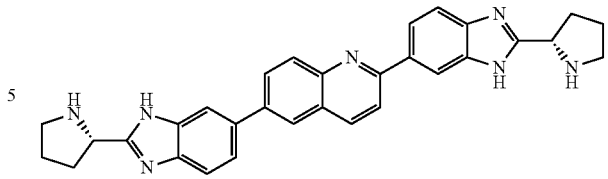

Intermediate 83

2,6-Bis(2-((S)-pyrrolidin-2-yl)-1H-benzo[d]imidazol-6-yl)quinoline

TFA (0.25 mL, 3.24 mmol) was added to a solution of a TFA salt of (2S,2'S)-tert-butyl 2,2'-(6,6'-(quinoline-2,6-diyl)bis(1H-benzo[d]imidazole-6,2-diyl))dipyrrolidine-1-carboxylate (65 mg) in DCM (0.5 mL) and the mixture was stirred at rt for 2 h. The volatiles were removed under vacuum and the residue was triturated with Et$_2$O. The resulting solid was collected via filtration and rinsed with Et$_2$O to yield a TFA salt of 2,6-bis(2-((S)-pyrrolidin-2-yl)-1H-benzo[d]imidazol-6-yl)quinoline (61 mg) as yellow solid. LC-MS retention time 1.12 min; m/z 500 [M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 8.89 (1H, d, J=8.8 Hz), 8.48 (1H, d, J=1.3 Hz), 8.45 (1H, s), 8.34-8.41 (2H, m), 8.31 (1H, d, J=8.8 Hz), 8.12 (1H, dd, J=8.5, 1.8 Hz), 8.09 (1H, s), 7.89 (1H, d, J=8.5 Hz), 7.77-7.85 (2H, m), 5.05-5.19 (2H, m), 3.44-3.72 (4H, m), 2.61-2.75 (2H, m), 2.19-2.49 (6H, m).

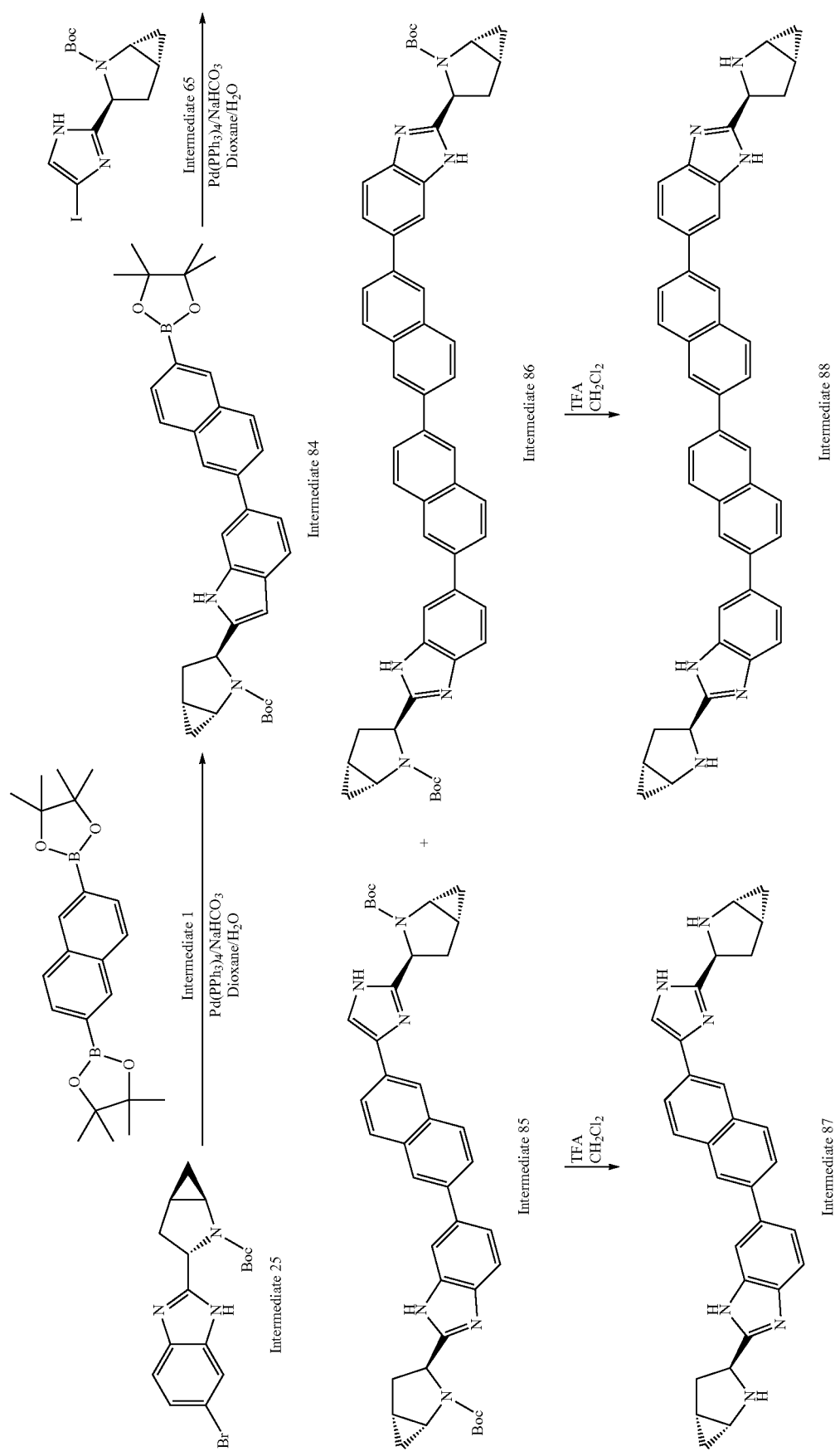

Intermediate 84

(1R,3S,5R)-tert-Butyl 3-(6-(6-(4,4,5,5-tetramethyl-1,3,2-dioxaborolan-2-yl)naphthalen-2-yl)-1H-benzo[d]imidazol-2-yl)-2-azabicyclo[3.1.0]hexane-2-carboxylate Pd(Ph₃P)₄ (0.382 g, 0.330 mmol) was added to a degassed solution of 2,6-bis(4,4,5,5-tetramethyl-1,3,2-dioxaborolan-2-yl)naphthalene (2.51 g, 6.61 mmol), (1R,3S,5R)-tert-butyl 3-(5-bromo-1H-benzo[d]imidazol-2-yl)-2-azabicyclo[3.1.0]hexane-2-carboxylate (2.5 g, 6.6 mmol) and sodium carbonate (2.78 g, 33.0 mmol) in DME (52.9 mL) and water (13.2 mL) at 80° C. The reaction was backfilled with nitrogen, sealed and heated at 100° C. overnight. The volatiles were removed under vacuum and the residue was taken in EtOAc, washed with water, and the water layer was extracted with EtOAc. The combined organic layers were filtered through a pad of diatomaceous earth (CELITE®) and dried over Na₂SO₄, concentrated and purified on a BIOTAGE® (dry loaded on silica gel, charged to a 90 g silica gel cartridge and eluted with a gradient of 0 to 70% ethyl acetate in hexanes, then flushed with 10% MeOH/DCM) to yield (1R,3S,5R)-tert-butyl 3-(6-(6-(4,4,5,5-tetramethyl-1,3,2-dioxaborolan-2-yl)naphthalen-2-yl)-1H-benzo[d]imidazol-2-yl)-2-azabicyclo[3.1.0]hexane-2-carboxylate (1.8 g, 3.3 mmol, 49% yield) as yellowish solid. LC-MS retention time 1.905 min; m/z 552.47 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H₂O/0.1% TFA and Solvent B was 10% H₂O/90% MeOH/0.1% TFA. MS data was determined using a MICROMASS® Platform for LC in electrospray mode.

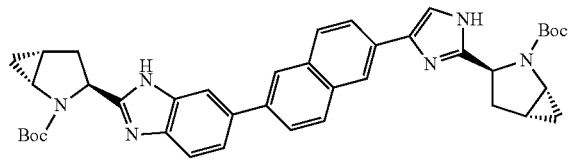 [SMILES: CC(C)(C)OC(=O)N1[C@@H]2C[C@@H]2C[C@H]1c1nc(-c2ccc3cc(-c4ccc5nc([C@@H]6C[C@H]7C[C@H]7N6C(=O)OC(C)(C)C)[nH]c5c4)ccc3c2)c[nH]1]

Intermediate 85 tert-Butyl (1R,3S,5R)-3-(4-(6-(2-((1R,3S,5R)-2-(tert-butoxycarbonyl)-2-azabicyclo[3.1.0]hex-3-yl)-1H-benzimidazol-5-yl)-2-naphthyl)-1H-imidazol-2-yl)-2-azabicyclo[3.1.0]hexane-2-carboxylate A 200 mL pressure round bottom flask equipped with a magnetic stir bar was charged with (1R,3S,5R)-tert-butyl 3-(5-(6-(4,4,5,5-tetramethyl-1,3,2-dioxaborolan-2-yl)naphthalen-2-yl)-1H-benzo[d]imidazol-2-yl)-2-azabicyclo[3.1.0]hexane-2-carboxylate (795 mg, 1.44 mmol), (1R,3S,5R)-tert-butyl 3-(5-iodo-1H-imidazol-2-yl)-2-azabicyclo[3.1.0]hexane-2-carboxylate (538 mg, 1.43 mmol) and sodium bicarbonate (502 mg, 5.97 mmol) in DME (9.5 mL) and water (2.4 mL). The solution was degassed under vacuum for 5 min and the reactor was back filled with N₂. Then, Pd(Ph₃P)₄ (110 mg, 0.096 mmol) was added under a stream of N₂ and the reactor was sealed and the heated overnight at 120° C. The reaction was cooled to room temperature and the volatiles were removed under vacuum. The residue was partitioned between EtOAc and water and the aqueous layer was extracted with EtOAc. The combined organics were filtered through a pad of diatomaceous earth (CELITE®), dried over Na₂SO₄ and the volatiles were removed under vacuum. The residue was purified by flash column chromatography (BIOTAGE®), eluting with a gradient of 50 to 100% EtOAc/Hexanes and then 10% methanol/DCM to afford the partially pure target product contaminated with starting material, reduced starting material and other reaction side products. The residue was further purified by prep HPLC (ACN/water, 0.1% TFA) to yield a TFA salt of tert-butyl (1R,3S,5R)-3-(4-(6-(2-((1R,3S,5R)-2-(tert-butoxycarbonyl)-2-azabicyclo[3.1.0]hex-3-yl)-1H-benzimidazol-5-yl)-2-naphthyl)-1H-imidazol-2-yl)-2-azabicyclo[3.1.0]hexane-2-carboxylate (200.5 mg). A side product was also collected form the same reaction mixture which was identified as a TFA salt (1R,3S,5R)-3-(5-(6'-(2-((1R,3S,5R)-2-(tert-butoxycarbonyl)-2-azabicyclo[3.1.0]hex-3-yl)-1H-benzimidazol-6-yl)-2,2'-binaphthalen-6-yl)-1H-benzimidazol-2-yl)-2-azabicyclo[3.1.0]hexane-2-carboxylate (108 mg) LC-MS retention time 1.497 min; m/z 673.52 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H₂O/0.1% TFA and Solvent B was 10% H₂O/90% MeOH/0.1% TFA. MS data was determined using a MICROMASS® Platform for LC in electrospray mode. ¹H NMR (TFA salt, 500 MHz, MeOD) δ ppm 8.33 (s, 1H), 8.31 (s, 1H), 8.09-8.20 (m, 3H), 7.96-8.08 (m, 2H), 7.87-7.94 (m, 2H), 5.07 (t, J=8.2 Hz, 1H), 4.91 (m, 1H), 3.69 (br s, 2H), 2.70-2.84 (m, 2H), 2.48 (br s, 2H), 1.81-1.94 (m, 2H), 1.51 (br s, 1H), 1.51 (br s, 9H), 1.31 (br s, 5H), 1.21 (br s, 4H), 0.89-0.99 (m, 2H), 0.82 (br s, 1H), 0.77 (br s, 1H).

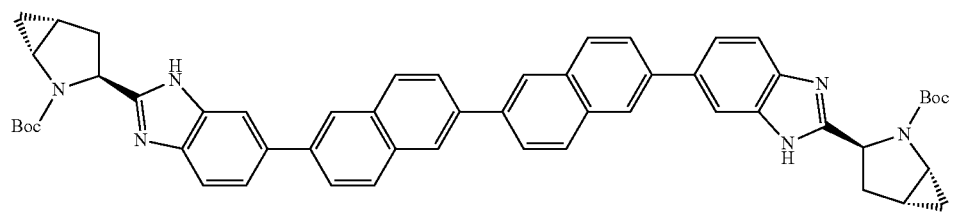 [SMILES: CC(C)(C)OC(=O)N1[C@@H]2C[C@@H]2C[C@H]1c1nc2ccc(-c3ccc4cc(-c5ccc6cc(-c7ccc8nc([C@@H]9C[C@H]%10C[C@H]%10N9C(=O)OC(C)(C)C)[nH]c8c7)ccc6c5)ccc4c3)cc2[nH]1]

Intermediate 86

(1R,3S,5R)-3-(5-(6'-(2-((1R,3S,5R)-2-(tert-Butoxy-carbonyl)-2-azabicyclo[3.1.0]hex-3-yl)-1H-benzimi-dazol-6-yl)-2,2'-binaphthalen-6-yl)-1H-benzimida-zol-2-yl)-2-azabicyclo[3.1.0]hexane-2-carboxylate Side product obtained as TFA salt (108 mg) after purification of the reaction mixture from Intermediate 85 synthesis. LC-MS retention time 1.882 min; m/z 849.84 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% TFA and Solvent B was 10% $H_2O$/90% MeOH/0.1% TFA. MS data was determined using a MICROMASS® Platform for LC in electrospray mode. $^1$H NMR (TFA salt, 500 MHz, MeOD) δ ppm 8.36 (s, 2H), 8.28 (s, 2H), 8.11-8.19 (m, 6H), 8.03-8.09 (m, 4H), 7.87-7.96 (m, 4H), 5.07 (t, J=8.2 Hz, 2H), 3.71 (br s, 2H), 2.75-2.85 (m, 2H), 2.51 (br s, 2H), 1.86-1.94 (m, 2H), 1.52 (m, 10H), 1.22 (br s, 8H), 0.97 (ddd, J=8.4, 6.0, 5.8 Hz, 2H), 0.83 (br s, 2H).

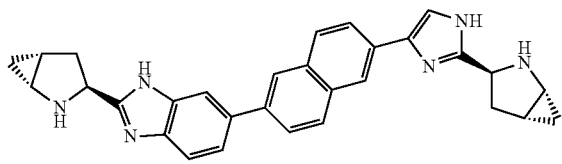 [SMILES: c1cc2cc(-c3c[nH]c([C@@H]4C[C@H]5C[C@H]5N4)n3)ccc2cc1-c1ccc2nc([C@@H]3C[C@H]4C[C@H]4N3)[nH]c2c1]

Intermediate 87

6-(6-(2-((1R,3S,5R)-2-Azabicyclo[3.1.0]hexan-3-yl)-1H-imidazol-4-yl)naphthalen-2-yl)-2-((1R,3S,5R)-2-azabicyclo[3.1.0]hexan-3-yl)-1H-benzo[d]imidazole 4M HCl in dioxane (10 mL, 40.0 mmol) was added to a stirred solution of a TFA salt of (1R,3S,5R)-tert-butyl 3-(5-(6-(2-((1R,3S,5R)-2-(tert-butoxycarbonyl)-2-azabicyclo[3.1.0]hexan-3-yl)-1H-benzo[d]imidazol-5-yl)naphthalen-2-yl)-1H-imidazol-2-yl)-2-azabicyclo[3.1.0]hexane-2-carboxylate (151 mg) in DCM (3 mL). Precipitate formed immediately. The suspension was agitated for 30 min. The volatile components were evaporated under vacuum. The crude residue was taken in DCM (3 mL) and TFA (2 mL) was added. The solution was agitated for 1 h. The volatile components were evaporated under reduced pressure. The residue was taken into MeOH and filtered through a Strata XC MCX cartridge. The cartridge was washed with methanol and the compound was release from the cartridge by eluting with a solution of 2M of ammonia/methanol. The ammonia/methanol filtrate was evaporated under reduced pressure to yield 6-(6-(2-((1R,3S,5R)-2-azabicyclo[3.1.0]hexan-3-yl)-1H-imidazol-4-yl)naphthalen-2-yl)-2-((1R,3S,5R)-2-azabicyclo[3.1.0]hexan-3-yl)-1H-benzo[d]imidazole (79 mg, 0.17 mmol) as yellow solid. LC-MS retention time 1.130 min; m/z 473.35 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% TFA and Solvent B was 10% $H_2O$/90% MeOH/0.1% TFA. MS data was determined using a MICROMASS® Platform for LC in electrospray mode. $^1$H NMR (500 MHz, MeOD) δ ppm 8.19 (s, 1H), 8.07 (s, 1H), 7.92 (dd, J=8.6, 5.8 Hz, 2H), 7.88 (s, 1H), 7.82 (dd, J=5.8, 1.5 Hz, 2H), 7.61-7.66 (m, 2H), 7.51 (s, 1H), 4.24-4.35 (m, 2H), 3.11 (td, J=6.1, 2.4 Hz, 1H), 3.06 (td, J=6.0, 2.6 Hz, 1H), 2.40-2.53 (m, 2H), 2.18-2.33 (m, 2H), 1.69-1.76 (m, 1H), 1.62-1.69 (m, 1H), 0.88 (ddd, J=6.6, 4.3, 2.6 Hz, 1H), 0.79-0.84 (m, 1H), 0.61-0.68 (m, 1H), 0.55-0.60 (m, 1H).

Intermediate 88

6,6'-Bis(2-((1R,3S,5R)-2-azabicyclo[3.1.0]hexan-3-yl)-1H-benzo[d]imidazol-5-yl)-2,2'-binaphthyl TFA (2.0 mL, 26 mmol) was added to a solution of a TFA salt (1R,3S,5R)-3-(5-(6'-(2-((1R,3S,5R)-2-(tert-butoxycarbonyl)-2-azabicyclo[3.1.0]hex-3-yl)-1H-benzimidazol-6-

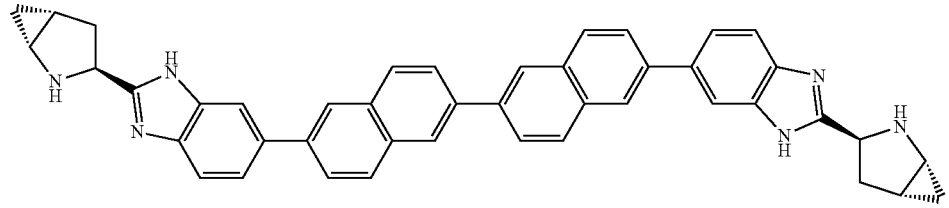 [SMILES: c1cc2cc(-c3ccc4nc([C@@H]5C[C@H]6C[C@H]6N5)[nH]c4c3)ccc2cc1-c1ccc2cc(-c3ccc4nc([C@@H]5C[C@H]6C[C@H]6N5)[nH]c4c3)ccc2c1]

yl)-2,2'-binaphthalen-6-yl)-1H-benzimidazol-2-yl)-2-azabicyclo[3.1.0]hexane-2-carboxylate (108 mg) in DCM (5 mL) and the reaction mixture was stirred for 2 h at rt. The reaction mixture was then concentrated to yield a TFA salt of 6,6'-bis(2-((1R,3S,5R)-2-azabicyclo[3.1.0]hexan-3-yl)-1H-benzo[d]imidazol-5-yl)-2,2'-binaphthyl (22 mg) as tan solid. LC-MS retention time 1.722 min; m/z 649.54 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H₂O/0.1% TFA and Solvent B was 10% H₂O/90% MeOH/0.1% TFA. MS data was determined using a MICROMASS® Platform for LC in electrospray mode. ¹H NMR (500 MHz, MeOD) δ ppm 8.33 (br s, 2H), 8.22 (br s, 2H), 8.09-8.15 (m, 4H), 8.01-8.07 (m, 4H), 7.89-7.95 (m, 2H), 7.77-7.87 (m, 4H), 4.85-4.98 (m, 2H), 3.51-3.57 (m, 2H), 2.79-2.87 (m, 2H), 2.59-2.68 (m, 2H), 2.07-2.14 (m, 2H), 1.23-1.30 (m, 2H), 1.01-1.09 (m, 2H).

Intermediate 89 tert-Butyl (1R,3S,5R)-3-(5-(6-(2-((1R,3S,5R)-2-(tert-butoxycarbonyl)-2-azabicyclo[3.1.0]hex-3-yl)-1H-benzimidazol-6-yl)-1,5-naphthyridin-2-yl)-1H-benzimidazol-2-yl)-2-azabicyclo[3.1.0]hexane-2-carboxylate Tetrakis(triphenylphosphine)palladium(0) (17.4 mg, 0.015 mmol) was added to a solution of 2,6-dichloro-1,5-naphthyridine (30 mg, 0.151 mmol), sodium bicarbonate (38.0 mg, 0.452 mmol) and (1R,3S,5R)-tert-butyl 3-(6-(4,4,5,5-tetramethyl-1,3,2-dioxaborolan-2-yl)-1H-benzo[d]imidazol-2-yl)-2-azabicyclo[3.1.0]hexane-2-carboxylate (141 mg, 0.332 mmol) in dioxane (1.0 mL) and H₂O (0.2 mL) and the mixture was heated and stirred at 110° C. for 2 h. The reaction was diluted with MeOH, filtered, concentrated and purified by prep HPLC (H₂O-MeOH with 10 mM NH₄OAc buffer) to yield tert-butyl (1R,3S,5R)-3-(5-(6-(2-((1R,3S,5R)-2-(tert-butoxycarbonyl)-2-azabicyclo[3.1.0]hex-3-yl)-1H-benzimidazol-6-yl)-1,5-naphthyridin-2-yl)-1H-benzimidazol-2-yl)-2-azabicyclo[3.1.0]hexane-2-carboxylate (22.3 mg, 0.030 mmol) as a white solid. LC-MS retention time 2.11 min; m/z 725 [M+H]⁺. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220).

Scheme 22

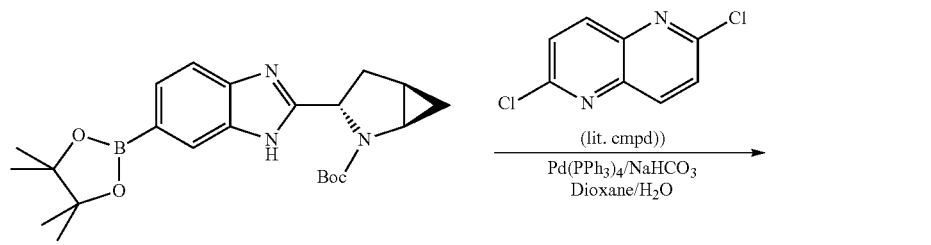

Intermediate 26

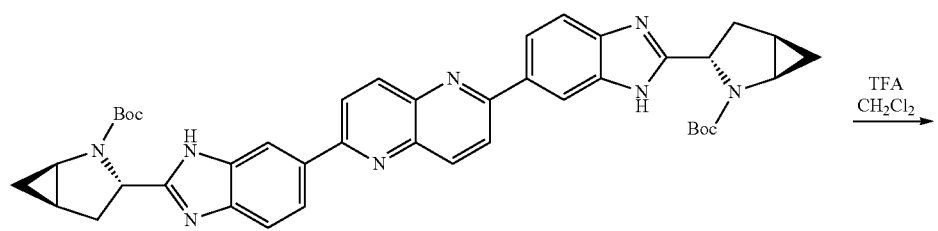

Intermediate 89

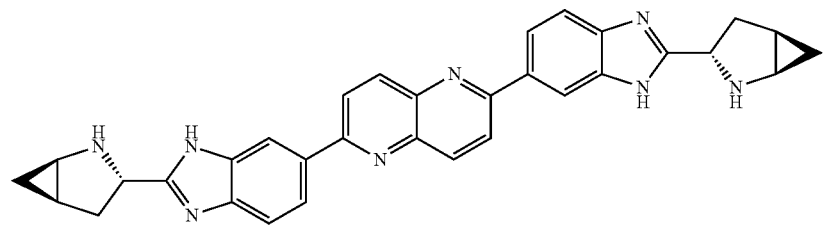

Intermediate 90

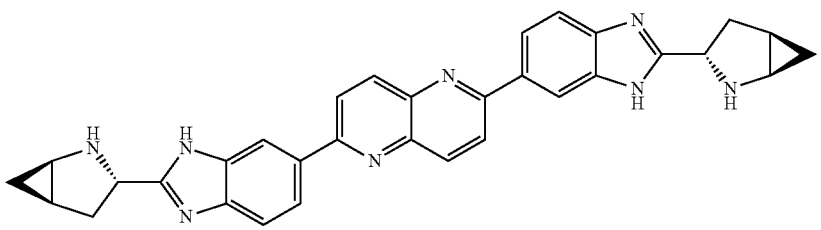 [SMILES: c1cc2nc([C@@H]3C[C@H]4C[C@H]4N3)[nH]c2cc1-c1ccc2nc(-c3ccc4nc([C@@H]5C[C@H]6C[C@H]6N5)[nH]c4c3)ccc2n1]

Intermediate 90

2,6-Bis(2-((1R,3S,5R)-2-azabicyclo[3.1.0]hexan-3-yl)-1H-benzo[d]imidazol-6-yl)-1,5-naphthyridine TFA (0.25 mL, 3.2 mmol) was added to a solution of tert-butyl (1R,3S,5R)-3-(5-(6-(2-((1R,3S,5R)-2-(tert-butoxycarbonyl)-2-azabicyclo[3.1.0]hex-3-yl)-1H-b enzimidazol-6-yl)-1,5-naphthyridin-2-yl)-1H-benzimidazol-2-yl)-2-azabicyclo[3.1.0]hexane-2-carboxylate (20 mg, 0.028 mmol) in DCM (0.5 mL) and the mixture was stirred at rt for 16 h. The volatile were removed under vacuum and the residue was triturated with Et$_2$O. The resulting solid was collected via filtration and rinsed with Et$_2$O to yield a TFA salt of 2,6-bis (2-((1R,3S,5R)-2-azabicyclo[3.1.0]hexan-3-yl)-1H-benzo [d]imidazol-6-yl)-1,5-naphthyridine (26 mg, 0.022 mmol, 78% yield) as a yellow solid. LC-MS retention time 1.41 min; m/z 525 [M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 8.61 (2H, d, J=8.8 Hz), 8.51 (2H, s), 8.40 (2H, d, J=9.0 Hz), 8.23 (2H, dd, J=8.5, 1.5 Hz), 7.81 (2H, d, J=8.5 Hz), 4.74-4.97 (2H, m), 3.47-3.57 (2H, m), 2.78-2.88 (2H, m), 2.52-2.65 (2H, m), 2.04-2.15 (2H, m), 1.22-1.33 (2H, m), 0.99-1.11 (2H, m).

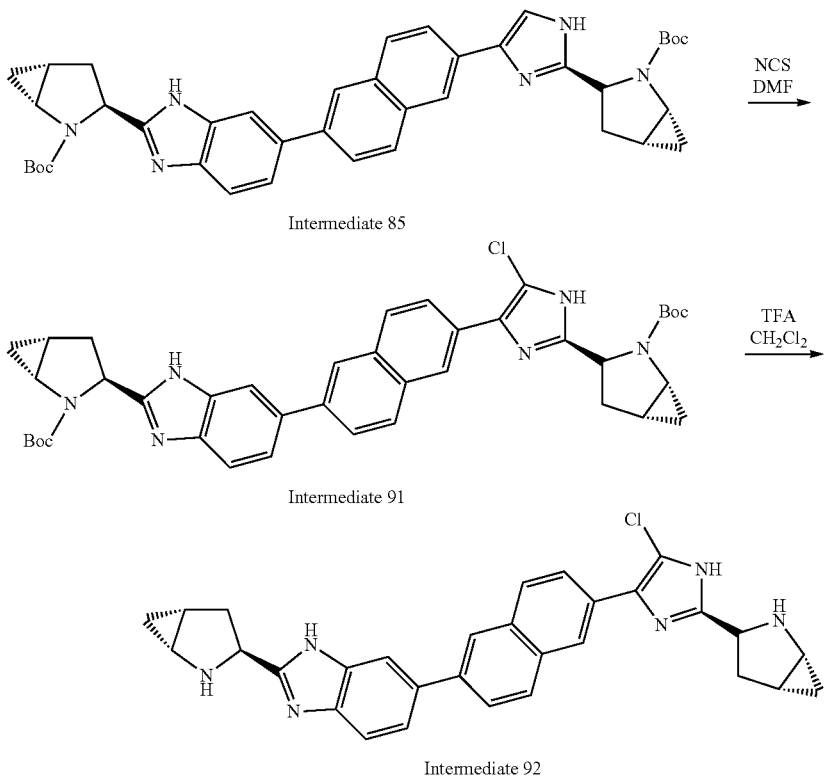

Scheme 23

Intermediate 91 tert-Butyl (1R,3S,5R)-3-(4-(6-(2-((1R,3S,5R)-2-(tert-butoxycarbonyl)-2-azabicyclo[3.1.0]hex-3-yl)-1H-benzimidazol-5-yl)-2-naphthyl)-5-chloro-1H-imidazol-2-yl)-2-azabicyclo[3.1.0]hexane-2-carboxylate NCS (20 mg, 0.15 mmol) was added portionwise to a stirring solution of tert-butyl (1R,3S,5R)-3-(4-(6-(2-((1R,3S, 5R)-2-(tert-butoxycarbonyl)-2-azabicyclo[3.1.0]hex-3-yl)-1H-benzimidazol-5-yl)-2-naphthyl)-1H-imidazol-2-yl)-2- azabicyclo[3.1.0]hexane-2-carboxylate (183 mg, 0.272 mmol) in DMF (5 mL) at rt. The reaction mixture was then heated at 50° C. for 3 h. The reaction was cooled to 0° C., additional NCS (15 mg, 0.112 mmol) was added, and the mixture was stirred for 2 h at 50° C. The reaction was diluted with water (2 mL) and methanol (2 mL), the volatiles were removed and the crude product was purified by prep HPLC (TFA) to yield a TFA salt of tert-butyl (1R,3S,5R)-3-(4-(6-(2-((1R,3S,5R)-2-(tert-butoxycarbonyl)-2-azabicyclo[3.1.0]hex-3-yl)-1H-benzimidazol-5-yl)-2-naphthyl)-5-chloro-1H-imidazol-2-yl)-2-azabicyclo[3.1.0]hexane-2-carboxylate (140.4 mg) as orange solid. LC-MS retention time 1.822 min; m/z 707.54 (1:1) (MH+). LC data was recorded on a Shimadzu LC-10AS liquid chromatograph equipped with a Waters Sunfire C18 4.6×30 mm 5 μm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (500 MHz, MeOD) δ ppm 8.27 (d, J=2.8 Hz, 2H), 8.03-8.18 (m, 4H), 7.87-7.98 (m, 3H), 5.04-5.10 (m, 1H), 4.63 (d, J=7.6 Hz, 1H), 3.71 (br s, 1H), 3.63 (br s, 1H), 2.74-2.87 (m, 1H), 2.59 (dd, J=13.3, 8.7 Hz, 1H), 2.51 (br s, 1H), 2.41 (ddd, J=13.6, 6.7, 6.6 Hz, 1H), 1.86-1.95 (m, 1H), 1.78 (br s, 1H), 1.12-1.63 (m, 18H), 0.97 (ddd, J=8.7, 6.0, 5.8 Hz, 1H), 0.79-0.91 (m, 2H), 0.66 (br s, 1H).

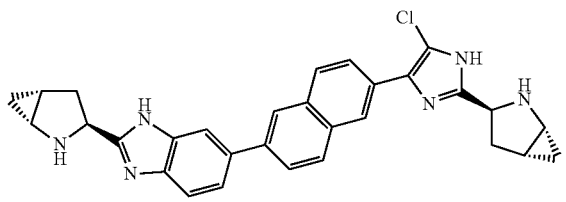 [SMILES: Clc1[nH]c([C@@H]2C[C@H]3C[C@H]3N2)nc1-c1ccc2cc(-c3ccc4nc([C@@H]5C[C@H]6C[C@H]6N5)[nH]c4c3)ccc2c1]

Intermediate 92

2-((1R,3S,5R)-2-Azabicyclo[3.1.0]hex-3-yl)-5-(6-(2-((1R,3S,5R)-2-azabicyclo[3.1.0]hex-3-yl)-4-chloro-1H-imidazol-5-yl)-2-naphthyl)-1H-benzimidazole TFA (2 mL, 26.0 mmol) was added to a solution of a TFA salt of tert-butyl (1R,3S,5R)-3-(4-(6-(2-((1R,3S,5R)-2-(tert-butoxycarbonyl)-2-azabicyclo[3.1.0]hex-3-yl)-1H-benzimidazol-5-yl)-2-naphthyl)-5-chloro-1H-imidazol-2-yl)-2-azabicyclo[3.1.0]hexane-2-carboxylate (131 mg, 0.140 mmol) in DCM (10 mL) and the mixture was stirred for 3 h at rt. The volatiles were removed under vacuum and the residue was taken into MeOH and filtered through a Strata XC MCX cartridge. The cartridge was washed with methanol and the compound was release from the cartridge by eluting with a solution of 2M of ammonia/methanol. The ammonia/methanol filtrate was evaporated under reduced pressure to yield 2-((1R,3S,5R)-2-azabicyclo[3.1.0]hex-3-yl)-5-(6-(2-((1R,3S,5R)-2-azabicyclo[3.1.0]hex-3-yl)-4-chloro-1H-imidazol-5-yl)-2-naphthyl)-1H-benzimidazole (55 mg, 0.11 mmol) as tan solid. LC-MS retention time 1.375 min; m/z 507.33 (1:1) (MH+). LC data was recorded on a Shimadzu LC-10AS liquid chromatograph equipped with a Waters Sunfire C18 4.6×30 mm 5 μm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (500 MHz, MeOD) δ ppm 8.26 (s, 1H), 8.19 (s, 1H), 8.00-8.09 (m, 3H), 7.92 (ddd, J=12.1, 8.6, 1.8 Hz, 2H), 7.85 (dd, J=8.6, 1.5 Hz, 1H), 7.81 (d, J=8.6 Hz, 1H), 4.96 (dd, J=11.0, 7.6 Hz, 1H), 4.64 (app t, J=9.3 Hz, 1H), 3.53-3.59 (m, 1H), 3.44-3.50 (m, 1H), 2.82 (dd, J=13.0, 7.5 Hz, 1H), 2.61-2.74 (m, 3H), 2.03-2.15 (m, 2H), 1.24-1.30 (m, 1H), 1.18-1.24 (m, 1H), 0.96-1.09 (m, 2H).

Scheme 24

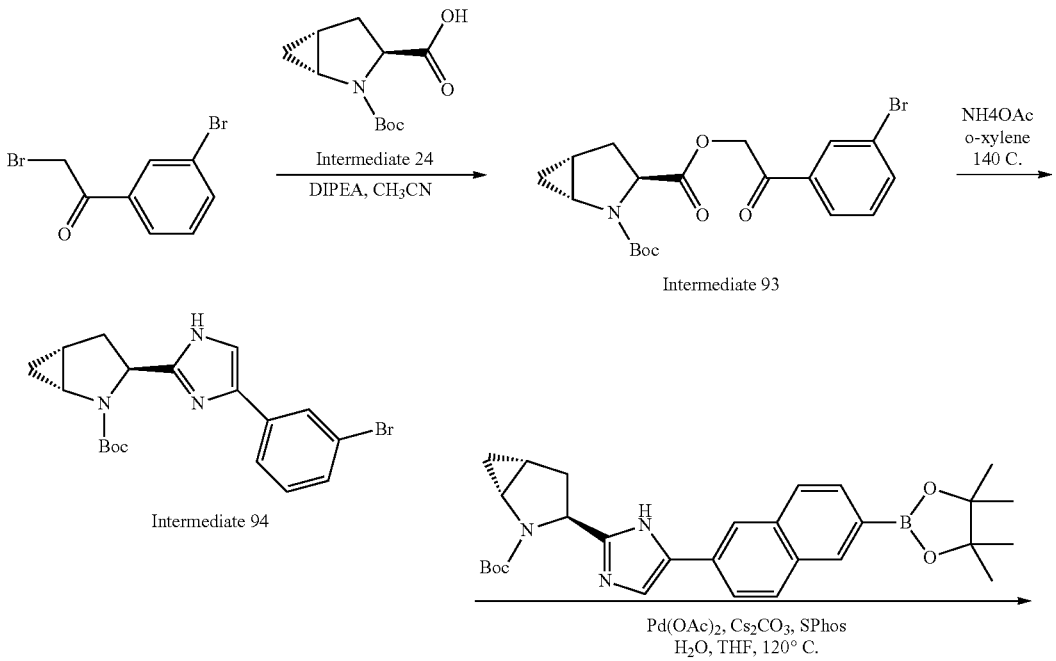

Intermediate 93

Intermediate 94

-continued

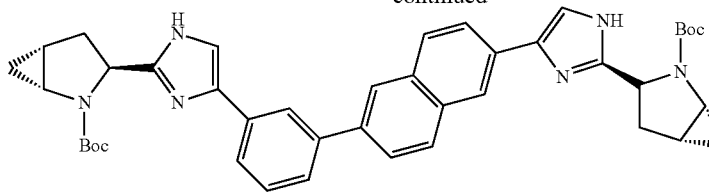

Intermediate 95

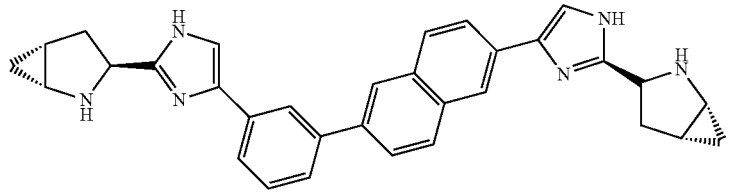

Intermediate 96

Intermediate 93

(1R,3S,5R)-3-(2-(3-Bromophenyl)-2-oxoethyl) 2-tert-butyl 2-azabicyclo[3.1.0]hexane-2,3-dicarboxylate DIPEA (2.79 mL, 16.0 mmol) was added to a stirring slurry of (1R,3S,5R)-2-(tert-butoxycarbonyl)-2-azabicyclo[3.1.0] hexane-3-carboxylic acid (2.00 g, 8.80 mmol) and 2-bromo-1-(3-bromophenyl)ethanone (2.22 g, 8.00 mmol) in acetonitrile (25 mL) (the solution became clear and amber colored) and the reaction mixture was stirred overnight. The reaction was concentrated and purified via BIOTAGE® (80 g SiO$_2$, 10-25% EtOAc/hexanes) to yield (1R,3S,5R)-3-(2-(3-bromophenyl)-2-oxoethyl) 2-tert-butyl 2-azabicyclo[3.1.0]hexane-2,3-dicarboxylate (3.37 g, 7.94 mmol) as a viscous light yellow oil. LC-MS retention time 1.853 min; m/z 423 and 425.98 (1:1) (MH+). LC data was recorded on a Shimadzu LC-10AS liquid chromatograph equipped with a waters XTERRA® MS 7u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, CDCl$_3$) δ ppm 8.04 (d, J=1.8 Hz, 1H), 7.83 (d, J=7.8 Hz, 1H), 7.75 (d, J=8.0 Hz, 1H), 7.38 (dd, J=8.0, 7.8 Hz, 1H), 5.58-5.10 (m, 2H), 4.23 (br s, 1H), 3.62-3.39 (m, 1H), 2.58 (dt, J=13.3, 6.5 Hz, 1H), 2.46 (dd, J=13.3, 9.5 Hz, 1H), 1.73-1.51 (m, 1H), 1.47 (s, 9H), 0.85 (br s, 1H), 0.51 (s, 1H).

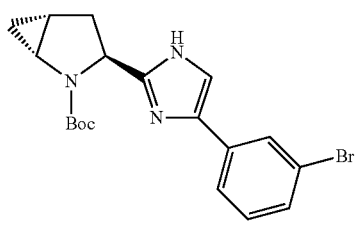 [SMILES: CC(C)(C)OC(=O)N1[C@@H]2C[C@@H]2C[C@H]1c1nc(-c2cccc(Br)c2)c[nH]1]

Intermediate 94

(1R,3S,5R)-tert-Butyl 3-(4-(3-bromophenyl)-1H-imidazol-2-yl)-2-azabicyclo[3.1.0]hexane-2-carboxylate In a 350 mL high pressure vessel ammonium acetate (5.94 g, 77 mmol) was added to a solution of (1R,3S,5R)-3-(2-(3-bromophenyl)-2-oxoethyl) 2-tert-butyl 2-azabicyclo[3.1.0] hexane-2,3-dicarboxylate (3.33 g, 7.85 mmol) in xylene (75 mL) and stirred under nitrogen for 5 minutes. The vessel was sealed and then placed into an oil bath which had been heated to 140° C. (reaction became dark brown) and the reaction was held at 140° C. for 11 h. Additional ammonium acetate (3.0 g) was added and the reaction was stirred at 145° C. for 8 hrs, cooled to rt and stirred (>90% conversion by LC-MS). The reaction was concentrated under high vacuum to a brown oil which was partitioned between DCM (~200 mL) and ½ sat. sodium bicarbonate (~200 mL). The organic layer was dried (MgSO$_4$), filtered and concentrated. The crude orange solidified foam was purified on a BIOTAGE® Horizon (20-50% EtOAc/hexanes, 160 g SiO$_2$) to yield (1R,3S,5R)-tert-butyl 3-(4-(3-bromophenyl)-1H-imidazol-2-yl)-2-azabicyclo [3.1.0]hexane-2-carboxylate (2.03 g, 5.02 mmol) as a yellow solidified foam. LC-MS retention time 2.450 min; m/z 404 and 406.06 (1:1) (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, CDCl$_3$) δ ppm 7.89 (s, 1H), 7.65 (d, J=6.5 Hz, 1H), 7.42-7.32 (m 2H), 7.26 (t, J=7.8 Hz, 1H), 4.72-4.61 (m, 1H), 3.62-3.53 (m, 1H), 2.51 (dd, J=13.0, 7.8 Hz, 1H), 2.36-2.26 (m, 1H), 1.75-1.66 (m, 1H), 1.29 (br s, 9H), 0.84 (dt, J=8.0, 5.7 Hz, 1H), 0.63-0.57 (m, 1H).

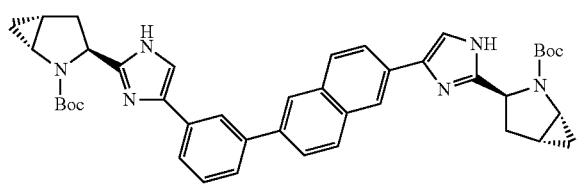 [SMILES: CC(C)(C)OC(=O)N1[C@@H]2C[C@@H]2C[C@H]1c1nc(-c2cccc(-c3ccc4cc(-c5c[nH]c([C@@H]6C[C@H]7C[C@H]7N6C(=O)OC(C)(C)C)n5)ccc4c3)c2)c[nH]1]

Intermediate 95 tert-Butyl (1R,3S,5R)-3-(4-(3-(6-(2-((1S,3R,5S)-2-(tert-butoxycarbonyl)-2-azabicyclo[3.1.0]hex-3-yl)-1H-imidazol-4-yl)-2-naphthyl)phenyl)-1H-imidazol-2-yl)-2-azabicyclo[3.1.0]hexane-2-carboxylate A solution of (1R,3S,5R)-tert-butyl 3-(5-(6-(4,4,5,5-tetramethyl-1,3,2-dioxaborolan-2-yl)naphthalen-2-yl)-1H-imidazol-2-yl)-2-azabicyclo[3.1.0]hexane-2-carboxylate (220 mg, 0.395 mmol) (prepared in the same manner as Intermediate 51 from Intermediate 55), (1R,3S,5R)-tert-butyl 3-(4-(3-bromophenyl)-1H-imidazol-2-yl)-2-azabicyclo[3.1.0]hexane-2-carboxylate (192 mg, 0.474 mmol) and cesium carbonate (386 mg, 1.185 mmol) in THF (4 mL) and water (4 mL) in a 100 mL pressure flask was degassed under vacuum for 5 min and then backfilled with nitrogen. Palladium (II) acetate (8.9 mg, 0.039 mmol) was added and the mixture was heated for 4 h at 120° C. The reaction mixture was cooled to RT, diluted with water and extracted with EtOAC and DCM. The combined organic layers were washed with brine, dried (Na$_2$SO$_4$), filtered and concentrated. The crude residue was purified on a BIOTAGE® system (90 g silica gel cartridge, eluted with a gradient of 0 to 100% EtOAc in hexanes) to yield tert-butyl (1R,3S,5R)-3-(4-(3-(6-(2-((1S,3R,5S)-2-(tert-butoxycarbonyl)-2-azabicyclo[3.1.0]hex-3-yl)-1H-imidazol-4-yl)-2-naphthyl)phenyl)-1H-imidazol-2-yl)-2-azabicyclo[3.1.0]hexane-2-carboxylate (142 mg, 0.203 mmol) as a yellow solid. LC-MS retention time 1.585 min; m/z 699.57 (MH+). LC data was recorded on a Shimadzu LC-10AS liquid chromatograph equipped with a Waters Sunfire C18 4.6× 30 mm Sum column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (500 MHz, MeOD) δ ppm 8.33 (d, J=1.2 Hz, 1H), 8.31 (s, 1H), 8.20-8.24 (m, 1H), 8.14-8.20 (m, 1H), 8.10-8.14 (m, 1H), 7.97-8.07 (m, 3H), 7.94 (d, J=7.9 Hz, 1H), 7.87-7.92 (m, 1H), 7.77-7.82 (m, 1H), 7.67-7.74 (m, 1H), 4.84-4.96 (m, 2H), 3.67 (br s, 2H), 2.69-2.80 (m, 2H), 2.47 (br s, 2H), 1.82-1.91 (m, 2H), 1.19-1.63 (m, 18H), 0.89-0.97 (m, 2H), 0.77 (br s, 2H).

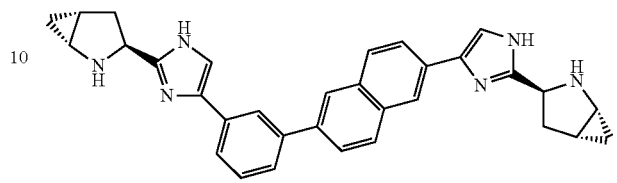

Intermediate 96

(1R,3S,5R)-3-(4-(3-(6-(2-((1S,3R,5S)-2-Azabicyclo[3.1.0]hex-3-yl)-1H-imidazol-4-yl)-2-naphthyl)phenyl)-1H-imidazol-2-yl)-2-azabicyclo[3.1.0]hexane TFA (2 mL, 26.0 mmol) was added to a solution of tert-butyl (1R,3S,5R)-3-(4-(3-(6-(2-((1S,3R,5S)-2-(tert-butoxycarbonyl)-2-azabicyclo[3.1.0]hex-3-yl)-1H-imidazol-4-yl)-2-naphthyl)phenyl)-1H-imidazol-2-yl)-2-azabicyclo[3.1.0]hexane-2-carboxylate (130 mg, 0.20 mmol) in DCM (2 mL) and the mixture was stirred for 2 h at RT. The volatiles were removed under vacuum and the crude product was purified by prep HPLC (methanol/water, 0.1% TFA) to yield a TFA salt of (1R,3S,5R)-3-(4-(3-(6-(2-((1S,3R,5S)-2-azabicyclo[3.1.0]hex-3-yl)-1H-imidazol-4-yl)-2-naphthyl)phenyl)-1H-imidazol-2-yl)-2-azabicyclo[3.1.0]hexane (103 mg) as a tan solid. LC-MS retention time 1.303 min; m/z 499.13 (MH+). LC data was recorded on a Shimadzu LC-10AS liquid chromatograph equipped with a Waters Sunfire C18 4.6×30 mm 5 µM column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (500 MHz, MeOD) δ ppm 8.33 (s, 1H), 8.22 (d, J=12.5 Hz, 2H), 8.02 (dd, J=8.6, 5.8 Hz, 2H), 7.90-7.97 (m, 2H), 7.75-7.82 (m, 4H), 7.58 (t, J=7.8 Hz, 1H), 4.74-4.78 (m, 2H), 3.46-3.53 (m, 2H), 2.64-2.74 (m, 4H), 2.04-2.12 (m, 2H), 1.19-1.26 (m, 2H), 1.02 (ddd, J=14.2, 7.3, 7.2 Hz, 2H).

Scheme 25

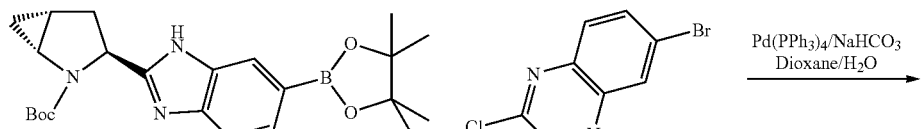

Intermediate 26

-continued

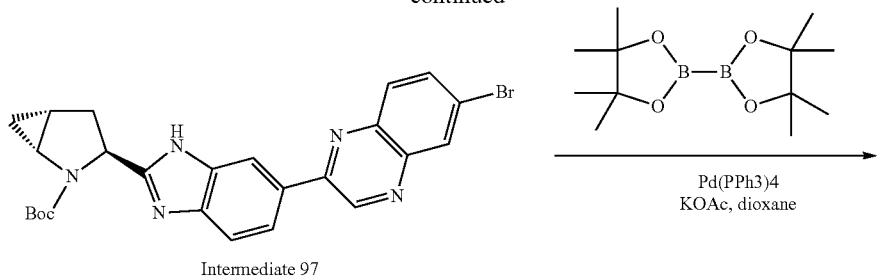

Intermediate 97

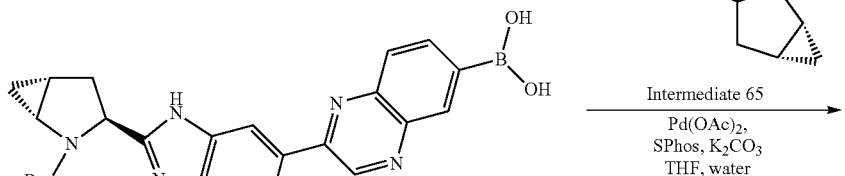

Intermediate 98

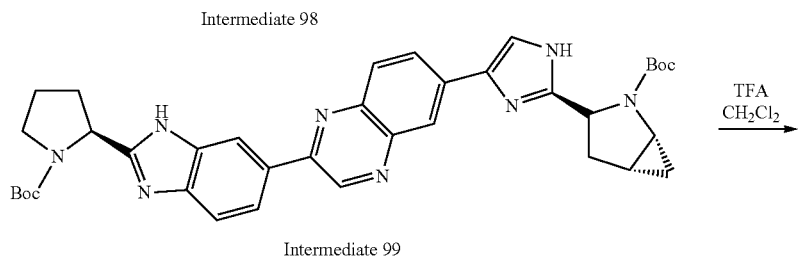

Intermediate 99

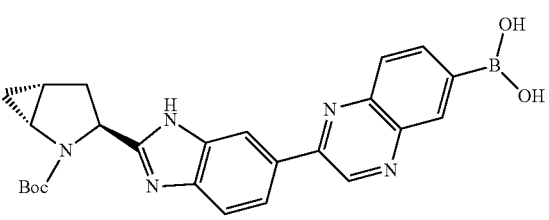 [SMILES: CC(C)(C)OC(=O)N1[C@@H]2C[C@@H]2C[C@H]1c1nc2ccc(-c3cnc4cc(B(O)O)ccc4n3)cc2[nH]1]

Intermediate 100

Intermediate 97

(1R,3S,5R)-tert-Butyl 3-(6-(6-bromoquinoxalin-2-yl)-1H-benzo[d]imidazol-2-yl)-2-azabicyclo[3.1.0]hexane-2-carboxylate Pd(Ph₃P)₄ (28.5 mg, 0.025 mmol) was added to a degassed solution of 6-bromo-2-chloroquinoxaline (60 mg, 0.246 mmol), (1R,3S,5R)-tert-butyl 3-(6-(4,4,5,5-tetramethyl-1,3,2-dioxaborolan-2-yl)-1H-benzo[d]imidazol-2-yl)-2-azabicyclo[3.1.0]hexane-2-carboxylate (115 mg, 0.271 mmol) and sodium bicarbonate (62.1 mg, 0.739 mmol) in dioxane (1 mL) and H₂O (0.2 mL) and the mixture was stirred at 110° C. for 2 h and then at 120° C. for 2 h. The reaction was diluted with MeOH, filtered and purified by prep HPLC (H₂O-MeOH with 10 mM NH₄OAc buffer) to yield (1R,3S,5R)-tert-butyl 3-(6-(6-bromoquinoxalin-2-yl)-1H-benzo[d]imidazol-2-yl)-2-azabicyclo[3.1.0]hexane-2-carboxylate (102.2 mg, 0.202 mmol, 82% yield) as bright yellow solid. LC-MS retention time 2.31 min; m/z 506 [M+H]⁺. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220).

Intermediate 98

2-(2-((1R,3S,5R)-2-(tert-Butoxycarbonyl)-2-azabicyclo[3.1.0]hexan-3-yl)-1H-benzo[d]imidazol-6-yl) quinoxalin-6-ylboronic acid Pd(Ph₃P)₄ (23.28 mg, 0.020 mmol) was added to a degassed solution of (1R,3S,5R)-tert-butyl 3-(6-(6-bromoquinoxalin-2-yl)-1H-benzo[d]imidazol-2-yl)-2-azabicyclo[3.1.0]hexane-2-carboxylate (102 mg, 0.201 mmol), KOAc (49.4 mg, 0.504 mmol) and bis(pinacolato)diboron (113 mg, 0.443 mmol) in dioxane (2 mL) and the reaction was stirred at 83° C. for 16 h. The reaction mixture was partitioned between EtOAc (20 mL) and sat. NH₄Cl(aq.) (5 mL). The organic layer was dried (MgSO₄), filtered and concentrated to an orange oil, which was purified by prep HPLC (H₂O-MeOH with 0.1% TFA buffer) to yield 2-(2-((1R,3S,5R)-2-(tert-butoxycarbonyl)-2-azabicyclo[3.1.0]hexan-3-yl)-1H-benzo[d]imidazol-6-yl)quinoxalin-6-ylboronic acid (57 mg, 0.121 mmol, 60.0% yield) as orange solid. LC-MS retention time 1.94 min; m/z 472 [M+H]⁺. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220).

Rate=4 mL/min. Start % B=0. Final % B=100. Gradient Time=2 min. Wavelength=220). ¹H NMR (400 MHz, MeOD) δ ppm 9.44 (s, 1H), 8.45 (br s, 1H), 8.39 (s, 1H), 8.23 (d, J=8.8 Hz, 1H), 8.18 (d, J=8.5 Hz, 1H), 8.13 (d, J=8.8 Hz, 1H), 7.69-7.76 (m, 1H), 7.64 (s, 1H), 4.69-4.78 (m, 1H), 4.49-4.57 (m, 1H), 3.56-3.70 (m, 2H), 2.50-2.73 (m, 2H), 2.31-2.47 (m, 2H), 1.67-1.86 (m, 2H), 1.31 (br s, 18H), 0.82-0.95 (m, 2H), 0.54-0.75 (m, 2H).

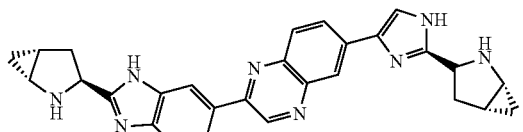

Intermediate 100

2-(2-((1R,3S,5R)-2-Azabicyclo[3.1.0]hex-3-yl)-1H-benzimidazol-5-yl)-6-(2-((1R,3S,5R)-2-azabicyclo[3.1.0]hex-3-yl)-1H-imidazol-4-yl)quinoxaline TFA (0.25 mL, 3.24 mmol) was added to a solution of (1R,3S,5R)-tert-butyl 3-(5-(2-(2-((1R,3S,5R)-2-(tert-butoxycarbonyl)-2-azabicyclo[3.1.0]hexan-3-yl)-1H-benzo[d]imidazol-6-yl)quinoxalin-6-yl)-1H-imidazol-2-yl)-2-azabicyclo[3.1.0]hexane-2-carboxylate (30 mg, 0.044 mmol) in DCM (0.5 mL) and the mixture was stirred at rt for 16 h. The volatiles were removed under vacuum and the residue was triturated with Et₂O to yield a TFA salt of 2-(2-((1R,3S,5R)-2-azabicyclo[3.1.0]hexan-3-yl)-1H-benzo[d]imidazol-6-yl)-6-(2-((1R,3S,5R)-2-azabicyclo[3.1.0]hexan-3-yl)-1H-imidazol-5-yl)quinoxaline (32.7 mg) as yellow solid. LC-MS retention time 1.33 min; m/z 475 [M+H]⁺. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). ¹H NMR (400 MHz, MeOD) δ ppm 9.47 (s, 1H), 8.54 (s, 1H), 8.50 (s, 1H), 8.31 (dd, J=8.8, 1.8 Hz, 1H), 8.26 (dd, J=8.5, 1.3 Hz, 1H), 8.15 (d, J=8.8 Hz, 1H), 7.83 (s, 1H), 7.82 (d, J=8.8 Hz, 1H), 4.85-4.97 (m, 1H), 4.67 (dd, J=10.8, 7.5 Hz, 1H), 3.45-3.57 (m, 2H), 2.77-2.86 (m, 1H), 2.65-2.74 (m, 1H), 2.52-2.65 (m, 2H), 2.02-2.15 (m, 2H), 1.18-1.30 (m, 2H), 0.95-1.09 (m, 2H).

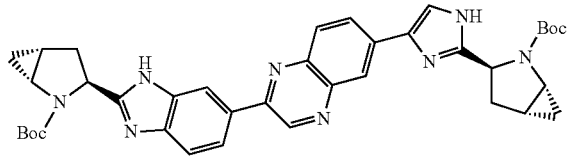 [SMILES: CC(C)(C)OC(=O)N1[C@@H]2C[C@@H]2C[C@H]1c1nc(-c2ccc3nc(-c4ccc5nc([C@@H]6C[C@H]7C[C@H]7N6C(=O)OC(C)(C)C)[nH]c5c4)cnc3c2)c[nH]1]

Intermediate 99 tert-Butyl (1R,3S,5R)-3-(4-(2-(2-((1R,3S,5R)-2-(tert-butoxycarbonyl)-2-azabicyclo[3.1.0]hex-3-yl)-1H-benzimidazol-5-yl)-6-quinoxalinyl)-1H-imidazol-2-yl)-2-azabicyclo[3.1.0]hexane-2-carboxylate Pd(OAc)₂ (2.67 mg, 0.012 mmol) was added to a degassed solution of 2-(2-((1R,3S,5R)-2-(tert-butoxycarbonyl)-2-azabicyclo[3.1.0]hexan-3-yl)-1H-benzo[d]imidazol-6-yl)quinoxalin-6-ylboronic acid (56 mg, 0.119 mmol), (1R,3S,5R)-tert-butyl 3-(5-iodo-1H-imidazol-2-yl)-2-azabicyclo[3.1.0]hexane-2-carboxylate (66.9 mg, 0.178 mmol), dicyclohexyl(2',6'-dimethoxybiphenyl-2-yl)phosphine (9.76 mg, 0.024 mmol) and K₂CO₃ (49.3 mg, 0.356 mmol) in THF (1 mL) and water (0.25 mL) and the mixture was stirred at 120° C. for 2 h. The reaction was diluted with MeOH, filtered and purified by prep HPLC (H₂O-MeOH with 10 mM NH₄OAc buffer) to yield (1R,3S,5R)-tert-butyl 3-(5-(2-(2-((1R,3S,5R)-2-(tert-butoxycarbonyl)-2-azabicyclo[3.1.0]hexan-3-yl)-1H-benzo[d]imidazol-6-yl)quinoxalin-6-yl)-1H-imidazol-2-yl)-2-azabicyclo[3.1.0]hexane-2-carboxylate (32 mg, 0.047 mmol) as yellow solid. LC-MS retention time 1.89 min; m/z 675 [M+H]⁺. (Column PHENOMENEX® Luna 3.0×50 mm S10. Solvent A=95% water/5% methanol/10 mM ammonium acetate. Solvent B=5% water/95% methanol/10 mM ammonium acetate. Flow Scheme 26

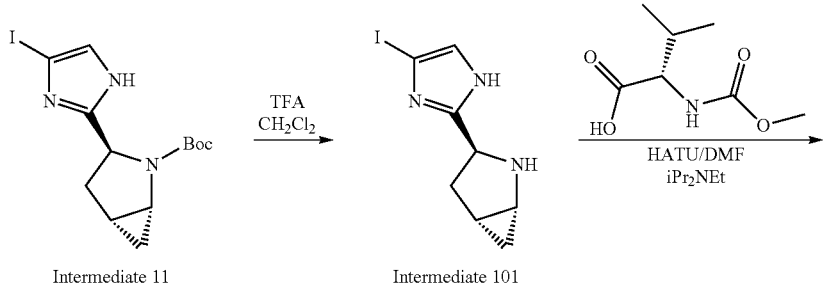

Intermediate 11     Intermediate 101

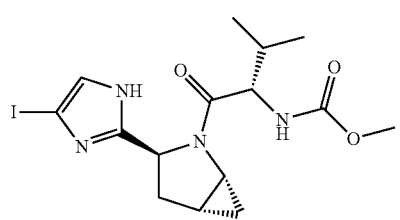 [SMILES: COC(=O)N[C@H](C(=O)N1[C@@H]2C[C@@H]2C[C@H]1c1nc(I)c[nH]1)C(C)C]

Intermediate 102

-continued

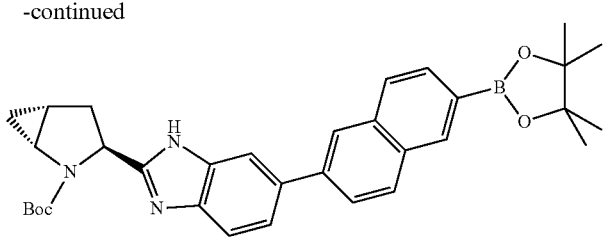

Intermediate 84

$$\xrightarrow{\text{Pd(OAc)}_2,\ \text{SPhos, Cs}_2\text{CO}_3}_{\text{THF, water}}$$

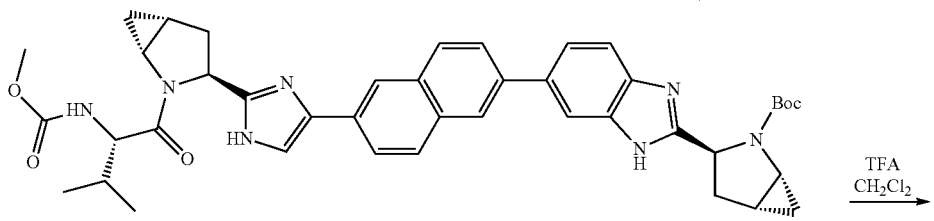

Intermediate 103

$$\xrightarrow{\text{TFA}}_{\text{CH}_2\text{Cl}_2}$$

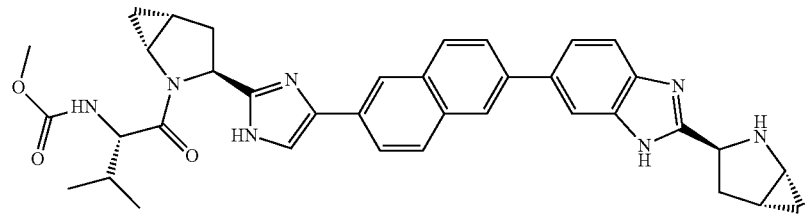

Intermediate 104

Intermediate 101

(1R,3S,5R)-3-(4-Iodo-1H-imidazol-2-yl)-2-azabicyclo[3.1.0]hexane

TFA (1 mL, 12.98 mmol) was added dropwise to a solution of (1R,3S,5R)-tert-butyl 3-(5-iodo-1H-imidazol-2-yl)-2-azabicyclo[3.1.0]hexane-2-carboxylate (450 mg, 1.20 mmol) in DCM (5 mL) at room temperature. The mixture was stirred for 2 h at room temperature, then, the volatiles were removed and the residue was taken in MeOH (5 mL) and filtered through a Strata XC MCX cartridge. The cartridge was washed with methanol (30 mL) and the compound was release from the cartridge by eluting with a solution of 2M of ammonia/methanol (40 mL) and concentrated to give (1R,3S,5R)-3-(5-iodo-1H-imidazol-2-yl)-2-azabicyclo[3.1.0]hexane (283 mg, 1.03 mmol, 86% yield) as white solid. LC-MS retention time 0.448 min; m/z 275.94 (MH+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (500 MHz, MeOD) δ ppm 7.17 (s, 1H), 4.20 (dd, J=10.4, 7.3 Hz, 1H), 3.08 (td, J=6.2, 2.6 Hz, 1H), 2.38 (dd, J=12.5, 7.3 Hz, 1H), 2.19 (ddd, J=12.7, 10.5, 4.9 Hz, 1H), 1.68-1.74 (m, 1H), 0.85 (ddd, J=6.6, 4.4, 2.8 Hz, 1H), 0.61-0.67 (m, 1H).

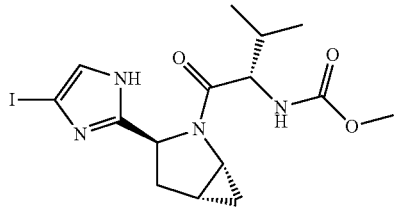

Intermediate 102

Methyl (S)-1-((1R,3S,5R)-3-(4-iodo-1H-imidazol-2-yl)-2-azabicyclo[3.1.0]hexan-2-yl)-3-methyl-1-oxobutan-2-ylcarbamate HATU (464 mg, 1.22 mmol) was added to a solution of (1R,3S,5R)-3-(5-iodo-1H-imidazol-2-yl)-2-azabicyclo[3.1.0]hexane (280 mg, 1.02 mmol), (S)-2-(methoxycarbonylamino)-3-methylbutanoic acid (214 mg, 1.22 mmol) and DIEA (1.8 mL, 10 mmol) in DMF (3 mL). The reaction mixture was stirred 2 h at room temperature and then diluted with MeOH (5 mL) and water (5 mL). The volatiles were removed under vacuum and the residue was purified with flash chromatography (sample was dry loaded on silica gel and eluted with 0-100 ethyl acetate/hexanes) to afford methyl (S)-1-((1R,3S,5R)-3-(5-iodo-1H-imidazol-2-yl)-2-azabicyclo[3.1.0]hexan-2-yl)-3-methyl-1-oxobutan-2-ylcarbamate (500 mg, 0.925 mmol, 91% yield) as yellowish oil. LC-MS retention time 0.850 min; m/z 432.97 (MH+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (500 MHz, MeOD) δ ppm 7.09 (s, 1H), 5.09 (dd, J=8.9, 4.6 Hz, 1H), 4.47-4.60 (m, 1H), 3.67 (s, 3H), 3.59-3.62 (m, 1H), 2.39-2.49 (m, 1H), 2.29-2.39 (m, 1H), 2.12 (dq, J=13.6, 6.8 Hz, 1H), 1.95-2.06 (m, 1H), 1.11 (dt, J=8.6, 5.5 Hz, 1H), 0.94-1.02 (m, 3H), 0.91 (d, J=6.7 Hz, 3H), 0.76 (br s, 1H).

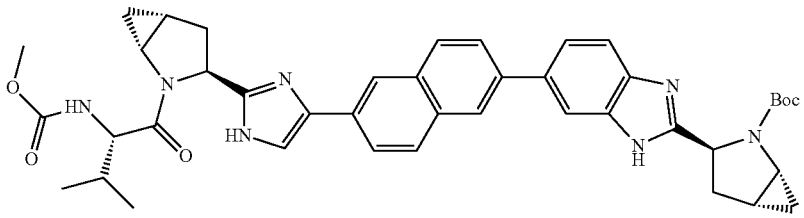 [SMILES: COC(=O)N[C@H](C(=O)N1[C@@H]2C[C@@H]2C[C@H]1c1nc(-c2ccc3cc(-c4ccc5nc([C@@H]6C[C@H]7C[C@H]7N6C(=O)OC(C)(C)C)[nH]c5c4)ccc3c2)c[nH]1)C(C)C]

Intermediate 103

(1R,3S,5R)-tert-Butyl 3-(6-(6-(2-((1R,3S,5R)-2-((S)-2-(methoxycarbonylamino)-3-methylbutanoyl)-2-azabicyclo[3.1.0]hexan-3-yl)-1H-imidazol-4-yl) naphthalen-2-yl)-1H-benzo[d]imidazol-2-yl)-2-azabicyclo[3.1.0]hexane-2-carboxylate A solution of (1R,3S,5R)-tert-butyl 3-(6-(6-(4,4,5,5-tetramethyl-1,3,2-dioxaborolan-2-yl)naphthalen-2-yl)-1H-benzo[d]imidazol-2-yl)-2-azabicyclo[3.1.0]hexane-2-carboxylate (573 mg, 1.04 mmol), methyl (S)-1-((1R,3S,5R)-3-(5-iodo-1H-imidazol-2-yl)-2-azabicyclo[3.1.0]hexan-2-yl)-3-methyl-1-oxobutan-2-ylcarbamate (374 mg, 0.87 mmol), dicyclohexyl(2',6'-dimethoxybiphenyl-2-yl)phosphine (SPHOS, 71.0 mg, 0.173 mmol) and cesium carbonate (846 mg, 2.60 mmol) in THF (7.9 mL) and water (0.8 mL) was degassed at 0° C. under vacuum for 5 min and the reactor was then back filled with nitrogen. Palladium(II) acetate (19.4 mg, 0.087 mmol) was added and the reaction mixture was heated at 100° C. for 3 h. water was added to the cooled solution and the reaction was further diluted with EtOAc (15 mL). The phases were separated and the aqueous layer was extracted with EtOAc (15 mL). The combined organic layers were dried over Na$_2$SO$_4$, filtered through a pad of diatomaceous earth (CELITE®) and the volatiles were removed under reduced pressure. The residue was purified with flash chromatography (sample was dry loaded on silica gel and eluted with 20-100% ethyl acetate/hexanes then 5% MeOH/DCM) to afford (1R,3S,5R)-tert-butyl 3-(6-(6-(2-((1R,3S,5R)-2-((S)-2-(methoxycarbonylamino)-3-methylbutanoyl)-2-azabicyclo[3.1.0]hexan-3-yl)-1H-imidazol-5-yl)naphthalen-2-yl)-1H-benzo[d]imidazol-2-yl)-2-azabicyclo[3.1.0] hexane-2-carboxylate (246 mg, 0.337 mmol, 39.0% yield). LC-MS retention time 1.448 min; m/z 730.21 (MH+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (500 MHz, MeOD) δ ppm 8.32 (br s, 1H), 8.30 (s, 1H), 8.03-8.19 (m, 4H), 7.96-8.03 (m, 1H), 8.01 (s, 1H), 7.85-7.96 (m, 2H), 5.18 (dd, J=9.0, 7.0 Hz, 1H), 5.09 (dd, J=8.9, 7.6 Hz, 1H), 4.58 (d, J=6.5 Hz, 1H), 3.81-3.89 (m, 1H), 3.65-3.75 (m, 1H), 3.69 (s, 3H), 2.68-2.86 (m, 2H), 2.52 (dt, J=13.6, 6.8 Hz, 2H), 2.15-2.29 (m, 1H), 2.06-2.15 (m, 1H), 1.85-1.95 (m, 1H), 1.51 (br s, 4H), 1.41 (d, J=16.3 Hz, 1H), 1.27 (s, 1H), 1.20 (br s, 3H), 1.12 (ddd, J=8.7, 6.0, 5.9 Hz, 1H), 1.04 (d, J=6.8 Hz, 3H), 0.87-1.00 (m, 5H), 0.83 (br s, 1H).

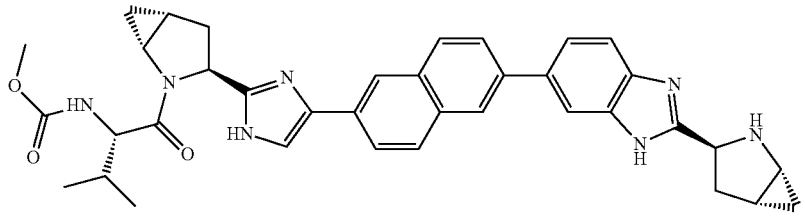 [SMILES: COC(=O)N[C@H](C(=O)N1[C@@H]2C[C@@H]2C[C@H]1c1nc(-c2ccc3cc(-c4ccc5nc([C@@H]6C[C@H]7C[C@H]7N6)[nH]c5c4)ccc3c2)c[nH]1)C(C)C]

Intermediate 104

Methyl (S)-1-((1R,3S,5R)-3-(4-(6-(2-((1R,3S,5R)-2-azabicyclo[3.1.0]hexan-3-yl)-1H-benzo[d]imidazol-6-yl)naphthalen-2-yl)-1H-imidazol-2-yl)-2-azabicyclo[3.1.0]hexan-2-yl)-3-methyl-1-oxobutan-2-ylcarbamate TFA (2 mL,) was added to a solution of (1R,3S,5R)-tert-butyl 3-(6-(6-(2-((1R,3S,5R)-2-((S)-2-(methoxycarbonylamino)-3-methylbutanoyl)-2-azabicyclo[3.1.0]hexan-3-yl)-1H-imidazol-5-yl)naphthalen-2-yl)-1H-benzo[d]imidazol-2-yl)-2-azabicyclo[3.1.0]hexane-2-carboxylate (226 mg, 0.310 mmol) in DCM (5 mL) and the reaction was stirred for 2 h at room temperature. The solution was concentrated under vacuum and the residue was taken in MeOH (10 mL) and filtered through a Strata XC MCX cartridge and washed with methanol (25 mL). The compound was released from the cartridge by washing the column with a solution of 2M of ammonia/methanol (10 mL) and concentrated under reduced pressure to give a methyl (S)-1-((1R,3S,5R)-3-(5-(6-(2-((1R,3S,5R)-2-azabicyclo[3.1.0]hexan-3-yl)-1H-benzo[d]imidazol-6-yl)naphthalen-2-yl)-1H-imidazol-2-yl)-2-azabicyclo[3.1.0]hexan-2-yl)-3-methyl-1-oxobutan-2-ylcarbamate (131 mg, 0.208 mmol) as tan solid. LC-MS retention time 1.235 min; m/z 630.17 (MH+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (500 MHz, MeOD) δ ppm 8.16 (s, 1H), 8.07 (s, 1H), 7.92 (dd, J=8.3, 6.3 Hz, 2H), 7.87 (s, 1H), 7.78-7.85 (m, 2H), 7.60-7.69 (m, 2H), 7.44 (s, 1H), 5.20 (dd, J=8.8, 4.8 Hz, 1H), 4.62 (d, J=6.8 Hz, 1H), 4.28 (dd, J=9.8, 7.8 Hz, 1H), 3.66-3.76 (m, 4H), 3.35-3.41 (m, 2H), 3.03 (td, J=6.0, 2.5 Hz, 1H), 2.40-2.59 (m, 3H), 2.12-2.25 (m, 2H), 1.99-2.09 (m, 1H), 1.59-1.68 (m, 1H), 1.10-1.18 (m, 1H), 1.00-1.08 (m, 3H), 1.04 (d, J=6.8 Hz, 3H), 0.91-1.04 (m, 1H), 0.95 (d, J=6.8 Hz, 3H), 0.76-0.84 (m, 2H), 0.50-0.59 (m, 1H).

Scheme 27

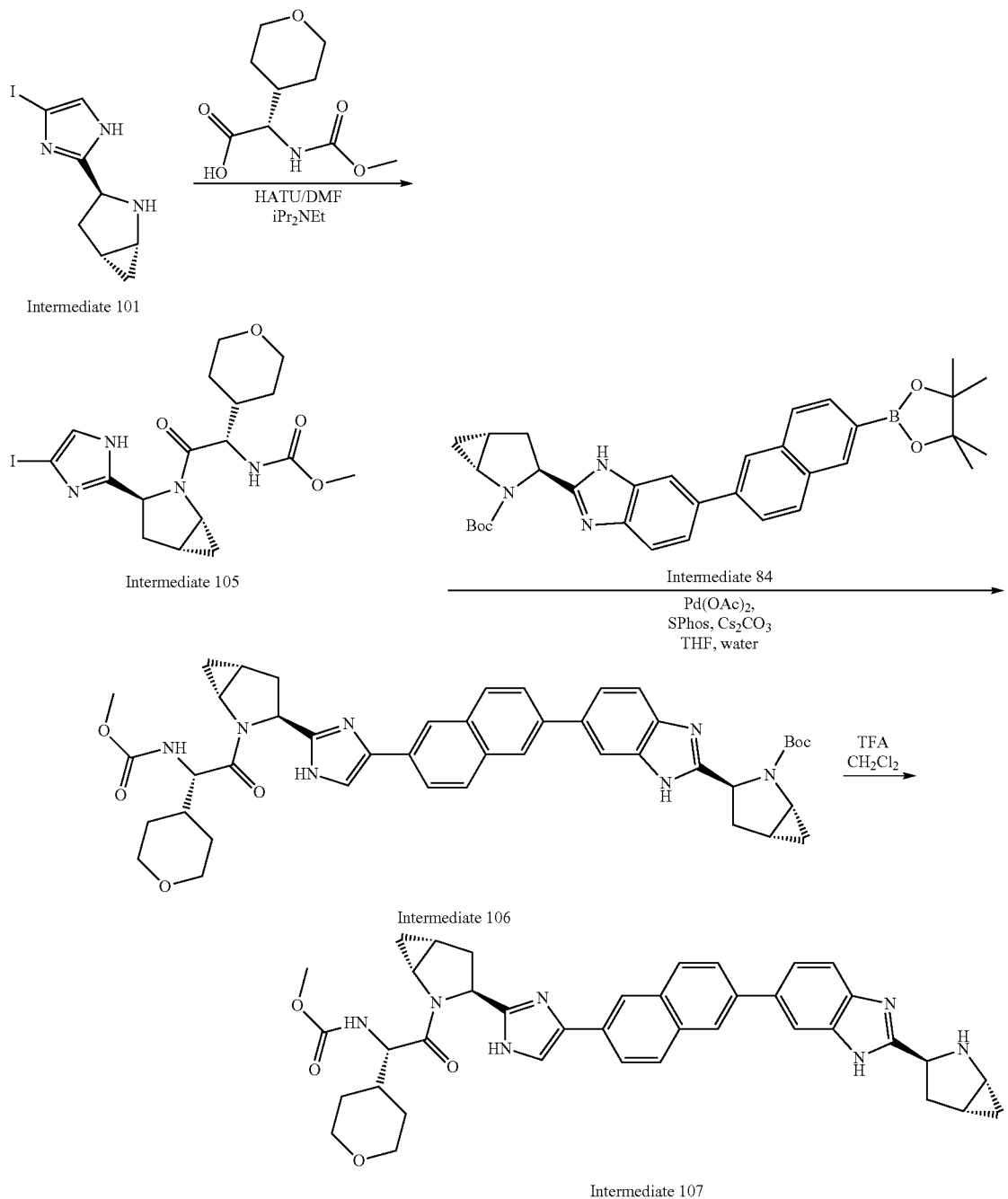

Intermediate 105

Methyl (S)-2-((1R,3S,5R)-3-(4-iodo-1H-imidazol-2-yl)-2-azabicyclo[3.1.0]hexan-2-yl)-2-oxo-1-(tetrahydro-2H-pyran-4-yl)ethylcarbamate HATU (846 mg, 2.23 mmol) was added to a solution of (1R,3S,5R)-3-(5-iodo-1H-imidazol-2-yl)-2-azabicyclo[3.1.0]hexane (510 mg, 1.85 mmol), (S)-2-(methoxycarbonylamino)-2-(tetrahydro-2H-pyran-4-yl)acetic acid (483 mg, 2.23 mmol) and DIEA (3.24 mL, 18.5 mmol) in DMF (5 mL) and the reaction was stirred 2 h at room temperature. The reaction mixture was diluted with MeOH (5 mL) and water (5 mL). The volatiles were removed under vacuum and the residue was purified with flash chromatography (sample was dry loaded on silica gel and eluted with 0-100% ethyl acetate/hexanes then 10% MeOH/DCM) to afford the methyl (S)-2-((1R,3S,5R)-3-(5-iodo-1H-imidazol-2-yl)-2-azabicyclo[3.1.0]hexan-2-yl)-2-oxo-1-(tetrahydro-2H-pyran-4-yl)ethylcarbamate (370 mg, 0.780 mmol, 42.1% yield) as white foam. Impure material was further purified on reverse phase HPLC (water/methanol, 0.1% TFA) to afford the TFA salt of methyl (S)-2-((1R,3S,5R)-3-(5-iodo-1H-imidazol-2-yl)-2-azabicyclo[3.1.0]hexan-2-yl)-2-oxo-1-(tetrahydro-2H-pyran-4-yl)ethylcarbamate, (387 mg) as colorless oil. LC-MS retention time 0.690 min; m/z 474.95 (MH+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (TFA salt, 500 MHz, MeOD) δ ppm 7.58 (s, 1H), 5.04 (dd, J=9.2, 6.7 Hz, 1H), 4.56 (d, J=7.8 Hz, 1H), 3.96 (td, J=11.7, 3.1 Hz, 2H), 3.74-3.81 (m, 1H), 3.65-3.73 (m, 3H), 3.35-3.44 (m, 2H), 2.61 (dd, J=13.6, 9.3 Hz, 1H), 2.37 (ddd, J=13.6, 6.7, 6.5 Hz, 1H), 1.96-2.09 (m, 2H), 1.37-1.62 (m, 4H), 1.06 (dt, J=8.8, 5.9 Hz, 1H), 0.84 (td, J=5.6, 2.4 Hz, 1H).

Intermediate 106

(1R,3S,5R)-tert-Butyl 3-(6-(6-(2-((1R,3S,5R)-2-((S)-2-(methoxycarbonylamino)-2-(tetrahydro-2H-pyran-4-yl)acetyl)-2-azabicyclo[3.1.0]hexan-3-yl)-1H-imidazol-4-yl)naphthalen-2-yl)-1H-benzo[d]imidazol-2-yl)-2-azabicyclo[3.1.0]hexane-2-carboxylate A slurry of (1R,3S,5R)-tert-butyl 3-(6-(6-(4,4,5,5-tetramethyl-1,3,2-dioxaborolan-2-yl)naphthalen-2-yl)-1H-benzo[d]imidazol-2-yl)-2-azabicyclo[3.1.0]hexane-2-carboxylate (407 mg, 0.738 mmol), a TFA salt of methyl (S)-2-((1R,3S,5R)-3-(5-iodo-1H-imidazol-2-yl)-2-azabicyclo[3.1.0]hexan-2-yl)-2-oxo-1-(tetrahydro-2H-pyran-4-yl)ethylcarbamate (350 mg), dicyclohexyl(2',6'-dimethoxybiphenyl-2-yl)phosphine (60.6 mg, 0.148 mmol) and cesium carbonate (721 mg, 2.21 mmol) in THF (6.7 mL) and water (0.7 mL) was degassed at 0° C. under vacuum for 5 min and then the reactor was back filled with nitrogen. Palladium(II) acetate (16.6 mg, 0.074 mmol) was added and the mixture was heated at 100° C. for 3 h. The volatiles were removed under vacuum and the mixture was diluted with water (20 mL) and EtOAc (20 mL). The phases were separated and the aqueous layer was extracted with EtOAc (20 mL). The combined organic layers were dried over $Na_2SO_4$, filtered and evaporated under vacuum. The residue was purified with flash chromatography (sample was dry loaded on silica gel and eluted with 20-100% ethyl acetate/hexanes, then 10% MeOH/DCM). The residue was purified again by on reverse phase HPLC (water/methanol, 0.1% TFA) to afford the TFA salt of (1R,3S,5R)-tert-butyl 3-(6-(6-(2-((1R,3S,5R)-2-((S)-2-(methoxycarbonylamino)-2-(tetrahydro-2H-pyran-4-yl)acetyl)-2-azabicyclo[3.1.0]hexan-3-yl)-1H-imidazol-5-yl)naphthalen-2-yl)-1H-benzo[d]imidazol-2-yl)-2-azabicyclo[3.1.0]hexane-2-carboxylate (231 mg) as yellow solid. LC-MS retention time 1.395 min; m/z 772.31 (MH+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (TFA salt, 500 MHz, MeOD) δ ppm 8.31 (s, 2H), 8.09-8.18 (m, 3H), 8.05 (dd, J=8.7, 1.7 Hz, 1H), 7.97-8.02 (m, 2H), 7.91 (d, J=8.6 Hz, 1H), 7.88 (dd, J=8.7, 1.7 Hz, 1H), 5.16 (dd, J=9.2, 7.0 Hz, 1H), 5.01-5.09 (m, 1H), 4.62 (d, J=7.6 Hz, 1H), 3.91-4.02 (m, 3H), 3.83-3.89 (m, 1H), 3.70 (br s, 4H), 3.35-3.45 (m, 2H), 2.68-2.83 (m, 2H), 2.45-2.57 (m, 2H), 2.04-2.16 (m, 2H), 1.90 (br s, 1H), 1.43-1.61 (m, 8H), 1.14-1.31 (m, 4H), 1.07-1.13 (m, 1H), 0.97 (dt, J=8.8, 5.8 Hz, 1H), 0.91 (br s, 1H), 0.82 (br s, 1H).

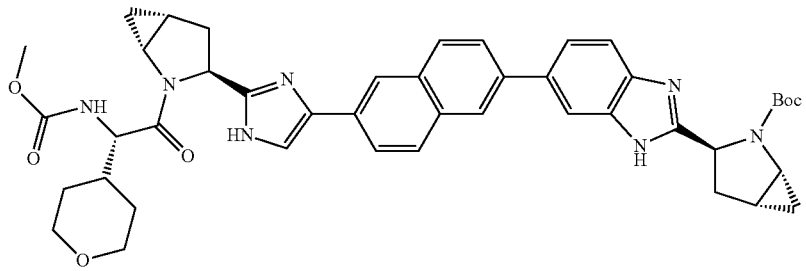 [SMILES: COC(=O)N[C@H](C(=O)N1[C@@H]2C[C@@H]2C[C@H]1c1nc(-c2ccc3cc(-c4ccc5nc([C@@H]6C[C@H]7C[C@H]7N6C(=O)OC(C)(C)C)[nH]c5c4)ccc3c2)c[nH]1)C1CCOCC1]

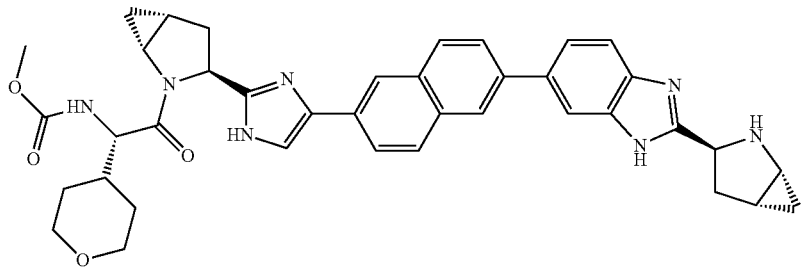 [SMILES: COC(=O)N[C@H](C(=O)N1[C@@H]2C[C@@H]2C[C@H]1c1nc(-c2ccc3cc(-c4ccc5nc([C@@H]6C[C@H]7C[C@H]7N6)[nH]c5c4)ccc3c2)c[nH]1)C1CCOCC1]

Intermediate 107

Methyl (S)-2-((1R,3S,5R)-3-(4-(6-(2-((1R,3S,5R)-2-azabicyclo[3.1.0]hexan-3-yl)-1H-benzo[d]imidazol-6-yl)naphthalen-2-yl)-1H-imidazol-2-yl)-2-azabicyclo[3.1.0]hexan-2-yl)-2-oxo-1-(tetrahydro-2H-pyran-4-yl)ethylcarbamate TFA (2 mL, 26.0 mmol) was added to a solution of a TFA salt of (1R,3S,5R)-tert-butyl 3-(6-(6-(2-((1R,3S,5R)-2-((S)-2-(methoxycarbonylamino)-2-(tetrahydro-2H-pyran-4-yl)acetyl)-2-azabicyclo[3.1.0]hexan-3-yl)-1H-imidazol-5-yl)naphthalen-2-yl)-1H-benzo[d]imidazol-2-yl)-2-azabicyclo[3.1.0]hexane-2-carboxylate (150 mg) in DCM and the mixture was stirred for 2 h at rt. The volatiles were removed under vacuum and the residue was taken in MeOH (15 mL), filtered through a Strata XC MCX cartridge (1 g) and washed with methanol. The compound was release from the cartridge by washing the column with a solution of 2M of ammonia/methanol (20 mL) and concentrated to give methyl (S)-2-((1R,3S,5R)-3-(5-(6-(2-((1R,3S,5R)-2-azabicyclo[3.1.0]hexan-3-yl)-1H-benzo[d]imidazol-6-yl)naphthalen-2-yl)-1H-imidazol-2-yl)-2-azabicyclo[3.1.0]hexan-2-yl)-2-oxo-1-(tetrahydro-2H-pyran-4-yl)ethylcarbamate (100 mg, 0.149 mmol) as white solid. LC-MS retention time 1.772 min; m/z 670.36 (M−H+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/10 mM ammonium acetate and solvent and Solvent B was 10% water/90% methanol/10 mM ammonium acetate and solvent. MS data was determined using a MICROMASS® Platform for LC in electrospray mode. $^1$H NMR (TFA salt, 500 MHz, MeOD) δ ppm 8.28 (s, 1H), 8.24 (s, 1H), 8.13 (d, J=8.9 Hz, 1H), 8.05-8.10 (m, 1H), 8.03 (s, 1H), 7.96-8.00 (m, 2H), 7.84 (dd, J=8.7, 1.7 Hz, 1H), 7.75-7.82 (m, 2H), 5.16 (dd, J=9.2, 7.3 Hz, 1H), 4.84-4.88 (partially shaded by MeOD, m, 1H), 4.62 (d, J=7.6 Hz, 1H), 3.91-4.01 (m, 2H), 3.84-3.89 (m, 1H), 3.66-3.76 (m, 3H), 3.51-3.56 (m, 1H), 3.35-3.46 (m, 2H), 2.82 (dd, J=12.8, 7.3 Hz, 1H), 2.73 (dd, J=13.7, 9.2 Hz, 1H), 2.61 (td, J=12.0, 4.7 Hz, 1H), 2.53 (ddd, J=13.8, 6.8, 6.6 Hz, 1H), 2.06-2.16 (m, 3H), 1.58-1.64 (m, 1H), 1.44-1.57 (m, 3H), 1.23-1.30 (m, 1H), 1.08-1.16 (m, 1H), 1.05 (q, J=7.8 Hz, 1H), 0.88-0.93 (m, 1H).

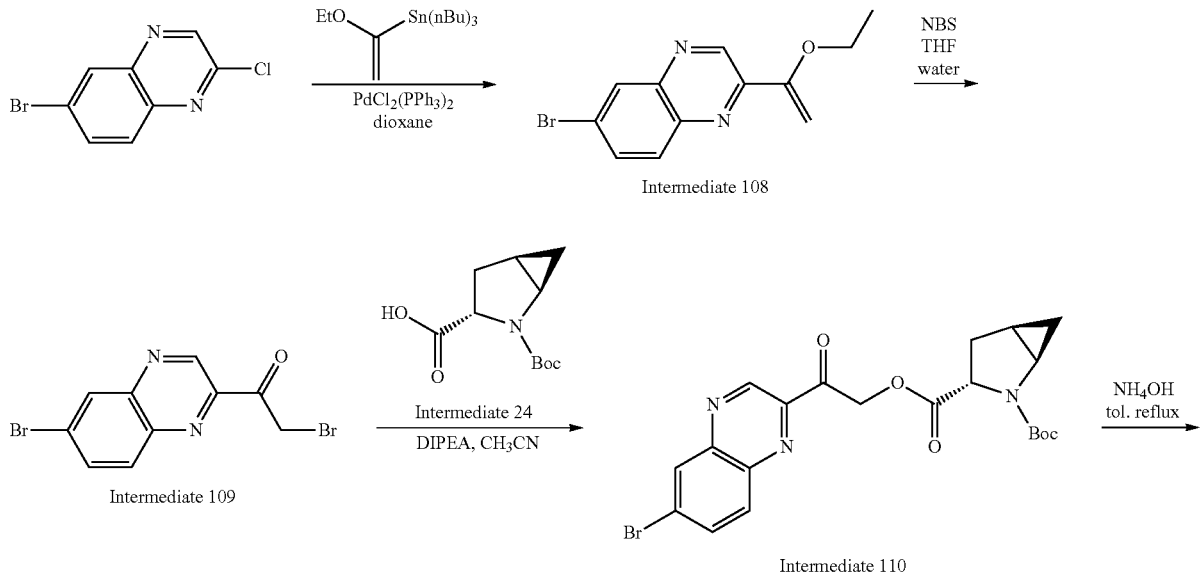

Scheme 28

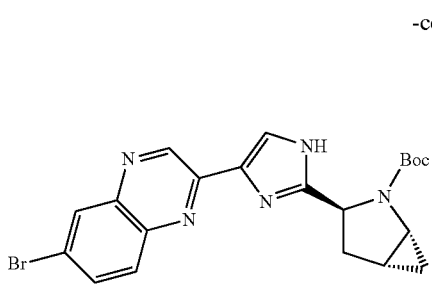

Intermediate 111

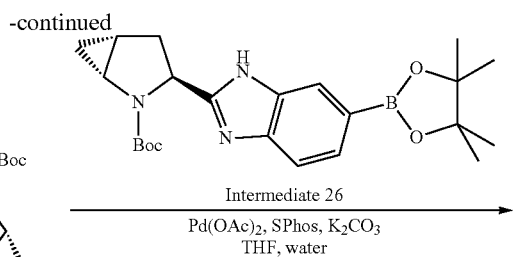

Intermediate 26

Pd(OAc)₂, SPhos, K₂CO₃
THF, water

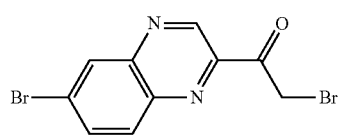

Intermediate 112

TFA
CH₂Cl₂

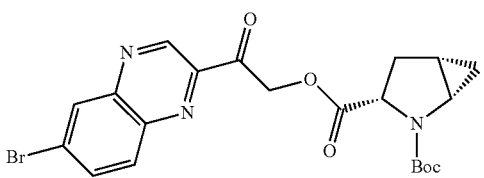 [SMILES: CC(C)(C)OC(=O)N1[C@H](C(=O)OCC(=O)c2cnc3cc(Br)ccc3n2)C[C@@H]2C[C@@H]21]

Intermediate 113

Intermediate 108

6-Bromo-2-(1-ethoxyvinyl)quinoxaline

Dichlorobis(triphenylphosphine)-palladium(II) (17.30 mg, 0.025 mmol) was added to a solution of 6-bromo-2-chloroquinoxaline (60 mg, 0.246 mmol) and tributyl(1-ethoxyvinyl)stannane (107 mg, 0.296 mmol) in dioxane (1.5 mL) and the mixture was stirred at 110° C. for 2 h. The reaction was diluted with MeOH, and purified by prep HPLC (H₂O-MeOH with 10 mM NH₄OAc buffer) to yield 6-bromo-2-(1-ethoxyvinyl)quinoxaline (36 mg, 0.129 mmol, 52.3% yield) as white solid. LC-MS retention time 2.76 min; m/z 279 [M+H]⁺. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220).

Intermediate 109

2-Bromo-1-(6-bromoquinoxalin-2-yl)ethanone

NBS (55.1 mg, 0.310 mmol) was added to a solution of 6-bromo-2-(1-ethoxyvinyl)quinoxaline (72 mg, 0.26 mmol) in THF (2 mL) and water (0.500 mL) and the mixture was stirred at rt for 2 h. The reaction was diluted with MeOH and purified by prep HPLC (H₂O-MeOH with 10 mM NH₄OAc buffer) to yield 2-bromo-1-(6-bromoquinoxalin-2-yl)ethanone (50 mg, 0.15 mmol, 59% yield) as white solid. LC-MS retention time 2.40 min; m/z 329 [M+H]⁺. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220).

Intermediate 110

(1S,3S,5S)-3-(2-(6-Bromoquinoxalin-2-yl)-2-oxoethyl) 2-tert-butyl 2-azabicyclo[3.1.0]hexane-2,3-dicarboxylate DIPEA (0.040 mL, 0.227 mmol) was added to a solution of 2-bromo-1-(6-bromoquinoxalin-2-yl)ethanone (50 mg, 0.152 mmol) and (1R,3S,5R)-2-(tert-butoxycarbonyl)-2-azabicyclo[3.1.0]hexane-3-carboxylic acid (37.9 mg, 0.167 mmol) in acetonitrile (1.5 mL) and the mixture was stirred at rt for 16 h. The solvent was evaporated and the residue was partitioned between EtOAc (20 mL)/aq. sat. NaHCO₃ (5 mL). The organic layer was dried (MgSO₄), filtered and concentrated to yield crude (1R,3S,5R)-3-(2-(6-bromoquinoxalin-2-yl)-2-oxoethyl) 2-tert-butyl 2-azabicyclo[3.1.0]hexane-2,3- dicarboxylate (63 mg) as orange solid. LC-MS retention time 2.74 min; m/z 476 [M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220).

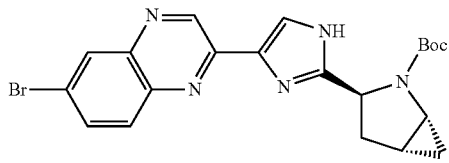 [SMILES: CC(C)(C)OC(=O)N1[C@@H]2C[C@@H]2C[C@H]1c1nc(-c2cnc3cc(Br)ccc3n2)c[nH]1]

Intermediate 111

(1R,3S,5R)-tert-Butyl 3-(4-(6-bromoquinoxalin-2-yl)-1H-imidazol-2-yl)-2-azabicyclo[3.1.0]hexane-2-carboxylate NH$_4$OAc (102 mg, 1.323 mmol) was added to a solution of (1R,3S,5R)-3-(2-(6-bromoquinoxalin-2-yl)-2-oxoethyl) 2-tert-butyl 2-azabicyclo[3.1.0]hexane-2,3-dicarboxylate (63 mg, 0.13 mmol) in toluene (3 mL) and the mixture was stirred at 120° C. for 4 h. Additional NH$_4$OAc (102 mg, 1.323 mmol) was added and the reaction was further heated at 120° C. for 4 h. The reaction was diluted with EtOAc (20 mL) and aq. sat. NaHCO$_3$ (5 mL). The organic layer was dried (MgSO$_4$), filtered, concentrated and then purified by flash silica chromatography (eluted with 1:2 EtOAc/hexane) to yield (1R,3S,5R)-tert-butyl 3-(4-(6-bromoquinoxalin-2-yl)-1H-imidazol-2-yl)-2-azabicyclo[3.1.0]hexane-2-carboxylate (25 mg, 0.055 mmol) as red orange solid. LC-MS retention time 2.07 min; m/z 456 [M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220).

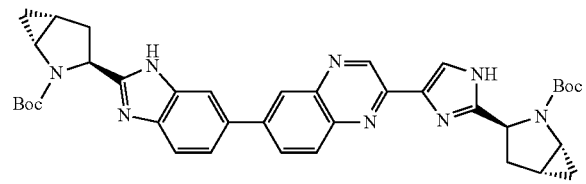 [SMILES: CC(C)(C)OC(=O)N1[C@@H]2C[C@@H]2C[C@H]1c1nc(-c2cnc3cc(-c4ccc5nc([C@@H]6C[C@H]7C[C@H]7N6C(=O)OC(C)(C)C)[nH]c5c4)ccc3n2)c[nH]1]

Intermediate 112

(1R,3S,5R)-3-(4-(6-(2-((1R,3S,5R)-2-(tert-Butoxycarbonyl)-2-azabicyclo[3.1.0]hex-3-yl)-1H-benzimidazol-5-yl)-2-quinoxalinyl)-1H-imidazol-2-yl)-2-azabicyclo[3.1.0]hexane-2-carboxylate Pd(OAc)$_2$ (1.230 mg, 5.48 μmol) was added to a degassed suspension of (1R,3S,5R)-tert-butyl 3-(4-(6-bromoquinoxalin-2-yl)-1H-imidazol-2-yl)-2-azabicyclo[3.1.0]hexane-2-carboxylate (25 mg, 0.055 mmol), K$_2$CO$_3$ (22.71 mg, 0.164 mmol), dicyclohexyl(2',6'-dimethoxybiphenyl-2-yl)phosphine (4.50 mg, 10.96 μmol) and (1R,3S,5R)-tert-butyl 3-(6-(4,4,5,5-tetramethyl-1,3,2-dioxaborolan-2-yl)-1H-benzo[d]imidazol-2-yl)-2-azabicyclo[3.1.0]hexane-2-carboxylate (30.3 mg, 0.071 mmol) in THF (1 mL) and water (0.250 mL) and the mixture was stirred at 110° C. for 2 h. The reaction was diluted with MeOH, filtered and purified by prep HPLC (H$_2$O-MeOH with 10 mM NH$_4$OAc buffer) to yield (1R,3S,5R)-tert-butyl 3-(5-(6-(2-((1R,3S,5R)-2-(tert-butoxycarbonyl)-2-azabicyclo[3.1.0]hexan-3-yl)-1H-benzo[d]imidazol-6-yl)quinoxalin-2-yl)-1H-imidazol-2-yl)-2-azabicyclo[3.1.0]hexane-2-carboxylate (12 mg, 0.018 mmol, 33% yield) as yellow solid. LC-MS retention time 1.90 min; m/z 675 [M+H]$^+$. (Column PHENOMENEX® Luna 3.0×50 mm S10. Solvent A=95% water/5% methanol/10 mM ammonium acetate. Solvent B=5% water/95% methanol/10 mM ammonium acetate. Flow Rate=4 mL/min. Start % B=0. Final % B=100. Gradient Time=2 min. Wavelength=220). $^1$H NMR (400 MHz, MeOD) δ ppm 9.38 (s, 1H), 8.28 (d, J=2.0 Hz, 1H), 8.16-8.22 (m, 1H), 8.10-8.15 (m, 1H), 7.95 (s, 2H), 7.66-7.76 (m, 2H), 3.54-3.73 (m, 2H), 2.52-2.69 (m, 2H), 2.33-2.47 (m, 2H), 1.71-1.84 (m, 2H), 1.08-1.57 (m, 20H), 0.83-0.95 (m, 2H), 0.60-0.74 (m, 2H).

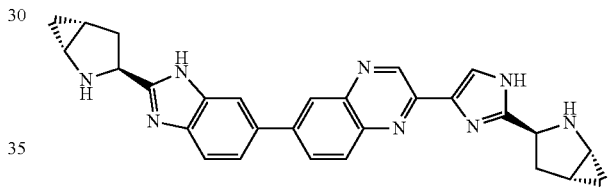

Intermediate 113

6-(2-((1R,3S,5R)-2-Azabicyclo[3.1.0]hexan-3-yl)-1H-benzo[d]imidazol-6-yl)-2-(2-((1R,3S,5R)-2-azabicyclo[3.1.0]hexan-3-yl)-1H-imidazol-4-yl)quinoxaline TFA (0.25 mL, 3.24 mmol) was added to a solution of (1R,3S,5R)-tert-butyl 3-(5-(6-(2-((1R,3S,5R)-2-(tert-butoxycarbonyl)-2-azabicyclo[3.1.0]hexan-3-yl)-1H-benzo[d]imidazol-6-yl)quinoxalin-2-yl)-1H-imidazol-2-yl)-2-azabicyclo[3.1.0]hexane-2-carboxylate (10 mg, 0.015 mmol) in DCM (0.5 mL) and the mixture was stirred at rt for 16 h. The volatiles were removed under vacuum and the residue was triturated with Et$_2$O. The resulting solid was rinsed with Et$_2$O to yield a TFA salt of 6-(2-((1R,3S,5R)-2-azabicyclo[3.1.0]hexan-3-yl)-1H-benzo[d]imidazol-6-yl)-2-(2-((1R,3S,5R)-2-azabicyclo[3.1.0]hexan-3-yl)-1H-imidazol-5-yl)quinoxaline (10.5 mg) as yellow solid. LC-MS retention time 1.32 min; m/z 475 [M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220).

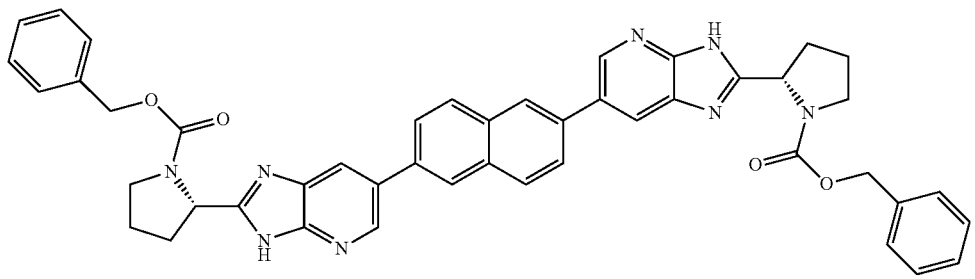 [SMILES: O=C(OCc1ccccc1)N1CCC[C@H]1c1nc2cc(-c3ccc4cc(-c5cnc6[nH]c([C@@H]7CCCN7C(=O)OCc7ccccc7)nc6c5)ccc4c3)cnc2[nH]1]

Intermediate 114

Benzyl (2S)-2-(6-(6-(2-((2S)-1-((benzyloxy)carbonyl)-2-pyrrolidinyl)-1H-imidazo[4,5-b]pyridin-6-yl)-2-naphthyl)-3H-imidazo[4,5-b]pyridin-2-yl)-1-pyrrolidinecarboxylate Prepared in a similar manner as Intermediate 39 using (S)-1-(benzyloxycarbonyl)pyrrolidine-2-carboxylic acid as a starting material rather than (S)-1-(tert-butoxycarbonyl)pyrrolidine-2-carboxylic acid and the intermediates were not SEM protected. Prepared benzyl (2S)-2-(6-(6-(2-((2S)-1-((benzyloxy)carbonyl)-2-pyrrolidinyl)-1H-imidazo[4,5-b]pyridin-6-yl)-2-naphthyl)-3H-imidazo[4,5-b]pyridin-2-yl)-1-pyrrolidinecarboxylate (20.8 mg) as a white solid. LC-MS retention time 1.742 min; m/z 769.41 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% H$_2$O/10 mM ammonium acetate and Solvent B was 5% H$_2$O/95% acetonitrile/10 mM ammonium acetate. MS data was determined using a MICROMASS® Platform for LC in electrospray mode.

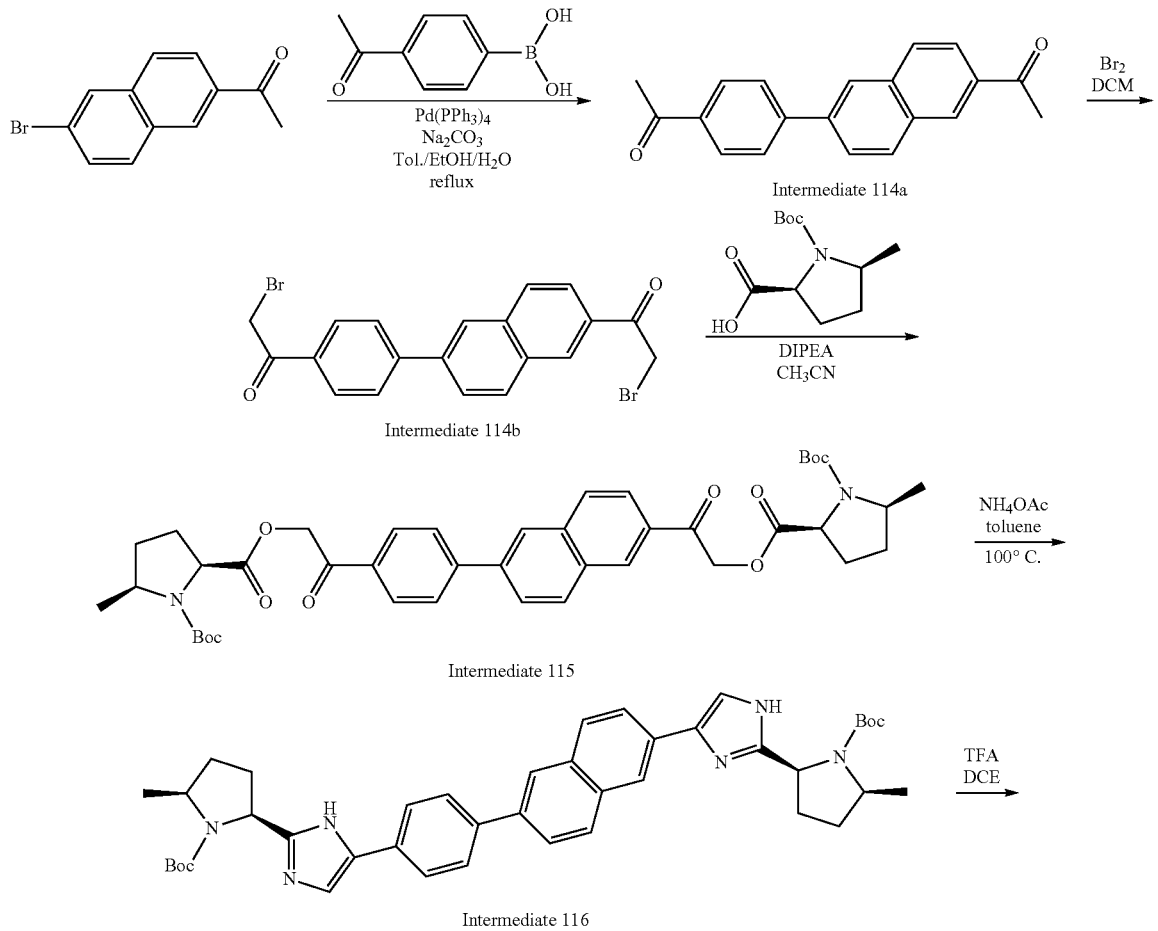

Scheme 29

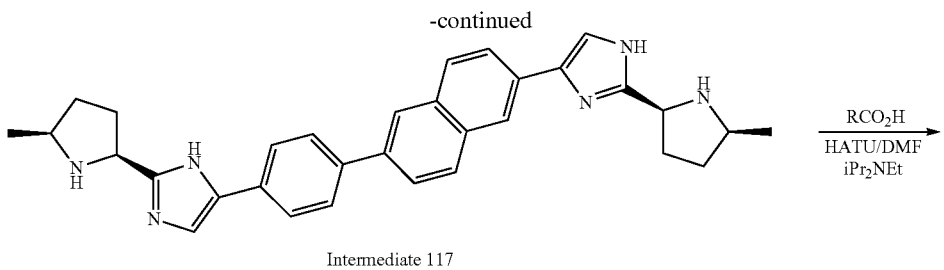

Intermediate 117

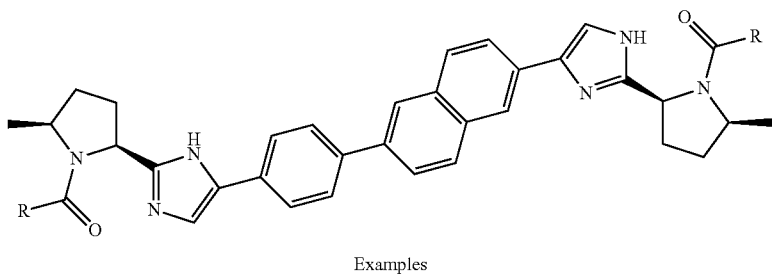

Examples

Intermediate 114a

1-(4-(6-Acetylnaphthalen-2-yl)phenyl)ethanone

A solution of sodium carbonate (5.43 g, 51.3 mmol) in water (35 mL) was added to a stirred solution of 1-(6-bromonaphthalen-2-yl)ethanone (2.554 g, 10.25 mmol) and 4-acetylphenylboronic acid (2.017 g, 12.30 mmol) in toluene (35.0 mL) and ethanol (35.0 mL) and nitrogen was bubbled through the reaction mixture for 15 min. Then $Pd(PPh_3)_4$ (0.237 g, 0.205 mmol) was added, and the reaction was flushed with nitrogen and heated at 95° C. under nitrogen for 8 h and then stirred overnight at rt. The reaction was concentrated to dryness under high vacuum and then partitioned between DCM (~200 mL) and water (~150 mL). The organic layer was then washed with brine (~100 mL), dried ($MsSO_4$), filtered and concentrated. The residue was triturated with MeOH (~120 mL) and the remaining solids were redissolved into DCM and concentrated to dryness (~2.7 g of orange solid). This material was dissolved into hot EtOAc (80 mL) and allowed to cool. The resulting solids were collected by filtration and rinsed with $Et_2O$ to yield 1-(4-(6-acetylnaphthalen-2-yl)phenyl)ethanone (1.84 g). LC-MS retention time 2.443 min; m/z 288.98 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1H$ NMR (400 MHz, chloroform-d) δ ppm 8.51 (s, 1H), 8.05-8.16 (m, 5H), 7.98 (d, J=8.8 Hz, 1H), 7.81-7.88 (m, 3H), 2.76 (s, 3H), 2.68 (s, 3H).

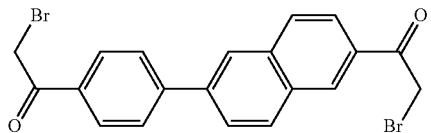

Intermediate 114b

2-Bromo-1-(4-(6-(2-bromoacetyl)naphthalen-2-yl)phenyl)ethanone

A solution of bromine (0.669 mL, 13.0 mmol) in DCM (10 mL) was added to a stirred solution of 1-(4-(6-acetylnaphthalen-2-yl)phenyl)ethanone (1.827 g, 6.34 mmol) in DCM (30 mL) and the reaction was stirred at rt for 1 d. The reaction mixture was diluted with DCM (~20 mL) and concentrated to dryness to yield 2-bromo-1-(4-(6-(2-bromoacetyl)naphthalen-2-yl)phenyl)ethanone (2.83 g) which was used without further purification. LC-MS retention time 2.708 min; m/z 446.71 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1H$ NMR (400 MHz, chloroform-d) δ ppm 8.57 (s, 1H), 8.07-8.17 (m, 5H), 8.02 (d, J=8.8 Hz, 1H), 7.88 (d, J=8.8 Hz, 3H), 4.60 (s, 2H), 4.51 (s, 2H).

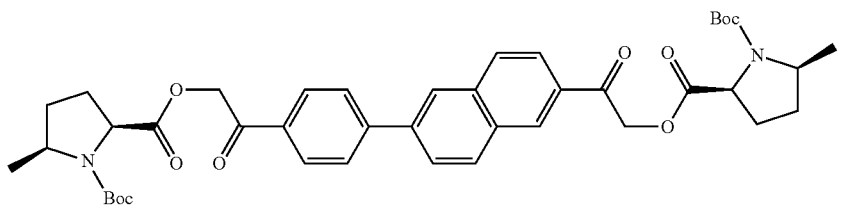

Intermediate 115

(2S,5S)-2-(2-(4-(6-(2-((2S,5S)-1-(tert-Butoxycarbonyl)-5-methylpyrrolidine-2-carbonyloxy)acetyl)naphthalen-2-yl)phenyl)-2-oxoethyl) 1-tert-butyl 5-methylpyrrolidine-1,2-dicarboxylate Hunig's Base (1.662 mL, 9.52 mmol) was added to a stirred slurry of 2-bromo-1-(4-(6-(2-bromoacetyl)naphthalen-2-yl)phenyl)ethanone (1.42 g, 3.17 mmol) and (2S,5S)-1-(tert-butoxycarbonyl)-5-methylpyrrolidine-2-carboxylic acid (1.45 g, 6.34 mmol) in acetonitrile (60 mL). The reaction was stirred at rt for 1 d (slowly became clear) and the clear orange solution was concentrated and purified on a BIOTAGE® Horizon (160 g SiO$_2$, 30-40% EtOAc/hexanes) to yield (2S,5S)-2-(2-(4-(6-(2-((2S,5S)-1-(tert-butoxycarbonyl)-5-methylpyrrolidine-2-carbonyloxy)acetyl)naphthalen-2-yl)phenyl)-2-oxoethyl) 1-tert-butyl 5-methylpyrrolidine-1,2-dicarboxylate (1.81 g) as an off-white solidified foam. LC-MS retention time 3.126 min; m/z 765.87 (M+Na). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, chloroform-d) δ ppm 8.48 (s, 1H), 8.13 (s, 1H), 7.99-8.11 (m, 5H), 7.86 (d, J=8.3 Hz, 3H), 5.24-5.76 (m, 4H), 4.41-4.59 (m, 2H), 3.93-4.11 (m, 2H), 2.28-2.42 (m, 4H), 2.11 (br. s., 2H), 1.77 (br. s., 2H), 1.49 (br. s., 9H), 1.48 (br. s., 9H), 1.35 (br. s., 6H).

Intermediate 116 tert-Butyl (2S,5S)-2-(4-(4-(6-(2-((2S,5S)-1-(tert-butoxycarbonyl)-5-methyl-2-pyrrolidinyl)-1H-imidazol-4-yl)-2-naphthyl)phenyl)-1H-imidazol-2-yl)-5-methyl-1-pyrrolidinecarboxylate Ammonium acetate (3.76 g, 48.7 mmol) was added to a stirred solution of (2S,5S)-2-(2-(4-(6-(2-((2S,5S)-1-(tert-butoxycarbonyl)-5-methylpyrrolidine-2-carbonyloxy)acetyl)naphthalen-2-yl)phenyl)-2-oxoethyl) 1-tert-butyl 5-methylpyrrolidine-1,2-dicarboxylate (1.81 g, 2.437 mmol) in toluene (40 mL) and the slurry was stirred at rt for 10 min before being heated at 100° C. for 12 h. The reaction was cooled to rt, concentrated to dryness and the residue was partitioned between DCM (~150 mL) and ½ sat NaHCO$_3$ (aq) (~150 mL). The organic layer was washed with brine (~100 mL), dried (MgSO$_4$), filter and concentrated to a solidified brown foam which was purified by BIOTAGE® Horizon (160 g SiO$_2$, 1.5-3% MeOH/DCM) to yield tert-butyl (2S,5S)-2-(4-(4-(6-(2-((2S,5S)-1-(tert-butoxycarbonyl)-5-methyl-2-pyrrolidinyl)-1H-imidazol-4-yl)-2-naphthyl)phenyl)-1H-imidazol-2-yl)-5-methyl-1-pyrrolidinecarboxylate (1.46 g) as a yellow-orange solidified foam. LC-MS retention time 2.92 min; m/z 703.32 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode.

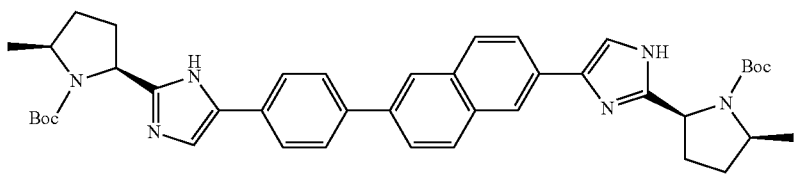

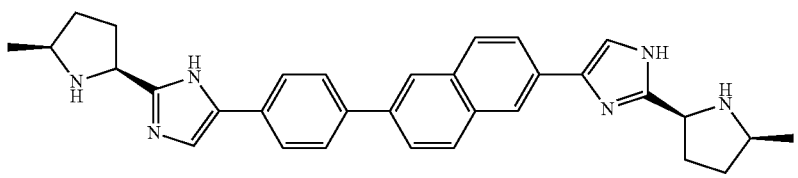

Intermediate 117

2-((2S,5S)-5-Methyl-2-pyrrolidinyl)-4-(4-(6-(2-((2S,5S)-5-methyl-2-pyrrolidinyl)-1H-imidazol-4-yl)-2-naphthyl)phenyl)-1H-imidazole TFA (0.500 mL, 6.49 mmol) was added dropwise to a stirred solution of tert-butyl (2S,5S)-2-(4-(4-(6-(2-((2S,5S)-1-(tert-butoxycarbonyl)-5-methyl-2-pyrrolidinyl)-1H-imidazol-4-yl)-2-naphthyl)phenyl)-1H-imidazol-2-yl)-5-methyl-1-pyrrolidinecarboxylate (228 mg, 0.324 mmol) in DCE (6 mL). During the addition, precipitate formed which hindered the stirring. DCM (~10 mL) was added and the slurry was stirred while the remaining TFA was added. The reaction was stirred at rt for 30 min, additional TFA was added (~0.5 mL) and the reaction was stirred 3 h. The reaction was concentrated to yield a TFA salt of 2-((2S,5S)-5-methyl-2-pyrrolidinyl)-4-(4-(6-(2-((2S,5S)-5-methyl-2-pyrrolidinyl)-1H-imidazol-4-yl)-2-naphthyl)phenyl)-1H-imidazole (102 mg, 113 mg, 114 mg) as an orange solid. LC-MS retention time 2.756 min; m/z 503.14 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, MeOD) δ ppm 8.32 (s, 1H), 8.17 (s, 1H), 8.01 (app t, J=8.2 Hz, 2H), 7.85-7.95 (m, 6H), 7.80 (s, 1H), 7.73 (s, 1H), 5.02 (app q, J=8.0 Hz, 2H), 3.92 (dddd, J=8.7, 7.0, 6.9, 4.8 Hz, 2H), 2.52-2.67 (m, 4H), 2.38-2.49 (m, 2H), 1.95-2.07 (m, 2H), 1.55 (app dd, J=6.7, 4.4 Hz, 6H).

Scheme 30

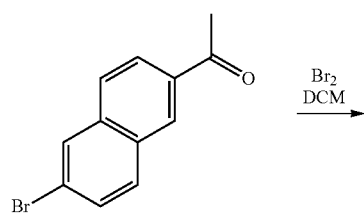

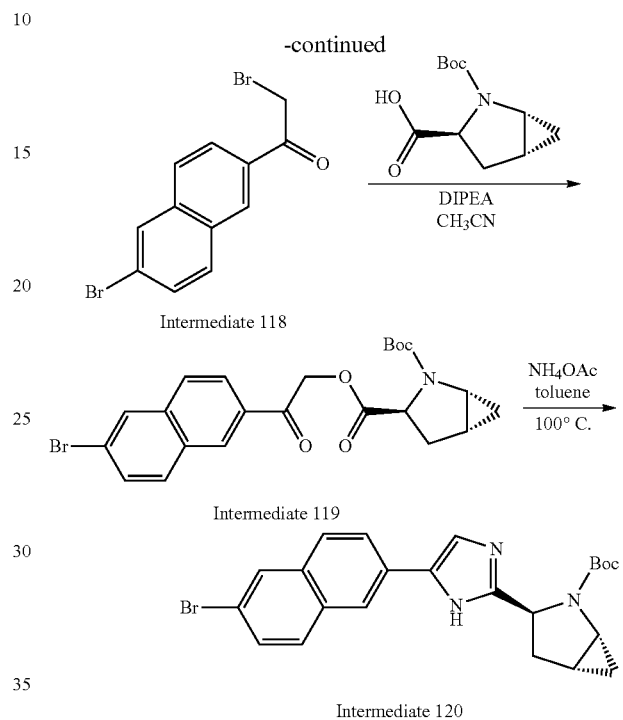

Intermediate 118

2-Bromo-1-(6-bromonaphthalen-2-yl)ethanone

A solution of bromine (0.682 mL, 13.3 mmol) in DCM (20 mL) was added to a solution of 1-(6-bromonaphthalen-2-yl)ethanone (3.30 g, 13.3 mmol) (>90% purity) in DCM (60 mL) and the reaction was stirred at rt overnight. The reaction mixture was concentrated to yield 2-bromo-1-(6-bromonaphthalen-2-yl)ethanone (4.35 g) as an off white solid which was used without further purification. LC-MS retention time 2.177 min; m/z 342.92 (MNa+). LC data was recorded on a Shimadzu LC-10AS liquid chromatograph equipped with a PHENOMENEX® Luna 10u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, chloroform-d) δ ppm 8.49 (s, 1H), 8.03-8.10 (m, 2H), 7.86 (d, J=8.5 Hz, 1H), 7.85 (d, J=8.8 Hz, 1H), 7.67 (dd, J=8.8, 2.0 Hz, 1H), 4.56 (s, 2H).

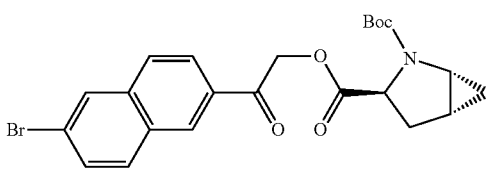 [SMILES: CC(C)(C)OC(=O)N1[C@@H]2C[C@@H]2C[C@H]1C(=O)OCC(=O)c1ccc2cc(Br)ccc2c1]

Intermediate 119

(1R,3S,5R)-3-(2-(6-Bromonaphthalen-2-yl)-2-oxoethyl) 2-tert-butyl 2-azabicyclo[3.1.0]hexane-2,3-dicarboxylate DIPEA (3.47 mL, 19.88 mmol) was added to a stirred slurry of crude 2-bromo-1-(6-bromonaphthalen-2-yl)ethanone (4.35 g, 13.3 mmol) and (1R,3S,5R)-2-(tert-butoxycarbonyl)-2-azabicyclo[3.1.0]hexane-3-carboxylic acid (3.01 g, 13.25 mmol) in acetonitrile (80 mL) and the reaction was stirred at rt overnight. The reaction was concentrated to dryness and purified by BIOTAGE® Horizon (160 g SiO$_2$, 10-20% EtOAc/hexanes). The fractions containing the desired product were allowed to stand for 3 d. Some fractions had crashed large crystals (collected 240 mg, pure desired product by $^1$H NMR). All fractions containing the desired product were collected and concentrated to a yellow solidified foam which was slurried with Et$_2$O (~40 mL). The white solid that formed was collected by filtration and rinsed with Et$_2$O to yield (1R,3S,5R)-3-(2-(6-bromonaphthalen-2-yl)-2-oxoethyl) 2-tert-butyl 2-azabicyclo[3.1.0]hexane-2,3-dicarboxylate (3.24 g). LC-MS retention time 2.760 min; m/z 472, 474.02 (1:1) (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 mHz, MeOD) d ppm 8.61 (br s, 1H), 8.17 (s, 1H), 8.03 (d, J=8.6 Hz, 1H), 8.00 (d, J=8.9 Hz, 1H), 7.94 (d, J=8.9 Hz, 1H), 7.71 (dd, J=8.6, 1.8 Hz, 1H), 5.75-5.66 (m, 1H), 5.61-5.46 (m, 1H), 4.34-4.26 (m, 1H), 3.46 (br s, 1H), 2.69-2.59 (m, 1H), 2.55-2.44 (m, 1H), 1.73 (br s, 1H), 1.54-1.43 (m, 9H), 0.88 (br s, 1H), 0.59-0.53 (m, 1H).

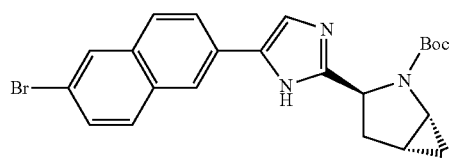 [SMILES: CC(C)(C)OC(=O)N1[C@@H]2C[C@@H]2C[C@H]1c1ncc(-c2ccc3cc(Br)ccc3c2)[nH]1]

Intermediate 120

(1R,3S,5R)-tert-Butyl 3-(5-(6-bromonaphthalen-2-yl)-1H-imidazol-2-yl)-2-azabicyclo[3.1.0]hexane-2-carboxylate (1R,3S,5R)-3-(2-(6-Bromonaphthalen-2-yl)-2-oxoethyl) 2-tert-butyl 2-azabicyclo[3.1.0]hexane-2,3-dicarboxylate (3.46 g, 7.28 mmol) and ammonium acetate (11.2 g, 146 mmol) were dissolved into toluene (100 mL) and stirred. Then the reaction was placed into an oil bath which had been preheated to 100° C. and stirred at that temperature for 12 h. The reaction was allowed to cool to rt, concentrated and partitioned between DCM (~200 mL) and ½ sat. aq. NaHCO$_3$ (~150 mL). The organic layer was washed with brine (~100 mL), dried (MgSO$_4$), filtered and concentrated to a solidified tan foam. This material was purified on a BIOTAGE® Horizon (160 g SiO$_2$, loaded with DCM, 30-50% EtOAc/hexanes) to yield (1R,3S,5R)-tert-butyl 3-(5-(6-bromonaphthalen-2-yl)-1H-imidazol-2-yl)-2-azabicyclo[3.1.0]hexane-2-carboxylate (3.05 g) as a solidified yellow foam. LC-MS retention time 2.238 min; m/z 452.07, 454.02 (1:1) (MH−). LC data was recorded on a Shimadzu LC-10AS liquid chromatograph equipped with a PHENOMENEX® Luna 3u C18 2.0× 30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 5% acetonitrile/95% H$_2$O/10 mM ammonium acetate and Solvent B was 5% H$_2$O/ 95% acetonitrile/10 mM ammonium acetate. MS data was determined using a MICROMASS® Platform for LC in electrospray mode. $^1$H NMR (400 MHz, chloroform-d) δ ppm 8.14 (br. s., 1H), 7.96 (d, J=1.8 Hz, 1H), 7.79 (d, J=9.0 Hz, 1H), 7.72 (d, J=9.8 Hz, 2H), 7.53 (dd, J=8.8, 2.0 Hz, 1H), 7.38 (s, 1H), 4.91 (dd, J=9.0, 5.3 Hz, 1H), 3.25-3.56 (m, 2H), 2.40-2.51 (m, 1H), 1.75-1.85 (m, 1H), 1.38 (br. s., 1H), 0.86-0.93 (m, 1H), 0.47-0.55 (m, 1H).

Scheme 31

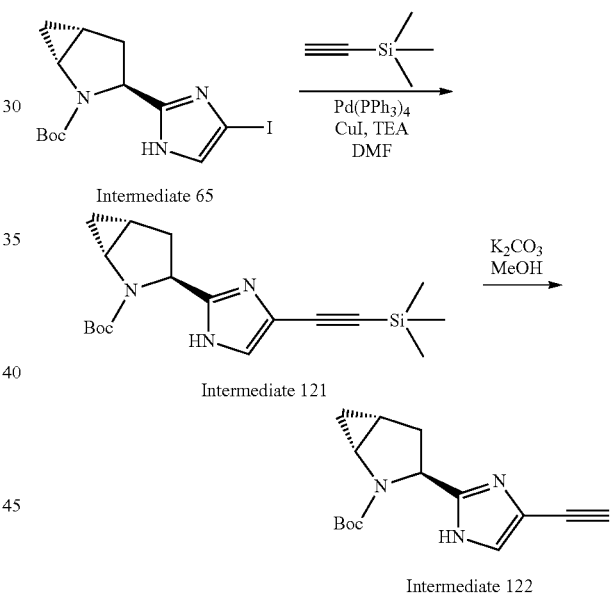

Intermediate 65

Intermediate 121

Intermediate 122

Intermediate 121

(1R,3S,5R)-tert-Butyl 3-(4-((trimethylsilyl)ethynyl)-1H-imidazol-2-yl)-2-azabicyclo[3.1.0]hexane-2-carboxylate Nitrogen was bubbled through a solution of (1R,3S,5R)-tert-butyl 3-(5-iodo-1H-imidazol-2-yl)-2-azabicyclo[3.1.0] hexane-2-carboxylate (1.65 g, 4.40 mmol) and Cu(I)I (168 mg, 0.880 mmol) in triethylamine (3.07 mL, 22.0 mmol) and DMF (40 mL) for 20 min. Then, ethynyltrimethylsilane (2.16 g, 22.0 mmol) and Pd(PPh$_3$)$_4$ (254 mg, 0.220 mmol) were added, the reaction was flushed with nitrogen, sealed and stirred at rt for 24 h. The reaction was concentrated to a brown oil, and purified by BIOTAGE® Horizon (160 g SiO$_2$, 20-40% EtOAc/hexanes) to yield (1R,3S,5R)-tert-butyl 3-(5-((trimethylsilyl)ethynyl)-1H-imidazol-2-yl)-2-azabicyclo [3.1.0]hexane-2-carboxylate (980 mg) as a yellow solid. LC-MS retention time 3.230 min; m/z 346.17 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, chloroform-d) δ ppm 7.18 (s, 1H), 4.77 (dd, J=9.2, 5.1 Hz, 1H), 3.20 (br. s., 1H), 3.14-3.39 (m, 1H), 2.33 (dd, J=13.2, 9.4 Hz, 1H), 1.69-1.78 (m, 1H), 1.34-1.56 (m, 1H), 1.49 (s, 9H), 0.85 (dt, J=8.5, 5.7 Hz, 1H), 0.41-0.47 (m, 1H), 0.22-0.24 (m, 9H).

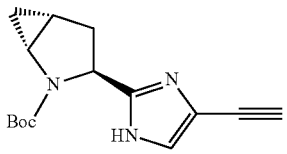 [SMILES: C#Cc1c[nH]c([C@@H]2C[C@H]3C[C@H]3N2C(=O)OC(C)(C)C)n1]

Intermediate 122

(1R,3S,5R)-tert-Butyl 3-(4-ethynyl-1H-imidazol-2-yl)-2-azabicyclo[3.1.0]hexane-2-carboxylate Potassium carbonate (194 mg, 1.40 mmol) was added to a solution of (1R,3S,5R)-tert-butyl 3-(5-((trimethylsilyl)ethynyl)-1H-imidazol-2-yl)-2-azabicyclo[3.1.0]hexane-2-carboxylate (970 mg, 2.81 mmol) in MeOH (30 mL) and the reaction was stirred under nitrogen and then heated at 50° C. (bath temp) for 4 h. The reaction was concentrated to ~5 mL of volume, diluted with DCM (~40 mL) and washed with ½ sat brine (~20 mL). The organics were dried ($MgSO_4$) filtered and concentrated to a tan solid. This material was purified by BIOTAGE® Horizon (40 g $SiO_2$, loaded with DCM, 35-45% EtOAc/hexanes) to yield (1R,3S,5R)-tert-butyl 3-(5-ethynyl-1H-imidazol-2-yl)-2-azabicyclo[3.1.0]hexane-2-carboxylate (747 mg) as a light yellow solid. LC-MS retention time 2.866 min; m/z 272.12 (MH−). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, MeOD) δ ppm 7.18 (br. s., 1H), 4.59 (br. s., 1H), 3.36-3.64 (m, 2H), 2.46 (dd, J=13.2, 8.9 Hz, 1H), 2.18-2.31 (m, 1H), 1.64-1.74 (m, 1H), 1.18-1.45 (m, 9H), 0.83 (dt, J=8.5, 5.8 Hz, 1H), 0.56 (br. s., 1H).

Scheme 32

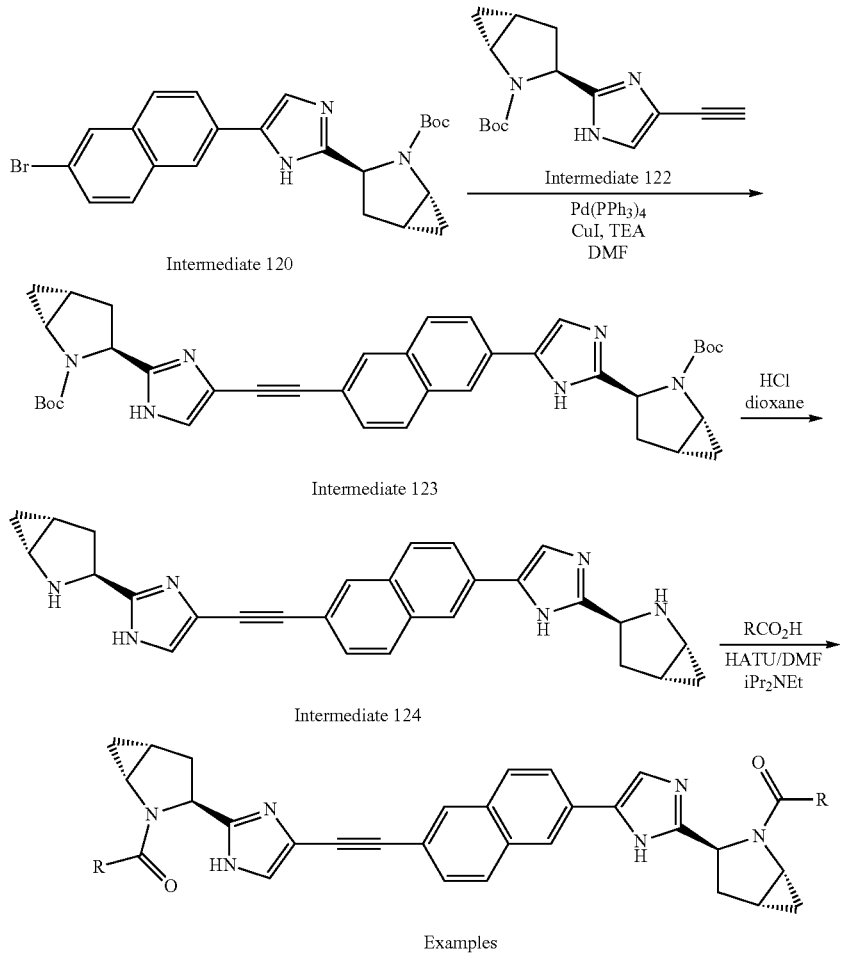

Examples

Intermediate 123 tert-Butyl (1R,3S,5R)-3-(4-(6-((2-((1R,3S,5R)-2-(tert-butoxycarbonyl)-2-azabicyclo[3.1.0]hex-3-yl)-1H-imidazol-4-yl)ethynyl)-2-naphthyl)-1H-imidazol-2-yl)-2-azabicyclo[3.1.0]hexane-2-carboxylate Nitrogen was bubbled through a solution of (1R,3S,5R)-tert-butyl 3-(5-(6-bromonaphthalen-2-yl)-1H-imidazol-2-yl)-2-azabicyclo[3.1.0]hexane-2-carboxylate (400 mg, 0.880 mmol), (1R,3S,5R)-tert-butyl 3-(5-ethynyl-1H-imidazol-2-yl)-2-azabicyclo[3.1.0]hexane-2-carboxylate (313 mg, 1.14 mmol) and Cu(I)I (8.4 mg, 0.044 mmol) in triethylamine (0.37 mL, 2.6 mmol) and DMF (8 mL) for 10 min. Then Pd(PPh₃)4 (50.9 mg, 0.044 mmol) was added, nitrogen was bubbled through the reaction mixture for 1 min, and then the flask was sealed and heated at 50° C. for 16 h. The reaction was concentrated to under high vacuum) and the residual solids were triturated with EtOAc (~5 mL) and collected by filtration (rinsing with EtOAc and hexanes) to yield tert-butyl (1R,3S,5R)-3-(4-(6-((2-((1R,3S,5R)-2-(tert-butoxycarbonyl)-2-azabicyclo[3.1.0]hex-3-yl)-1H-imidazol-4-yl)ethynyl)-2-naphthyl)-1H-imidazol-2-yl)-2-azabicyclo[3.1.0]hexane-2-carboxylate (595 mg) as a light yellow solid. The material was used without further purification. LC-MS retention time 3.140 min; m/z 647.35 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode.

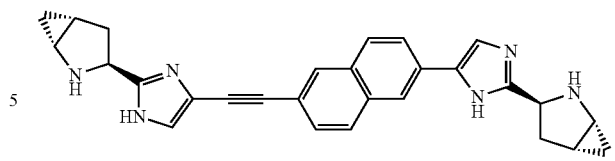

Intermediate 124

(1R,3S,5R)-3-(5-(6-((2-((1R,3S,5R)-2-Azabicyclo[3.1.0]hexan-3-yl)-1H-imidazol-4-yl)ethynyl)naphthalen-2-yl)-1H-imidazol-2-yl)-2-azabicyclo[3.1.0]hexane 4M HCl (1.546 mL, 6.18 mmol) in dioxane was added to a solution of tert-butyl (1R,3S,5R)-3-(4-(6-((2-((1R,3S,5R)-2-(tert-butoxycarbonyl)-2-azabicyclo[3.1.0]hex-3-yl)-1H-imidazol-4-yl)ethynyl)-2-naphthyl)-1H-imidazol-2-yl)-2-azabicyclo[3.1.0]hexane-2-carboxylate (200 mg, 0.309 mmol) in dioxane (3 mL) and the reaction was vigorously stirred for 4 h. The reaction slurry was concentrated to yield an HCl salt of (1R,3S,5R)-3-(5-(6-((2-((1R,3S,5R)-2-azabicyclo[3.1.0]hexan-3-yl)-1H-imidazol-4-yl)ethynyl)naphthalen-2-yl)-1H-imidazol-2-yl)-2-azabicyclo[3.1.0]hexane (177 mg) as a yellow solid. LC-MS retention time 3.403 min; m/z 893.29 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode. ¹H NMR (400 MHz, MeOD) d ppm 8.42 (s, 1H), 8.16 (s, 2H), 8.05 (d, J=8.8 Hz, 1H), 8.03 (d, J=8.8 Hz, 1H), 7.97 (dd, J=8.8, 1.8 Hz, 1H), 7.74 (s, 1H), 7.66 (dd, J=8.5, 1.5 Hz, 1H), 5.01 (dd, J=10.8, 7.8 Hz, 1H), 4.78 (dd, J=10.8, 8.3 Hz, 1H), 3.57-3.77 (m, 2H), 3.50-3.56 (m, 1H), 2.61-2.92 (m, 4H), 2.13-2.21 (m, 1H), 2.06-2.13 (m, 1H), 1.25 (ddd, J=7.8, 5.0, 2.5 Hz, 1H), 0.99-1.14 (m, 2H).

Scheme 33

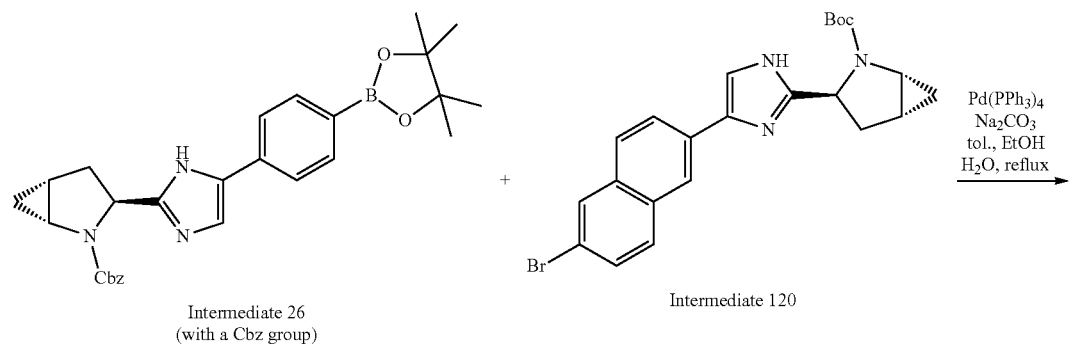

Intermediate 26 (with a Cbz group) + Intermediate 120

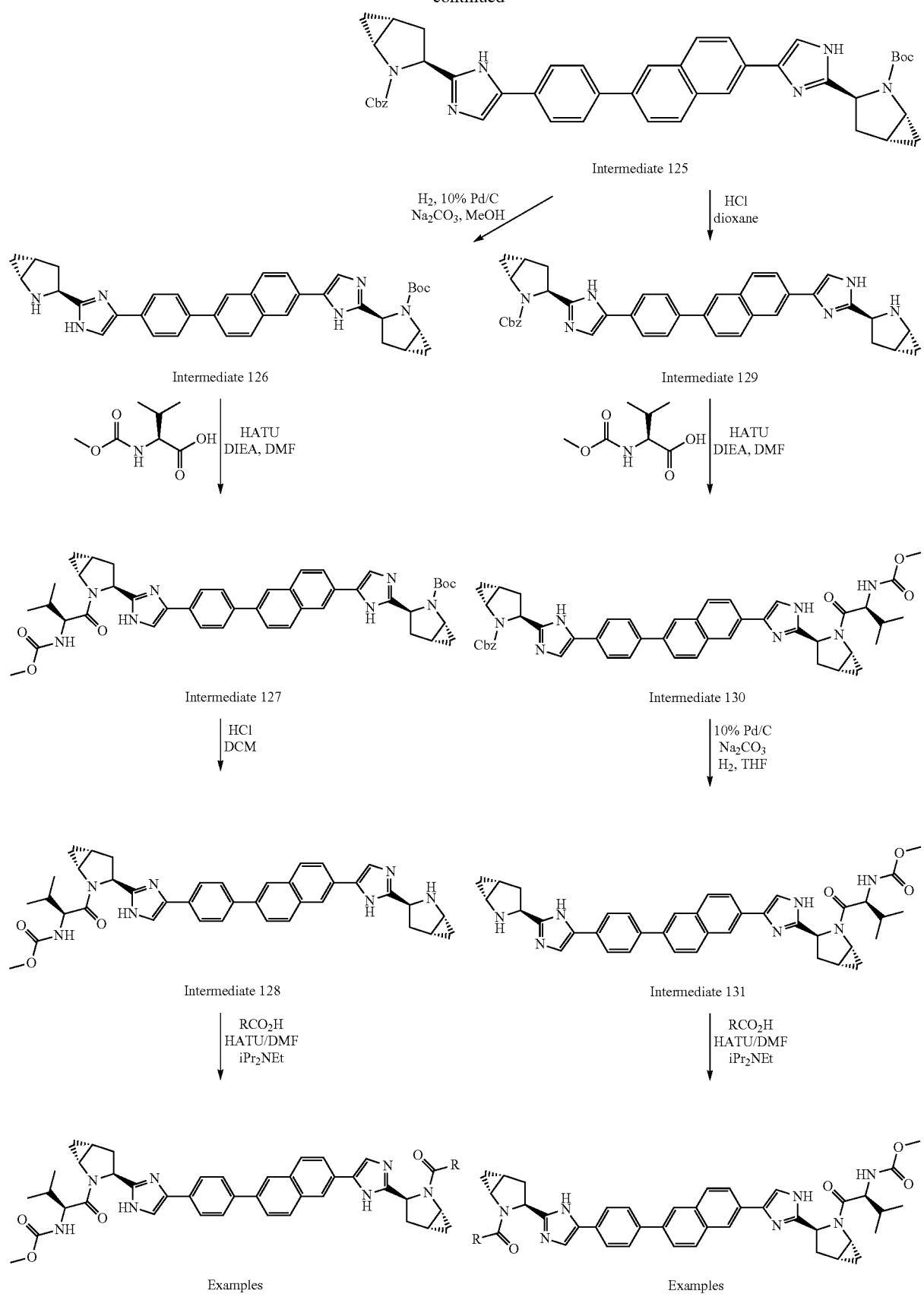

Intermediate 125

(1R,3S,5R)-Benzyl 3-(5-(4-(6-(2-((1R,3S,5R)-2-(tert-butoxycarbonyl)-2-azabicyclo[3.1.0]hexan-3-yl)-1H-imidazol-4-yl)naphthalen-2-yl)phenyl)-1H-imidazol-2-yl)-2-azabicyclo[3.1.0]hexane-2-carboxylate Nitrogen was bubbled through a biphasic solution of (1R,3S,5R)-benzyl 3-(5-(4-(4,4,5,5-tetramethyl-1,3,2-dioxaborolan-2-yl)phenyl)-1H-imidazol-2-yl)-2-azabicyclo[3.1.0]hexane-2-carboxylate (prepared in an analogous manner to Intermediate 26) (2.0 g, 4.12 mmol), (1R,3S,5R)-tert-butyl 3-(5-(6-bromonaphthalen-2-yl)-1H-imidazol-2-yl)-2-azabicyclo[3.1.0]hexane-2-carboxylate (1.872 g, 4.12 mmol) and Na$_2$CO$_3$ (2.184 g, 20.60 mmol) in a mixture of EtOH (16.0 mL), toluene (16.0 mL) and water (16.0 mL) for 15 min. Then, Pd(PPh$_3$)$_4$ (0.143 g, 0.124 mmol) was added, the reaction was flushed with nitrogen, sealed and then heated at 95° C. for 10 h. The crude slurry was diluted with water (~20 mL) and extracted with EtOAc (~100 mL). The organic layer was washed with brine, dried (MgSO$_4$), filtered and concentrated to a yellow foam. This material was dissolved into a minimal amount of DCM, and purified on a BIOTAGE® Horizon (110 g of SiO$_2$, 70-85% EtOAc/hexanes) to yield (1R,3S,5R)-benzyl 3-(5-(4-(6-(2-((1R,3S,5R)-2-(tert-butoxycarbonyl)-2-azabicyclo[3.1.0]hexan-3-yl)-1H-imidazol-5-yl)naphthalen-2-yl)phenyl)-1H-imidazol-2-yl)-2-azabicyclo[3.1.0]hexane-2-carboxylate (2.257 g) as a light yellow solidified foam. LC-MS retention time 4.158 min; m/z 733.17 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, MeOD) δ ppm 8.17 (br. s., 1H), 8.07 (s, 1H), 7.86-7.94 (m, 2H), 7.71-7.86 (m, 6H), 7.44 (s, 1H), 7.32 (s, 1H), 7.20 (br. s., 5H), 5.14 (d, J=12.3 Hz, 1H), 4.91-5.05 (m, 1H), 4.63-4.77 (m, 1H), 3.55-3.69 (m, 2H), 3.29-3.34 (m, 1H), 2.46-2.59 (m, 2H), 2.29-2.44 (m, 2H), 1.66-1.80 (m, 2H), 1.30 (br. s., 9H), 0.80-0.93 (m, 2H), 0.61 (br. s., 2H).

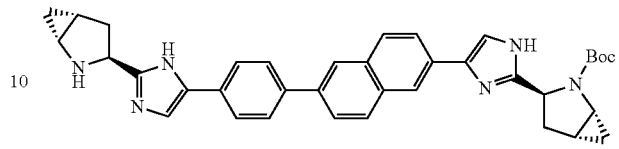

Intermediate 126

(1R,3S,5R)-tert-Butyl 3-(5-(6-(4-(2-((1R,3S,5R)-2-azabicyclo[3.1.0]hexan-3-yl)-1H-imidazol-4-yl)phenyl)naphthalen-2-yl)-1H-imidazol-2-yl)-2-azabicyclo[3.1.0]hexane-2-carboxylate A reaction mixture of (1R,5R)-benzyl 3-(5-(4-(6-(2-((1R,3S,5R)-2-(tert-butoxycarbonyl)-2-azabicyclo[3.1.0]hexan-3-yl)-1H-imidazol-5-yl)naphthalen-2-yl)phenyl)-1H-imidazol-2-yl)-2-azabicyclo[3.1.0]hexane-2-carboxylate (0.305 g, 0.416 mmol) and NaHCO$_2$ (0.070 g, 0.832 mmol) in MeOH (15 mL) was charged with 10% Pd/C (0.022 g, 0.021 mmol). The resulting suspension was vacuum flushed with N$_2$ (3×) and placed under 1 atm of H$_2$ (balloon) for 3 h at room temperature. The mixture was then filtered though a pad of diatomaceous earth (CELITE®) and concentrated under vacuum. An off-white solid corresponding to (1R,3S,5R)-tert-butyl 3-(5-(6-(4-(2-((1R,5R)-2-azabicyclo[3.1.0]hexan-3-yl)-1H-imidazol-5-yl)phenyl)naphthalen-2-yl)-1H-imidazol-2-yl)-2-azabicyclo[3.1.0]hexane-2-carboxylate (0.235 g) was recovered and used without further purification. LC-MS [M+H]$^+$=599; Rt=1.96 min is product. Column Luna 3u C18 2×50 mm; start % B: 0, final % B: 100 Solvent A: 10% Acetonitrile/90% H$_2$O+1% TFA; Solvent B: 90% Acetonitrile/10% H$_2$O+1% TFA; flow rate 4 ml/min. Run time: 5 min. Purity=94%. $^1$H NMR (500 MHz, DMSO-d$_6$) δ ppm 12.00 (2H, br. s.), 8.11-8.32 (3H, m), 7.88-8.02 (5H, m), 7.72-7.88 (9H, m), 7.63 (4H, br. s.), 4.64 (2H, br. s.), 4.42 (1H, t, J=7.93 Hz), 3.97-4.18 (1H, m), 3.45 (1H, br. s.), 3.17 (3H, s), 2.96 (1H, dd, J=13.43, 6.71 Hz), 2.08-2.43 (6H, m), 1.66 (2H, br. s.), 1.07-1.50 (20H, m), 0.81-0.89 (3H, m), 0.77 (1H, br. s.), 0.45-0.61 (3H, m), 0.30 (1H, br. s.).

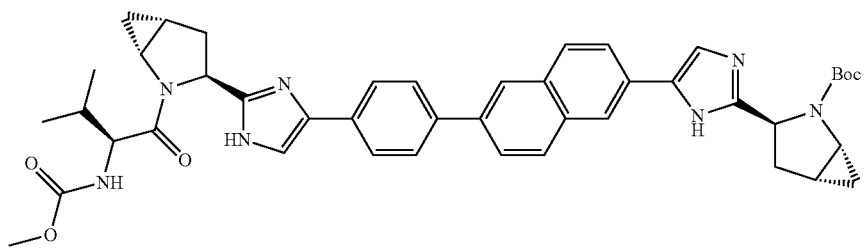 [SMILES: COC(=O)N[C@H](C(=O)N1[C@@H]2C[C@@H]2C[C@H]1c1nc(-c2ccc(-c3ccc4cc(-c5cnc([C@@H]6C[C@H]7C[C@H]7N6C(=O)OC(C)(C)C)[nH]5)ccc4c3)cc2)c[nH]1)C(C)C]

Intermediate 127

(1R,3S,5R)-tert-Butyl 3-(5-(6-(4-(2-((1R,3S,5R)-2-((S)-2-(methoxycarbonylamino)-3-methylbutanoyl)-2-azabicyclo[3.1.0]hexan-3-yl)-1H-imidazol-4-yl)phenyl)naphthalen-2-yl)-1H-imidazol-2-yl)-2-azabicyclo[3.1.0]hexane-2-carboxylate HATU (0.164 g, 0.432 mmol) was added to a solution of (1R,3S,5R)-tert-butyl 3-(5-(6-(4-(2-((1R,3S,5R)-2-azabicyclo[3.1.0]hexan-3-yl)-1H-imidazol-5-yl)phenyl)naphthalen-2-yl)-1H-imidazol-2-yl)-2-azabicyclo[3.1.0]hexane-2-carboxylate (0.235 g, 0.392 mmol), (S)-2-(methoxycarbonylamino)-3-methylbutanoic acid (0.069 g, 0.39 mmol) and DIEA (0.137 mL, 0.785 mmol) in DMF (10 mL) and the resulting yellow solution was stirred at rt overnight. The solvent was removed under reduced pressure and the residue was dissolved into methanol, filtered and purified by preparative HPLC (Solvent A: 10% MeOH/90% water/0.1% TFA; Solvent B: 90% MeOH/10% water/0.1% TFA; Column: Sunfire Prep MS C18 30×100 mm 5u; Wavelength: 220 nM; Flow rate: 30 ml/min; Gradient: 0% B to 100% B over 30 min. with a 2 min hold time) to yield a TFA salt of (1R,3S,5R)-tert-butyl 3-(5-(6-(4-(2-((1R,3S,5R)-2-((S)-2-(methoxycarbonylamino)-3-methylbutanoyl)-2-azabicyclo[3.1.0]hexan-3-yl)-1H-imidazol-5-yl)phenyl)naphthalen-2-yl)-1H-imidazol-2-yl)-2-azabicyclo[3.1.0]hexane-2-carboxylate (0.10 g) as a white solid. LC-MS [M+H]$^+$=756; Rt=2.14 min is product. Column Luna 3u C18 2×50 mm; start % B: 0, final % B: 100 Solvent A: 10% Acetonitrile/90% $H_2O$+1% TFA; Solvent B: 90% Acetonitrile/10% $H_2O$+1% TFA; flow rate 4 ml/min. Run time: 5 min. Purity=96%. $^1$H NMR (500 MHz, DMSO-$d_6$) δ ppm 14.60 (1H, br. s.), 8.39 (3H, d, J=4.88 Hz), 8.09-8.24 (4H, m), 7.99-8.08 (6H, m), 7.89-7.98 (5H, m), 7.27 (1H, d, J=8.55 Hz), 4.98-5.07 (1H, m), 4.84 (1H, br. s.), 4.42 (1H, t, J=7.32 Hz), 3.74 (1H, br. s.), 3.55 (4H, s), 2.55 (2H, d, J=9.77 Hz), 2.32-2.44 (3H, m), 2.13 (1H, dq, J=13.43, 6.71 Hz), 1.94 (1H, dt, J=13.28, 6.79 Hz), 1.75 (1H, dt, J=12.89, 6.22 Hz), 1.40 (4H, d, J=10.07 Hz), 1.11-1.30 (10H, m), 0.90-1.00 (5H, m), 0.73-0.88 (10H, m).

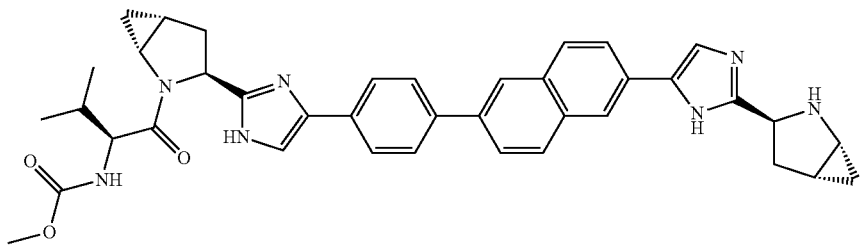 [SMILES: COC(=O)N[C@H](C(=O)N1[C@@H]2C[C@@H]2C[C@H]1c1nc(-c2ccc(-c3ccc4cc(-c5cnc([C@@H]6C[C@H]7C[C@H]7N6)[nH]5)ccc4c3)cc2)c[nH]1)C(C)C]

Intermediate 128

Methyl (S)-1-((1R,3S,5R)-3-(4-(4-(6-(2-((1R,3S,5R)-2-azabicyclo[3.1.0]hexan-3-yl)-1H-imidazol-5-yl)naphthalen-2-yl)phenyl)-1H-imidazol-2-yl)-2-azabicyclo[3.1.0]hexan-2-yl)-3-methyl-1-oxobutan-2-ylcarbamate 4N HCl in dioxane (2 mL, 8.00 mmol) was added to a stirred solution of a TFA salt of (1R,3S,5R)-tert-butyl 3-(5-(6-(4-(2-((1R,3S,5R)-2-((S)-2-(methoxycarbonylamino)-3-methylbutanoyl)-2-azabicyclo[3.1.0]hexan-3-yl)-1H-imidazol-5-yl)phenyl)naphthalen-2-yl)-1H-imidazol-2-yl)-2-azabicyclo[3.1.0]hexane-2-carboxylate (0.10 g, 0.12 mmol) in $CH_2Cl_2$ (20 mL) and the resulting yellow suspension was stirred at rt for 2 h. The reaction was concentrated under vacuum and the resulting residue was triturated with $Et_2O$ to yield an HCl salt of methyl (S)-1-((1R,3S,5R)-3-(5-(4-(6-(2-((1R,3S,5R)-2-azabicyclo[3.1.0]hexan-3-yl)-1H-imidazol-5-yl)naphthalen-2-yl)phenyl)-1H-imidazol-2-yl)-2-azabicyclo[3.1.0]hexan-2-yl)-3-methyl-1-oxobutan-2-ylcarbamate HCl (47 mg) as a yellow solid. LC-MS [M+H]$^+$=656; Rt=1.73 min is product. Column Luna 3u C18 2×50 mm; start % B: 0, final % B: 100 Solvent A: 10% Acetonitrile/90% $H_2O$+1% TFA; Solvent B: 90% Acetonitrile/10% $H_2O$+1% TFA; flow rate 4 ml/min. Run time: 5 min. Purity=95%. $^1$H NMR (500 MHz, DMSO-$d_6$) δ ppm 14.47-15.18 (2H, m), 9.77-10.61 (2H, m), 8.30-8.42 (2H, m), 8.17 (1H, s), 7.93-8.10 (10H, m), 7.27 (1H, d, J=8.55 Hz), 5.08 (1H, t, J=7.93 Hz), 4.71 (1H, t, J=8.39 Hz), 4.40-4.46 (1H, m), 3.77 (1H, br. s.), 3.52-3.58 (3H, m), 3.38-3.44 (1H, m), 2.52-2.61 (3H, m), 2.39 (1H, dt, J=13.58, 6.64 Hz), 2.14-2.21 (1H, m), 1.94 (2H, dd, J=8.24, 4.88 Hz), 1.15 (1H, d, J=5.80 Hz), 0.93 (4H, d, J=6.71 Hz), 0.75-0.89 (6H, m).

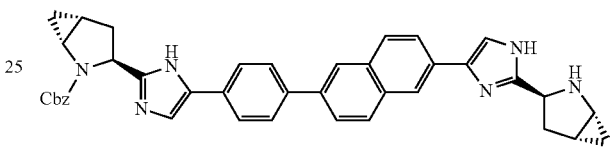

Intermediate 129

(1R,3S,5R)-Benzyl 3-(5-(4-(6-(2-((1R,3S,5R)-2-azabicyclo[3.1.0]hexan-3-yl)-1H-imidazol-4-yl)naphthalen-2-yl)phenyl)-1H-imidazol-2-yl)-2-azabicyclo[3.1.0]hexane-2-carboxylate A solution of 4.0 M HCl (1.167 mL, 4.67 mmol) in dioxane was added to a stirred solution of (1R,3S,5R)-benzyl 3-(5-(4-(6-(2-((1R,3S,5R)-2-(tert-butoxycarbonyl)-2-azabicyclo[3.1.0]hexan-3-yl)-1H-imidazol-5-yl)naphthalen-2-yl)phenyl)-1H-imidazol-2-yl)-2-azabicyclo[3.1.0]hexane-2-carboxylate (228 mg, 0.311 mmol) in dioxane (3 mL) and the reaction was stirred vigorously at rt for 3 h. The reaction was concentrated to yield an HCl salt of (1R,3S,5R)-benzyl 3-(5-(4-(6-(2-((1R,3S,5R)-2-azabicyclo[3.1.0]hex an-3-yl)-1H-imidazol-5-yl)naphthalen-2-yl)phenyl)-1H-imidazol-2-yl)-2-azabicyclo[3.1.0]hexane-2-carboxylate (233 mg) as a yellow solid. LC-MS retention time 3.988 min; m/z 633.18 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 1 mL/min, a gradient of 100%

Solvent A/0% Solvent B to 0% Solvent A/100% Solvent B, a gradient time of 4 min, a hold time of 1 min, and an analysis time of 5 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode. ¹H NMR (400 MHz, MeOD) δ ppm 8.44 (s, 1H), 8.28 (s, 1H), 8.08-8.18 (m, 3H), 7.92-8.02 (m, 4H), 7.84 (br. s., 3H), 7.31 (br. s., 5H), 5.21 (d, J=12.1, 1 H), 4.95-5.05 (m, 2H), 4.80-4.91 (m, 1H), 3.70-3.77 (m, 1H), 3.59-3.67 (m, 1H), 2.77-2.93 (m, 2H), 2.74 (dd, J=13.4, 9.2 Hz, 1H), 2.46 (dt, J=13.5, 6.7 Hz, 1H), 2.12-2.22 (m, 1H), 1.83-1.96 (m, 1H), 1.27-1.35 (m, 1H), 1.09 (q, J=7.9 Hz, 1H), 0.95 (ddd, J=8.7, 5.9, 5.8 Hz, 1H), 0.75-0.83 (m, 1H).

[3.1.0]hexane-2-carboxylate (200 mg) as a yellow solid. LC-MS retention time 4.053 min; m/z 790.25 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray

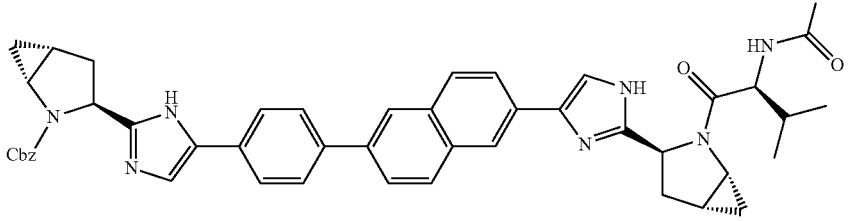

Intermediate 130

(1R,3S,5R)-Benzyl 3-(5-(4-(6-(2-((1R,3S,5R)-2-((S)-2-(methoxycarbonylamino)-3-methylbutanoyl)-2-azabicyclo[3.1.0]hexan-3-yl)-1H-imidazol-4-yl)naphthalen-2-yl)phenyl)-1H-imidazol-2-yl)-2-azabicyclo[3.1.0]hexane-2-carboxylate HATU (203 mg, 0.533 mmol) was added to a stirred solution of (1R,5R)-benzyl 3-(5-(4-(6-(2-((1R,3S,5R)-2-azabicyclo[3.1.0]hexan-3-yl)-1H-imidazol-5-yl)naphthalen-2-yl) phenyl)-1H-imidazol-2-yl)-2-azabicyclo[3.1.0]hexane-2-carboxylate (225 mg) and (S)-2-(methoxycarbonylamino)-3-methylbutanoic acid (93 mg, 0.53 mmol) in DMF (3 mL) and DIPEA (0.37 mL, 2.1 mmol) and the reaction was stirred at rt for 3 hr. The crude reaction was concentrated under a stream of nitrogen and the residue was dissolved into MeOH and purified by preparative HPLC (MeOH/water with an ammonium acetate buffer) to yield (1R,5R)-benzyl 3-(5-(4-(6-(2-((1R,3S,5R)-2-((S)-2-(methoxycarbonylamino)-3-methylbutanoyl)-2-azabicyclo[3.1.0]hexan-3-yl)-1H-imidazol-5-yl)naphthalen-2-yl)phenyl)-1H-imidazol-2-yl)-2-azabicyclo mode. ¹H NMR (400 MHz, MeOD) δ ppm 8.28 (s, 2H), 8.13 (d, J=8.8 Hz, 1H), 8.08 (d, J=8.8 Hz, 1H), 7.94-8.02 (m, 4H), 7.76-7.92 (m, 3H), 7.85 (dd, J=8.7, 1.6 Hz, 1H), 7.29 (br. s., 5H), 5.21 (d, J=12.1 Hz 1H), 5.16 (dd, J=9.2, 6.9 Hz, 1H), 4.97 (t, J=8.2 Hz, 1H), 4.57 (d, J=6.5 Hz, 1H), 3.78-3.87 (m, 1H), 3.68 (s, 3H), 3.64-3.77 (m, 2H), 2.66-2.77 (m, 2H), 2.40-2.56 (m, 2H), 2.14-2.25 (m, 1H), 2.05-2.14 (m, 1H), 1.87 (d, J=6.5 Hz, 1H), 1.06-1.16 (m, 1H), 1.02 (d, J=6.8 Hz, 3H), 0.94 (d, J=6.8 Hz, 3H), 0.87-0.99 (m, 2H), 0.74-0.82 (m, 1H).

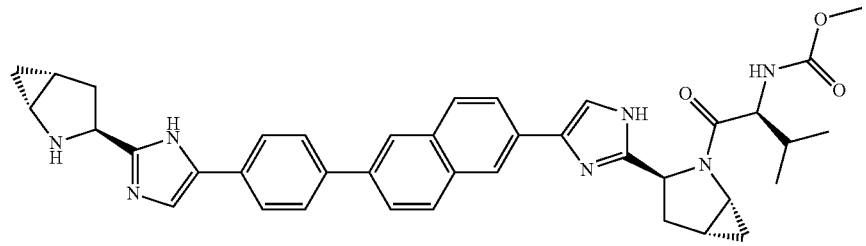 [SMILES: COC(=O)N[C@H](C(=O)N1[C@@H]2C[C@@H]2C[C@H]1c1nc(-c2ccc3cc(-c4ccc(-c5cnc([C@@H]6C[C@H]7C[C@H]7N6)[nH]5)cc4)ccc3c2)c[nH]1)C(C)C]

Intermediate 131

Methyl (S)-1-((1R,3S,5R)-3-(4-(6-(4-(2-((1R,3S,5R)-2-azabicyclo[3.1.0]hexan-3-yl)-1H-imidazol-5-yl)phenyl)naphthalen-2-yl)-1H-imidazol-2-yl)-2-azabicyclo[3.1.0]hexan-2-yl)-3-methyl-1-oxobutan-2-ylcarbamate 10% Palladium on carbon (100 mg, 0.094 mmol) was added to a solution of (1R,5R)-benzyl 3-(5-(4-(6-(2-((1R,3S,5R)-2-((S)-2-(methoxycarbonylamino)-3-methylbutanoyl)-

2-azabicyclo[3.1.0]hexan-3-yl)-1H-imidazol-5-yl)naphthalen-2-yl)phenyl)-1H-imidazol-2-yl)-2-azabicyclo[3.1.0]hexane-2-carboxylate (190 mg, 0.241 mmol) and Na$_2$CO$_3$ (50 mg, 0.472 mmol) in THF (10 mL) and the reaction mixture was vacuum flushed with nitrogen (3×) and then with hydrogen (5×). The reaction mixture was allowed to stir under a balloon of hydrogen for 2 h, filtered through diatomaceous earth (CELITE®) and concentrated. The residue was resubmitted to the reaction conditions (50 mg of 10% Pd/C used) overnight at rt before being filtered through diatomaceous earth (CELITE®) and concentrated. The residue was dissolved into DMSO/MeOH, filtered and purified by preparative HPLC (MeOH/H$_2$O w/0.1% TFA) to yield a TFA salt of methyl (2S)-1-((1R,3S,5R)-3-(5-(6-(4-(2-((1R,5R)-2-azabicyclo[3.1.0]hexan-3-yl)-1H-imidazol-5-yl)phenyl)naphthalen-2-yl)-1H-imidazol-2-yl)-2-azabicyclo[3.1.0]hexan-2-yl)-3-methyl-1-oxobutan-2-ylcarbamate (55 mg). LC-MS retention time 2.147 min; m/z 656.21 (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (500 MHz, MeOD) δ ppm 8.28 (s, 1H), 8.24 (s, 1H), 8.12 (d, J=8.9 Hz, 1H), 8.07 (d, J=8.9 Hz, 1H), 7.91-8.01 (m, 4H), 7.83-7.90 (m, 3H), 7.66 (s, 1H), 5.17 (dd, J=9.2, 7.0 Hz, 1H), 4.67 (dd, J=10.7, 7.6 Hz, 1H), 4.58 (d, J=6.7 Hz, 1H), 3.82-3.87 (m, 1H), 3.69 (s, 3H), 3.44-3.49 (m, 1H), 2.59-2.77 (m, 3H), 2.48-2.56 (m, 1H), 2.16-2.25 (m, 1H), 2.03-2.15 (m, 2H), 1.21 (ddd, J=7.5, 4.9, 2.6 Hz, 1H), 1.09-1.15 (m, 1H), 1.04 (d, J=6.7 Hz, 3H), 0.98-1.03 (m, 1H), 0.95 (d, J=6.7 Hz, 3H), 0.89-0.95 (m, 1H).

Scheme 34

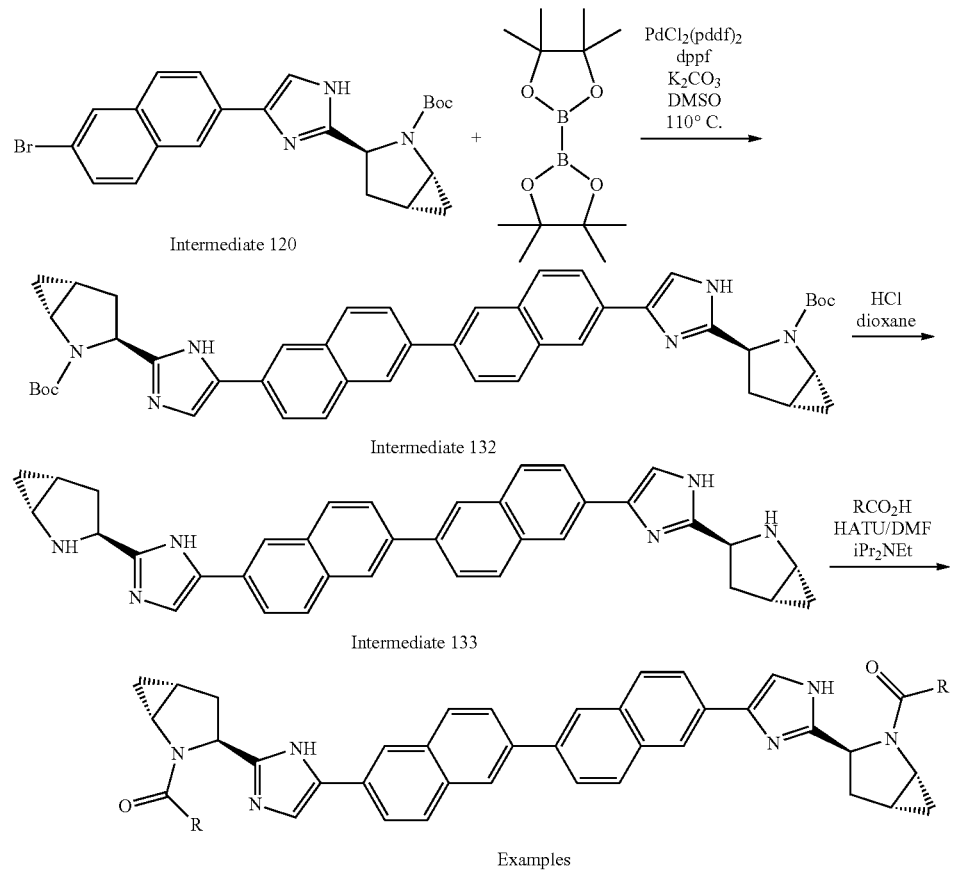

Examples

Intermediate 132

(1R,1'R,3S,3'S,5R,5'R)-tert-Butyl 3,3'-(4,4'-(2,2'-binaphthyl-6,6'-diyl)bis(1H-imidazole-4,2-diyl))bis(2-azabicyclo[3.1.0]hexane-2-carboxylate)

Nitrogen was bubbled a solution of (1R,3S,5R)-tert-butyl 3-(4-(6-bromonaphthalen-2-yl)-1H-imidazol-2-yl)-2-azabicyclo[3.1.0]hexane-2-carboxylate (250 mg, 0.550 mmol), 4,4,4',4',5,5,5',5'-octamethyl-2,2'-bi(1,3,2-dioxaborolane) (69.9 mg, 0.275 mmol), 1,1'-bis-(diphenylphosphino)-ferrocene (15.42 mg, 0.028 mmol) and K$_2$CO$_3$ (228 mg, 1.651 mmol) in DMSO (12 mL) for 10 min. Then 1,1'-Bis-(diphenylphosphino)-ferrocene) palladium dichloride (22.63 mg, 0.028 mmol) was added to the reaction mixture and the nitrogen bubbling was continued for 10 min before the reaction was sealed and then heated at 110° C. for 20 h. The reaction was partitioned between water (60 mL) and DCM (60 mL) and the organics were separated, dried (MgSO$_4$), filtered and concentrated. The crude residue was purified by BIOTAGE® Horizon (40 g SiO$_2$, 70-100% EtOAc/hexanes) to yield (1R,1'R,3S,3'S,5R,5'R)-tert-butyl 3,3'-(4,4'-(2,2'-binaphthyl-6,6'- diyl)bis(1H-imidazole-4,2-diyl))bis(2-azabicyclo[3.1.0]hexane-2-carboxylate) (67 mg) as a yellow solid. LC-MS retention time 4.348 min; m/z 749.29 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, MeOD) δ ppm 8.22 (s, 4H), 7.91-8.02 (m, 6H), 7.87 (d, J=8.5 Hz, 2H), 7.48 (br. s., 2H), 4.68-4.77 (m, 2H), 3.61 (br. s., 2H), 2.56 (dd, J=13.1, 8.8 Hz, 2H), 2.33-2.43 (m, 2H), 1.70-1.79 (m, 2H), 1.31 (br. s., 18H), 0.87 (dt, J=8.5, 5.8 Hz, 2H), 0.63 (br. s., 2H).

4'-(2,2'-binaphthyl-6,6'-diyl)bis(1H-imidazole-4,2-diyl))bis(2-azabicyclo[3.1.0]hexane-2-carboxylate) (62 mg, 0.083 mmol) in dioxane (2 mL) and the reaction slurry was stirred vigorously for 3 h. The slurry was diluted with MeOH and concentrated to dryness to yield an HCl salt of 6,6'-bis(2-((1R,3S,5R)-2-azabicyclo[3.1.0]hexan-3-yl)-1H-imidazol-4-yl)-2,2'-binaphthyl (56 mg) as a light yellow solid. LC-MS retention time 3.971 min; m/z 547.25 (MH−). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% H$_2$O/10 mM ammonium acetate and Solvent B was 5% H$_2$O/95% MeOH/10 mM ammonium acetate. MS data was determined using a

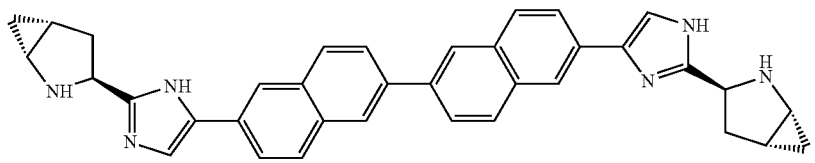 [SMILES: c1cc2cc(-c3c[nH]c([C@@H]4C[C@H]5C[C@H]5N4)n3)ccc2cc1-c1ccc2cc(-c3cnc([C@@H]4C[C@H]5C[C@H]5N4)[nH]3)ccc2c1]

Intermediate 133

6,6'-Bis(2-((1R,3S,5R)-2-azabicyclo[3.1.0]hexan-3-yl)-1H-imidazol-4-yl)-2,2'-binaphthyl 4.0M HCl (1.0 mL, 4.00 mmol) in dioxane was added to a stirred solution of (1R,1'R,3S,3'S,5R,5'R)-tert-butyl 3,3'-(4, MICROMASS® Platform for LC in electrospray mode. $^1$H NMR (500 MHz, MeOD) δ ppm 8.44 (s, 2H), 8.38 (s, 2H), 8.12-8.19 (m, 6H), 8.09 (dd, 2H), 7.97 (dd, J=8.5, 1.5 Hz, 2H), 4.97 (dd, J=10.5, 8.1 Hz, 2H), 3.62-3.66 (m, 2H), 2.79-2.89 (m, 4H), 2.15-2.22 (m, 2H), 1.29-1.34 (m, 2H), 1.11 (q, J=7.9 Hz, 2H).

Scheme 35

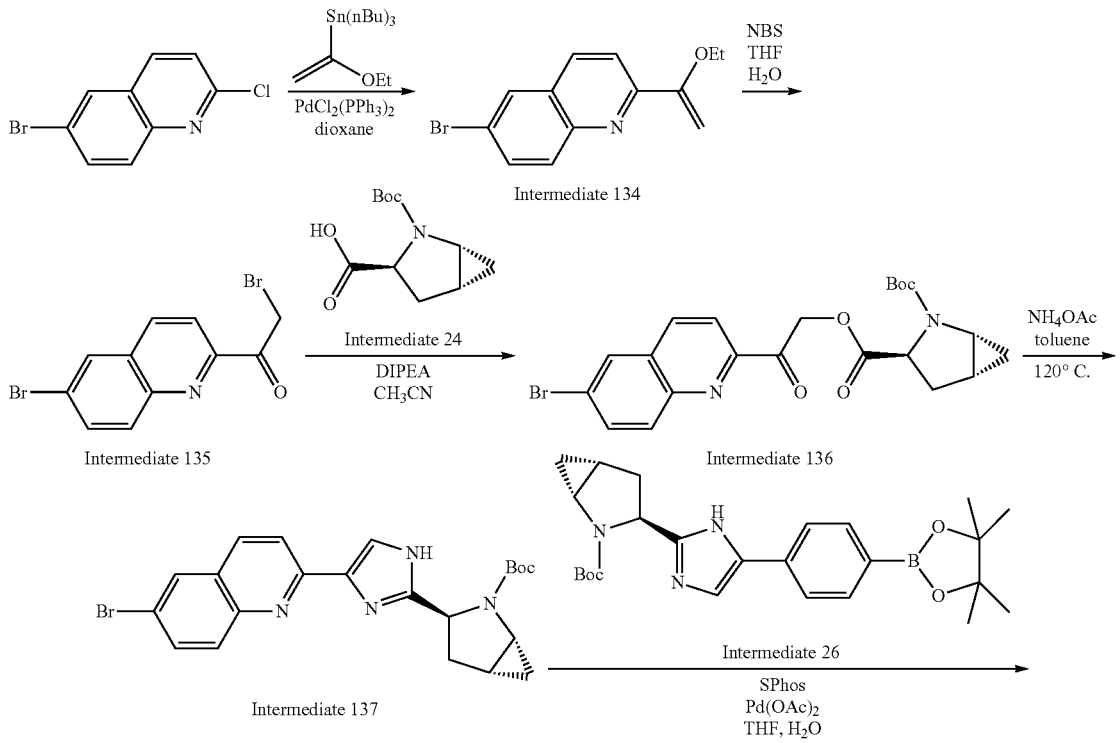

-continued

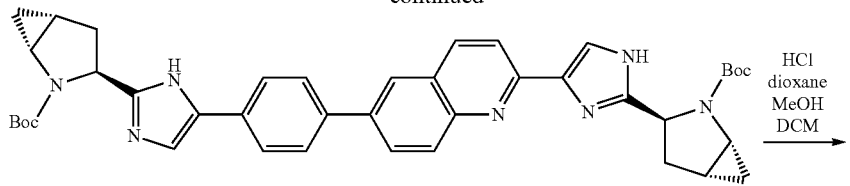

Intermediate 138

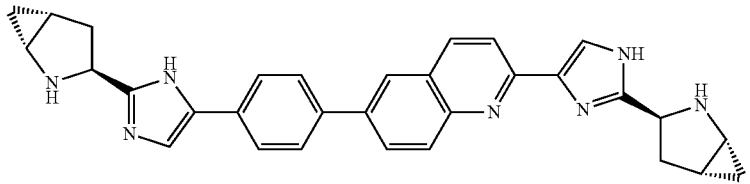

Intermediate 139

Intermediate 134

6-Bromo-2-(1-ethoxyvinyl)quinoline

Dichlorobis(triphenylphosphine)-palladium(II) (0.289 g, 0.412 mmol) was added to a solution of 6-bromo-2-chloroquinoline (1.0 g, 4.1 mmol) and tributyl(1-ethoxyvinyl)stannane (1.79 g, 4.95 mmol) in dioxane (8 mL) and the mixture was stirred at 100° C. for 5 h, desired product was identified by LC-MS. The crude reaction mixture was concentrated and purified by flash silica gel chromatography (eluted with 1:1 hexanes/DCM) to yield product 6-bromo-2-(1-ethoxyvinyl) quinoline (720 mg) as white solid. LC-MS retention time 4.091 min; m/z 279.84 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode.

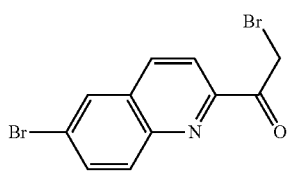

Intermediate 135

2-Bromo-1-(6-bromoquinolin-2-yl)ethanone

NBS (407 mg, 2.287 mmol) was added to a solution of 6-bromo-2-(1-ethoxyvinyl)quinoline (530 mg, 1.91 mmol) in THF (10 mL) and water (2.5 mL) and the mixture was stirred at rt for 2 h. The reaction mixture was partitioned between EtOAc and brine and the organic layer was concentrated. The crude material was purified by flash silica gel chromatography (eluted with $Et_2O$/hexanes, gradient from 0 to 5% $Et_2O$) to yield 2-bromo-1-(6-bromoquinolin-2-yl)ethanone (380 mg) as white solid. LC-MS retention time 3.988 min; m/z 329.84 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode.

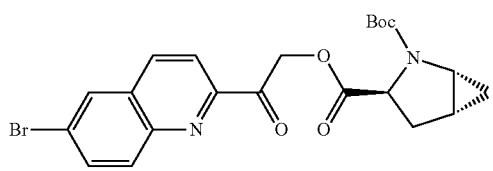 [SMILES: CC(C)(C)OC(=O)N1[C@@H]2C[C@@H]2C[C@H]1C(=O)OCC(=O)c1ccc2cc(Br)ccc2n1]

Intermediate 136

(1R,3S,5R)-3-(2-(6-Bromoquinolin-2-yl)-2-oxoethyl) 2-tert-butyl 2-azabicyclo[3.1.0]hexane-2,3-dicarboxylate DIPEA (0.21 mL, 1.2 mmol) was added to a solution of 2-bromo-1-(6-bromoquinolin-2-yl)ethanone (268 mg, 0.815 mmol)) and (1R,3S,5R)-2-(tert-butoxycarbonyl)-2-azabicyclo[3.1.0]hexane-3-carboxylic acid (204 mg, 0.896 mmol) in acetonitrile (8 mL) and the reaction mixture was stirred at rt for 16 h. The reaction mixture was diluted with sat. aq. $NaHCO_3$ (5 mL) and extracted with EtOAc (2×20 mL). The combined organic layers were washed with brine, dried ($MgSO_4$), filtered and concentrated. The crude product was purified by flash silica gel chromatography (used DCM as loading solvent, eluted with $Et_2O$/hexanes, gradient from 10% to 30% $Et_2O$) to yield (1R,3S,5R)-3-(2-(6-bromoquinolin-2-yl)-2-oxoethyl) 2-tert-butyl 2-azabicyclo[3.1.0]hexane-2,3-dicarboxylate (332 mg) as white solid. LC-MS retention time 4.283 min; m/z 476.88 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode.

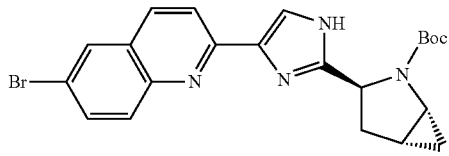 [SMILES: CC(C)(C)OC(=O)N1[C@@H]2C[C@@H]2C[C@H]1c1nc(-c2ccc3cc(Br)ccc3n2)c[nH]1]

Intermediate 137 tert-Butyl (1R,3S,5R)-3-(4-(6-bromo-2-quinolinyl)-1H-imidazol-2-yl)-2-azabicyclo[3.1.0]hexane-2-carboxylate Ammonium acetate (990 mg, 12.8 mmol) was added to a solution of (1R,3S,5R)-3-(2-(6-bromoquinolin-2-yl)-2-oxoethyl) 2-tert-butyl 2-azabicyclo[3.1.0]hexane-2,3-dicarboxylate (407 mg, 0.856 mmol) in toluene (10 mL) and the mixture was stirred at 120° C. for 3 h. The reaction mixture was diluted with sat. aq $NaHCO_3$ (10 mL) and extracted with EtOAc (50 mL). The organic layer was washed with brine, dried ($MgSO_4$), filtered and concentrated. The crude material was purified by flash silica gel chromatography (eluted with 1:1 EtOAc/hexanes) to yield tert-butyl (1R,3S,5R)-3-(4-(6-bromo-2-quinolinyl)-1H-imidazol-2-yl)-2-azabicyclo[3.1.0]hexane-2-carboxylate (272 mg) as light yellow solid. LC-MS retention time 3.306 min; m/z 456.99 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, chloroform-d) δ ppm 8.08 (d, J=8.5 Hz, 1H), 7.95 (d, J=2.2 Hz, 1H), 7.78 (dd, J=8.9, 2.2 Hz, 1H), 7.73-8.14 (m, 3H), 4.86-4.98 (m, 1H), 3.70-3.82 (m, 0.5H), 3.26-3.39 (m, 1H), 2.46 (dd, J=13.3, 9.3 Hz, 1H), 1.84-1.91 (m, 0.5H), 1.74-1.84 (m, 1H), 1.52 (s, 9H), 0.87-0.97 (m, 1H), 0.48-0.61 (m, 1H).

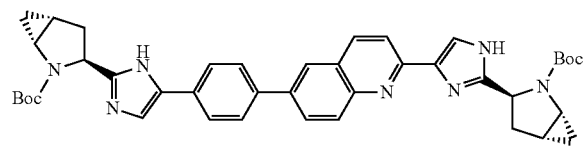 [SMILES: CC(C)(C)OC(=O)N1[C@@H]2C[C@@H]2C[C@H]1c1nc(-c2ccc3cc(-c4ccc(-c5cnc([C@@H]6C[C@H]7C[C@H]7N6C(=O)OC(C)(C)C)[nH]5)cc4)ccc3n2)c[nH]1]

Intermediate 138 tert-Butyl (1R,3S,5R)-3-(4-(6-(4-(2-((1R,3S,5R)-2-(tert-butoxycarbonyl)-2-azabicyclo[3.1.0]hex-3-yl)-1H-imidazol-4-yl)phenyl)-2-quinolinyl)-1H-imidazol-2-yl)-2-azabicyclo[3.1.0]hexane-2-carboxylate $Pd(OAc)_2$ (7.40 mg, 0.033 mmol) was added to a solution of tert-butyl (1R,3S,5R)-3-(4-(6-bromo-2-quinolinyl)-1H-imidazol-2-yl)-2-azabicyclo[3.1.0]hexane-2-carboxylate (150 mg, 0.329 mmol), (1R,3S,5R)-tert-butyl 3-(5-(4-(4,4,5,5-tetramethyl-1,3,2-dioxaborolan-2-yl)phenyl)-1H-imidazol-2-yl)-2-azabicyclo[3.1.0]hexane-2-carboxylate (149 mg, 0.329 mmol), dicyclohexyl(2',6'-dimethoxybiphenyl-2-yl) phosphine (27.0 mg, 0.066 mmol) and $K_2CO_3$ (137 mg, 0.988 mmol) in THF (2 mL) and water (0.50 mL) and the reaction mixture was stirred at 110° C. for 2 h. The reaction mixture was diluted with MeOH, filtered and purified by preparative HPLC ($H_2O$-MeOH with 10 mM $NH_4OAc$ buffer) to yield tert-butyl (1R,3S,5R)-3-(4-(6-(4-(2-((1R,3S,5R)-2-(tert-butoxycarbonyl)-2-azabicyclo[3.1.0]hex-3-yl)-1H-imidazol-4-yl)phenyl)-2-quinolinyl)-1H-imidazol-2-yl)-2-azabicyclo[3.1.0]hexane-2-carboxylate (140 mg) as bright yellow solid. LC-MS retention time 3.150 min; m/z 700.36 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode.

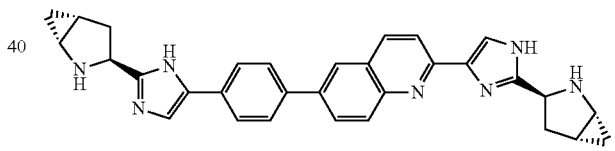

Intermediate 139

2-(2-((1R,3S,5R)-2-Azabicyclo[3.1.0]hex-3-yl)-1H-imidazol-4-yl)-6-(4-(2-((1R,3S,5R)-2-azabicyclo[3.1.0]hex-3-yl)-1H-imidazol-4-yl)phenyl)quinoline A solution of 4M HCl (1 mL, 4.00 mmol) in dioxane was added to a suspension of tert-butyl (1R,3S,5R)-3-(4-(6-(4-(2-((1R,3S,5R)-2-(tert-butoxycarbonyl)-2-azabicyclo[3.1.0] hex-3-yl)-1H-imidazol-4-yl)phenyl)-2-quinolinyl)-1H-imidazol-2-yl)-2-azabicyclo[3.1.0]hexane-2-carboxylate (130 mg, 0.186 mmol) in dioxane (3 mL), MeOH (0.5 mL) and DCM (3 mL) and the mixture was stirred at rt for 2 h. The reaction was concentrated to yield an HCl salt of 2-(2-((1R,3S,5R)-2-azabicyclo[3.1.0]hex-3-yl)-1H-imidazol-4-yl)-6-(4-(2-((1R,3S,5R)-2-azabicyclo[3.1.0]hex-3-yl)-1H-imidazol-4-yl)phenyl)quinoline (140 mg) as yellow solid. LC-MS retention time 2.063 min; m/z 500.37 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode. $^1$H NMR (400 MHz, MeOD) δ ppm 9.09 (d, J=9.0 Hz, 1H), 8.66 (s, 1H), 8.56-8.62 (m, 2H), 8.47-8.53 (m, 2H), 8.07 (s, 1H), 8.02-8.06 (m, 4H), 4.97 (dd, J=10.8, 8.0 Hz, 1H), 3.65-3.71 (m, 1H), 3.55-3.65 (m, 2H), 2.73-2.86 (m, 3H), 2.61-2.72 (m, 1H), 2.07-2.20 (m, 2H), 1.25-1.35 (m, 2H), 1.07 (t, 2H).

Scheme 36

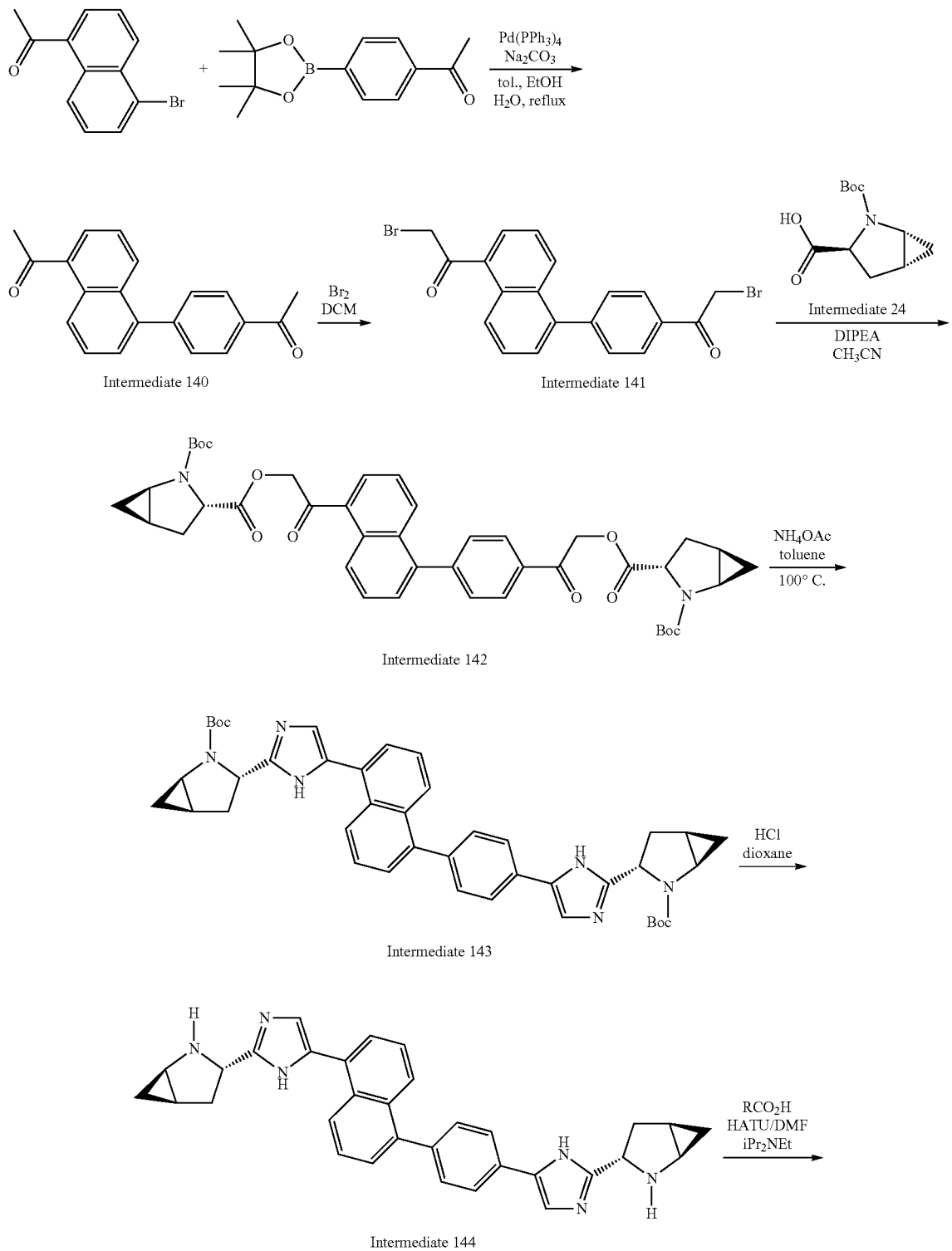

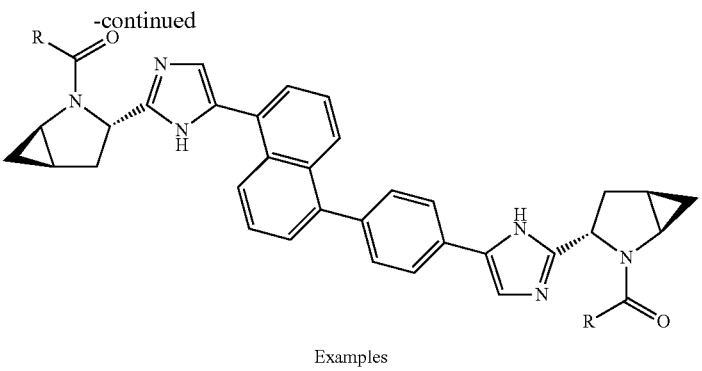

Examples

Intermediate 140

1-(4-(5-Acetylnaphthalen-1-yl)phenyl)ethanone

A solution of sodium carbonate (2.55 g, 24.09 mmol) in water (20 mL) was added to a solution of 1-(5-bromonaphthalen-1-yl)ethanone (1.2 g, 4.8 mmol) and 4-acetylphenylboronic acid (1.03 g, 6.26 mmol) in toluene (20 mL) and ethanol (20 mL) and then heterogeneous solution was vigorously stirred with bubbling nitrogen for 15 min. Then Pd(PPh$_3$)$_4$ (0.111 g, 0.096 mmol) was added and the reaction vessel was sealed and heated at reflux for 6 h. The reaction was cooled and concentrated to dryness. The crude residue was taken into EtOAc (~150 mL) and water (~100 mL). The layers were separated and the organic layer was washed with brine, dried (MgSO$_4$), filtered and concentrated to an orange solid. The orange solid was purified on a BIOTAGE® Horizon (40 g SiO$_2$, DCM) to yield 1-(4-(5-acetylnaphthalen-1-yl)phenyl)ethanone (1.31 g) as an off-white solid. LC-MS retention time 3.736 min; m/z 289.19 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, chloroform-d) δ ppm 8.75 (d, J=8.8 Hz, 1H), 8.11 (d, J=8.5 Hz, 2H), 7.99 (d, J=8.5 Hz, 1H), 7.94 (dd, J=7.2, 1.1 Hz, 1H), 7.67 (dd, J=8.5, 7.0 Hz, 1H), 7.58 (d, J=8.3 Hz, 2H), 7.45-7.51 (m, 2H), 2.79 (s, 3H), 2.70 (s, 3H).

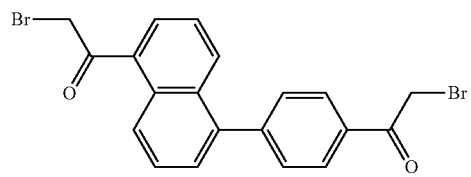 [SMILES: O=C(CBr)c1ccc(-c2cccc3c(C(=O)CBr)cccc23)cc1]

Intermediate 141

2-Bromo-1-(4-(5-(2-bromoacetyl)naphthalen-1-yl)phenyl)ethanone

A solution of bromine (0.47 mL, 9.1 mmol) in DCM (10 mL) was added to a solution of 1-(4-(5-acetylnaphthalen-1-yl)phenyl)ethanone (1.285 g, 4.46 mmol) in DCM (20 mL) and the reaction was stirred at rt for 1 d. The reaction was concentrated to a viscous light orange oil (~1.92 g). By $^1$H NMR the major product appears to be the desired product with peaks corresponding to the two mono brominated regioisomers (~10%). The material was used without purification. $^1$H NMR (400 MHz, chloroform-d) δ ppm 8.64 (d, J=8.5 Hz, 1H), 8.13-8.17 (m, 2H), 8.05 (d, J=8.5 Hz, 1H), 7.94 (dd, J=7.2, 1.1 Hz, 1H), 7.71 (dd, J=8.8, 7.0 Hz, 1H), 7.60-7.64 (m, 2H), 7.48-7.55 (m, 2H), 4.60 (s, 2H), 4.53 (s, 2H).

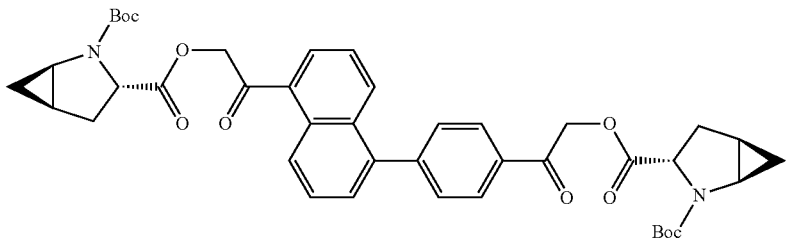 [SMILES: CC(C)(C)OC(=O)N1[C@@H]2C[C@@H]2C[C@H]1C(=O)OCC(=O)c1ccc(-c2cccc3c(C(=O)COC(=O)[C@@H]4C[C@H]5C[C@H]5N4C(=O)OC(C)(C)C)cccc23)cc1]

Intermediate 142

(1R,3S,5R)-3-(2-(4-(5-(2-((1R,3S,5R)-2-(tert-Butoxycarbonyl)-2-azabicyclo[3.1.0]hexane-3-carbonyloxy)acetypnaphthalen-1-yl)phenyl)-2-oxoethyl) 2-tert-butyl 2-azabicyclo[3.1.0]hexane-2,3-dicarboxylate DIPEA (2.337 mL, 13.38 mmol) was added to a solution of crude 2-bromo-1-(4-(5-(2-bromoacetyl)naphthalen-1-yl)phenyl)ethanone (1.99 g, 4.46 mmol) and (1R,3S,5R)-2-(tert-butoxycarbonyl)-2-azabicyclo[3.1.0]hexane-3-carboxylic acid (2.03 g, 8.92 mmol) in acetonitrile (50 mL) and the clear yellow solution was stirred at rt overnight. The reaction was concentrated to a yellow solidified foam which was purified on a BIOTAGE® Horizon (SiO$_2$, EtOAc/hexanes) to yield (1R,3S,5R)-3-(2-(4-(5-(2-((1R,3S,5R)-2-(tert-butoxycarbonyl)-2-azabicyclo[3.1.0]hexane-3-carbonyloxy)acetyl)naphthalen-1-yl)phenyl)-2-oxoethyl) 2-tert-butyl 2-azabicyclo[3.1.0]hexane-2,3-dicarboxylate (2.95 g) as a white fluffy solid. LC-MS retention time 4.363 min; m/z 737.38 (MH−). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% acetonitrile/95% H$_2$O/10 mM ammonium acetate and Solvent B was 5% H$_2$O/95% acetonitrile/10 mM ammonium acetate. MS data was determined using a MICROMASS® Platform for LC in electrospray mode. $^1$H NMR (400 MHz, MeOD) δ ppm 8.57 (d, J=8.8 Hz, 1H), 8.14 (d, J=8.0 Hz, 2H), 7.99-8.06 (m, 2H), 7.68 (dd, J=8.8, 7.0 Hz, 1H), 7.64 (d, J=8.3 Hz, 2H), 7.52-7.60 (m, 2H), 5.60-5.70 (m, 1H), 5.32-5.56 (m, 3H), 4.24-4.34 (m, 2H), 3.38-3.49 (m, 2H), 2.59-2.69 (m, 1H), 2.38-2.55 (m, 3H), 1.61-1.77 (m, 2H), 1.47 (br. s., 18H), 0.81-0.94 (m, 2H), 0.50-0.58 (m, 2H).

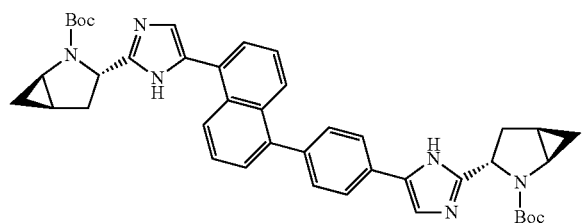 [SMILES: CC(C)(C)OC(=O)N1[C@@H]2C[C@@H]2C[C@H]1c1ncc(-c2ccc(-c3cccc4c(-c5cnc([C@@H]6C[C@H]7C[C@H]7N6C(=O)OC(C)(C)C)[nH]5)cccc34)cc2)[nH]1]

Intermediate 143

(1R,3S,5R)-tert-Butyl 3-(5-(4-(5-(2-((1R,3S,5R)-2-(tert-butoxycarbonyl)-2-azabicyclo[3.1.0]hexan-3-yl)-1H-imidazol-5-yl)naphthalen-1-yl)phenyl)-1H-imidazol-2-yl)-2-azabicyclo[3.1.0]hexane-2-carboxylate A solution of (1R,3S,5R)-3-(2-(4-(5-(2-((1R,3S,5R)-2-(tert-butoxycarbonyl)-2-azabicyclo[3.1.0]hexane-3-carbonyloxy)acetyl)naphthalen-1-yl)phenyl)-2-oxoethyl) 2-tert-butyl 2-azabicyclo[3.1.0]hexane-2,3-dicarboxylate (2.01 g, 2.72 mmol) and ammonium acetate (4.19 g, 54.4 mmol) in toluene (40 mL) was stirred and heated at 100° C. overnight. The reaction was concentrated to dryness and the brown solids were partitioned between DCM (150 mL) and ½ sat. aq. NaHCO$_3$ (100 mL). The organics were dried (MgSO$_4$), filtered and concentrated. The crude material was not easily purified by flash column chromatography so all fractions containing the desired product or starting material were collected, concentrated and resubmitted to the reaction conditions (now 110° C. overnight). The reaction was concentrated and the brown solids were partitioned between DCM (150 mL) and ½ sat NaHCO$_3$ (100 mL). The organics were dried (MgSO$_4$), filtered and concentrated. Approximately ~30-35% of the material was purified by preparative HPLC (dissolved into MeOH, filtered, 80-100% MeOH/water, ammonium acetate buffer) to yield (1R,3S,5R)-tert-butyl 3-(5-(4-(5-(2-((1R,3S,5R)-2-(tert-butoxycarbonyl)-2-azabicyclo[3.1.0]hexan-3-yl)-1H-imidazol-5-yl)naphthalen-1-yl)phenyl)-1H-imidazol-2-yl)-2-azabicyclo[3.1.0]hexane-2-carboxylate (148 mg) as a yellow solid. The remaining material was purified by preparative HPLC (dissolved into MeOH, filtered, 60-100% MeOH/water, TFA buffer) to yield a TFA salt (1R,3S,5R)-tert-butyl 3-(5-(4-(5-(2-((1R,3S,5R)-2-(tert-butoxycarbonyl)-2-azabicyclo[3.1.0]hexan-3-yl)-1H-imidazol-5-yl)naphthalen-1-yl)phenyl)-1H-imidazol-2-yl)-2-azabicyclo[3.1.0]hexane-2-carboxylate (299 mg). LC-MS retention time 3.100 min; m/z 699.56 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 8.29 (d, J=8.5 Hz, 1H), 7.90 (d, J=8.5 Hz, 1H), 7.83 (d, J=8.3 Hz, 2H), 7.59 (dd, J=7.0, 1.0 Hz, 1H), 7.53 (dd, J=8.5, 7.0 Hz, 1H), 7.43-7.50 (m, 4H), 7.42 (s, 1H), 7.23 (s, 1H), 4.66-4.80 (m, 2H), 3.60 (br. s., 2H), 2.56 (dt, J=13.1, 8.9 Hz, 2H), 2.32-2.46 (m, 2H), 1.70-1.78 (m, 2H), 1.38 (br. s., 18H), 0.82-0.90 (m, 2H), 0.63 (br. s., 2H).

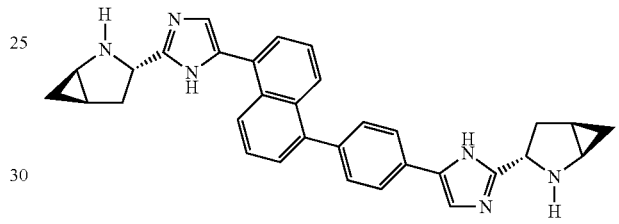

Intermediate 144

(1R,3S,5R)-3-(5-(4-(5-(2-((1R,3S,5R)-2-Azabicyclo[3.1.0]hexan-3-yl)-1H-imidazol-5-yl)naphthalen-1-yl)phenyl)-1H-imidazol-2-yl)-2-azabicyclo[3.1.0]hexane 4M HCl (0.757 mL, 3.03 mmol) in dioxane was added to a solution of (1R,3S,5R)-tert-butyl 3-(5-(4-(5-(2-((1R,3S,5R)-2-(tert-butoxycarbonyl)-2-azabicyclo[3.1.0]hexan-3-yl)-1H-imidazol-5-yl)naphthalen-1-yl)phenyl)-1H-imidazol-2-yl)-2-azabicyclo[3.1.0]hexane-2-carboxylate (141 mg, 0.202 mmol) in dioxane (3.0 mL) and the reaction was stirred at rt for 6 h. The solids were washed down the sides of the vial with MeOH and the reaction was concentrated under a stream nitrogen to yield an HCl salt of (1R,3S,5R)-3-(5-(4-(5-(2-((1R,3S,5R)-2-azabicyclo[3.1.0]hexan-3-yl)-1H-imidazol-4-yl)naphthalen-1-yl)phenyl)-1H-imidazol-2-yl)-2-azabicyclo[3.1.0]hexane (119 mg) as a yellow solid. LC-MS retention time 2.333 min; m/z 499.57 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 8.15 (d, J=8.3 Hz, 1H), 8.03-8.08 (m, 2H), 8.01 (d, J=8.0 Hz, 2H), 7.95 (s, 1H), 7.77 (d, J=6.5 Hz, 1H), 7.68-7.74 (m, 1H), 7.65 (d, J=8.0 Hz, 2H), 7.57-7.64 (m, 2H), 5.03 (t, J=9.4 Hz, 1H), 4.97 (dd, J=10.8, 8.0 Hz, 1H), 3.57-3.66 (m, 2H), 2.76-2.89 (m, 4H), 2.11-2.21 (m, 2H), 1.27-1.34 (m, J=7.7, 5.1, 5.1, 2.6 Hz, 2H), 1.05-1.14 (m, 2H).

Scheme 37

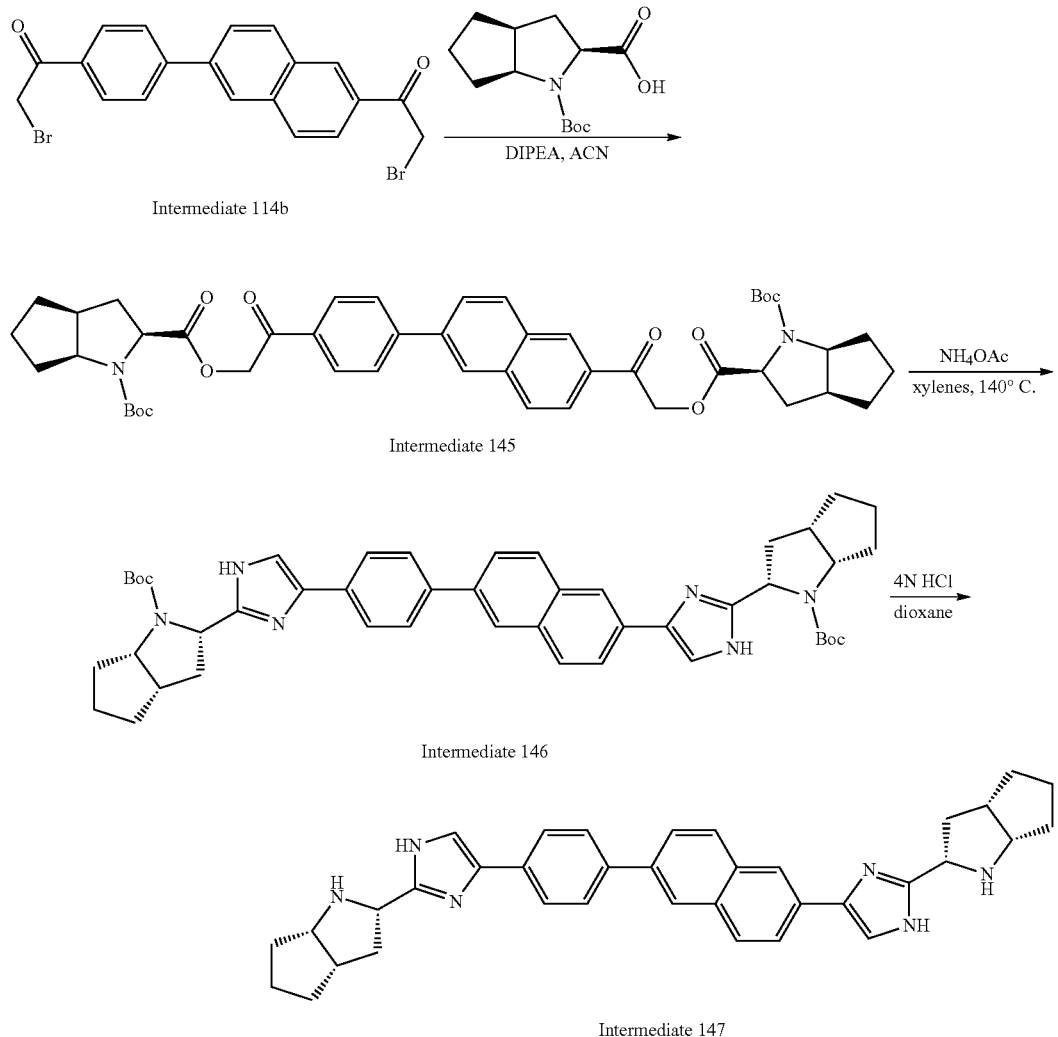

Intermediate 114b

Intermediate 145

Intermediate 146

Intermediate 147

Intermediate 145

(2S,3aS,6aS)-2-(2-(4-(6-(2-((2S,3aS,6aS)-1-(tert-Butoxycarbonyl)-octahydrocyclopenta[b]pyrrole-2-carbonyloxy)acetyl)naphthalen-2-yl)phenyl)-2-oxo-ethyl)1-tert-butyl hexahydrocyclopenta[b]pyrrole-1,2 (2H)-dicarboxylate Neat DIPEA (0.068 mL, 0.388 mmol) was added to a stirred suspension of 2-bromo-1-(4-(6-(2-bromoacetyl)naph-thalen-2-yl)phenyl)ethanone (79 mg, 0.176 mmol) and (2S,3aS,6aS)-1-(tert-butoxycarbonyl)octahydrocyclopenta [b]pyrrole-2-carboxylic acid (90 mg, 0.353 mmol) in an. acetonitrile (1.5 mL) and chloroform (1.5 mL) and the mixture was stirred at r.t. overnight. Reaction mixture was evaporated to dryness and then purified by silica gel FCC (3% MeOH in DCM) to afford the Intermediate 145 as a tan solid. LC-MS retention time: 2.480 min; m/z 793.7 (M−H)⁻.

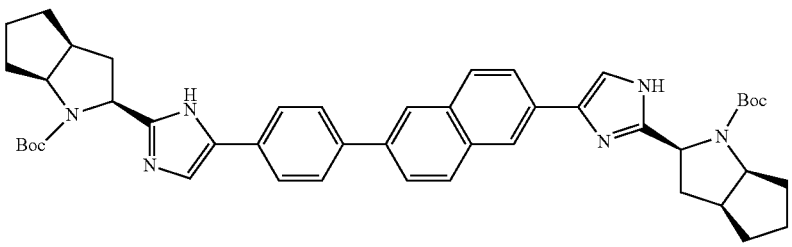 [SMILES: CC(C)(C)OC(=O)N1[C@H](c2nc(-c3ccc4cc(-c5ccc(-c6cnc([C@@H]7C[C@@H]8CCC[C@@H]8N7C(=O)OC(C)(C)C)[nH]6)cc5)ccc4c3)c[nH]2)C[C@@H]2CCC[C@@H]21]

Intermediate 146

(2S,3aS,6aS)-tert-Butyl 2-(4-(4-(6-(2-((2S,3aS,6aS)-1-(tert-butoxycarbonyl)-octahydrocyclopenta[b]pyrrol-2-yl)-1H-imidazol-4-yl)naphthalen-2-yl)phenyl)-1H-imidazol-2-yl)hexahydrocyclopenta[b]pyrrole-1(2H)-carboxylate A stirred suspension of (2S,3aS,6aS)-2-(2-(4-(6-(2-((2S,3aS,6aS)-1-(tert-butoxycarbonyl)octahydrocyclopenta[b]pyrrole-2-carbonyloxy)acetyl)naphthalen-2-yl)phenyl)-2-oxoethyl) 1-tert-butyl hexahydrocyclopenta[b]pyrrole-1,2 (2H)-dicarboxylate (140 mg, 0.176 mmol) and ammonium acetate (272 mg, 3.52 mmol) in xylene (4 mL) was heated at 140° C. for 2 h. Reaction mixture was cooled to r.t. and diluted with EtOAc (20 ml) and washed with satd. NaHCO₃, water, brine and dried (Na₂SO₄) to afford a brown solid which was purified by silica gel FCC (3-5% MeOH in DCM) to afford the (2S,3aS,6aS)-tert-butyl 2-(4-(4-(6-(2-((2S,3aS,6aS)-1-(tert-butoxycarbonyl)-octahydrocyclopenta[b]pyrrol-2-yl)-1H-imidazol-4-yl)naphthalen-2-yl)phenyl)-1H-imidazol-2-yl)hexahydrocyclopenta[b]pyrrole-1(2H)-carboxylate. LC-MS retention time: 2.577 min; m/z 755.7 (M+H)⁺.

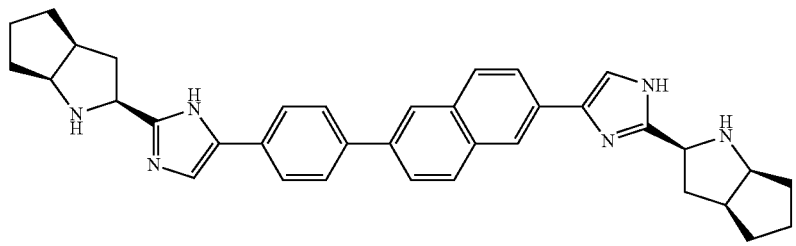 [SMILES: c1cc(-c2cnc([C@@H]3C[C@@H]4CCC[C@@H]4N3)[nH]2)ccc1-c1ccc2cc(-c3c[nH]c([C@@H]4C[C@@H]5CCC[C@@H]5N4)n3)ccc2c1]

Intermediate 147

(2S,3aS,6aS)-2-(4-(4-(6-(2-((2S,3aS,6aS)-Octahydrocyclopenta[b]pyrrol-2-yl)-1H-imidazol-4-yl)naphthalen-2-yl)phenyl)-1H-imidazol-2-yl)octahydrocyclopenta[b]pyrrole 4N HCl in dioxane (20 equiv) was added to a solution of (2S,3aS,6aS)-tert-butyl 2-(4-(4-(6-(2-((2S,3aS,6aS)-1-(tert-butoxycarbonyl)-octahydrocyclopenta[b]pyrrol-2-yl)-1H-imidazol-4-yl)naphthalen-2-yl)phenyl)-1H-imidazol-2-yl)hexahydrocyclopenta[b]pyrrole-1(2H)-carboxylate in an. DCM and the mixture was stirred at rt for 2-3 h Anhydrous toluene was added to the resultant yellow suspension and then evaporated to dryness to an HCl salt of (2S,3aS,6aS)-2-(4-(4-(6-(2-((2S,3aS,6aS)-octahydrocyclopenta[b]pyrrol-2-yl)-1H-imidazol-4-yl)naphthalen-2-yl)phenyl)-1H-imidazol-2-yl)octahydrocyclopenta[b]pyrrole as a beige solid: LC-MS retention time: 2.343 min; m/z 555 (M+H)⁺.

Scheme 38

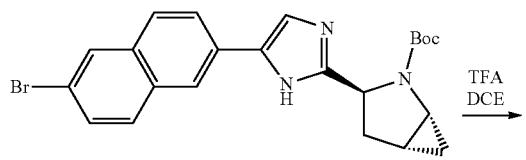

Intermediate 120

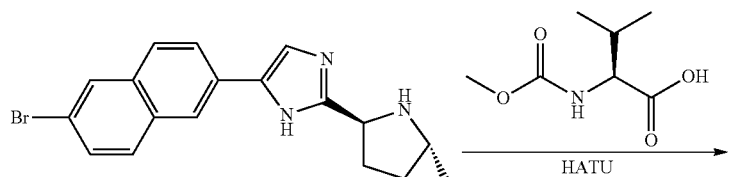

Intermediate 148

-continued

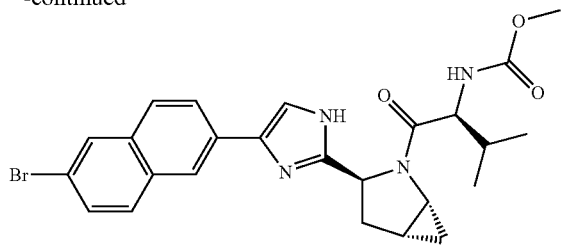

Intermediate 149

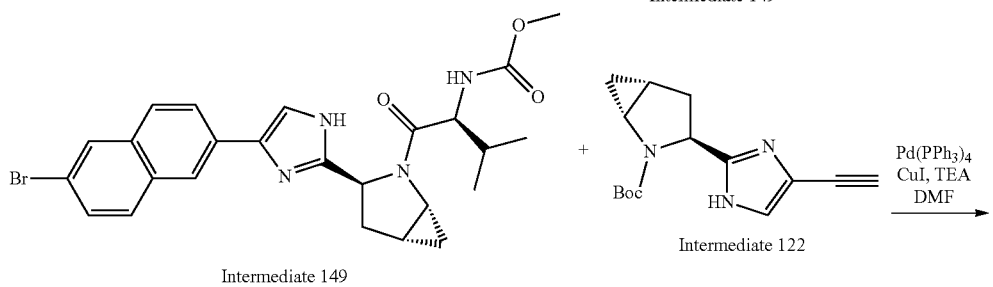

Intermediate 150

Intermediate 148

(1R,3S,5R)-3-(4-(6-Bromonaphthalen-2-yl)-1H-imidazol-2-yl)-2-azabicyclo[3.1.0]hexane TFA (1.028 mL, 13.34 mmol) was added to a solution of (1R,3S,5R)-tert-butyl 3-(4-(6-bromonaphthalen-2-yl)-1H-imidazol-2-yl)-2-azabicyclo[3.1.0]hexane-2-carboxylate (Intermediate 120) (606 mg, 1.334 mmol) in DCE (20 mL) and reaction was stirred at rt for 2 h. Then additional TFA (1 mL) was added and the reaction was stirred at rt for 4 h. The reaction was concentrated to dryness and the crude brown oil was dissolved into diethyl ether and concentrated under vacuum (2×) to yield a TFA salt of (1R,3S,5R)-3-(4-(6-bromonaphthalen-2-yl)-1H-imidazol-2-yl)-2-azabicyclo[3.1.0]hexane (786 mg) as a yellow solid. The material was used without further purification. LC-MS retention time 2.558 min; m/z 352.03, 354.05 (1:1) (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) δ ppm 10.55 (br. s., 1H), 8.02 (s, 1H), 7.93 (d, J=1.5 Hz, 1H), 7.72 (d, J=8.5 Hz, 1H), 7.65 (d, J=8.8 Hz, 1H), 7.59 (dd, J=8.8, 2.0 Hz, 1H), 7.52 (dd, J=8.7, 1.6 Hz, 1H), 7.44 (s, 1H), 5.10 (dd, J=11.8, 7.3 Hz, 1H), 3.49-3.54 (m, 1H), 2.94 (td, J=12.7, 4.6 Hz, 1H), 2.68 (dd, J=13.2, 7.2 Hz, 1H), 2.06-2.14 (m, 1H), 1.20-1.26 (m, 1H), 1.00-1.09 (m, 1H).

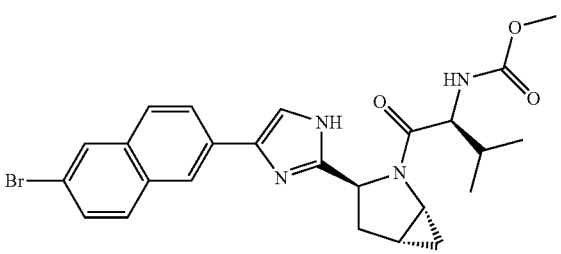 [SMILES: COC(=O)N[C@H](C(=O)N1[C@@H]2C[C@@H]2C[C@H]1c1nc(-c2ccc3cc(Br)ccc3c2)c[nH]1)C(C)C]

Intermediate 149

Methyl (S)-1-((1R,3S,5R)-3-(4-(6-bromonaphthalen-2-yl)-1H-imidazol-2-yl)-2-azabicyclo[3.1.0]hexan-2-yl)-3-methyl-1-oxobutan-2-ylcarbamate HATU (411 mg, 1.082 mmol) was added to a solution of a TFA salt of (1R,3S,5R)-3-(4-(6-bromonaphthalen-2-yl)-1H-imidazol-2-yl)-2-azabicyclo[3.1.0]hexane (525 mg, 0.902 mmol) and (S)-2-(methoxycarbonylamino)-3-methylbutanoic acid (190 mg, 1.08 mmol) in DMF (10 mL) and DIPEA (0.79 mL, 4.5 mmol) and the reaction was stirred at rt for 4 h. The reaction was diluted with EtOAc (~80 mL) and washed with sat. aq. NaHCO$_3$, water (30 mL) and brine (30 mL). The organics were then dried (MgSO$_4$), filtered and concentrated to a brown oil (625 mg). This material was purified on a BIOTAGE® Horizon (40 g SiO$_2$, 40-80% EtOAc/hexanes) to yield methyl (S)-1-((1R,3S,5R)-3-(4-(6-bromonaphthalen-2-yl)-1H-imidazol-2-yl)-2-azabicyclo[3.1.0]hexan-2-yl)-3-methyl-1-oxobutan-2-ylcarbamate (412 mg) as a yellow glass. LC-MS retention time 1.843 min; m/z 511.24, 513.12 (1:1) (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1.0 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode.

0.332 mmol) and CuI (3.17 mg, 0.017 mmol) in DMF (4 mL) and TEA (0.14 mL, 0.10 mmol) for 15 min. Then Pd(PPh$_3$)$_4$ (19.2 mg, 0.017 mmol) was added and the reaction vessel was sealed and heated at 60° C. overnight. The reaction was cooled and then additional CuI (5 mg) and TEA (100 µL) were added to the reaction and nitrogen was bubbled through the reaction for 15 min. Then additional Pd(PPh$_3$)$_4$ (12 mg) was added and the reaction was sealed and stirred at 70° C. for 24 h. The reaction was concentrated under high vacuum and the residue was partitioned between DCM (25 mL) and water (25 mL). The aqueous was extracted with DCM (2×10 mL) and the combined organics were washed with brine (~20 mL), dried (MgSO$_4$), filtered and concentrated to a viscous dark oil. The material was dissolved into MeOH, filtered and purified by preparative HPLC (MeOH/water, ammonium acetate buffer) to yield (1R,3S,5R)-tert-butyl 3-(4-((6-(2-((1R,3S,5R)-2-((S)-2-(methoxycarbonylamino)-3-methylbutanoyl)-2-azabicyclo[3.1.0]hexan-3-yl)-1H-imidazol-4-yl)naphthalen-2-yl)ethynyl)-1H-imidazol-2-yl)-2-azabicyclo[3.1.0]

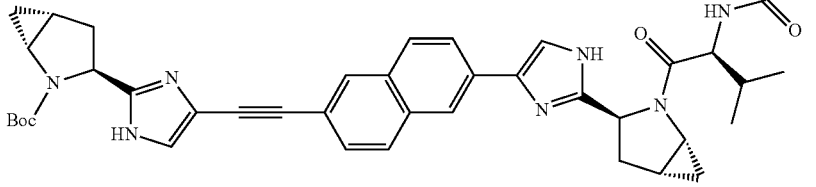

Intermediate 150

(1R,3S,5R)-tert-Butyl 3-(4-((6-(2-((1R,3S,5R)-2-((S)-2-(methoxycarbonylamino)-3-methylbutanoyl)-2-azabicyclo[3.1.0]hexan-3-yl)-1H-imidazol-4-yl)naphthalen-2-yl)ethynyl)-1H-imidazol-2-yl)-2-azabicyclo[3.1.0]hexane-2-carboxylate Nitrogen was bubbled through a mixture of (1R,3S,5R)-tert-butyl 3-(5-ethynyl-1H-imidazol-2-yl)-2-azabicyclo[3.1.0]hexane-2-carboxylate (Intermediate 122) (118 mg, 0.432 mmol), methyl (S)-1-((1R,3S,5R)-3-(5-(6-bromonaphthalen-2-yl)-1H-imidazol-2-yl)-2-azabicyclo[3.1.0]hexan-2-yl)-3-methyl-1-oxobutan-2-ylcarbamate (170 mg, hexane-2-carboxylate (187.4 mg) as a yellow solid. The material was used without further purification. LC-MS retention time 1.720 min; m/z 704.59 (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1.0 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode.

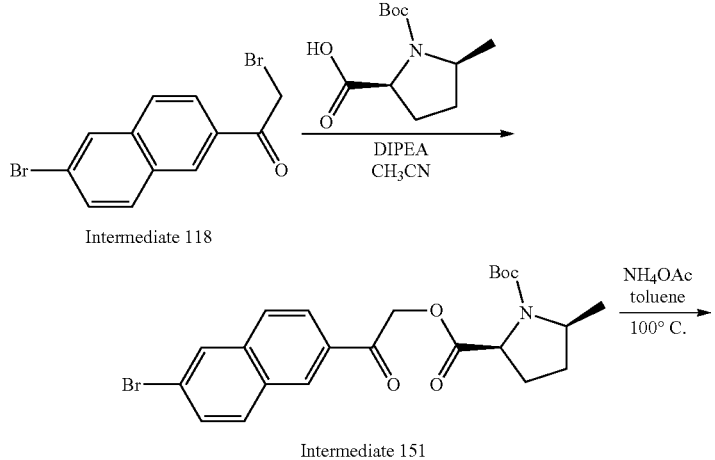

Scheme 39

Intermediate 118

Intermediate 151

-continued

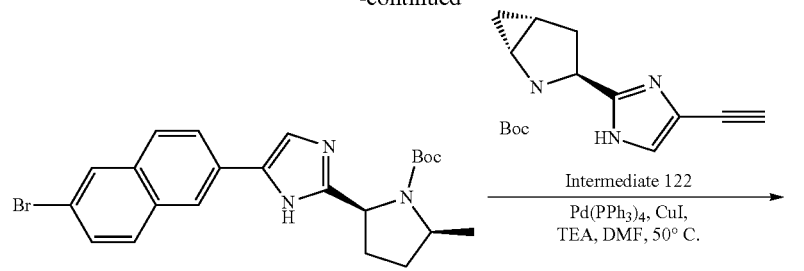

Intermediate 152

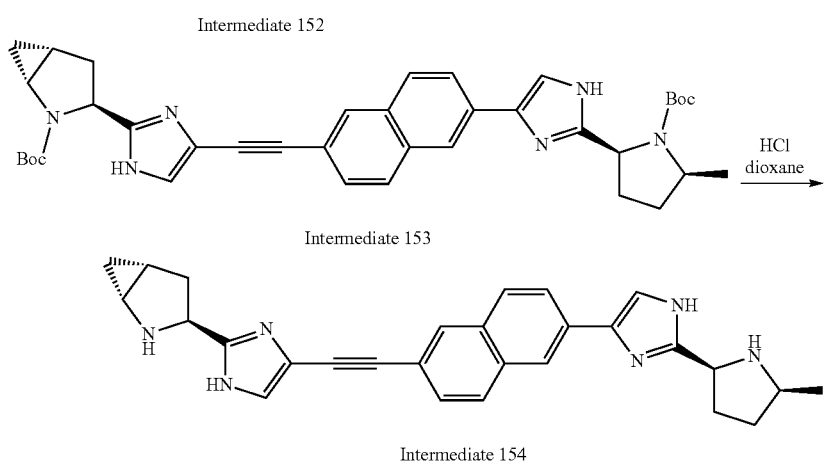

Intermediate 153

Intermediate 154

Intermediate 151

(2S,5S)-2-(2-(6-Bromonaphthalen-2-yl)-2-oxoethyl) 1-tert-butyl 5-methylpyrrolidine-1,2-dicarboxylate DIPEA (0.823 mL, 4.71 mmol) was added to a stirred slurry of 2-bromo-1-(6-bromonaphthalen-2-yl)ethanone (Intermediate 118) (1.03 g, 3.14 mmol) and (2S,5S)-1-(tert-butoxycarbonyl)-5-methylpyrrolidine-2-carboxylic acid (0.720 g, 3.14 mmol) in acetonitrile (50 mL) and the reaction was stirred at rt overnight. The reaction was concentrated to dryness and purified by BIOTAGE® Horizon (40 g SiO$_2$, 10-20% EtOAc/hexanes) to yield (2S,5S)-2-(2-(6-bromonaphthalen-2-yl)-2-oxoethyl) 1-tert-butyl 5-methylpyrrolidine-1,2-dicarboxylate (1.09 g) as a yellow solidified foam. LC-MS retention time 4.413 min; m/z 476, 478.20 (1:1) (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 8.57 (br. s., 1H), 8.14 (d, J=1.5 Hz, 1H), 8.01 (d, J=8.5 Hz, 1H), 7.96 (d, J=8.8 Hz, 1H), 7.91 (d, J=8.8 Hz, 1H), 7.68 (dd, J=8.8, 1.8 Hz, 1H), 5.62-5.70 (m, 1H), 5.47-5.60 (m, 1H), 4.46 (t, J=7.3 Hz, 1H), 3.92-4.06 (m, 1H), 2.26-2.37 (m, 2H), 2.05-2.19 (m, 1H), 1.67-1.82 (m, 1H), 1.46 (d, J=6.8 Hz, 9H), 1.30 (d, J=6.5 Hz, 3H).

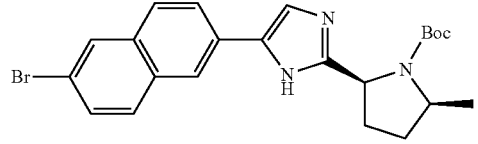 [SMILES: C[C@H]1CC[C@@H](c2ncc(-c3ccc4cc(Br)ccc4c3)[nH]2)N1C(=O)OC(C)(C)C]

Intermediate 152

(2S,5S)-tert-Butyl 2-(5-(6-bromonaphthalen-2-yl)-1H-imidazol-2-yl)-5-methylpyrrolidine-1-carboxylate Ammonium acetate (3.79 g, 49.1 mmol) was added to a solution of (2S,5S)-2-(2-(6-bromonaphthalen-2-yl)-2-oxoethyl) 1-tert-butyl 5-methylpyrrolidine-1,2-dicarboxylate (1.17 g, 2.47 mmol) in toluene (30 mL) and the reaction was placed into an oil bath which had been preheated to 100° C. and stirred at that temperature overnight. The reaction was allowed to cool to rt, concentrated and partitioned between DCM (100 mL) and ½ sat. aq. NaHCO$_3$ (75 mL). The organics layer was washed with brine (~50 mL), dried (MgSO$_4$), filtered and concentrated to a solidified tan foam. This material was purified on a BIOTAGE® Horizon (160 g SiO$_2$, loaded with DCM, 20-35% EtOAc/hexanes) to yield (2S,5S)-tert-butyl 2-(5-(6-bromonaphthalen-2-yl)-1H-imidazol-2-yl)-5-methylpyrrolidine-1-carboxylate (893 mg) as a solidified tan foam. LC-MS retention time 3.410 min; m/z 456, 458.22 (1:1) (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent A/100% Solvent B, a gradient time of 3 min, a hold time of 1 min, and an analysis time of 4 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode. $^1$H NMR (400 MHz, MeOD) δ ppm 8.19 (br. s., 1H), 8.01 (s, 1H), 7.83-7.93 (m, 1H), 7.76-7.83 (m, 2H), 7.55 (dd, J=8.7, 1.6 Hz, 1H), 7.47 (br. s., 1H), 4.94 (br. s., 1H), 3.99-4.09 (m, 1H), 2.22-2.36 (m, 2H), 2.09-2.21 (m, 1H), 1.72 (br. s., 1H), 1.42 (d, J=6.0 Hz, 3H), 1.34 (br. s., 9H).

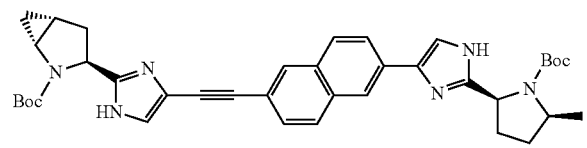 [SMILES: C[C@H]1CC[C@@H](c2nc(-c3ccc4cc(C#Cc5c[nH]c([C@@H]6C[C@H]7C[C@H]7N6C(=O)OC(C)(C)C)n5)ccc4c3)c[nH]2)N1C(=O)OC(C)(C)C]

Intermediate 153

(1R,3S,5R)-tert-Butyl 3-(4-((6-(2-((2S,5S)-1-(tert-butoxycarbonyl)-5-methylpyrrolidin-2-yl)-1H-imidazol-4-yl)naphthalen-2-yl)ethynyl)-1H-imidazol-2-yl)-2-azabicyclo[3.1.0]hexane-2-carboxylate Nitrogen was bubbled through a solution of (2S,5S)-tert-butyl 2-(5-(6-bromonaphthalen-2-yl)-1H-imidazol-2-yl)-5-methylpyrrolidine-1-carboxylate (127 mg, 0.277 mmol), (1R,3S,5R)-tert-butyl 3-(5-ethynyl-1H-imidazol-2-yl)-2-azabicyclo[3.1.0]hexane-2-carboxylate (91 mg, 0.33 mmol) and CuI (2.6 mg, 0.014 mmol) in DMF (3 mL) and TEA (0.12 mL, 0.83 mmol) for 15 min. Then Pd(PPh₃)₄ (16 mg, 0.014 mmol) was added and the reaction vessel was flushed with nitrogen, sealed and heated at 50° C. overnight. The reaction was cooled to rt, nitrogen was bubbled through the reaction mixture for 20 min., and then additional CuI (~4 mg) and Pd(PPh₃)₄ (15 mg) were added. The reaction was flushed with nitrogen for 5 min., sealed and heated at 60° C. for 1 d. The reaction was cooled to rt, diluted with methanol, filtered and purified by preparative HPLC (MeOH/water with TFA buffer) to yield a TFA salt of (1R,3S,5R)-tert-butyl 3-(5-((6-(2-((2S,5S)-1-(tert-butoxycarbonyl)-5-methylpyrrolidin-2-yl)-1H-imidazol-5-yl)naphthalen-2-yl)ethynyl)-1H-imidazol-2-yl)-2-azabicyclo[3.1.0]hexane-2-carboxylate (56.7 mg) as a yellow solid. LC-MS retention time 3.161 min; m/z 649.62 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode. $^1$H NMR (400 MHz, MeOD) δ ppm 8.31 (s, 1H), 8.21 (s, 1H), 8.07 (d, J=8.8 Hz, 1H), 7.99-8.04 (m, 2H), 7.91 (dd, J=8.8, 1.8 Hz, 1H), 7.77-7.87 (m, 1H), 7.69 (dd, J=8.7, 1.4 Hz, 1H), 5.13 (t, J=7.5 Hz, 1H), 4.12 (br. s., 1H), 3.61 (br. s., 1H), 2.66 (br. s., 1H), 2.45-2.54 (m, 1H), 2.33-2.42 (m, 1H), 2.22-2.32 (m, 2H), 1.75-1.86 (m, 2H), 1.25-1.59 (m, 21H), 1.06 (none, 1H), 0.90 (dt, J=8.5, 5.8 Hz, 1H), 0.71 (br. s., 1H).

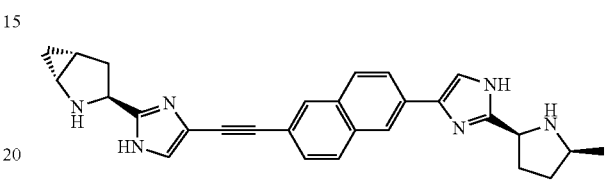

Intermediate 154

(1R,3S,5R)-3-(4-((6-(2-((2S,5S)-5-Methylpyrrolidin-2-yl)-1H-imidazol-4-yl)naphthalen-2-yl)ethynyl)-1H-imidazol-2-yl)-2-azabicyclo[3.1.0]hexane 4M HCl (0.611 mL, 2.445 mmol) in dioxane was added to a mixture of a TFA salt of (1R,3S,5R)-tert-butyl 3-(5-((6-(2-((2S,5S)-1-(tert-butoxycarbonyl)-5-methylpyrrolidin-2-yl)-1H-imidazol-5-yl)naphthalen-2-yl)ethynyl)-1H-imidazol-2-yl)-2-azabicyclo[3.1.0]hexane-2-carboxylate (53.6 mg, 0.061 mmol) in dioxane (1.5 mL) and the reaction was vigorously stirred for 2 h. The reaction was concentrated under a steam of nitrogen overnight to yield an HCl salt of (1R,3S,5R)-3-(4-((6-(2-((2S,5S)-5-methylpyrrolidin-2-yl)-1H-imidazol-4-yl)naphthalen-2-yl)ethynyl)-1H-imidazol-2-yl)-2-azabicyclo[3.1.0]hexane (37 mg) which was used without further purification. LC-MS retention time 2.302 min; m/z 449.40 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode.

Scheme 40

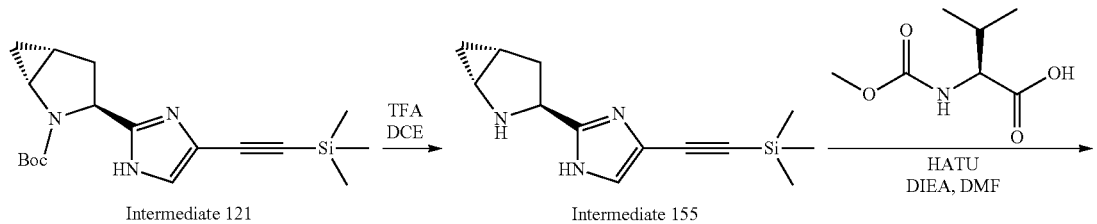

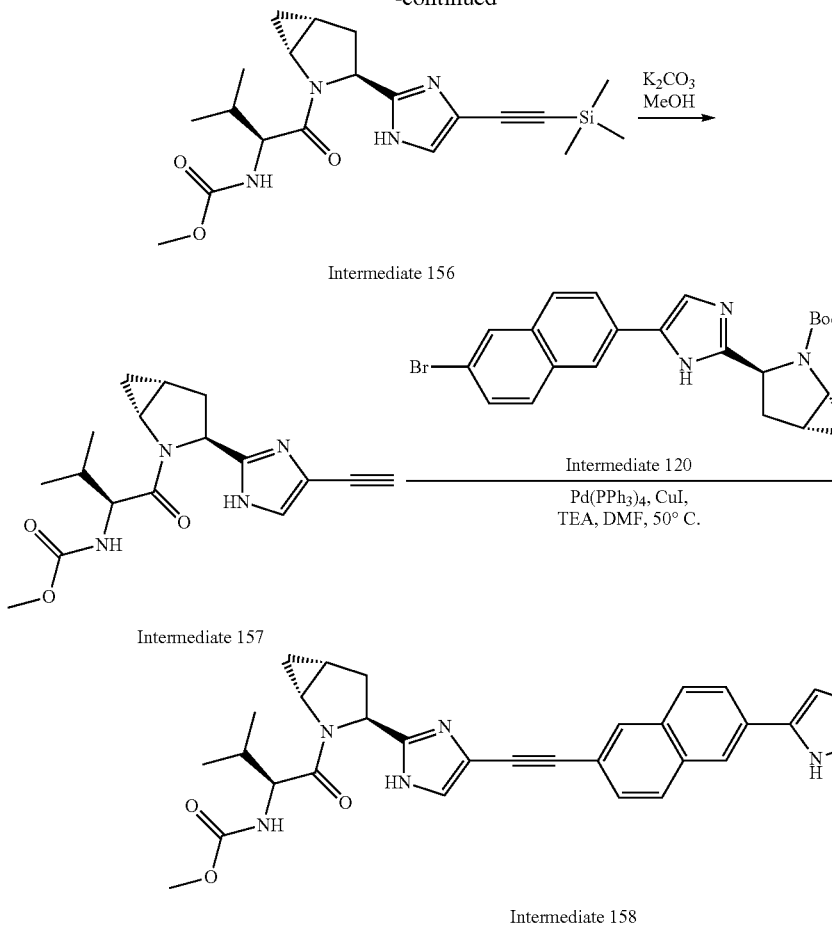

Intermediate 156

Intermediate 157

Intermediate 158

Intermediate 155

(1R,3S,5R)-3-(4-((Trimethylsilyl)ethynyl)-1H-imidazol-2-yl)-2-azabicyclo[3.1.0]hexane TFA (500 μl, 6.49 mmol) was added to a solution of (1R, 3S,5R)-tert-butyl 3-(5-((trimethylsilyl)ethynyl)-1H-imidazol-2-yl)-2-azabicyclo[3.1.0]hexane-2-carboxylate (299 mg, 0.865 mmol) in DCE (5 mL) and the reaction was stirred at rt for 30 min. The reaction was concentrated to dryness and then resubmitted to the reaction conditions for 5 h. The reaction was concentrated to yield a TFA salt of (1R,3S,5R)-3-(4-((trimethylsilyl)ethynyl)-1H-imidazol-2-yl)-2-azabicyclo [3.1.0]hexane as a viscous brown oil which was used without further purification. LC-MS retention time 2.755 min; m/z 246.25 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode.

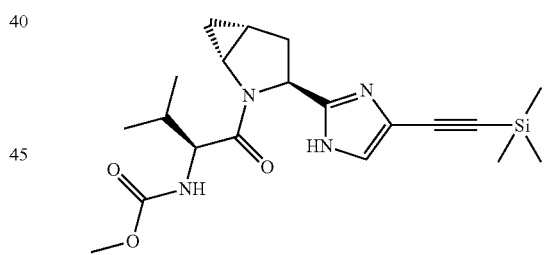

Intermediate 156

Methyl (S)-3-methyl-1-oxo-1-((1R,3S,5R)-3-(4-((trimethylsilyl)ethynyl)-1H-imidazol-2-yl)-2-azabicyclo[3.1.0]hexan-2-yl)butan-2-ylcarbamate HATU (428 mg, 1.125 mmol) was added to a stirred solution of (1R,3S,5R)-3-(5-((trimethylsilyl)ethynyl)-1H-imidazol-2-yl)-2-azabicyclo[3.1.0]hexane (212 mg, 0.865 mmol) and (S)-2-(methoxycarbonylamino)-3-methylbutanoic acid (197 mg, 1.125 mmol) in DMF (3 mL) and DIPEA (1.2 mL, 6.9 mmol) and the reaction was stirred at rt overnight. The reaction was concentrated to dryness and then purified with a BIOTAGE® Horizon (25 g SiO$_2$, 40-60% EtOAc/hexanes) to yield methyl (S)-3-methyl-1-oxo-1-((1R,3S,5R)-3-(5-((trimethylsilyl)ethynyl)-1H-imidazol-2-yl)-2-azabicyclo[3.1.0]

hexan-2-yl)butan-2-ylcarbamate (203 mg) as a yellow glass. LC-MS retention time 3.095 min; m/z 403.29 (MH+). LC data was recorded on a Shimadzu LC-10AS liquid chromatograph equipped with a PHENOMENEX® Luna 3u C18 2.0× 50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/ 0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 7.17 (br. s., 1H), 5.04-5.11 (m, 1H), 4.54 (d, J=6.8 Hz, 1H), 3.65 (s, 3H), 3.54-3.61 (m, 1H), 2.82 (s, 1H), 2.39-2.50 (m, 1H), 2.27-2.36 (m, 1H), 2.04-2.15 (m, 1H), 1.94-2.04 (m, 1H), 1.11 (dt, J=8.7, 5.6 Hz, 1H), 0.95 (d, J=6.8 Hz, 3H), 0.90 (d, J=6.8 Hz, 3H), 0.73-0.79 (m, 1H), 0.21 (s, 9H).

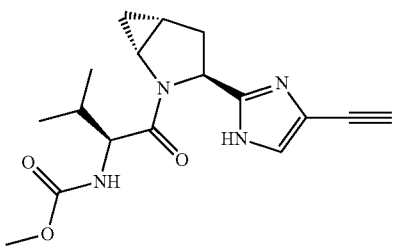 [SMILES: C#Cc1c[nH]c([C@@H]2C[C@H]3C[C@H]3N2C(=O)[C@@H](NC(=O)OC)C(C)C)n1]

Intermediate 157

Methyl (S)-1-((1R,3S,5R)-3-(4-ethynyl-1H-imidazol-2-yl)-2-azabicyclo[3.1.0]hexan-2-yl)-3-methyl-1-oxobutan-2-ylcarbamate Potassium carbonate (34.3 mg, 0.248 mmol) was added to a solution of methyl (S)-3-methyl-1-oxo-1-((1R,3S,5R)-3-(5-((trimethylsilyl)ethynyl)-1H-imidazol-2-yl)-2-azabicyclo[3.1.0]hexan-2-yl)butan-2-ylcarbamate (200 mg, 0.497 mmol) in methanol (5 mL) and the reaction was flushed with nitrogen, sealed and then heated at 50° C. for 4 h. and then stirred at rt overnight. The reaction was concentrated to dryness and then purified on a BIOTAGE® Horizon (12 g $SiO_2$, 70-90% EtOAc/hexanes) to yield methyl (S)-1-((1R,3S,5R)-3-(5-ethynyl-1H-imidazol-2-yl)-2-azabicyclo[3.1.0]hexan-2-yl)-3-methyl-1-oxobutan-2-ylcarbamate (151 mg) as a yellow glass. LC-MS retention time 1.788 min; m/z 331.32 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/ 0.1% trifluoroacetic acid and Solvent B was 10% $H_2O$/90% MeOH/0.1% trifluoroacetic acid. MS data was determined using a MICROMASS® Platform for LC in electrospray mode.

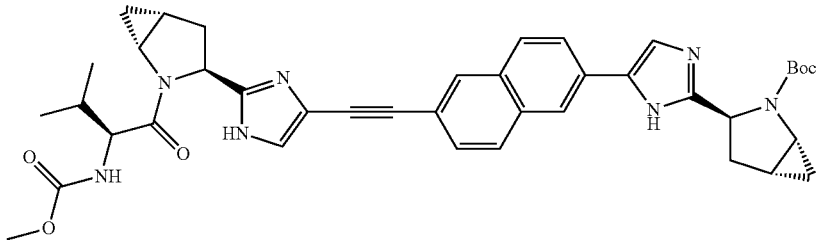 [SMILES: COC(=O)N[C@H](C(=O)N1[C@@H]2C[C@@H]2C[C@H]1c1nc(C#Cc2ccc3cc(-c4cnc([C@@H]5C[C@H]6C[C@H]6N5C(=O)OC(C)(C)C)[nH]4)ccc3c2)c[nH]1)C(C)C]

Intermediate 158

(1R,3S,5R)-tert-Butyl 3-(5-(6-((2-((1R,3S,5R)-2-((S)-2-(methoxycarbonylamino)-3-methylbutanoyl)-2-azabicyclo[3.1.0]hexan-3-yl)-1H-imidazol-4-yl)ethynyl)naphthalen-2-yl)-1H-imidazol-2-yl)-2-azabicyclo[3.1.0]hexane-2-carboxylate A mixture of (1R,3S,5R)-tert-butyl 3-(5-(6-bromonaphthalen-2-yl)-1H-imidazol-2-yl)-2-azabicyclo[3.1.0]hexane-2-carboxylate (208 mg, 0.457 mmol), methyl (S)-1-((1R,3S,5R)-3-(5-ethynyl-1H-imidazol-2-yl)-2-azabicyclo[3.1.0] hexan-2-yl)-3-methyl-1-oxobutan-2-ylcarbamate (151 mg, 0.457 mmol) and CuI (8.70 mg, 0.046 mmol) in DMF (4 mL) and TEA (0.19 mL, 1.4 mmol) was vacuum flushed with nitrogen (6×) over 10 minutes. Then Pd(PPh$_3$)$_4$ (53 mg, 0.046 mmol) was added and the reaction mixture was vacuum flushed with nitrogen (3×), sealed and heated at 60° C. for 20 h. The reaction was concentrated under a steam of nitrogen overnight and then purified preparative HPLC (40-80% MeOH/water with a TFA buffer) to yield a TFA salt of (1R, 3S,5R)-tert-butyl 3-(5-(6-((2-((1R,3S,5R)-2-((S)-2-(methoxycarbonylamino)-3-methylbutanoyl)-2-azabicyclo[3.1.0] hexan-3-yl)-1H-imidazol-5-yl)ethynyl)naphthalen-2-yl)-1H-imidazol-2-yl)-2-azabicyclo[3.1.0]hexane-2-carboxylate (270 mg) as a yellow solid. LC-MS retention time 2.995 min; m/z 704.70 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 8.28 (s, 1H), 8.18 (s, 1H), 8.06 (d, J=8.8 Hz, 1H), 7.98-8.03 (m, 2H), 7.89 (dd, J=8.5, 1.8 Hz, 1H), 7.69-7.85 (m, 1H), 7.67 (dd, J=8.7, 1.4 Hz, 1H), 5.11 (br. s., 1H), 4.84-4.91 (m, 2H), 4.55 (d, J=5.8 Hz, 1H), 3.70-3.77 (m, 1H), 3.67 (s, 3H), 2.72 (dd, J=13.6, 9.0 Hz, 1H), 2.55-2.63 (m, 1H), 2.39-2.50 (m, 2H), 2.11-2.20 (m, 1H), 2.02-2.11 (m, 1H), 1.81-1.89 (m, 1H), 1.45 (br. s., 9H), 1.07-1.14 (m, 1H), 1.00 (d, J=6.8 Hz, 3H), 0.93 (d, J=6.8 Hz, 3H), 0.84-0.93 (m, 2H), 0.74 (br. s., 1H).

Scheme 41
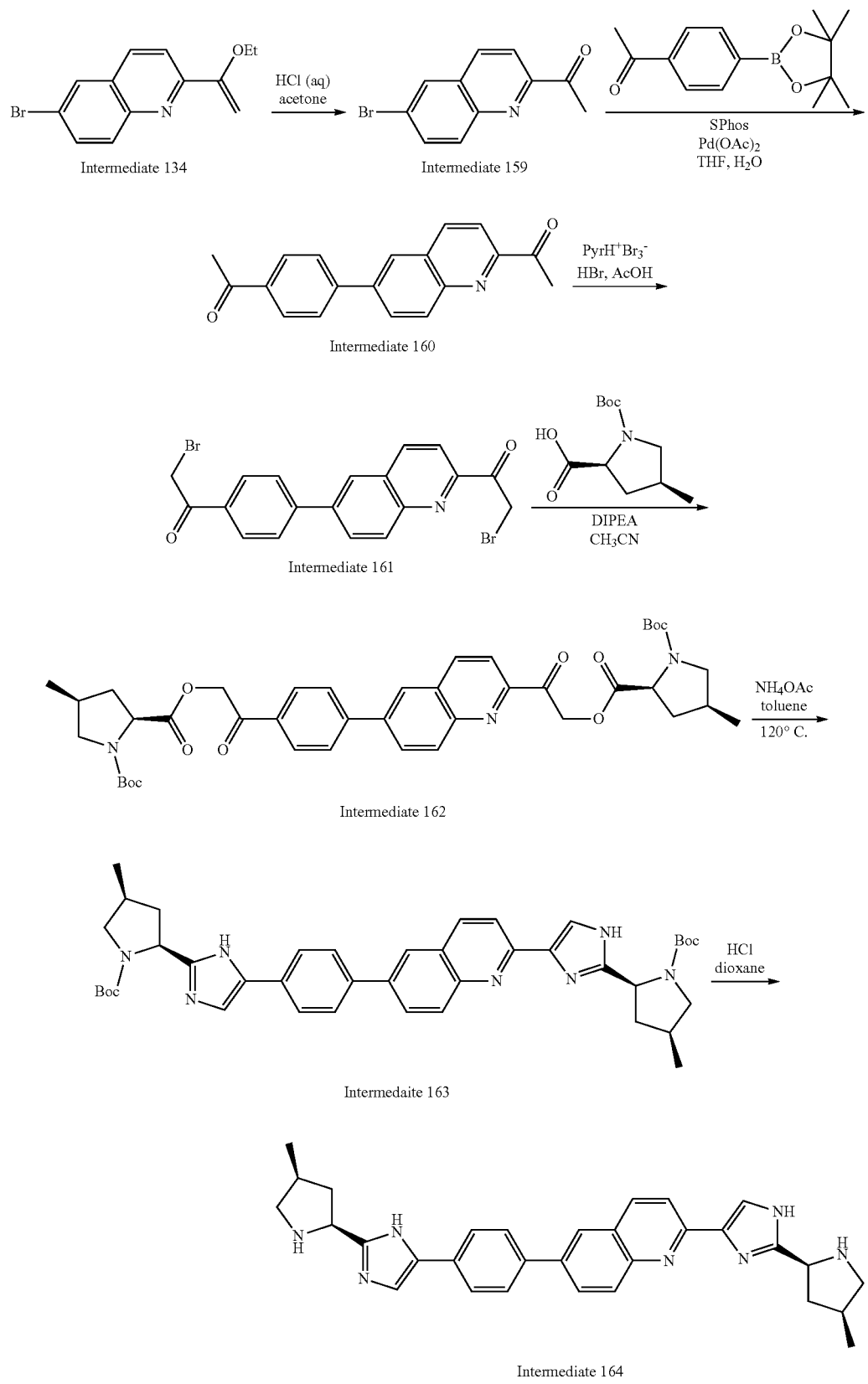

Intermediate 159

1-(6-Bromoquinolin-2-yl)ethanone

3M HCl (aq.) (10 mL, 30.0 mmol) was added to a suspension of 6-bromo-2-(1-ethoxyvinyl)quinoline (780 mg, 2.80 mmol) in acetone (20 mL) and the reaction mixture was stirred at rt for 5 h. The reaction mixture was concentrated, dissolved into THF (20 mL) and treated with 3N HCl (aq.) (5 mL) was clear reaction solution was stirred at 60° C. for 5 h. The reaction was, cooled, neutralized with aq. NaOH and NaHCO$_3$ and extracted with EtOAc. The organic layer was dried, and concentrated to yield crude 1-(6-bromoquinolin-2-yl)ethanone (710 mg) as white solid. LC-MS retention time 3.703 min; m/z 250, 251.99 (1:1) (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode.

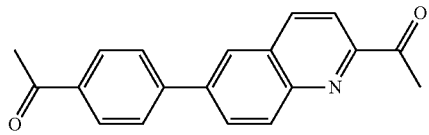

Intermediate 160

1-(6-(4-Acetylphenyl)quinolin-2-yl)ethanone

Pd(OAc)$_2$ (62.9 mg, 0.280 mmol) was added to a solution of 4-acetylphenylboronic acid (689 mg, 4.20 mmol), 1-(6-bromoquinolin-2-yl)ethanone (700 mg, 2.8 mmol), dicyclohexyl(2',6'-dimethoxybiphenyl-2-yl)phosphine (230 mg, 0.560 mmol) and K$_2$CO$_3$ (1.16 g, 8.40 mmol) in dioxane (10 mL) and water (2.500 mL) and the reaction mixture was refluxed at 110° C. for 5 h. The reaction mixture was cooled to rt and partitioned between sat.aq NH$_4$Cl and EtOAc. The organic layer was washed with NaHCO$_3$ and brine and then dried (MgSO$_4$), filtered, concentrated and purified by flash silica gel chromatography (loading solvent: DCM, eluted with 0~20% EtOAc/hexanes) to yield 1-(6-(4-acetylphenyl)quinolin-2-yl)ethanone (781 mg) as white solid. LC-MS retention time 3.776 min; m/z 290.29 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, chloroform-d) δ ppm 8.35 (d, J=8.3 Hz, 1H), 8.34 (d, J=8.3 Hz, 1H), 8.19 (d, J=8.5 Hz, 1H), 8.12 (d, J=8.3 Hz, 1H), 8.08-8.16 (m, 3H), 7.85 (d, J=8.3 Hz, 1H), 7.82-7.89 (m, 1H), 2.91 (s, 3H), 2.69 (s, 3H).

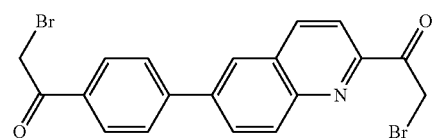 [SMILES: O=C(CBr)c1ccc(-c2ccc3nc(C(=O)CBr)ccc3c2)cc1]

Intermediate 161

2-Bromo-1-(6-(4-(2-bromoacetyl)phenyl)quinolin-2-yl)ethanone

Pyridinium tribromide (221 mg, 0.691 mmol) was added to a suspension of 1-(6-(4-acetylphenyl)quinolin-2-yl)ethanone (100 mg, 0.346 mmol) and HBr (0.061 mL, 0.35 mmol) in acetic acid (3 mL) the reaction mixture was stirred at 70° C.) for 6 h. The reaction was concentrated under vacuum and the residue was partitioned between aq NaHCO$_3$ (15 mL) and EtOAc (30 mL+10 mL+10 mL). The organic layers were combined, washed with brine, dried, filtered and concentrated to yield crude 2-bromo-1-(6-(4-(2-bromoacetyl)phenyl)quinolin-2-yl)ethanone (120 mg) as white solid. LC-MS retention time 4.138 min; m/z 448.01 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode.

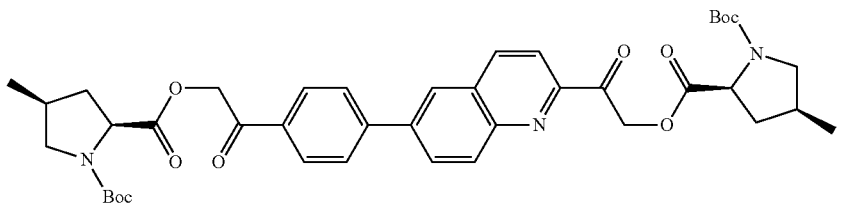

Intermediate 162

(2S,4S)-2-(2-(6-(4-(2-((2S,4S)-1-(tert-Butoxycarbonyl)-4-methylpyrrolidine-2-carbonyloxy)acetyl)phenyl)quinolin-2-yl)-2-oxoethyl) 1-tert-butyl 4-methylpyrrolidine-1,2-dicarboxylate DIPEA (0.094 mL, 0.537 mmol) was added to a solution of 2-bromo-1-(6-(4-(2-bromoacetyl)phenyl)quinolin-2-yl) ethanone (60 mg, 0.134 mmol) and (2S,4S)-1-(tert-butoxycarbonyl)-4-methylpyrrolidine-2-carboxylic acid (64.6 mg, 0.282 mmol) in acetonitrile (2 mL) and the mixture was stirred at rt for 16 h. The reaction mixture was partitioned between EtOAc (20 mL+20 mL)/aq NaHCO₃ (5 mL). The combined organic layers were washed with aq NaHCO₃, brine, dried, filtered and concentrated to yield crude (2S,4S)-2-(2-(6-(4-(2-((2S,4S)-1-(tert-butoxycarbonyl)-4-methylpyrrolidine-2-carbonyloxy)acetyl)phenyl)quinolin-2-yl)-2-oxoethyl) 1-tert-butyl 4-methylpyrrolidine-1,2-dicarboxylate (100 mg) as orange solid. This material was used without further purification. LC-MS retention time 4.558 min; m/z 742.36 (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode.

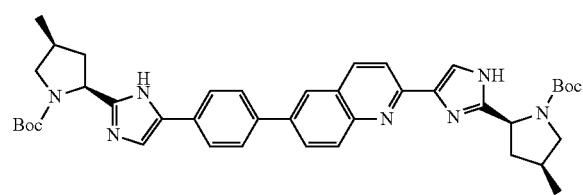 [SMILES: C[C@H]1C[C@@H](c2nc(-c3ccc4cc(-c5ccc(-c6cnc([C@@H]7C[C@H](C)CN7C(=O)OC(C)(C)C)[nH]6)cc5)ccc4n3)c[nH]2)N(C(=O)OC(C)(C)C)C1]

Intermediate 163

(2S,4S)-tert-Butyl 2-(5-(4-(2-(2-((2S,4S)-1-(tert-butoxycarbonyl)-4-methylpyrrolidin-2-yl)-1H-imidazol-4-yl)quinolin-6-yl)phenyl)-1H-imidazol-2-yl)-4-methylpyrrolidine-1-carboxylate Ammonium acetate (207 mg, 2.69 mmol) was added to a solution of (2S,4S)-2-(2-(6-(4-(2-((2S,4S)-1-(tert-butoxycarbonyl)-4-methylpyrrolidine-2-carbonyloxy)acetyl)phenyl)quinolin-2-yl)-2-oxoethyl) 1-tert-butyl 4-methylpyrrolidine-1,2-dicarboxylate (100 mg, 0.134 mmol) in toluene (3 mL) and the reaction mixture was stirred at 120° C. (microwave reactor) for 3 h. The reaction was partitioned between EtOAc (20 mL+10 mL+10 mL) and aq NaHCO₃ (10 mL) and the combined organic layers were dried, filtered and concentrated. This crude product was purified by preparative HPLC (H₂O—CH₃CN with 10 mM NH₄OAc buffer) to yield product (2S,4S)-tert-butyl 2-(5-(6-(4-(2-((2S,4S)-1-(tert-butoxycarbonyl)-4-methylpyrrolidin-2-yl)-1H-imidazol-5-yl)phenyl)quinolin-2-yl)-1H-imidazol-2-yl)-4-methylpyrrolidine-1-carboxylate (16.6 mg) as a yellow solid. LC-MS retention time 3.270 min; m/z 704.72 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode.

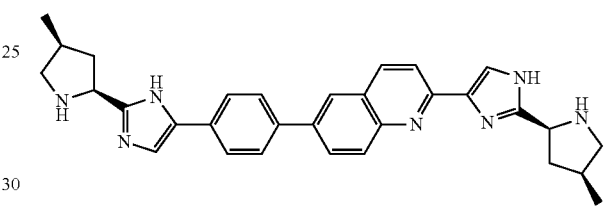

Intermediate 164

2-(2-((2S,4S)-4-Methylpyrrolidin-2-yl)-1H-imidazol-4-yl)-6-(4-(2-((2S,4S)-4-methylpyrrolidin-2-yl)-1H-imidazol-5-yl)phenyl)quinoline 4M HCl (0.2 mL, 0.800 mmol) in dioxane was added to a solution of (2S,4S)-tert-butyl 2-(5-(6-(4-(2-((2S,4S)-1-(tert-butoxycarbonyl)-4-methylpyrrolidin-2-yl)-1H-imidazol-5-yl)phenyl)quinolin-2-yl)-1H-imidazol-2-yl)-4-methylpyrrolidine-1-carboxylate (16.6 mg, 0.024 mmol) in dioxane (1 mL) and the reaction mixture was stirred at rt for 3 d. The reaction mixture was concentrated to yield a crude HCl salt of 2-(2-((2S,4S)-4-methylpyrrolidin-2-yl)-1H-imidazol-5-yl)-6-(4-(2-((2S,4S)-4-methylpyrrolidin-2-yl)-1H-imidazol-5-yl)phenyl)quinoline (19.1 mg) as yellow solid. LC-MS retention time 2.765 min; m/z 504.47 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode.

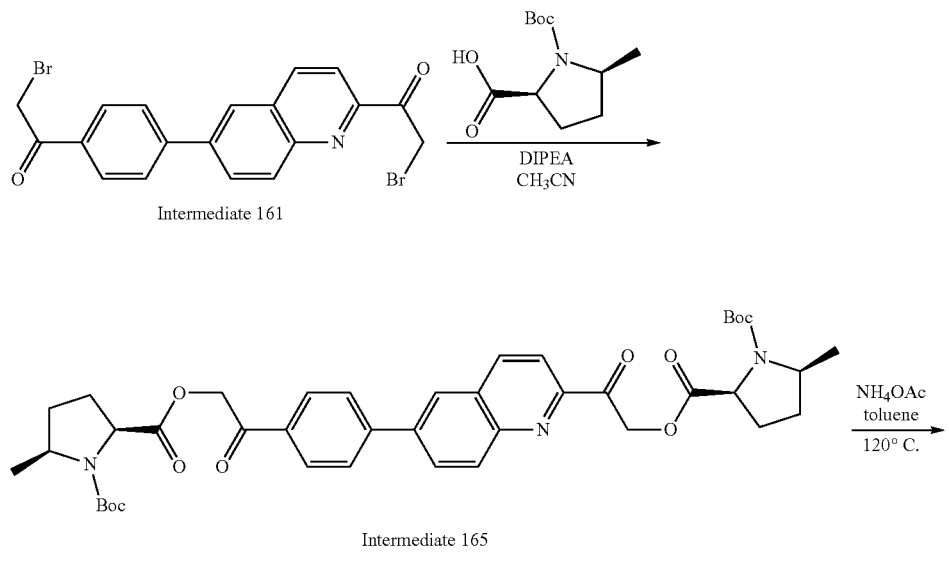

Scheme 42

Intermediate 165

(2S,5S)-2-(2-(6-(4-(2-((2S,4S)-1-(tert-Butoxycarbonyl)-4-methylpyrrolidine-2-carbonyloxy)acetyl)phenyl)quinolin-2-yl)-2-oxoethyl) 1-tert-butyl 5-methylpyrrolidine-1,2-dicarboxylate

DIPEA (0.059 mL, 0.335 mmol) was added to a solution of 2-bromo-1-(6-(4-(2-bromoacetyl)phenyl)quinolin-2-yl)ethanone (50 mg, 0.11 mmol) and (2S,5S)-1-(tert-butoxycarbonyl)-5-methylpyrrolidine-2-carboxylic acid (54 mg, 0.24 mmol) in acetonitrile (2 mL) and the reaction mixture was stirred at rt for 16 h. The reaction was partitioned between EtOAc (20+20 mL)/aq NaHCO₃ (5 mL). The combined organic layers were washed with sat. aq NaHCO₃, brine, dried, filtered and concentrated to yield crude (2S,5S)-2-(2-(6-(4-(2-((2S,5S)-1-(tert-butoxycarbonyl)-5-methylpyrrolidine-2-carbonyloxy)acetyl)phenyl)quinolin-2-yl)-2-oxoethyl) 1-tert-butyl 5-methylpyrrolidine-1,2-dicarboxylate (69 mg) as orange solid. This crude was used without further purification. LC-MS retention time 4.483 min; m/z 744.61 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode.

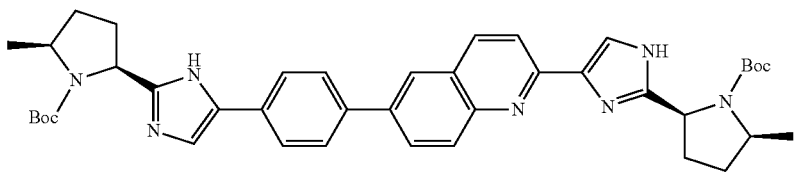

Intermediate 166

(2S,5S)-tert-Butyl 2-(5-(4-(2-(2-((2S,5S)-1-(tert-butoxycarbonyl)-5-methylpyrrolidin-2-yl)-1H-imidazol-4-yl)quinolin-6-yl)phenyl)-1H-imidazol-2-yl)-5-methylpyrrolidine-1-carboxylate Ammonium acetate (107 mg, 1.39 mmol) was added to a suspension of (2S,5S)-2-(2-(6-(4-(2-((2S,5S)-1-(tert-butoxycarbonyl)-5-methylpyrrolidine-2-carbonyloxy)acetyl)phenyl)quinolin-2-yl)-2-oxoethyl) 1-tert-butyl 5-methylpyrrolidine-1,2-dicarboxylate (69 mg, 0.093 mmol) in toluene (Volume: 2 mL) and the reaction mixture was stirred at 120° C. (microwave reactor) for 3 h. The reaction was partitioned between EtOAc (10 mL+5 mL+5 mL) and aq NaHCO3 (5 mL). The combined organic layers were dried, filtered and concentrated and the crude product was purified by preparative HPLC (H$_2$O—CH$_3$CN with 10 mM NH$_4$OAc buffer) to yield product (2S,5S)-tert-butyl 2-(4-(6-(4-(2-((2S,5S)-1-(tert-butoxycarbonyl)-5-methylpyrrolidin-2-yl)-1H-imidazol-4-yl)phenyl)quinolin-2-yl)-1H-imidazol-2-yl)-5-methylpyrrolidine-1-carboxylate (13.4 mg) as a yellow solid. LC-MS retention time 4.350 min; m/z 702.29 (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, MeOD) δ ppm 8.37 (d, J=8.8 Hz, 1H), 8.16 (s, 1H), 8.07-8.10 (m, 2H), 8.03 (d, J=8.8 Hz, 1H), 7.79-7.88 (m, 5H), 7.40 (s, 1H), 4.90-5.07 (m, 2H), 3.99-4.13 (m, 2H), 2.10-2.39 (m, 6H), 1.68-1.82 (m, 2H), 1.43 (d, J=6.0 Hz, 6H), 1.24-1.59 (m, 22H).

Intermediate 167

2-(2-((2S,5S)-5-Methylpyrrolidin-2-yl)-1H-imidazol-4-yl)-6-(4-(2-((2S,5S)-5-methylpyrrolidin-2-yl)-1H-imidazol-5-yl)phenyl)quinoline 4M HCl (0.2 mL, 0.8 mmol) in dioxane was added to a solution of (2S,5S)-tert-butyl 2-(5-(6-(4-(2-((2S,5S)-1-(tert-butoxycarbonyl)-5-methylpyrrolidin-2-yl)-1H-imidazol-5-yl)phenyl)quinolin-2-yl)-1H-imidazol-2-yl)-5-methylpyrrolidine-1-carboxylate (12.7 mg, 0.018 mmol) in dioxane (1 mL) and the mixture was stirred at rt for 3 d. The reaction mixture was concentrated to yield a crude HCl salt of 2-(2-((2S,5S)-5-methylpyrrolidin-2-yl)-1H-imidazol-5-yl)-6-(4-(2-((2S,5S)-5-methylpyrrolidin-2-yl)-1H-imidazol-5-yl)phenyl)quinoline (18.1 mg) as yellow solid. LC-MS retention time 2.597 min; m/z 504.46 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 9.09 (d, J=9.0 Hz, 1H), 8.66 (s, 1H), 8.54-8.61 (m, 2H), 8.51 (d, J=9.0 Hz, 1H), 8.50 (d, J=8.8 Hz, 1H), 8.00-8.08 (m, 4H), 7.99 (s, 1H), 5.14 (t, J=8.5 Hz, 1H), 5.07 (t, J=8.0 Hz, 1H), 3.90-4.04 (m, 2H), 2.52-2.75 (m, 4H), 2.39-2.53 (m, 2H), 1.98-2.14 (m, 2H), 1.59 (dd, J=9.7, 6.7 Hz, 6H).

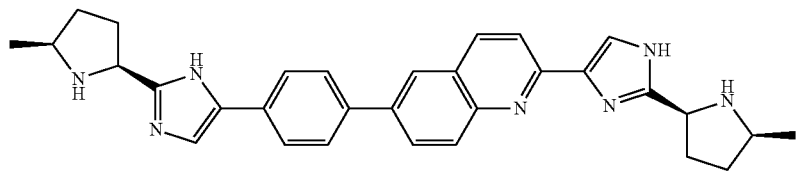

Scheme 43

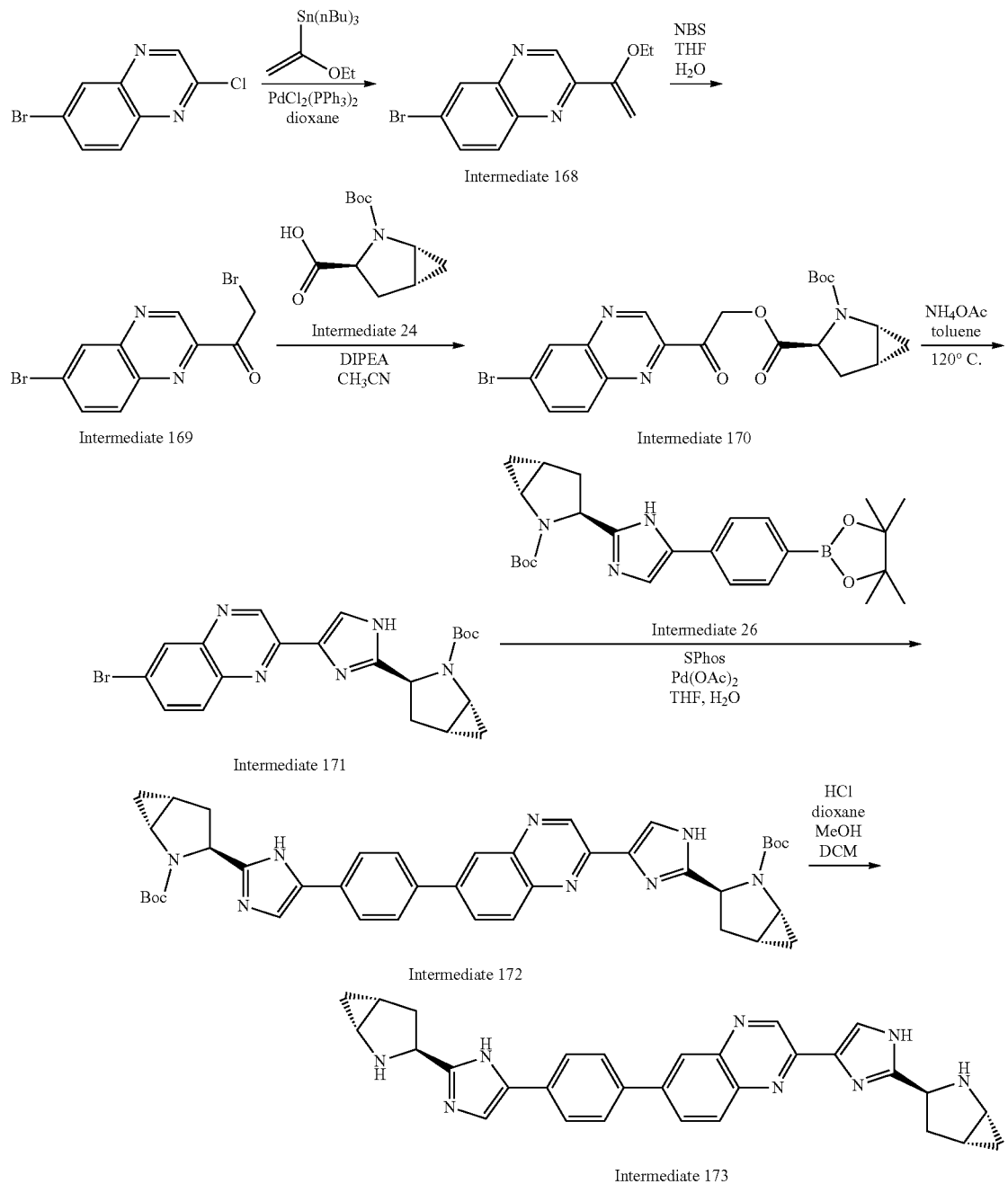

Intermediate 173 was prepared in an analogous manner to Intermediate 139 in Scheme 35 by utilizing 6-bromo-2-chloroquinoxaline as the starting material rather than 6-bromo-2-chloroquinoline. Analytical data shown below.

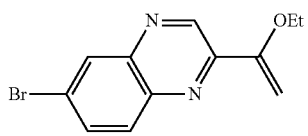 [SMILES: C=C(OCC)c1cnc2cc(Br)ccc2n1]

Intermediate 168

6-Bromo-2-(1-ethoxyvinyl)quinoxaline

The reaction yielded the desired product (380 mg) as a white solid. LC-MS retention time 4.178 min; m/z 278.9, 280.98 (1:1) (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode.

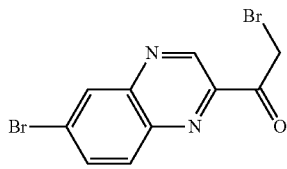 [SMILES: O=C(CBr)c1cnc2cc(Br)ccc2n1]

Intermediate 169

2-Bromo-1-(6-bromoquinoxalin-2-yl)ethanone

The reaction yielded the desired product (390 mg) as a white solid. LC-MS retention time 3.743 min; m/z 331.12 (1:2:1) (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode.

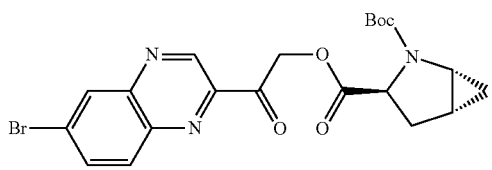 [SMILES: CC(C)(C)OC(=O)N1[C@@H]2C[C@@H]2C[C@H]1C(=O)OCC(=O)c1cnc2cc(Br)ccc2n1]

Intermediate 170

(1R,3S,5R)-3-(2-(6-Bromoquinoxalin-2-yl)-2-oxoethyl) 2-tert-butyl 2-azabicyclo[3.1.0]hexane-2,3-dicarboxylate The reaction yielded the desired product (270 mg) as a pink/orange solid. LC-MS retention time 4.115 min; m/z 473, 475.81 (1:1) (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode.

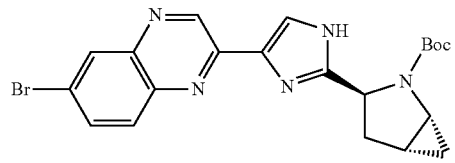 [SMILES: CC(C)(C)OC(=O)N1[C@@H]2C[C@@H]2C[C@H]1c1nc(-c2cnc3cc(Br)ccc3n2)c[nH]1]

Intermediate 171 tert-Butyl (1R,3S,5R)-3-(4-(6-bromo-2-quinoxalinyl)-1H-imidazol-2-yl)-2-azabicyclo[3.1.0]hexane-2-carboxylate The reaction yielded the desired product (125 mg) as a red/orange solid. LC-MS retention time 3.958 min; m/z 453.90, 455.87 (1:1) (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode. ¹H NMR (400 MHz, MeOD) δ ppm 9.40 (br. s., 1H), 8.22 (d, J=2.0 Hz, 1H), 7.96 (d, J=8.8 Hz, 1H), 7.93-7.99 (m, 1H), 7.90 (dd, J=8.8, 2.0 Hz, 1H), 4.71-4.81 (m, 1H), 3.59 (br. s., 1H), 2.49-2.63 (m, 1H), 2.31-2.45 (m, 1H), 1.68-1.82 (m, 1H), 1.16-1.53 (m, 5H), 0.81-0.94 (m, 1H), 0.64 (br. s., 1H).

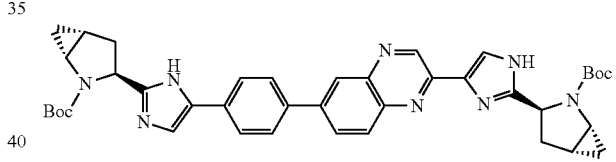

Intermediate 172 tert-Butyl (1R,3S,5R)-3-(4-(6-(4-(2-((1R,3S,5R)-2-(tert-butoxycarbonyl)-2-azabicyclo[3.1.0]hex-3-yl)-1H-imidazol-4-yl)phenyl)-2-quinoxalinyl)-1H-imidazol-2-yl)-2-azabicyclo[3.1.0]hexane-2-carboxylate The reaction yielded the desired product (64.4 mg) as a bright yellow solid. LC-MS retention time 3.696 min; m/z 699.3 (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode. ¹H NMR (400 MHz, DMSO-d₆) δ ppm 9.45 (s, 1H), 8.31 (s, 1H), 8.19 (d, J=8.3 Hz, 1H), 8.07 (d, J=8.8 Hz, 1H), 7.97 (s, 1H), 7.81-7.95 (m, 4H), 7.60 (s, 1H), 4.57-4.80 (m, 2H), 3.23-3.60 (m, 2H), 2.23-2.48 (m, 4H), 1.61-1.75 (m, 2H), 1.28 (br. s., 18H), 0.73-0.87 (m, 2H), 0.59 (br. s., 2H).

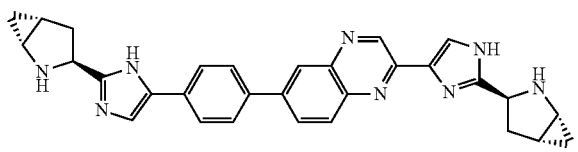 [SMILES: c1cc(-c2cnc([C@@H]3C[C@H]4C[C@H]4N3)[nH]2)ccc1-c1ccc2nc(-c3c[nH]c([C@@H]4C[C@H]5C[C@H]5N4)n3)cnc2c1]

min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 9.54 (s, 1H), 8.40-8.43 (m, 1H), 8.34 (s, 1H), 8.23-8.30 (m, 2H), 8.13 (s, 1H), 8.00-8.08 (m, 4H), 4.88-5.08 (m, 2H), 3.53-3.77 (m, 2H), 2.64-2.90 (m, 4H), 2.08-2.22 (m, 2H), 1.23-1.36 (m, 2H), 1.02-1.14 (m, 2H).

Scheme 44

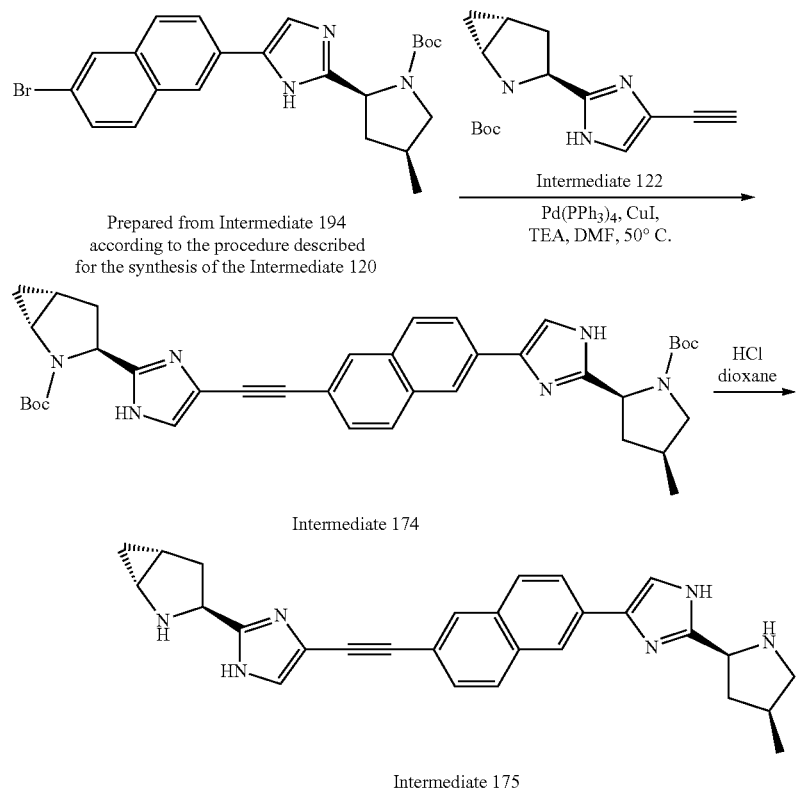

Intermediate 173

Methyl ((1S)-1-(((2S,4S)-2-(4-(6-(4-(2-((2S,4S)-1-((2S)-2-((methoxycarbonyl)amino)-3-methylbutanoyl)-4-methyl-2-pyrrolidinyl)-1H-imidazol-4-yl)phenyl)-2-quinolinyl)-1H-imidazol-2-yl)-4-methyl-1-pyrrolidinyl)carbonyl)-2-methylpropyl)carbamate The reaction yielded an HCl salt of the desired product (80 mg) as a yellow solid. LC-MS retention time 2.915 min; m/z 501.42 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1

Intermediate 174

(1R,3S,5R)-tert-Butyl 3-(4-((6-(2-((2S,4S)-1-(tert-butoxycarbonyl)-4-methylpyrrolidin-2-yl)-1H-imidazol-4-yl)naphthalen-2-yl)ethynyl)-1H-imidazol-2-yl)-2-azabicyclo[3.1.0]hexane-2-carboxylate Compound was prepared in an analogous manner to Intermediate 153 with the appropriate starting materials to yield a TFA salt of the title compound (121 mg) as a yellow glass. LC-MS retention time 4.100 min; m/z 647.37 (MH−). LC data was recorded on a Shimadzu LC-10AS liquid chromatograph equipped with a PHENOMENEX® Luna 3u C18 2.0× 50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode.

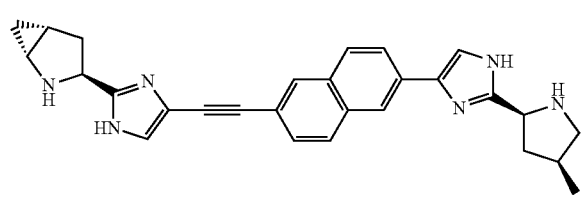 [SMILES: C[C@@H]1CN[C@H](c2nc(-c3ccc4cc(C#Cc5c[nH]c([C@@H]6C[C@H]7C[C@H]7N6)n5)ccc4c3)c[nH]2)C1]

Intermediate 175

(1R,3S,5R)-3-(4-((6-(2-((2S,4S)-4-Methylpyrrolidin-2-yl)-1H-imidazol-4-yl)naphthalen-2-yl)ethynyl)-1H-imidazol-2-yl)-2-azabicyclo[3.1.0]hexane 2M HCl (0.33 mL, 0.66 mmol) in dioxane was added to a solution of a TFA salt of (1R,3S,5R)-tert-butyl 3-(5-((6-(2-((2S,4S)-1-(tert-butoxycarbonyl)-4-methylpyrrolidin-2-yl)-1H-imidazol-4-yl)naphthalen-2-yl)ethynyl)-1H-imidazol-2-yl)-2-azabicyclo[3.1.0]hexane-2-carboxylate (115 mg, 0.131 mmol) in dioxane (2 mL) and the reaction was stirred vigorously overnight. The reaction was concentrated to yield an HCl salt of (1R,3S,5R)-3-(4-((6-(2-((2S,4S)-4-methylpyrrolidin-2-yl)-1H-imidazol-4-yl)naphthalen-2-yl)ethynyl)-1H-imidazol-2-yl)-2-azabicyclo[3.1.0]hexane (87 mg) which was used without further purification. LC-MS retention time 2.793 min; m/z 449.41 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode.

Scheme 45

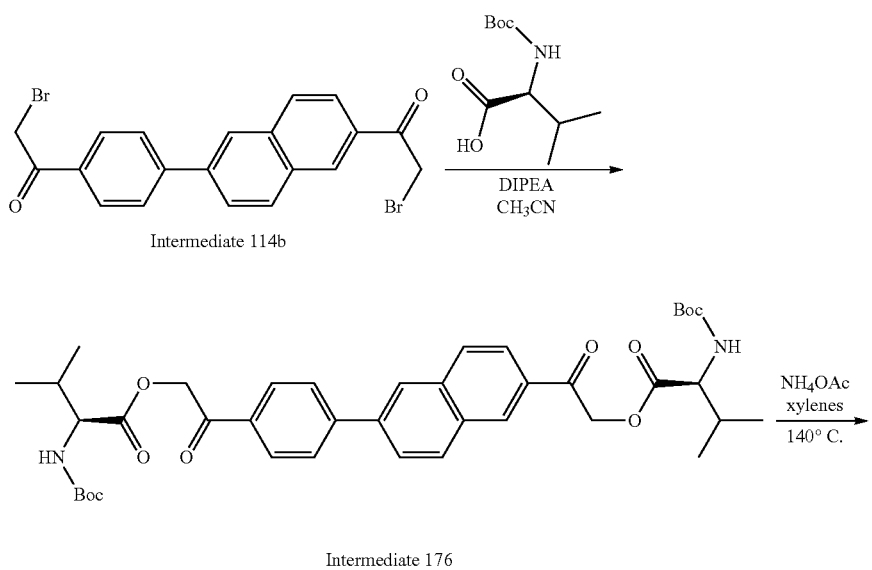

Intermediate 176

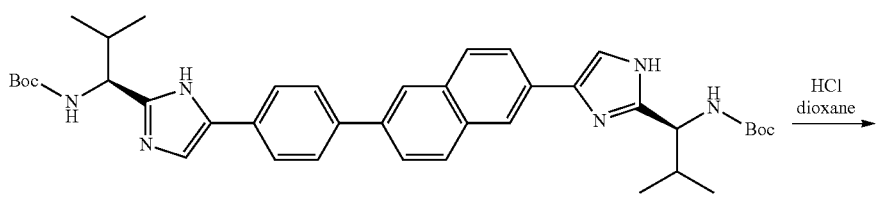

Intermediate 177

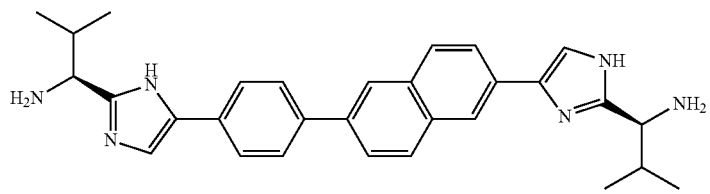

Intermediate 178

Intermediate 178 was prepared in an analogous manner to the preparation of Intermediate 117 in Scheme 29 utilizing (S)-2-(tert-butoxycarbonylamino)-3-methylbutanoic acid as a starting material rather than (2S,5S)-1-(tert-butoxycarbonyl)-5-methylpyrrolidine-2-carboxylic acid. Analytical data for the intermediates shown below.

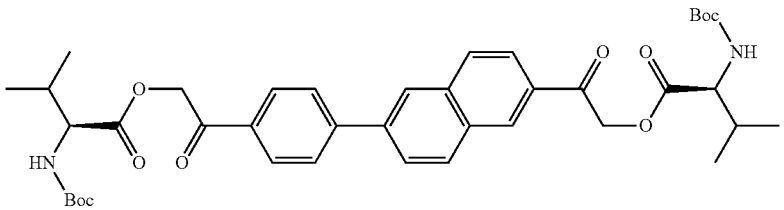 [SMILES: CC(C)[C@H](NC(=O)OC(C)(C)C)C(=O)OCC(=O)c1ccc(-c2ccc3cc(C(=O)COC(=O)[C@@H](NC(=O)OC(C)(C)C)C(C)C)ccc3c2)cc1]

Intermediate 176

(S)-2-(4-(6-(2-((S)-2-(tert-Butoxycarbonylamino)-3-methylbutanoyloxy)acetyl)naphthalen-2-yl)phenyl)-2-oxoethyl 2-(tert-butoxycarbonylamino)-3-methylbutanoate The reaction yielded the desired product (700 mg) as a tan solid. LC-MS retention time 2.243 min; m/z 717.5 (MH−). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1.0 mL/min, a gradient of 100% Solvent A/0% Solvent B to 0% Solvent A/100% Solvent B, a gradient time of 2 min, a hold time of 1 min, and an analysis time of 3 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode.

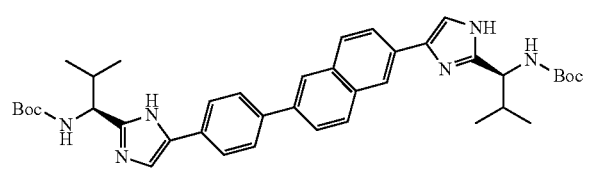 [SMILES: CC(C)[C@H](NC(=O)OC(C)(C)C)c1nc(-c2ccc3cc(-c4ccc(-c5cnc([C@@H](NC(=O)OC(C)(C)C)C(C)C)[nH]5)cc4)ccc3c2)c[nH]1]

Intermediate 177 tert-Butyl ((1S)-1-(4-(4-(6-(2-((1S)-1-((tert-butoxycarbonyl)amino)-2-methylpropyl)-1H-imidazol-4-yl)-2-naphthyl)phenyl)-1H-imidazol-2-yl)-2-methylpropyl)carbamate The reaction yielded the desired product (453 mg) as a yellow solid. LC-MS retention time 2.407 min; m/z 677.6 (MH−). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1.0 mL/min, a gradient of 100% Solvent A/0% Solvent B to 0% Solvent A/100% Solvent B, a gradient time of 2 min, a hold time of 1 min, and an analysis time of 3 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode.

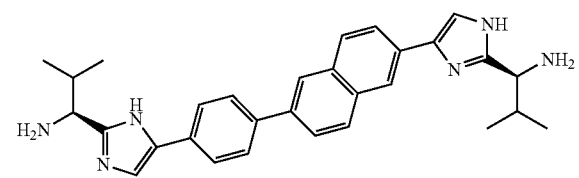 [SMILES: CC(C)[C@H](N)c1nc(-c2ccc3cc(-c4ccc(-c5cnc([C@@H](N)C(C)C)[nH]5)cc4)ccc3c2)c[nH]1]

Intermediate 178

(S)-1-(5-(4-(6-(2-((S)-1-Amino-2-methylpropyl)-1H-imidazol-4-yl)naphthalen-2-yl)phenyl)-1H-imidazol-2-yl)-2-methylpropan-1-amine The reaction yielded an HCl salt of the desired product (390 mg) as a yellow solid. LC-MS retention time 2.080 min; m/z 477.4 (MH−). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1.0 mL/min, a gradient of 100% Solvent A/0% Solvent B to 0% Solvent A/100% Solvent B, a gradient time of 2 min, a hold time of 1 min, and an analysis time of 3 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode.

Scheme 46

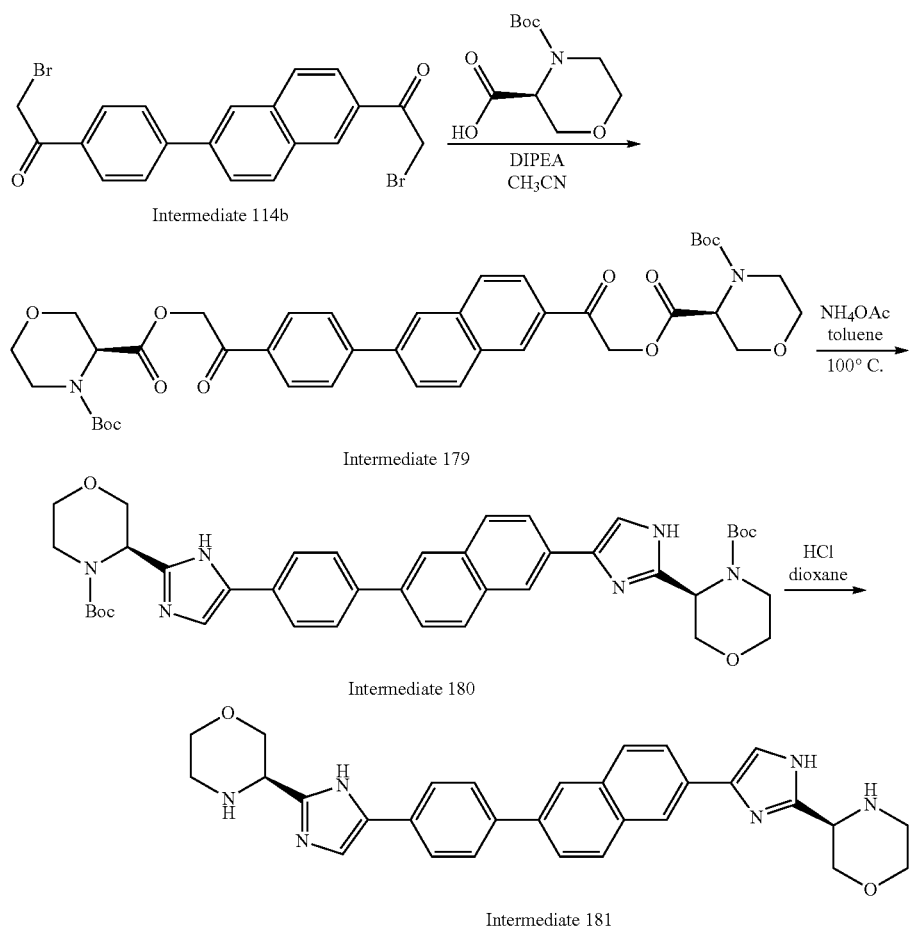

Intermediate 181 was prepared in an analogous manner to the preparation of Intermediate 117 in Scheme 29 utilizing (S)-4-(tert-butoxycarbonyl)morpholine-3-carboxylic acid as a starting material rather than (2S,5S)-1-(tert-butoxycarbonyl)-5-methylpyrrolidine-2-carboxylic acid. Analytical data for the intermediates shown below.

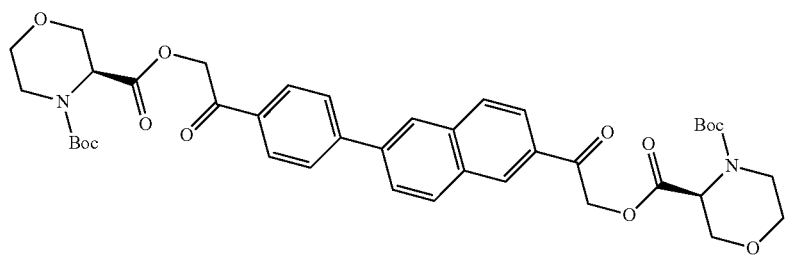 [SMILES: CC(C)(C)OC(=O)N1CCOC[C@H]1C(=O)OCC(=O)c1ccc(-c2ccc3cc(C(=O)COC(=O)[C@@H]4COCCN4C(=O)OC(C)(C)C)ccc3c2)cc1]

Intermediate 179

(S)-3-(2-(4-(6-(2-((S)-4-(tert-Butoxycarbonyl)morpholine-3-carbonyloxy)acetyl)naphthalen-2-yl)phenyl)-2-oxoethyl) 4-tert-butyl morpholine-3,4-dicarboxylate The reaction yielded an HCl salt of the desired product (1.60 g) as an off-white solid foam. LC-MS retention time 4.413 min; m/z 770.29 (MNa+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, chloroform-d) δ ppm 8.47 (s, 1H), 8.13 (s, 1H), 7.98-8.11 (m, 5H), 7.86 (d, J=8.3 Hz, 3H), 5.39-5.70 (m, 4H), 4.66-4.83 (m, 2H), 4.46-4.63 (m, 2H), 3.91-4.03 (m, 2H), 3.68-3.85 (m, 4H), 3.49-3.59 (m, 3H), 3.27-3.40 (m, 1H), 1.51 (s, 18H).

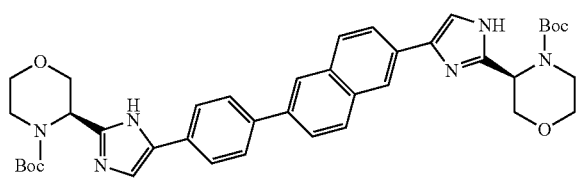 [SMILES: CC(C)(C)OC(=O)N1CCOC[C@H]1c1nc(-c2ccc3cc(-c4ccc(-c5cnc([C@@H]6COCCN6C(=O)OC(C)(C)C)[nH]5)cc4)ccc3c2)c[nH]1]

Intermediate 180

(R)-tert-Butyl 3-(5-(4-(6-(2-((R)-4-(tert-butoxycarbonyl)morpholin-3-yl)-1H-imidazol-4-yl)naphthalen-2-yl)phenyl)-1H-imidazol-2-yl)morpholine-4-carboxylate The reaction yielded the desired product (1.12 g) as an orange solid. LC-MS retention time 3.608 min; m/z 707.94 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode. ¹H NMR (400 MHz, MeOD) δ ppm 8.22 (br. s., 1H), 8.09 (s, 1H), 7.90-7.97 (m, 2H), 7.75-7.89 (m, 6H), 7.49 (br. s., 1H), 7.41 (br. s., 1H), 5.17-5.24 (m, 2H), 4.42 (t, J=11.2 Hz, 2H), 3.82-3.95 (m, 6H), 3.59 (tt, J=11.6, 3.0 Hz, 2H), 3.39-3.51 (m, 2H), 1.50 (d, J=2.8 Hz, 18H).

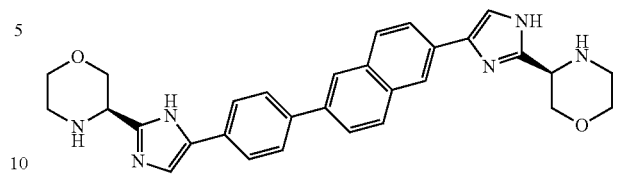

Intermediate 181

(R)-3-(5-(4-(6-(2-((R)-Morpholin-3-yl)-1H-imidazol-4-yl)naphthalen-2-yl)phenyl)-1H-imidazol-2-yl)morpholine The reaction yielded an HCl salt of the desired product (312 mg) as a yellow solid. LC-MS retention time 2.988 min; m/z 507.72 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode.

Scheme 47

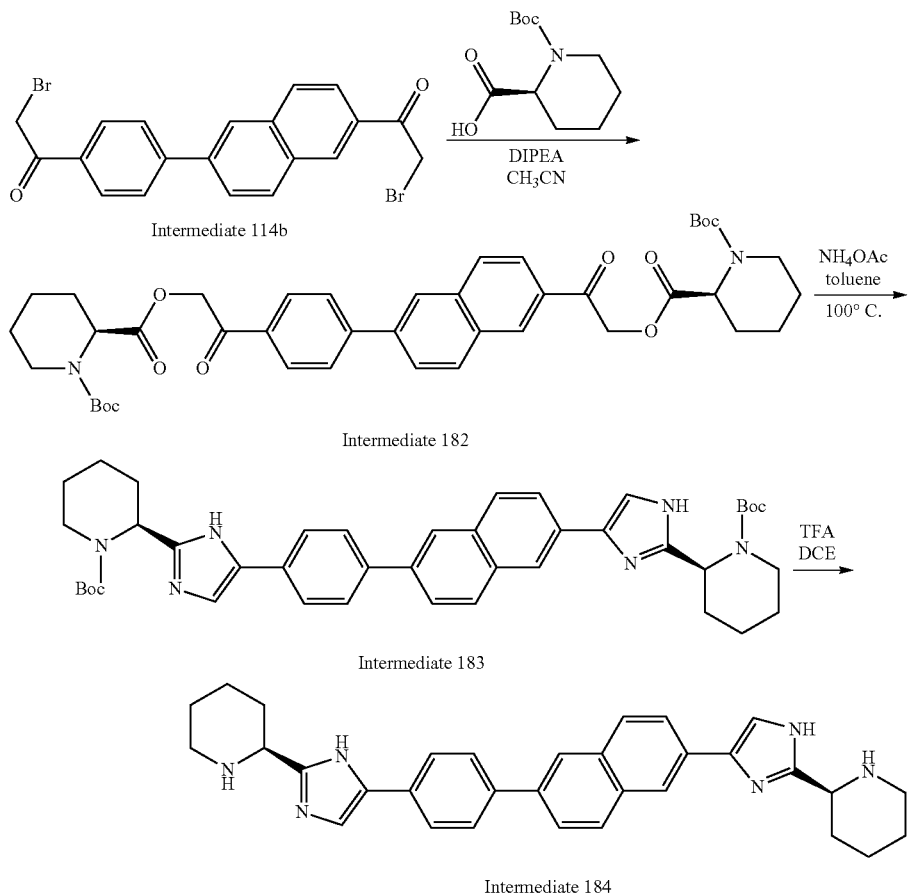

Intermediate 184 was prepared in an analogous manner to the preparation of Intermediate 117 in Scheme 29 utilizing (S)-1-(tert-butoxycarbonyl)piperidine-2-carboxylic acid as a starting material rather than (2S,5S)-1-(tert-butoxycarbonyl)-5-methylpyrrolidine-2-carboxylic acid. Analytical data for the intermediates shown below.

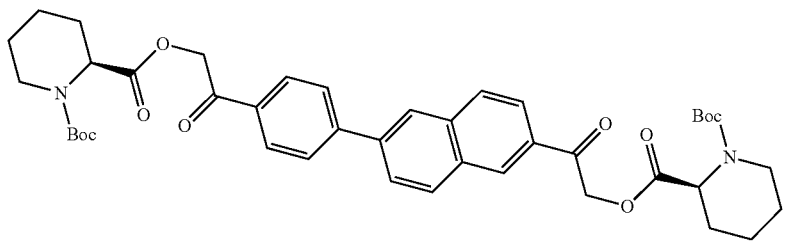 [SMILES: CC(C)(C)OC(=O)N1CCCC[C@H]1C(=O)OCC(=O)c1ccc(-c2ccc3cc(C(=O)COC(=O)[C@@H]4CCCCN4C(=O)OC(C)(C)C)ccc3c2)cc1]

Intermediate 182

(S)-2-(2-(4-(6-(2-((S)-1-(tert-Butoxycarbonyl)piperidine-2-carbonyloxy)acetyl)naphthalen-2-yl)phenyl)-2-oxoethyl) 1-tert-butyl piperidine-1,2-dicarboxylate The reaction yielded the desired product (1.67 g) as a solidified light yellow foam. LC-MS retention time 4.850 min; m/z 766.37 (MNa+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, chloroform-d) δ ppm 8.47 (s, 1H), 8.13 (s, 1H), 7.99-8.10 (m, 5H), 7.83-7.89 (m, 3H), 5.32-5.67 (m, 4H), 4.92-5.13 (m, 2H), 3.93-4.11 (m, 2H), 3.00-3.28 (m, 2H), 2.40 (br. s., 2H), 1.68-1.84 (m, 6H), 1.49 (s, 18H), 1.39-1.67 (m, 4H)

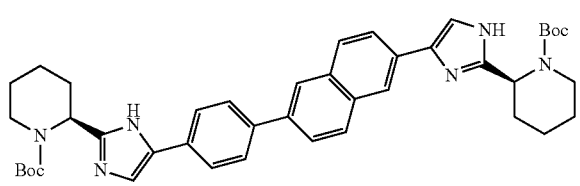 [SMILES: CC(C)(C)OC(=O)N1CCCC[C@H]1c1nc(-c2ccc3cc(-c4ccc(-c5cnc([C@@H]6CCCCN6C(=O)OC(C)(C)C)[nH]5)cc4)ccc3c2)c[nH]1]

Intermediate 183

(S)-tert-Butyl 2-(5-(4-(6-(2-((S)-1-(tert-butoxycarbonyl)piperidin-2-yl)-1H-imidazol-4-yl)naphthalen-2-yl)phenyl)-1H-imidazol-2-yl)piperidine-1-carboxylate The reaction yielded the desired product (1.18 g) as a bright yellow solid. LC-MS retention time 3.778 min; m/z 703.97 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 8.22 (br. s., 1H), 8.09 (s, 1H), 7.93 (t, J=7.7 Hz, 2H), 7.73-7.88 (m, 6H), 7.46 (br. s., 1H), 7.38 (br. s., 1H), 5.47 (br. s., 2H), 4.03-4.15 (m, 2H), 2.99-3.12 (m, 2H), 2.46 (br. s., 2H), 1.80-1.94 (m, 2H), 1.50 (d, J=2.3 Hz, 18H), 1.44-1.76 (m, 8H).

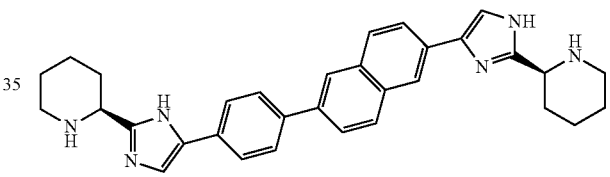

Intermediate 184

(S)-2-(5-(4-(6-(2-((S)-Piperidin-2-yl)-1H-imidazol-4-yl)naphthalen-2-yl)phenyl)-1H-imidazol-2-yl)piperidine The reaction yielded an HCl salt of the desired product (280 mg) as a yellow solid. LC-MS retention time 3.015 min; m/z 503.69 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, DMSO-$d_6$) δ ppm 10.06 (br. s., 2H), 9.85 (br. s., 2H), 8.48 (s, 1H), 8.36 (s, 1H), 8.09-8.19 (m, 3H), 7.96-8.09 (m, 7H), 4.70 (br. s., 2H), 3.42-3.53 (m, 2H), 3.14 (br. s., 2H), 2.10-2.37 (m, 4H), 1.60-2.00 (m, 8H).

Scheme 48

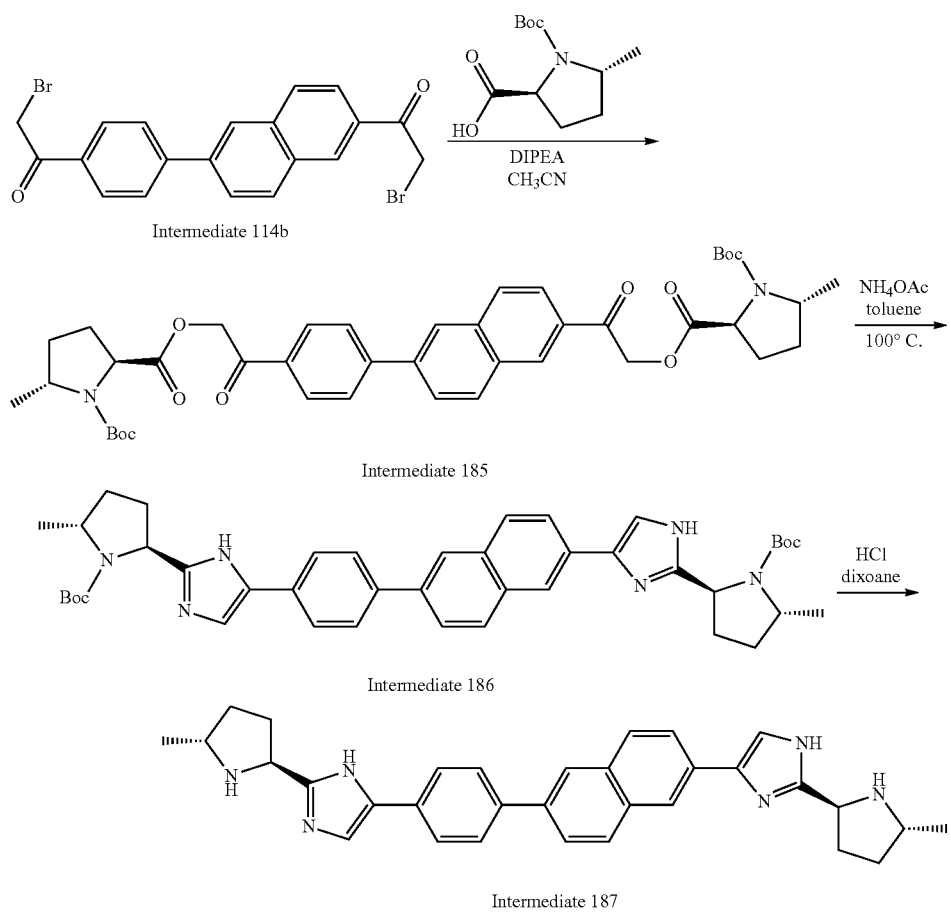

Intermediate 187 was prepared in an analogous manner to the preparation of Intermediate 117 in Scheme 29 utilizing (2S,5R)-1-(tert-butoxycarbonyl)-5-methylpyrrolidine-2-carboxylic acid (prepared according to JOC 1995, p. 5011) as a starting material rather than (2S,5S)-1-(tert-butoxycarbonyl)-5-methylpyrrolidine-2-carboxylic acid. Analytical data for the intermediates shown below.

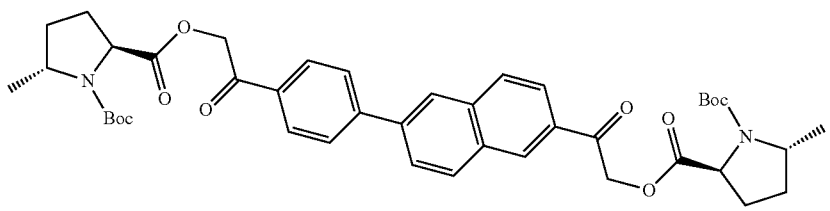

Intermediate 185

(2S,5R)-2-(2-(4-(6-(2-((2S,5R)-1-(tert-Butoxycarbonyl)-5-methylpyrrolidine-2-carbonyloxy)acetyl) naphthalen-2-yl)phenyl)-2-oxoethyl) 1-tert-butyl 5-methylpyrrolidine-1,2-dicarboxylate The reaction yielded the desired product (979 mg). LC-MS retention time 4.796 min; m/z 766.19 (MNa+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1H$ NMR (400 MHz, chloroform-d) δ ppm 8.47 (br. s., 1H), 8.13 (d, J=2.5 Hz, 1H), 7.99-8.11 (m, 5H), 7.86 (dd, J=7.8, 2.3 Hz, 3H), 5.21-5.77 (m, 4H), 4.51-4.58 (m, 1H), 4.47 (dd, J=7.8, 4.5 Hz, 1H), 4.17-4.26 (m, 1H), 4.07-4.14 (m, 1H), 2.23-2.48 (m, 6H), 1.60-1.68 (m, 2H), 1.44-1.52 (m, 18H), 1.25 (d, J=6.3 Hz, 3H), 1.21 (d, J=6.3 Hz, 3H).

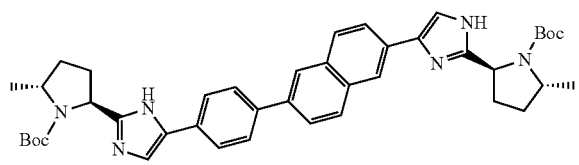

Intermediate 186

(2S,5R)-tert-Butyl 2-(5-(4-(6-(2-((2S,5R)-1-(tert-butoxycarbonyl)-5-methylpyrrolidin-2-yl)-1H-imidazol-4-yl)naphthalen-2-yl)phenyl)-1H-imidazol-2-yl)-5-methylpyrrolidine-1-carboxylate The reaction yielded the desired product (561 mg) as an orange solid foam. LC-MS retention time 3.673 min; m/z 703.95 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode.

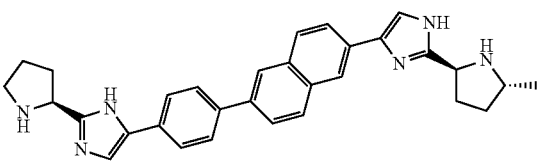

Intermediate 187

2-((2S,5R)-5-Methylpyrrolidin-2-yl)-5-(4-(6-(2-((2S,5R)-5-methylpyrrolidin-2-yl)-1H-imidazol-4-yl)naphthalen-2-yl)phenyl)-1H-imidazole The reaction yielded an HCl salt of the desired product (157 mg) as a light orange solid. LC-MS retention time 2.975 min; m/z 503.71 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, DMSO-$d_6$) δ ppm 9.84-10.25 (m, 4H), 8.54 (s, 1H), 8.36 (s, 1H), 7.95-8.22 (m, 10H), 5.15 (br. s., 2H), 4.00 (br. s., 2H), 2.53-2.63 (m, 4H), 2.30-2.41 (m, 2H), 1.67-1.82 (m, 2H), 1.43 (d, J=4.3 Hz, 6H).

Scheme 49

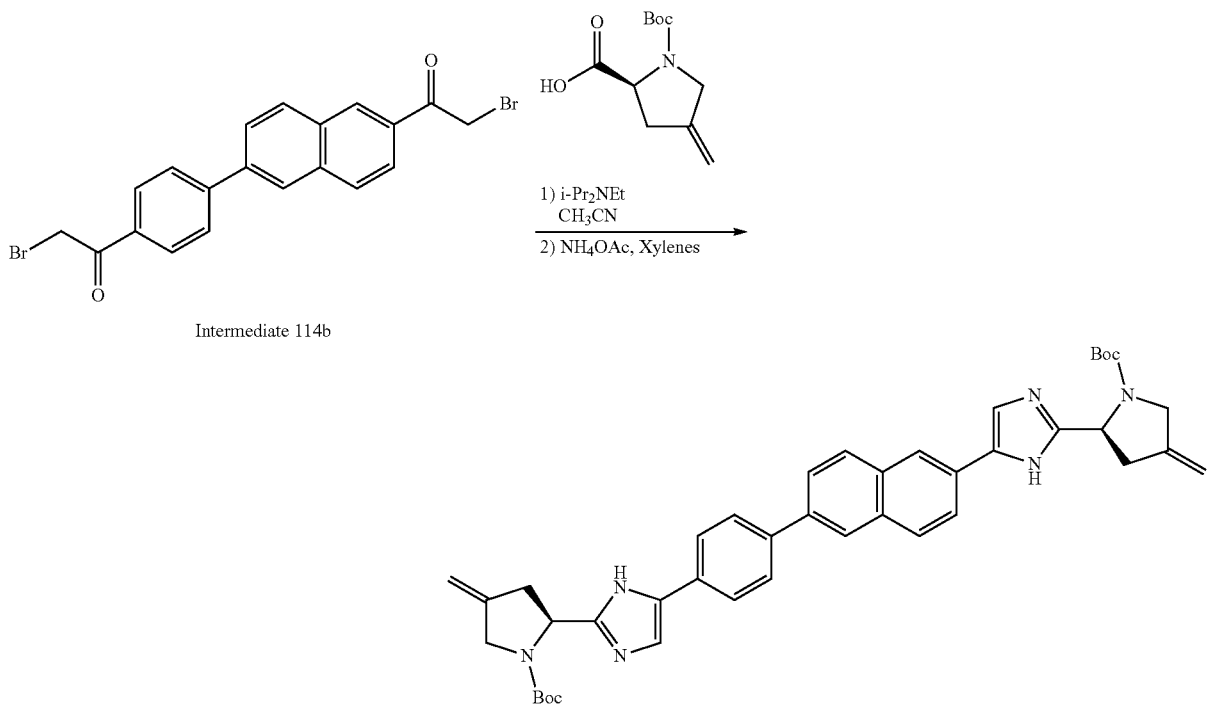

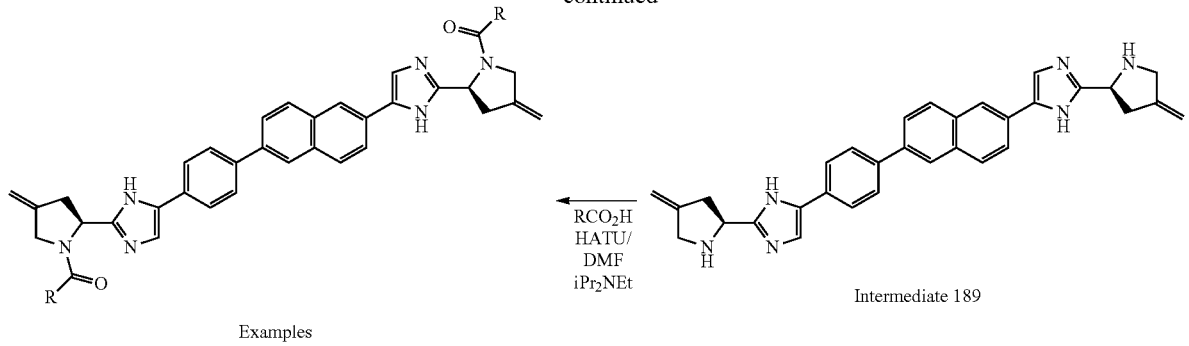

Examples

Intermediate 189 was prepared as shown in Scheme 49 utilizing (S)-1-(tert-butoxycarbonyl)-4-methylenepyrrolidine-2-carboxylic acid as starting material. Analytical data for the intermediates shown below.

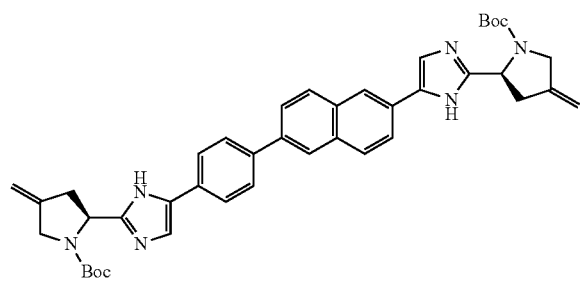

Intermediate 188 tert-Butyl (2S)-2-(4-(4-(6-(2-((2S)-1-(tert-butoxycarbonyl)-4-methylene-2-pyrrolidinyl)-1H-imidazol-4-yl)-2-naphthyl)phenyl)-1H-imidazol-2-yl)-4-methylene-1-pyrrolidinecarboxylate Hunig's base (0.43 mL, 2.47 mmol) was added to a stirred solution of (S)-1-(tert-butoxycarbonyl)-4-methylenepyrrolidine-2-carboxylic acid (509 mg, 2.241 mmol) and 2-bromo-1-(4-(6-(2-bromoacetyl)naphthalen-2-yl)phenyl)ethanone (500 mg, 1.121 mmol) in MeCN (25 mL). The mixture was stirred for 18 h at RT. The solvent was removed in vacuo and the residue was taken up in ethyl acetate and washed with water, saturated sodium bicarbonate solution, and brine. After being concentrated, the residue was taken up in xylene (25 mL) and ammonium acetate (1.3 g, 16.85 mmol) was added. The pressure vessel was sealed and heated at 140° C. for 2.5 h. The reaction mixture was taken up in ethyl acetate and washed with saturated sodium bicarbonate solution and brine. After being concentrated, the crude product was charged (methylene chloride) to a 80 g Thompson silica gel cartridge (eluted with 15% B to 100% B over 1 L where Solvent B=ethyl acetate and Solvent A=hexanes) to yield tert-butyl (2S)-2-(4-(4-(6-(2-((2S)-1-(tert-butoxycarbonyl)-4-methylene-2-pyrrolidinyl)-1H-imidazol-4-yl)-2-naphthyl)phenyl)-1H-imidazol-2-yl)-4-methylene-1-pyrrolidinecarboxylate (380 mg, 45% yield). LC-MS retention time 3.32 min; calcd. for $C_{42}H_{47}N_6O_4$: 699.36 m/z Found 699.41 [M+H]$^+$. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 8.21 (s, 1H), 8.14 (s, 1H), 7.98 (s, 1H), 7.97 (s, 1H), 7.87-7.83 (m, 6H), 7.54 (s, 1H), 7.46 (s, 1H), 5.14 (s, 2H), 5.19 (s, 2H), 4.30 (br s, 2H), 4.15 (br s, 2H), 3.22-3.16 (m, 2H), 2.81-2.76 (m, 2H), 1.51/1.31 (s, 18H).

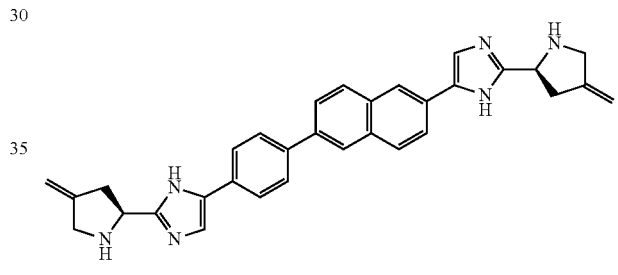

Intermediate 189

2-((S)-4-Methylenepyrrolidin-2-yl)-4-(4-(6-(2-((S)-4-methylenepyrrolidin-2-yl)-1H-imidazol-4-yl)naphthalen-2-yl)phenyl)-1H-imidazole A solution of 4N HCl in dioxane (10 mL) was added to tert-butyl (2S)-2-(4-(4-(6-(2-((2S)-1-(tert-butoxycarbonyl)-4-methylene-2-pyrrolidinyl)-1H-imidazol-4-yl)-2-naphthyl)phenyl)-1H-imidazol-2-yl)-4-methylene-1-pyrrolidinecarboxylate (380 mg. 0.544 mmol) in MeOH (10 mL) and stirred at ambient conditions for 4 hours, concentrated, and dried under vacuum. Tetra HCl salt (assume theoretical: 350 mg). LC-MS retention time 2.68 min; calcd. for $C_{32}H_{31}N_6$: 499.26 m/z Found 499.21 [M+H]$^+$. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode.

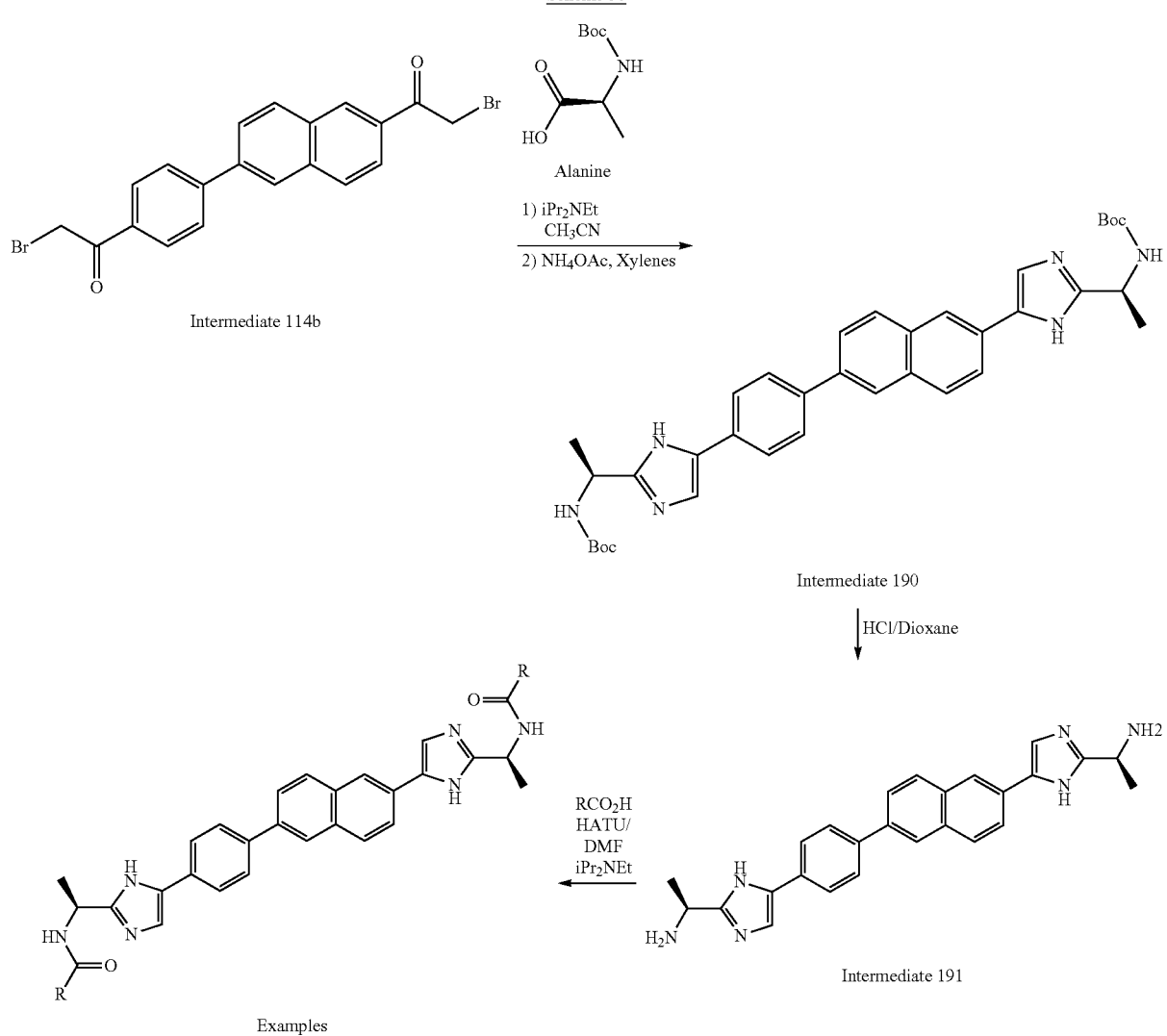

Intermediate 191 was prepared as shown in Scheme 50 utilizing (S)-2-(tert-butoxycarbonylamino)propanoic acid as starting material. Analytical data for the intermediates shown below.

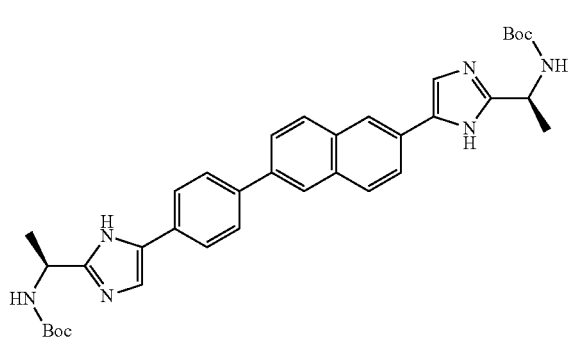 [SMILES: C[C@H](NC(=O)OC(C)(C)C)c1ncc(-c2ccc(-c3ccc4cc(-c5cnc([C@H](C)NC(=O)OC(C)(C)C)[nH]5)ccc4c3)cc2)[nH]1]

Intermediate 190 tert-Butyl ((1S)-1-(4-(4-(6-(2-((1S)-1-((tert-butoxy-carbonyl)amino)ethyl)-1H-imidazol-4-yl)-2-naph-thyl)phenyl)-1H-imidazol-2-yl)ethyl)carbamate Hunig's base (0.39 mL, 2.24 mmol) was added to a stirred solution of (S)-2-(tert-butoxycarbonylamino)propanoic acid (424 mg, 2.24 mmol) and 2-bromo-1-(4-(6-(2-bromoacetyl) naphthalen-2-yl)phenyl)ethanone (500 mg, 1.121 mmol) in MeCN (50 mL). The mixture was stirred for 18 h at RT. The solvent was removed in vacuo and the residue was taken up in ethyl acetate and washed with water, saturated sodium bicarbonate solution, and brine. After being concentrated, the residue was taken up in xylene (25 mL) and ammonium acetate (1.5 g, 20.18 mmol) was added. The pressure vessel was sealed and heated at 140° C. for 3.5 h. The reaction mixture was taken up in ethyl acetate and washed with saturated sodium bicarbonate solution and brine. After being concentrated, the crude product was charged (methylene chloride) to a 90 g Thompson silica gel cartridge (eluted with 15% B to 100% B over 1 L where Solvent B=ethyl acetate and Solvent A=hexanes) to provide tert-Butyl ((1S)-1-(4-(4-(6-(2-((1S)-1-((tert-butoxycarbonyl)amino)ethyl)-1H-imidazol-4-yl)-2-naphthyl)phenyl)-1H-imidazol-2-yl)ethyl)carbamate (368 mg, 47% yield). NOTE: Sample was only partially soluble in methylene chloride. LC-MS retention time 3.24 min; calcd. for $C_{36}H_{43}N_6O_4$: 623.33 m/z. Found 623.37 $[M+H]^+$. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 8.20 (s, 1H), 8.11 (s, 1H), 7.95 (t, J=8.24 Hz, 2H), 7.86-7.79 (m, 6H), 7.46 (s, 1H), 7.37 (s, 1H), 4.93-4.89 (m, 2H), 1.57-1.48 (m, 24H).

Intermediate 191

(S)-1-(4-(4-(6-(2-((S)-1-Aminoethyl)-1H-imidazol-4-yl)naphthalen-2-yl)phenyl)-1H-imidazol-2-yl)ethanamine A solution of 4N HCl in dioxane (10 mL) was added to tert-butyl ((1S)-1-(4-(4-(6-(2-((1S)-1-((tert-butoxycarbonyl)amino)ethyl)-1H-imidazol-4-yl)-2-naphthyl)phenyl)-1H-imidazol-2-yl)ethyl)carbamate (368 mg. 0.59 mmol) in MeOH (10 mL) and stirred at ambient conditions for 5 hours, concentrated, and dried under vacuum. Tetra HCl salt (assume theoretical: 334 mg). LC-MS retention time 1.33 min; calcd. for $C_{26}H_{27}N_6$: 423.23 m/z Found 423.17 $[M+H]^+$. LC data was recorded on a Shimadzu LC-10AS liquid chromatograph equipped with a PHENOMENEX® Luna 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min and an analysis time of 3 min where Solvent A was 5% methanol/95% water/0.1% TFA and Solvent B was 95% methanol/5% water/0.1% TFA. MS data was determined using a MICROMASS® Platform for LC in electrospray mode.

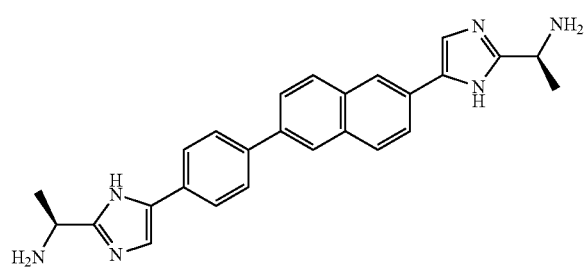 [SMILES: C[C@H](N)c1ncc(-c2ccc(-c3ccc4cc(-c5cnc([C@H](C)N)[nH]5)ccc4c3)cc2)[nH]1]

Scheme 51

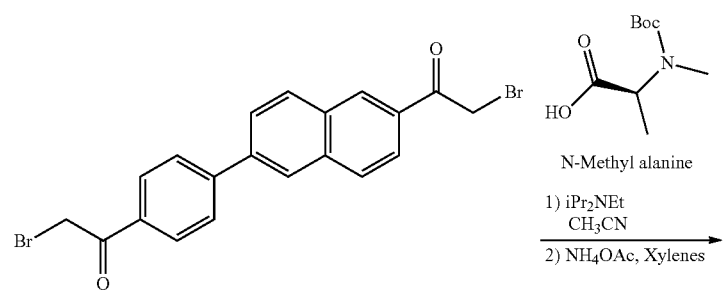

Intermediate 114b

N-Methyl alanine 1) iPr₂NEt CH₃CN
2) NH₄OAc, Xylenes

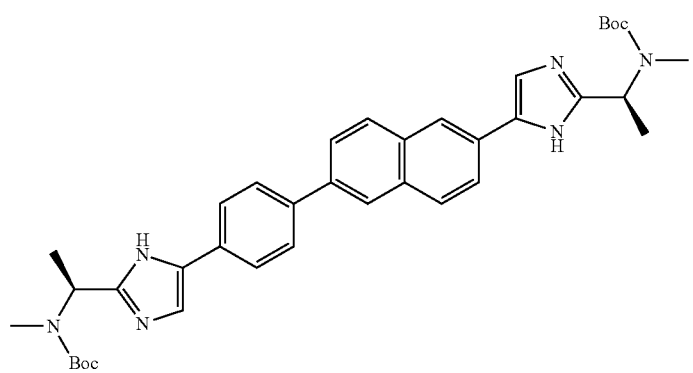

Intermediate 192

HCl/Dioxane

-continued

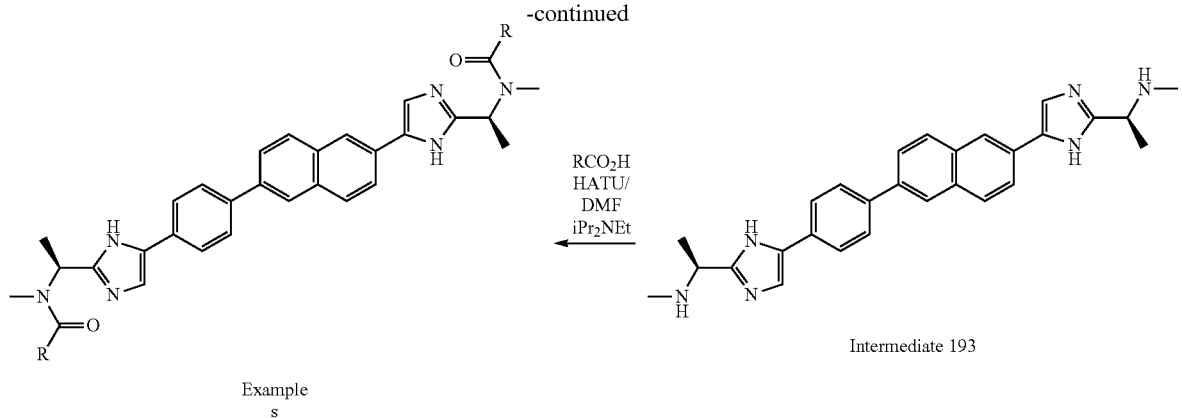

Examples

Intermediate 193 was prepared as shown in Scheme 51 utilizing (S)-2-(tert-butoxycarbonyl(methyl)amino)propanoic acid as starting material. Analytical data for the intermediates shown below.

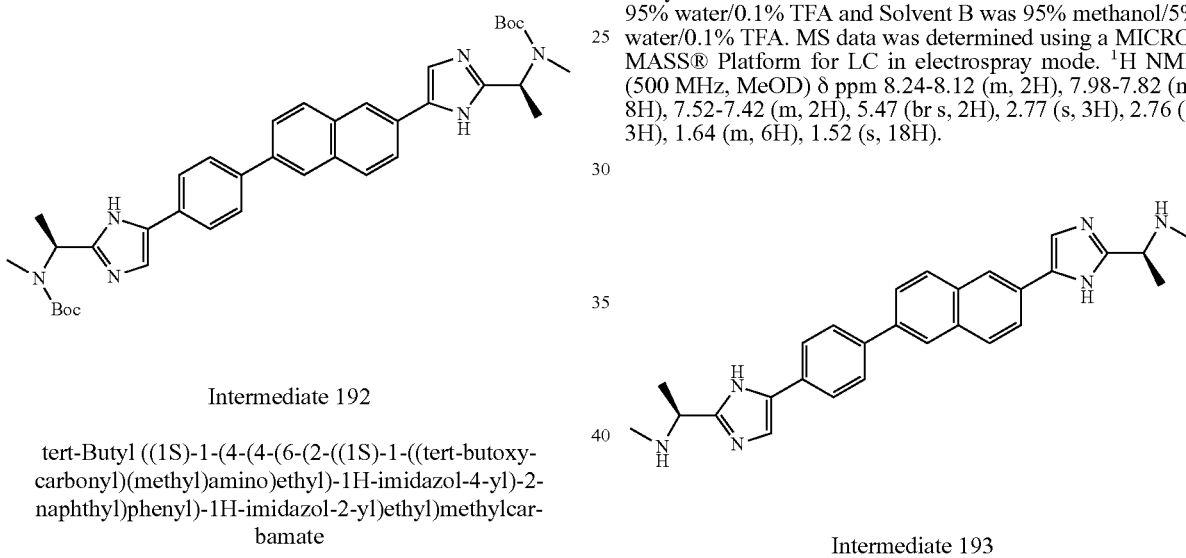

Intermediate 192 tert-Butyl ((1S)-1-(4-(4-(6-(2-((1S)-1-((tert-butoxycarbonyl)(methyl)amino)ethyl)-1H-imidazol-4-yl)-2-naphthyl)phenyl)-1H-imidazol-2-yl)ethyl)methylcarbamate Hunig's base (0.78 mL, 4.48 mmol) was added to a stirred solution of (S)-2-(tert-butoxycarbonyl(methyl)amino)propanoic acid (456 mg, 2.241 mmol) and 2-bromo-1-(4-(6-(2-bromoacetyl)naphthalen-2-yl)phenyl)ethanone (500 mg, 1.121 mmol) in MeCN (50 mL). The mixture was stirred for 18 h at RT. The solvent was removed in vacuo and the residue was taken up in ethyl acetate and washed with water, saturated sodium bicarbonate solution, and brine. After being concentrated, the residue was taken up in xylene (25 mL) and ammonium acetate (859 mg, 11.15 mmol) was added. The pressure vessel was sealed and heated at 140° C. for 3 h. The reaction mixture was taken up in ethyl acetate and washed with saturated sodium bicarbonate solution and brine. After being concentrated, the crude product was charged (methylene chloride) to a 90 g Thompson silica gel cartridge (eluted with 15% B to 100% B over 1 L where Solvent B=ethyl acetate and Solvent A=hexanes) to yield tert-butyl ((1S)-1-(4-(4-(6-(2-((1S)-1-((tert-butoxycarbonyl)(methyl)amino)ethyl)-1H-imidazol-4-yl)-2-naphthyl)phenyl)-1H-imidazol-2-yl)ethyl)methylcarbamate (460 mg, 58% yield). LC-MS retention time 3.28 min; calcd. for $C_{38}H_{47}N_6O_4$: 651.37 m/z Found 651.34 [M+H]$^+$. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 8.24-8.12 (m, 2H), 7.98-7.82 (m, 8H), 7.52-7.42 (m, 2H), 5.47 (br s, 2H), 2.77 (s, 3H), 2.76 (s, 3H), 1.64 (m, 6H), 1.52 (s, 18H).

Intermediate 193

(S)—N-Methyl-1-(4-(4-(6-(2-((S)-1-(methylamino)ethyl)-1H-imidazol-4-yl)naphthalen-2-yl)phenyl)-1H-imidazol-2-yl)ethanamine A solution of 4N HCl in dioxane (10 mL) was added to tert-butyl ((1S)-1-(4-(4-(6-(2-((1S)-1-((tert-butoxycarbonyl)(methyl)amino)ethyl)-1H-imidazol-4-yl)-2-naphthyl)phenyl)-1H-imidazol-2-yl)ethyl)methylcarbamate (434 mg. 0.667 mmol) in MeOH (10 mL) and stirred at ambient conditions for 3 hours, concentrated and dried under vacuum. Tetra HCl salt (assume theoretical: 396 mg). LC-MS retention time 1.44 min; calcd. for $C_{28}H_{31}N_6$: 451.26 m/z Found 451.17 [M+H]$^+$. LC data was recorded on a Shimadzu LC-10AS liquid chromatograph equipped with a PHENOMENEX® Luna 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min and an analysis time of 3 min where Solvent A was 5% methanol/95% water/0.1% TFA and Solvent B was 95% methanol/5% water/0.1% TFA. MS data was determined using a MICROMASS® Platform for LC in electrospray mode.

Scheme 52

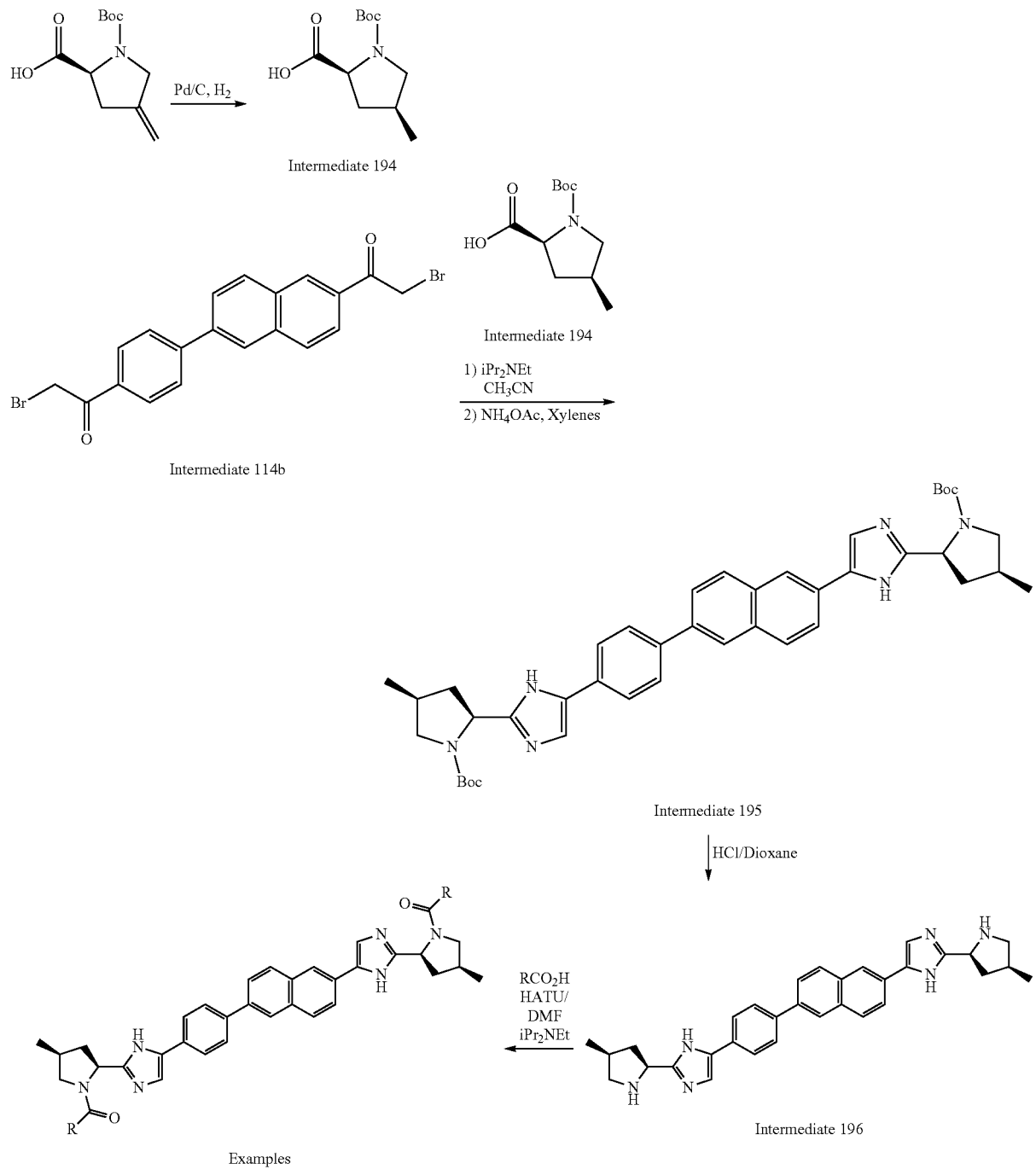

Intermediate 196 was prepared as shown in Scheme 52 utilizing (2S,4S)-1-(tert-butoxycarbonyl)-4-methylpyrrolidine-2-carboxylic acid as starting material. Analytical data for the intermediates shown below.

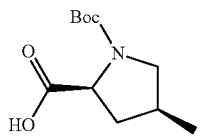 [SMILES: C[C@H]1C[C@@H](C(=O)O)N(C(=O)OC(C)(C)C)C1]

Intermediate 194

(2S,4S)-1-(tert-Butoxycarbonyl)-4-methylpyrrolidine-2-carboxylic acid

A solution of (S)-1-(tert-butoxycarbonyl)-4-methylenepyrrolidine-2-carboxylic acid (4 g, 17.60 mmol) in 2-propanol (10 mL) was added to a nitrogen purged suspension of 10% palladium on carbon (936 mg) in 2-propanol (240 mL) and the flask was charged with hydrogen gas (1 atm). After being stirred 18, the catalyst was removed by filtration over CELITE® and the filtrate concentrated. LC analysis showed the sample contained ~14% of the trans-isomer, and recrystallization from toluene enriched the cis-isomer to 96% (16:1). LC-MS retention time 3.26 min; calcd. for $C_{11}H_{20}N_6O_4$: 230.14 m/z Found 252.14 [M+Na]$^+$. LC data was recorded on a Shimadzu LC-10AS liquid chromatograph equipped with a PHENOMENEX® 2×5 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 10% methanol/90% water/0.1% TFA and Solvent B was 90% methanol/10% water/0.1% TFA. MS data was determined using a MICROMASS® Platform for LC in electrospray mode. $^1$H NMR (500 MHz, MeOD) δ ppm 4.21-4.17 (m, 1H), 3.76-3.67 (m, 1H), 2.96-2.92 (m, 1H), 2.49-2.46 (m, 1H), 2.30-2.29 (m, 1H), 1.59-1.51 (m, 1H), 1.47/1.43 (m, 9H), 1.10-1.06 (m, 3H).

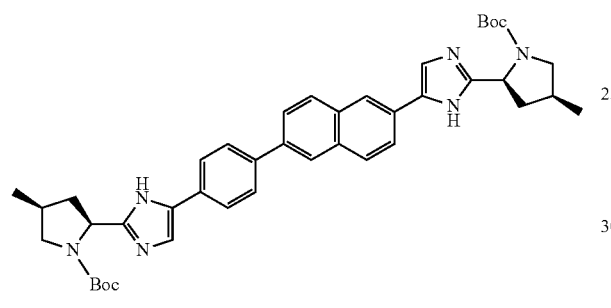

Intermediate 195 tert-Butyl (2S,4S)-2-(4-(4-(6-(2-((2S,4S)-1-(tert-butoxycarbonyl)-4-methyl-2-pyrrolidinyl)-1H-imidazol-4-yl)-2-naphthyl)phenyl)-1H-imidazol-2-yl)-4-methyl-1-pyrrolidinecarboxylate Hunig's base (0.381 mL, 2.181 mmol) was added to a stirred solution of (2S,4S)-1-(tert-butoxycarbonyl)-4-methylpyrrolidine-2-carboxylic acid (500 mg, 2.18 mmol) and 2-bromo-1-(4-(6-(2-bromoacetyl)naphthalen-2-yl)phenyl)ethanone (486 mg, 1.09 mmol) in acetonitrile (11 mL). The heterogeneous mixture was stirred for 18 h at RT and additional Hunig's base (1 equiv) was added and the mixture was stirred for 24 h. The solvent was removed in vacuo and the residue was taken up in methylene chloride and washed with saturated sodium bicarbonate solution, brine, and dried over sodium sulfate. Wash was repeated 2×. The crude product, isolated as a tan foam, was taken up in xylene (15 mL) and ammonia acetate (1.261 g, 16.36 mmol) was added. The pressure vessel was sealed and placed into a preheated oil bath (140° C.) and stirred for 2 h. The reaction mixture was taken up in ethyl acetate and washed with saturated sodium bicarbonate solution and brine. After being concentrated, the crude product was charged (methylene chloride) to a 80 g Thompson silica gel cartridge (eluted with 25% B to 100% B over 1.5 L and hold 0.5 L B. Solvent B=ethyl acetate and Solvent A=hexanes) to yield tert-butyl (2S,4S)-2-(4-(4-(6-(2-((2S,4S)-1-(tert-butoxycarbonyl)-4-methyl-2-pyrrolidinyl)-1H-imidazol-4-yl)-2-naphthyl)phenyl)-1H-imidazol-2-yl)-4-methyl-1-pyrrolidinecarboxylate (214.2 mg 27.9%) as a yellow foam. LC-MS retention time 3.32 min; calcd. for $C_{42}H_{51}N_6O_4$: 703.40 m/z Found 703.28 [M+H]$^+$. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 8.20 (s, 1H), 8.12 (s, 1H), 7.96-7.94 (m, 2H), 7.87-7.82 (m, 6H), 7.50 (s, 1H), 7.42 (s, 1H), 4.87 (br. s, 2H), 3.81 (br. s, 2H), 3.24-3.18 (m, 2H), 2.53-2.50 (m, 2H), 2.36 (br s, 2H), 1.82-1.74 (m, 2H), 1.46/1.23 (s, 18H), 1.17-1.16 (m, 6H).

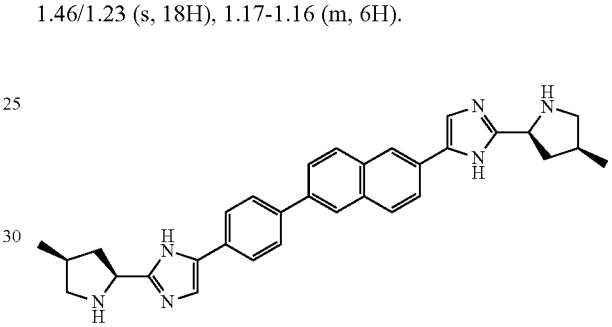

Intermediate 196

2-((2S,4S)-4-Methyl-2-pyrrolidinyl)-4-(4-(6-(2-((2S,4S)-4-methyl-2-pyrrolidinyl)-1H-imidazol-4-yl)-2-naphthyl)phenyl)-1H-imidazole A solution of 4N HCl in dioxane (15 mL) was added to tert-butyl (2S,4S)-2-(4-(4-(6-(2-((2S,4S)-1-(tert-butoxycarbonyl)-4-methyl-2-pyrrolidinyl)-1H-imidazol-4-yl)-2-naphthyl)phenyl)-1H-imidazol-2-yl)-4-methyl-1-pyrrolidinecarboxylate (200 mg. 0.285 mmol) in MeOH (5 mL) and stirred at ambient conditions for 2 hours, concentrated, and dried under vacuum. Tetra HCl salt (assume theoretical: 185 mg). LC-MS retention time 2.64 min; calcd. for $C_{32}H_{35}N_6$: 503.29 m/z Found 503.20 [M+H]$^+$. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode.

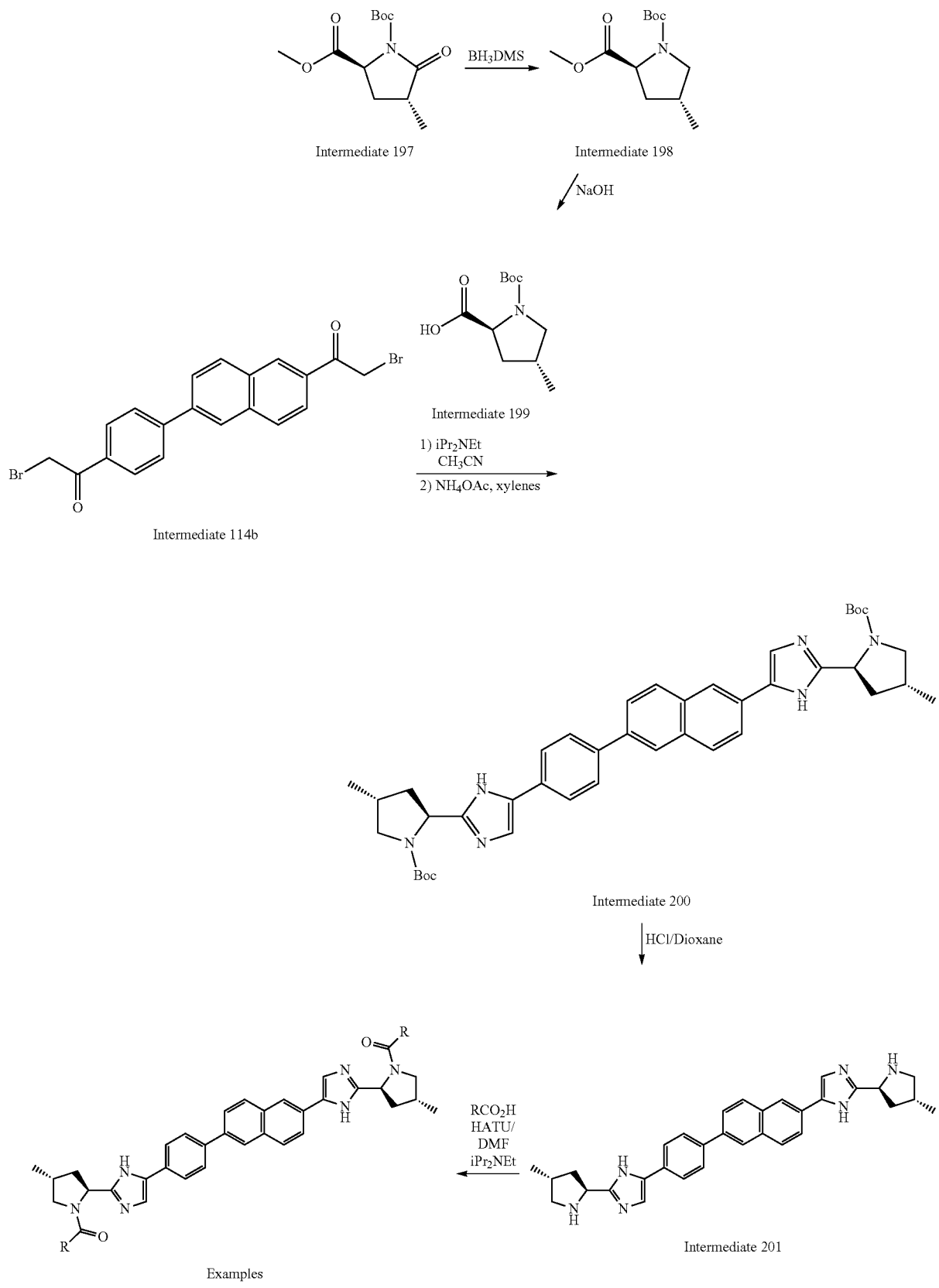

Intermediate 201 was prepared as shown in Scheme 53 utilizing (2S,4R)-1-(tert-butoxycarbonyl)-4-methylpyrrolidine-2-carboxylic acid as starting material. Analytical data for the intermediates shown below.

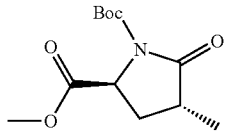

Intermediate 197

The trans-isomer was isolated from a mixture of cis, trans, and the dimethyl analog which could be obtained from methyl iodide alkylation of (S)-1-tert-butyl 2-methyl-5-oxopyrrolidine-1,2-dicarboxylate according to the procedure described in Tetrahedron Letters, 2003, 3203-3205. $^1$H NMR (500 MHz, MeOD) δ ppm 4.66-4.64 (m, 1H), 3.80 (s, 3H), 2.34-2.29 (m, 1H), 2.04-1.99 (m, 1H), 1.49 (s, 9H), 1.21-1.19 (m, 3H).

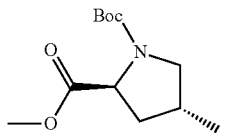

Intermediate 198

Borane-methyl sulfide complex (17.67 mL, 35.3 mmol) was added to a solution of Intermediate 197 (6.06 g, 23.55 mmol) in THF (180 mL), and the reaction mixture was heated at 40° C. for 16 hr. The solvent was removed in vacuo and the residue was partitioned between EtOAc and water (250 mL each). The aqueous layer was extracted with EtOAc (2×60 mL), and the combined organic phase was dried with Na$_2$SO$_4$, and concentrated in vacuo. The resultant colorless oil was purified with a flash chromatography (10-65% EtOAc/Hexane) to afford Intermediate 198 as a colorless oil (3.65 g). $^1$H NMR (CDCl$_3$, δ=7.24 ppm, 400 MHz): 4.36-4.33 (dd, J=2.4, 10, 0.4H), 4.26-4.23 (dd, J=3, 8.9, 0.6H), 3.73-3.63 ('s' overlapped with 'm', 4H), 2.97-2.85 (m, 1H), 2.37 (m, 1H), 2.04 (m, 1H), 1.81 (m, 1H), 1.44-1.39 (two 's', 9H), 1.03-1.00 (two 's', 3H).

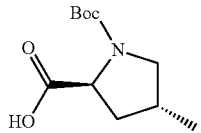 [SMILES: C[C@@H]1C[C@@H](C(=O)O)N(C(=O)OC(C)(C)C)C1]

Intermediate 199

(2S,4R)-1-(tert-Butoxycarbonyl)-4-methylpyrrolidine-2-carboxylic acid

To a solution of ester Intermediate 198 (3.63 g, 14.92 mmol) in ethanol (36 mL) was added solution of LiOH (0.393 g, 10.42 mmol) in water (18.00 mL), and the reaction mixture was stirred at room temperature for 22 hr. The organic solvent was evaporated in vacuo and the residue was diluted with water (30 mL) and washed with ethylacetate (50 mL). It was chilled in ice-water bath, and acidified to a pH range of ~2 with 1N HCl. It was then extracted with EtOAc (50 mL, 2×). The organic layer was dried with Na$_2$SO$_4$ and concentrated in vacuo to afford Intermediate 199 as a colorless oil, which became a white solid upon extended exposure to high vacuum (3.3 g). $^1$H NMR (CDCl$_3$, δ=7.24 ppm, 400 MHz): 4.37-4.27 (overlapped 'm' 1H), 3.72-3.50 (m, 1H), 3.01-2.83 (overlapped 'm', 1H), 2.50-2.11 (m, 2H), 1.89-1.57 (m, 1H), 1.47-1.39 (two 's', 9H), 1.04-1.03 (two 's', 3H).

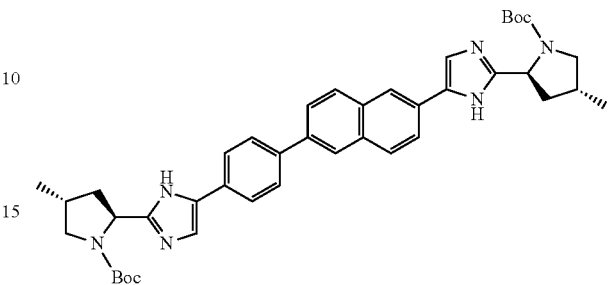

Intermediate 200 tert-Butyl (2S,4R)-2-(4-(4-(6-(2-((2S,4R)-1-(tert-butoxycarbonyl)-4-methyl-2-pyrrolidinyl)-1H-imidazol-4-yl)-2-naphthyl)phenyl)-1H-imidazol-2-yl)-4-methyl-1-pyrrolidinecarboxylate Hunig's base (0.381 mL, 2.181 mmol) was added to a stirred solution of (2S,4R)-1-(tert-butoxycarbonyl)-4-methylpyrrolidine-2-carboxylic acid (500 mg, 2.18 mmol) and 2-bromo-1-(4-(6-(2-bromoacetyl)naphthalen-2-yl)phenyl) ethanone (486 mg, 1.09 mmol) in acetonitrile (11 mL). The heterogeneous mixture was stirred for 18 h at RT and additional Hunig's base (1 eqv) was added and the mixture was stirred for 24 h. The solvent was removed in vacuo and the residue was taken up in methylene chloride and washed with saturated sodium bicarbonate solution, brine, and dried over sodium sulfate. Wash was repeated 2×. The crude product, isolated as a tan foam, was taken up in xylene (15 mL) and ammonia acetate (1.261 g, 16.36 mmol) was added. The pressure vessel was sealed and placed into a preheated oil bath (140° C.) and stirred for 2 h. The reaction mixture was taken up in ethyl acetate and washed with saturated sodium bicarbonate solution and brine. After being concentrated, the crude product was charged (methylene chloride) to a 80 g Thompson silica gel cartridge (eluted with 25% B to 100% B over 1.5 L and hold 0.5 L B. Solvent B=ethyl acetate and Solvent A=hexanes) to yield tert-butyl (2S,4R)-2-(4-(4-(6-(2-((2S,4R)-1-(tert-butoxycarbonyl)-4-methyl-2-pyrrolidinyl)-1H-imidazol-4-yl)-2-naphthyl)phenyl)-1H-imidazol-2-yl)-4-methyl-1-pyrrolidinecarboxylate (214.2 mg 27.9%) as a yellow foam. LC-MS retention time 3.32 min; calcd. for C$_{42}$H$_{51}$N$_6$O$_4$: 703.40 m/z Found 703.28 [M+H]$^+$. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 8.20 (s, 1H), 8.12 (s, 1H), 7.96-7.94 (m, 2H), 7.87-7.82 (m, 6H), 7.50 (s, 1H), 7.42 (s, 1H), 4.87 (br. s, 2H), 3.81 (br. s, 2H), 3.24-3.18 (m, 2H), 2.53-2.50 (m, 2H), 2.36 (br s, 2H), 1.82-1.74 (m, 2H), 1.46/1.23 (s, 18H), 1.17-1.16 (m, 6H).

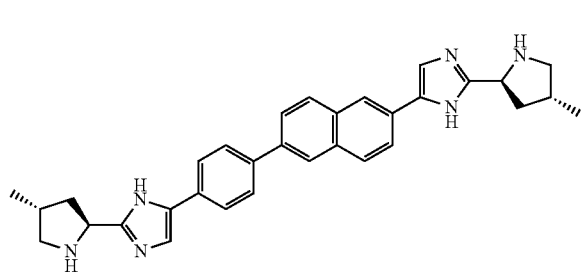

Intermediate 201

2-((2S,4R)-4-Methyl-2-pyrrolidinyl)-4-(4-(6-(2-((2S,4R)-4-methyl-2-pyrrolidinyl)-1H-imidazol-4-yl)-2-naphthyl)phenyl)-1H-imidazole A solution of 4N HCl in dioxane (15 mL) was added to tert-butyl (2S,4R)-2-(4-(4-(6-(2-((2S,4R)-1-(tert-butoxycarbonyl)-4-methyl-2-pyrrolidinyl)-1H-imidazol-4-yl)-2-naphthyl)phenyl)-1H-imidazol-2-yl)-4-methyl-1-pyrrolidinecarboxylate (200 mg. 0.285 mmol) in MeOH (5 mL) and stirred at ambient conditions for 2 hours, concentrated, and dried under vacuum. Tetra HCl salt (assume theoretical: 185 mg). LC-MS retention time 2.64 min; calcd. for $C_{32}H_{35}N_6$: 503.29 m/z Found 503.20 $[M+H]^+$. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode.

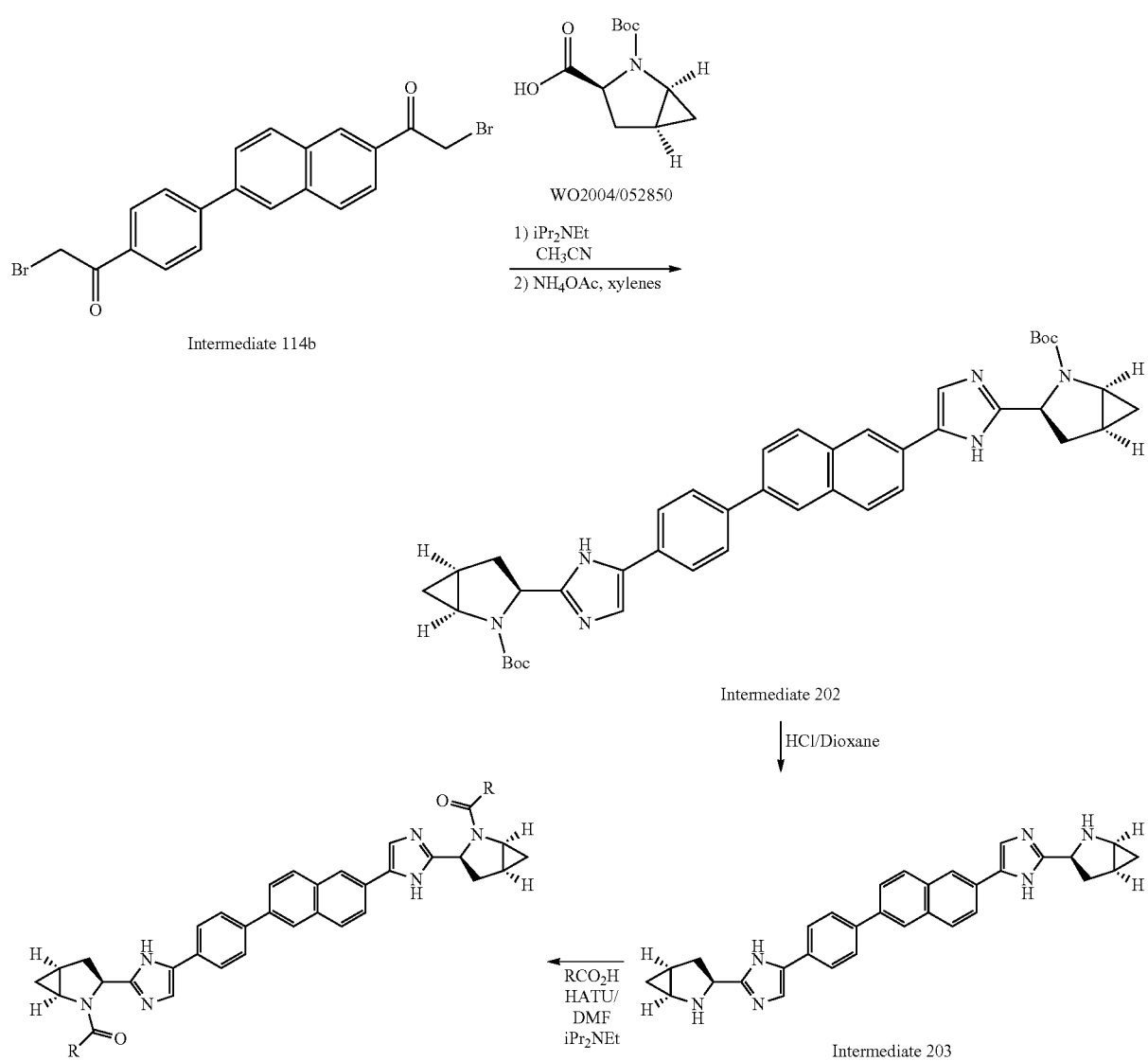

Intermediate 203 was prepared as shown in Scheme 54 utilizing as starting material (1S,3S,5S)-2-(tert-butoxycarbonyl)-2-azabicyclo[3.1.0]hexane-3-carboxylic acid (which could be prepared according to WO 2004/052850). Analytical data for the intermediates shown below.

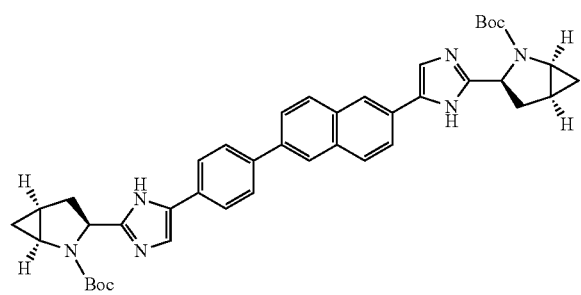 [SMILES: CC(C)(C)OC(=O)N1[C@H](c2ncc(-c3ccc(-c4ccc5cc(-c6cnc([C@@H]7C[C@@H]8C[C@@H]8N7C(=O)OC(C)(C)C)[nH]6)ccc5c4)cc3)[nH]2)C[C@@H]2C[C@@H]21]

Intermediate 202 tert-Butyl (1S,3S,5S)-3-(4-(4-(6-(2-((1S,3S,5S)-2-(tert-butoxycarbonyl)-2-azabicyclo[3.1.0]hex-3-yl)-1H-imidazol-4-yl)-2-naphthyl)phenyl)-1H-imidazol-2-yl)-2-azabicyclo[3.1.0]hexane-2-carboxylate Hunig's base (0.384 mL, 2.2 mmol) was added to a stirred solution of 2-bromo-1-(4-(6-(2-bromoacetyl)naphthalen-2-yl)phenyl)ethanone (0.491 g, 1.100 mmol) and (1S,3S,5S)-2-(tert-butoxycarbonyl)-2-azabicyclo[3.1.0]hexane-3-carboxylic acid (500 mg, 1.1 mmol) in acetonitrile (11 mL). The heterogeneous mixture was stirred for 20 h at RT the solvent was removed in vacuo. The residue was taken up in ethyl acetate and washed with saturated sodium bicarbonate solution, brine, and dried over sodium sulfate. Wash was repeated 2×. The crude product was taken up in xylene (11 mL) and ammonia acetate (1.27 g, 16.5 mmol) was added. The pressure vessel was sealed and placed into a preheated oil bath (140° C.) and stirred for 2 h. The solvent was removed in vacuo and the residue was taken up in ethyl acetate and washed with saturated sodium bicarbonate solution and brine. After being concentrated, the crude product was charged (methylene chloride) to a 80 g Thompson silica gel cartridge (eluted with 25% B to 100% B over 1.5 L and hold 0.5 L B. Solvent B=ethyl acetate and Solvent A=hexanes) to yield tert-butyl (1S,3S,5S)-3-(4-(4-(6-(2-((1S,3S,5S)-2-(tert-butoxycarbonyl)-2-azabicyclo[3.1.0]hex-3-yl)-1H-imidazol-4-yl)-2-naphthyl)phenyl)-1H-imidazol-2-yl)-2-azabicyclo[3.1.0]hexane-2-carboxylate (418.9 mg, 43%) as a light yellow solid. LC-MS retention time 3.46 min; calcd. for $C_{42}H_{47}N_6O_4$: 699.37 m/z Found 699.33 [M+H]$^+$. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 8.18 (s, 1H), 8.11 (s, 1H), 7.96-7.93 (m, 2H), 7.85-7.80 (m, 6H), 7.45 (br. s, 1H), 7.37 (br. s, 1H), 5.36 (br. s, 2H), 3.72 (br. s, 1H), 3.64 (br. s, 1H), 2.82 (br. s, 1H), 2.72 (br s, 1H), 2.43 (br. s, 1H), 2.15 (br. s, 1H), 1.70 (br. s, 2H), 1.55/1.33 (s, 18H), 1.10 (br. s, 1H), 0.94 (br. s, 1H), 0.88 (br. s, 1H), 0.81 (br. s, 1H).

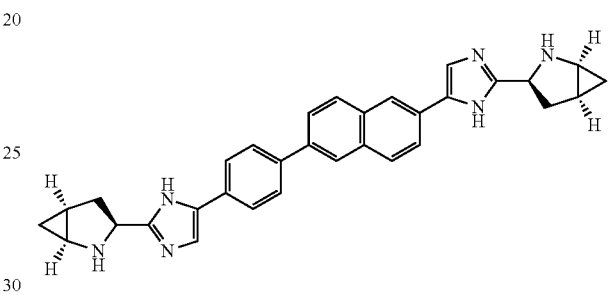

Intermediate 203

(1S,3S,5S)-3-(4-(4-(6-(2-((1S,3S,5S)-2-Azabicyclo[3.1.0]hex-3-yl)-1H-imidazol-4-yl)-2-naphthyl)phenyl)-1H-imidazol-2-yl)-2-azabicyclo[3.1.0]hexane A solution of 4N HCl in dioxane (10 mL) was added to tert-butyl (1S,3S,5S)-3-(4-(4-(6-(2-((1S,3S,5S)-2-(tert-butoxycarbonyl)-2-azabicyclo[3.1.0]hex-3-yl)-1H-imidazol-4-yl)-2-naphthyl)phenyl)-1H-imidazol-2-yl)-2-azabicyclo[3.1.0]hexane-2-carboxylate (375 mg. 0.537 mmol) in MeOH (3 mL) and stirred at ambient conditions for 2 hours, concentrated, and dried under vacuum. Tetra HCl salt (assume theoretical: 346 mg). LC-MS retention time 2.75 min; calcd. for $C_{32}H_{31}N_6$: 499.26 m/z Found 499.22 [M+H]$^+$. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode.

Scheme 55
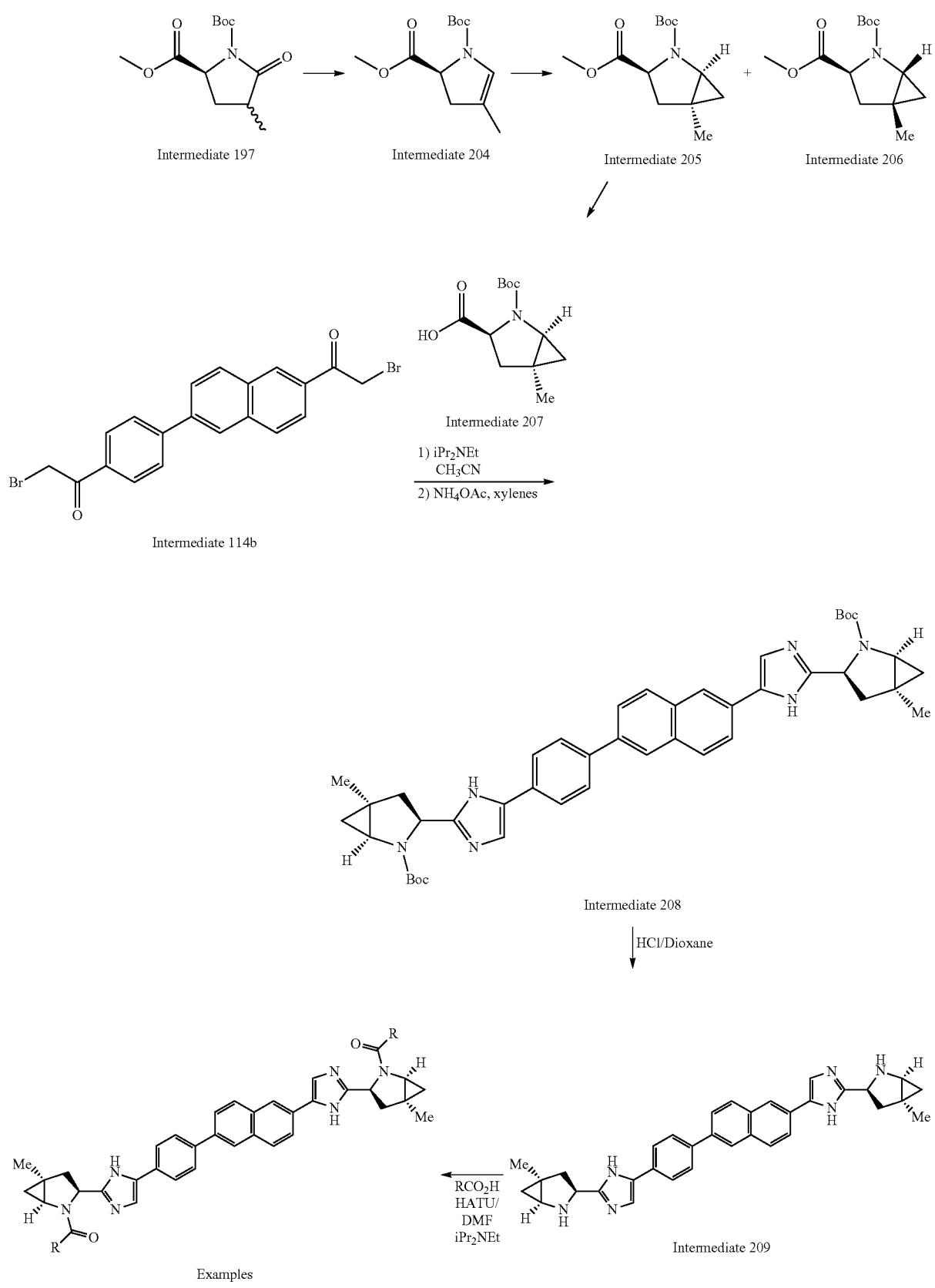

Intermediate 209 was prepared as shown in Scheme 55 utilizing as starting material (1S,3S,5S)-2-(tert-butoxycarbonyl)-5-methyl-2-azabicyclo[3.1.0]hexane-3-carboxylic acid (which could be prepared according to WO 2004/052850). Analytical data for the intermediates shown below.

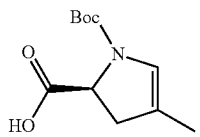 [SMILES: CC1=CN(C(=O)OC(C)(C)C)[C@H](C(=O)O)C1]

Intermediate 204

To a solution of the diastereomeric mixture (at the carbon carrying the methyl group) of Intermediate 197 (4.75 g, 18.46 mmol) was added superhydride (19.20 mL, 19.20 mmol) dropwise at −50° C. in a dry ice/acetone bath over 10 min. Hunig's base (13.58 mL, 78 mmol) was added, stirred for 10 min, DMAP (0.122 g, 0.997 mmol) was added as a solid, stirred for 15 min, and trifluoroacetic anhydride (2.98 mL, 21.08 mmol) was added dropwise over 15 mins. The dry ice/acetone bath was removed and the reaction mixture was stirred for 4 h while being allowed to warm to room temperature. The reaction mixture was washed with water (50 mL), sat. NaCl (30 mL), and concentrated in vacuo. The resulting crude material was purified by flash chromatography (8-60% EtOAc/Hexane) to afford ester Intermediate 204 as a yellow oil (2.85 g). $^1$H NMR (CDCl$_3$, 400 MHz): 6.36 (s, 0.5H), 6.25 (s, 0.5H), 4.70-4.57 (m, 1H), 3.78 (s, 3H), 2.96 (m, 1H), 2.54 (m, 1H), 1.70 (s, 3H), 1.50 (s, 4.5H), 1.44 (s, 4.5H).

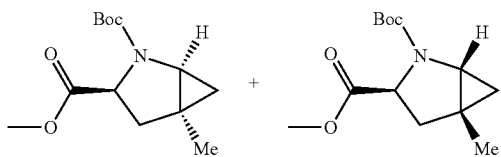 [SMILES: COC(=O)[C@@H]1C[C@]2(C)C[C@@H]2N1C(=O)OC(C)(C)C ; COC(=O)[C@@H]1C[C@@]2(C)C[C@H]2N1C(=O)OC(C)(C)C]

Intermediate 205 and Intermediate 206

Diethylzinc (1.1 M in toluene, 59.1 mL, 65.0 mmol) was added dropwise over 20 min to a cooled (−23° C.) toluene (60 mL) solution of Intermediate 203 (5.23 g, 21.68 mmol), and stirred for 10 min. Chloroiodomethane (9.44 mL, 130 mmol) was added dropwise over 10 min, and the reaction mixture was stirred at −21° C. for 16 hr. Sat. NaHCO$_3$ (60 mL) was added to the reaction mixture, the cooling bath was removed, and the mixture was stirred for 10 min. It was then filtered, and the filter cake was washed with toluene (50 mL). The filterate was partitioned, and the organic layer was dried with Na$_2$SO$_4$, and concentrated in vacuo. The resulting crude material was purified with flash chromatography (2-10% EtOAc/Hexane) to afford Intermediate 205 (first elute; colorless oil; 2.88 g) and Intermediate 206 (second elute; colorless oil; 1.01 g). Relative stereochemical assignment was made based on NOE studies. Intermediate 205: $^1$H NMR (CDCl$_3$, 400 MHz): 4.65-4.52 (m, 1H), 3.72 (s, 3H), 3.28-3.17 (m, 1H), 2.44-2.32 (m, 1H), 2.16-2.10 (m, 1H), 1.51-1.42 (two s, 9H), 1.24 (s, 3H), 1.07 (m, 1H), 0.69-0.60 (m, 1H).

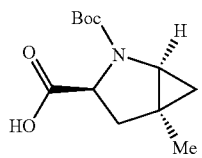

Intermediate 207

(1S,3S,5S)-2-(tert-Butoxycarbonyl)-5-methyl-2-azabicyclo[3.1.0]hexane-3-carboxylic acid To a solution of Intermediate 205 (2.88 g, 11.28 mmol) in ethanol (20 mL) was added a solution of LiOH (0.324 g, 13.54 mmol) in water (10.00 mL), and the mixture was stirred at room temperature for 6 hr. Most of the volatile component was removed in vacuo, and the residue was partitioned between water (20 mL) and ether (20 mL). The aqueous layer was chilled in an ice-water bath, acidified with a 1N HCl to a pH region of 2, and extracted with EtOAc (30 mL, 4×). The combined organic phase was dried with Na$_2$SO$_4$, evaporated in vacuo to give Intermediate 207 as a sticky solid (2.55 g). $^1$H NMR (CDCl$_3$, 400 MHz): 4.64 (m, 1H), 3.25 (appt s, 1H), 2.70-2.40 (m, 1H), 2.14 (m, 1H), 1.54-1.44 (m, 9H), 1.27 (s, 3H), 1.10-0.80 (m, 1H), 0.67 (m, 1H).

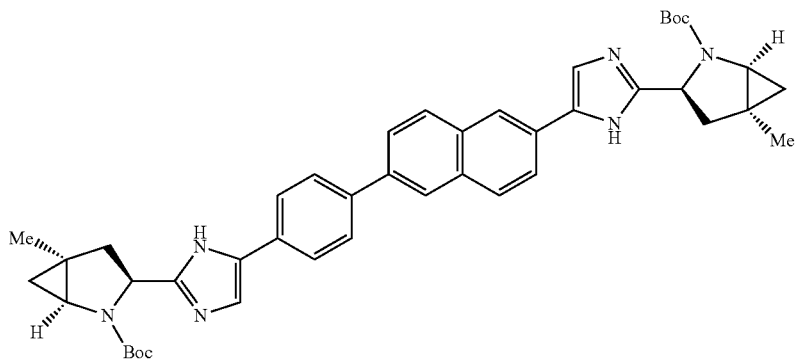 [SMILES: CC(C)(C)OC(=O)N1[C@H]2C[C@@]2(C)C[C@H]1c1ncc(-c2ccc(-c3ccc4cc(-c5cnc([C@@H]6C[C@]7(C)C[C@@H]7N6C(=O)OC(C)(C)C)[nH]5)ccc4c3)cc2)[nH]1]

Intermediate 208 tert-Butyl (1S,3S,5S)-3-(4-(4-(6-(2-((1S,3S,5S)-2-(tert-butoxycarbonyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hexane-2-carboxylate Hunig's base (0.475 mL, 2.72 mmol) was added to a stirred solution of 2-bromo-1-(4-(6-(2-bromoacetyl)naphthalen-2-yl)phenyl)ethanone (0.607 g, 1.36 mmol) and (1S,3S,5S)-2-(tert-butoxycarbonyl)-5-methyl-2-azabicyclo[3.1.0]hexane-3-carboxylic acid (729.0 mg, 2.72 mmol) in dry acetonitrile (12 mL). The heterogeneous mixture was stirred for 20 h at RT the solvent was removed in vacuo. The residue was taken up in ethyl acetate and washed with saturated sodium bicarbonate solution, brine, and dried over sodium sulfate. Wash was repeated 2×. The crude product was taken up in xylene (12 mL) and ammonia acetate (1.57 g, 20.39 mmol) was added. The pressure vessel was sealed and placed into a preheated oil bath (140° C.) and stirred for 2 h. The solvent was removed in vacuo and the residue was taken up in ethyl acetate and washed with saturated sodium bicarbonate solution and brine. After being concentrated, the crude product was charged (methylene chloride) to a 80 g Thompson silica gel cartridge (eluted with 25% B to 100% B over 1.5 L and hold 0.5 L B. Solvent B=ethyl acetate and Solvent A=hexanes) to yield tert-butyl (1S,3S,5S)-3-(4-(4-(6-(2-((1S,3S,5S)-2-(tert-butoxycarbonyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hexane-2-carboxylate (279 mg, 27%) as a light yellow solid. LC-MS retention time 3.56 min; calcd. for $C_{44}H_{51}N_6O_4$: 727.40 m/z Found 727.41 [M+H]$^+$. LC data was recorded on a Shimadzu LC-10AS liquid chromatograph equipped with a PHENOMENEX® 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 8.18 (s, 1H), 8.11 (s, 1H), 7.96-7.93 (m, 2H), 7.83-7.80 (m, 6H), 7.43 (br. s, 1H), 7.35 (br. s, 1H), 5.35 (br. s, 2H), 3.42 (br. s, 1H), 3.36 (br. s, 1H), 2.61 (br. s, 1H), 2.53 (br.s, 2H), 2.72 (br s, 1H), 1.55/1.33 (s, 25H), 1.06 (br. s, 1H), 0.85 (br. s, 1H), 0.72 (br. s, 1H).

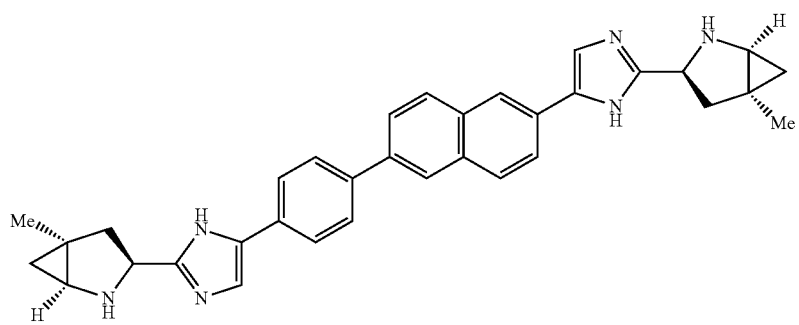 [SMILES: C[C@]12C[C@@H](c3ncc(-c4ccc(-c5ccc6cc(-c7cnc([C@@H]8C[C@]9(C)C[C@@H]9N8)[nH]7)ccc6c5)cc4)[nH]3)N[C@H]1C2]

Intermediate 209

(1S,3S,5S)-5-Methyl-3-(4-(4-(6-(2-((1S,3S,5S)-5-methyl-2-azabicyclo[3.1.0]hex-3-yl)-1H-imidazol-4-yl)-2-naphthyl)phenyl)-1H-imidazol-2-yl)-2-azabicyclo[3.1.0]hexane A solution of 4N HCl in dioxane (15 mL) was added to tert-butyl (1S,3S,5S)-3-(4-(4-(6-(2-((1S,3S,5S)-2-(tert-butoxycarbonyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hexane-2-carboxylate (250 mg. 0.344 mmol) in MeOH (5 mL) and stirred at ambient conditions for 2 hours, concentrated, and dried under vacuum. Tetra HCl salt (assume theoretical: 231 mg). LC-MS retention time 3.09 min; calcd. for $C_{34}H_{35}N_6$: 527.29 m/z Found 527.35 [M+H]$^+$. LC data was recorded on a Shimadzu LC-10AS liquid chromatograph equipped with a PHENOMENEX® 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode.

Scheme 56
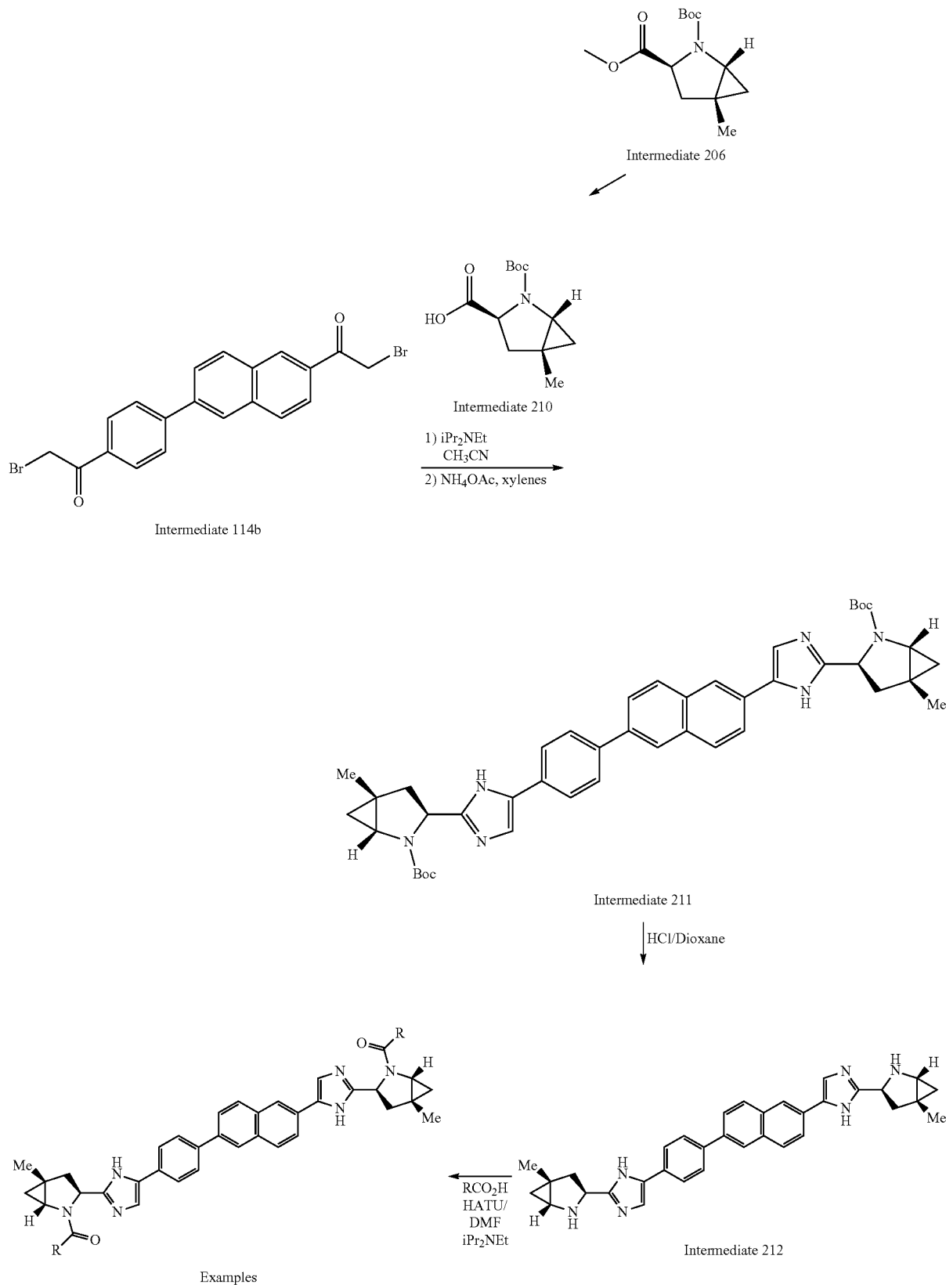

Intermediate 212 was prepared as shown in Scheme 56 utilizing (1R,3S,5R)-2-(tert-butoxycarbonyl)-5-methyl-2-azabicyclo[3.1.0]hexane-3-carboxylic acid (which could be prepared according to WO 2004/052850 as starting material. Analytical data for the intermediates shown below.

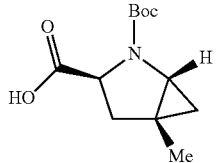 [SMILES: CC(C)(C)OC(=O)N1[C@H](C(=O)O)C[C@@]2(C)C[C@@H]12]

Intermediate 210

(1R,3S,5R)-2-(tert-Butoxycarbonyl)-5-methyl-2-azabicyclo[3.1.0]hexane-3-carboxylic acid Intermediate 210 was prepared from Intermediate 206 as described above for Intermediate 207. $^1$H NMR (CDCl$_3$, 400 MHz): 4.13 (app br s, 1H), 3.06 (app br s, 1H), 2.55/2.41 (overlapping app br s, 2H), 1.51 (s, 9H), 1.27 (s, 3H), 0.76 (app t, J=5.6, 1H), 0.60 (app br s, 1H).

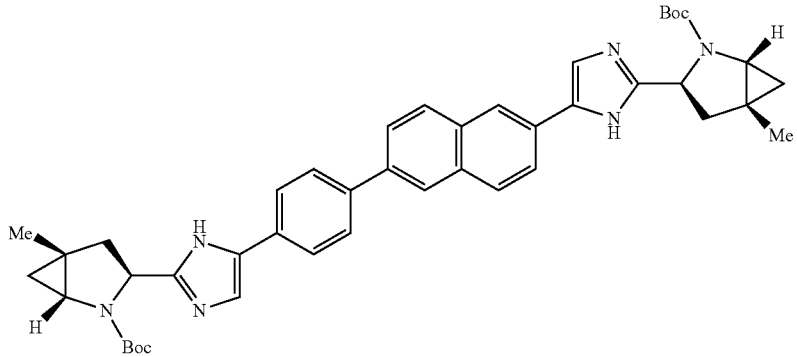 [SMILES: CC(C)(C)OC(=O)N1[C@H](c2ncc(-c3ccc(-c4ccc5cc(-c6cnc([C@@H]7C[C@@]8(C)C[C@H]8N7C(=O)OC(C)(C)C)[nH]6)ccc5c4)cc3)[nH]2)C[C@@]2(C)C[C@@H]12]

Intermediate 211 tert-Butyl (1R,3S,5R)-3-(4-(4-(6-(2-((1R,3S,5R)-2-(tert-butoxycarbonyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hexane-2-carboxylate Hunig's base (0.29 mL, 1.66 mmol) was added to a stirred solution of 2-bromo-1-(4-(6-(2-bromoacetyl)naphthalen-2-yl)phenyl)ethanone (0.37 g, 0.83 mmol) and (1R,3R,5S)-2-(tert-butoxycarbonyl)-5-methyl-2-azabicyclo[3.1.0]hexane-3-carboxylic acid (0.40 g, 1.66 mmol) in dry acetonitrile (9 mL). The heterogeneous mixture was stirred for 20 h at RT the solvent was removed in vacuo. The residue was taken up in ethyl acetate and washed with saturated sodium bicarbonate solution, brine, and dried over sodium sulfate. Wash was repeated 2×. The crude product was taken up in xylene (9 mL) and ammonia acetate (1.3 g, 16.6 mmol) was added. The pressure vessel was sealed and placed into a preheated oil bath (140° C.) and stirred for 2 h. The solvent was removed in vacuo and the residue was taken up in ethyl acetate and washed with saturated sodium bicarbonate solution and brine. After being concentrated, the crude product was charged (methylene chloride) to a 90 g Thompson silica gel cartridge (eluted with 25% B to 100% B over 1.5 L and hold 0.5 L B. Solvent B=ethyl acetate and Solvent A=hexanes) to yield tert-butyl (1R,3S,5R)-3-(4-(4-(6-(2-((1R,3S,5R)-2-(tert-butoxycarbonyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hexane-2-carboxylate (80 mg, 10%). LC-MS retention time 3.37 min; calcd. for C$_{44}$H$_{51}$N$_6$O$_4$: 727.40 m/z. Found 727.38 [M+H]$^+$. LC data was recorded on a Shimadzu LC-10AS liquid chromatograph equipped with a PHENOMENEX® 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 8.19 (s, 1H), 8.08 (s, 1H), 7.92-7.91 (m, 2H), 7.85-7.77 (m, 6H), 7.47 (s, 1H), 7.38 (s, 1H), 4.67 (br. s, 2H), 3.93-3.90 (m, 2H), 2.63-2.57 (m, 2H), 2.20-2.14 (m, 2H), 1.31-1.23 (m, 24H), 0.92 (app. d, J=6.7 Hz, 1H), 0.82 (br. s, 1H), 0.77-0.75 (m, 2H).

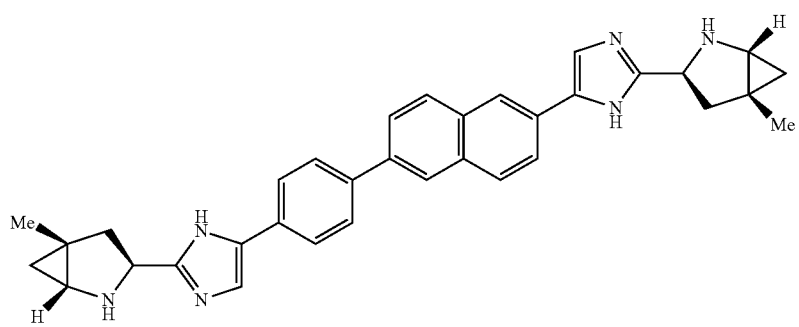 [SMILES: C[C@@]12C[C@@H](c3ncc(-c4ccc(-c5ccc6cc(-c7cnc([C@@H]8C[C@@]9(C)C[C@H]9N8)[nH]7)ccc6c5)cc4)[nH]3)N[C@@H]1C2]

Intermediate 212

(1R,3S,5R)-5-Methyl-3-(4-(4-(6-(2-((1R,3S,5R)-5-methyl-2-azabicyclo[3.1.0]hex-3-yl)-1H-imidazol-4-yl)-2-naphthyl)phenyl)-1H-imidazol-2-yl)-2-azabicyclo[3.1.0]hexane A solution of 4N HCl in dioxane (5 mL) was added to tert-butyl (1R,3S,5R)-3-(4-(4-(6-(2-((1R,3S,5R)-2-(tert-butoxycarbonyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hexane-2-carboxylate (48 mg. 0.066 mmol) in MeOH (1 mL) and stirred at ambient conditions for 2 hours, concentrated, and dried under vacuum. Tetra HCl salt (assume theoretical: 44 mg). LC-MS retention time 2.82 min; calcd. for $C_{34}H_{35}N_6$: 527.29 m/z Found 527.26 [M+H]$^+$. LC data was recorded on a Shimadzu LC-10AS liquid chromatograph equipped with a PHENOMENEX® 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/ 0.1% TFA and Solvent B was 95% methanol/5% water/0.1% TFA. MS data was determined using a MICROMASS® Platform for LC in electrospray mode.

Scheme 57

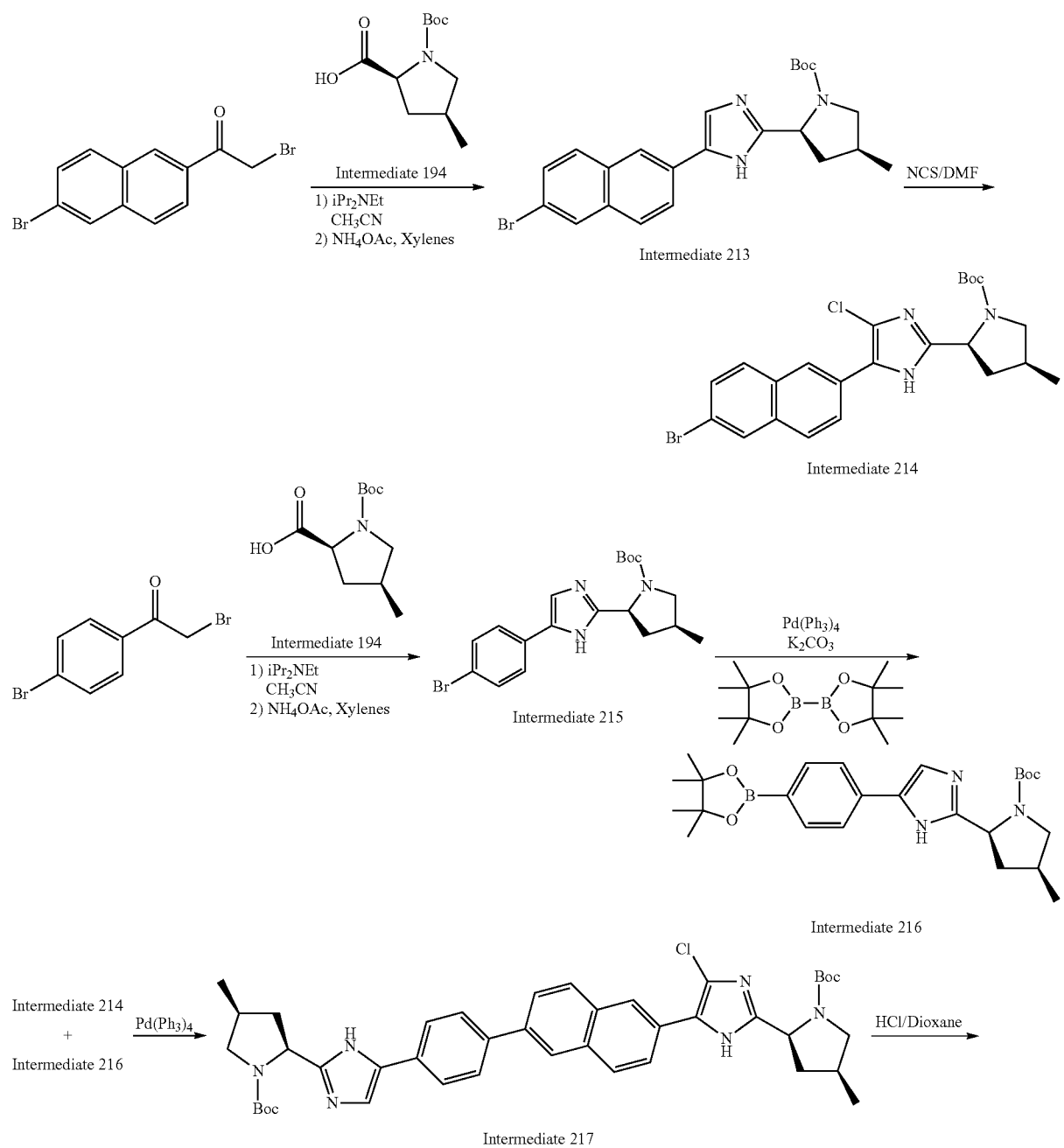

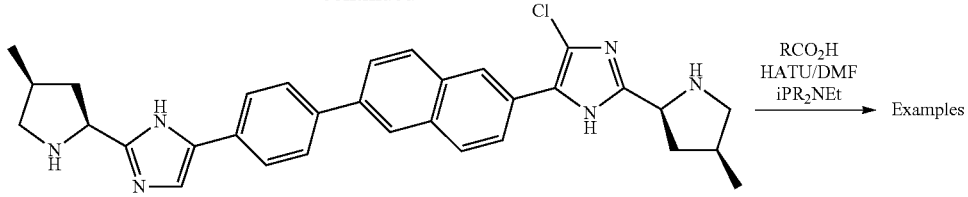

Intermediate 218

Intermediate 218 was prepared as shown in Scheme 57 utilizing (2S,4S)-1-(tert-butoxycarbonyl)-4-methylpyrrolidine-2-carboxylic acid (Intermediate 194) as starting material. Analytical data for the intermediates shown below:

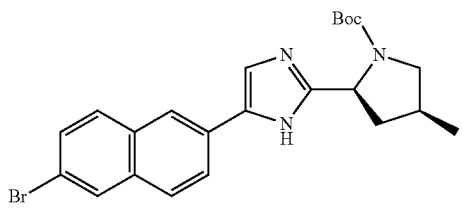 [SMILES: C[C@H]1C[C@@H](c2ncc(-c3ccc4cc(Br)ccc4c3)[nH]2)N(C(=O)OC(C)(C)C)C1]

Intermediate 213

(2S,4S)-tert-Butyl 2-(5-(6-bromonaphthalen-2-yl)-1H-imidazol-2-yl)-4-methylpyrrolidine-1-carboxylate Hunig's base (1.6 mL, 9.0 mmol) was added to a stirred mixture of 2-bromo-1-(6-bromonaphthalen-2-yl)ethanone (3.0 g, 9.0 mmol) and (2S,4S)-1-(tert-butoxycarbonyl)-4-methylpyrrolidine-2-carboxylic acid (2.062 g, 8.99 mmol) in dry acetonitrile (100 mL) and stirred at rt for 16 h. Additional (S)-1-(tert-butoxycarbonyl)-4-methylpyrrolidine-2-carboxylic acid (500 mg) and Hunig's base (0.4 mL) were added and stirring was continued for 15 h. The solvent was removed by rotary evaporation and the residue was taken up in EtOAc and washed with sat'd NaHCO₃ soln, brine, and dried (Na₂SO₄). The ester was taken up in xylene (100 mL) and treated with NH₄OAc (10.40 g, 135 mmol) in a sealed pressure vessel which was immersed in an oil bath at 140° C. and stirred for 2 h. The solvent was removed by rotary evaporation under high vacuum and the residue was taken up in EtOAc and washed with sat'd NaHCO₃ soln, brine, and dried (Na₂SO₄).

This residue was purified with a Thompson 300 g silica gel cartridge (gradient elution 3% B to 100% B over 4.5 L and hold 0.5 L B; Solvent B=ethyl acetate and Solvent A=hexanes) to yield (2S,4S)-tert-butyl 2-(5-(6-bromonaphthalen-2-yl)-1H-imidazol-2-yl)-4-methylpyrrolidine-1-carboxylate (2 g) as a foam. For the purpose of characterization, approximately 25 mg was dissolved in methanol (2 mL) and subjected to prep HPLC (gradient 0-100% B over a 25 min at 40 mL/min) on a PHENOMENEX® Luna column (30×100 mm, 10u); Solvent B=95% CH₃CN-5% H₂O-10 mM NH₄OAc and A=5% CH₃CN-95% H₂O-10 mM NH₄OAc. LC-MS retention time 2.61 min; calcd. for C₂₃H₂₇BrN₃O₂: 456.13 m/z. found 456.09 [M+H]+. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. ¹H NMR (500 MHz, MeOD) δ ppm 8.18 (s, 1H), 8.03 (s, 1H), 7.89 (d, J=8.6 Hz, 1H), 7.82 (d, J=8.6 Hz, 1H), 7.79 (d, J=8.6 Hz, 1H), 7.57 (d, J=10.4 Hz, 1H), 7.51 (s, 1H), 4.91 (br. s, 1H), 3.81 (t, J=8.3 Hz, 1H), 3.21 (t, J=8.3 Hz, 1H), 2.53-2.48 (m, 1H), 2.37-2.34 (m, 1H), 1.81-1.73 (m, 1H), 1.46/1.21 (s, 9H), 1.16 (d, J=6.1 Hz, 3H).

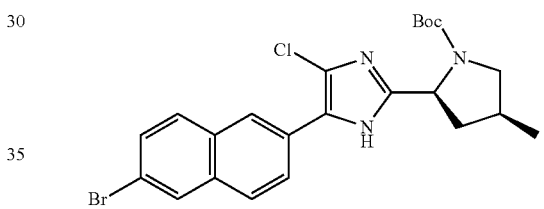

Intermediate 214

(2S,4S)-tert-Butyl 2-(4-(6-bromonaphthalen-2-yl)-5-chloro-1H-imidazol-2-yl)-4-methylpyrrolidine-1-carboxylate NCS (203 mg, 1.52 mmol) was added to a solution of (2S,4S)-tert-butyl 2-(5-(6-bromonaphthalen-2-yl)-1H-imidazol-2-yl)-4-methylpyrrolidine-1-carboxylate (560 mg, 1.39 mmol) in dry DMF (15 mL) and the mixture was heated at 50° C. for 16 h. The solvent was removed by nitrogen purge and the residue was purified with a Thompson 90 g silica gel cartridge (gradient elution 5%-100% B over 2 L; Solvent B=ethyl acetate and Solvent A=hexanes) to yield (2S,4S)-tert-butyl 2-(4-(6-bromonaphthalen-2-yl)-5-chloro-1H-imidazol-2-yl)-4-methylpyrrolidine-1-carboxylate (255 mg) as a tan foam. For purpose of characterization, approximately 20 mg was dissolved in methanol (2 mL) and subject to prep HPLC (gradient 0-100% B over a 25 min at 40 ml/min) on a PHENOMENEX® Luna column (30×100 mm, 10u); Solvent B=95% CH₃CN-5% H₂O-10 mM NH₄OAc and A=5% CH₃CN-95% H₂O-10 mM NH₄OAc. LC-MS retention time 2.61 min; calcd. for C₂₃H₂₆BrClN₃O₂: 492.09 m/z. found 492.03 [M+H]. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 8.18 (s, 1H), 8.09 (s, 1H), 7.91 (br. s, 2H), 7.83 (d, J=8.6 Hz, 1H), 7.63 (d, J=8.6 Hz, 1H), 4.79-4.75 (m, 1H), 3.78 (t, J=8.9 Hz, 1H), 3.19 (t, J=10.4 Hz, 1H), 2.49 (quin, J=6.1 Hz, 1H), 2.36-2.32 (m, 1H), 1.78 (q, J=11.9 Hz, 1H), 1.45/1.24 (s, 9H), 1.15 (d, J=6.1 Hz, 3H).

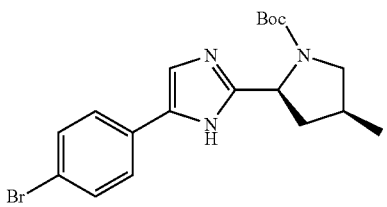 [SMILES: C[C@H]1C[C@@H](c2ncc(-c3ccc(Br)cc3)[nH]2)N(C(=O)OC(C)(C)C)C1]

Intermediate 215

(2S,4S)-tert-Butyl 2-(5-(4-bromophenyl)-1H-imidazol-2-yl)-4-methylpyrrolidine-1-carboxylate Hunig's base (2.3 mL, 13.1 mmol) was added to a stirred mixture of 2-bromo-1-(4-bromophenyl)ethanone (3.64 g, 13.1 mmol) and (2S,4S)-1-(tert-butoxycarbonyl)-4-methylpyrrolidine-2-carboxylic acid (3.0 g, 13 mmol) in dry acetonitrile (150 mL) and stirred at rt for 16 h. The solvent was removed by rotary evaporation and the residue was taken up in EtOAc and washed with water, sat'd NaHCO$_3$ soln, brine, and dried (Na$_2$SO$_4$). The resulting ester was taken up in xylene (150 mL) and treated with NH$_4$OAc (15.1 g, 196 mmol) in a sealed pressure vessel which was immersed in an oil bath at 140° C. and stirred for 2 h. The solvent was removed by rotary evaporation under high vacuum and the residue was taken up in EtOAc and washed with sat'd NaHCO$_3$ soln, brine, and dried (Na$_2$SO$_4$), filtered and concentrated. The crude product was purified with a Thompson 300 g silica gel cartridge (gradient elution 3% B to 100% B over 4.5 L and hold 0.5 L B; Solvent B=ethyl acetate and Solvent A=hexanes) to yield (2S,4S)-tert-butyl 2-(5-(4-bromophenyl)-1H-imidazol-2-yl)-4-methylpyrrolidine-1-carboxylate (3.5 g, 59%) as a foam. For purpose of characterization, approximately 25 mg was dissolved in methanol (2 mL) and subject to prep HPLC (gradient 0-100% B over a 25 min at 40 ml/min) on a PHENOMENEX® Luna column (30×100 mm, 10u); Solvent B=95% CH$_3$CN-5% H$_2$O-10 mM NH$_4$OAc and A=5% CH$_3$CN-95% H$_2$O-10 mM NH$_4$OAc. LC-MS retention time 3.06 min; calcd. for C$_{19}$H$_{25}$BrN$_3$O$_2$: 408.11 m/z. found 408.16 [M+H]. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 7.62 (d, J=8.2 Hz, 2H), 7.51 (d, J=8.6 Hz, 2H), 7.38 (s, 1H), 4.84-4.81 (m, 1H), 3.79 (t, J=8.6 Hz, 1H), 3.17 (t, J=10.4 Hz, 1H), 2.50-2.45 (m, 1H), 2.36-2.31 (m, 1H), 1.76-1.69 (m, 1H), 1.45/1.20 (s, 9H), 1.14 (d, J=6.1 Hz, 3H).

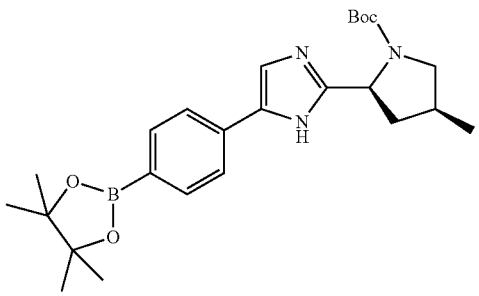

Intermediate 216

(2S,4S)-tert-Butyl 4-methyl-2-(5-(4-(4,4,5,5-tetramethyl-1,3,2-dioxaborolan-2-yl)phenyl)-1H-imidazol-2-yl)pyrrolidine-1-carboxylate Pd(Ph$_3$P)$_4$ (213 mg, 0.185 mmol) was added to a nitrogen purged suspension of (2S,4S)-tert-butyl 2-(5-(4-bromophenyl)-1H-imidazol-2-yl)-4-methylpyrrolidine-1-carboxylate, (1.5 g, 3.7 mmol), 4,4,4',4',5,5,5',5'-octamethyl-2,2'-bi(1,3,2-dioxaborolane) (1.88 g, 7.38 mmol) and potassium acetate (906 mg, 9.23 mmol) in dioxane (35 mL). The pressure reaction vessel was degassed, sealed, and immersed in an oil bath at 85° C. for 16 hours. The mixture was diluted with EtOAc and washed with sat'd NaHCO$_3$ soln, brine, and dried (Na$_2$SO$_4$), filtered and concentrated. The crude product was purified with a Thompson 160 g silica gel cartridge (gradient elution 10% to 100% B over 1 L. Solvent B=ethyl acetate and Solvent A=hexanes) to yield (2S,4S)-tert-butyl 4-methyl-2-(5-(4-(4,4,5,5-tetramethyl-1,3,2-dioxaborolan-2-yl)phenyl)-1H-imidazol-2-yl)pyrrolidine-1-carboxylate (1.8 g, 97%) as a foam. LC-MS retention time 1.78 min; calcd. for C$_{19}$H$_{27}$BN$_3$O$_4$: 372.21 m/z. found 372.18 [M+H]. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode.

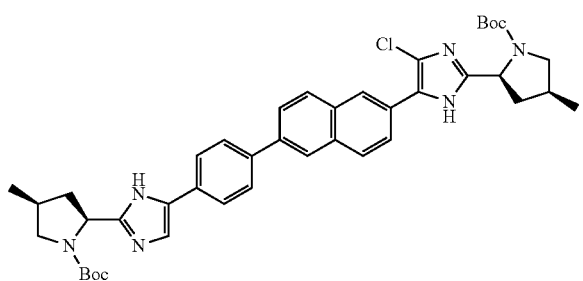

Intermediate 217

(2S,4S)-tert-Butyl 2-(5-(6-(4-(2-((2S,4S)-1-(tert-butoxycarbonyl)-4-methylpyrrolidin-2-yl)-1H-imidazol-5-yl)phenyl)naphthalen-2-yl)-4-chloro-1H-imidazol-2-yl)-4-methylpyrrolidine-1-carboxylate Pd(Ph$_3$P)$_4$ (27.1 mg, 0.023 mmol) was added to a nitrogen purged suspension of (2S,4S)-tert-butyl 2-(5-(6-bromonaphthalen-2-yl)-4-chloro-1H-imidazol-2-yl)-4-methylpyrrolidine-1-carboxylate, (230 mg, 0.469 mmol), (2S,4S)-tert-butyl 4-methyl-2-(5-(4-(4,4,5,5-tetramethyl-1,3,2-dioxaborolan-2-yl)phenyl)-1H-imidazol-2-yl)pyrrolidine-1-carboxylate (234 mg, 0.515 mmol) and NaHCO$_3$ (197 mg, 2.34 mmol) in an argon-degassed solution of DME (4 mL) and water (1 mL). The pressure vessel was charged with argon, sealed, and immersed into a pre-heated oil bath (85° C.) and stirred for 14 h. The mixture was diluted with EtOAc (Note: THF and MeOH were added to aid dissolution) and washed with sat'd NaHCO$_3$ soln, brine, dried (Na$_2$SO$_4$), filtered and concentrated. The residue was purified utilizing a Thompson 90 g SiO$_2$ column (Gradient elution 5% to 100% B for 2 L and hold for 0.5 L Solvent B=ethyl acetate and Solvent A=hexanes) to yield (2S,4S)-tert-butyl 2-(5-(6-(4-(2-((2S,4S)-1-(tert-butoxycarbonyl)-4-methylpyrrolidin-2-yl)-1H-imidazol-5-yl)phenyl)naphthalen-2-yl)-4-chloro-1H-imidazol-2-yl)-4-methylpyrrolidine-1-carboxylate (270 mg, 70%) as a foam. For the purpose of characterization approx. 20 mg was dissolved in MeOH (up to 2 mL) and subject to prep HPLC vial (0 to 100% B over a 30 min gradient at 40 ml/min) using a PHENOMENEX® Luna column (30×100 mm, S10) where B=95% CH$_3$CN-5% H$_2$O-10 mM NH$_4$OAc and A=5% CH$_3$CN-95% H$_2$O-10 mM NH$_4$OAc. LC-MS retention time 3.90 min; calcd. for C$_{42}$H$_{50}$ClN$_6$O$_4$: 737.36 m/z. found 737.43 [M+H]. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD) δ ppm 8.21 (s, 1H), 8.16 (s, 1H), 8.03 (d, J=8.6 Hz, 1H), 7.99 (d, J=8.6 Hz, 2H), 7.91-7.81 (m, 6H), 7.42 (s, 1H), 4.86 (under MeOH, 1H), 4.80-4.877 (m, 1H), 3.82-3.77 (m, 2H), 3.20 (t, J=10.4 Hz, 2H), 2.52-2.47 (m, 2H), 2.37-2.34 (m, 2H), 1.83-1.73 (m, 2H), 1.46/1.26/1.23 (s, 18H), 1.16 (m, 6H).

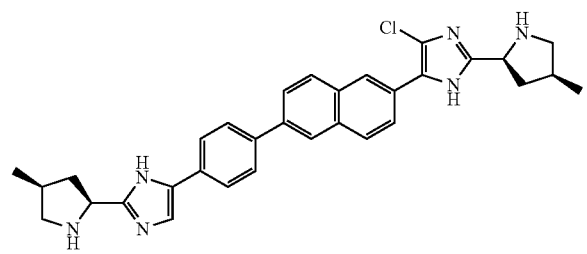

Intermediate 218

4-Chloro-2-((2S,4S)-4-methylpyrrolidin-2-yl)-5-(6-(4-(2-((2S,4S)-4-methylpyrrolidin-2-yl)-1H-imidazol-5-yl)phenyl)naphthalen-2-yl)-1H-imidazole 4N HCl in dioxane (5 mL) was added to a stirred solution of (2S,4S)-tert-butyl 2-(5-(6-(4-(2-((2S,4S)-1-(tert-butoxycarbonyl)-4-methylpyrrolidin-2-yl)-1H-imidazol-5-yl)phenyl)naphthalen-2-yl)-4-chloro-1H-imidazol-2-yl)-4-methylpyrrolidine-1-carboxylate (30 mg, 0.041 mmol) in MeOH (1 mL) and the mixture was stirred at RT for 2 h, concentrated, and dried under high vacuum for 2 h. LC-MS retention time 3.31 min; calcd. for C$_{32}$H$_{34}$ClN$_6$: 537 26 m/z Found 537.37 [M+H]. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode.

Scheme 58

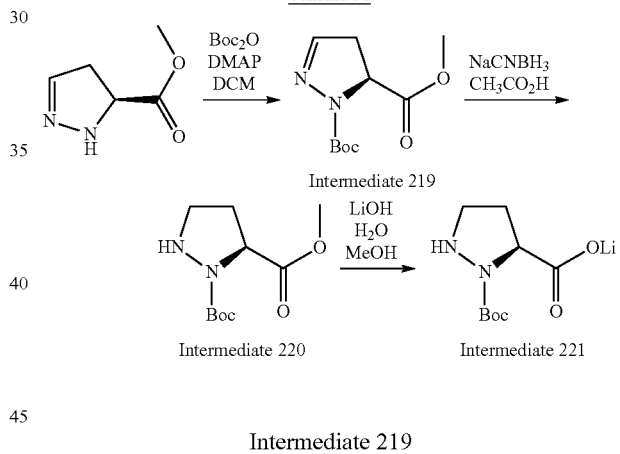

Intermediate 219

(S)-Methyl 4,5-dihydro-1H-pyrazole-5-carboxylate

DMAP (2.83 g, 23.2 mmol) was added to a solution of (S)-methyl 4,5-dihydro-1H-pyrazole-5-carboxylate (prepared according to J. Am. Chem. Soc., 119:8379-8380 (1997); 2.95 g, 23.02 mmol) and Boc$_2$O (11.9 mL, 51.2 mmol) in CH$_2$Cl$_2$ (40 mL) and stirred at ambient condition for 22.5 hr. Additional Boc$_2$O (1.83 g) was added and stirring was continued for 15 hr. Silica gel was added to the reaction mixture and the solvent was removed in vacuo, and the resultant mesh was submitted to a BIOTAGE® purification (300 g silica gel; column was eluted with 30-50% EtOAc/hexanes) to afford (S)-methyl 4,5-dihydro-1H-pyrazole-5-carboxylate as a yellow oil (3.956 g). A sample of the starting pyrazoline, contaminated with the product, was also retrieved (695 mg). $^1$H NMR (CDCl$_3$, δ=7.24 ppm, 400 MHz): 6.80 (s, 1H), 4.67 (dd, J=12.6, 6.1 Hz, 1H), 3.75 (s, 3H), 3.22 (ddd, J=18.5, 12.6, 1.4 Hz, 1H), 2.94 (ddd, J=18.5, 6.1, 1.7 Hz, 1H), 1.5 (s, 9H). LC-MS: Anal. Calcd. for [M+Na]$^+$ C$_{10}$H$_{16}$N$_2$NaO$_4$: 251.10. found 251.26.

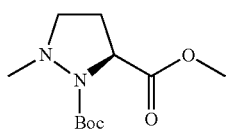

Intermediate 220

(S)-1-tert-Butyl 5-methyl 1H-pyrazole-1,5(4H,5H)-dicarboxylate

Sodium cyanoborohydride (0.769 g, 12.2 mmol) was added in batches over 1 min to an acetic acid (7.0 mL) solution of (S)-methyl 4,5-dihydro-1H-pyrazole-5-carboxylate (1.05 g, 4.61 mmol), and stirred at ambient condition for 20 h. Formaldehyde (1mL of 37% in water) was added dropwise over 4 min, and stirring was continued for 4.5 h. The volatile component was removed in vacuo and the residue was treated with saturated NaHCO₃ (10 mL) and CH₂Cl₂ (30 mL), the mixture was shaken and the phases were separated. The organic layer was washed with an additional saturated NaHCO₃ solution (10 mL), dried (MgSO₄), filtered and concentrated in vacuo. The resultant crude material was purified with a BIOTAGE® (240 g silica gel; sample was loaded with CH₂Cl₂; eluted with 60-100% EtOAc/hexanes) to afford (S)-1-tert-butyl 5-methyl 1H-pyrazole-1,5(4H,5H)-dicarboxylate as a colorless oil (861 mg). ¹H NMR (CDCl₃, δ=7.24 ppm, 400 MHz): 4.39 (app br t, J=7.7, 1H), 3.74 (s, 3H), 3.15-3.02 (m, 2H), 2.64 (s, 3H), 2.48-2.40 (m, 1H), 2.30-2.21 (m, 1H), 1.45 (s, 9H). LC-MS: Anal. Calcd. for [M+Na]⁺ C₁₁H₂₀N₂NaO₄: 267.13. found 267.28.

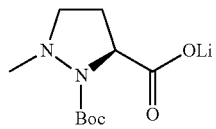

Intermediate 221

Lithium (S)-2-(tert-butoxycarbonyl)pyrazolidine-3-carboxylate

A water (5 mL) solution of LiOH (0.146 g, 6.09 mmol) was added to a methanol (5 mL) solution of (S)-1-tert-butyl 5-methyl 1H-pyrazole-1,5(4H,5H)-dicarboxylate (0.76 g, 3.11 mmol), and stirred at ambient conditions for ~7 h. The reaction mixture was cooled with an ice-water bath, and HCl/H₂O (3 mL of 1.00 N; 3.0 mmol) was added dropwise and stirred for a few minutes. Then, the volatile component was removed in vacuo and the resultant viscous oil was exposed to high vacuum to afford lithium (S)-2-(tert-butoxycarbonyl)pyrazolidine-3-carboxylate as a white foam, which was used without further purification. ¹H NMR (DMSO-d₆, δ=2.50 ppm, 400 MHz) for crude sample: 3.98 (dd, J=8.5, 6.3, 1H), 2.86-2.74 (m, 2H), 2.45 (s, 3H), 2.25-2.17 (m, 1H), 2.10-2.02 (m, 1H), 1.35 (s, 9H). LC-MS: Anal. Calcd. for [M+H]⁺ C₁₀H₁₉N₂O₄: 231.13. found 231.21.

Scheme 59

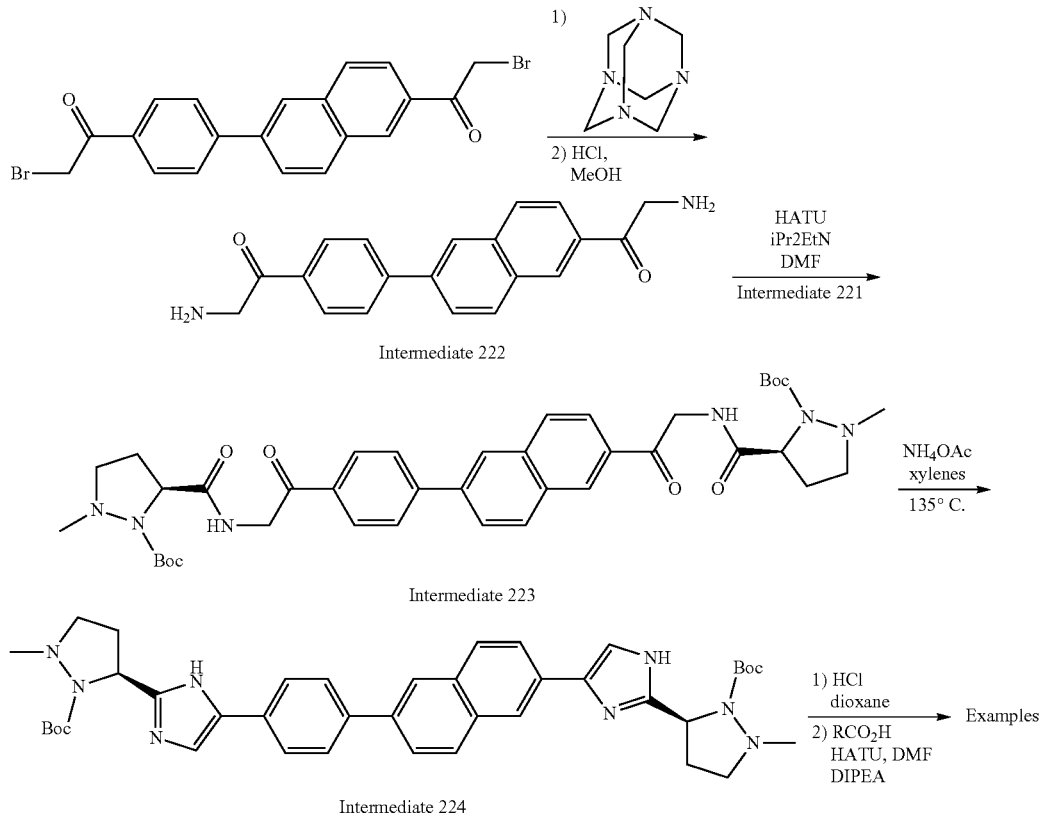

Intermediate 222

2-Amino-1-(4-(6-(2-aminoacetyl)naphthalen-2-yl)phenyl)ethanone

A slurry of 2-bromo-1-(4-(6-(2-bromoacetyl)naphthalen-2-yl)phenyl)ethanone (1.0 g, 2.2 mmol) and hexamethylenetetramine (0.660 g, 4.71 mmol) were slurried into chloroform (30 mL) and heated at 50° C. for 2 h. The reaction was cooled to rt and the solids were collected by filtration (rinsed with chloroform, 3×25 mL). The resulting bright yellow solid was slurried into MeOH (15.0 mL) and then conc HCl (3.0 mL, 99 mmol) was added dropwise and the reaction was stirred in the dark for 2 d. The reaction was concentrated to a solid which was slurried into water and stirred for 1 h. The solids were collected by filtration and the cake was dried in a vacuum oven to yield an HCl salt of 2-amino-1-(4-(6-(2-aminoacetyl)naphthalen-2-yl)phenyl)ethanone (787 mg). LC-MS retention time 2.342 min; m/z 319.09 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode.

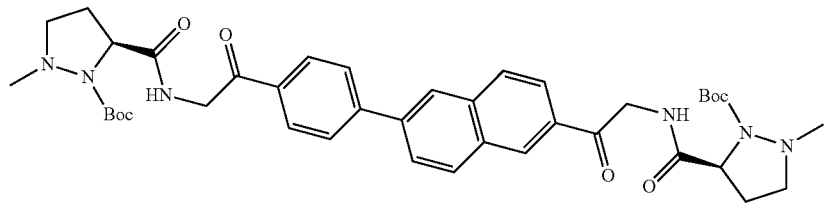

Intermediate 223

(S)-tert-Butyl 5-(2-(4-(6-(2-((S)-2-(tert-butoxycarbonyl)-1-methylpyrazolidine-3-carboxamido)acetyl)naphthalen-2-yl)phenyl)-2-oxoethylcarbamoyl)-2-methylpyrazolidine-1-carboxylate HATU (1577 mg, 4.15 mmol) was added to a stirred solution of a n HCl salt of 2-amino-1-(4-(6-(2-aminoacetyl)naphthalen-2-yl)phenyl)ethanone (773 mg, 1.98 mmol) and lithium (S)-2-(tert-butoxycarbonyl)-1-methylpyrazolidine-3-carboxylate (980 mg, 4.15 mmol) in DMF (15 mL) and Hunig's Base (2.070 mL, 11.85 mmol) and the reaction mixture was stirred for 2 h. The reaction was concentrated to ~20% volume, diluted with MeOH, filtered and purified by HPLC (MeOH/water with an ammonium acetate buffer) to yield (S)-tert-butyl 5-(2-(4-(6-(2-((S)-2-(tert-butoxycarbonyl)-1-methylpyrazolidine-3-carboxamido)acetyl)naphthalen-2-yl)phenyl)-2-oxoethylcarbamoyl)-2-methylpyrazolidine-1-carboxylate (537 mg) as a bright yellow solid. LC-MS retention time 3.758 min; m/z 741.55 (MH−). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode.

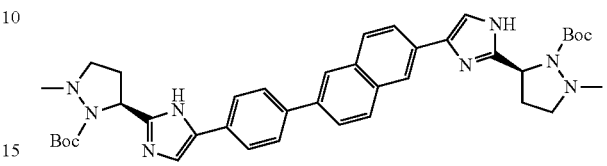

Intermediate 224

(S)-tert-Butyl 5-(5-(4-(6-(2-((S)-2-(tert-butoxycarbonyl)-1-methylpyrazolidin-3-yl)-1H-imidazol-4-yl)naphthalen-2-yl)phenyl)-1H-imidazol-2-yl)-2-methylpyrazolidine-1-carboxylate In a 25 mL pressure tube, (S)-tert-butyl 5-(2-(4-(6-(2-((S)-2-(tert-butoxycarbonyl)-1-methylpyrazolidine-3-carboxamido)acetyl)naphthalen-2-yl)phenyl)-2-oxoethylcarbamoyl)-2-methylpyrazolidine-1-carboxylate (420 mg, 0.565 mmol) and ammonium acetate (872 mg, 11.3 mmol) were slurried into xylenes (7 mL). The reaction vessel was sealed and heated at 135° C. for 5 h then at rt ON. The crude reaction was diluted with ½ sat aq. NaHCO$_3$ (40 mL) and extracted with DCM (3×30 mL). The combine organics were dried (MgSO$_4$), filtered and concentrated to yield (S)-tert-butyl 5-(5-(4-(6-(2-((S)-2-(tert-butoxycarbonyl)-1-methylpyrazolidin-3-yl)-1H-imidazol-4-yl)naphthalen-2-yl)phenyl)-1H-imidazol-2-yl)-2-methylpyrazolidine-1-carboxylate (95 mg, ~80% purity) as a dark yellow glass. LC-MS retention time 4.026 min; m/z 703.63 (MH−). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, MeOD) δ ppm 8.32 (s, 1H), 8.28 (s, 1H), 8.15 (d, J=8.8 Hz, 1H), 8.10 (d, J=8.8 Hz, 1H), 7.86-8.03 (m, 8H), 5.31-5.39 (m, 2H), 3.22-3.35 (m, 4H), 2.82-2.93 (m, 2H), 2.77 (s, 3H), 2.76 (s, 3H), 2.53-2.65 (m, 2H), 1.43 (s, 18H).

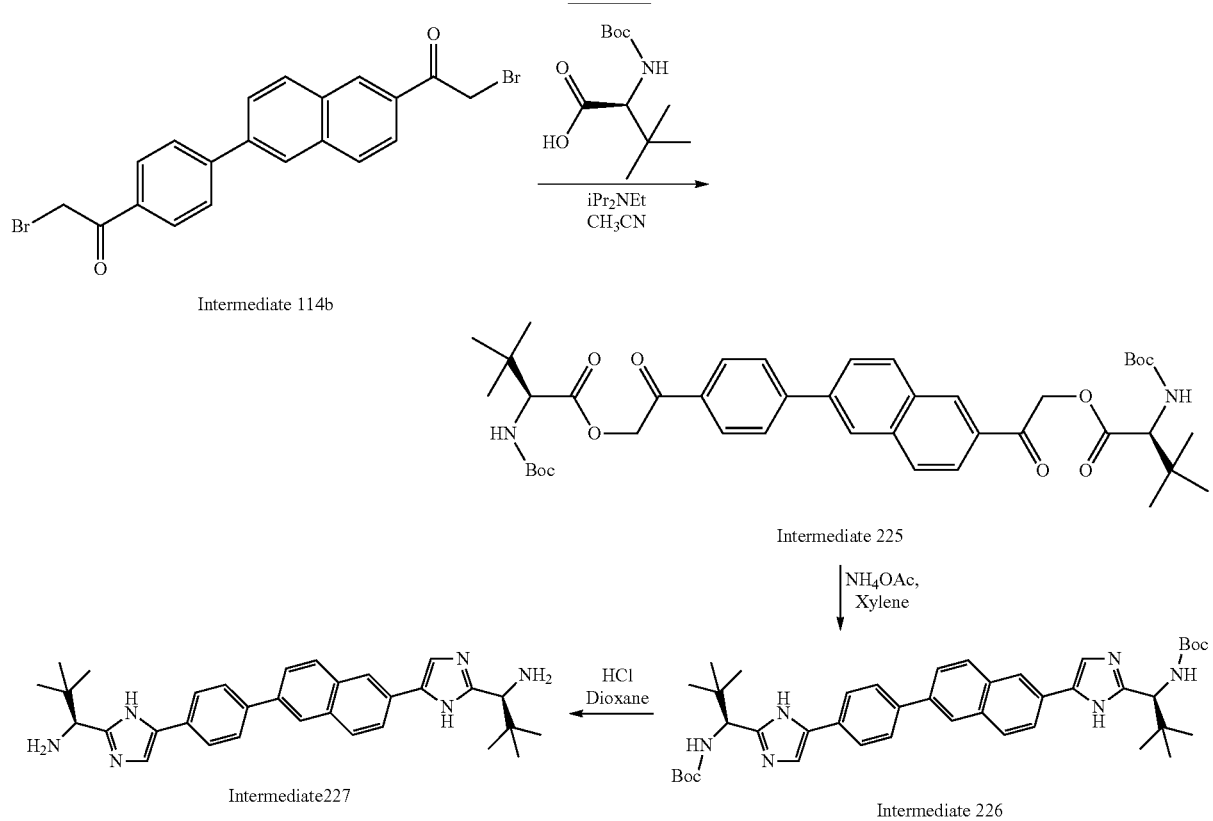

Scheme 60

Condition 1
Column=PHENOMENEX®, 2.0×50 mm, 3 μm
Start % B=0
Final % B=100
Gradient time=4 min
Stop time=5 min
Flow Rate=0.8 mL/min
Wavelength=220 nm
Solvent A=0.1% TFA in 10% methanol/90% water
Solvent B=0.1% TFA in 90% methanol/10% water
Oven temp.=40° C.
Condition 2
Column=Sunfire, C18, 3.0×150 mm, 3.5 μm
Start % B=0
Final % B=100
Gradient time=15 min
Stop time=18 min
Flow Rate=1 mL/min
Wavelength 1=220 nm
Wavelength 2=254 nm
Solvent A=0.1% TFA in 5% MeCN/95% water
Solvent B=0.1% TFA in 95% MeCN/5% water

Intermediate 225

(S)-2-(4-(6-(2-((S)-2-(tert-Butoxycarbonylamino)-3,3-dimethylbutanoyloxy)acetyl)naphthalen-2-yl)phenyl)-2-oxoethyl 2-(tert-butoxycarbonylamino)-3,3-dimethylbutanoate To a solution of 2-bromo-1-(4-(6-(2-bromoacetyl)naphthalen-2-yl)phenyl)ethanone (0.2 g, 0.448 mmol) and (S)-2-(tert-butoxycarbonylamino)-3,3-dimethylbutanoic acid (0.207 g, 0.897 mmol) in DCM was added DIPEA (0.172 mL, 0.986 mmol). The reaction mixture was stirred at rt for 16 h and then diluted with EtOAc, washed with sat. NaHCO$_3$, water, sat. NaCl and dried over anhydrous Na$_2$SO$_4$. Then it was filtered and concentrated to yield (S)-2-(4-(6-(2-((S)-2-(tert-butoxycarbonylamino)-3,3-dimethylbutanoyloxy)acetyl)naphthalen-2-yl)phenyl)-2-oxoethyl 2-(tert-butoxycarbonylamino)-3,3-dimethylbutanoate as a pale yellow solid. LC-MS (Cond. 1): [M+H]$^+$ 747.50, R$_f$=4.67 min.

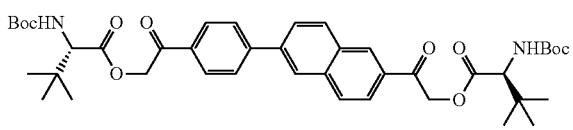 [SMILES: CC(C)(C)OC(=O)N[C@H](C(=O)OCC(=O)c1ccc(-c2ccc3cc(C(=O)COC(=O)[C@@H](NC(=O)OC(C)(C)C)C(C)(C)C)ccc3c2)cc1)C(C)(C)C]

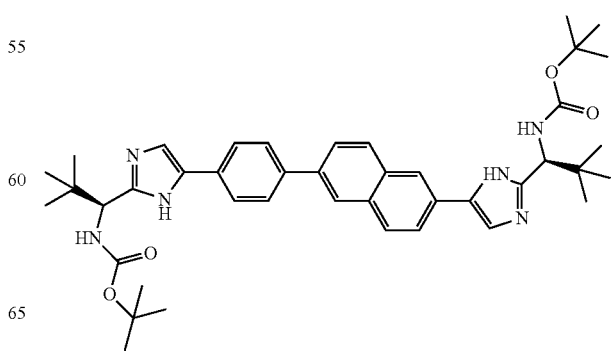

Intermediate 226 tert-Butyl (S)-1-(5-(4-(6-(2-((S)-2,2-dimethyl-1-(tert-butoxycarbonylamino)propyl)-1H-imidazol-5-yl)naphthalen-2-yl)phenyl)-1H-imidazol-2-yl)-2,2-dimethylpropylcarbamate In a sealed tube, a reaction mixture of (S)-2-(4-(6-(2-((S)-2-(tert-butoxycarbonylamino)-3,3-dimethylbutanoyloxy)

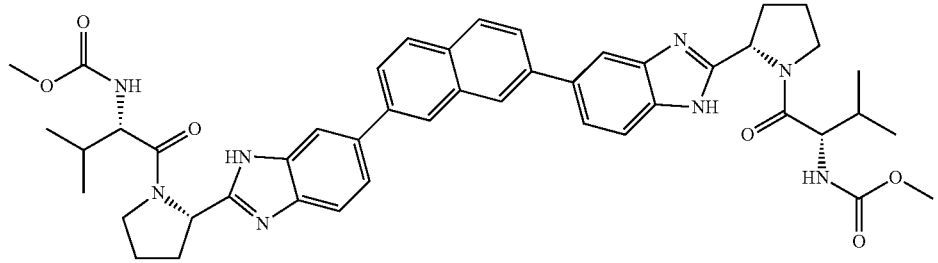

acetyl)naphthalen-2-yl)phenyl)-2-oxoethyl 2-(tert-butoxycarbonylamino)-3,3-dimethylbutanoate (0.35 g, 0.469 mmol) in xylenes (5 mL) and ammonium acetate (0.361 g, 4.69 mmol) was heated at 130° C. for 3 h. The reaction mixture was diluted with EtOAc and water. The organic layer was washed with sat. NaHCO₃ and sat. NaCl, dried over anhydrous Na₂SO₄, filtered and concentrated. The residue was charged into a 40 g silica gel cartridge which was eluted with a 15 min gradient of 0-100% EtOAc/Hex to yield tert-butyl (S)-1-(5-(4-(6-(2-((S)-2,2-dimethyl-1-(tert-butoxycarbonylamino)propyl)-1H-imidazol-5-yl)naphthalen-2-yl)phenyl)-1H-imidazol-2-yl)-2,2-dimethylpropylcarbamate (0.2 g) as a yellow solid. LC-MS (Cond. 1): [M+H]⁺ 707.6, R$_t$=3.44 min.

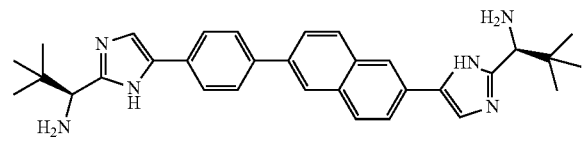 [SMILES: CC(C)(C)[C@H](N)c1ncc(-c2ccc(-c3ccc4cc(-c5cnc([C@@H](N)C(C)(C)C)[nH]5)ccc4c3)cc2)[nH]1]

Intermediate 226

(S)-1-(5-(4-(6-(2-((S)-1-Amino-2,2-dimethylpropyl)-1H-imidazol-5-yl)naphthalen-2-yl)phenyl)-1H-imidazol-2-yl)-2,2-dimethylpropan-1-amine To a reaction mixture of tert-butyl (S)-1-(5-(4-(6-(2-((S)-2,2-dimethyl-1-(tert-butoxycarbonylamino)propyl)-1H-imidazol-5-yl)naphthalen-2-yl)phenyl)-1H-imidazol-2-yl)-2,2-dimethylpropylcarbamate (0.2 g, 0.283 mmol) in DCM was added 4M hydrogen chloride in dioxane (2 mL, 8 mmol). The reaction mixture was stirred at rt for 4 h and then concentrated to dryness to yield an HCl salt of (S)-1-(5-(4-(6-(2-((S)-1-amino-2,2-dimethylpropyl)-1H-imidazol-5-yl)naphthalen-2-yl)phenyl)-1H-imidazol-2-yl)-2,2-dimethylpropan-1-amine as a yellow solid. LC-MS (Cond. 1): [M+H]⁺ 507.43, R$_t$=3.241 min.

EXAMPLES

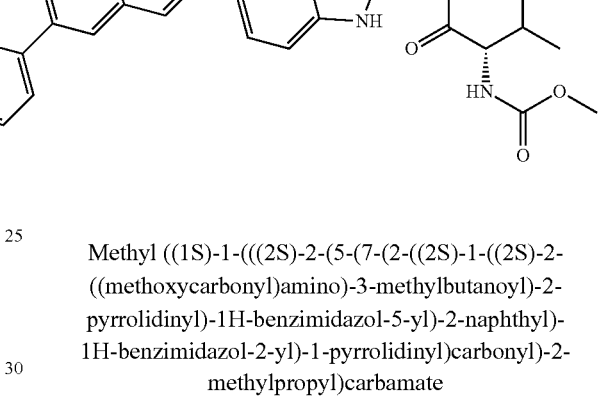

Methyl ((1S)-1-(((2S)-2-(5-(7-(2-((2S)-1-((2S)-2-((methoxycarbonyl)amino)-3-methylbutanoyl)-2-pyrrolidinyl)-1H-benzimidazol-5-yl)-2-naphthyl)-1H-benzimidazol-2-yl)-1-pyrrolidinyl)carbonyl)-2-methylpropyl)carbamate HATU (59 mg, 0.15 mmol) was added to a mixture of a TFA salt of 2,7-bis(2-((S)-pyrrolidin-2-yl)-1H-benzo[d]imidazol-6-yl)naphthalene (37 mg), diisopropylethylamine (68 μL, 0.40 mmol) and (S)-2-(methoxycarbonylamino)-3-methylbutanoic acid (27 mg, 0.15 mmol) in DMF (2 mL) and the resulting mixture was stirred at ambient conditions for 2.5 hours. The reaction mixture was diluted with methanol (2 mL) and water (2 mL) and stirred for 15 min. The volatile component was removed in vacuo and the residue was purified twice by a reverse phase HPLC (water/acetonitrile/TFA) and reverse phase HPLC (water/acetonitrile/NH₄OAc) to provide the desired product which was suspended in methanol and TFA. The volatiles were removed in vacuo to afford a TFA salt of methyl ((1S)-1-(((2S)-2-(5-(7-(2-((2S)-1-((2S)-2-((methoxycarbonyl)amino)-3-methylbutanoyl)-2-pyrrolidinyl)-1H-benzimidazol-5-yl)-2-naphthyl)-1H-benzimidazol-2-yl)-1-pyrrolidinyl)carbonyl)-2-methylpropyl)carbamate (11.3 mg) as tan solid. LC-MS retention time 1.34 min; calcd. for $C_{46}H_{52}N_8O_6$ 812.4. found m/z 813.42 [M+H]⁺. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. ¹H NMR (TFA salt, 500 MHz, MeOD) δ ppm 8.31 (s, 2H), 8.03-8.10 (m, 4H), 7.96-8.02 (m, Hz, 2H), 7.89 (dd, J=8.6, 1.5 Hz, 2H), 7.85 (m, 2H), 5.36 (t, J=7.0 Hz, 2H), 4.22-4.32 (m, 2H), 4.09-4.19 (m, 2H), 3.89-4.00 (m, 2H), 3.63-3.74 (m, 6H), 2.56-2.70 (m, 2H), 2.31-2.40 (m, 2H), 2.19-2.31 (m, 4H), 2.08 (dd, J=13.6, 6.9 Hz, 2H), 0.95 (d, J=7.0 Hz, 6H), 0.89 (d, J=6.7 Hz, 6H).

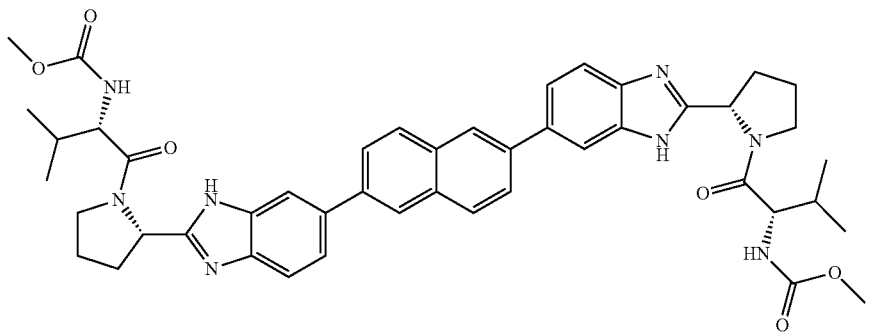

Methyl ((1S)-1-(((2S)-2-(5-(6-(2-((2S)-1-((2S)-2-((methoxycarbonyl)amino)-3-methylbutanoyl)-2-pyrrolidinyl)-1H-benzimidazol-5-yl)-2-naphthyl)-1H-benzimidazol-2-yl)-1-pyrrolidinyl)carbonyl)-2-methylpropyl)carbamate HATU (82 mg, 0.217 mmol) was added to a TFA salt of 2,6-bis(2-((S)-pyrrolidin-2-yl)-1H-benzo[d]imidazol-6-yl)naphthalene (69 mg), diisopropylethylamine (126 μL, 0.723 mmol) and (S)-2-(methoxycarbonylamino)-3-methylbutanoic acid (51 mg, 0.29 mmol) in DMF (2 mL) and the resulting mixture was stirred at ambient conditions for 2.5 hours. The reaction mixture was diluted with methanol (2 mL) and water (2 mL). Then the volatile component was removed in vacuo and the residue was purified by a reverse phase HPLC (water/acetonitrile/TFA) to provide a TFA salt of methyl ((1S)-1-(((2S)-2-(5-(6-(2-((2S)-1-((2S)-2-((methoxycarbonyl)amino)-3-methylbutanoyl)-2-pyrrolidinyl)-1H-benzimidazol-5-yl)-2-naphthyl)-1H-benzimidazol-2-yl)-1-pyrrolidinyl)carbonyl)-2-methylpropyl)carbamate (47 mg) as tan solid. LC-MS retention time 1.30 min; calcd. for $C_{46}H_{52}N_8O_6$: 812.40. found m/z 813.42 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.25 (s, 2H), 8.07-8.16 (m, 4H), 8.02 (m, J=8.6 Hz, 2H), 7.91 (m, J=8.6 Hz, 2H), 7.87 (d, J=8.6 Hz, 2H), 5.37 (t, J=7.2 Hz, 2H), 4.28 (d, J=7.0 Hz, 2H), 4.09-4.18 (m, 2H), 3.90-4.01 (m, 2H), 3.63-3.73 (m, 6H), 2.57-2.70 (m, 2H), 2.32-2.45 (m, 2H), 2.19-2.32 (m, 4H), 2.09 (dq, J=13.6, 6.9 Hz, 2H), 0.95 (d, J=6.7 Hz, 6H), 0.89 (d, J=6.7 Hz, 6H).

Methyl ((1S)-1-(((2S)-2-(4-(4-(6-(2-(1-((2S)-2-((methoxycarbonyl)amino)-3-methylbutanoyl)-2-pyrrolidinyl)-1H-benzimidazol-5-yl)-2-naphthyl)phenyl)-1H-imidazol-2-yl)-1-pyrrolidinyl)carbonyl)-2-methylpropyl)carbamate HATU (39 mg, 0.10 mmol) was added to a mixture of a TFA salt of 2-((S)-pyrrolidin-2-yl)-6-(6-(4-(2-((S)-pyrrolidin-2-yl)-1H-imidazol-5-yl)phenyl)naphthalen-2-yl)-1H-benzo[d]imidazole (50 mg), diisopropylethylamine (89 μL, 0.51 mmol) and (S)-2-(methoxycarbonylamino)-3-methylbutanoic acid (27 mg, 0.15 mmol) in DMF (2 mL) and the resulting mixture was stirred at ambient conditions for 2.5 hours. The reaction mixture was diluted with methanol (2 mL) and water (2 mL). The volatile component was removed in vacuo and the residue was purified by a reverse phase HPLC (water/acetonitrile/TFA) to provide a TFA salt of methyl ((1S)-1-(((2S)-2-(4-(4-(6-(2-(1-((2S)-2-((methoxycarbonyl)amino)-3-methylbutanoyl)-2-pyrrolidinyl)-1H-benzimidazol-5-yl)-2-naphthyl)phenyl)-1H-imidazol-2-yl)-1-pyrrolidinyl)carbonyl)-2-methylpropyl)carbamate (31.4 mg) as tan solid. LC-MS retention time 1.37 min; calcd. for $C_{48}H_{54}N_8O_6$ 838.42. found m/z 839.36 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.23-8.28 (m, 2H), 8.08-8.15 (m, 3H), 8.02 (d, J=8.6 Hz, 1H), 7.95-8.00 (m, 2H), 7.85-7.95 (m, 6H), 5.40 (t, J=7.2 Hz, 1H), 5.29 (t, J=7.5 Hz, 1H), 4.29 (dd, J=19.4, 7.2 Hz, 2H), 4.10-4.19 (m, 2H), 3.96-4.03 (m, 1H),

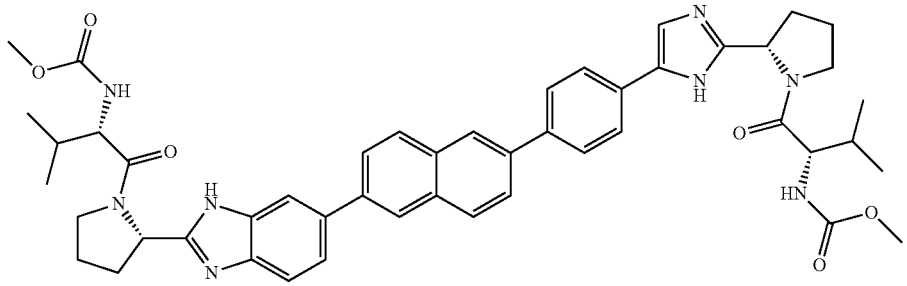

3.87-3.96 (m, 1H), 3.69 (m, 6H), 2.55-2.73 (m, 2H), 2.04-2.42 (m, 8H), 0.89-1.05 (m, 12H).

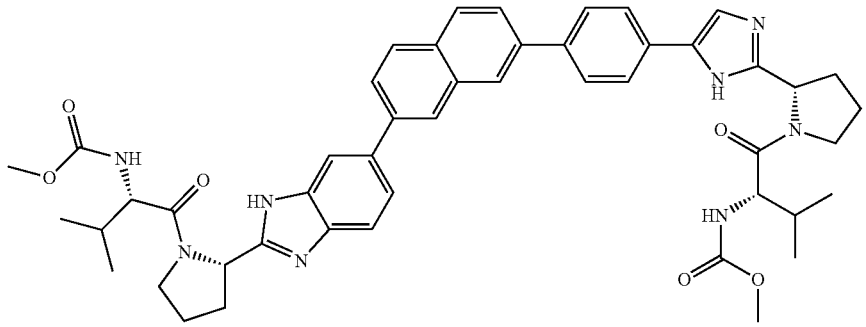 [SMILES: COC(=O)N[C@H](C(=O)N1CCC[C@H]1c1ncc(-c2ccc(-c3ccc4ccc(-c5ccc6nc([C@@H]7CCCN7C(=O)[C@@H](NC(=O)OC)C(C)C)[nH]c6c5)cc4c3)cc2)[nH]1)C(C)C]

Methyl ((1S)-1-(((2S)-2-(4-(4-(7-(2-((2S)-1-((2S)-2-((methoxycarbonyl)amino)-3-methylbutanoyl)-2-pyrrolidinyl)-1H-benzimidazol-5-yl)-2-naphthyl)phenyl)-1H-imidazol-2-yl)-1-pyrrolidinyl)carbonyl)-2-methylpropyl)carbamate HATU (29 mg, 0.076 mmol) was added to a mixture of a TFA salt of 2-((S)-pyrrolidin-2-yl)-6-(7-(4-(2-((S)-pyrrolidin-2-yl)-1H-imidazol-5-yl)phenyl)naphthalen-2-yl)-1H-benzo[d]imidazole (25 mg), diisopropylethylamine (45 μL, 0.26 mmol) and (S)-2-(methoxycarbonylamino)-3-methylbutanoic acid (13 mg, 0.76 mmol) in DMF (2 mL) and the resulting mixture was stirred at ambient conditions for 2.5 hours. The reaction mixture was diluted with methanol (2 mL) and water (2 mL). The volatile component was removed in vacuo and the residue was purified by a reverse phase HPLC (water/acetonitrile/TFA) to provide a TFA salt of methyl ((1S)-1-(((2S)-2-(4-(4-(7-(2-((2S)-1-((2S)-2-((methoxycarbonyl)amino)-3-methylbutanoyl)-2-pyrrolidinyl)-1H-benzimidazol-5-yl)-2-naphthyl)phenyl)-1H-imidazol-2-yl)-1-pyrrolidinyl)carbonyl)-2-methylpropyl)carbamate (14.2 mg) as yellow solid. LC-MS retention time 1.40 min; calcd. for $C_{48}H_{54}N_8O_6$ 838.42. found m/z 839.36 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.33 (br s, 2H), 8.13 (s, 1H), 8.03-8.10 (m, 3H), 8.00 (d, J=8.2 Hz, 2H), 7.86-7.94 (m, 6H), 5.40 (t, J=7.2 Hz, 1H), 5.29 (t, J=7.6 Hz, 1H), 4.31 (d, J=7.3 Hz, 1H), 4.27 (d, J=7.3 Hz, 1H), 4.10-4.20 (m, 2H), 3.85-4.10 (m, 2H), 3.69 (s, 6H), 2.55-2.74 (m, 2H), 2.03-2.37 (m, 8H), 0.85-1.05 (m, 12H).

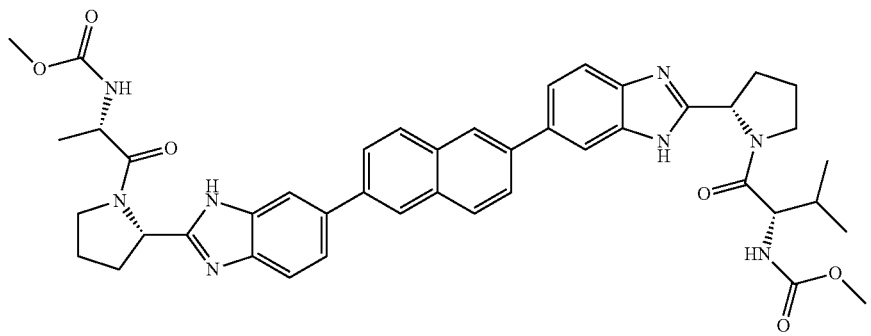

Methyl ((1S)-2-((2S)-2-(5-(6-(2-((2S)-1-(N-(methoxycarbonyl)-L-alanyl)-2-pyrrolidinyl)-1H-benzimidazol-5-yl)-2-naphthyl)-1H-benzimidazol-2-yl)-1-pyrrolidinyl)-1-methyl-2-oxoethyl)carbamate HATU (74.5 mg, 0.196 mmol) was added to a stirring solution of a TFA salt of 2,6-bis(2-((S)-pyrrolidin-2-yl)-1H-benzo[d]imidazol-6-yl)naphthalene (40 mg), (S)-2-(methoxycarbonylamino)propanoic acid (28.8 mg, 0.196 mmol) and DIEA (0.114 mL, 0.653 mmol) in DMF (2 mL). The reaction was stirred 9 h at room temperature, diluted with MeOH (2 mL) and water (2 mL), concentrated to remove the volatiles and purified by preparative HPLC (acetonitrile/water with 0.1% TFA) to afford a TFA salt of methyl ((1S)-2-((2S)-2-(5-(6-(2-((2S)-1-(N-(methoxycarbonyl)-L-alanyl)-2-pyrrolidinyl)-1H-benzimidazol-5-yl)-2-naphthyl)-1H-benzimidazol-2-yl)-1-pyrrolidinyl)-1-methyl-2-oxoethyl)carbamate (35.9 mg) as white solid. LC-MS retention time 1.12 min; calcd. for $C_{42}H_{44}N_8O_6$ 756.34. found m/z 757.20 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.22-8.30 (m, 2H), 8.08-8.18 (m, 4H), 7.99-8.07 (m, 2H), 7.83-7.96 (m, 4H), 5.44 (dd, J=8.6, 5.2 Hz, 2H), 4.56 (q, J=6.9 Hz, 2H), 4.0-4.09 (m, 2H), 3.94-4.02 (m, 2H), 3.61-3.75 (m, 6H), 2.58-2.72 (m, 2H), 2.21-2.38 (m, 6H), 1.32-1.45 (m, 6H).

A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.25-8.35 (m, 2H), 8.12-8.21 (m, 4H), 8.05-8.12 (m, 2H), 7.90-8.00 (m, 4H), 7.38-7.54 (m, 10H), 5.62 (s, 2H), 5.38-5.53 (m, 2H), 4.04-4.18 (m, 2H), 3.67 (s, 6H), 2.34-2.41 (m, 2H), 2.46-2.58 (m, 2H), 2.15-2.35 (m, 4H), 2.02-2.13 (m, 2H).

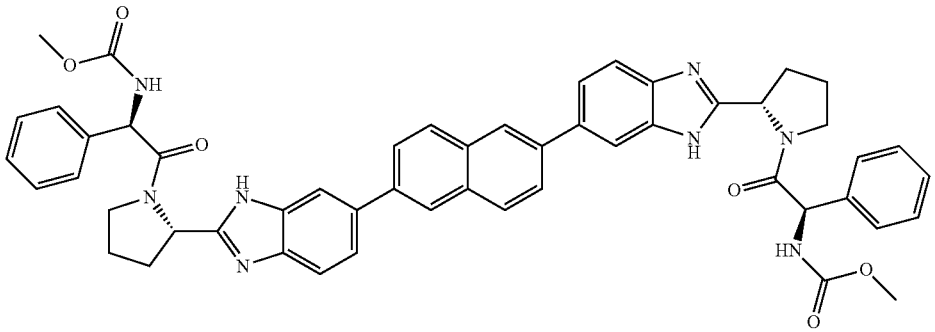 [SMILES: COC(=O)N[C@@H](C(=O)N1CCC[C@H]1c1nc2ccc(-c3ccc4cc(-c5ccc6nc([C@@H]7CCCN7C(=O)[C@H](NC(=O)OC)c7ccccc7)[nH]c6c5)ccc4c3)cc2[nH]1)c1ccccc1]

Dimethyl (2,6-naphthalenediylbis(1H-benzimidazole-5,2-diyl(2S)-2,1-pyrrolidinediyl((1R)-2-oxo-1-phenyl-2,1-ethanediyl)))biscarbamate HATU (74.5 mg, 0.196 mmol) was added to a stirring solution of a TFA salt of 2,6-bis(2-((S)-pyrrolidin-2-yl)-1H-

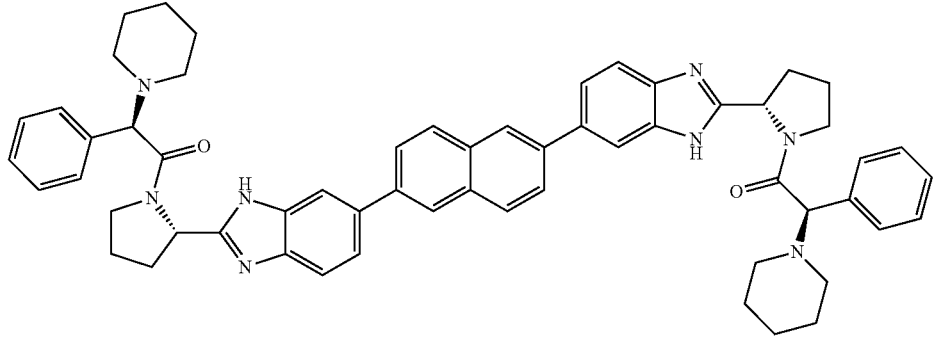 [SMILES: O=C([C@@H](c1ccccc1)N1CCCCC1)N1CCC[C@H]1c1nc2ccc(-c3ccc4cc(-c5ccc6nc([C@@H]7CCCN7C(=O)[C@@H](c7ccccc7)N7CCCCC7)[nH]c6c5)ccc4c3)cc2[nH]1]

benzo[d]imidazol-6-yl)naphthalene (40 mg), (R)-2-(methoxycarbonylamino)-2-phenylacetic acid (41.0 mg, 0.196 mmol) and DIEA (0.114 mL, 0.653 mmol) in DMF (2 mL). The reaction was stirred 9 h at room temperature, diluted with MeOH (2 mL) and water (2 mL), concentrated to remove the volatiles and purified by preparative HPLC (acetonitrile/water with 0.1% TFA) and then by preparative HPLC (acetonitrile/water with 10 mM ammonium acetate) to afford dimethyl (2,6-naphthalenediylbis(1H-benzimidazole-5,2-diyl (2S)-2,1-pyrrolidinediyl((1R)-2-oxo-1-phenyl-2,1-ethanediyl)))biscarbamate (32.3 mg) as white solid. LC-MS retention time 1.43 min; calcd. for $C_{52}H_{48}N_8O_6$ 880.37. found m/z 881.23 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent 5,5'-(2,6-Naphthalenediyl)bis(2-((2S)-1-((2R)-2-phenyl-2-(1-piperidinyl)acetyl)-2-pyrrolidinyl)-1H-benzimidazole)

HATU (74.5 mg, 0.196 mmol) was added to a stirring solution of a TFA salt of 2,6-bis(2-((S)-pyrrolidin-2-yl)-1H-benzo[d]imidazol-6-yl)naphthalene (40 mg), (R)-2-phenyl-2-(piperidin-1-yl)acetic acid (43.0 mg, 0.196 mmol) and DIEA (0.114 mL, 0.653 mmol) in DMF (2 mL). The reaction was stirred 9 h at room temperature, diluted with MeOH (2 mL) and water (2 mL), concentrated to remove the volatiles and purified by preparative HPLC (acetonitrile/water with 0.1% TFA) and then by preparative HPLC (acetonitrile/water with 10 mM ammonium acetate) to afford 5,5'-(2,6-naphthalenediyl)bis(2-((2S)-1-((2R)-2-phenyl-2-(1-piperidinyl) acetyl)-2-pyrrolidinyl)-1H-benzimidazole) (44.3 mg) as white solid. LC-MS retention time 1.18 min; calcd. for [M+H]$^+$ $C_{58}H_{50}N_8O_2$ 900.48. found m/z 451.33 [½M+H]$^+$.

LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA.

min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.31 (s, 2H), 8.20-8.24 (m, 2H), 8.13-8.20 (m, 2H), 8.07-8.13 (m, 2H), 7.89-8.05 (m, 4H), 7.60-7.70 (m, 10H), 5.55-5.59 (m, 2H), 5.52 (dd, J=8.7, 3.8 Hz, 2H), 4.11-4.19 (m, 2H), 2.42-3.18 (m, 13H), 2.17-2.36 (m, 5H), 1.98-2.08 (m, 4H).

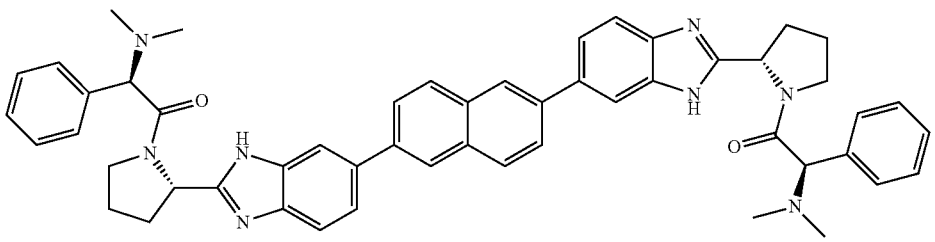 [SMILES: CN(C)[C@@H](C(=O)N1CCC[C@H]1c1nc2ccc(-c3ccc4cc(-c5ccc6nc([C@@H]7CCCN7C(=O)[C@@H](c7ccccc7)N(C)C)[nH]c6c5)ccc4c3)cc2[nH]1)c1ccccc1]

(1R)-2-((2S)-2-(5-(6-(2-((2S)-1-((2R)-2-(Dimethylamino)-2-phenylacetyl)-2-pyrrolidinyl)-1H-benzimidazol-6-yl)-2-naphthyl)-1H-benzimidazol-2-yl)-1-pyrrolidinyl)-N,N-dimethyl-2-oxo-1-phenylethanamine HATU (74.5 mg, 0.196 mmol) was added to a stirring solution of a TFA salt of 2,6-bis(2-((S)-pyrrolidin-2-yl)-1H-

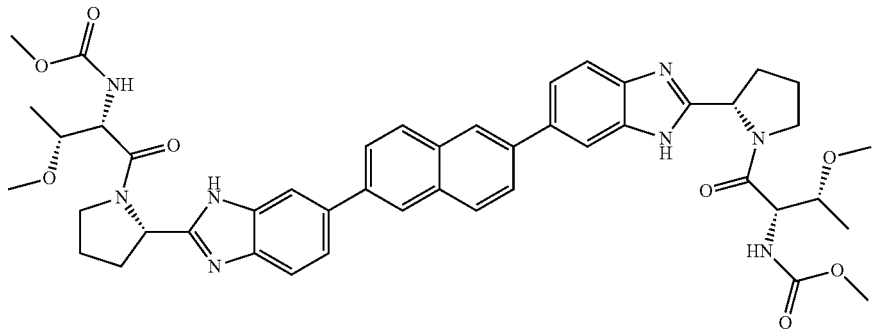

Methyl ((1S,2R)-2-methoxy-1-(((2S)-2-(5-(6-(2-((2S)-1-(N-(methoxycarbonyl)-O-methyl-L-threonyl)-2-pyrrolidinyl)-1H-benzimidazol-5-yl)-2-naphthyl)-1H-benzimidazol-2-yl)-1-pyrrolidinyl)carbonyl)propyl)carbamate benzo[d]imidazol-6-yl)naphthalene (40 mg, 0.065 mmol), (R)-2-(dimethylamino)-2-phenylacetic acid (35.1 mg) and DIEA (0.114 mL, 0.653 mmol) in DMF (2 mL). The reaction was stirred 9 h at room temperature, diluted with MeOH (2 mL) and water (2 mL), concentrated to remove the volatiles and purified by preparative HPLC (acetonitrile/water with 0.1% TFA) and then by preparative HPLC (acetonitrile/water with 10 mM ammonium acetate) to afford (1R)-2-((2S)-2-(5-(6-(2-((2S)-1-((2R)-2-(dimethylamino)-2-phenylacetyl)-2-pyrrolidinyl)-1H-benzimidazol-6-yl)-2-naphthyl)-1H-benzimidazol-2-yl)-1-pyrrolidinyl)-N,N-dimethyl-2-oxo-1-phenylethanamine (44.3 mg) as off-white solid. LC-MS retention time 1.07 min; calcd. for $C_{52}H_{52}N_8O_2$ 820.42. found m/z 821.29 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1

HATU (74.5 mg, 0.196 mmol) was added to a stirring solution of a TFA salt of 2,6-bis(2-((S)-pyrrolidin-2-yl)-1H-benzo[d]imidazol-6-yl)naphthalene (40 mg), (2S,3R)-3-methoxy-2-(methoxycarbonylamino)butanoic acid (37.4 mg, 0.196 mmol) and DIEA (0.114 mL, 0.653 mmol) in DMF (2 mL). The reaction was stirred 9 h at room temperature, diluted with MeOH (2 mL) and water (2 mL), concentrated to remove the volatiles and purified by preparative HPLC (acetonitrile/water with 0.1% TFA) and then by preparative HPLC (acetonitrile/water with 10 mM ammonium acetate) to afford methyl ((1S,2R)-2-methoxy-1-(((2S)-2-(5-(6-(2-((2S)-1-(N-(methoxycarbonyl)-O-methyl-L-threonyl)-2-pyrrolidinyl)-1H-benzimidazol-5-yl)-2-naphthyl)-1H-benzimidazol-2-yl)-1-pyrrolidinyl)carbonyl)propyl)carbamate (9.3 mg) as white solid. LC-MS retention time 1.22 min; calcd. for [M+H]+ $C_{46}H_{52}N_8O_8$ 844.39. found m/z 845.25 [M+H]+. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.10-8.21 (m, 2H), 7.99-8.08 (m, 2H), 7.83-7.96 (m, 4H), 7.58-7.77 (m, 4H), 5.70-5.75 (m, 0.4H), 5.35 (dd, J=7.9, 4.9 Hz, 1.6H), 4.58-4.61 (m, 0.2H), 4.51 (d, J=4.9 Hz, 1.5H), 4.37-4.43 (m, 0.3H), 3.89-4.08 (m, 3H), 3.61-3.78 (m, 7H), 3.38-3.45 (m, 2H), 3.23-3.31 (m, 5H), 1.93-2.57 (m, 9H), 1.10-1.28 (m, 6H).

the volatiles and purified by preparative HPLC (acetonitrile/water with 0.1% TFA) to afford a TFA salt of methyl ((1S)-3-methoxy-1-((((2S)-2-(5-(6-(2-((2S)-1-(N-(methoxycarbonyl)-O-methyl-L-homoseryl)-2-pyrrolidinyl)-1H-benzimidazol-5-yl)-2-naphthyl)-1H-benzimidazol-2-yl)-1-pyrrolidinyl)carbonyl)propyl)carbamate (28.6 mg) as yellow solid. LC-MS retention time 1.18 min; calcd. for [M+H]+ $C_{46}H_{52}N_8O_8$ 844.39. found m/z 845.22 [M+H]+. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold

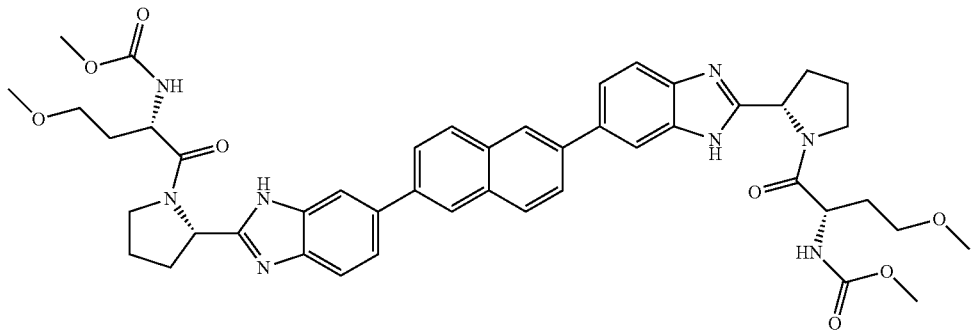

Methyl ((1S)-3-methoxy-1-(((2S)-2-(5-(6-(2-((2S)-1-(N-(methoxycarbonyl)-O-methyl-L-homoseryl)-2-pyrrolidinyl)-1H-benzimidazol-5-yl)-2-naphthyl)-1H-benzimidazol-2-yl)-1-pyrrolidinyl)carbonyl)propyl)carbamate HATU (74.5 mg, 0.196 mmol) was added to a stirring solution of a TFA salt of 2,6-bis(2-((S)-pyrrolidin-2-yl)-1H-benzo[d]imidazol-6-yl)naphthalene (40 mg), (S)-4-methoxy-2-(methoxycarbonylamino)butanoic acid (37.4 mg, 0.196 mmol) and DIEA (0.114 mL, 0.653 mmol) in DMF (2 mL). The reaction was stirred 9 h at room temperature, diluted with MeOH (2 mL) and water (2 mL), concentrated to remove time of 1 min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.23-8.30 (m, 2H), 8.09-8.18 (m, 4H), 8.00-8.09 (m, 2H), 7.84-7.97 (m, 4H), 5.84-5.90 (m, 0.2H), 5.44 (dd, J=8.2, 4.9 Hz, 1.8H), 4.65 (dd, J=9.2, 4.0 Hz, 1.8H), 4.38-4.45 (m, 0.2H), 3.91-4.11 (m, 4H), 3.66-3.78 (m, 6H), 3.39-3.55 (m, 4H), 3.27-3.38 (m, 7H), 2.59-2.75 (m, 2H), 2.25-2.40 (m, 5H), 2.16 (dddd, J=14.3, 7.0, 6.8, 4.3 Hz, 2H), 1.74-1.93 (m, 2H).

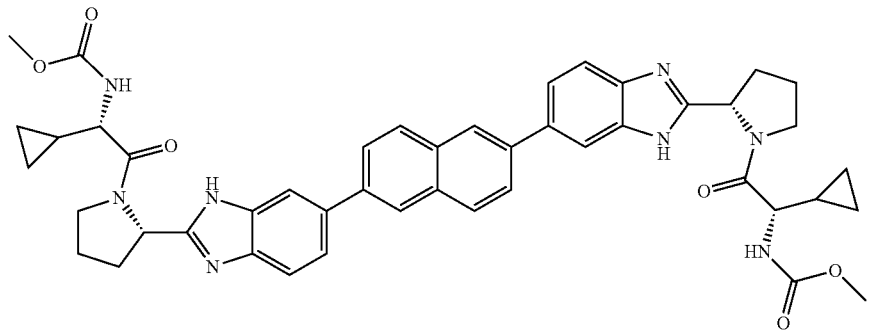

Dimethyl (2,6-naphthalenediylbis(1H-benzimidazole-5,2-diyl(2S)-2,1-pyrrolidinediyl((1S)-1-cyclopropyl-2-oxo-2,1-ethanediyl)))biscarbamate HATU (74.5 mg, 0.196 mmol) was added to a stirring solution of a TFA salt of 2,6-bis(2-((S)-pyrrolidin-2-yl)-1H-benzo[d]imidazol-6-yl)naphthalene (40 mg, 0.065 mmol), (S)-2-cyclopropyl-2-(methoxycarbonylamino)acetic acid (33.9 mg, 0.196 mmol) and DIEA (0.114 mL, 0.653 mmol) in DMF (2 mL). The reaction was stirred 9 h at room temperature, diluted with MeOH (2 mL) and water (2 mL), concentrated to remove the volatiles and purified by preparative HPLC (acetonitrile/water with 0.1% TFA) to afford a TFA salt of dimethyl (1S,1'S)-2,2'-((2S,2'S)-2,2'-(5,5'-(naphthalene-2,6-diyl)bis(1H-benzo[d] imidazole-5,2-diyl))bis(pyrrolidine-2,1-diyl))bis(1-cyclopropyl-2-oxo ethane-2,1-diyl) dicarbamate (34.9 mg, 0.038 mmol, 58% yield) as white solid. LC-MS retention time 1.23 min; calcd. for $C_{46}H_{48}N_8O_6$ 808.37. found m/z 809.22 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.20-8.29 (m, 2H), 8.07-8.16 (m, 4H), 7.98-8.07 (m, 2H), 7.84-7.95 (m, 4H), 5.37-5.48 (m, 2H), 4.03-4.13 (m, 2H), 3.87-4.03 (m, 4H), 3.64-3.74 (m, 6H), 2.65-2.74 (m, 2H), 2.20-2.40 (m, 6H), 1.09-1.22 (m, 2H), 0.47-0.67 (m, 6H), 0.30-0.46 (m, 2H).

imidazol-5-yl)-7-(2-((S)-pyrrolidin-2-yl)-1H-benzo[d]imidazol-6-yl)naphthalene (47 mg), (R)-2-(methoxycarbonylamino)-2-phenylacetic acid (30.9 mg, 0.148 mmol) and DIEA (0.086 mL, 0.49 mmol) in DMF (2 mL). The reaction was stirred 4 h at room temperature, diluted with MeOH (2 mL) and water (2 mL) concentrated to remove the volatiles and purified by preparative HPLC (acetonitrile/water with 0.1% TFA) to afford a TFA salt of dimethyl (1R,1'R)-2,2'-((2S,2'S)-2,2'-(5,5'-(naphthalene-2,7-diyl)bis(1H-benzo[d]imidazole-5,2-diyl))bis(pyrrolidine-2,1-diyl))bis(2-oxo-1-phenylethane-2,1-diyl)dicarbamate (38 mg) as light yellow solid. LC-MS retention time 1.45 min; calcd. for $C_{52}H_{48}N_8O_6$ 880.37. found m/z 881.26 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.31-8.39 (m, 2H), 8.03-8.17 (m, 6H), 7.84-8.00 (m, 4H), 7.33-7.53 (m, 10H), 5.55-5.63 (m, 2H), 5.40-5.54 (m, 2H), 4.01-4.17 (m, 2H), 3.67 (s, 6H), 3.27-4.41 (m, 2H), 2.44-2.75 (m, 2H), 2.01-2.33 (m, 6H).

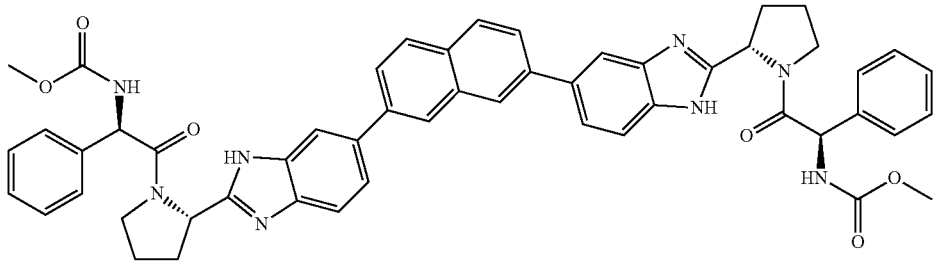 [SMILES: COC(=O)N[C@@H](C(=O)N1CCC[C@H]1c1nc2cc(-c3ccc4ccc(-c5ccc6nc([C@@H]7CCCN7C(=O)[C@H](NC(=O)OC)c7ccccc7)[nH]c6c5)cc4c3)ccc2[nH]1)c1ccccc1]

Dimethyl (2,7-naphthalenediylbis(1H-benzimidazole-5,2-diyl(2S)-2,1-pyrrolidinediyl((1R)-2-oxo-1-phenyl-2,1-ethanediyl)))biscarbamate HATU (56.2 mg, 0.148 mmol) was added to a stirred solution of a TFA salt of 2-(2-((S)-pyrrolidin-2-yl)-1H-benzo[d]

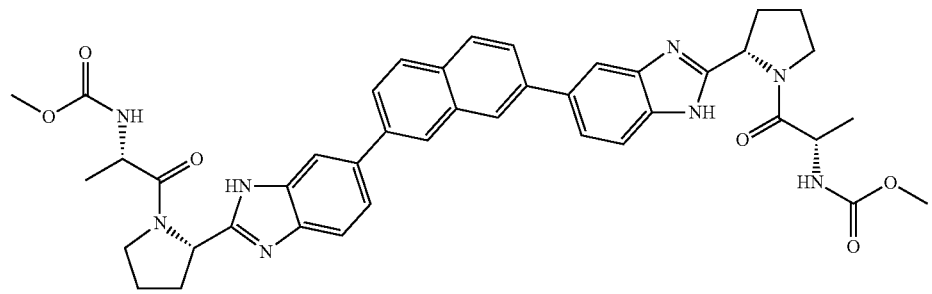

Methyl ((1S)-2-((2S)-2-(5-(7-(2-((2S)-1-(N-(methoxycarbonyl)-L-alanyl)-2-pyrrolidinyl)-1H-benzimidazol-5-yl)-2-naphthyl)-1H-benzimidazol-2-yl)-1-pyrrolidinyl)-1-methyl-2-oxoethyl)carbamate HATU (56.2 mg, 0.148 mmol) was added to a stirred solution of a TFA salt of 2-(2-((S)-pyrrolidin-2-yl)-1H-benzo[d]imidazol-5-yl)-7-(2-((S)-pyrrolidin-2-yl)-1H-benzo[d]imidazol-6-yl)naphthalene (47 mg), (S)-2-(methoxycarbonylamino)propanoic acid (21.7 mg, 0.148 mmol) and DIEA (0.086 mL, 0.49 mmol) in DMF (2 mL). The reaction was stirred 5 h at room temperature, diluted with MeOH (2 mL) and water (2 mL) concentrated to remove the volatiles and purified by preparative HPLC (acetonitrile/water with 0.1% TFA) and then by preparative HPLC (acetonitrile/water with 10 mM ammonium acetate) to afford methyl ((1S)-2-((2S)-2-(5-(7-(2-((2S)-1-(N-(methoxycarbonyl)-L-alanyl)-2-pyrrolidinyl)-1H-benzimidazol-5-yl)-2-naphthyl)-1H-benzimidazol-2-yl)-1-pyrrolidinyl)-1-methyl-2-oxoethyl)carbamate (20.9 mg) as white solid. LC-MS retention time 1.16 min; calcd. for $C_{42}H_{44}N_8O_6$ 756.34. found m/z 757.27 $[M+H]^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 8.16-8.24 (m, 2H), 7.87-8.02 (m, 4H), 7.80-7.87 (m, 2H), 7.60-7.75 (m, 4H), 5.42-5.46 (m, 0.3H), 5.34 (dd, J=7.9, 4.0 Hz, 1.7H), 4.55 (q, J=7.0 Hz, 1.7H), 4.31-4.37 (m, 0.3H), 3.80-3.98 (m, 4H), 3.67 (s, 5H), 3.47 (s, 1H), 2.39-2.55 (m, 2H), 2.04-2.36 (m, 4H), 1.92-2.01 (m, 2H), 1.31-1.42 (m, 6H).

Methyl ((1R)-1-(((2S)-2-(5-(7-(2-((2S)-1-((2R)-2-((methoxycarbonyl)amino)-3-methylbutanoyl)-2-pyrrolidinyl)-1H-benzimidazol-5-yl)-2-naphthyl)-1H-benzimidazol-2-yl)-1-pyrrolidinyl)carbonyl)-2-methylpropyl)carbamate HATU (56.2 mg, 0.148 mmol) was added to a stirred solution of a TFA salt of 2-(2-((S)-pyrrolidin-2-yl)-1H-benzo[d]imidazol-5-yl)-7-(2-((S)-pyrrolidin-2-yl)-1H-benzo[d]imidazol-6-yl)naphthalene (47 mg), (R)-2-(methoxycarbonylamino)-3-methylbutanoic acid (25.9 mg, 0.148 mmol) and DIEA (0.086 mL, 0.49 mmol) in DMF (2 mL). The reaction was stirred 5 h at room temperature, diluted with MeOH (2 mL) and water (2 mL) concentrated to remove the volatiles and purified by preparative HPLC (acetonitrile/water with 0.1% TFA) and then by preparative HPLC (acetonitrile/water with 10 mM ammonium acetate) to afford a TFA salt of methyl ((1R)-1-(((2S)-2-(5-(7-(2-((2S)-1-((2R)-2-((methoxycarbonyl)amino)-3-methylbutanoyl)-2-pyrrolidinyl)-1H-benzimidazol-5-yl)-2-naphthyl)-1H-benzimidazol-2-yl)-1-pyrrolidinyl)carbonyl)-2-methylpropyl)carbamate (25 mg) as beige solid. LC-MS retention time 1.36 min; calcd. for $C_{46}H_{52}N_8O_6$ 812.40. found m/z 813.36 $[M+H]^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (TFA salt, 500 MHz, MeOD) δ ppm 8.33 (s, 2H), 8.07-8.13 (m, 4H), 8.05 (dd, J=8.5, 1.2 Hz, 2H), 7.84-7.96 (m, 4H), 5.49 (dd, J=8.6, 3.7 Hz, 2H), 4.36 (d, J=7.3 Hz, 2H), 4.15-4.23 (m, 2H), 3.83-3.97 (m, 2H), 3.72 (s, 6H), 2.58-2.71 (m, 2H), 2.21-2.38 (m, 6H), 2.05-2.18 (m, 2H), 1.07 (d, J=6.7 Hz, 6H), 1.04 (d, J=6.7 Hz, 6H).

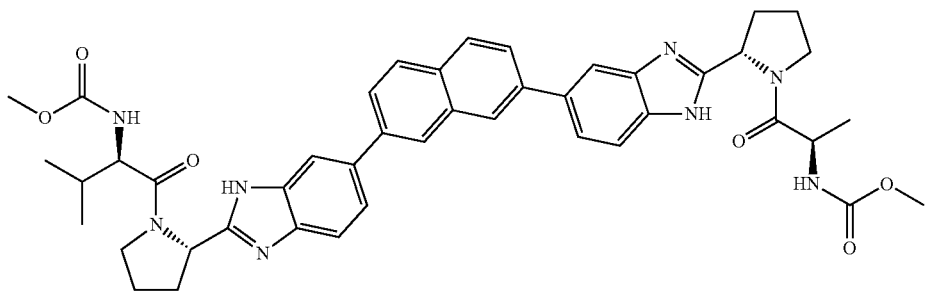

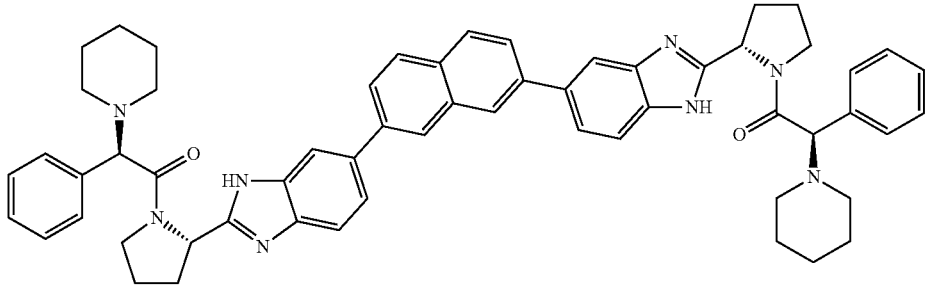 [SMILES: O=C([C@@H](c1ccccc1)N1CCCCC1)N1CCC[C@H]1c1nc2cc(-c3ccc4ccc(-c5ccc6nc([C@@H]7CCCN7C(=O)[C@@H](c7ccccc7)N7CCCCC7)[nH]c6c5)cc4c3)ccc2[nH]1]

5,5'-(2,7-Naphthalenediyl)bis(2-((2S)-1-((2R)-2-phenyl-2-(1-piperidinyl)acetyl)-2-pyrrolidinyl)-1H-benzimidazole)

HATU (56.2 mg, 0.148 mmol) was added to a stirred solution of a TFA salt of 2-(2-((S)-pyrrolidin-2-yl)-1H-benzo[d]imidazol-5-yl)-7-(2-((S)-pyrrolidin-2-yl)-1H-benzo[d]imidazol-6-yl)naphthalene (47 mg), (R)-2-phenyl-2-(piperidin-1-yl)acetic acid (32.4 mg, 0.148 mmol) and DIEA (0.086 mL, 0.49 mmol) in DMF (2 mL). The reaction was stirred 5 h at room temperature, diluted with MeOH (2 mL) and water (2 mL) concentrated to remove the volatiles and purified by preparative HPLC (acetonitrile/water with 0.1% TFA) and then by preparative HPLC (acetonitrile/water with 10 mM ammonium acetate) to afford 5,5'-(2,7-naphthalenediyl)bis(2-((2S)-1-((2R)-2-phenyl-2-(1-piperidinyl)acetyl)-2-pyrrolidinyl)-1H-benzimidazole) (16.4 mg) as white solid. LC-MS retention time 1.21 min; calcd. for [M+H]$^+$ C$_{58}$H$_{60}$N$_8$O$_6$ 900.48. found m/z 451.43½[M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (400 MHz, MeOD) δ ppm 8.18-8.28 (m, 2H), 7.96-8.05 (m, 2.2H), 7.92 (d, J=1.0 Hz, 1.5H), 7.80-7.90 (m, 2.2H), 7.65-7.76 (m, 3.8H), 7.55-7.64 (m, 3.2H), 7.46-7.55 (m, 4.5H), 6.85-6.97 (m, 1.6H), 6.76-6.83 (m, 1H), 5.65-5.70 (m, 0.5H), 5.28 (dd, J=7.5, 3.3 Hz, 1.5H), 4.48 (br s, 0.5H), 4.02-4.12 (m, 1.5H), 3.90-3.98 (m, 0.5H), 3.74-3.84 (m, 0.5H), 3.25-3.40 (m, 3H), 2.51-2.93 (m, 8H), 1.89-2.33 (m, 8H), 1.62-1.75 (m, 8H), 1.47-1.59 (m 4H).

Methyl ((1S)-1-(((2S)-2-(4-(6-(2-((2S)-1-((2S)-2-((methoxycarbonyl)amino)-3-methylbutanoyl)-2-pyrrolidinyl)-1H-benzimidazol-5-yl)-2-naphthyl)-1H-imidazol-2-yl)-1-pyrrolidinyl)carbonyl)-2-methylpropyl)carbamate HATU (40 mg, 0.11 mmol) was added to a mixture of a TFA salt of 2-((S)-pyrrolidin-2-yl)-6-(6-(2-((S)-pyrrolidin-2-yl)-1H-imidazol-5-yl)naphthalen-2-yl)-1H-benzo[d]imidazole (32 mg), diisopropylethylamine (62 μL, 0.35 mmol) and (S)-2-(methoxycarbonylamino)-3-methylbutanoic acid (19 mg, 0.106 mmol) in DMF (2 mL) and the resulting mixture was stirred at ambient conditions for 9 hours. The reaction mixture was diluted with methanol (2 mL) and water (2 mL). The volatile component was removed in vacuo and the residue was purified by reverse phase HPLC (once with water/acetonitrile 10 mM ammonium acetate and twice with water/acetonitrile 0.1% TFA) to provide a TFA salt of methyl ((1S)-1-(((2S)-2-(4-(6-(2-((2S)-1-((2S)-2-((methoxycarbonyl)amino)-3-methylbutanoyl)-2-pyrrolidinyl)-1H-benzimidazol-5-yl)-2-naphthyl)-1H-imidazol-2-yl)-1-pyrrolidinyl)carbonyl)-2-methylpropyl)carbamate (21 mg) as white solid. LC-MS retention time 1.17 min; calcd. for C$_{42}$H$_{50}$N$_8$O$_6$ 762.39. found m/z 763.34 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90%

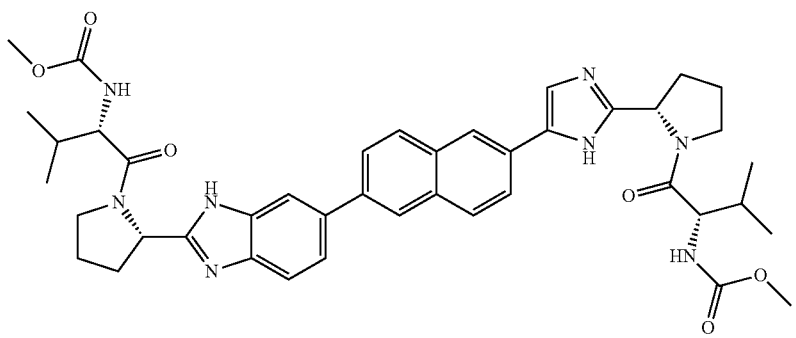

acetonitrile/10% water/0.1% TFA. $^1$H NMR (500 MHz, MeOD) δ ppm 8.30 (s, 1H), 8.27 (s, 1H), 8.15 (d, J=8.9 Hz, 1H), 8.10 (d, J=8.9 Hz, 1H), 8.07 (s, 1H), 7.94-8.01 (m, 3H), 7.82-7.89 (m, 2H), 5.38 (t, J=7.2 Hz, 1H), 5.31 (t, J=7.6 Hz, 1H), 4.28 (dd, J=14.5, 7.2 Hz, 2H), 4.15 (br s, 2H), 3.86-4.01 (m, 2H), 3.69 (s, 6H), 2.55-2.69 (m, 2H), 2.19-2.39 (m, 6H), 2.04-2.15 (m, 2H), 0.86-1.05 (m, 12H).

acetonitrile/10% water/0.1% TFA. $^1$H NMR (500 MHz, MeOD) δ ppm 8.35 (s, 1H), 8.25 (s, 1H), 8.09 (dd, J=8.4, 3.2 Hz, 2H), 8.04 (s, 1H), 7.89-8.00 (m, 3H), 7.77-7.87 (m, 2H), 5.37 (t, J=7.0 Hz, 1H), 5.30 (t, J=7.3 Hz, 1H), 4.28 (dd, J=15.4, 7.2 Hz, 2H), 4.08-4.20 (m, 2H), 3.86-4.01 (m, 2H), 3.69 (s, 6H), 2.56-2.68 (m, 3H), 2.39-2.02 (m, 7H), 0.87-1.04 (m, 12H).

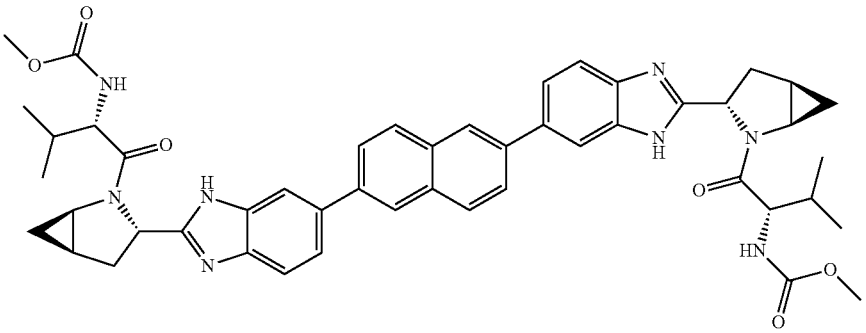

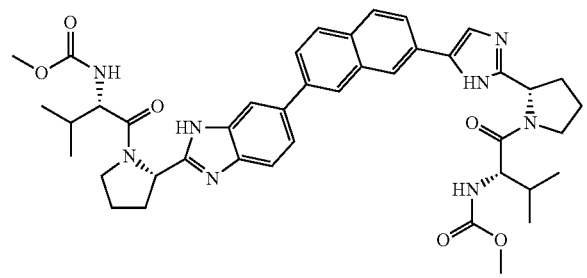 [SMILES: COC(=O)N[C@H](C(=O)N1CCC[C@H]1c1ncc(-c2ccc3ccc(-c4ccc5nc([C@@H]6CCCN6C(=O)[C@@H](NC(=O)OC)C(C)C)[nH]c5c4)cc3c2)[nH]1)C(C)C]

Methyl ((1S)-1-(((2S)-2-(4-(7-(2-((2S)-1-((2S)-2-((methoxycarbonyl)amino)-3-methylbutanoyl)-2-pyrrolidinyl)-1H-benzimidazol-5-yl)-2-naphthyl)-1H-imidazol-2-yl)-1-pyrrolidinyl)carbonyl)-2-methylpropyl)carbamate HATU (20 mg, 0.053 mmol) was added to a mixture of a TFA salt of 2-((S)-pyrrolidin-2-yl)-6-(7-(2-((S)-pyrrolidin-2-yl)-1H-imidazol-4-yl)naphthalen-2-yl)-1H-benzo[d]imidazole (16 mg), diisopropylethylamine (31 μL, 0.18 mmol) and (S)-2-(methoxycarbonylamino)-3-methylbutanoic acid (9.3 mg, 0.053 mmol) in DMF (2 mL) and the resulting mixture was stirred at ambient for 9 hours. The reaction mixture was diluted with methanol (2 mL) and water (2 mL). The volatile component was removed in vacuo and the residue was purified by a reverse phase HPLC (water/acetonitrile 0.1% TFA) to provide a TFA salt of methyl ((1S)-1-(((2S)-2-(4-(7-(2-((2S)-1-((2S)-2-((methoxycarbonyl)amino)-3-methylbutanoyl)-2-pyrrolidinyl)-1H-benzimidazol-5-yl)-2-naphthyl)-1H-imidazol-2-yl)-1-pyrrolidinyl)carbonyl)-2-methylpropyl)carbamate (7.9 mg) as white solid. LC-MS retention time 1.20 min; calcd. for $C_{42}H_{50}N_8O_6$ 762.39. found m/z 763.35 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90%

Methyl ((1S)-1-(((1R,3S,5R)-3-(5-(6-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-2-naphthyl)-1H-benzimidazol-2-yl)-2-azabicyclo[3.1.0]hex-2-yl)carbonyl)-2-methylpropyl)carbamate HATU (218 mg, 0.574 mmol) was added to a mixture of 2,6-bis(2-((1R,3S,5R)-2-azabicyclo[3.1.0]hexan-3-yl)-1H-benzo[d]imidazol-6-yl)naphthalene (100 mg), diisopropylethylamine (334 μL, 1.91 mmol) and (S)-2-(methoxycarbonylamino)-3-methylbutanoic acid (101 mg, 0.574 mmol) in DMF (2 mL) and the resulting mixture was stirred at ambient for 4 hours. The reaction mixture was diluted with methanol (2 mL) and water (2 mL). Then, the volatile component was removed in vacuo and the residue was purified by a reverse phase HPLC (water/acetonitrile 0.1% TFA) to provide a TFA salt of methyl ((1S)-1-(((1R,3S,5R)-3-(5-(6-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-2-naphthyl)-1H-benzimidazol-2-yl)-2-azabicyclo[3.1.0]hex-2-yl)carbonyl)-2-methylpropyl)carbamate (85 mg) as yellow solid. LC-MS retention time 1.33 min; calcd. for $C_{48}H_{52}N_8O_6$: 836.4. found m/z 837.32 [M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD) δ ppm 8.22 (s, 2H), 8.05-8.13 (m, 4H), 7.96-8.02 (m, 2H), 7.82-7.92 (m, 4H), 5.22-5.32 (m, 2H), 4.59 (d, J=6.4 Hz, 2H), 3.86 (t, J=6.0 Hz, 2H), 3.60-3.75 (m, 6H), 2.66-2.79 (m, 2H), 2.54 (m, 2H), 2.16-2.26 (m, 2H), 2.02-2.16 (m, 2H), 1.10-1.16 (m, 2H), 0.98-1.05 (m, 6H), 0.94-0.97 (m, 2H), 0.91 (d, J=6.7 Hz, 6H).

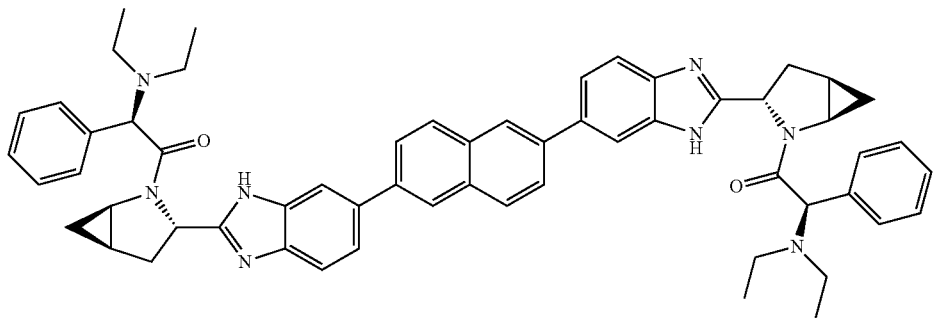 [SMILES: CCN(CC)[C@@H](C(=O)N1[C@@H]2C[C@@H]2C[C@H]1c1nc2ccc(-c3ccc4cc(-c5ccc6nc([C@@H]7C[C@H]8C[C@H]8N7C(=O)[C@@H](c7ccccc7)N(CC)CC)[nH]c6c5)ccc4c3)cc2[nH]1)c1ccccc1]

(1R)-2-((1R,3S,5R)-3-(5-(6-(2-((1R,3S,5R)-2-((2R)-2-(Diethylamino)-2-phenylacetyl)-2-azabicyclo[3.1.0]hex-3-yl)-1H-benzimidazol-6-yl)-2-naphthyl)-1H-benzimidazol-2-yl)-2-azabicyclo[3.1.0]hex-2-yl)-N,N-diethyl-2-oxo-1-phenylethanamine HATU (109 mg, 0.287 mmol) was added to a mixture of 2,6-bis(2-((1R,3S,5R)-2-azabicyclo[3.1.0]hexan-3-yl)-1H-benzo[d]imidazol-6-yl)naphthalene (50 mg), diisopropylethylamine (0.167 mL, 0.957 mmol) and (R)-2-(diethylamino)-2-phenylacetic acid, HCl (70.0 mg, 0.287 mmol) in DMF (2 mL) and the resulting mixture was stirred at ambient for 5 hours. The reaction mixture was diluted with methanol (2 mL) and water (2 mL). Then, the volatile component was removed in vacuo and the residue was purified by a reverse phase HPLC (water/acetonitrile 0.1% TFA) then by reverse phase HPLC (water/acetonitrile 10 mM ammonium acetate) and finally by reverse phase HPLC (water/acetonitrile 0.1% TFA) to provide a TFA salt of (1R)-2-((1R,3S,5R)-3-(5-(6-(2-((1R,3S,5R)-2-((2R)-2-(diethylamino)-2-phenylacetyl)-2-azabicyclo[3.1.0]hex-3-yl)-1H-benzimidazol-6-yl)-2-naphthyl)-1H-benzimidazol-2-yl)-2-azabicyclo[3.1.0]hex-2-yl)-N,N-diethyl-2-oxo-1-phenylethanamine (25.2 mg) as white powder. LC-MS retention time 1.15 min; calcd. for [M+H]$^+$ C$_{58}$H$_{60}$N$_8$O$_2$: 900.48. found m/z 451.46 [½M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (TFA salt, 500 MHz, MeOD) δ ppm 8.27 (s, 2H), 8.08-8.17 (m, 4H), 7.96 (td, J=8.7, 1.5 Hz, 4H), 7.87 (d, J=8.6 Hz, 2H), 7.68-7.72 (m, 4H), 7.57-7.68 (m, 6H), 5.79 (s, 2H), 5.23 (dd, J=9.0, 6.3 Hz, 2H), 3.95-4.05 (m, 2H), 3.25-3.48 (m, 4H), 3.06 (br s, 4H), 2.43-2.61 (m, 4H), 2.01-2.11 (m, 2H), 1.31 (t, J=6.9 Hz, 12H), 0.62 (ddd, J=8.7, 6.0, 5.8 Hz, 2H), −0.21 (td, J=5.7, 2.4 Hz, 2H).

Example 20

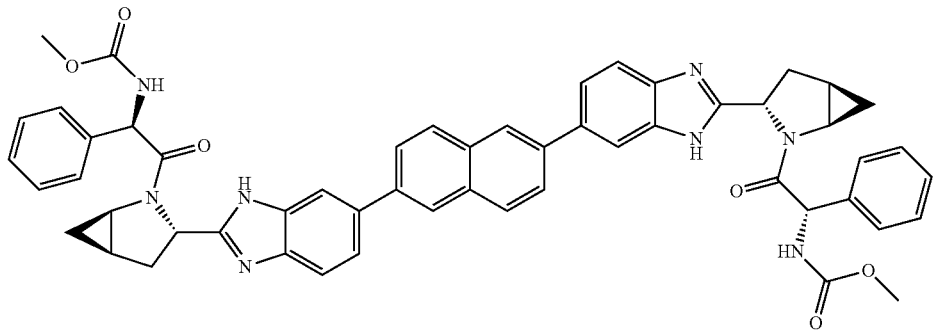

Example 21

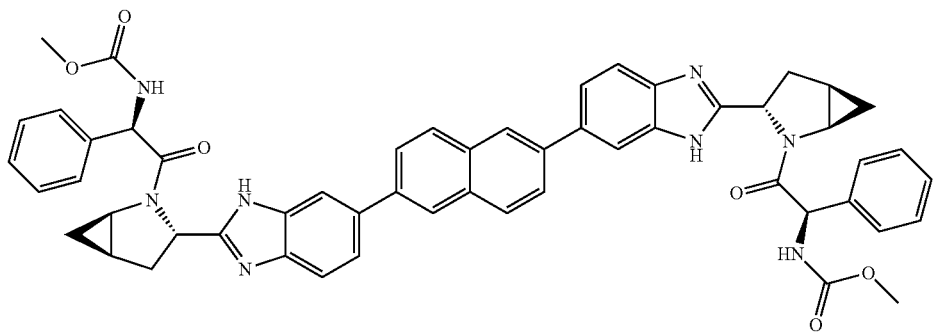

Example 20

Methyl ((1R)-2-((1R,3S,5R)-3-(5-(6-(2-((1R,3S,5R)-2-((2S)-2-((methoxycarbonyl)amino)-2-phenylacetyl)-2-azabicyclo[3.1.0]hex-3-yl)-1H-benzimidazol-5-yl)-2-naphthyl)-1H-benzimidazol-2-yl)-2-azabicyclo[3.1.0]hex-2-yl)-2-oxo-1-phenylethyl) carbamate and

Example 21

Dimethyl (2,6-naphthalenediylbis(1H-benzimidazole-5,2-diyl(1R,3S,5R)-2-azabicyclo[3.1.0]hexane-3,2-diyl((1R)-2-oxo-1-phenyl-2,1-ethanediyl)))biscarbamate HATU (109 mg, 0.287 mmol) was added to a mixture of 2,6-bis(2-((1R,3S,5R)-2-azabicyclo[3.1.0]hexan-3-yl)-1H-benzo[d]imidazol-6-yl)naphthalene (50 mg), diisopropylethylamine (0.167 mL, 0.957 mmol) and (R)-2-(methoxycarbonylamino)-2-phenylacetic acid (60.0 mg, 0.287 mmol) in DMF (2 mL) and the resulting mixture was stirred at ambient for 5 hours. The reaction mixture was diluted with methanol (2 mL) and water (2 mL). Then, the volatile component was removed in vacuo and the residue was purified by a reverse phase HPLC (water/acetonitrile 0.1% TFA) then by reverse phase HPLC (water/acetonitrile 10 mM ammonium acetate) and finally by reverse phase HPLC (water/acetonitrile 0.1% TFA) to provide a TFA salt of methyl ((1R)-2-((1R,3S,5R)-3-(5-(6-(2-((1R,3S,5R)-2-((2S)-2-((methoxycarbonyl)amino)-2-phenylacetyl)-2-azabicyclo[3.1.0]hex-3-yl)-1H-benzimidazol-5-yl)-2-naphthyl)-1H-benzimidazol-2-yl)-2-azabicyclo[3.1.0]hex-2-yl)-2-oxo-1-phenylethyl)carbamate (6.9 mg) as white solid and a TFA salt of dimethyl (2,6-naphthalenediylbis(1H-benzimidazole-5,2-diyl(1R,3S,5R)-2-azabicyclo[3.1.0]hexane-3,2-diyl((1R)-2-oxo-1-phenyl-2,1-ethanediyl)))biscarbamate (12.5 mg) as white solid. Analytical data for Example 20: LC-MS retention time 1.46 min; calcd. for $C_{54}H_{48}N_8O_6$: 904.37. found m/z 453.35 [½M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (TFA salt, 500 MHz, MeOD) δ ppm 8.28 (d, J=4.6 Hz, 2H), 8.15 (d, J=8.6 Hz, 2H), 8.12 (s, 1H), 8.07 (s, 1H), 8.03 (t, J=8.9 Hz, 2H), 7.92-7.98 (m, 2H), 7.90 (d, J=8.6 Hz, 1H), 7.85 (d, J=8.6 Hz, 1H), 7.48-7.54 (m, 2H), 7.37-7.48 (m, 8H), 5.85 (s, 1H), 5.78 (s, 1H), 5.39 (dd, J=9.0, 6.3 Hz, 1H), 5.29 (dd, J=9.2, 5.8 Hz, 1H), 3.91-3.97 (m, 1H), 3.68 (s, 3H), 3.66 (s, 3H), 3.52-3.61 (m, 1H), 2.73 (dd, J=13.7, 9.2 Hz, 1H), 2.46-2.65 (m, 3H), 2.06-2.14 (m, 1H), 1.98-2.06 (m, 1H), 1.23-1.30 (m, 1H), 1.10 (br s, 1H), 0.66-0.72 (m, 1H), 0.01-0.10 (m, 1H).

Analytical data for Example 21: LC-MS retention time 1.48 min; calcd. for [M+H]$^+$ $C_{54}H_{48}N_8O_6$: 904.37. found m/z 453.35 [½M+H]$^+$. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (TFA salt, 500 MHz, MeOD) δ ppm 8.29 (s, 2H), 8.16 (d, J=8.6 Hz, 2H), 8.11 (s, 2H), 8.01-8.06 (m, 2H), 7.95 (d, J=8.6 Hz, 2H), 7.90 (m, J=8.6 Hz, 2H), 7.48-7.55 (m, 4H), 7.36-7.48 (m, 6H), 5.85 (s, 2H), 5.29 (dd, J=9.2, 5.8 Hz, 2H), 3.92-3.97 (m, 2H), 3.66 (s, 6H), 2.55-2.66 (m, 2H), 2.51 (ddd, J=13.3, 6.6, 6.4 Hz, 2H), 1.97-2.07 (m, 2H), 0.63-0.74 (m, 2H), −0.02-0.10 (m, 2H).

Example 22

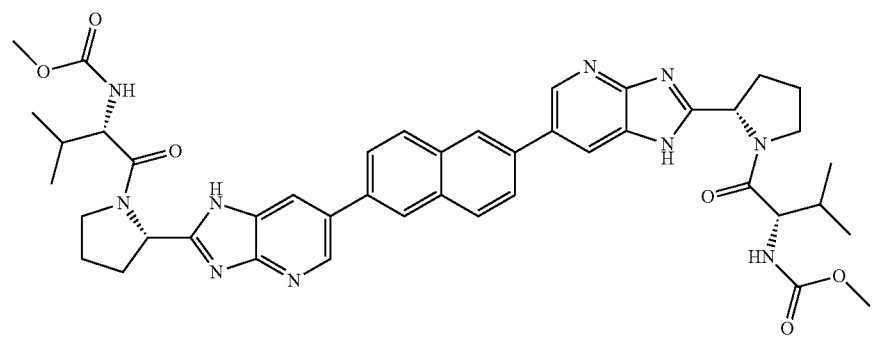

Example 23

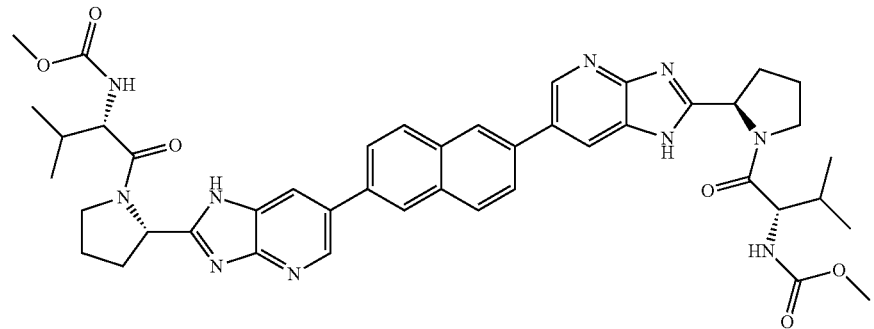

Example 22

Methyl ((1S)-1-(((2S)-2-(6-(6-(2-((2S)-1-((2S)-2-((methoxycarbonyl)amino)-3-methylbutanoyl)-2-pyrrolidinyl)-1H-imidazo[4,5-b]pyridin-6-yl)-2-naphthyl)-1H-imidazo[4,5-b]pyridin-2-yl)-1-pyrrolidinyl)carbonyl)-2-methylpropyl)carbamate and

Example 23

Methyl ((1S)-1-(((2R)-2-(6-(6-(2-((2S)-1-((2S)-2-((methoxycarbonyl)amino)-3-methylbutanoyl)-2-pyrrolidinyl)-1H-imidazo[4,5-b]pyridin-6-yl)-2-naphthyl)-1H-imidazo[4,5-b]pyridin-2-yl)-1-pyrrolidinyl)carbonyl)-2-methylpropyl)carbamate HATU (63.5 mg, 0.167 mmol) was added to a stirred slurry of a hydrochloride salt of 2,6-bis(2-((S)-pyrrolidin-2-yl)-3H-imidazo[4,5-b]pyridin-6-yl)naphthalene (45 mg) and (S)-2-(methoxycarbonylamino)-3-methylbutanoic acid (29.3 mg, 0.167 mmol) in DMF (1 mL) and DIPEA (0.122 mL, 0.696 mmol). The reaction mixture was stirred at room temperature for 16 h, diluted with MeOH, filtered and purified by preparative HPLC (acetonitrile/water with 10 mM ammonium acetate) to provide methyl ((1S)-1-(((2S)-2-(6-(6-(2-((2S)-1-((2S)-2-((methoxycarbonyl)amino)-3-methylbutanoyl)-2-pyrrolidinyl)-1H-imidazo[4,5-b]pyridin-6-yl)-2-naphthyl)-1H-imidazo[4,5-b]pyridin-2-yl)-1-pyrrolidinyl)carbonyl)-2-methylpropyl)carbamate (19.2 mg) as white solid and methyl ((1S)-1-(((2R)-2-(6-(6-(2-((2S)-1-((2S)-2-((methoxycarbonyl)amino)-3-methylbutanoyl)-2-pyrrolidinyl)-1H-imidazo[4,5-b]pyridin-6-yl)-2-naphthyl)-1H-imidazo[4,5-b]pyridin-2-yl)-1-pyrrolidinyl)carbonyl)-2-methylpropyl)carbamate (16.5 mg) as white solid (uncertain if pyrrolidine stereocenter racemized during this step or in a previous step). Resolution of 2,6-bis(2-((S)-pyrrolidin-2-yl)-3H-imidazo[4,5-b]pyridin-6-yl)naphthalene by chiral HPLC showed a broad peak, but individual diastereomers could not be resolved under the attempted conditions.

Analytical data for Example 22: LC-MS retention time 1.407 min; m/z 815.60 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. $^1$H NMR (500 MHz, MeOD) δ ppm 8.82-8.71 (m, 2H), 8.32-8.18 (m, 4H), 8.14-8.07 (m, 2H), 7.92-7.84 (m, 2H), 5.37-5.29 (m, 2H), 4.30 (d, J=7.3 Hz, 2H), 4.13-4.04 (m, 2H), 4.02-3.92 (m, 2H), 3.68 (s, 6H), 2.54-1.98 (m, 10H), 1.03-0.89 (m, 12H).

Analytical data for Example 23: LC-MS retention time 1.442 min; m/z 815.59 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. $^1$H NMR (500 MHz, MeOD) δ ppm 8.89-8.66 (m, 2H), 8.36-8.20 (m, 4H), 8.15-8.10 (m, 2H), 7.94-7.86 (m, 2H), 5.44-5.29 (m, 2H), 4.34 (d, J=7.6 Hz, 1H), 4.30 (d, J=7.6 Hz, 1H), 4.21-3.80 (m, 4H), 3.74 (s, 3H), 3.68 (s, 3H), 2.69-1.95 (m, 10H), 1.09-0.41 (m, 12H).

Example 24

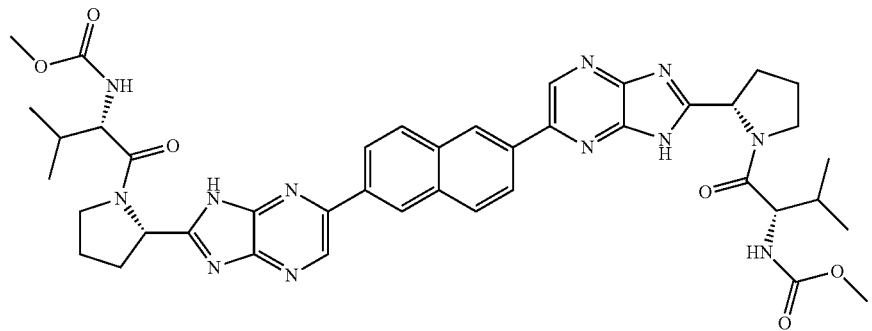

Example 25A

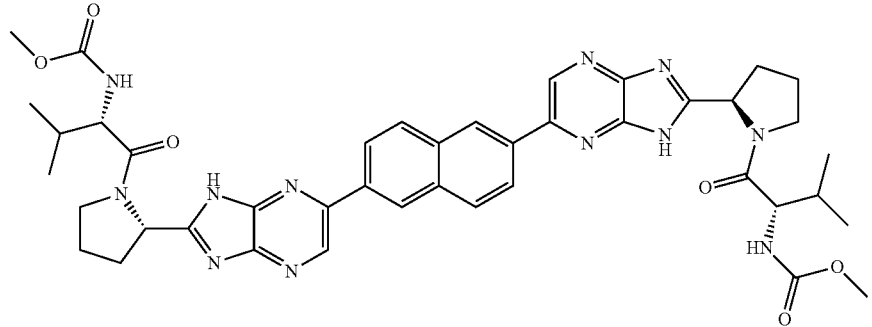

-continued

Example 25B

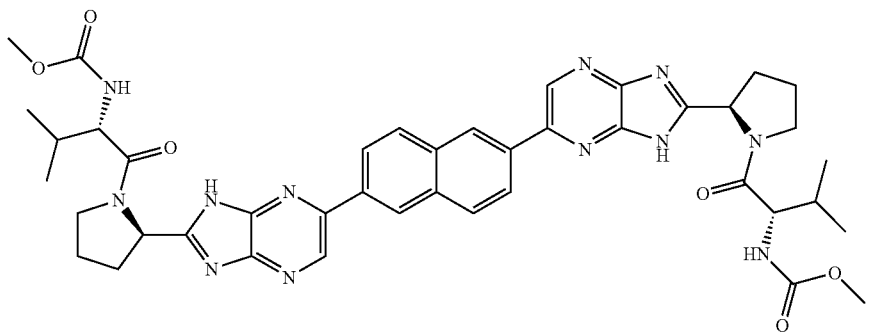

Example 24

Methyl ((1S)-1-(((2S)-2-(5-(6-(2-((2S)-1-((2S)-2-((methoxycarbonyl)amino)-3-methylbutanoyl)-2-pyrrolidinyl)-1H-imidazo[4,5-b]pyrazin-5-yl)-2-naphthyl)-1H-imidazo[4,5-b]pyrazin-2-yl)-1-pyrrolidinyl)carbonyl)-2-methylpropyl)carbamate and

Example 25A

Methyl ((1S)-1-(((2S)-2-(5-(6-(2-((2R)-1-((2S)-2-((methoxycarbonyl)amino)-3-methylbutanoyl)-2-pyrrolidinyl)-1H-imidazo[4,5-b]pyrazin-5-yl)-2-naphthyl)-1H-imidazo[4,5-b]pyrazin-2-yl)-1-pyrrolidinyl)carbonyl)-2-methylpropyl)carbamate and

Example 25B

Methyl ((1S)-1-(((2R)-2-(5-(6-(2-((2R)-1-((2S)-2-((methoxycarbonyl)amino)-3-methylbutanoyl)-2-pyrrolidinyl)-1H-imidazo[4,5-b]pyrazin-5-yl)-2-naphthyl)-1H-imidazo[4,5-b]pyrazin-2-yl)-1-pyrrolidinyl)carbonyl)-2-methylpropyl)carbamate HATU (63 mg, 0.17 mmol) was added to a stirred slurry of an HCl salt of 2,6-bis(2-((S)-pyrrolidin-2-yl)-1H-imidazo[4,5-b]pyrazin-5-yl)naphthalene (45 mg) and (S)-2-(methoxycarbonylamino)-3-methylbutanoic acid (29 mg, 0.17 mmol) in DMF (1 mL) and DIPEA (0.12 mL, 0.69 mmol). The reaction mixture was stirred at room temperature for 16 h diluted with MeOH, filtered and purified by preparative HPLC (acetonitrile/water with 10 mM ammonium acetate) to yield methyl ((1S)-1-(((2S)-2-(5-(6-(2-((2S)-1-((2S)-2-((methoxycarbonyl)amino)-3-methylbutanoyl)-2-pyrrolidinyl)-1H-imidazo[4,5-b]pyrazin-5-yl)-2-naphthyl)-1H-imidazo[4,5-b]pyrazin-2-yl)-1-pyrrolidinyl)carbonyl)-2-methylpropyl)carbamate (11.2 mg) as yellow solid, methyl ((1S)-1-(((2S)-2-(5-(6-(2-((2R)-1-((2S)-2-((methoxycarbonyl)amino)-3-methylbutanoyl)-2-pyrrolidinyl)-1H-imidazo[4,5-b]pyrazin-5-yl)-2-naphthyl)-1H-imidazo[4,5-b]pyrazin-2-yl)-1-pyrrolidinyl)carbonyl)-2-methylpropyl)carbamate (17.3 mg) as yellow solid and methyl ((1S)-1-(((2R)-2-(5-(6-(2-((2R)-1-((2S)-2-((methoxycarbonyl)amino)-3-methylbutanoyl)-2-pyrrolidinyl)-1H-imidazo[4,5-b]pyrazin-5-yl)-2-naphthyl)-1H-imidazo[4,5-b]pyrazin-2-yl)-1-pyrrolidinyl)carbonyl)-2-methylpropyl)carbamate (6.7 mg) as yellow solid (uncertain if pyrrolidine stereocenter racemized during this step or in a previous step). Resolution of 2,6-bis(2-((S)-pyrrolidin-2-yl)-1H-imidazo[4,5-b]pyrazin-5-yl)naphthalene by chiral HPLC showed a broad peak, but individual diastereomers could not be resolved under the attempted conditions.

Analytical data for Example 24: LC-MS retention time 1.420 min; m/z 817.59 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. $^1$H NMR (500 MHz, MeOD) δ ppm 9.14-9.06 (m, 2H), 8.71-8.64 (m, 2H), 8.37-8.29 (m, 2H), 8.18-8.11 (m, 2H), 5.59-5.30 (m, 2H), 4.30 (d, J=7.3 Hz, 2H), 4.13-3.96 (m, 4H), 3.78-3.64 (m, 6H), 2.57-2.01 (m, 10H), 1.07-0.92 (m, 12H).

Analytical data for Example 25A: LC-MS retention time 1.507 min; m/z 817.56 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICROMASS® Platform for LC in electrospray mode. $^1$H NMR (500 MHz, MeOD) δ ppm 9.14-9.02 (m, 2H), 8.69-8.60 (m, 2H), 8.36-8.27 (m, 2H), 8.15-8.08 (m, 2H), 5.41-5.36 (m, 1H), 5.34-5.29 (m, 1H), 4.35 (d, J=7.9 Hz, 1H), 4.31 (d, J=7.3 Hz, 1H), 4.24-3.81 (m, 4H), 3.78 (s, 3H), 3.68 (s, 3H), 2.62-1.97 (m, 10H), 1.09-0.46 (m, 12H).

Analytical data for Example 25B: LC-MS retention time 1.562 min; m/z 817.58 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 5% water/95% acetonitrile/10 mM ammonium acetate. MS data was determined using a MICRO-MASS® Platform for LC in electrospray mode.

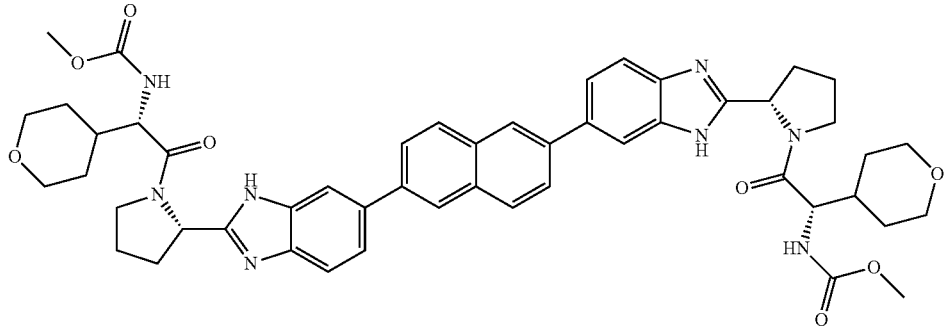 [SMILES: COC(=O)N[C@H](C(=O)N1CCC[C@H]1c1nc2ccc(-c3ccc4cc(-c5ccc6nc([C@@H]7CCCN7C(=O)[C@@H](NC(=O)OC)C7CCOCC7)[nH]c6c5)ccc4c3)cc2[nH]1)C1CCOCC1]

Dimethyl (2,6-naphthalenediylbis(1H-benzimidazole-5,2-diyl(2S)-2,1-pyrrolidinediyl((1S)-2-oxo-1-(tetrahydro-2H-pyran-4-yl)-2,1-ethanediyl)))biscarbamate HATU (114 mg, 0.301 mmol) was added to a stirred solution of 2,6-bis(2-((S)-pyrrolidin-2-yl)-1H-benzo[d]imidazol-6-yl)naphthalene (50 mg), diisopropylethylamine (175 µL, 1.0 mmol) and (S)-2-(methoxycarbonylamino)-2-(tetrahydro-2H-pyran-4-yl)acetic acid (65 mg, 0.30 mmol) in DMF (5 mL) and the resulting mixture was stirred at ambient conditions for 2 hours. The reaction mixture was diluted with methanol (2 mL) and water (2 mL). Then, the volatile component was removed in vacuo and the residue was purified by a reverse phase HPLC (water/acetonitrile/TFA) to provide a TFA salt of dimethyl (2,6-naphthalenediylbis(1H-benzimidazole-5,2-diyl(2S)-2,1-pyrrolidinediyl((1S)-2-oxo-1-(tetrahydro-2H-pyran-4-yl)-2,1-ethanediyl)))biscarbamate (51.5 mg) as pale yellow solid. LC-MS retention time 1.117 min; m/z 897.31 (MH+). LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (TFA salt 500 MHz, MeOD) δ ppm 8.27 (br s, 2H), 8.10-8.18 (m, 4H), 8.01-8.07 (m, 2H), 7.86-7.96 (m, 4H), 5.88-5.93 (m, 0.2H), 5.39 (t, J=7.0 Hz, 1.8H), 4.33-4.38 (m, 2H), 4.12-4.22 (m, 2H), 3.89-4.05 (m, 7H), 3.70 (s, 6H), 3.35-3.45 (m, 2H), 2.60-2.75 (m, 2H), 2.14-2.47 (m, 6.5H), 1.94-2.12 (m, 2.5H), 1.32-1.69 (m, 8H).

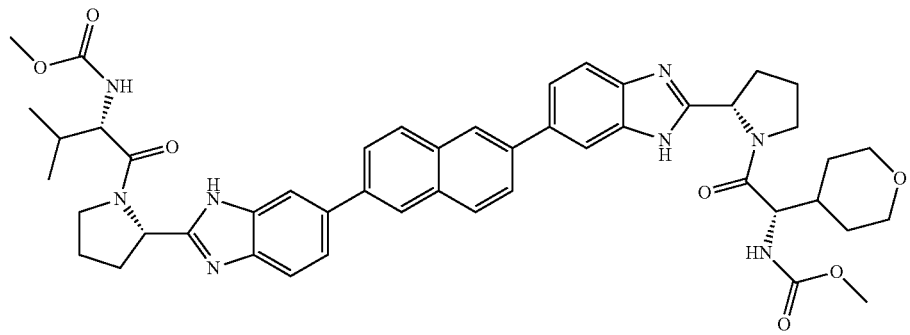 [SMILES: COC(=O)N[C@H](C(=O)N1CCC[C@H]1c1nc2ccc(-c3ccc4cc(-c5ccc6nc([C@@H]7CCCN7C(=O)[C@@H](NC(=O)OC)C7CCOCC7)[nH]c6c5)ccc4c3)cc2[nH]1)C(C)C]

Methyl ((1S)-2-((2S)-2-(5-(6-(2-((2S)-1-((2S)-2-((methoxycarbonyl)amino)-3-methylbutanoyl)-2-pyrrolidinyl)-1H-benzimidazol-5-yl)-2-naphthyl)-1H-benzimidazol-2-yl)-1-pyrrolidinyl)-2-oxo-1-(tetrahydro-2H-pyran-4-yl)ethyl)carbamate HATU (87 mg, 0.23 mmol) was added to a stirred solution of methyl ((1S)-2-methyl-1-(((2S)-2-(5-(6-(2-((2S)-2-pyrrolidinyl)-1H-benzimidazol-5-yl)-2-naphthyl)-1H-benzimidazol-2-yl)-1-pyrrolidinyl)carbonyl)propyl)carbamate (50 mg), diisopropylethylamine (133 µL, 0.76 mmol) and (S)-2-(methoxycarbonylamino)-2-(tetrahydro-2H-pyran-4-yl)acetic acid (50 mg, 0.23 mmol) in DMF (3 mL) and the resulting mixture was stirred at ambient conditions for 2 hours. The reaction mixture was diluted with methanol (2 mL) and water (2 mL). Then the volatile component was removed in vacuo and the residue was purified by a reverse phase HPLC (water/acetonitrile/TFA) to provide a TFA salt of methyl ((1S)-2-((2S)-2-(5-(6-(2-((2S)-1-((2S)-2-((methoxycarbonyl)amino)-3-methylbutanoyl)-2-pyrrolidinyl)-1H-benzimidazol-5-yl)-2-naphthyl)-1H-benzimidazol-2-yl)-1-pyrrolidinyl)-2-oxo-1-(tetrahydro-2H-pyran-4-yl)ethyl)carbamate (36 mg) as yellow solid. LC-MS retention time 1.177 min; m/z 855.30 (MH+). LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (TFA salt, 500 MHz, MeOD) δ ppm 8.22-8.30 (m, 1.8H), 8.20 (br s, 0.2H), 8.07-8.17 (m, 4H), 8.00-8.06 (m, 1.8H), 7.98 (br s, 0.2H), 7.85-7.95 (m, 4H), 5.86 (m, 0.1H), 5.35-5.44 (m, 1.8H), 5.25-5.31 (m, 0.1H), 4.36 (d, J=7.6 Hz, 0.5H), 4.31 (d, J=6.7 Hz, 1H), 4.15 (br s, 1.5H), 3.87-4.05 (m, 4H), 3.69 (br s, 6H), 3.34-3.47 (m, 1H), 2.96-3.23 (m, 2H), 2.61-2.77 (m, 2.5H), 2.21-2.47 (m, 6H), 1.95-2.16 (m, 2H), 1.33-1.69 (m, 3.5H), 1.00-1.05 (m, 0.3H), 0.94-0.99 (m, 3H), 0.91 (d, J=6.7 Hz, 2.7H).

mmol) and (S)-2-(methoxycarbonylamino)-2-(tetrahydro-2H-pyran-4-yl)acetic acid (21 mg, 0.10 mmol) in DMF (2 mL) and the resulting mixture was stirred at ambient conditions for 2 hours. The reaction mixture was diluted with methanol (2 mL) and water (2 mL). Then the volatile component was removed in vacuo and the residue was purified by a reverse phase HPLC (water/acetonitrile/TFA) to provide a TFA salt of methyl ((1S)-2-((2S)-2-(4-(6-(2-((2S)-1-((2S)-2-((methoxycarbonyl)amino)-2-(tetrahydro-2H-pyran-4-yl)acetyl)-2-pyrrolidinyl)-1H-benzimidazol-5-yl)-2-naphthyl)-1H-imidazol-2-yl)-1-pyrrolidinyl)-2-oxo-1-(tetrahydro-2H-pyran-4-yl)ethyl)carbamate (16.3 mg) as yellow solid. LC-MS retention time 1.023 min; m/z 847.31 (MH+). LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time

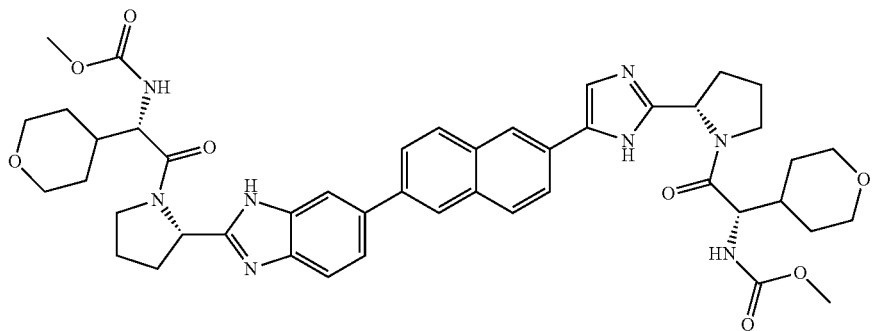 [SMILES: COC(=O)N[C@H](C(=O)N1CCC[C@H]1c1ncc(-c2ccc3cc(-c4ccc5nc([C@@H]6CCCN6C(=O)[C@@H](NC(=O)OC)C6CCOCC6)[nH]c5c4)ccc3c2)[nH]1)C1CCOCC1]

Methyl ((1S)-2-((2S)-2-(4-(6-(2-((2S)-1-((2S)-2-((methoxycarbonyl)amino)-2-(tetrahydro-2H-pyran-4-yl)acetyl)-2-pyrrolidinyl)-1H-benzimidazol-5-yl)-2-naphthyl)-1H-imidazol-2-yl)-1-pyrrolidinyl)-2-oxo-1-(tetrahydro-2H-pyran-4-yl)ethyl)carbamate HATU (36.6 mg, 0.096 mmol) was added to a stirred solution of a TFA salt of 2-((S)-pyrrolidin-2-yl)-6-(6-(2-((S)-pyrrolidin-2-yl)-1H-imidazol-5-yl)naphthalen-2-yl)-1H-benzo[d]imidazole (29 mg), diisopropylethylamine (56 μL, 0.32 of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (TFA salt, 500 MHz, MeOD) δ ppm 8.29 (d, J=12.5 Hz, 2H), 8.15 (d, J=8.6 Hz, 1H), 8.10 (d, J=8.5 Hz, 1H), 8.07 (s, 1H), 7.92-8.01 (m, 3H), 7.81-7.90 (m, 2H), 5.37 (dd, J=7.9, 6.1 Hz, 1H), 5.30 (t, J=7.5 Hz, 1H), 4.28-4.39 (m, 2H), 4.12-4.22 (m, 2H), 3.88-4.04 (m, 7H), 3.65-3.77 (m, 6H), 3.38-3.45 (m, 1H), 2.56-2.69 (m, 2H), 2.20-2.40 (m, 6.5H), 2.01 (br s, 2.5H), 1.57-1.69 (m, 2.5H), 1.35-1.53 (m, 6.5H).

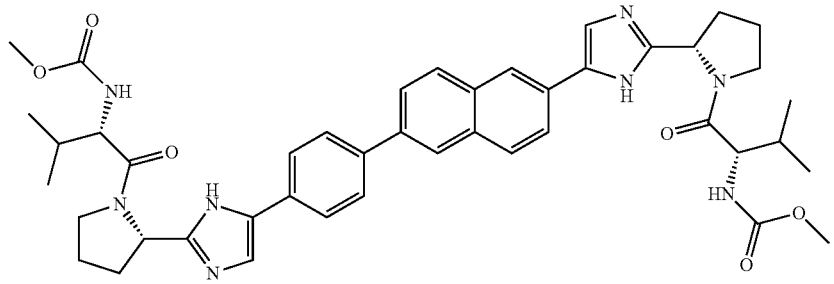

443

Methyl ((1S)-1-(((2S)-2-(4-(4-(6-(2-((2S)-1-((2S)-2-((methoxycarbonyl)amino)-3-methylbutanoyl)-2-pyrrolidinyl)-1H-imidazol-4-yl)-2-naphthyl)phenyl)-1H-imidazol-2-yl)-1-pyrrolidinyl)carbonyl)-2-methylpropyl)carbamate HATU (57.6 mg, 0.152 mmol) was added to a stirred solution of a TFA salt of 2-((S)-pyrrolidin-2-yl)-5-(4-(6-(2-((S)-pyrrolidin-2-yl)-1H-imidazol-5-yl)naphthalen-2-yl)phenyl)-1H-imidazole (47 mg), diisopropylethylamine (88 μL, 0.51 mmol) and (S)-2-(methoxycarbonylamino)-3-methylbutanoic acid (26.5 mg, 0.152 mmol) in DMF (4 mL) and the resulting mixture was stirred at ambient conditions for 2 hours. The reaction mixture was diluted with methanol (2 mL) and water (2 mL). The volatile component was removed in vacuo and the residue was purified by a reverse phase HPLC (water/methanol/TFA), repurified by a reverse phase HPLC (water/acetonitrile/ammonium acetate) and finally repurified by a reverse phase HPLC (water/methanol/TFA) to provide a TFA salt of methyl ((1S)-1-(((2S)-2-(4-(4-(6-(2-((2S)-1-((2S)-2-((methoxycarbonyl)amino)-3-methylbutanoyl)-2-pyrrolidinyl)-1H-imidazol-4-yl)-2-naphthyl)phenyl)-1H-imidazol-2-yl)-1-pyrrolidinyl)carbonyl)-2-methylpropyl)carbamate (33.3 mg) as yellow solid. LC-MS retention time 1.237 min; m/z 789.29 (MH+). LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (TFA salt, 500 MHz, MeOD) δ ppm 8.29 (d, J=8.9 Hz, 2H), 8.15 (d, J=8.5 Hz, 1H), 8.10 (d, J=8.9 Hz, 1H), 7.95-8.03 (m, 4H), 7.93 (s, 1H), 7.84-7.91 (m, 3H), 5.69-5.72 (m, 0.2H), 5.24-5.35 (m, 1.8H), 4.27 (dd, J=7.2, 2.6 Hz, 2H), 4.09-4.19 (m, 2H), 3.85-3.97 (m, 2H), 3.67-3.76 (m, 6H), 2.55-2.68 (m, 2H), 2.27-2.38 (m, 2H), 2.14-2.27 (m, 4H), 2.02-2.14 (m, 2H), 0.86-1.06 (m, 12H).

444

Dimethyl (2,6-naphthalenediylbis(1H-benzimidazole-5,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate HATU (54.6 mg, 0.144 mmol) was added to a stirred solution of 2,6-bis(2-((1R,3S,5R)-2-azabicyclo[3.1.0]hexan-3-yl)-1H-benzo[d]imidazol-6-yl)naphthalene (25 mg), diisopropylethylamine (84 μL, 0.48 mmol) and (S)-2-(methoxycarbonylamino)-2-(tetrahydro-2H-pyran-4-yl) acetic acid (31.2 mg, 0.144 mmol) in DMF (5 mL) and the resulting mixture was stirred at ambient conditions for 4 hours. The reaction mixture was diluted with methanol (2 mL) and water (2 mL). The volatile component was removed in vacuo and the residue was purified by a reverse phase HPLC (water/methanol/TFA), repurified by a reverse phase HPLC (water/acetonitrile/ammonium acetate) and finally repurified by a reverse phase HPLC (water/methanol/TFA) to provide a TFA salt of dimethyl (2,6-naphthalenediylbis(1H-benzimidazole-5,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate (8.2 mg) as off-white solid. LC-MS retention time 1.220 min; m/z 461.3 [½M+H$^+$]. LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (TFA salt, 500 MHz, MeOD) δ ppm 8.28 (br s, 2H), 8.07-8.18 (m, 4H), 8.00-8.07 (m, 2H), 7.84-7.96 (m, 4H), 5.23-5.31 (m, 2H), 4.59-4.67 (m, 2H), 3.85-4.01 (m, 6H), 3.70 (s, 6H), 3.28-3.44 (m, 4H), 2.71-2.80 (m, 2H), 2.58 (ddd, J=13.2, 6.5, 6.3 Hz, 2H), 2.03-2.20 (m, 4H), 1.41-1.65 (m, 8H), 1.13 (br s, 2H), 0.97 (br s, 2H).

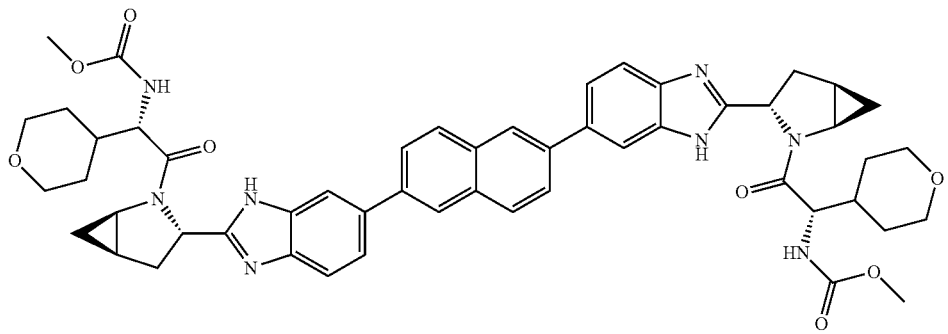 [SMILES: COC(=O)N[C@H](C(=O)N1[C@@H]2C[C@@H]2C[C@H]1c1nc2ccc(-c3ccc4cc(-c5ccc6nc([C@@H]7C[C@H]8C[C@H]8N7C(=O)[C@@H](NC(=O)OC)C7CCOCC7)[nH]c6c5)ccc4c3)cc2[nH]1)C1CCOCC1]

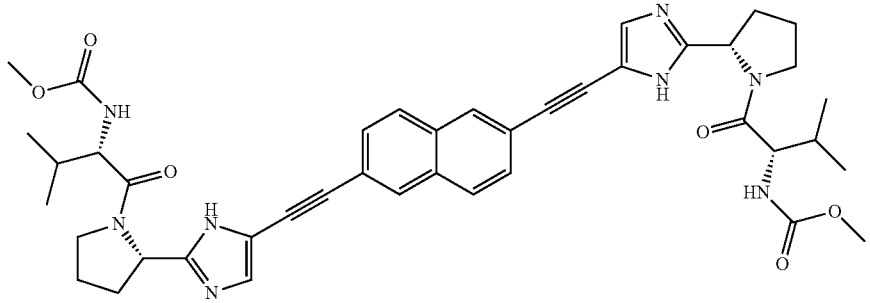

Methyl ((1S)-1-(((2S)-2-(4-((6-((2-((2S)-1-((2S)-2-((methoxycarbonyl)amino)-3-methylbutanoyl)-2-pyrrolidinyl)-1H-imidazol-4-yl)ethynyl)-2-naphthyl)ethynyl)-1H-imidazol-2-yl)-1-pyrrolidinyl)carbonyl)-2-methylpropyl)carbamate HATU (47.6 mg, 0.125 mmol) was added to a TFA salt of 2,6-bis((2-((S)-pyrrolidin-2-yl)-1H-imidazol-5-yl)ethynyl)naphthalene (38 mg) and (S)-2-(methoxycarbonylamino)-3-methylbutanoic acid (22 mg, 0.13 mmol) in DMF (0.7 mL) and TEA (0.047 mL, 0.33 mmol) and the clear yellow solution was at rt ON. The reaction was diluted with MeOH (1 mL), filtered and purified by prep HPLC 15-100% MeOH/water/TFA buffer) to yield a TFA salt of methyl ((1S)-1-(((2S)-2-(4-((6-((2-((2S)-1-((2S)-2-((methoxycarbonyl)amino)-3-methylbutanoyl)-2-pyrrolidinyl)-1H-imidazol-4-yl)ethynyl)-2-naphthyl)ethynyl)-1H-imidazol-2-yl)-1-pyrrolidinyl)carbonyl)-2-methylpropyl)carbamate (37.1 mg) as light yellow solid. LC-MS retention time 2.530 min; m/z 759.61 (MH-). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode.

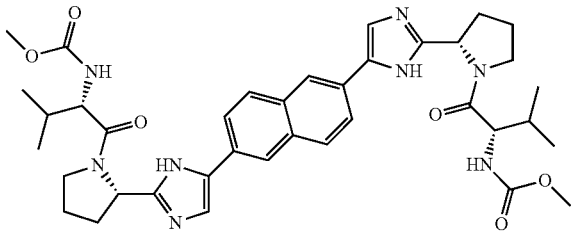

Methyl ((1S)-1-(((2S)-2-(4-((6-((2-((2S)-1-((2S)-2-((methoxycarbonyl)amino)-3-methylbutanoyl)-2-pyrrolidinyl)-1H-imidazol-4-yl)ethynyl)-2-naphthyl)ethynyl)-1H-imidazol-2-yl)-1-pyrrolidinyl)carbonyl)-2-methylpropyl)carbamate A TFA salt of 4,4'-(2,6-naphthalenediyl)bis(2-((2S)-2-pyrrolidinyl)-1H-imidazole) (21 mg, 0.025 mmol) and (S)-2-(methoxycarbonylamino)-3-methylbutanoic acid (12.9 mg) were dissolved into DMF (3 mL) and DIEA (0.043 mL, 0.246 mmol). Then HATU (28.0 mg, 0.074 mmol) was added and the reaction mixture was stirred at room temperature for 2 h. The volatiles were removed under vacuum and the crude product was purified by prep HPLC (Waters Sunfire C18 column 30×100 mm 5u eluted with a gradient of 0 to 90% MeOH-Water+0.1% TFA) to yield a TFA salt of methyl ((1S)-1-(((2S)-2-(4-((6-((2-((2S)-1-((2S)-2-((methoxycarbonyl)amino)-3-methylbutanoyl)-2-pyrrolidinyl)-1H-imidazol-4-yl)ethynyl)-2-naphthyl)ethynyl)-1H-imidazol-2-yl)-1-pyrrolidinyl)carbonyl)-2-methylpropyl)carbamate (10.4 mg) as off white solid. LC-MS retention time 1.158 min; m/z 713.60 (MH+). LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (TFA salt, 500 MHz, MeOD) δ ppm 8.31 (s, 2H), 8.11 (d, J=8.6 Hz, 2H), 7.94-8.03 (m, 2H), 7.84-7.94 (m, 2H), 5.29 (t, J=7.3 Hz, 2H), 4.26 (d, J=7.02 Hz, 2H), 4.14 (t, J=10.2 Hz, 2H), 3.85-3.96 (m, 2H), 3.68 (s, 6H), 2.53-2.67 (m, 2H), 2.31 (d, J=10.4 Hz, 2H), 2.16-2.28 (m, 4H), 2.03-2.15 (m, 2H), 0.88-1.08 (m, 12H).

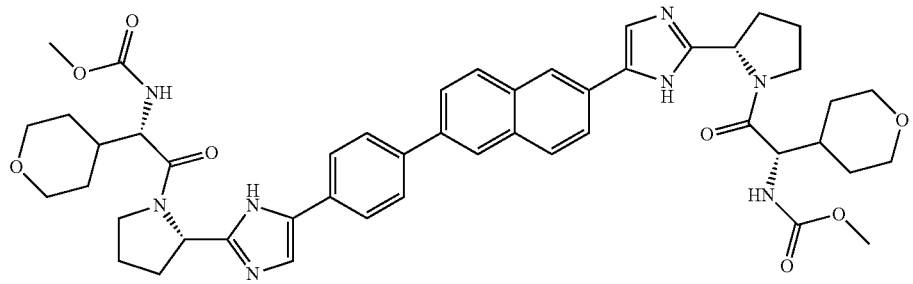 [SMILES: COC(=O)N[C@H](C(=O)N1CCC[C@H]1c1ncc(-c2ccc(-c3ccc4cc(-c5cnc([C@@H]6CCCN6C(=O)[C@@H](NC(=O)OC)C6CCOCC6)[nH]5)ccc4c3)cc2)[nH]1)C1CCOCC1]

447

Methyl ((1S)-2-((2S)-2-(4-(4-(6-(2-((2S)-1-((2S)-2-((methoxycarbonyl)amino)-2-(tetrahydro-2H-pyran-4-yl)acetyl)-2-pyrrolidinyl)-1H-imidazol-4-yl)-2-naphthyl)phenyl)-1H-imidazol-2-yl)-1-pyrrolidinyl)-2-oxo-1-(tetrahydro-2H-pyran-4-yl)ethyl)carbamate HATU (120 mg, 0.316 mmol) was added to a stirred solution of a TFA salt of 2-((2S)-2-pyrrolidinyl)-4-(4-(6-(2-((2S)-2-pyrrolidinyl)-1H-imidazol-4-yl)-2-naphthyl)phenyl)-1H-imidazole (50 mg) and (S)-2-(methoxycarbonylamino)-2-(tetrahydro-2H-pyran-4-yl)acetic acid (68.7 mg, 0.316 mmol) in DMF (5 mL) and DIEA (0.18 mL, 1.1 mmol) and the reaction mixture was stirred at room temperature for 2 h. The reaction mixture was diluted with MeOH (2 mL) and water (2 mL) and the volatiles were removed under vacuum. The residue was purified by prep HPLC (Waters Sunfire C18 column 30×100 mm 5u eluted with a gradient of 10 to 90% MeOH-Water+0.1% TFA) and then repurified by prep HPLC (Waters Sunfire C18 column 30×150 mm 5u eluted with a gradient of to % ACN-Water+0.1% TFA) to yield a TFA salt of methyl ((1S)-2-((2S)-2-(4-(4-(6-(2-((2S)-1-((2S)-2-((methoxycarbonyl)amino)-2-(tetrahydro-2H-pyran-4-yl)acetyl)-2-pyrrolidinyl)-1H-imidazol-4-yl)-2-naphthyl)phenyl)-1H-imidazol-2-yl)-1-pyrrolidinyl)-2-oxo-1-(tetrahydro-2H-pyran-4-yl)ethyl)carbamate (96 mg) as yellow solid. LC-MS retention time 1.207 min; m/z 873.63 (MH+). LC data was recorded on a Shimadzu LC-10AS liquid chromatograph equipped with a Waters Sunfire 5u C18 4.6×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% TFA and Solvent B was 10% $H_2O$/90% MeOH/0.1% TFA. MS data was determined using a MICROMASS® Platform for LC in electrospray mode. $^1$H NMR (TFA salt, 500 MHz, MeOD) δ ppm 8.29 (d, J=7.9 Hz, 2H), 8.14 (d, J=8.9 Hz, 1H), 8.06-8.11 (m, 1H), 7.94-8.03 (m, 4H), 7.90-7.94 (m, 1H), 7.80-7.90 (m, 3H), 5.74 (br s, 0.2H), 5.23-5.35 (m, 1.8H), 4.32 (dd, J=8.1, 4.7 Hz, 2H), 4.16 (d, J=2.8 Hz, 2H), 3.94 (dd, J=9.5, 7.3 Hz, 6H), 3.69 (s, 6H), 3.31-3.48 (m, 4H), 2.55-2.68 (m, 2H), 2.16-2.35 (m, 6H), 1.92-2.10 (m, 2H), 1.63 (d, J=12.8 Hz, 2H), 1.34-1.54 (m, 6H).

448

Methyl ((1S)-2-((1R,3S,5R)-3-(4-(4-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)-2-oxo-1-(tetrahydro-2H-pyran-4-yl)ethyl)carbamate HATU (57 mg, 0.150 mmol) was added to a stirred solution of (1R,3S,5R)-3-(5-(4-(6-(2-((1R,3S,5R)-2-azabicyclo[3.1.0]hexan-3-yl)-1H-imidazol-5-yl)naphthalen-2-yl)phenyl)-1H-imidazol-2-yl)-2-azabicyclo[3.1.0]hexane (25 mg, 0.050 mmol) and (S)-2-(methoxycarbonylamino)-2-(tetrahydro-2H-pyran-4-yl)acetic acid (33 mg) in DMF (3 mL) and DIEA (0.078 mL, 0.50 mmol) and the reaction mixture was stirred at room temperature for 2 h. The reaction mixture was diluted with MeOH (2 mL) and water (2 mL) and the volatiles were removed under vacuum. The residue was purified by prep HPLC (Waters Sunfire C18 column 30×100 mm 5u eluted with a gradient of 10 to 100% MeOH-Water+0.1% TFA) to yield a TFA salt of methyl ((1S)-2-((1R,3S,5R)-3-(4-(4-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)-2-oxo-1-(tetrahydro-2H-pyran-4-yl)ethyl)carbamate (27 mg) as pale yellow solid. LC-MS retention time 1.280 min; m/z 897.65 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% TFA and Solvent B was 10% $H_2O$/90% MeOH/0.1% TFA. MS data was determined using a MICROMASS® Platform for LC in electrospray mode. $^1$H NMR (TFA salt, 500 MHz, MeOD) δ ppm 8.28-8.32 (m, 2H), 8.14 (d, J=8.6 Hz, 1H), 8.07-8.11 (m, 1H), 7.95-8.02 (m, 4H), 7.84-7.93 (m, 4H), 5.12-5.23 (m, 2H), 4.62 (dd, J=7.6, 4.0 Hz, 2H), 3.92-4.00 (m, 4H), 3.83-3.89 (m, 2H), 3.72-3.78 (m, 2H), 3.70 (s, 6H), 3.35-3.46 (masked with methanol, m, 4H), 2.68-2.77 (m, 2H), 2.47-2.57 (m, 2H), 2.00-2.15 (m, 4H), 1.42-1.65 (m, 6H), 1.06-1.17 (m, 2H), 0.84-0.93 (m, 2H).

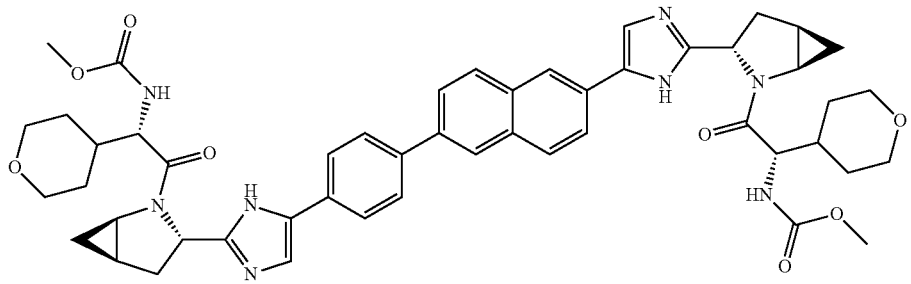 [SMILES: COC(=O)N[C@H](C(=O)N1[C@@H]2C[C@@H]2C[C@H]1c1ncc(-c2ccc(-c3ccc4cc(-c5cnc([C@@H]6C[C@H]7C[C@H]7N6C(=O)[C@@H](NC(=O)OC)C6CCOCC6)[nH]5)ccc4c3)cc2)[nH]1)C1CCOCC1]

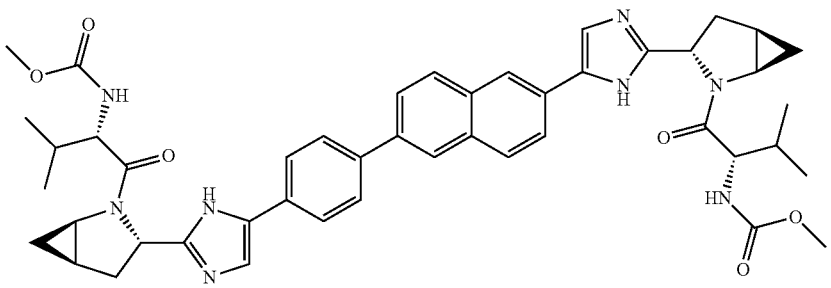

Methyl ((1S)-1-(((1R,3S,5R)-3-(4-(4-(6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)carbonyl)-2-methylpropyl)carbamate HATU (57 mg, 0.150 mmol) was added to a stirred solution of (1R,3S,5R)-3-(5-(4-(6-(2-((1R,3S,5R)-2-azabicyclo [3.1.0]hexan-3-yl)-1H-imidazol-5-yl)naphthalen-2-yl)phenyl)-1H-imidazol-2-yl)-2-azabicyclo[3.1.0]hexane (25 mg) and (S)-2-(methoxycarbonylamino)-3-methylbutanoic acid (26 mg, 0.15 mmol) in DMF (3 mL) and DIEA (0.070 mL, 0.40 mmol) and the reaction mixture was stirred at room temperature for 2 h. The reaction mixture was diluted with MeOH (2 mL) and water (2 mL) and the volatiles were removed under vacuum. The residue was purified by prep HPLC (Waters Sunfire C18 column 30×100 mm 5u eluted with a gradient of 10 to 100% MeOH-Water+0.1% TFA) to yield a TFA salt of methyl ((1S)-1-(((1R,3S,5R)-3-(4-(4-(6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)phenyl)-1H-imidazol-2-yl)-2-azabicyclo [3.1.0]hex-2-yl)carbonyl)-2-methylpropyl)carbamate (34.8 mg) as pale yellow solid. LC-MS retention time 1.402 min; m/z 813.69 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% TFA and Solvent B was 10% $H_2O$/90% MeOH/ 0.1% TFA. MS data was determined using a MICROMASS® Platform for LC in electrospray mode. $^1$H NMR (TFA salt, 500 MHz, MeOD) δ ppm 8.29 (d, J=7.9 Hz, 2H), 8.14 (d, J=8.9 Hz, 1H), 8.09 (d, J=8.9 Hz, 1H), 7.95-8.01 (m, 4H), 7.92 (s, 1H), 7.84-7.90 (m, 3H), 5.16 (ddd, J=11.6, 9.2, 7.0 Hz, 2H), 4.58 (dd, J=6.4, 2.1 Hz, 2H), 3.81-3.88 (m, 2H), 3.66-3.75 (m, 6H), 2.67-2.77 (m, 2H), 2.46-2.57 (m, 2H), 2.21 (dq, J=12.9, 6.5 Hz, 2H), 2.06-2.14 (m, 2H), 1.08-1.18 (m, 2H), 1.04 (d, J=6.7 Hz, 6H), 0.95 (d, J=6.7 Hz, 6H), 0.91 (br s, 2H).

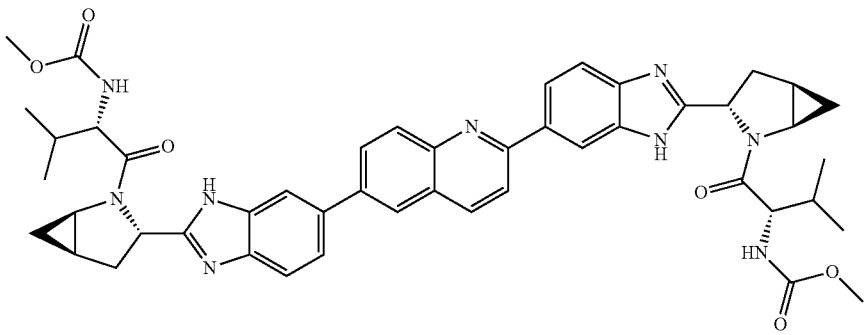

Methyl ((1S)-1-(((1R,3S,5R)-3-(5-(6-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-2-quinolinyl)-1H-benzimidazol-2-yl)-2-azabicyclo[3.1.0]hex-2-yl)carbonyl)-2-methylpropyl)carbamate HATU (32.7 mg, 0.086 mmol) was added to a solution of a hydrochloride salt of 2,6-bis(2-((1R,3S,5R)-2-azabicyclo [3.1.0]hexan-3-yl)-1H-benzo[d]imidazol-6-yl)quinoline (25 mg) and (S)-2-(methoxycarbonylamino)-3-methylbutanoic acid (15 mg, 0.086 mmol) in DMF (1 mL) and DIPEA (0.059 mL, 0.34 mmol) and the mixture was stirred at rt for 16 h. The reaction was diluted with MeOH, and purified by prep HPLC ($H_2O$-MeOH with 0.1% TFA buffer) to yield a TFA salt of dimethyl (2S,2'S)-1,1'-(((1R,1'R,3S,3'S,5R,5'R)-3,3'-(6,6'-(quinoline-2,6-diyl)bis(1H-benzo[d]imidazole-6,2-diyl))bis (2-azabicyclo[3.1.0]hexane-3,2-diyl))bis(3-methyl-1-oxobutane-2,1-diyl)dicarbamate (8.3 mg) as a yellow solid. LC-MS retention time 1.88 min; m/z 838 [M+H]$^+$. (Column PHENOMENEX® Luna3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 8.64-8.80 (1H, m), 8.49-8.62 (1H, m), 7.45-8.48 (9H, m), 5.21-5.52 (2H, m), 4.50-4.68 (2H, m), 3.82-4.13 (2H, m), 3.70-3.79 (2H, m), 3.68, 3.66 (6H, s, s), 2.48-2.83 (3H, m), 2.02-2.28 (3H, m), 1.09-1.30 (2H, m), 0.83-1.08 (14H, m).

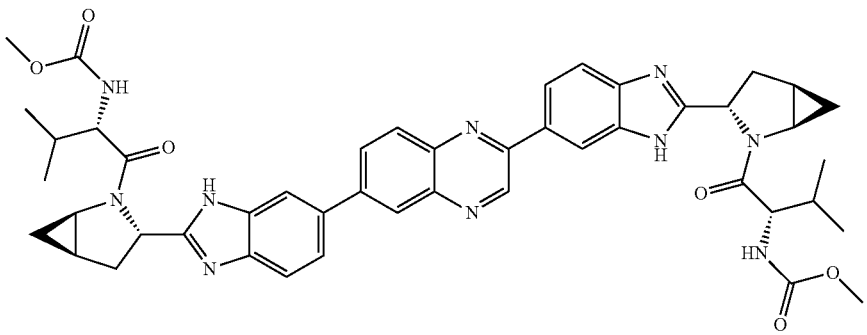

Methyl ((1S)-1-((((1R,3S,5R)-3-(5-(6-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-2-quinoxalinyl)-1H-benzimidazol-2-yl)-2-azabicyclo[3.1.0]hex-2-yl)carbonyl)-2-methylpropyl)carbamate HATU (25 mg, 0.066 mmol) was added to a solution of a TFA salt of 2,6-bis(2-((1R,3S,5R)-2-azabicyclo[3.1.0]hexan-3-yl)-1H-benzo[d]imidazol-6-yl)quinoxaline (28 mg) and (S)-2-(methoxycarbonylamino)-3-methylbutanoic acid (11.5 mg, 0.066 mmol) in DMF (0.5 mL) and DIPEA (0.045 mL, 0.26 mmol) and the mixture was stirred at rt for 2 h. The reaction was diluted with MeOH, and purified by prep HPLC (H$_2$O-MeOH with 0.1% TFA buffer) to yield a TFA salt of dimethyl (2S,2'S)-1,1'-((1R,1'R,3S,3'S,5R,5'R)-3,3'-(6,6'-(quinoxaline-2,6-diyl)bis(1H-benzo[d]imidazole-6,2-diyl))bis(2-azabicyclo[3.1.0]hexane-3,2-diyl))bis(3-methyl-1-oxobutane-2,1-diyl)dicarbamate (27 mg) as a yellow solid. LC-MS retention time 1.94 min; m/z 839 [M+H]$^+$. (Column PHENOMENEX® Luna3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (TFA salt, 400 MHz, MeOD) δ ppm 9.56 (s, 1H), 8.67 (s, 1H), 8.52 (d, J=8.8 Hz, 1H), 8.40 (s, 1H), 8.26 (d, J=8.8 Hz, 1H), 8.24 (d, J=8.8 Hz, 1H), 8.17 (s, 1H), 8.05 (d, J=8.5 Hz, 1H), 7.93 (d, J=8.5 Hz, 1H), 7.90 (d, J=8.8 Hz, 1H), 5.30 (app dd, J=9.0, 6.8 Hz, 2H), 4.60 (app d, J=6.0 Hz, 2H), 3.93-3.84 (m, 2H), 3.68 (s, 6H), 2.80-2.70 (m, 2H), 2.63-2.51 (m, 2H), 2.29-2.09 (m, 4H), 1.21-1.11 (m, 2H), 1.03 (d, J=6.8 Hz, 6H), 1.00-0.90 (m, 2H), 0.93 (d, J=6.5 Hz, 6H).

Dimethyl (2,6-quinoxalinediylbis(1H-benzimidazole-5,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate HATU (25.9 mg, 0.068 mmol) was added to a solution of a TFA salt of 2,6-bis(2-((1R,3S,5R)-2-azabicyclo[3.1.0]hexan-3-yl)-1H-benzo[d]imidazol-6-yl)quinoxaline (29 mg) and (S)-2-(methoxycarbonylamino)-2-(tetrahydro-2H-pyran-4-yl)acetic acid (14.8 mg, 0.068 mmol) in DMF (0.5 mL) and DIPEA (0.046 mL, 0.27 mmol) and the mixture was stirred at rt for 16 h. The reaction was diluted with MeOH, and purified by prep HPLC (H$_2$O-MeOH with 0.1% TFA buffer) to yield a TFA salt of dimethyl (1S,1'S)-2,2'-((1R,1'R,3S,3'S,5R,5'R)-3,3'-(6,6'-(quinoxaline-2,6-diyl)bis(1H-benzo[d]imidazole-6,2-diyl))bis(2-azabicyclo[3.1.0]hexane-3,2-diyl))bis(2-oxo-1-(tetrahydro-2H-pyran-4-yl)ethane-2,1-diyl)dicarbamate (32.5 mg) as a yellow solid. LC-MS retention time 1.74 min; m/z 462 [½M+H]$^+$. (Column PHENOMENEX® Luna3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (TFA salt, 400 MHz, MeOD) δ ppm 9.53 (s, 1H), 8.70 (s, 1H), 8.55 (dd, J=8.8, 1.5 Hz, 1H), 8.44 (d, J=1.8 Hz, 1H), 8.31 (d, J=8.8 Hz, 1H), 8.27 (dd, J=8.8, 1.8 Hz, 1H), 8.19 (br s, 1H), 8.08 (dd, J=8.8, 1.5 Hz, 1H), 7.96 (d, J=8.8 Hz, 1H), 7.92 (d, J=8.8 Hz, 1H), 5.28 (app dd, J=8.8, 6.8 Hz, 2H), 4.63 (app d, J=7.3 Hz, 2H), 3.99-3.86 (m, 6H), 3.69 (s, 6H), 3.44-3.29 (m, 4H), 2.81-2.71 (m, 2H), 2.63-2.52 (m, 2H), 2.20-2.03 (m, 4H), 1.68-1.37 (m, 8H), 1.17-1.08 (m, 2H), 0.99-0.92 (m, 2H).

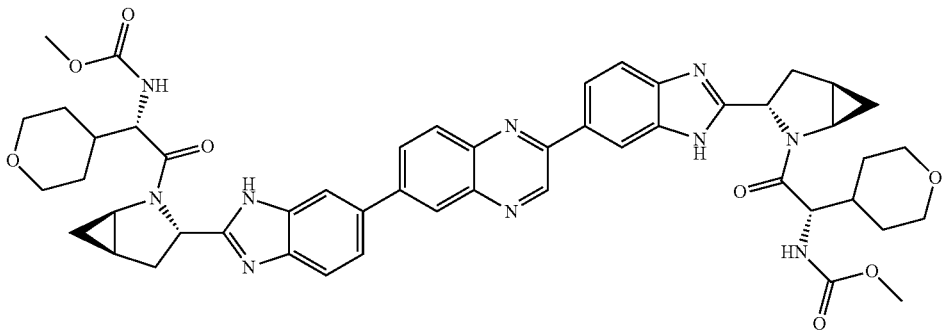 [SMILES: COC(=O)N[C@H](C(=O)N1[C@@H]2C[C@@H]2C[C@H]1c1nc2ccc(-c3ccc4nc(-c5ccc6nc([C@@H]7C[C@H]8C[C@H]8N7C(=O)[C@@H](NC(=O)OC)C7CCOCC7)[nH]c6c5)cnc4c3)cc2[nH]1)C1CCOCC1]

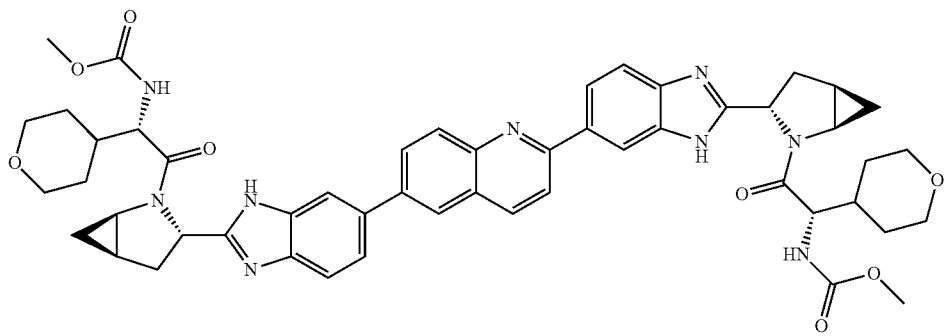 [SMILES: COC(=O)N[C@H](C(=O)N1[C@@H]2C[C@@H]2C[C@H]1c1nc2ccc(-c3ccc4nc(-c5ccc6nc([C@@H]7C[C@H]8C[C@H]8N7C(=O)[C@@H](NC(=O)OC)C7CCOCC7)[nH]c6c5)ccc4c3)cc2[nH]1)C1CCOCC1]

Dimethyl (2,6-quinolinediylbis(1H-benzimidazole-5,
2-diyl(1R,3S,5R)-2-azabicyclo[3.1.0]hexane-3,2-diyl
((1S)-2-oxo-1-(tetrahydro-2H-pyran-4-yl)-2,1-
ethanediyl)))biscarbamate HATU (34.0 mg, 0.089 mmol) was added to a solution of a hydrochloride salt of 2,6-bis(2-((1R,3S,5R)-2-azabicyclo [3.1.0]hexan-3-yl)-1H-benzo[d]imidazol-6-yl)quinoline (26 mg) and (S)-2-(methoxycarbonylamino)-2-(tetrahydro-2H-pyran-4-yl)acetic acid (19.4 mg, 0.089 mmol) in DMF (0.5 mL) and DIPEA (0.061 mL, 0.350 mmol) and the mixture was stirred at rt for 16 h. The reaction was diluted with MeOH and purified by prep HPLC ($H_2O$-MeOH with 0.1% TFA buffer) to yield a TFA salt of dimethyl (1S,1'S)-2,2'-((1R,1'R, 3S,3'S,5R,5'R)-3,3'-(6,6'-(quinoline-2,6-diyl)bis(1H-benzo [d]imidazole-6,2-diyl))bis(2-azabicyclo[3.1.0]hexane-3,2-diyl))bis(2-oxo-1-(tetrahydro-2H-pyran-4-yl)ethane-2,1-diyl)dicarbamate (6.0 mg) as a yellow solid. LC-MS retention time 1.65 min; m/z 462 [½M+H]$^+$. (Column PHENOMENEX® Luna3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 8.70 (1H, d, J=8.5 Hz), 8.57 (1H, s), 8.23-8.45 (5H, m), 8.17 (1H, s), 8.01-8.12 (1H, m), 7.88-7.97 (2H, m), 5.27 (2H, t, J=7.8 Hz), 4.33-4.68 (2H, m), 3.84-4.02 (6H, m), 3.69 (6H, s), 3.35-3.47 (4H, m), 2.67-2.81 (2H, m), 2.49-2.64 (2H, m), 1.91-2.21 (4H, m), 1.35-1.71 (8H, m), 1.07-1.17 (2H, m), 0.85-1.00 (2H, m).

2-yl)-1H-imidazol-5-yl)naphthalen-2-yl)phenyl)-1H-imidazole (20 mg) and (S)-2-(methoxycarbonylamino)-2-(tetrahydro-2H-pyran-4-yl)acetic acid (25.6 mg, 0.118 mmol) in DMF (3 mL) and DIEA (0.070 mL, 0.40 mmol) and the reaction mixture was stirred at room temperature for 2 h. The reaction mixture was diluted with MeOH (2 mL) and water (2 mL) and the volatiles were removed under vacuum. The residue was purified by prep HPLC (Waters Sunfire C18 column 30×100 mm 5u eluted with a gradient of 10 to 100% MeOH-Water+0.1%TFA) and then repurified by HPLC (Waters Sunfire C18 column 30×150 mm 5u eluted with a gradient of 10 to 100% ACN-Water+0.1% TFA) to yield a TFA salt of methyl ((1S)-2-((2S)-2-(4-chloro-5-(4-(6-(2-((2S)-1-((2S)-2-((methoxycarbonyl)amino)-2-(tetrahydro-2H-pyran-4-yl) acetyl)-2-pyrrolidinyl)-1H-imidazol-4-yl)-2-naphthyl)phenyl)-1H-imidazol-2-yl)-1-pyrrolidinyl)-2-oxo-1-(tetrahydro-2H-pyran-4-yl)ethyl)carbamate (12.9 mg) as yellow solid. LC-MS retention time 1.595 min; m/z 907.39 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/ 0.1% TFA and Solvent B was 10% $H_2O$/90% MeOH/0.1%

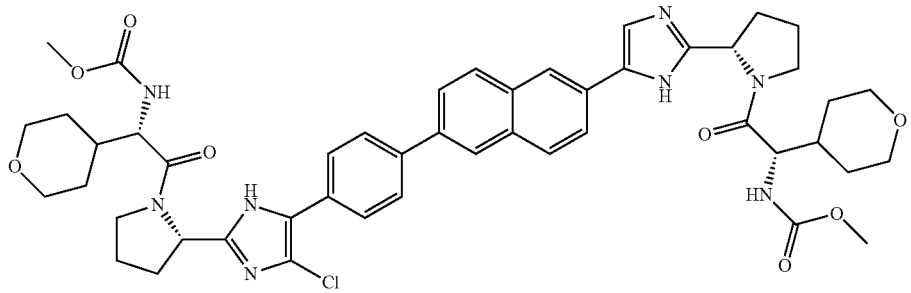 [SMILES: COC(=O)N[C@H](C(=O)N1CCC[C@H]1c1ncc(-c2ccc3cc(-c4ccc(-c5[nH]c([C@@H]6CCCN6C(=O)[C@@H](NC(=O)OC)C6CCOCC6)nc5Cl)cc4)ccc3c2)[nH]1)C1CCOCC1]

Methyl ((1S)-2-((2S)-2-(4-chloro-5-(4-(6-(2-((2S)-1-
((2S)-2-((methoxycarbonyl)amino)-2-(tetrahydro-
2H-pyran-4-yl)acetyl)-2-pyrrolidinyl)-1H-imidazol-
4-yl)-2-naphthyl)phenyl)-1H-imidazol-2-yl)-1-
pyrrolidinyl)-2-oxo-1-(tetrahydro-2H-pyran-4-yl)
ethyl)carbamate HATU (45 mg, 0.118 mmol) was added to a solution of 4-chloro-2-((S)-pyrrolidin-2-yl)-5-(4-(6-(2-((S)-pyrrolidin- TFA. MS data was determined using a MICROMASS® Platform for LC in electrospray mode. $^1$H NMR (TFA salt, 500 MHz, MeOD) δ ppm 8.20-8.28 (m, 2H), 8.09-8.12 (m, 1H), 8.02-8.08 (m, 1H), 7.91-8.00 (m, 3H), 7.87-7.91 (m, 2H), 7.80-7.87 (m, 2H), 5.28 (t, J=7.5 Hz, 1H), 5.06-5.14 (m, 1H), 4.25-4.35 (m, 2H), 4.11-4.19 (m, 1H), 4.00-4.07 (m, 1H), 3.85-4.00 (m, 6H), 3.63-3.69 (m, 6H), 3.32-3.43 (m, 4H), 2.57-2.64 (m, 1H), 2.34-2.40 (m, 1H), 2.26-2.32 (m, 2H), 2.12-2.25 (m, 4H), 1.95-2.09 (m, 2H), 1.34-1.64 (m, 8H).

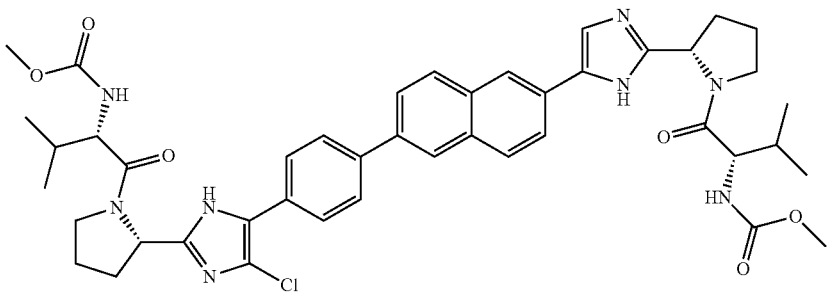

Methyl ((1S)-1-(((2S)-2-(4-(6-(4-(4-chloro-2-((2S)-1-((2S)-2-((methoxycarbonyl)amino)-3-methylbutanoyl)-2-pyrrolidinyl)-1H-imidazol-5-yl)phenyl)-2-naphthyl)-1H-imidazol-2-yl)-1-pyrrolidinyl)carbonyl)-2-methylpropyl)carbamate HATU (45 mg, 0.118 mmol) was added to a solution of 4-chloro-2-((S)-pyrrolidin-2-yl)-5-(4-(6-(2-((S)-pyrrolidin-2-yl)-1H-imidazol-5-yl)naphthalen-2-yl)phenyl)-1H-imidazole (20 mg) and (S)-2-(methoxycarbonylamino)-3-methylbutanoic acid (20.7 mg, 0.118 mmol) in DMF (3 mL) and DIEA (0.070 mL, 0.40 mmol) and the reaction mixture was stirred at room temperature for 2 h. The reaction mixture was diluted with MeOH (2 mL) and water (2 mL) and the volatiles were removed under vacuum. The residue was purified by prep HPLC (Waters Sunfire C18 column 30×100 mm 5u eluted with a gradient of 10 to 100% MeOH-Water+0.1% TFA) and then repurified by HPLC (Waters Sunfire C18 column 30×150 mm 5u eluted with a gradient of 10 to 100% ACN-Water+0.1% TFA) to yield a TFA salt of methyl ((1S)-1-(((2S)-2-(4-(6-(4-(4-chloro-2-((2S)-1-((2S)-2-((methoxycarbonyl)amino)-3-methylbutanoyl)-2-pyrrolidinyl)-1H-imidazol-5-yl)phenyl)-2-naphthyl)-1H-imidazol-2-yl)-1-pyrrolidinyl)carbonyl)-2-methylpropyl)carbamate (3.6 mg) as yellow solid. LC-MS retention time 1.715 min; m/z 823.49 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (TFA salt, 500 MHz, MeOD) δ ppm 8.24-8.29 (m, 1H), 8.22 (s, 1H), 8.08-8.15 (m, 1H), 8.03-8.08 (m, 1H), 7.81-8.01 (m, 7H), 5.31 (t, J=7.5 Hz, 1H), 5.12 (app t, J=7.5 Hz, 1H), 4.21-4.32 (m, 2H), 4.08-4.19 (m, 1H), 3.99-4.08 (m, 1H), 3.85-3.96 (m, 2H), 3.57-3.74 (m, 6H), 2.56-2.67 (m, 1H), 2.35-2.46 (m, 1H), 2.28-2.35 (m, 2H), 2.20-2.26 (m, 2H), 2.05-2.19 (m, 4H), 0.90-1.09 (m, 12H).

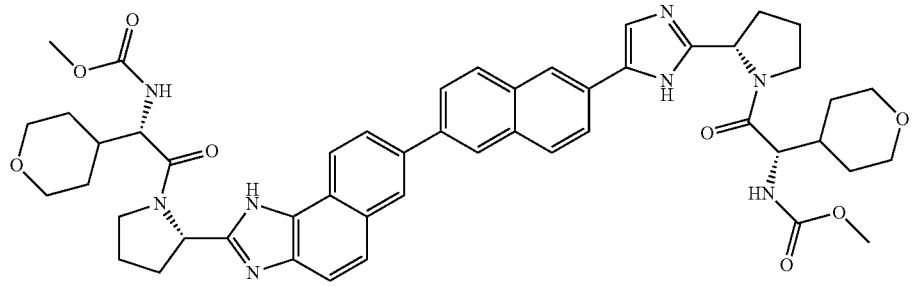 [SMILES: COC(=O)N[C@H](C(=O)N1CCC[C@H]1c1ncc(-c2ccc3cc(-c4ccc5c(ccc6nc([C@@H]7CCCN7C(=O)[C@@H](NC(=O)OC)C7CCOCC7)[nH]c65)c4)ccc3c2)[nH]1)C1CCOCC1]

Methyl ((1S)-2-((1R,3S,5R)-3-(7-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-naphthyl)-1H-naphtho[1,2-d]imidazol-2-yl)-2-azabicyclo[3.1.0]hex-2-yl)-2-oxo-1-(tetrahydro-2H-pyran-4-yl)ethyl)carbamate HATU (103 mg, 0.271 mmol) was added to a solution of 2-((S)-pyrrolidin-2-yl)-7-(6-(2-((S)-pyrrolidin-2-yl)-1H-imidazol-5-yl)naphthalen-2-yl)-1H-naphtho[1,2-d]imidazole (45 mg) and (S)-2-(methoxycarbonylamino)-2-(tetrahydro-2H-pyran-4-yl)acetic acid (58.8 mg, 0.271 mmol) in DMF (3 mL) and DIEA (0.16 mL, 0.90 mmol) and the reaction mixture was stirred at room temperature for 2 h. The reaction mixture was diluted with MeOH (2 mL) and water (2 mL) and the volatiles were removed under vacuum. The residue was purified by prep HPLC (Waters Sunfire C18 column 30×100 mm 5u eluted with a gradient of 10 to 100% MeOH-Water+0.1% TFA) and then repurified by HPLC (Waters Sunfire C18 column 30×150 mm 5u eluted with a gradient of 0 to 90% ACN-Water+0.1% TFA) to yield a TFA salt of methyl ((1S)-2-((1R,3S,5R)-3-(7-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-naphthyl)-1H-naphtho[1,2-d]imidazol-2-yl)-2-azabicyclo[3.1.0]hex-2-yl)-2-oxo-1-(tetrahydro-2H-pyran-4-yl)ethyl)carbamate (8.7 mg) as white solid. LC-MS retention time 1.307 min; m/z 897.67 (MH+). LC data was recorded on a Shimadzu LC-10AS liquid chromatograph equipped with a Waters Sunfire 5u C18 4.6×30 mm column using a SPD- 10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H₂O/0.1% TFA and Solvent B was 10% H₂O/90% MeOH/0.1% TFA. MS data was determined using a MICROMASS® Platform for LC in electrospray mode. $^1$H NMR (TFA salt, 500 MHz, MeOD) δ ppm 8.51-8.57 (m, 2H), 8.40 (s, 1H), 8.30 (s, 1H), 8.23 (d, J=10.1 Hz, 1H), 8.18 (d, J=8.6 Hz, 1H), 8.05-8.15 (m, 3H), 8.00 (s, 1H), 7.87 (dd, J=8.6, 1.8 Hz, 1H), 7.79-7.85 (m, 1H), 5.43 (t, J=7.3 Hz, 1H), 5.30 (t, J=7.3 Hz, 1H), 4.28-4.40 (m, 2H), 4.19 (br s, 2H), 3.88-4.07 (m, 6H), 3.70 (d, J=1.5 Hz, 6H), 3.26-3.45 (overlap with methanol, m, 4H), 2.57-2.71 (m, 2H), 2.30-2.42 (m, 3H), 2.20-2.29 (m, 3H), 1.93-2.10 (m, 2H), 1.58-1.68 (m., 2H), 1.34-1.58 (m, 6H).

LC-MS retention time 1.82 min; m/z 814 [M+H]⁺. (Column PHENOMENEX® Luna3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 8.71 (1H, d, J=8.8 Hz), 8.57 (1H, s), 8.21-8.43 (5H, m), 8.18 (1H, s), 8.04 (1H, dd, J=8.5, 1.5 Hz), 7.88-7.96 (2H, m), 5.40 (2H, t, J=7.03 Hz), 4.31 (2H, d, J=6.8 Hz), 4.09-4.21 (2H, m), 3.91-4.06 (2H, m), 3.68 (6H, s), 2.58-2.73 (2H, m), 2.20-2.49 (6H, m), 2.02-2.19 (2H, m), 0.96 (6H, dd, J=6.8, 1.8 Hz), 0.90 (6H, dd, J=6.7, 1.6 Hz).

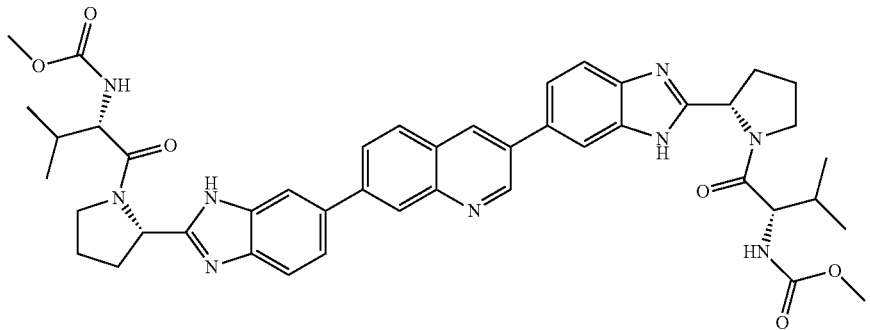

Methyl ((1S)-2-((1R,3S,5R)-3-(7-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-naphthyl)-1H-naphtho[1,2-d]imidazol-2-yl)-2-azabicyclo[3.1.0]hex-2-yl)-2-oxo-1-(tetrahydro-2H-pyran-4-yl)ethyl)carbamate HATU (24.5 mg, 0.065 mmol) was added to a solution of a TFA salt of 2,6-bis(2-((S)-pyrrolidin-2-yl)-1H-benzo[d]imi-

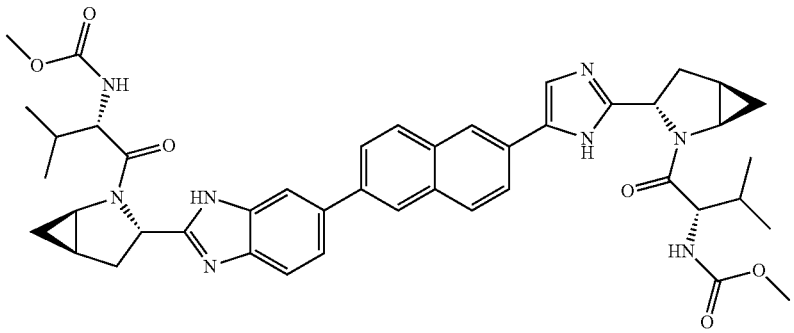

dazol-6-yl)quinoline (30 mg) and (S)-2-(methoxycarbonylamino)-3-methylbutanoic acid (11.3 mg, 0.065 mmol) in DMF (1 mL) and DIPEA (0.044 mL, 0.252 mmol) and the mixture was stirred at rt for 2 h. The reaction was diluted with MeOH and purified by prep HPLC (H₂O-MeOH with 0.1% TFA buffer) to yield a TFA salt of dimethyl (2S,2'S)-1,1'-((2S,2'S)-2,2'-(6,6'-(quinoline-2,6-diyl)bis(1H-benzo[d]imidazole-6,2-diyl))bis(pyrrolidine-2,1-diyl))bis(3-methyl-1-oxobutane-2,1-diyl)dicarbamate (34 mg) as a yellow solid.

Methyl ((1S)-1-(((1R,3S,5R)-3-(5-(6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)-1H-benzimidazol-2-yl)-2-azabicyclo[3.1.0]hex-2-yl)carbonyl)-2-methylpropyl)carbamate HATU (82 mg, 0.22 mmol) was added to a solution of 6-(6-(2-((1R,3S,5R)-2-azabicyclo[3.1.0]hexan-3-yl)-1H-imidazol-4-yl)naphthalen-2-yl)-2-((1R,3S,5R)-2-azabicyclo[3.1.0]hexan-3-yl)-1H-benzo[d]imidazole (34 mg), (S)-2-(methoxycarbonylamino)-3-methylbutanoic acid (37.8 mg, 0.216 mmol) and DIEA (0.13 mL, 0.72 mmol) in DMF (3 mL) and the reaction was stirred 2 h at room temperature. The reaction mixture was diluted with MeOH (2 ml) and water (2 mL). The volatiles were removed under vacuum. The residue was purified by prep HPLC (Waters Sunfire C18 column 30×150 mm 5u eluted with a gradient of 10 to 80% ACN-Water+0.1% TFA) to afford a TFA salt of methyl ((1S)-1-(((1R,3S,5R)-3-(5-(6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)-1H-benzimidazol-2-yl)-2-azabicyclo[3.1.0]hex-2-yl)carbonyl)-2-methylpropyl)carbamate (49.8 mg) as pale yellow solid. LC-MS retention time 1.357 min; m/z 787.65 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (TFA salt, 500 MHz, MeOD) δ ppm 8.29 (d, J=10.7 Hz, 2H), 8.07-8.19 (m, 3H), 7.94-8.05 (m, 3H), 7.84-7.92 (m, 2H), 5.29 (dd, J=9.2, 6.7 Hz, 1H), 5.18 (dd, J=9.2, 7.0 Hz, 1H), 4.59 (dd, J=12.4, 6.6 Hz, 2H), 3.81-3.91 (m, 2H), 3.69 (s, 6H), 2.67-2.80 (m, 2H), 2.48-2.61 (m, 2H), 2.07-2.27 (m, 4H), 1.09-1.19 (m, 2H), 0.99-1.06 (m, 6H), 0.88-1.00 (m, 8H).

imidazol-4-yl)naphthalen-2-yl)-2-((1R,3S,5R)-2-azabicyclo[3.1.0]hexan-3-yl)-1H-benzo[d]imidazole (34 mg), (S)-2-(methoxycarbonylamino)-2-(tetrahydro-2H-pyran-4-yl) acetic acid (46.9 mg, 0.216 mmol) and DIEA (0.13 mL, 0.72 mmol) in DMF (3 mL) and the reaction was stirred for 2 h at room temperature. The reaction mixture was diluted with MeOH (2 ml) and water (2 mL). The volatiles were removed under vacuum. The residue was purified by prep HPLC (Waters Sunfire C18 column 30×150 mm 5u eluted with a gradient of 10 to 80% ACN-Water+0.1% TFA) to afford a TFA salt of methyl ((1S)-2-((1R,3S,5R)-3-(4-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-benzimidazol-5-yl)-2-naphthyl)-1H-imidazol-2-yl)-2-azabicyclo[3.1.0]hex-2-yl)-2-oxo-1-(tetrahydro-2H-pyran-4-yl)ethyl)carbamate (38 mg) as pale yellow solid. LC-MS retention time 1.240 min; m/z 871.66 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a

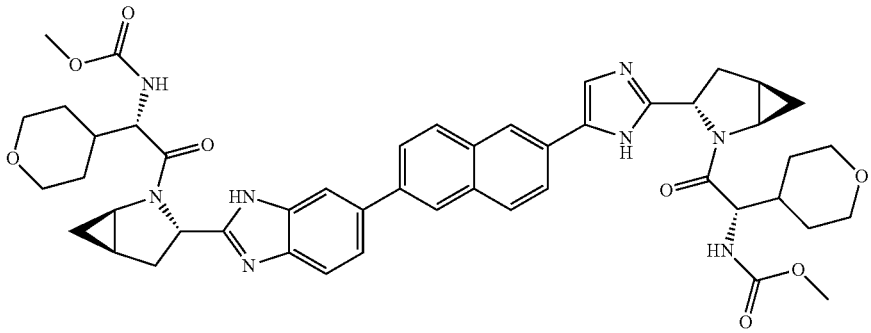 [SMILES: COC(=O)N[C@H](C(=O)N1[C@@H]2C[C@@H]2C[C@H]1c1ncc(-c2ccc3cc(-c4ccc5nc([C@@H]6C[C@H]7C[C@H]7N6C(=O)[C@@H](NC(=O)OC)C6CCOCC6)[nH]c5c4)ccc3c2)[nH]1)C1CCOCC1]

Methyl ((1S)-2-((1R,3S,5R)-3-(4-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-benzimidazol-5-yl)-2-naphthyl)-1H-imidazol-2-yl)-2-azabicyclo[3.1.0]hex-2-yl)-2-oxo-1-(tetrahydro-2H-pyran-4-yl)ethyl)carbamate HATU (82 mg, 0.216 mmol) was added to a solution of 6-(6-(2-((1R,3S,5R)-2-azabicyclo[3.1.0]hexan-3-yl)-1H-

MICROMASS® Platform for LC in electrospray mode. $^1$H NMR (TFA salt, 500 MHz, MeOD) δ ppm 8.30 (d, J=6.1 Hz, 2H), 8.08-8.18 (m, 3H), 8.04 (dd, J=8.6, 1.5 Hz, 1H), 7.95-8.01 (m, 2H), 7.85-7.92 (m, 2H), 5.27 (dd, J=9.2, 6.7 Hz, 1H), 5.16 (dd, J=9.2, 7.0 Hz, 1H), 4.59-4.66 (m, 2H), 3.84-4.01 (m, 6H), 3.70 (s, 6H), 3.35-3.45 (m, 4H), 2.69-2.80 (m, 2H), 2.48-2.61 (m, 2H), 2.03-2.20 (m, 4H), 1.57-1.65 (m, 2H), 1.40-1.56 (m, 6H), 1.07-1.17 (m, 2H), 0.97 (br s, 1H), 0.91 (br s, 1H).

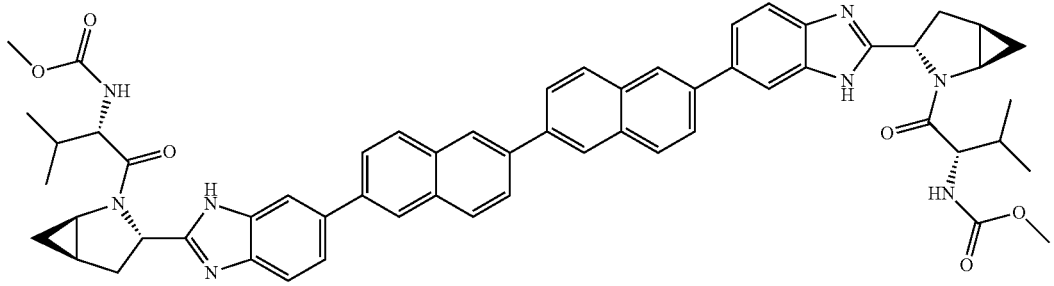

461

Methyl ((1S)-1-(((1R,3S,5R)-3-(5-(6'-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-2,2'-binaphthalen-6-yl)-1H-benzimidazol-2-yl)-2-azabicyclo[3.1.0]hex-2-yl)carbonyl)-2-methylpropyl)carbamate HATU (22.7 mg, 0.060 mmol) was added to a solution of a TFA salt of 6,6'-bis(2-((1R,3S,5R)-2-azabicyclo[3.1.0]hexan-3-yl)-1H-benzo[d]imidazol-5-yl)-2,2'-binaphthyl (22 mg), (S)-2-(methoxycarbonylamino)-3-methylbutanoic acid (10.5 mg, 0.060 mmol) and DIEA (0.035 mL, 0.20 mmol) in DMF (3 mL) and the reaction was stirred at rt for 2 h. The reaction mixture was diluted with MeOH (2 ml) and water (2 mL) and the volatiles were removed under vacuum. The residue was purified by prep HPLC (Waters Sunfire C18 column 30×100 mm 5u eluted with a gradient of 10 to 80% MeOH-Water+0.1% TFA) to afford a TFA salt of methyl ((1S)-1-(((1R,3S,5R)-3-(5-(6'-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-2,2'-binaphthalen-6-yl)-1H-benzimidazol-2-yl)-2-azabicyclo[3.1.0]hex-2-yl)carbonyl)-2-methylpropyl)carbamate (15.6 mg) as tan solid. LC-MS retention time 1.765 min; m/z 482.68 (½M+H+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% TFA and Solvent B was 10% $H_2O$/90% MeOH/0.1% TFA. MS data was determined using a MICROMASS® Platform for LC in electrospray mode. $^1$H NMR (TFA salt, 500 MHz, MeOD) δ ppm 8.36 (s, 2H), 8.27 (s, 2H), 8.12-8.18 (m, 4H), 8.11 (s, 2H), 8.05 (app t, J=8.6 Hz, 4H), 7.91-7.96 (m, 2H), 7.86-7.91 (m, 2H), 5.29 (dd, J=9.2, 6.7 Hz, 2H), 4.61 (d, J=6.4 Hz, 2H), 3.85-3.91 (m, 2H), 3.70 (s, 6H), 2.72-2.80 (m, 2H), 2.53-2.62 (m, 2H), 2.12-2.26 (m, 4H), 1.13-1.21 (m, 2H), 1.04 (d, J=6.7 Hz, 6H), 0.99 (br s, 2H), 0.95 (d, J=6.7 Hz, 6H).

462

Methyl ((1S)-1-(((1R,3S,5R)-3-(5-(6-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-1,5-naphthyridin-2-yl)-1H-benzimidazol-2-yl)-2-azabicyclo[3.1.0]hex-2-yl)carbonyl)-2-methylpropyl)carbamate HATU (8.7 mg, 0.023 mmol) was added to a solution of a TFA salt of 2,6-bis(2-((1R,3S,5R)-2-azabicyclo[3.1.0]hexan-3-yl)-1H-benzo[d]imidazol-6-yl)-1,5-naphthyridine (12 mg, 9.93 μmol) and (S)-2-(methoxycarbonylamino)-3-methylbutanoic acid (4.2 mg) in DMF (0.5 mL) and DIPEA (0.017 mL, 0.099 mmol) and the mixture was stirred at rt for 16 h. The reaction was diluted with MeOH, and purified by prep HPLC ($H_2O$-MeOH with 0.1% TFA buffer) to yield a TFA salt of dimethyl (2S,2'S)-1,1'-((1R,1'R,3S,3'S,5R,5'R)-3,3'-(6,6'-(1,5-naphthyridine-2,6-diyl)bis(1H-benzo[d]imidazole-6,2-diyl))bis(2-azabicyclo[3.1.0]hexane-3,2-diyl))bis(3-methyl-1-oxobutane-2,1-diyl)dicarbamate (5.6 mg) as yellow solid. LC-MS retention time 1.91 min; m/z 420 [½M+H]$^+$. (Column PHENOMENEX® Luna3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 8.59-8.67 (4H, m), 8.48 (2H, dd, J=8.8, 1.3 Hz), 8.44 (2H, d, J=8.8 Hz), 7.92 (2H, d, J=8.5 Hz), 5.29 (2H, dd, J=9.2, 6.7 Hz), 4.60 (2H, d, J=6.5 Hz), 3.84-3.92 (2H, m), 3.68 (6H, s), 2.69-2.80 (2H, m), 2.51-2.62 (2H, m), 2.07-2.27 (4H, m), 1.10-1.21 (2H, m), 1.02 (6H, d, J=6.8 Hz), 0.95-1.00 (2H, m), 0.93 (6H, d, J=6.8 Hz).

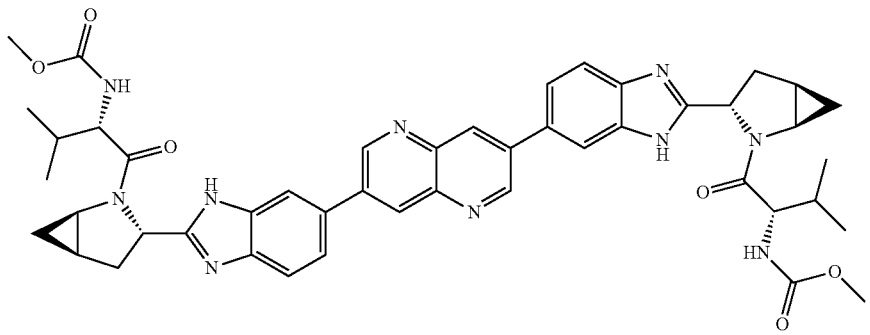

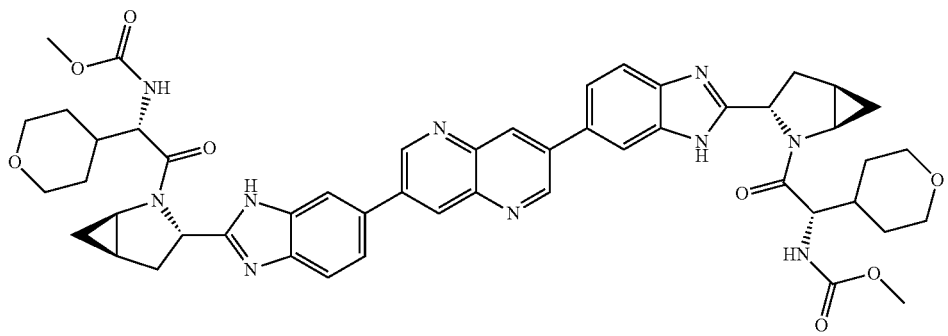 [SMILES: COC(=O)N[C@H](C(=O)N1[C@@H]2C[C@@H]2C[C@H]1c1nc2ccc(-c3cnc4cc(-c5ccc6nc([C@@H]7C[C@H]8C[C@H]8N7C(=O)[C@@H](NC(=O)OC)C7CCOCC7)[nH]c6c5)cnc4c3)cc2[nH]1)C1CCOCC1]

Dimethyl (1,5-naphthyridine-2,6-diylbis(1H-benzimidazole-5,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate HATU (8.68 mg, 0.023 mmol) was added to a solution of a TFA salt of 2,6-bis(2-((1R,3S,5R)-2-azabicyclo[3.1.0]hexan-3-yl)-1H-benzo[d]imidazol-6-yl)-1,5-naphthyridine (12 mg) and (S)-2-(methoxycarbonylamino)-2-(tetrahydro-2H-pyran-4-yl)acetic acid (5.0 mg, 0.023 mmol) in DMF (0.5 mL) and DIPEA (0.016 mL, 0.089 mmol) and the mixture was stirred at rt for 3 h. The reaction was diluted with MeOH and purified by prep HPLC ($H_2O$-MeOH with 0.1% TFA buffer) to yield a TFA salt of dimethyl (1S,1'S)-2,2'-((1R,1'R,3S,3'S,5R,5'R)-3,3'-(6,6'-(1,5-naphthyridine-2,6-diyl)bis(1H-benzo[d]imidazole-6,2-diyl))bis(2-azabicyclo[3.1.0]hexane-3,2-diyl))bis(2-oxo-1-(tetrahydro-2H-pyran-4-yl)ethane-2,1-diyl)dicarbamate (11 mg) as yellow solid. LC-MS retention time 1.73 min; m/z 462 [½M+H]$^+$. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 8.61-8.68 (4H, m), 8.50 (2H, dd, J=8.8, 1.51 Hz), 8.45 (2H, d, J=8.8 Hz), 7.93 (2H, d, J=8.8 Hz), 5.28 (2H, dd, J=9.3, 6.8 Hz), 4.64 (2H, d, J=7.5 Hz), 3.84-4.02 (6H, m), 3.69 (6H, s), 3.35-3.46 (4H, m), 2.75 (2H, dd, J=13.7, 9.2 Hz), 2.58 (2H, d, J=6.8 Hz), 1.99-2.22 (4H, m), 1.36-1.69 (8H, m), 1.07-1.19 (2H, m), 0.96 (2H, m).

3S,5R)-2-azabicyclo[3.1.0]hex-3-yl)-4-chloro-1H-imidazol-5-yl)-2-naphthyl)-1H-benzimidazole (34 mg), (S)-2-(methoxycarbonylamino)-3-methylbutanoic acid (35.2 mg, 0.201 mmol) and DIEA (0.12 mL, 0.67 mmol) in DMF (3 mL) and the resulting mixture was stirred at ambient temperature for 2 hours. The reaction mixture was diluted with methanol (2 mL) and water (2 mL) and the volatile component was removed in vacuo. The residue was purified by a reverse phase preparative HPLC (water/methanol, 0.1% TFA) to yield a TFA salt of methyl ((1S)-1-(((1R,3S,5R)-3-(5-(6-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)-2-naphthyl)-1H-benzimidazol-2-yl)-2-azabicyclo[3.1.0]hex-2-yl)carbonyl)-2-methylpropyl)carbamate (41.3 mg) as yellow solid. LC-MS retention time 1.717 min; m/z 821.58 (MH+). LC data was recorded on a Shimadzu LC-10AS liquid chromatograph equipped with a Waters Sunfire C18 4.6×30 mm 5 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray

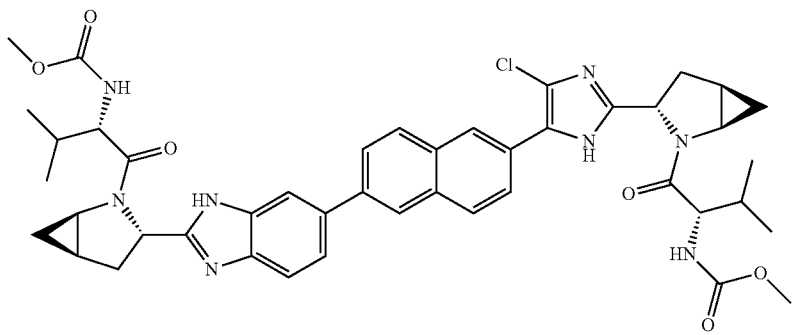

Methyl ((1S)-1-(((1R,3S,5R)-3-(5-(6-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)-2-naphthyl)-1H-benzimidazol-2-yl)-2-azabicyclo[3.1.0]hex-2-yl)carbonyl)-2-methylpropyl)carbamate HATU (76 mg, 0.20 mmol) was added to a solution of 2-((1R,3S,5R)-2-azabicyclo[3.1.0]hex-3-yl)-5-(6-(2-((1R, mode. $^1$H NMR (500 MHz, MeOD) δ ppm 8.24 (d, J=1.8 Hz, 2H), 8.01-8.13 (m, 4H), 7.84-7.98 (m, 3H), 5.29 (dd, J=9.2, 6.7 Hz, 1H), 5.09 (t, J=7.2 Hz, 1H), 4.60 (t, J=7.2 Hz, 2H), 3.86-3.91 (m, 1H), 3.71-3.76 (m, 1H), 3.69 (s, 3H), 3.68 (m, 3H), 2.77 (dd, J=13.6, 9.3 Hz, 1H), 2.57 (ddd, J=13.6, 6.7, 6.6 Hz, 1H), 2.44-2.53 (m, 2H), 2.11-2.26 (m, 3H), 1.99-2.10 (m, 1H), 1.10-1.22 (m, 2H), 0.89-1.09 (m, 13H), 0.80-0.84 (m, 1H).

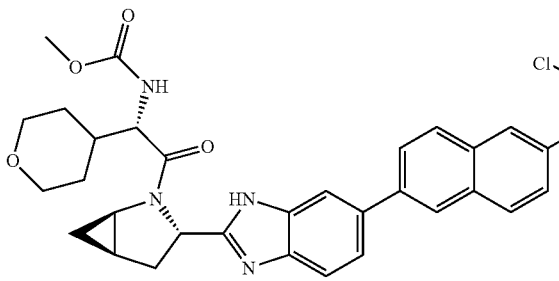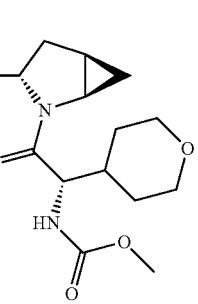

Methyl ((1S)-2-(((1R,3S,5R)-3-(4-chloro-5-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-benzimidazol-5-yl)-2-naphthyl)-1H-imidazol-2-yl)-2-azabicyclo[3.1.0]hex-2-yl)-2-oxo-1-(tetrahydro-2H-pyran-4-yl)ethyl)carbamate HATU (45.0 mg, 0.118 mmol) was added to a solution of 2-((1R,3S,5R)-2-azabicyclo[3.1.0]hex-3-yl)-5-(6-(2-((1R,3S,5R)-2-azabicyclo[3.1.0]hex-3-yl)-4-chloro-1H-imidazol-5-yl)-2-naphthyl)-1H-benzimidazole (20 mg, 0.039 mmol), (S)-2-(methoxycarbonylamino)-2-(tetrahydro-2H-pyran-4-yl)acetic acid (25.7 mg) and DIEA (0.069 mL, 0.39 mmol) in DMF (3 mL) and the resulting mixture was stirred at ambient temperature for 2 hours. The reaction mixture was diluted with methanol (2 mL) and water (2 mL) and the volatile component was removed in vacuo. The residue was purified by a reverse phase preparative HPLC (water/methanol, 0.1% TFA) to yield a TFA salt of methyl ((1S)-2-((1R,3S,5R)-3-(4-chloro-5-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-benzimidazol-5-yl)-2-naphthyl)-1H-imidazol-2-yl)-2-azabicyclo[3.1.0]hex-2-yl)-2-oxo-1-(tetrahydro-2H-pyran-4-yl)ethyl)carbamate (28.1 mg) as pale yellow solid. LC-MS retention time 1.597 min; m/z 905.67 (MH+). LC data was recorded on a Shimadzu LC-10AS liquid chromatograph equipped with a Waters Sunfire C18 4.6×30 mm 5 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (500 MHz, MeOD) δ ppm 8.24 (s, 2H), 8.02-8.13 (m, 4H), 7.86-7.97 (m, 3H), 5.27 (dd, J=9.2, 7.0 Hz, 1H), 5.08 (t, J=7.2 Hz, 1H), 4.65 (t, J=7.3 Hz, 2H), 3.88-4.02 (m, 5H), 3.75-3.83 (m, 1H), 3.70 (s, 3H), 3.68 (s, 3H), 3.36-3.49 (m, 4H), 2.77 (dd, J=13.7, 9.5 Hz, 1H), 2.57 (ddd, J=13.7, 6.7, 6.4 Hz, 1H), 2.46-2.53 (m, 2H), 2.00-2.20 (m, 4H), 1.55-1.69 (m, 4H), 1.40-1.70 (m, 4H), 1.08-1.20 (m, 2H), 0.94-1.00 (m, 1H), 0.80-0.84 (m, 1H).

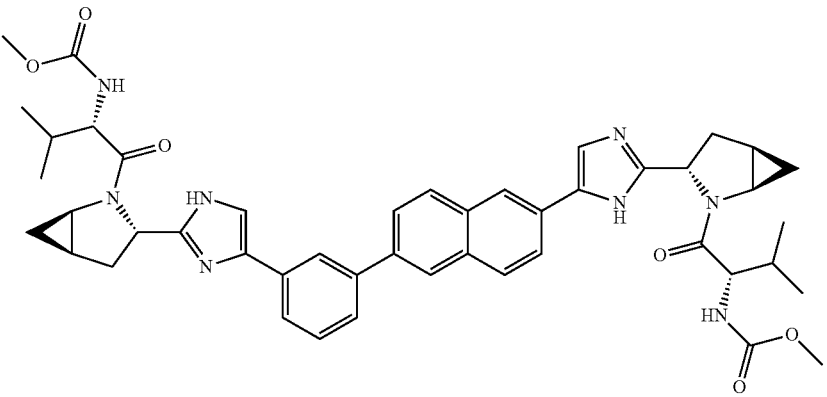

Methyl ((1S)-1-(((1S,3R,5S)-3-(4-(6-(3-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)carbonyl)-2-methylpropyl)carbamate HATU (47.8 mg, 0.126 mmol) was added to a mixture of a TFA salt of (1R,3S,5R)-3-(4-(3-(6-(2-((1S,3R,5S)-2-azabicyclo[3.1.0]hex-3-yl)-1H-imidazol-4-yl)-2-naphthyl)phenyl)-1H-imidazol-2-yl)-2-azabicyclo[3.1.0]hexane (40 mg), (S)-2-(methoxycarbonylamino)-3-methylbutanoic acid (22 mg, 0.13 mmol) and DIEA (0.073 mL, 0.42 mmol) in DMF (3 mL) and the resulting mixture was stirred at ambient temperature for 2 hours. The reaction mixture was diluted with methanol (2 mL) and water (2 mL) and the volatile component was removed in vacuo. The residue was partially purified by a reverse phase HPLC (water/methanol, 0.1% TFA) and then repurified by reverse phase HPLC (water/acetonitrile, 0.1% TFA) to yield a TFA salt of methyl ((1S)-1-((((1S,3R,5S)-3-(4-(6-(3-(2-(((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)carbonyl)-2-methylpropyl)carbamate (45 mg) as a white solid. LC-MS retention time 1.458 min; m/z 813.30 (MH+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/10 mM ammonium acetate and Solvent B was 10% water/90% methanol/10 mM ammonium acetate. MS data was determined using a MICROMASS® Platform for LC in electrospray mode. $^1$H NMR (500 MHz, MeOD) δ ppm 8.30 (d, J=4.6 Hz, 2H), 8.18 (s, 1H), 8.14 (d, J=8.9 Hz, 1H), 8.10 (d, J=8.9 Hz, 1H), 7.98-8.02 (m, 2H), 7.98 (s, 1H), 7.93 (d, J=8.2 Hz, 1H), 7.88 (dd, J=8.7, 1.7 Hz, 1H), 7.77 (d, J=8.2 Hz, 1H), 7.69 (t, J=7.8 Hz, 1H), 5.13-5.20 (m, 2H), 4.57 (t, J=6.1 Hz, 2H), 3.80-3.88 (m, 2H), 3.69 (d, J=6.1 Hz, 6H), 2.67-2.77 (m, 2H), 2.51 (dq, J=13.7, 6.8 Hz, 2H), 2.15-2.25 (m, 2H), 2.10 (dq, J=13.8, 6.8 Hz, 2H), 1.08-1.18 (m, 2H), 1.03 (dd, J=6.7, 4.6 Hz, 6H), 0.95 (dd, J=6.7, 3.4 Hz, 6H), 0.92 (dd, J=5.3, 2.0 Hz, 2H).

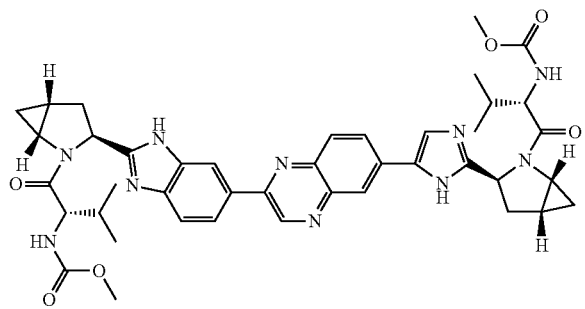 [SMILES: COC(=O)N[C@H](C(=O)N1[C@@H]2C[C@@H]2C[C@H]1c1ncc(-c2ccc3nc(-c4ccc5nc([C@@H]6C[C@H]7C[C@H]7N6C(=O)[C@@H](NC(=O)OC)C(C)C)[nH]c5c4)cnc3c2)[nH]1)C(C)C]

Methyl ((1S)-1-(((1R,3S,5R)-3-(4-(2-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-6-quinoxalinyl)-1H-imidazol-2-yl)-2-azabicyclo[3.1.0]hex-2-yl)carbonyl)-2-methylpropyl) carbamate HATU (13.16 mg, 0.035 mmol) was added to a solution of a TFA salt of 2-(2-((1R,3S,5R)-2-azabicyclo[3.1.0]hexan-3-yl)-1H-benzo[d]imidazol-6-yl)-6-(2-((1R,3S,5R)-2-azabicyclo[3.1.0]hexan-3-yl)-1H-imidazol-5-yl)quinoxaline (14 mg, 0.015 mmol) and (S)-2-(methoxycarbonylamino)-3-methylbutanoic acid (6.1 mg) in DMF (0.5 mL) and DIPEA (0.024 mL, 0.135 mmol) and the mixture was stirred at rt for 16 h. The reaction was diluted with MeOH and purified by prep HPLC (H$_2$O-MeOH with 0.1% TFA buffer) to yield a TFA salt of methyl ((1S)-1-(((1R,3S,5R)-3-(4-(2-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-6-quinoxalinyl)-1H-imidazol-2-yl)-2-azabicyclo[3.1.0]hex-2-yl)carbonyl)-2-methylpropyl)carbamate (11.8 mg,) as a yellow solid. LC-MS retention time 1.77 min; m/z 789 [M+H]$^+$. (Column PHENOMENEX® Luna3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). $^1$H NMR (400 MHz, MeOD) δ ppm 9.59 (s, 1H), 8.67 (s, 1H), 8.51 (d, J=8.8 Hz, 1H), 8.46 (d, J=1.8 Hz, 1H), 8.27 (d, J=8.8 Hz, 1H), 8.19 (dd, J=8.8, 2.0 Hz, 1H), 8.11 (s, 1H), 7.92 (d, J=8.5 Hz, 1H), 5.29 (dd, J=9.2, 6.7 Hz, 1H), 5.17 (dd, J=9.2, 7.2 Hz, 1H), 4.58 (dd, J=13.2, 6.7 Hz, 2H), 3.78-3.92 (m, 2H), 3.68 (s, 6H), 2.67-2.79 (m, 2H), 2.45-2.62 (m, 2H), 2.03-2.27 (m, 4H), 1.07-1.21 (m, 2H), 1.03 (d, J=6.8 Hz, 6H), 0.93-1.00 (m, 2H), 0.93 (dd, J=6.3, 5.8 Hz, 6H).

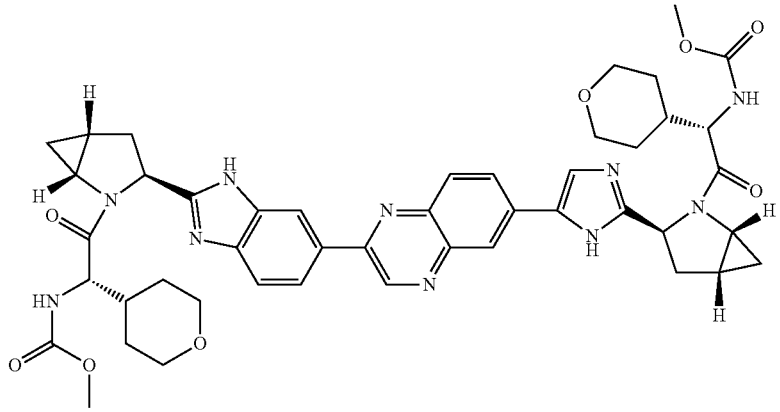 [SMILES: COC(=O)N[C@H](C(=O)N1[C@@H]2C[C@@H]2C[C@H]1c1ncc(-c2ccc3nc(-c4ccc5nc([C@@H]6C[C@H]7C[C@H]7N6C(=O)[C@@H](NC(=O)OC)C6CCOCC6)[nH]c5c4)cnc3c2)[nH]1)C1CCOCC1]

Methyl ((1S)-2-((1R,3S,5R)-3-(4-(2-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-benzimidazol-5-yl)-6-quinoxalinyl)-1H-imidazol-2-yl)-2-azabicyclo[3.1.0]hex-2-yl)-2-oxo-1-(tetrahydro-2H-pyran-4-yl)ethyl)carbamate HATU (15.0 mg, 0.040 mmol) was added to a solution of a TFA salt of 2-(2-((1R,3S,5R)-2-azabicyclo[3.1.0]hexan-3-yl)-1H-benzo[d]imidazol-6-yl)-6-(2-((1R,3S,5R)-2-azabicyclo[3.1.0]hexan-3-yl)-1H-imidazol-5-yl)quinoxaline (16 mg) and (S)-2-(methoxycarbonylamino)-2-(tetrahydro-2H-pyran-4-yl)acetic acid (8.6 mg, 0.040 mmol) in DMF (0.5 mL) and DIPEA (0.027 mL, 0.16 mmol) and the mixture was stirred at rt for 16 h. The reaction was diluted with MeOH, and purified by prep HPLC (H₂O-MeOH with 10 mM NH₄OAc buffer) to yield methyl ((1S)-2-((1R,3S,5R)-3-(4-(2-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-benzimidazol-5-yl)-6-quinoxalinyl)-1H-imidazol-2-yl)-2-azabicyclo[3.1.0]hex-2-yl)-2-oxo-1-(tetrahydro-2H-pyran-4-yl)ethyl)carbamate (14.5 mg) as yellow solid. LC-MS retention time 1.58 min; m/z 873 [M+H]⁺. (Column PHENOMENEX® Luna 3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). ¹H NMR (400 MHz, MeOD) δ ppm 9.34 (s, 1H), 8.36 (s, 1H), 8.28 (d, J=1.0 Hz, 1H), 8.08-8.19 (m, 2H), 8.03 (d, J=8.8 Hz, 1H), 7.66 (d, J=8.5 Hz, 1H), 7.54 (s, 1H), 5.27 (t, J=6.9 Hz, 1H), 5.18 (dd, J=8.9, 4.9 Hz, 1H), 4.69 (d, J=5.5 Hz, 2H), 3.87-4.03 (m, 4H), 3.73-3.85 (m, 2H), 3.68 (s, 6H), 3.32-3.47 (m, 4H), 2.50-2.61 (m, 3H), 2.40-2.49 (m, 1H), 1.99-2.16 (m, 4H), 1.51-1.72 (m, 6H), 1.38-1.51 (m, 2H), 1.09-1.22 (m, 2H), 0.76-0.92 (m, 2H).

Methyl ((1S)-2-((1R,3S,5R)-3-(5-(6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)-1H-benzimidazol-2-yl)-2-azabicyclo[3.1.0]hex-2-yl)-2-oxo-1-(tetrahydro-2H-pyran-4-yl)ethyl)carbamate HATU (157 mg, 0.413 mmol) was added to a solution of methyl (S)-1-((1R,3S,5R)-3-(5-(6-(2-((1R,3S,5R)-2-azabicyclo[3.1.0]hexan-3-yl)-1H-benzo[d]imidazol-6-yl)naphthalen-2-yl)-1H-imidazol-2-yl)-2-azabicyclo[3.1.0]hexan-2-yl)-3-methyl-1-oxobutan-2-ylcarbamate (130 mg), (S)-2-(methoxycarbonylamino)-2-(tetrahydro-2H-pyran-4-yl) acetic acid (90 mg, 0.41 mmol) and DIEA (0.36 mL, 2.1 mmol) in DMF (4 mL) and the reaction was stirred 2 h at room temperature. The reaction mixture was diluted with MeOH (2 mL) and water (2 mL). The volatiles were removed under vacuum. The material was purified on reverse phase HPLC (water/methanol, 0.1% TFA) to afford a TFA salt of methyl ((1S)-2-((1R,3S,5R)-3-(5-(6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)-1H-benzimidazol-2-yl)-2-azabicyclo[3.1.0]hex-2-yl)-2-oxo-1-(tetrahydro-2H-pyran-4-yl)ethyl)carbamate (194 mg) as yellow solid. LC-MS retention time 1.307 min; m/z 829.27 (MH+). LC data was recorded on a Shimadzu LC-10AS liquid chromatograph equipped with a Waters Sunfire C18 4.6× 30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. ¹H NMR (TFA salt, 500 MHz, MeOD) δ ppm 8.31 (s, 1H), 8.29 (s, 1H), 8.16 (d, J=8.5 Hz, 1H), 8.11 (d, J=0.9 Hz, 1H), 8.11 (d, J=8.9 Hz, 1H), 8.02 (dd, J=8.5, 1.5 Hz, 1H), 8.00 (s, 1H), 7.98 (dd, J=8.5, 1.5 Hz, 1H), 7.89 (d, J=8.5 Hz, 1H), 7.88 (dd, J=8.5, 1.8 Hz, 1H), 5.27 (dd, J=9.2, 6.7 Hz, 1H), 5.18 (dd, J=9.2, 7.0 Hz, 1H), 4.62-4.67 (m, 1H), 4.58 (d, J=6.4 Hz, 1H), 3.87-4.01 (m, 3H), 3.82-3.87 (m, 1H), 3.70 (m, 6H), 3.36-3.44 (m, 2H), 2.74 (td, J=13.3, 9.5 Hz, 2H), 2.48-2.62 (m, 2H), 2.04-2.24 (m, 4H), 1.40-1.60 (m, 4H), 1.09-1.19 (m, 2H), 1.04 (d, J=6.7 Hz, 3H), 0.89-0.99 (m, 5H).

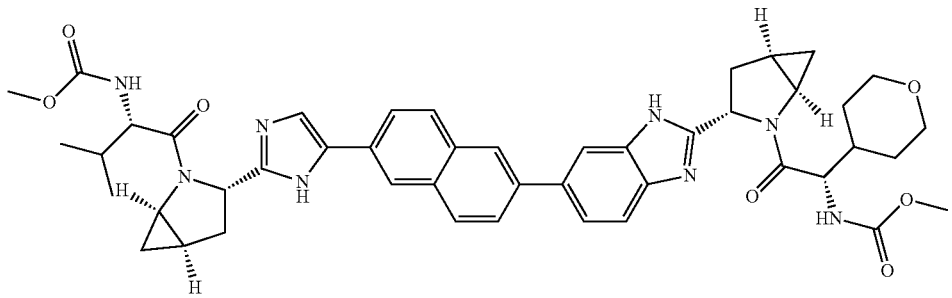

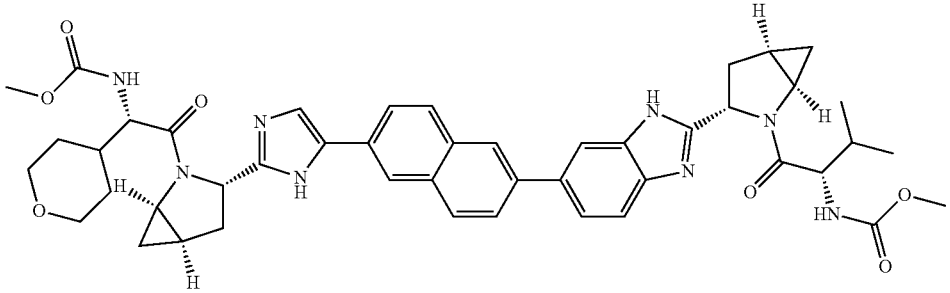

Methyl ((1S)-1-(((1R,3S,5R)-3-(5-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-naphthyl)-1H-benzimidazol-2-yl)-2-azabicyclo[3.1.0]hex-2-yl)carbonyl)-2-methylpropyl)carbamate HATU (100 mg, 0.263 mmol) was added to a solution of methyl (S)-2-((1R,3S,5R)-3-(5-(6-(2-((1R,3S,5R)-2-azabicyclo[3.1.0]hexan-3-yl)-1H-benzo[d]imidazol-6-yl)naphthalen-2-yl)-1H-imidazol-2-yl)-2-azabicyclo[3.1.0]hexan-2-yl)-2-oxo-1-(tetrahydro-2H-pyran-4-yl)ethylcarbamate (118 mg), (S)-2-(methoxycarbonylamino)-3-methylbutanoic acid (46.2 mg, 0.263 mmol) and DIEA (0.31 mL, 1.8 mmol) in DMF (4 mL) and the reaction was stirred 2 h at room temperature. The reaction mixture was diluted with MeOH (2 mL) and water (2 mL). The volatiles were removed under vacuum using a rotavap and the residue was purified on reverse phase HPLC (water/methanol, 0.1% TFA) to afford the a TFA salt of methyl ((1S)-1-(((1R,3S,5R)-3-(5-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-naphthyl)-1H-benzimidazol-2-yl)-2-azabicyclo[3.1.0]hex-2-yl)carbonyl)-2-methylpropyl)carbamate (55.3 mg). LC-MS retention time 1.320 min; m/z 829.42 (MH+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (TFA salt, 500 MHz, MeOD) δ ppm 8.31 (s, 1H) 8.29 (s, 1H), 8.08-8.18 (m, 3H), 8.04 (dd, J=8.9, 1.5 Hz, 1H), 7.95-8.00 (m, 2H), 7.90 (d, J=8.6 Hz, 1H), 7.87 (dd, J=8.6, 1.8 Hz, 1H), 5.29 (dd, J=9.3, 6.9 Hz, 1H), 5.17 (dd, J=9.2, 7.0 Hz, 1H), 4.62 (dd, J=9.2, 7.3 Hz, 2H), 3.96 (td, J=10.8, 2.9 Hz, 2H), 3.83-3.92 (m, 2H), 3.64-3.77 (m, 6H), 3.35-3.46 (m, 2H), 2.74 (ddd, J=19.3, 13.5, 9.3 Hz, 2H), 2.48-2.62 (m, 2H), 2.06-2.26 (m, 4H), 1.45-1.63 (m, 4H), 1.06-1.22 (m, 2H), 1.03 (d, J=6.7 Hz, 3H), 0.96-1.01 (m, 1H), 0.93 (d, J=6.7 Hz, 3H), 0.88-091 (m, 1H).

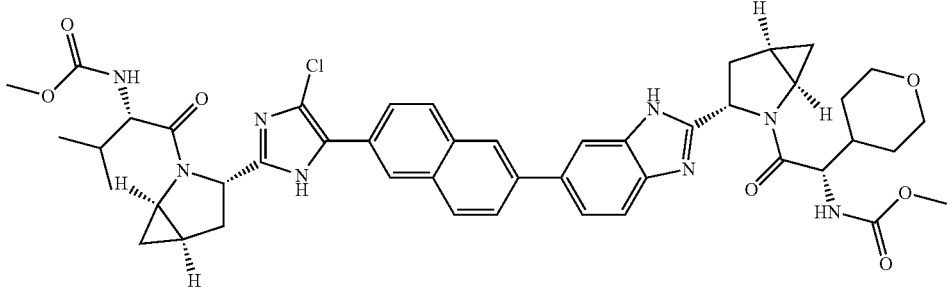

Methyl ((1S)-2-((1R,3S,5R)-3-(5-(6-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)-2-naphthyl)-1H-benzimidazol-2-yl)-2-azabicyclo[3.1.0]hex-2-yl)-2-oxo-1-(tetrahydro-2H-pyran-4-yl)ethyl)carbamate NCS (14.98 mg, 0.112 mmol) was added to a solution of methyl ((1S)-2-((1R,3S,5R)-3-(5-(6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)-1H-benzimidazol-2-yl)-2-azabicyclo[3.1.0]hex-2-yl)-2-oxo-1-(tetrahydro-2H-pyran-4-yl)ethyl)carbamate (93 mg) in DMF and the reaction mixture was heated at 50° C. (oil bath temp) for 2 h. The crude reaction mixture was purified on reverse phase HPLC (water/methanol, 0.1% TFA) to afford a TFA salt of methyl ((1S)-2-((1R,3S,5R)-3-(5-(6-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)-2-naphthyl)-1H-benzimidazol-2-yl)-2-azabicyclo[3.1.0]hex-2-yl)-2-oxo-1-(tetrahydro-2H-pyran-4-yl)ethyl)carbamate (102.8 mg). LC-MS retention time 1.648 min; m/z 863.32 (MH+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (TFA salt, 500 MHz, MeOD) δ ppm 8.22 (br s, 2H), 8.10 (s, 1H), 8.00-8.06 (m, 3H), 7.85-7.94 (m, 3H), 5.28 (dd, J=9.2, 7.0 Hz, 1H), 5.09 (t, J=7.2 Hz, 1H), 4.65 (d, J=7.3 Hz, 1H), 4.59 (d, J=7.0 Hz, 1H), 3.89-3.99 (m, 3H), 3.66-3.77 (m, 7H), 3.35-3.44 (m, 2H), 2.77 (dd, J=13.6, 9.3 Hz, 1H), 2.57 (ddd, J=13.8, 6.8, 6.6 Hz, 1H), 2.47-2.52 (m, 2H), 2.02-2.22 (m, 4H), 1.44-1.63 (m, 4H), 1.13 (dt, J=8.6, 5.8 Hz, 2H), 1.05 (d, J=7.0 Hz, 3H), 0.92-1.02 (m, 4H), 0.83 (d, J=1.8 Hz, 1H).

50° C. for 2 h. The crude reaction mixture was purified on reverse phase HPLC (water/methanol, 0.1% TFA) and repurified on reverse phase HPLC (water/ACN, 0.1% TFA) to afford the TFA salt of methyl ((1S)-1-(((1R,3S,5R)-3-(5-(6-(4-chloro-2-((1R,3S,5R)-2-((2S)-2-((methoxycarbonyl) amino)-2-(tetrahydro-2H-pyran-4-yl)acetyl)-2-azabicyclo [3.1.0]hex-3-yl)-1H-imidazol-5-yl)-2-naphthyl)-1H-benzimidazol-2-yl)-2-azabicyclo[3.1.0]hex-2-yl)carbonyl)-2-methylpropyl)carbamate (44.7 mg) as tan solid. LC-MS retention time 1.63 min; m/z 863.39 (MH+). LC data was recorded on a Shimadzu LC-10AS liquid chromatograph equipped with a Waters Sunfire C18 4.6×30 mm column using a SPD-10AV UV-Vis detector at a detector wave length of 220 nM. The elution conditions employed a flow rate of 4

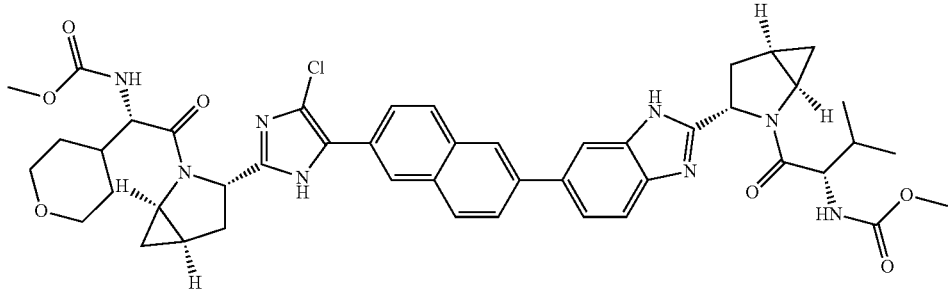

Methyl ((1S)-1-(((1R,3S,5R)-3-(5-(6-(4-chloro-2-((1R,3S,5R)-2-((2S)-2-((methoxycarbonyl)amino)-2-(tetrahydro-2H-pyran-4-yl)acetyl)-2-azabicyclo [3.1.0]hex-3-yl)-1H-imidazol-5-yl)-2-naphthyl)-1H-benzimidazol-2-yl)-2-azabicyclo[3.1.0]hex-2-yl) carbonyl)-2-methylpropyl)carbamate NCS (10.31 mg, 0.077 mmol) was added to a solution of methyl ((1S)-1-(((1R,3S,5R)-3-(5-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-naphthyl)-1H-benzimidazol-2-yl)-2-azabicyclo [3.1.0]hex-2-yl)carbonyl)-2-methylpropyl)carbamate (64 mg) in DMF (2 mL) and the reaction mixture was heated at mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 10% water/90% methanol/0.1% TFA. MS data was determined using a MICROMASS® Platform for LC in electrospray mode. $^1$H NMR (TFA salt, 500 MHz, MeOD) δ ppm 8.24 (br s, 2H), 8.02-8.12 (m, 4H), 7.86-7.95 (m, 3H), 5.28 (dd, J=9.2, 6.7 Hz, 1H), 5.08 (t apparent, J=7.0 Hz, 1H), 4.65 (d, J=7.6 Hz, 1H), 4.60 (d, J=6.7 Hz, 1H), 3.93-4.01 (m, 2H), 3.86-3.91 (m, 1H), 3.75-3.81 (m, 1H), 3.65-3.74 (m, 6H), 3.36-3.46 (m, 2H), 2.77 (dd, J=13.7, 9.2 Hz, 1H), 2.57 (ddd, J=13.7, 6.7, 6.4 Hz, 1H), 2.49 (dd, J=7.8, 3.2 Hz, 2H), 2.12-2.25 (m, 2H), 2.00-2.12 (m, 2H), 1.54-1.67 (m, 3H), 1.41-1.51 (m, 1H), 1.09-1.19 (m, 2H), 0.97-1.06 (m, 4H), 0.94 (d, J=6.7 Hz, 3H), 0.82 (br s, 1H).

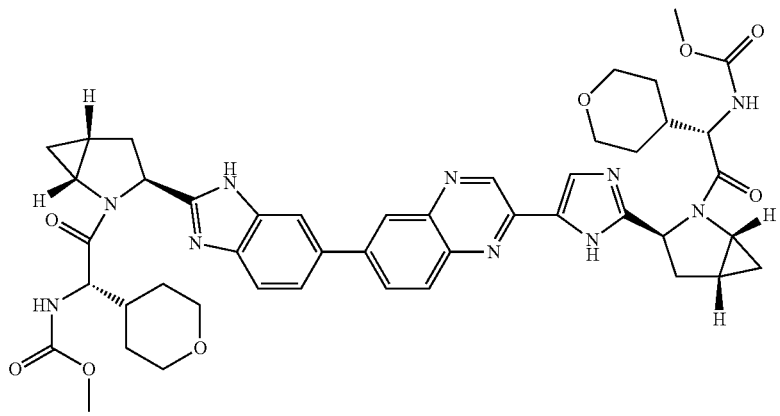 [SMILES: COC(=O)N[C@H](C(=O)N1[C@@H]2C[C@@H]2C[C@H]1c1ncc(-c2cnc3cc(-c4ccc5nc([C@@H]6C[C@H]7C[C@H]7N6C(=O)[C@@H](NC(=O)OC)C6CCOCC6)[nH]c5c4)ccc3n2)[nH]1)C1CCOCC1]

475

Methyl ((1S)-2-((1R,3S,5R)-3-(4-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-benzimidazol-5-yl)-2-quinoxalinyl)-1H-imidazol-2-yl)-2-azabicyclo[3.1.0]hex-2-yl)-2-oxo-1-(tetrahydro-2H-pyran-4-yl)ethyl)carbamate HATU (5.64 mg, 0.015 mmol) was added to a solution of a TFA salt of 6-(2-((1R,3S,5R)-2-azabicyclo[3.1.0]hexan-3-yl)-1H-benzo[d]imidazol-6-yl)-2-(2-((1R,3S,5R)-2-azabicyclo[3.1.0]hexan-3-yl)-1H-imidazol-5-yl)quinoxaline (6.0 mg) and (S)-2-(methoxycarbonylamino)-2-(tetrahydro-2H-pyran-4-yl)acetic acid (3.2 mg) in DMF (0.5 mL) and DIPEA (10.13 µL, 0.058 mmol) and the mixture was stirred at rt for 16 h. The solvent was removed and the residue was purified by prep HPLC (H₂O-MeOH with 0.1% TFA buffer) to yield a TFA salt of methyl ((1S)-2-((1R,3S,5R)-3-(4-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-benzimidazol-5-yl)-2-quinoxalinyl)-1H-imidazol-2-yl)-2-azabicyclo[3.1.0]hex-2-yl)-2-oxo-1-(tetrahydro-2H-pyran-4-yl)ethyl)carbamate (5.5 mg) as a yellow solid. LC-MS retention time 1.60 min; m/z 873 [M+H]⁺. (Column PHENOMENEX® Luna3.0×50 mm S10. Solvent A=95% water/5% methanol/10 mM ammonium acetate. Solvent B=5% water/95% methanol/10 mM ammonium acetate. Flow Rate=4 mL/min. Start % B=0. Final % B=100. Gradient Time=2 min. Wavelength=220). ¹H NMR (400 MHz, MeOD) δ ppm 9.42 (s, 1H), 8.41-8.50 (m, 2H), 8.30 (d, J=1.3 Hz, 2H), 8.19 (d, J=1.0 Hz, 1H), 8.07 (dd, J=8.5, 1.5 Hz, 1H), 7.92 (d, J=8.5 Hz, 1H), 5.13-5.33 (m, 3H), 4.57-4.70 (m, 1H), 3.81-4.04 (m, 6H), 3.62-3.77 (m, 6H), 3.34-3.46 (m, 4H), 2.65-2.82 (m, 2H), 2.45-2.61 (m, 2H), 2.01-2.22 (m, 4H), 1.40-1.65 (m, 8H), 1.03-1.17 (m, 2H), 0.83-0.98 (m, 2H).

476

Methyl ((1S)-1-(((1R,3S,5R)-3-(4-(6-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-2-quinoxalinyl)-1H-imidazol-2-yl)-2-azabicyclo[3.1.0]hex-2-yl)carbonyl)-2-methylpropyl)carbamate HATU (5.64 mg, 0.015 mmol) was added to a solution of a TFA salt of 6-(2-((1R,3S,5R)-2-azabicyclo[3.1.0]hexan-3-yl)-1H-benzo[d]imidazol-6-yl)-2-(2-((1R,3S,5R)-2-azabicyclo[3.1.0]hexan-3-yl)-1H-imidazol-5-yl)quinoxaline (6.0 mg) and (S)-2-(methoxycarbonylamino)-3-methylbutanoic acid (2.60 mg, 0.015 mmol) in DMF (0.5 mL) and DIPEA (10.13 µL, 0.058 mmol) and the mixture was stirred at rt for 16 h. The solvent was removed and the residue was purified by prep HPLC (H₂O-MeOH with 0.1% TFA buffer) to yield a TFA salt of methyl ((1S)-1-(((1R,3S,5R)-3-(4-(6-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-2-quinoxalinyl)-1H-imidazol-2-yl)-2-azabicyclo[3.1.0]hex-2-yl)carbonyl)-2-methylpropyl)carbamate (3.6 mg) as yellow solid. LC-MS retention time 1.75 min; m/z 789 [M+H]⁺. (Column PHENOMENEX® Luna3.0×50 mm S10. Solvent A=90% water: 10% methanol: 0.1% TFA. Solvent B=10% water: 90% methanol: 0.1% TFA. Flow Rate=4 mL/min. Start % B=0. Final % B=100. Gradient Time=3 min. Wavelength=220). ¹H NMR (400 MHz, MeOD) δ ppm 9.42 (s, 1H), 8.41-8.48 (m, 2H), 8.30 (d, J=1.3 Hz, 2H), 8.18 (d, J=1.0 Hz, 1H), 8.06 (dd, J=8.7, 1.6 Hz, 1H), 7.92 (d, J=8.5 Hz, 1H), 5.24-5.33 (m, 1H), 5.16-5.24 (m, 1H), 4.52-4.63 (m, 2H), 3.78-3.91 (m, 2H), 3.68 (d, J=1.0 Hz, 6H), 2.65-2.79 (m, 2H), 2.46-2.61 (m, 2H), 2.05-2.26 (m, 4H), 1.07-1.20 (m, 2H), 0.99-1.06 (m, 6H), 0.94-1.01 (m, 2H), 0.92 (dd, J=6.8, 3.3 Hz, 6H).

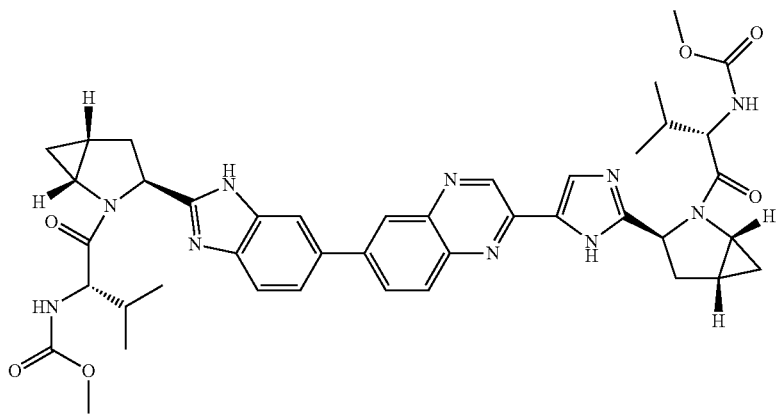 [SMILES: COC(=O)N[C@H](C(=O)N1[C@@H]2C[C@@H]2C[C@H]1c1ncc(-c2cnc3cc(-c4ccc5nc([C@@H]6C[C@H]7C[C@H]7N6C(=O)[C@@H](NC(=O)OC)C(C)C)[nH]c5c4)ccc3n2)[nH]1)C(C)C]

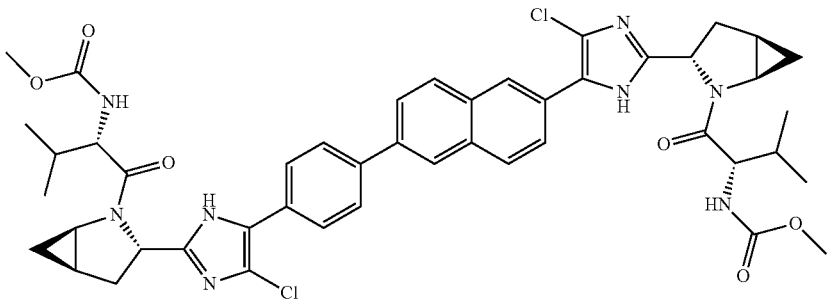

Methyl ((1S)-1-((((1R,3S,5R)-3-(4-chloro-5-(6-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)-2-naphthyl)-1H-imidazol-2-yl)-2-azabicyclo[3.1.0]hex-2-yl)carbonyl)-2-methylpropyl)carbamate

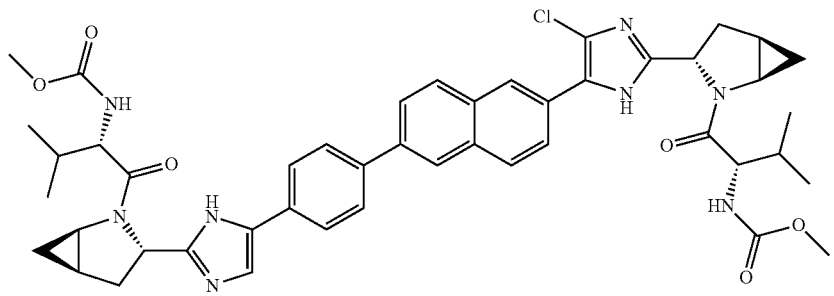

Methyl ((1S)-1-((((1R,3S,5R)-3-(4-chloro-5-(6-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)carbonyl)-2-methylpropyl)carbamate

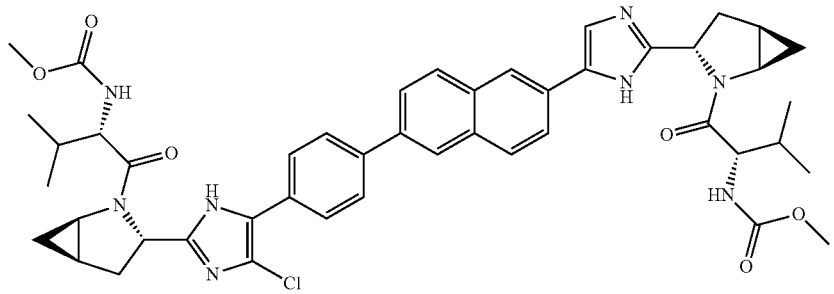

Methyl ((1S)-1-((((1R,3S,5R)-3-(4-(6-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)-2-naphthyl)-1H-imidazol-2-yl)-2-azabicyclo[3.1.0]hex-2-yl)carbonyl)-2-methylpropyl)carbamate NCS (13.0 mg, 0.097 mmol) was added to a solution of methyl ((1S)-1-((((1R,3S,5R)-3-(4-(4-(6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)carbonyl)-2-methylpropyl)carbamate (79 mg) in DMF (2 mL) at room temperature and the mixture was heated at 50° C. for 16 h. The crude product was purified by prep HPLC (TFA) using a Waters Sunfire C18 column 30×150 mm 5u eluted with a gradient of 30 to 90% MeOH-Water+0.1% TFA to yield a TFA salt of methyl ((1S)-1-((((1R,3S,5R)-3-(4-chloro-5-(6-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)-2-naphthyl)-1H-imidazol-2-yl)-2-azabicyclo[3.1.0]hex-2-yl)carbonyl)-2-methylpropyl)carbamate (20.2 mg) as yellow solid and a mixture of the two monochloride products which were separated by SFC on a CHIRALPAK® IB column and then repurified individually by prep HPLC (TFA) using a Waters Sunfire C18 column 30×150 mm 5u eluted with a gradient of 25 to 100% MeOH-Water+0.1% TFA to yield a TFA of methyl ((1S)-1-(((1R,3S,5R)-3-(4-chloro-5-(6-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)carbonyl)-2- methylpropyl)carbamate (11.1 mg) as a yellow solid and a TFA salt of methyl ((1S)-1-(((1R,3S,5R)-3-(4-chloro-5-(6-(4-(2-(((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)carbonyl)-2-methylpropyl)carbamate (11.4 mg) as a yellow solid.

For Example 60: LC-MS retention time 2.133 min; m/z 883.35 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (500 MHz, MeOD) δ ppm 8.22 (s, 2H), 8.07 (d, J=8.5 Hz, 1H), 8.03 (d, J=8.9 Hz, 1H), 7.83-7.95 (m, 6H), 5.08 (td, J=9.1, 6.0 Hz, 2H), 4.59 (dd, J=6.7, 1.8 Hz, 2H), 3.71-3.79 (m, 2H), 3.68 (s, 6H), 2.44-2.57 (m, 4H), 2.13-2.25 (m, 2H), 2.00-2.10 (m, 2H), 1.09-1.16 (m, 2H), 1.05 (dd, J=6.7, 1.5 Hz, 6H), 0.91-1.02 (m, 6H), 0.79-0.87 (m, 2H).

For Example 62: LC-MS retention time 1.745 min; m/z 847.33 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (500 MHz, MeOD) δ ppm 8.23 (s, 2H), 8.02-8.09 (m, 2H), 7.98 (d, J=8.2 Hz, 2H), 7.89-7.94 (m, 3H), 7.86 (d, J=8.6 Hz, 2H), 5.15 (dd, J=9.2, 7.0 Hz, 1H), 5.09 (t, J=7.0 Hz, 1H), 4.58 (t, J=6.7 Hz, 2H), 3.84 (t, J=4.7 Hz, 1H), 3.71-3.77 (m, 1H), 3.69 (d, J=3.1 Hz, 6H), 2.72 (dd, J=13.7, 9.5 Hz, 1H), 2.45-2.54 (m, 3H), 2.14-2.24 (m, 2H), 2.00-2.14 (m, 2H), 1.09-1.18 (m, 2H), 1.00-1.08 (m, 6H), 0.96 (t, J=7.6 Hz, 6H), 0.92 (br s, 1H), 0.83 (br s, 1H).

For Example 63: LC-MS retention time 1.753 min; m/z 847.32 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (500 MHz, MeOD) δ ppm 8.26 (d, J=7.0 Hz, 2H), 8.13 (d, J=8.9 Hz, 1H), 8.04-8.10 (m, 1H), 7.95-8.01 (m, 2H), 7.89-7.95 (m, 2H), 7.82-7.89 (m, 3H), 5.17 (dd, J=9.2, 7.0 Hz, 1H), 5.07 (t, J=7.2 Hz, 1H), 4.58 (d, J=6.4 Hz, 2H), 3.81-3.88 (m, 1H), 3.71-3.76 (m, 1H), 3.69 (d, J=4.6 Hz, 6H), 2.73 (dd, J=13.4, 9.5 Hz, 1H), 2.44-2.56 (m, 3H), 2.14-2.25 (m, 2H), 2.08-2.14 (m, 1H), 1.09-1.18 (m, 2H,) 1.00-1.08 (m, 6H), 0.96 (t, J=6.4 Hz, 6H), 0.92 (br s, 1H) 0.78-0.85 (m, 1H).

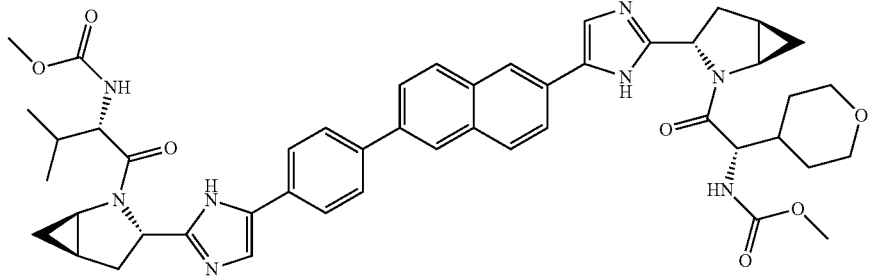 [SMILES: COC(=O)N[C@H](C(=O)N1[C@@H]2C[C@@H]2C[C@H]1c1ncc(-c2ccc(-c3ccc4cc(-c5cnc([C@@H]6C[C@H]7C[C@H]7N6C(=O)[C@@H](NC(=O)OC)C6CCOCC6)[nH]5)ccc4c3)cc2)[nH]1)C(C)C]

Methyl ((1S)-2-((1R,3S,5R)-3-(4-(6-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)-2-oxo-1-(tetrahydro-2H-pyran-4-yl)ethyl)carbamate The reaction of Intermediate 105 and the appropriate boronic acid (prepared in a similar manner as Intermediate 66 using the appropriate starting materials) via a coupling reaction similar to the preparation of Intermediate 106 yielded a TFA salt of methyl ((1S)-2-((1R,3S,5R)-3-(4-(6-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl) phenyl)-2-naphthyl)-1H-imidazol-2-yl)-2-azabicyclo[3.1.0] hex-2-yl)-2-oxo-1-(tetrahydro-2H-pyran-4-yl)ethyl) carbamate (91 mg) as a pale yellow solid. LC-MS retention time 1.362 min; m/z 855.31 (MH+). LC data was recorded on a Shimadzu LC-10AS liquid chromatograph equipped with a Waters Sunfire 5u C18 4.6×30 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% TFA and Solvent B was 10% H$_2$O/90% MeOH/0.1% TFA. MS data was determined using a MICROMASS® Platform for LC in electrospray mode. $^1$H NMR (500 MHz, MeOD) δ ppm 8.29 (s, 1H), 8.28 (s, 1H), 8.14 (d, J=8.9 Hz, 1H), 8.09 (d, J=8.9 Hz, 1H), 8.01-7.94 (m, 4H), 7.93-7.91 (m, 1H), 7.90-7.83 (m, 3H), 5.19-5.12 (m, 2H), 4.62 (d, J=7.6 Hz, 1H), 4.58 (d, J=6.4 Hz, 1H), 3.99-3.91 (m, 2H), 3.89-3.80 (m, 2H), 3.70 (s, 3H), 3.69 (s, 3H), 3.46-3.35 (m, 2H), 2.76-2.67 (m, 2H), 2.57-2.46 (m, 2H), 2.25-2.16 (m, 1H), 2.15-2.05 (m, 3H), 1.65-1.40 (m, 4H), 1.16-1.07 (m, 2H), 1.04 (d, J=6.7 Hz, 3H), 0.95 (d, J=6.7 Hz, 3H), 0.93-0.87 (m, 2H).

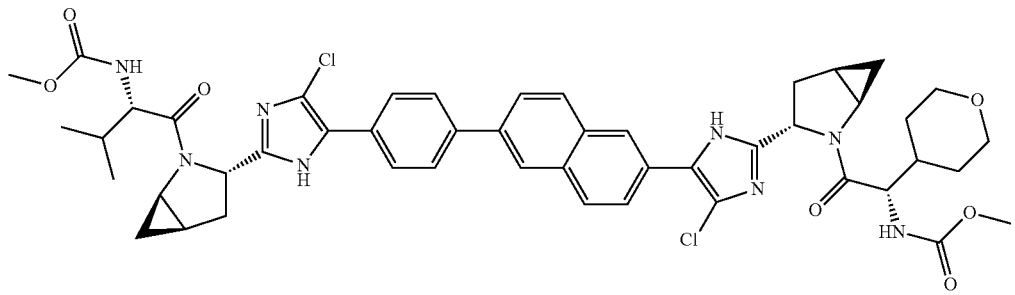

Methyl ((1S)-2-((1R,3S,5R)-3-(4-chloro-5-(6-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)-2-naphthyl)-1H-imidazol-2-yl)-2-azabicyclo[3.1.0]hex-2-yl)-2-oxo-1-(tetrahydro-2H-pyran-4-yl)ethyl)carbamate N-Chlorosuccinimide (10.4 mg, 0.078 mmol) was added to a stirred solution of methyl ((1S)-2-((1R,3S,5R)-3-(4-(6-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)-2-oxo-1-(tetrahydro-2H-pyran-4-yl)ethyl)carbamate (Example 61) (60 mg, 0.071 mmol) in DMF (1.5 mL) and the reaction vessel was sealed and heated at 50° C. for 16 h. The reaction was cooled, partially concentrated and then diluted with MeOH. The solution was filtered and purified by preparative HPLC (MeOH/H₂O, w 0.1% TFA) to yield a TFA salt of methyl ((1S)-2-((1R,3S,5R)-3-(4-chloro-5-(6-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)-2-naphthyl)-1H-imidazol-2-yl)-2-azabicyclo[3.1.0]hex-2-yl)-2-oxo-1-(tetrahydro-2H-pyran-4-yl)ethyl)carbamate (21.4 mg) as a yellow solid. LC-MS retention time 2.798 min; m/z 462.34 (½ MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode. ¹H NMR (400 MHz, MeOD) δ ppm 8.18 (s, 2H), 8.03 (d, J=8.8 Hz, 1H), 7.99 (d, J=8.8 Hz, 1H), 7.80-7.92 (m, 6H), 5.06 (ddd, J=9.0, 5.8, 3.5 Hz, 2H), 4.63 (d, J=7.5 Hz, 1H), 4.57 (d, J=6.5 Hz, 1H), 3.92-3.98 (m, 2H), 3.71-3.81 (m, 2 H), 3.67 (s, 6H), 3.35-3.44 (m, 2H), 2.42-2.57 (m, 4H), 1.99-2.24 (m, 4H), 1.40-1.66 (m, 4H), 1.06-1.14 (m, 2H), 1.03 (d, J=6.8 Hz, 3H), 0.95 (d, J=6.8 Hz, 3H), 0.82 (d, J=2.8 Hz, 2H).

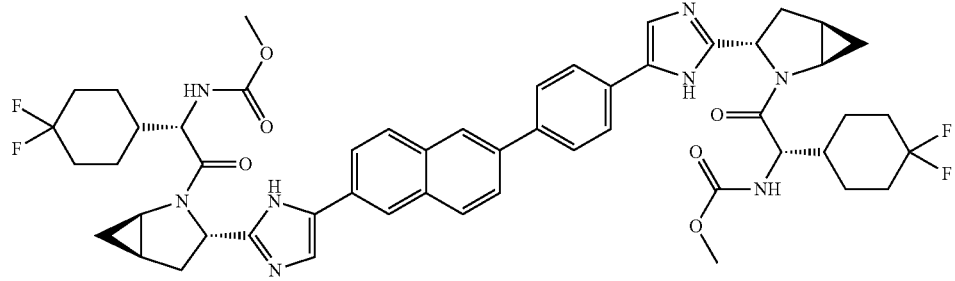 [SMILES: COC(=O)N[C@H](C(=O)N1[C@@H]2C[C@@H]2C[C@H]1c1ncc(-c2ccc(-c3ccc4cc(-c5cnc([C@@H]6C[C@H]7C[C@H]7N6C(=O)[C@@H](NC(=O)OC)C6CCC(F)(F)CC6)[nH]5)ccc4c3)cc2)[nH]1)C1CCC(F)(F)CC1]

Methyl ((1S)-1-(4,4-difluorocyclohexyl)-2-((1R,3S,5R)-3-(4-(4-(6-(2-((1R,3S,5R)-2-((2S)-2-(4,4-difluorocyclohexyl)-2-((methoxycarbonyl)amino)acetyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)-2-oxoethyl)carbamate HATU (67.3 mg, 0.177 mmol) was added to a stirred solution of an HCl salt of (1R,3S,5R)-3-(5-(4-(6-(2-((1R,3S,5R)-2-azabicyclo[3.1.0]hexan-3-yl)-1H-imidazol-5-yl)naphthalen-2-yl)phenyl)-1H-imidazol-2-yl)-2-azabicyclo[3.1.0] hexane (Intermediate 69) (38.0 mg, 0.059 mmol) and (S)-2-(4,4-difluorocyclohexyl)-2-(methoxycarbonylamino)acetic acid (44.5 mg, 0.177 mmol) in DMF (0.7 mL) and DIPEA (0.103 mL, 0.590 mmol). The reaction was diluted with MeOH, filtered, purified by preparative HPLC (water/MeOH w/0.1% TFA) and repurified by preparative HPLC (water/MeOH w/10 mM ammonium acetate) to yield methyl ((1S)-1-(4,4-difluorocyclohexyl)-2-((1R,3S,5R)-3-(4-(4-(6-(2-((1R,3S,5R)-2-((2S)-2-(4,4-difluorocyclohexyl)-2-((methoxycarbonyl)amino)acetyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)-2-oxoethyl)carbamate (22.1 mg) as a light yellow solid. LC-MS retention time 2.713 min; m/z 483.13 (½ MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, MeOD) δ ppm 8.16 (s, 1H), 8.11 (s, 1H), 7.94 (d, J=8.5 Hz, 2H), 7.77-7.85 (m, 5H), 7.47 (s, 1H), 7.39 (s, 1H), 7.08 (d, J=8.5 Hz, 1H), 5.15 (ddd, J=8.2, 6.3, 6.1 Hz, 2H), 4.68 (br. s., 2H), 3.69-3.76 (m, 2H), 3.68 (s, 6H), 2.41-2.57 (m, 4H), 1.65-2.12 (m, 16H), 1.33-1.59 (m, 4H), 1.06-1.17 (m, 2H), 0.78 (br. s., 2H).

pyl)carbamate (70.1 mg) as a light yellow solid. LC-MS retention time 1.688 min; m/z 785.55 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% MeOH/90% H$_2$O/0.1% trifluoroacetic acid and Solvent B was 10% H$_2$O/90% MeOH/0.1% trifluoroacetic acid. MS data was determined using a

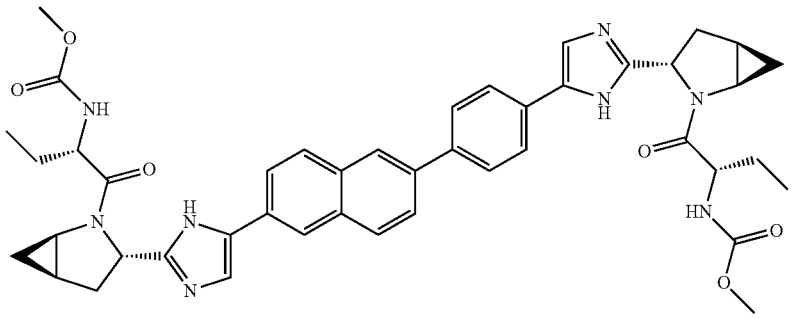 [SMILES: CC[C@H](NC(=O)OC)C(=O)N1[C@@H]2C[C@@H]2C[C@H]1c1ncc(-c2ccc(-c3ccc4cc(-c5cnc([C@@H]6C[C@H]7C[C@H]7N6C(=O)[C@H](CC)NC(=O)OC)[nH]5)ccc4c3)cc2)[nH]1]

Methyl ((1S)-1-(((1R,3S,5R)-3-(4-(4-(6-(2-((1R,3S,5R)-2-((2S)-2-((methoxycarbonyl)amino)butanoyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)carbonyl)propyl)carbamate HATU (89 mg, 0.24 mmol) was added to a stirred solution of a TFA salt of (1R,3S,5R)-3-(5-(4-(6-(2-((1R,3S,5R)-2-azabicyclo[3.1.0]hexan-3-yl)-1H-imidazol-5-yl)naphthalen-2-yl)phenyl)-1H-imidazol-2-yl)-2-azabicyclo[3.1.0]hexane (Intermediate 69) (80 mg, 0.084 mmol) and (S)-2-(methoxycarbonylamino)butanoic acid (37.8 mg, 0.235 mmol) in DMF (0.8 mL) and DIPEA (0.15 mL, 0.84 mmol). The reaction was diluted with MeOH, filtered and purified by preparative HPLC (water/MeOH w/0.1% TFA) to yield a TFA salt of methyl ((1S)-1-(((1R,3S,5R)-3-(4-(4-(6-(2-((1R,3S,5R)-2-((2S)-2-((methoxycarbonyl)amino)butanoyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)carbonyl)pro- MICROMASS® Platform for LC in electrospray mode. $^1$H NMR (400 MHz, MeOD) δ ppm 8.28 (s, 1H), 8.26 (s, 1H), 8.12 (d, J=8.8 Hz, 1H), 8.07 (d, J=8.5 Hz, 1H), 7.93-8.00 (m, 4H), 7.82-7.90 (m, 4H), 5.12-5.21 (m, 2H), 4.58-4.65 (m, 2H), 3.74-3.81 (m, 2H), 3.67 (s, 6H), 2.70 (ddd, J=13.7, 9.0, 4.9 Hz, 2H), 2.49 (dq, J=14.2, 7.1 Hz, 2H), 2.09 (br. s., 2H), 1.86-1.99 (m, 2H), 1.64-1.77 (m, 2H), 1.09-1.17 (m, 2H), 1.02 (t, J=7.4 Hz, 6H), 0.92 (br. s., 2H).

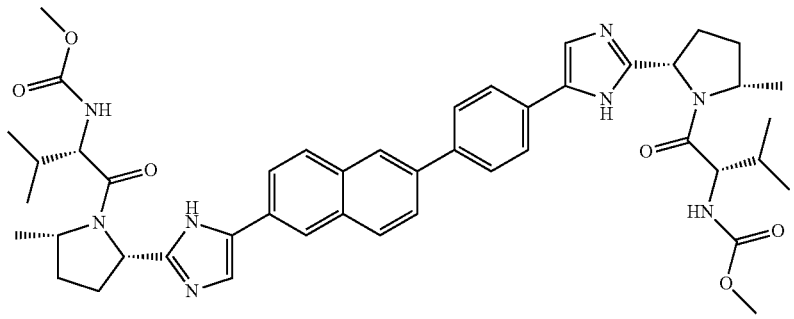 [SMILES: COC(=O)N[C@H](C(=O)N1[C@@H](C)CC[C@H]1c1ncc(-c2ccc(-c3ccc4cc(-c5cnc([C@@H]6CC[C@H](C)N6C(=O)[C@@H](NC(=O)OC)C(C)C)[nH]5)ccc4c3)cc2)[nH]1)C(C)C]

Methyl ((1S)-1-(((2S,5S)-2-(4-(4-(6-(2-((2S,5S)-1-((2S)-2-((methoxycarbonyl)amino)-3-methylbutanoyl)-5-methyl-2-pyrrolidinyl)-1H-imidazol-4-yl)-2-naphthyl)phenyl)-1H-imidazol-2-yl)-5-methyl-1-pyrrolidinyl)carbonyl)-2-methylpropyl)carbamate HATU (101 mg, 0.266 mmol) was added to a stirred solution of a TFA salt of 2-((2S,5S)-5-methyl-2-pyrrolidinyl)-4-(4-(6-(2-((2S,5S)-5-methyl-2-pyrrolidinyl)-1H-imidazol-4-yl)-2-naphthyl)phenyl)-1H-imidazole (Intermediate 117) (102 mg, 0.106 mmol) and (S)-2-(methoxycarbonylamino)-3-methylbutanoic acid (46.6 mg, 0.266 mmol) in DMF (1.0 mL) and DIPEA (0.189 mL, 1.1 mmol) and the reaction was stirred at rt for 2 h. The reaction mixture was diluted with MeOH and purified by preparative HPLC (MeOH/H$_2$O w/0.1% TFA) and then repurified by preparative HPLC (acetonitrile/water with 0.1% TFA) to yield a TFA salt of methyl ((1S)-1-(((2S,5S)-2-(4-(4-(6-(2-((2S,5S)-1-((2S)-2-((methoxycarbonyl)amino)-3-methylbutanoyl)-5-methyl-2-pyrrolidinyl)-1H-imidazol-4-yl)-2-naphthyl)phenyl)-1H-imidazol-2-yl)-5-methyl-1-pyrrolidinyl)carbonyl)-2-methylpropyl)carbamate (63.8 mg) as a light yellow solid. LC-MS retention time 1.900 min; m/z 817.59 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR presents as a ~4:1 mixture of regioisomers. $^1$H NMR (for major regioisomer) (400 MHz, MeOD) δ ppm 8.31 (s, 1H), 8.27 (s, 1H), 8.13 (d, J=8.5 Hz, 1H), 8.09 (d, J=8.5 Hz, 1H), 7.94-8.02 (m, 5H), 7.84-7.92 (m, 3H), 5.15-5.24 (m, 2H), 4.13 (dd, J=8.7, 1.4 Hz, 2H), 3.74 (d, J=2.8 Hz, 2H), 3.67 (s, 6H), 2.50-2.60 (m, 2H), 2.26-2.45 (m, 4H), 1.95-2.10 (m, 4H), 1.57 (dd, J=6.5, 3.0 Hz, 6H), 1.32 (t, J=6.4 Hz, 2H), 0.99 (d, J=6.8 Hz, 6H), 0.89 (d, J=6.8 Hz, 6H).

Methyl ((1S)-1-(((1R,3S,5R)-3-(4-chloro-5-(4-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)carbonyl)-2-methylpropyl)carbamate A mixture of two chloroimidazole regioisomers as TFA salts (Examples 68 and 69) (21.4 mg) was isolated from the same reaction that prepared a TFA salt of methyl ((1S)-2-((1R,3S,5R)-3-(4-chloro-5-(6-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)-2-naphthyl)-1H-imidazol-2-yl)-2-azabicyclo[3.1.0]hex-2-yl)-2-oxo-1-(tetrahydro-2H-pyran-4-yl)ethyl)carbamate (Example 64). The two regioisomeric compounds were separated in multiple injections using SCF chromatography (2-ethylpyridine SCF column (4.6×250 mm, 5 μm) and 80% CO$_2$-20% EtOH/0.1% DEA).

The absolute regiochemistry of the separated materials was determined by HMBC correlation. The reaction yielded methyl ((1S)-1-(((1R,3S,5R)-3-(4-(4-(6-(4-chloro-2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-5-yl)-2-naphthyl)phenyl)-1H-imidazol-2-yl)-2-azabicyclo[3.1.0]hex-2-yl)carbonyl)-2-methylpropyl)carbamate (7.4 mg) and methyl ((1S)-1-(((1R,3S,5R)-3-(4-chloro-5-(4-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-

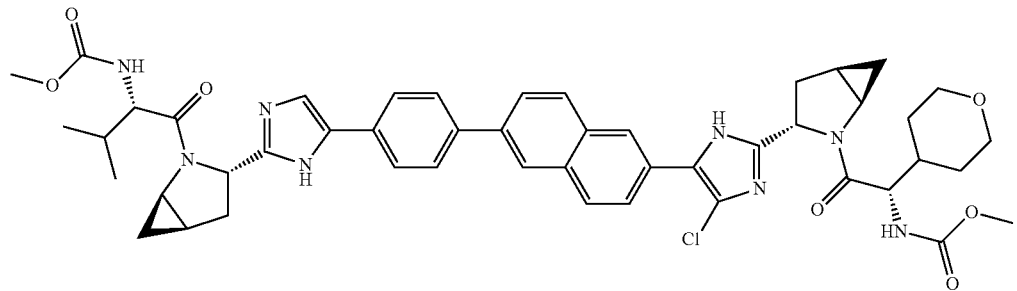

Methyl ((1S)-1-(((1R,3S,5R)-3-(4-(4-(6-(4-chloro-2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-5-yl)-2-naphthyl)phenyl)-1H-imidazol-2-yl)-2-azabicyclo[3.1.0]hex-2-yl)carbonyl)-2-methylpropyl)carbamate and naphthyl)phenyl)-1H-imidazol-2-yl)-2-azabicyclo[3.1.0]hex-2-yl)carbonyl)-2-methylpropyl)carbamate (4.5 mg), each as an off-white solid. For Example 68: LC-MS retention time 2.683 min; m/z 889.17 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220

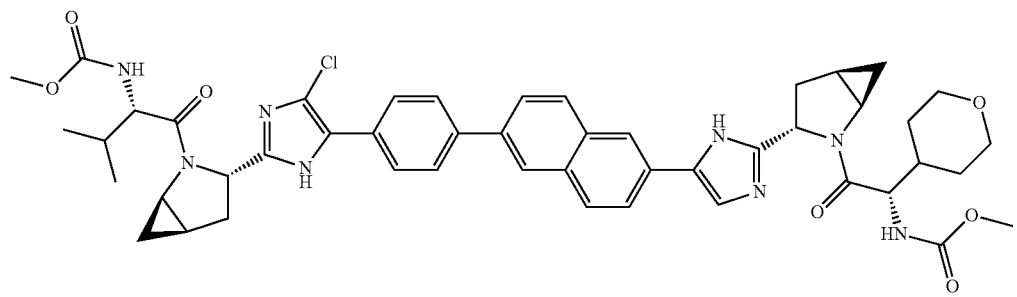

nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode. For Example 69: LC-MS retention time 2.695 min; m/z 889.22 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode.

(4-(6-(2-((2S,5S)-5-methyl-2-pyrrolidinyl)-1H-imidazol-4-yl)-2-naphthyl)phenyl)-1H-imidazole (Intermediate 117) (73.9 mg, 0.077 mmol) and (S)-2-(methoxycarbonylamino)-2-(tetrahydro-2H-pyran-4-yl)acetic acid (41.9 mg, 0.193 mmol) in DMF (1.0 mL) and DIPEA (0.14 mL, 0.77 mmol) and the reaction was stirred at rt for 30 min. The reaction mixture was diluted with MeOH, filtered and purified by preparative HPLC (MeOH/H₂O w/0.1% TFA) to yield a TFA salt of methyl ((1S)-2-((2S,5S)-2-(4-(4-(6-(2-((2S,5S)-1-((2S)-2-((methoxycarbonyl)amino)-2-(tetrahydro-2H-pyran-4-yl)acetyl)-5-methyl-2-pyrrolidinyl)-1H-imidazol-4-yl)-2-naphthyl)phenyl)-1H-imidazol-2-yl)-5-methyl-1-pyrrolidinyl)-2-oxo-1-(tetrahydro-2H-pyran-4-yl)ethyl) carbamate (51.2 mg) as a yellow solid. LC-MS retention time 1.897 min; m/z 901.39 (MH+). LC data was recorded on a Shimadzu LC-10AS liquid chromatograph equipped with a PHENOMENEX® Luna 10u C18 3.0×50 mm column using

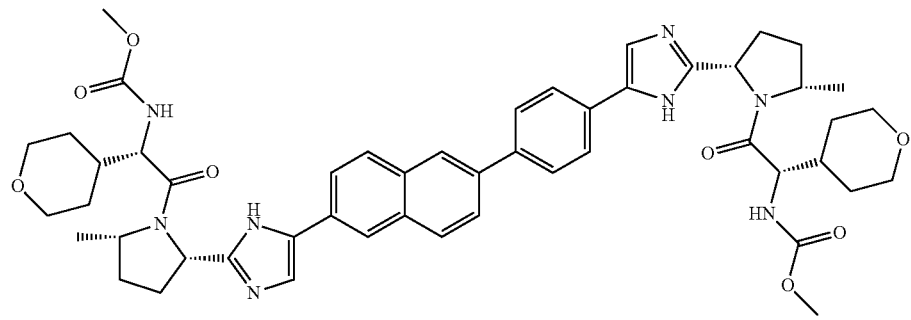 [SMILES: COC(=O)N[C@H](C(=O)N1[C@@H](C)CC[C@H]1c1ncc(-c2ccc(-c3ccc4cc(-c5cnc([C@@H]6CC[C@H](C)N6C(=O)[C@@H](NC(=O)OC)C6CCOCC6)[nH]5)ccc4c3)cc2)[nH]1)C1CCOCC1]

Methyl ((1S)-2-((2S,5S)-2-(4-(4-(6-(2-((2S,5S)-1-((2S)-2-((methoxycarbonyl)amino)-2-(tetrahydro-2H-pyran-4-yl)acetyl)-5-methyl-2-pyrrolidinyl)-1H-imidazol-4-yl)-2-naphthyl)phenyl)-1H-imidazol-2-yl)-5-methyl-1-pyrrolidinyl)-2-oxo-1-(tetrahydro-2H-pyran-4-yl)ethyl)carbamate HATU (73.3 mg, 0.193 mmol) was added to a stirred solution of a TFA salt of 2-((2S,5S)-5-methyl-2-pyrrolidinyl)-4- a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode.

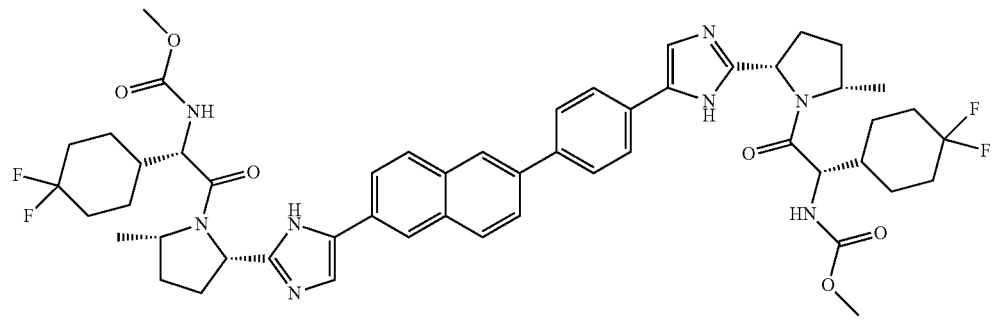 [SMILES: COC(=O)N[C@H](C(=O)N1[C@@H](C)CC[C@H]1c1ncc(-c2ccc(-c3ccc4cc(-c5cnc([C@@H]6CC[C@H](C)N6C(=O)[C@@H](NC(=O)OC)C6CCC(F)(F)CC6)[nH]5)ccc4c3)cc2)[nH]1)C1CCC(F)(F)CC1]

Methyl ((1S)-1-(4,4-difluorocyclohexyl)-2-((2S,5S)-2-(4-(4-(6-(2-((2S,5S)-1-((2S)-2-(4,4-difluorocyclohexyl)-2-((methoxycarbonyl)amino)acetyl)-5-methyl-2-pyrrolidinyl)-1H-imidazol-4-yl)-2-naphthyl)phenyl)-1H-imidazol-2-yl)-5-methyl-1-pyrrolidinyl)-2-oxoethyl)carbamate HATU (70.8 mg, 0.186 mmol) was added to a stirred solution of a TFA salt of 2-((2S,5S)-5-methyl-2-pyrrolidinyl)-4-(4-(6-(2-((2S,5S)-5-methyl-2-pyrrolidinyl)-1H-imidazol-4-yl)-2-naphthyl)phenyl)-1H-imidazole (Intermediate 117) (71.4 mg, 0.074 mmol) and (S)-2-(4,4-difluorocyclohexyl)-2-(methoxycarbonylamino)acetic acid (46.8 mg, 0.186 mmol) in DMF (1.0 mL) and DIPEA (0.13 mL, 0.75 mmol) and the reaction was stirred at rt for 1.5 h. The reaction was diluted with MeOH, filtered and purified in by preparative HPLC (MeOH/H$_2$O w/0.1% TFA) to yield the desired product a TFA salt of methyl ((1S)-1-(4,4-difluorocyclohexyl)-2-((2S,5S)-2-(4-(4-(6-(2-((2S,5S)-1-((2S)-2-(4,4-difluorocyclohexyl)-2-((methoxycarbonyl)amino)acetyl)-5-methyl-2-pyrrolidinyl)-1H-imidazol-4-yl)-2-naphthyl)phenyl)-1H-imidazol-2-yl)-5-methyl-1-pyrrolidinyl)-2-oxoethyl)carbamate (43.3 mg) as a light yellow solid. LC-MS retention time 2.828 min; m/z 485.22 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode.

Methyl ((1S)-2-((1R,3S,5R)-3-(4-chloro-5-(4-(6-(4-chloro-2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-5-yl)-2-naphthyl)phenyl)-1H-imidazol-2-yl)-2-azabicyclo[3.1.0]hex-2-yl)-2-oxo-1-(tetrahydro-2H-pyran-4-yl)ethyl) carbamate N-Chlorosuccinimide (7.1 mg, 0.053 mmol) was added to a stirred solution of methyl ((1S)-2-((1R,3S,5R)-3-(4-(4-(6-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)-2-oxo-1-(tetrahydro-2H-pyran-4-yl)ethyl)carbamate (Example 34) (22.7 mg, 0.025 mmol) in DMF (0.5 mL) and the reaction vessel was sealed and the reaction was heated at 50° C. for 12 h. The reaction was cooled to rt, additional N-chlorosuccinimide (~3 mg) was added and the reaction vessel was sealed and stirred at 50° C. for 2 h. The reaction was cooled to rt, diluted with MeOH, filtered and purified by preparative HPLC (Methanol/Water w/0.1% TFA) to yield methyl ((1S)-2-((1R,3S,5R)-3-(4-chloro-5-(4-(6-(4-chloro-2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-5-yl)-2-naphthyl)phenyl)-1H-imidazol-2-yl)-2-azabicyclo[3.1.0]hex-2-yl)-2-oxo-1-(tetrahydro-2H-pyran-4-yl)ethyl) carbamate (12 mg) as a yellow solid. LC-MS retention time 2.708 min; m/z 483.25 (½ MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, MeOD) δ ppm 8.18 (s, 2H), 8.04 (d, J=8.8 Hz, 1H), 7.99 (d, J=8.8 Hz, 1H), 7.80-7.92 (m, 6H), 5.02-5.09 (m, 2H), 4.63 (d, J=6.0 Hz, 2H), 3.91-3.99 (m, 4H), 3.73-3.80 (m, 2H), 3.67 (s, 6H), 3.34-3.45 (m, 4H), 2.43-2.54 (m, 4H), 1.98-2.13 (m, 4H), 1.38-1.67 (m, 8H), 1.06-1.15 (m, 2H), 0.81 (br. s., 2H).

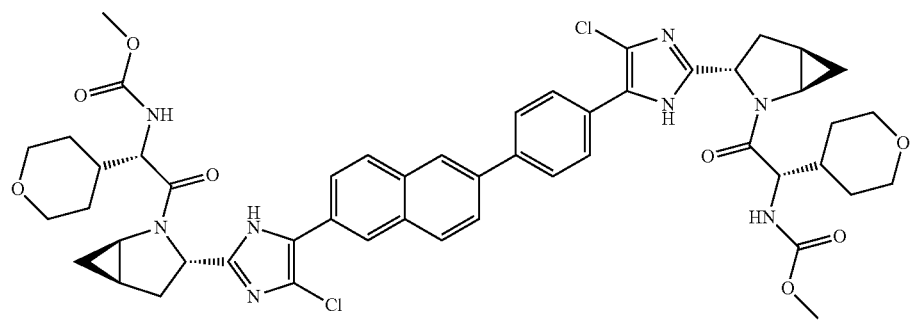 [SMILES: COC(=O)N[C@H](C(=O)N1[C@@H]2C[C@@H]2C[C@H]1c1nc(Cl)c(-c2ccc(-c3ccc4cc(-c5[nH]c([C@@H]6C[C@H]7C[C@H]7N6C(=O)[C@@H](NC(=O)OC)C6CCOCC6)nc5Cl)ccc4c3)cc2)[nH]1)C1CCOCC1]

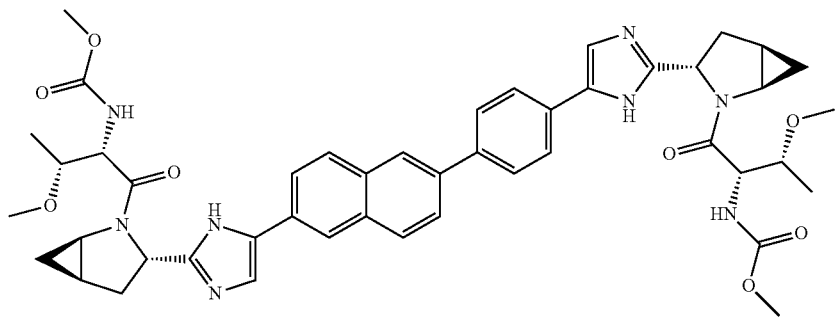

Methyl ((1S,2R)-2-methoxy-1-(((1R,3S,5R)-3-(4-(6-(4-(2-(((1R,3S,5R)-2-(N-(methoxycarbonyl)-O-methyl-L-threonyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)carbonyl)propyl) carbamate HATU (65.7 mg, 0.173 mmol) was added to a stirred solution of a TFA salt of 2-((2S,5S)-5-methyl-2-pyrrolidinyl)-4-(4-(6-(2-((2S,5S)-5-methyl-2-pyrrolidinyl)-1H-imidazol-4-yl)-2-naphthyl)phenyl)-1H-imidazole (Intermediate 133) (66 mg, 0.069 mmol) and (2S,3R)-3-methoxy-2-(methoxycarbonylamino)butanoic acid (33.0 mg, 0.173 mmol) in DMF (0.8 mL) and DIPEA (0.121 mL, 0.691 mmol) and the reaction was stirred at rt overnight. The reaction was diluted with MeOH, filtered and purified preparative HPLC (Methanol/water w/10 nM ammonium acetate) to yield a TFA salt of methyl ((1S,2R)-2-methoxy-1-(((1R,3S,5R)-3-(4-(6-(4-(2-(((1R,3S,5R)-2-(N-(methoxycarbonyl)-O-methyl-L-threonyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)carbonyl)propyl)carbamate (51.9 mg, 0.048 mmol, 98% yield) as an off-white solid. LC-MS retention time 2.383 min; m/z 845.42 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode. ¹H NMR (MeOD, 400 MHz) δ 8.29 (br s, 1H), 8.26 (s, 1H), 8.12 (d, J=8.8 Hz, 1H), 8.07 (d, J=8.8 Hz, 1H), 8.00-7.93 (m, 4H), 7.91-7.82 (m, 4H), 5.18 (td, J=9.0, 7.0 Hz, 2H), 4.78 (dd, J=3.9, 1.7 Hz, 2H), 3.92-3.79 (m, 4H), 3.68 (s, 6H), 3.35 (s, 3H), 3.35 (m, 3H), 2.76-2.65 (m, 2H), 2.59-2.47 (m, 2H), 2.15-2.05 (m, 2H), 1.19 (d, J=6.3 Hz, 6H), 1.16-1.07 (m, 2H), 0.94-0.84 (m, 2H).

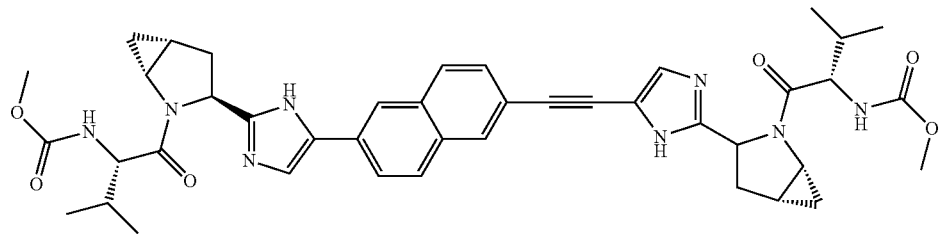 [SMILES: COC(=O)N[C@H](C(=O)N1C(c2ncc(C#Cc3ccc4cc(-c5cnc([C@@H]6C[C@H]7C[C@H]7N6C(=O)[C@@H](NC(=O)OC)C(C)C)[nH]5)ccc4c3)[nH]2)C[C@H]2C[C@H]21)C(C)C]

Methyl ((1S)-1-(((1R,3S,5R)-3-(4-(6-((2-((1R,3S,5R)-2-((2S)-2-((methoxycarbonyl)amino)-3-methylbutanoyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)carbonyl)-2-methylpropyl) carbamate HATU (193 mg, 0.506 mmol) was added to a stirred solution of an HCl salt of (1R,3S,5R)-3-(5-(6-((2-((1R,3S,5R)-2-azabicyclo[3.1.0]hexan-3-yl)-1H-imidazol-4-yl)ethynyl)naphthalen-2-yl)-1H-imidazol-2-yl)-2-azabicyclo[3.1.0]hexane (Intermediate 124) (100 mg, 0.169 mmol) and (R)-2-(methoxycarbonylamino)-3-methylbutanoic acid (89 mg, 0.51 mmol) in DMF (1.5 mL) and DIPEA (0.24 mL, 1.4 mmol) and the clear orange solution was stirred at rt for 3 h. The reaction was diluted with methanol, filtered and purified by preparative HPLC (MeOH/water with an ammonium acetate buffer) to yield methyl ((1S)-1-(((1R,3S,5R)-3-(4-(6-((2-((1R,3S,5R)-2-((2S)-2-((methoxycarbonyl)amino)-3-methylbutanoyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)carbonyl)-2-methylpropyl) carbamate (71 mg) as a light yellow solid. LC-MS retention time 3.706 min; m/z 761.22 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, MeOD) δ ppm 8.15 (s, 1H), 7.96 (s, 1H), 7.80-7.88 (m, 3H), 7.51 (dd, J=8.4, 1.6 Hz, 1H), 7.46 (s, 1H), 7.27 (s, 1H), 5.18 (dd, J=9.0, 4.8 Hz, 1H), 5.13 (dd, J=8.8, 4.3 Hz, 1H), 4.59 (dd, J=11.8, 6.8 Hz, 2H), 3.68-3.72 (m, 1H), 3.67 (s, 3H), 3.67 (s, 3H), 3.59-3.64 (m, 1H), 2.31-2.60 (m, 4H), 2.08-2.22 (m, 2H), 1.99-2.08 (m, 2H), 1.13 (ddd, J=8.6, 5.8, 5.5 Hz, 2H), 1.00 (dd, J=12.9, 6.9 Hz, 6H), 0.93 (dd, J=6.7, 2.9 Hz, 6H), 0.79 (br. s., 2H).

[3.1.0]hex-3-yl)-1H-imidazol-4-yl)ethynyl)-2-naphthyl)-1H-imidazol-2-yl)-2-azabicyclo[3.1.0]hex-2-yl)-2-oxo-1-(tetrahydro-2H-pyran-4-yl)ethyl)carbamate (37.3 mg) as a yellow solid and as a mixture of diastereomers. LC-MS retention time 1.522 min; m/z 845.36 (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% trifluoro-

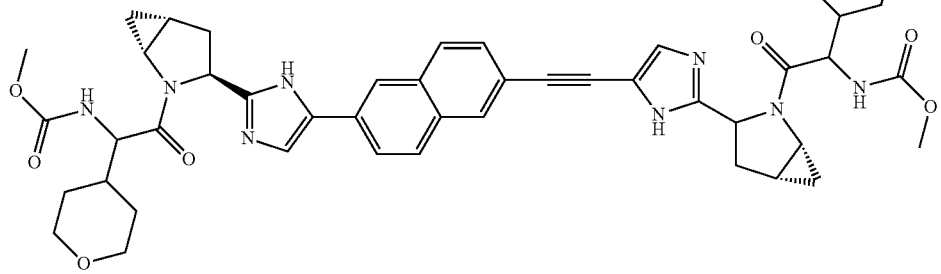

Mixture of Diastereomers

Methyl (2-((1R,3S,5R)-3-(4-(6-((2-((1R,3S,5R)-2-(((methoxycarbonyl)amino)(tetrahydro-2H-pyran-4-yl)acetyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)-2-oxo-1-(tetrahydro-2H-pyran-4-yl)ethyl)carbamate HATU (110 mg, 0.289 mmol) was added to a stirred solution of an HCl salt of (1R,3S,5R)-3-(5-(6-((2-((1R,3S,5R)-2-azabicyclo[3.1.0]hexan-3-yl)-1H-imidazol-4-yl)ethynyl)naphthalen-2-yl)-1H-imidazol-2-yl)-2-azabicyclo[3.1.0]hexane (Intermediate 124) (57 mg, 0.096 mmol) and racemic 2-(methoxycarbonylamino)-2-(tetrahydro-2H-pyran-4-yl)acetic acid (62.7 mg, 0.289 mmol) in DMF (1.0 mL) and DIPEA (0.134 mL, 0.770 mmol) and the clear orange solution was stirred at rt for 3 h. The reaction was diluted with methanol, filtered and purified by preparative HPLC (MeOH/water with an ammonium acetate buffer) to yield methyl (2-((1R,3S,5R)-3-(4-(6-((2-((1R,3S,5R)-2-(((methoxycarbonyl)amino)(tetrahydro-2H-pyran-4-yl)acetyl)-2-azabicyclo acetic acid and Solvent B was 10% H$_2$O/90% MeOH/0.1% trifluoroacetic acid. MS data was determined using a MICROMASS® Platform for LC in electrospray mode. Mixture of diastereomers. $^1$H NMR (400 MHz, MeOD) δ ppm 8.15 (d, J=12.8 Hz, 1H), 7.96 (s, 1H), 7.80-7.90 (m, 3H), 7.51 (dd, J=8.5, 1.5 Hz, 1H), 7.46 (d, J=5.5 Hz, 1H), 7.27 (d, J=5.3 Hz, 1H), 5.08-5.24 (m, 2H), 4.61-4.69 (m, 1H), 4.57 (dd, J=8.3, 4.5 Hz, 1H), 3.85-4.03 (m, 5H), 3.63-3.79 (m, 8H), 3.34-3.49 (m, 5H), 2.30-2.63 (m, 4H), 1.99-2.16 (m, 3H), 1.70-1.80 (m, 1H), 1.35-1.66 (m, 6H), 1.16-1.26 (m, 1H), 1.07-1.16 (m, 1H), 0.70-0.83 (m, 2H).

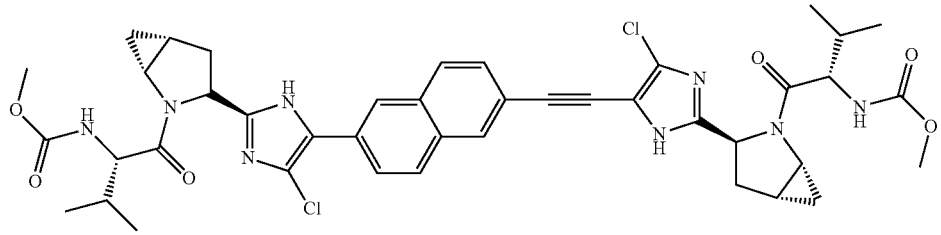

Methyl ((1S)-1-(((1R,3S,5R)-3-(4-chloro-5-(6-((4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)ethynyl)-2-naphthyl)-1H-imidazol-2-yl)-2-azabicyclo[3.1.0]hex-2-yl)carbonyl)-2-methylpropyl)carbamate N-Chlorosuccinimide (13.3 mg, 0.100 mmol) was added to a stirred solution of ((1S)-1-(((1R,3S,5R)-3-(4-(6-((2-((1R,3S,5R)-2-((2S)-2-((methoxycarbonyl)amino)-3-methylbutanoyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)carbonyl)-2-methylpropyl)carbamate (38 mg, 0.050 mmol) in DMF (1 mL) and then the reaction vessel was flushed with nitrogen, sealed and heated at 50° C. for 16 h. The reaction was cooled to rt and additional N-chlorosuccinimide (7.4 mg) was added. The reaction was reheated at 50° C. for 3 h, cooled to rt, diluted with MeOH (~0.5 mL), filtered and purified by preparative HPLC (MeOH/water, TFA buffer) to yield a TFA salt of methyl ((1S)-1-(((1R,3S,5R)-3-(4-chloro-5-(6-((4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)ethynyl)-2-naphthyl)-1H-imidazol-2-yl)-2-azabicyclo[3.1.0]hex-2-yl)carbonyl)-2-methylpropyl)carbamate (5.0 mg) as a yellow solid. LC-MS retention time 4.153 min; m/z 831.02 (MH+). LC data was recorded on a Shimadzu LC-10AS liquid chromatograph equipped with a PHENOMENEX® Luna 3u C18 2.0× 50 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 8.19 (s, 1H), 8.07 (s, 1H), 7.87-7.99 (m, 3H), 7.58 (dd, J=8.5, 1.3 Hz, 1H), 5.07 (t, J=7.2 Hz, 1H), 4.98-5.03 (m, 1H), 4.54-4.59 (m, 2H), 3.67 (s, 6H), 3.62-3.75 (m, 2H), 2.45-2.50 (m, 2H), 2.41 (dd, J=7.3, 3.5 Hz, 2H), 2.09-2.21 (m, 2H), 1.96-2.08 (m, 2H), 1.08-1.16 (m, 2H), 1.02 (t, J=6.1 Hz, 6H), 0.92-0.97 (m, 6H), 0.75-0.85 (m, 2H).

(2-((1R,3S,5R)-2-azabicyclo[3.1.0]hexan-3-yl)-1H-imidazol-5-yl)naphthalen-2-yl)phenyl)-1H-imidazol-2-yl)-2-azabicyclo[3.1.0]hexan-2-yl)-3-methyl-1-oxobutan-2-ylcarbamate (Intermediate 128) (42 mg, 0.061 mmol), 2-((2R,4r,6S)-2,6-dimethyltetrahydro-2H-pyran-4-yl)-2-(methoxycarbonylamino)acetic acid (Cap-179 stereoisomer 2) (14.9 mg, 0.061 mmol) and DIEA (0.053 mL, 0.30 mmol) in DMF (2 mL) and the resulting yellowish solution was stirred at rt for 2 h. The reaction was concentrated under reduced pressure and the residue was redissolved into methanol and purified by preparative HPLC. (Solvent A: 05% MeCN/95% water/10 mM NH$_4$Ac; Solvent B: 95% MeCN/5% water/10 mM NH$_4$Ac; Column: Sunfire Prep MS C18 30×100 mm S10; Wavelength: 220 nM; Flow rate: 40 ml/min; Gradient: 0% B to 80% B over 30 min with a 5 min. hold time) to yield methyl ((1S)-1-(((1R,3S,5R)-3-(4-(4-(6-(2-((1R,3S,5R)-2-(((2R,4r,6S)-2,6-dimethyltetrahydro-2H-pyran-4-yl)((methoxycarbonyl)amino)acetyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)carbonyl)-2-methylpropyl)carbamate (26 mg) as a white solid. LC-MS [M+H]$^+$=883; Rt=2.99 min is product. Column Luna 3u C18 2×50 mm; start % B: 0, final % B: 100 Solvent A: 5% ACN/95% H$_2$O+10 mM Ammonium Acetate; Solvent B: 95% ACN/5% H$_2$O+10 mM Ammonium Acetate; flow rate 4 ml/min. Run time: 5 min. Purity=97%. $^1$H NMR (500 MHz, DMSO-d$_6$) δ ppm 11.85 (1H, br. s.), 11.73 (1H, br. s.), 8.14-

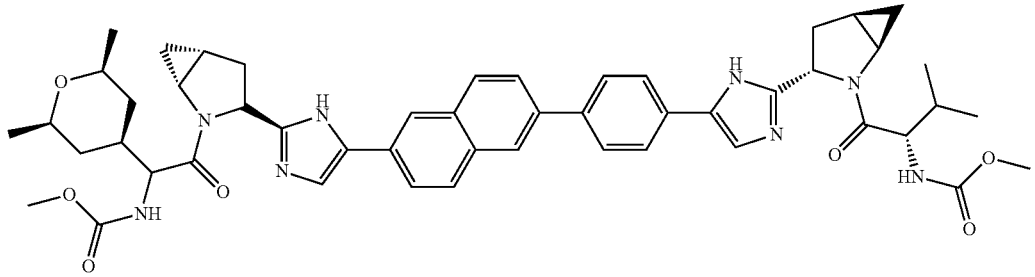

Methyl ((1S)-1-(((1R,3S,5R)-3-(4-(4-(6-(2-((1R,3S,5R)-2-(((2R,4r,6S)-2,6-dimethyltetrahydro-2H-pyran-4-yl)((methoxycarbonyl)amino)acetyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)carbonyl)-2-methylpropyl)carbamate HATU (25.4 mg, 0.067 mmol) was added to a stirred solution of an HCl salt of methyl (S)-1-((1R,3S,5R)-3-(5-(4-(6-

8.27 (2H, m), 7.90-7.98 (3H, m), 7.82-7.89 (3H, m), 7.79 (2H, d, J=8.24 Hz), 7.64 (1H, s), 7.57 (1H, s), 7.19 (2H, t, J=9.31 Hz), 5.03-5.13 (2H, m), 4.51 (1H, t, J=7.93 Hz), 4.44 (1H, t, J=7.78 Hz), 3.65 (1H, br. s.), 3.51-3.60 (7H, m), 3.29-3.42 (7H, m), 2.35-2.47 (2H, m), 2.20-2.33 (2H, m), 2.01-2.11 (2H, m), 1.83-1.92 (3H, m), 1.63 (1H, d, J=12.21 Hz), 1.57 (1H, d, J=11.60 Hz), 0.96-1.09 (12H, m), 0.89 (4H, d, J=6.71 Hz), 0.72 (2H, br. s.).

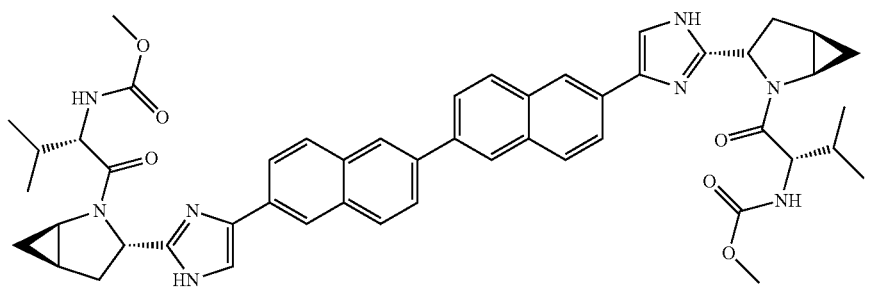

Methyl ((1S)-1-(((1R,3S,5R)-3-(4-(6'-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2,2'-binaphthalen-6-yl)-1H-imidazol-2-yl)-2-azabicyclo[3.1.0]hex-2-yl)carbonyl)-2-methylpropyl)carbamate HATU (91 mg, 0.240 mmol) was added to a stirred solution of 6,6'-bis(2-((1R,3S,5R)-2-azabicyclo[3.1.0]hexan-3-yl)-1H-imidazol-4-yl)-2,2'-binaphthyl (Intermediate 133) (43.9 mg, 0.080 mmol) and (S)-2-(methoxycarbonylamino)-3-methylbutanoic acid (42.0 mg, 0.240 mmol) in DMF (1 mL) and DIPEA (0.14 mL, 0.80 mmol) and the clear brown solution was stirred for 2 h. The reaction mixture was diluted with MeOH and purified by preparative HPLC (MeOH/water with 0.1% TFA) purified by to yield a TFA salt of methyl ((1S)-1-(((1R,3S,5R)-3-(4-(6'-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2,2'-binaphthalen-6-yl)-1H-imidazol-2-yl)-2-azabicyclo[3.1.0]hex-2-yl)carbonyl)-2-methylpropyl)carbamate (28.9 mg) as a yellow solid. LC-MS retention time 1.788 min; m/z 863.46 (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 8.37 (s, 2H), 8.29 (d, J=1.0 Hz, 2H), 8.15 (d, J=8.8 Hz, 2H), 8.06-8.13 (m, 4H), 7.97 (s, 2H), 7.86 (dd, J=8.7, 1.6 Hz, 2H), 5.17 (dd, J=9.3, 7.0 Hz, 2H), 4.57 (d, J=6.8 Hz, 2H), 3.80-3.86 (m, 2H), 3.68 (s, 6H), 2.71 (dd, J=13.7, 9.4 Hz, 2H), 2.46-2.56 (m, 2H), 2.15-2.25 (m, 2H), 2.09 (d, J=8.0 Hz, 2H), 1.08-1.16 (m, 2H), 1.03 (d, J=6.8 Hz, 6H), 0.92-0.96 (m, 6H), 0.88-0.96 (m, 2H).

Methyl ((1S)-1-(((1R,3S,5R)-3-(4-(6-(4-(2-((1R,5R)-2-((2S)-2-((2R,4r,6S)-2,6-dimethyltetrahydro-2H-pyran-4-yl)-2-((methoxycarbonyl)amino)acetyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)carbonyl)-2-methylpropyl)carbamate HATU (35.4 mg, 0.093 mmol) was added to a stirred solution of a TFA salt of methyl (2S)-1-((1R,3S,5R)-3-(5-(6-(4-(2-((1R,5R)-2-azabicyclo[3.1.0]hexan-3-yl)-1H-imidazol-5-yl)phenyl)naphthalen-2-yl)-1H-imidazol-2-yl)-2-azabicyclo[3.1.0]hexan-2-yl)-3-methyl-1-oxobutan-2-ylcarbamate (47 mg, 0.072 mmol) and (S)-2-((2R,4r,6S)-2,6-dimethyltetrahydro-2H-pyran-4-yl)-2-(methoxycarbonylamino)acetic acid (23 mg, 0.093 mmol) in DMF (1 mL) and DIPEA (0.050 mL, 0.29 mmol) and the reaction was stirred for 3 h. The reaction mixture was diluted with MeOH and purified by preparative HPLC (MeOH/water with 0.1% TFA) to yield a TFA salt of methyl ((1S)-1-(((1R,3S,5R)-3-(4-(6-(4-(2-((1R,5R)-2-((2S)-2-((2R,4r,6S)-2,6-dimethyltetrahydro-2H-pyran-4-yl)-2-((methoxycarbonyl)amino)acetyl)-2-azabicyclo[3.1.0]hex-3-yl)-1H-imidazol-4-yl)phenyl)-2-naphthyl)-1H-imidazol-2-yl)-2-azabicyclo[3.1.0]hex-2-yl)carbonyl)-2-methylpropyl)carbamate (31.3 mg) as a yellow solid. LC-MS retention time 1.670 min; m/z 883.43 (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 8.28 (d, J=1.0 Hz, 1H), 8.26 (s, 1H), 8.12 (d, J=8.8 Hz, 1H), 8.07 (d, J=8.5 Hz, 1H), 7.93-7.99 (m, 4H), 7.82-7.92 (m, 4H), 5.15 (td, J=9.6, 6.9 Hz, 2H), 4.58 (t, J=7.4 Hz, 2H), 3.79-3.86 (m, 2H), 3.68 (s, 6H), 3.43-3.53 (m, 2H), 2.65-2.75 (m, 2H), 2.50 (ddd, J=13.6, 6.7, 6.5 Hz, 2H), 2.04-2.24 (m, 4H), 1.54-1.62 (m, 1H), 1.45-1.53 (m, 1H), 0.84-1.21 (m, 18H).

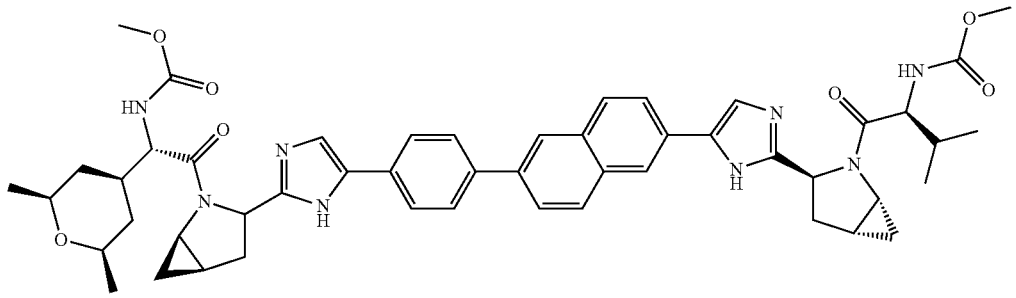

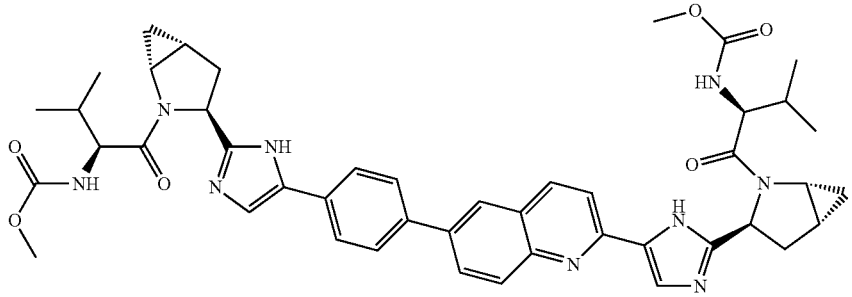 [SMILES: COC(=O)N[C@H](C(=O)N1[C@@H]2C[C@@H]2C[C@H]1c1ncc(-c2ccc(-c3ccc4nc(-c5cnc([C@@H]6C[C@H]7C[C@H]7N6C(=O)[C@@H](NC(=O)OC)C(C)C)[nH]5)ccc4c3)cc2)[nH]1)C(C)C]

Methyl ((1S)-1-((((1R,3S,5R)-3-(4-(6-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-quinolinyl)-1H-imidazol-2-yl)-2-azabicyclo[3.1.0]hex-2-yl)carbonyl)-2-methylpropyl)carbamate HATU (64.1 mg, 0.169 mmol) was added to a solution of an HCl salt of 2-(2-((1R,3S,5R)-2-azabicyclo[3.1.0]hex-3-yl)-1H-imidazol-4-yl)-6-(4-(2-((1R,3S,5R)-2-azabicyclo[3.1.0]hex-3-yl)-1H-imidazol-4-yl)phenyl)quinoline (Intermediate 139) (50 mg, 0.073 mmol) and (S)-2-(methoxycarbonylamino)-3-methylbutanoic acid (29.5 mg, 0.169 mmol) in DMF (1 mL) and DIPEA (0.115 mL, 0.660 mmol) and the reaction mixture was stirred at rt for 16 h. The reaction was diluted with MeOH, filtered and purified by preparative HPLC (H$_2$O-MeOH with 0.1% TFA buffer) to yield a TFA salt of methyl ((1S)-1-((((1R,3S,5R)-3-(4-(6-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-quinolinyl)-1H-imidazol-2-yl)-2-azabicyclo[3.1.0]hex-2-yl)carbonyl)-2-methylpropyl)carbamate (55.3 mg) as a yellow solid. LC-MS retention time 2.883 min; m/z 814.65 (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode.

Methyl ((1S)-2-((1R,3S,5R)-3-(4-(6-(4-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)phenyl)-2-quinolinyl)-1H-imidazol-2-yl)-2-azabicyclo[3.1.0]hex-2-yl)-2-oxo-1-(tetrahydro-2H-pyran-4-yl)ethyl)carbamate HATU (64.1 mg, 0.169 mmol) was added to a solution of an HCl salt of 2-(2-((1R,3S,5R)-2-azabicyclo[3.1.0]hex-3-yl)-1H-imidazol-4-yl)-6-(4-(2-((1R,3S,5R)-2-azabicyclo[3.1.0]hex-3-yl)-1H-imidazol-4-yl)phenyl)quinoline (Intermediate 139) (50 mg, 0.073 mmol) and (S)-2-(methoxycarbonylamino)-2-(tetrahydro-2H-pyran-4-yl)acetic acid (36.6 mg, 0.169 mmol) in DMF (1 mL) and DIPEA (0.12 mL, 0.66 mmol) and the reaction mixture was stirred at rt for 2 h. The reaction was diluted with MeOH, filtered and purified by preparative HPLC (H$_2$O-MeOH with 0.1% TFA buffer) to yield a TFA salt of methyl ((1S)-2-((1R,3S,5R)-3-(4-(6-(4-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)phenyl)-2-quinolinyl)-1H-imidazol-2-yl)-2-azabicyclo[3.1.0]hex-2-yl)-2-oxo-1-(tetrahydro-2H-pyran-4-yl)ethyl)carbamate (64.8 mg) as a yellow solid. LC-MS retention time 2.553 min; m/z 898.70 (MH+). LC data was recorded on a Shimadzu LC-10AS liquid chromatograph equipped with a PHENOMENEX® Luna 3u C18 2.0× 30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode.

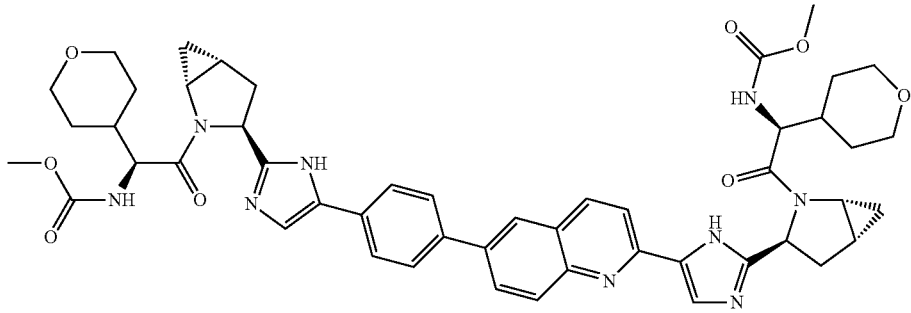 [SMILES: COC(=O)N[C@H](C(=O)N1[C@@H]2C[C@@H]2C[C@H]1c1ncc(-c2ccc(-c3ccc4nc(-c5cnc([C@@H]6C[C@H]7C[C@H]7N6C(=O)[C@@H](NC(=O)OC)C6CCOCC6)[nH]5)ccc4c3)cc2)[nH]1)C1CCOCC1]

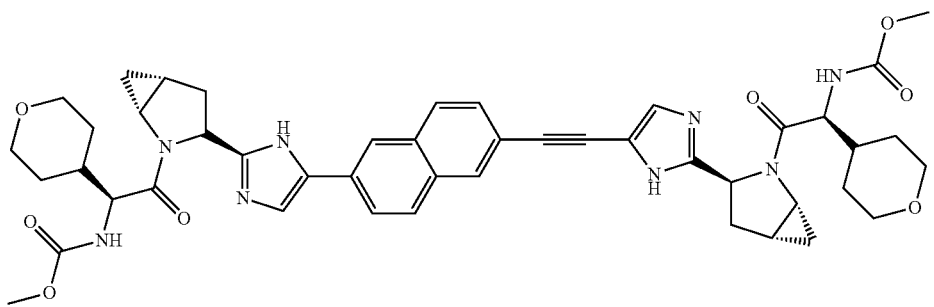

Methyl ((1S)-2-((1R,3S,5R)-3-(4-(6-((2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)-2-oxo-1-(tetrahydro-2H-pyran-4-yl)ethyl)carbamate HATU (102 mg, 0.269 mmol) was added to a stirred solution of an HCl salt of (1R,3S,5R)-3-(5-(6-((2-((1R,3S,5R)-2-azabicyclo[3.1.0]hexan-3-yl)-1H-imidazol-4-yl)ethynyl)naphthalen-2-yl)-1H-imidazol-2-yl)-2-azabicyclo[3.1.0]hexane (60 mg, 0.134 mmol) and (S)-2-(methoxycarbonylamino)-2-(tetrahydro-2H-pyran-4-yl)acetic acid (58.4 mg, 0.269 mmol) in DMF (1.2 mL) and DIPEA (0.19 mL, 1.1 mmol) and the reaction was stirred at rt for 2 h. The reaction was diluted with methanol and purified by preparative HPLC (MeOH/water, with an ammonium acetate buffer) to yield methyl ((1S)-2-((1R,3S,5R)-3-(4-(6-((2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)-2-oxo-1-(tetrahydro-2H-pyran-4-yl)ethyl)carbamate (48.9 mg) as a light yellow solid. LC-MS retention time 2.572 min; m/z 845.65 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 8.14 (s, 1H), 7.96 (s, 1H), 7.80-7.87 (m, 3H), 7.51 (dd, J=8.5, 1.5 Hz, 1H), 7.45 (s, 1H), 7.27 (s, 1H), 5.16 (dd, J=8.8, 5.0 Hz, 1H), 5.11 (dd, J=8.8, 4.5 Hz, 1H), 4.66 (d, J=7.5 Hz, 1H), 4.63 (d, J=7.8 Hz, 1H), 3.90-3.98 (m, 4H), 3.67 (s, 6H), 3.63-3.76 (m, 2H), 3.33-3.44 (m, 4H), 2.32-2.56 (m, 4H), 1.98-2.10 (m, 4H), 1.35-1.67 (m, 8H), 1.08-1.16 (m, 2H), 0.78 (br. s., 2H).

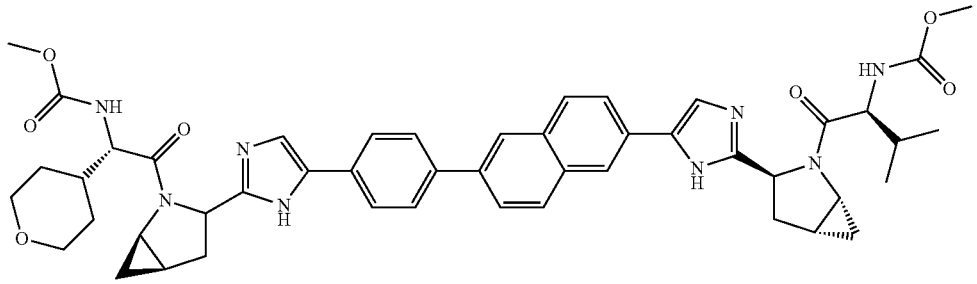

Methyl ((1S)-2-((1R,5R)-3-(4-(4-(6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)-2-oxo-1-(tetrahydro-2H-pyran-4-yl)ethyl)carbamate HATU (27.8 mg, 0.073 mmol) was added to a solution of methyl (2S)-1-((1R,3S,5R)-3-(5-(6-(4-(2-((1R,5R)-2-azabicyclo[3.1.0]hexan-3-yl)-1H-imidazol-5-yl)phenyl)naphthalen-2-yl)-1H-imidazol-2-yl)-2-azabicyclo[3.1.0]hexan-2-yl)-3-methyl-1-oxobutan-2-ylcarbamate (Intermediate 131) (40 mg, 0.061 mmol) and (S)-2-(methoxycarbonylamino)-2-(tetrahydro-2H-pyran-4-yl)acetic acid (15.90 mg, 0.073 mmol) were dissolved into DMF (0.5 mL) and DIPEA (0.053 mL, 0.31 mmol) and the reaction was stirred at rt for 2 h. The reaction was diluted with methanol and purified by preparative HPLC (MeOH/water with an ammonium acetate buffer) to yield methyl ((1S)-2-((1R,5R)-3-(4-(4-(6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)-2-oxo-1-(tetrahydro-2H-pyran-4-yl)ethyl)carbamate (3.5 mg) as a light yellow solid. LC-MS retention time 2.785 min; m/z 855.74 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode. ¹H NMR (400 MHz, MeOD) δ ppm 8.17 (s, 1H), 8.10 (s, 1H), 7.93 (dd, J=8.5, 3.0 Hz, 2H), 7.77-7.86 (m, 6H), 7.44 (s, 1H), 7.35 (s, 1H), 5.20 (dd, J=8.9, 4.6 Hz, 1H), 5.15 (dd, J=8.8, 5.0 Hz, 1H), 4.66 (d, J=7.8 Hz, 1H), 4.61 (d, J=6.8 Hz, 1H), 3.90-3.99 (m, 2H), 3.68 (s, 6H), 3.64-3.76 (m, 3H), 3.34-3.43 (m, 3H), 2.39-2.61 (m, 4H), 2.12-2.23 (m, 1H), 1.99-2.10 (m, 2H), 1.52-1.67 (m, 2H), 1.41-1.51 (m, 1H), 1.08-1.18 (m, 2H), 1.02 (d, J=6.8 Hz, 3H), 0.94 (d, J=6.8 Hz, 3H), 0.76-0.84 (m, 2H).

carbamate (Example 80) (26 mg, 0.022 mmol) in DMF (0.5 mL) and the reaction mixture was stirred at 50° C. for 16 h. The reaction was diluted with MeOH, filtered and purified by preparative HPLC (H₂O-MeOH with 0.1% TFA buffer) to yield two products: 1) A TFA salt of methyl ((1S)-1-(((1R,3S,5R)-3-(4-chloro-5-(6-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)-2-quinolinyl)-1H-imidazol-2-yl)-2-azabicyclo[3.1.0]hex-2-yl)carbonyl)-2-methylpropyl)carbamate (12.4 mg) as yellow solid. LC-MS retention time 3.871 min; m/z 882.55 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100%

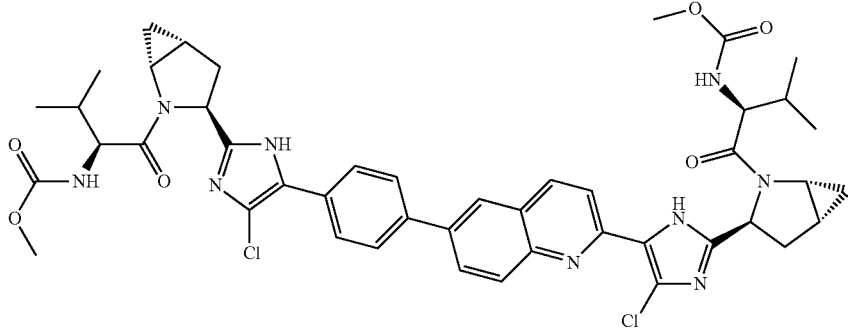 [SMILES: COC(=O)N[C@H](C(=O)N1[C@@H]2C[C@@H]2C[C@H]1c1nc(Cl)c(-c2ccc(-c3ccc4nc(-c5[nH]c([C@@H]6C[C@H]7C[C@H]7N6C(=O)[C@@H](NC(=O)OC)C(C)C)nc5Cl)ccc4c3)cc2)[nH]1)C(C)C]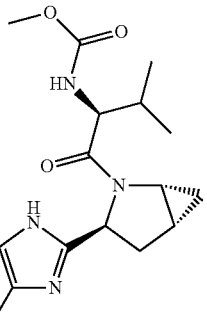

Methyl ((1S)-1-(((1R,3S,5R)-3-(4-chloro-5-(6-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)-2-quinolinyl)-1H-imidazol-2-yl)-2-azabicyclo[3.1.0]hex-2-yl)carbonyl)-2-methylpropyl)carbamate and Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode. ¹H NMR (400 MHz, MeOD) δ ppm 8.53 (d, J=8.8 Hz,

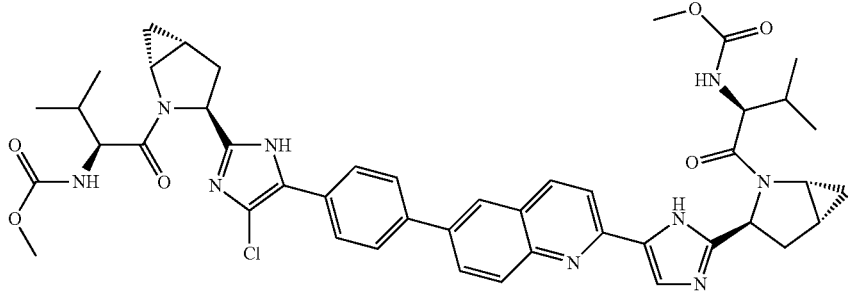 [SMILES: COC(=O)N[C@H](C(=O)N1[C@@H]2C[C@@H]2C[C@H]1c1ncc(-c2ccc3cc(-c4ccc(-c5[nH]c([C@@H]6C[C@H]7C[C@H]7N6C(=O)[C@@H](NC(=O)OC)C(C)C)nc5Cl)cc4)ccc3n2)[nH]1)C(C)C]

Methyl ((1S)-1-(((1R,3S,5R)-3-(4-(6-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)-2-quinolinyl)-1H-imidazol-2-yl)-2-azabicyclo[3.1.0]hex-2-yl)carbonyl)-2-methylpropyl)carbamate N-Chlorosuccinimide (6.01 mg, 0.045 mmol) was added to a stirred solution of a TFA salt of methyl ((1S)-1-(((1R,3S,5R)-3-(4-(6-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-quinolinyl)-1H-imidazol-2-yl)-2-azabicyclo[3.1.0]hex-2-yl)carbonyl)-2-methylpropyl)

1H), 8.26 (d, J=8.8 Hz, 1H), 8.23 (s, 1H), 8.17 (s, 2H), 7.82-7.93 (m, 4H), 5.16 (dd, J=8.8, 5.3 Hz, 1H), 5.06 (t, J=7.2 Hz, 1H), 4.53-4.63 (m, 2H), 3.68-3.76 (m, 2H), 3.67 (s, 6H), 2.44-2.60 (m, 4H), 2.11-2.24 (m, 2H), 1.97-2.09 (m, 2H), 1.09-1.18 (m, 2H), 1.03 (dd, J=6.8, 3.3 Hz, 6H), 0.95 (dd, J=6.8, 2.4 Hz, 6H), 0.75-0.87 (m, 2H). 2) A TFA salt of methyl ((1S)-1-(((1R,3S,5R)-3-(4-(6-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)-2-quinolinyl)-1H-imidazol-2-yl)-2-azabicyclo[3.1.0]hex-2-yl)carbonyl)-2-methylpropyl)carbamate (4.8 mg) as yellow solid. LC-MS retention time 2.98 min; m/z 848.60 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 8.64 (d, J=8.8 Hz, 1H), 8.34 (s, 1H), 8.32 (s, 1H), 8.25-8.29 (m, 2H), 8.09 (d, J=8.8 Hz, 1H), 7.86-7.96 (m, 4H), 5.18-5.25 (m, 1H), 5.03-5.09 (m, 1H), 4.53-4.62 (m, 2H), 3.64-3.83 (m, 2H), 3.64-3.69 (m, 6H), 2.42-2.70 (m, 4H), 1.97-2.24 (m, 4H), 1.08-1.17 (m, 2H), 1.02 (dd, J=6.8, 2.4 Hz, 6H), 0.94 (t, J=6.8 Hz, 6H), 0.76-0.91 (m, 2H).

hex-3-yl)-1H-imidazol-4-yl)phenyl)-2-quinolinyl)-1H-imidazol-2-yl)-2-azabicyclo[3.1.0]hex-2-yl)-2-oxo-1-(tetrahydro-2H-pyran-4-yl)ethyl)carbamate (Example 81) (31 mg, 0.025 mmol) in DMF (0.5 mL) and the reaction mixture was stirred at 50° C. for 16 h. The reaction was diluted with MeOH, filtered and purified by preparative HPLC (H$_2$O-MeOH with 0.1% TFA buffer) to yield methyl ((1S)-2-((1R,3S,5R)-3-(4-chloro-5-(6-(4-(4-chloro-2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-5-yl)phenyl)-2-quinolinyl)-1H-imidazol-2-yl)-2-azabicyclo[3.1.0]hex-2-yl)-2-oxo-1-(tetrahydro-2H-pyran-4-yl)ethyl)carbamate (12.1 mg) as yellow solid. LC-MS retention time 3.511 min; m/z 484.17 (½ MH+). LC data was recorded on a Shimadzu LC-10AS liquid chromatograph equipped with a PHENOMENEX® Luna 3u C18 2.0×50 mm column using a SPD-10AV UV-Vis detector at a detector

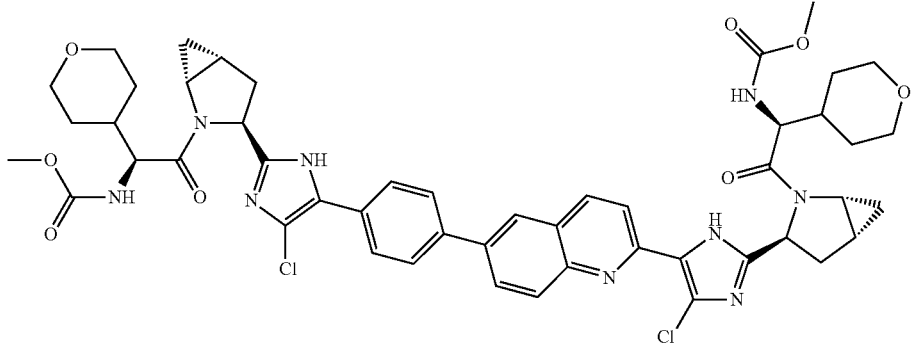 [SMILES: COC(=O)N[C@H](C(=O)N1[C@@H]2C[C@@H]2C[C@H]1c1nc(Cl)c(-c2ccc(-c3ccc4nc(-c5[nH]c([C@@H]6C[C@H]7C[C@H]7N6C(=O)[C@@H](NC(=O)OC)C6CCOCC6)nc5Cl)ccc4c3)cc2)[nH]1)C1CCOCC1]

Methyl ((1S)-2-((1R,3S,5R)-3-(4-chloro-5-(6-(4-(4-chloro-2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-5-yl)phenyl)-2-quinolinyl)-1H-imidazol-2-yl)-2-azabicyclo[3.1.0]hex-2-yl)-2-oxo-1-(tetrahydro-2H-pyran-4-yl)ethyl)carbamate N-Chlorosuccinimide (6.68 mg, 0.050 mmol) was added to a solution of a TFA salt of methyl ((1S)-2-((1R,3S,5R)-3-(4-(6-(4-(2-((1R,3S,5R)-2-((2S)-2-((methoxycarbonyl)amino)-2-(tetrahydro-2H-pyran-4-yl)acetyl)-2-azabicyclo[3.1.0]

wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 8.60 (d, J=8.8 Hz, 1H), 8.27-8.33 (m, 2H), 8.21 (s, 2H), 7.89-7.95 (m, 2H), 7.83-7.88 (m, 2H), 5.15 (dd, J=8.7, 5.6 Hz, 1H), 5.05 (dd, J=8.3, 6.3 Hz, 1H), 4.64 (dd, J=11.3, 7.8 Hz, 2H), 3.87-4.00 (m, 4H), 3.73-3.81 (m, 2H), 3.68 (s, 6H), 3.33-3.48 (m, 4H), 2.41-2.61 (m, 4H), 1.95-2.16 (m, 4H), 1.39-1.70 (m, 8H), 1.06-1.18 (m, 2H), 0.81 (m, 2H).

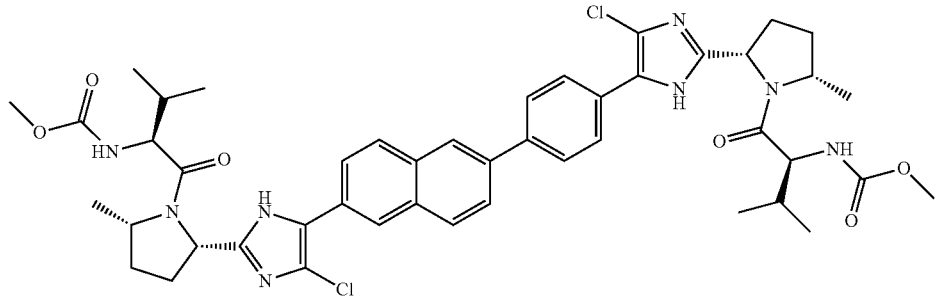

507
Methyl ((1S)-1-(((2S,5S)-2-(4-chloro-5-(4-(6-(4-chloro-2-((2S,5S)-1-((2S)-2-((methoxycarbonyl)amino)-3-methylbutanoyl)-5-methyl-2-pyrrolidinyl)-1H-imidazol-5-yl)-2-naphthyl)phenyl)-1H-imidazol-2-yl)-5-methyl-1-pyrrolidinyl)carbonyl)-2-methylpropyl)carbamate N-Chlorosuccinimide (18.88 mg, 0.141 mmol) was to a stirred solution of a TFA salt of methyl ((1S)-1-(((2S,5S)-2-(4-(4-(6-(2-((2S,5S)-1-((2S)-2-((methoxycarbonyl)amino)-3-methylbutanoyl)-5-methyl-2-pyrrolidinyl)-1H-imidazol-4-yl)-2-naphthyl)phenyl)-1H-imidazol-2-yl)-5-methyl-1-pyrrolidinyl)carbonyl)-2-methylpropyl)carbamate (105 mg, 0.129 mmol) in DMF (3.0 mL) and then and the reaction was flushed with nitrogen, sealed and heated at 50° C. overnight. By LC-MS a 1.3:1.6:1 of starting material: mono-Cl (presumably both regioisomers: dichloro). The reaction was concentrated, dissolved into MeOH, filtered and purified by preparative HPLC (MeOH/water with a TFA buffer) to yield recovered starting material (36.2 mg), a mixture of the two mono-chloroimidazole regioisomers (56.6 mg) (Example 94 and Example 95) and a TFA salt of methyl ((1S)-1-((2S,5S)-2-(4-chloro-5-(4-(6-(4-chloro-2-((2S,5S)-1-((2S)-2-((methoxycarbonyl)amino)-3-methylbutanoyl)-5-methyl-2-pyrrolidinyl)-1H-imidazol-5-yl)-2-naphthyl)phenyl)-1H-imidazol-2-yl)-5-methyl-1-pyrrolidinyl)carbonyl)-2-methylpropyl)carbamate (20.4 mg) as a yellow solid. LC-MS retention time 2.482 min; m/z 885.84 (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode.

508
Methyl ((1S)-1-(((1R,3S,5R)-3-(4-(4-(5-(2-((1R,3S,5R)-2-((2S)-2-((methoxycarbonyl)amino)-3-methylbutanoyl)-2-azabicyclo[3.1.0]hex-3-yl)-1H-imidazol-4-yl)-1-naphthyl)phenyl)-1H-imidazol-2-yl)-2-azabicyclo[3.1.0]hex-2-yl)carbonyl)-2-methylpropyl)carbamate HATU (62.8 mg, 0.165 mmol) was added to a stirred solution of an HCl salt of (1R,3S,5R)-3-(5-(4-(5-(2-((1R,3S,5R)-2-azabicyclo[3.1.0]hexan-3-yl)-1H-imidazol-4-yl)naphthalen-1-yl)phenyl)-1H-imidazol-2-yl)-2-azabicyclo[3.1.0]hexane (Intermediate 144) (42.6 mg, 0.066 mmol) and (S)-2-(methoxycarbonylamino)-3-methylbutanoic acid (28.9 mg, 0.165 mmol) in DMF (0.8 mL) and DIPEA (0.092 mL, 0.53 mmol) and the reaction was stirred at rt for 2 h. The reaction was diluted with MeOH, filtered and purified by preparative HPLC (MeOH/water with TFA buffer) to yield the a TFA salt of methyl ((1S)-1-(((1R,3S,5R)-3-(4-(4-(5-(2-((1R,3S,5R)-2-((2S)-2-((methoxycarbonyl)amino)-3-methylbutanoyl)-2-azabicyclo[3.1.0]hex-3-yl)-1H-imidazol-4-yl)-1-naphthyl)phenyl)-1H-imidazol-2-yl)-2-azabicyclo[3.1.0]hex-2-yl)carbonyl)-2-methylpropyl)carbamate (53.7 mg) as an off-white solid. LC-MS retention time 2.821 min; m/z 813.88 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (500 MHz, MeOD) δ ppm 8.06 (d, J=8.5 Hz, 1H), 7.98 (d, J=8.5 Hz, 1H), 7.95 (s, 1H), 7.91 (d, J=8.5 Hz, 2H), 7.78 (s, 1H), 7.65-7.73 (m, 4H), 7.59-7.64 (m, 2H), 5.18 (ddd, J=12.5, 9.2, 7.0 Hz, 2H), 4.59 (dd, J=6.4, 3.4 Hz, 2H), 3.80-3.87 (m, 2H), 3.69 (s, 6H), 2.73 (dt, J=13.4, 9.2 Hz, 2H), 2.48-2.59 (m, 2H), 2.18-2.28 (m, 2H), 2.10 (br. s., 2H), 1.08-1.15 (m, 2H), 1.06 (d, J=7.0 Hz, 3H), 1.04 (d, J=7.0 Hz, 3H), 0.99 (d, J=6.7 Hz, 3H), 0.95 (d, J=6.7 Hz, 3H), 0.89-0.94 (m, 2H).

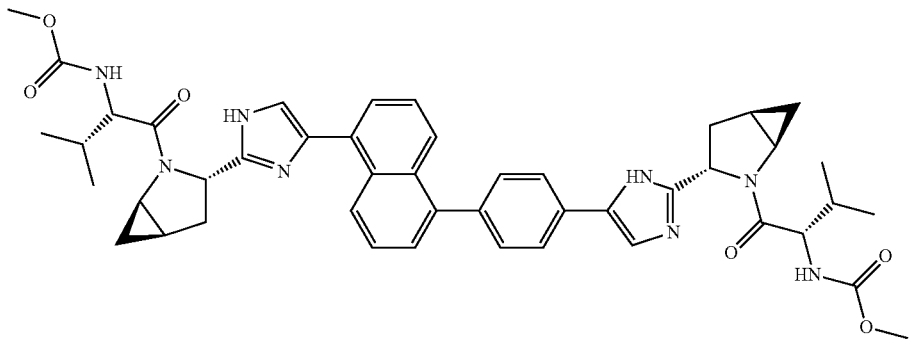

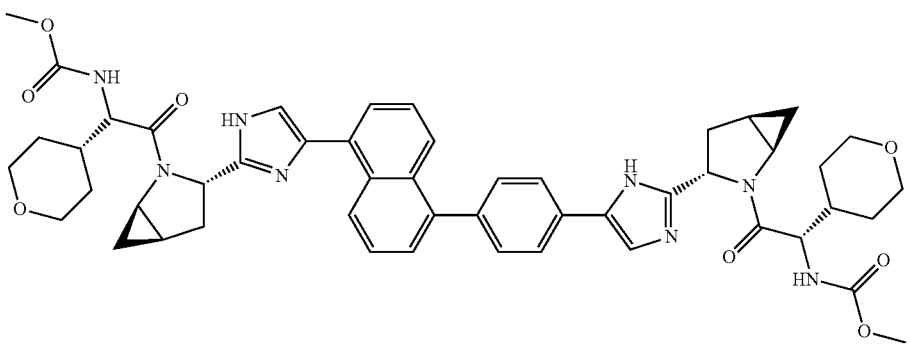

Methyl ((1S)-2-((1R,3S,5R)-3-(4-(4-(5-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-1-naphthyl)phenyl)-1H-imidazol-2-yl)-2-azabicyclo[3.1.0]hex-2-yl)-2-oxo-1-(tetrahydro-2H-pyran-4-yl)ethyl)carbamate HATU (62.8 mg, 0.165 mmol) was added to a stirred solution of an HCl salt of (1R,3S,5R)-3-(5-(4-(5-(2-((1R,3S,5R)-2-azabicyclo[3.1.0]hexan-3-yl)-1H-imidazol-4-yl)naphthalen-1-yl)phenyl)-1H-imidazol-2-yl)-2-azabicyclo[3.1.0]hexane (Intermediate 144) (42.6 mg, 0.066 mmol) and (S)-2-(methoxycarbonylamino)-2-(tetrahydro-2H-pyran-4-yl)acetic acid (35.9 mg, 0.165 mmol) in DMF (0.8 mL) and DIPEA (0.092 mL, 0.53 mmol) and the reaction was stirred at rt for 4 h. The reaction was diluted with MeOH, filtered and purified by preparative HPLC (MeOH/water with ammonium acetate buffer) to yield methyl ((1S)-2-((1R,3S,5R)-3-(4-(4-(5-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)-1-naphthyl)phenyl)-1H-imidazol-2-yl)-2-azabicyclo[3.1.0]hex-2-yl)-2-oxo-1-(tetrahydro-2H-pyran-4-yl)ethyl)carbamate (42.6 mg, 0.066 mmol) as an off-white solid. LC-MS retention time 1.965 min; m/z 897.59 (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (500 MHz, MeOD) δ ppm 8.23 (d, J=8.2 Hz, 1H), 7.91 (d, J=8.5 Hz, 1H), 7.82 (d, J=8.2 Hz, 2H), 7.52-7.59 (m, 2H), 7.44-7.51 (m, 4H), 7.41 (s, 1H), 7.21 (s, 1H), 5.23 (dd, J=8.9, 4.6 Hz, 1H), 5.18 (dd, J=8.9, 4.9 Hz, 1H), 4.68 (dd, J=7.5, 2.6 Hz, 2H), 3.89-4.01 (m, 4H), 3.70-3.77 (m, 2H), 3.69 (s, 6H), 3.35-3.45 (m, 4H), 2.43-2.63 (m, 4H), 2.00-2.14 (m, 4H), 1.52-1.71 (m, 6H), 1.41-1.52 (m, 2H), 1.10-1.18 (m, 2H), 0.79-0.86 (m, 2H).

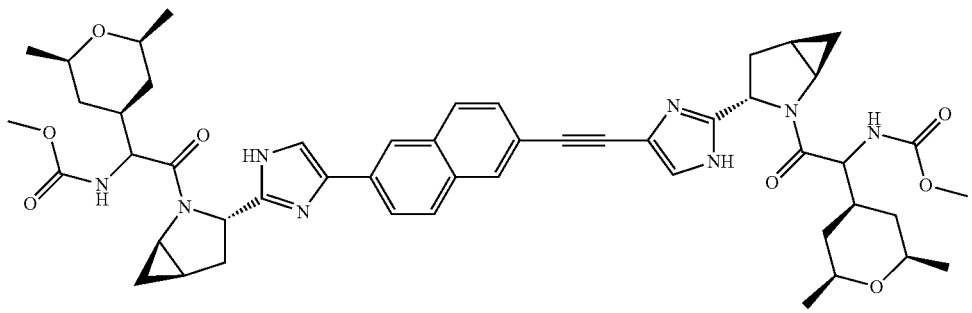

Methyl ((1S)-1-((2R,4r,6S)-2,6-dimethyltetrahydro-2H-pyran-4-yl)-2-((1R,3S,5R)-3-(4-((6-(2-((1R,3S,5R)-2-((2S)-2-((2R,4r,6S)-2,6-dimethyltetrahydro-2H-pyran-4-yl)-2-((methoxycarbonyl)amino)acetyl)-2-azabicyclo[3.1.0]hex-3-yl)-1H-imidazol-4-yl)-2-naphthyl)ethynyl)-1H-imidazol-2-yl)-2-azabicyclo[3.1.0]hex-2-yl)-2-oxoethyl)carbamate An HCl salt of (1R,3S,5R)-3-(5-(6-((2-((1R,3S,5R)-2-azabicyclo[3.1.0]hexan-3-yl)-1H-imidazol-4-yl)ethynyl)naphthalen-2-yl)-1H-imidazol-2-yl)-2-azabicyclo[3.1.0]hexane (Intermediate 124) (50 mg, 0.073 mmol), 2-((2R,4r,6S)-2,6-dimethyltetrahydro-2H-pyran-4-yl)-2-(methoxycarbonylamino)acetic acid (Cap-179 stereoisomer 2) (36.9 mg, 0.151 mmol), HATU (58.6 mg, 0.154 mmol) and DIEA (0.077 mL, 0.441 mmol) were combined in DMF (3 mL) and the resulting yellow solution was stirred at rt for 15 h. The volatiles were removed under reduced pressure and the residue was redissolved in methanol and purified by preparative HPLC (Solvent A: 10% MeOH/90% water/0.1% TFA; Solvent B: 90% MeOH/10% water/0.1% TFA; Column: Sunfire Prep MS C18 30×100 mm 5u; Wavelength: 220 nM; Flow rate: 40 ml/min; Gradient: 10% B to 80% B over 30 min. with a 5 min hold time) to yield a TFA salt of methyl ((1S)-1-((2R,4r,6S)-2,6-dimethyltetrahydro-2H-pyran-4-yl)-2-((1R,3S, 5R)-3-(4-((6-(2-(((1R,3S,5R)-2-((2S)-2-((2R,4r,6S)-2,6-dimethyltetrahydro-2H-pyran-4-yl)-2-((methoxycarbonyl)amino)acetyl)-2-azabicyclo[3.1.0]hex-3-yl)-1H-imidazol-4-yl)-2-naphthyl)ethynyl)-1H-imidazol-2-yl)-2-azabicyclo[3.1.0]hex-2-yl)-2-oxoethyl)carbamate (43 mg) as a white solid. LC-MS [M+H]⁺=902; Rt=1.93 min is product. Column PHENOMENEX® 10u C18 3.0×50 mm; start %B: 0, final %B: 100 Solvent A: 10% MeOH/90% H₂O+1% TFA; Solvent B: 90% MeOH/10% H₂O+1% TFA; flow rate 4 mL/min. Run time: 5 min. Purity=98%. ¹H NMR (500 MHz, DMSO-d₆) δ ppm 8.38 (1H, br. s.), 8.14-8.22 (1H, m), 8.09 (1H, d, J=8.85 Hz), 7.93-8.00 (2H, m), 7.62 (1H, d, J=8.85 Hz), 7.25 (2H, t, J=7.48 Hz), 5.02 (2H, t, J=6.87 Hz), 4.51 (1H, dd, J=7.78, 6.56 Hz), 4.45 (1H, t, J=7.93 Hz), 3.82 (1H, br. s.), 3.67 (1H, d, J=13.73 Hz), 3.54 (6H, s), 3.31-3.42 (3H, m), 2.33 (2H, br. s.), 1.85-1.97 (2H, m), 1.43-1.52 (1H, m), 1.22-1.31 (1H, m), 1.03-1.12 (10H, m), 0.89-1.01 (9H, m), 0.82 (1H, br. s.), 0.75 (1H, br. s.).

6aS)-octahydrocyclopenta[b]pyrrol-2-yl)-1H-imidazol-4-yl)naphthalen-2-yl)phenyl)-1H-imidazol-2-yl)octahydrocyclopenta[b]pyrrole (51 mg, 0.073 mmol), (S)-2-(methoxycarbonylamino)-3-methylbutanoic acid (Intermediate 147) (28.1 mg, 0.160 mmol) and DIPEA (0.076 mL, 0.44 mmol) in DCM (1.5 mL) and the reaction mixture was stirred at rt for 2 h. The crude reaction mixture was concentrated to dryness and purified by preparative HPLC (TFA buffer) to yield a TFA salt of methyl ((1S)-1-(((2S,3aS,6aS)-2-(4-(6-(4-(2-((2S,3aS,6aS)-1-((2S)-2-((methoxycarbonyl)amino)-3-methylbutanoyl)octahydrocyclopenta[b]pyrrol-2-yl)-1H-imidazol-4-yl)phenyl)-2-naphthyl)-1H-imidazol-2-yl)hexahydrocyclopenta[b]pyrrol-1(2H)-yl)carbonyl)-2-methylpropyl)carbamate (23.7 mg) as a white solid. LC-MS retention time 2.462 min; m/z 867.8 (MH−). LC data was recorded on a Shimadzu LC-10AS liquid chromatograph equipped with a PHENOMENEX® Luna 3u C18

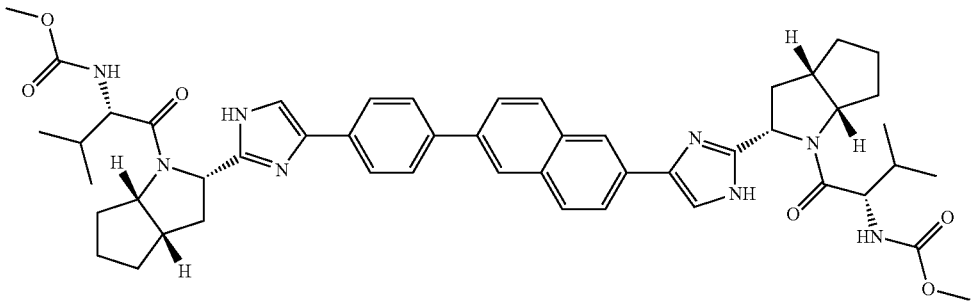

Methyl ((1S)-1-(((2S,3aS,6aS)-2-(4-(6-(4-(2-((2S,3aS,6aS)-1-((2S)-2-((methoxycarbonyl)amino)-3-methylbutanoyl)octahydrocyclopenta[b]pyrrol-2-yl)-1H-imidazol-4-yl)phenyl)-2-naphthyl)-1H-imidazol-2-yl)hexahydrocyclopenta[b]pyrrol-1(2H)-yl)carbonyl)-2-methylpropyl)carbamate HATU (60.9 mg, 0.160 mmol) was added to a stirred solution of an HCl salt of (2S,3aS,6aS)-2-(4-(4-(6-(2-((2S,3aS, 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 5% acetonitrile/95% H₂O/10 mM ammonium acetate and Solvent B was 5% H₂O/95% acetonitrile/10 mM ammonium acetate. MS data was determined using a MICROMASS® Platform for LC in electrospray mode.

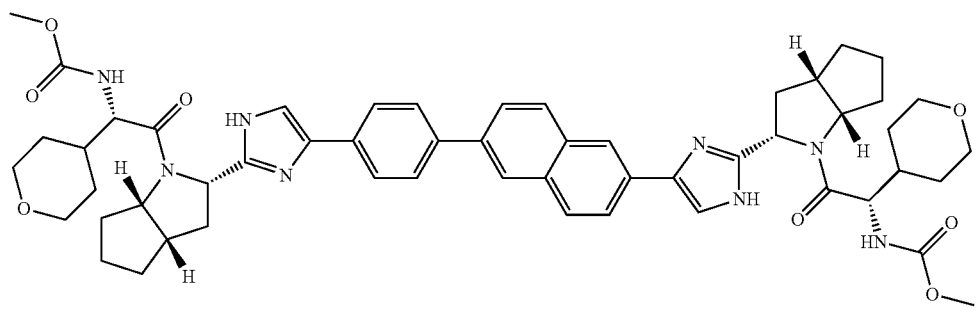

Methyl ((1S)-2-((2S,3aS,6aS)-2-(4-(4-(6-(2-((2S, 3aS,6aS)-1-((2S)-2-((methoxycarbonyl)amino)-2-(tetrahydro-2H-pyran-4-yl)acetyl)hexahydrocyclopenta[b]pyrrol-2(2H)-yl)-1H-imidazol-4-yl)-2-naphthyl)phenyl)-1H-imidazol-2-yl) hexahydrocyclopenta[b]pyrrol-1(2H)-yl)-2-oxo-1-(tetrahydro-2H-pyran-4-yl)ethyl)carbamate HATU (62.1 mg, 0.163 mmol) was added to a stirred solution of an HCl salt of (2S,3aS,6aS)-2-(4-(4-(6-(2-((2S,3aS, 6aS)-octahydrocyclopenta[b]pyrrol-2-yl)-1H-imidazol-4-yl)naphthalen-2-yl)phenyl)-1H-imidazol-2-yl) octahydrocyclopenta[b]pyrrole (51 mg, 0.073 mmol), (S)-2-(methoxycarbonylamino)-3-methylbutanoic acid (Intermediate 147) (52 mg, 0.074 mmol), (S)-2-(methoxycarbonylamino)-2-(tetrahydro-2H-pyran-4-yl)acetic acid (35.5 mg, 0.163 mmol) and DIPEA (0.078 mL, 0.45 mmol) in DCM (1.5 mL) and the mixture was stirred at rt for 2 h. The crude reaction mixture was concentrated to dryness and purified by preparative HPLC 9TFA buffer) to yield a TFA salt of methyl ((1S)-2-((2S,3aS,6aS)-2-(4-(4-(6-(2-((2S,3aS,6aS)-1-((2S)-2-((methoxycarbonyl)amino)-2-(tetrahydro-2H-pyran-4-yl)acetyl)hexahydrocyclopenta[b]pyrrol-2(2H)-yl)-1H-imidazol-4-yl)-2-naphthyl)phenyl)-1H-imidazol-2-yl) hexahydrocyclopenta[b]pyrrol-1(2H)-yl)-2-oxo-1-(tetrahydro-2H-pyran-4-yl)ethyl)carbamate (25.8 mg) as a white solid. LC-MS retention time 2.350 min; m/z 477.5 (½ MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 5% acetonitrile/95% $H_2O$/10 mM ammonium acetate and Solvent B was 5% $H_2O$/95% acetonitrile/10 mM ammonium acetate. MS data was determined using a MICROMASS® Platform for LC in electrospray mode.

3-Chloro-1-(((1R,3S,5R)-3-(4-(6-((2-((1R,3S,5R)-2-((3-chloro-5-methoxy-1-isoquinolinyl)carbonyl)-2-azabicyclo[3.1.0]hex-3-yl)-1H-imidazol-4-yl)ethynyl)-2-naphthyl)-1H-imidazol-2-yl)-2-azabicyclo [3.1.0]hex-2-yl)carbonyl)-5-methoxyisoquinoline HATU (48.1 mg, 0.127 mmol) was added to a solution of an HCl salt of (1R,3S,5R)-3-(5-(6-((2-((1R,3S,5R)-2-azabicyclo[3.1.0]hexan-3-yl)-1H-imidazol-4-yl)ethynyl)naphthalen-2-yl)-1H-imidazol-2-yl)-2-azabicyclo[3.1.0]hexane (Intermediate 124) (30 mg, 0.051 mmol) and 3-chloro-5-methoxyisoquinoline-1-carboxylic acid (30.1 mg, 0.127 mmol) in DMF (0.8 mL) and DIPEA (0.071 mL, 0.45 mmol) and stirred at rt overnight. The reaction was diluted with MeOH, filtered, and purified by preparative HPLC (MeOH/water with an $NH_4OAc$ buffer) and repurified by preparative HPLC (MeOH/water with a TFA buffer) to yield a TFA salt of 3-chloro-1-(((1R,3S,5R)-3-(4-(6-((2-((1R,3S,5R)-2-((3-chloro-5-methoxy-1-isoquinolinyl)carbonyl)-2-azabicyclo [3.1.0]hex-3-yl)-1H-imidazol-4-yl)ethynyl)-2-naphthyl)-1H-imidazol-2-yl)-2-azabicyclo[3.1.0]hex-2-yl)carbonyl)-5-methoxyisoquinoline (40.9 mg) as a yellow solid. LC-MS retention time 3.621 min; m/z 887.34 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode.

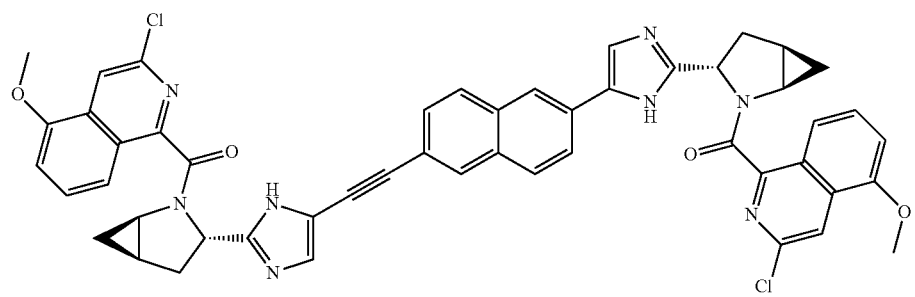 [SMILES: COc1cccc2c(C(=O)N3[C@@H]4C[C@@H]4C[C@H]3c3ncc(C#Cc4ccc5cc(-c6cnc([C@@H]7C[C@H]8C[C@H]8N7C(=O)c7nc(Cl)cc8c(OC)cccc78)[nH]6)ccc5c4)[nH]3)nc(Cl)cc12]

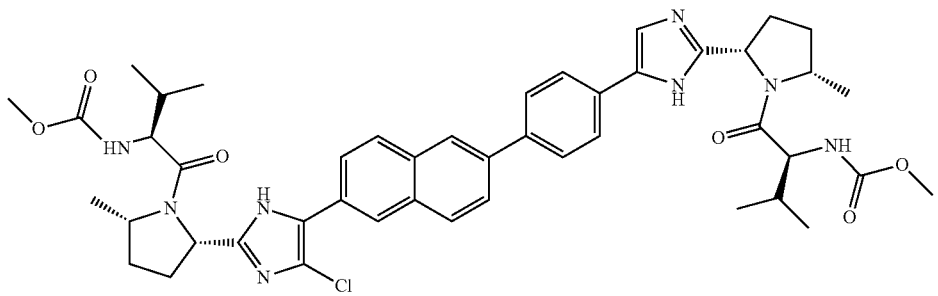

Methyl ((1S)-1-(((2S,5S)-2-(4-(4-(6-(4-chloro-2-((2S,5S)-1-((2S)-2-((methoxycarbonyl)amino)-3-methylbutanoyl)-5-methyl-2-pyrrolidinyl)-1H-imidazol-5-yl)-2-naphthyl)phenyl)-1H-imidazol-2-yl)-5-methyl-1-pyrrolidinyl)carbonyl)-2-methylpropyl) carbamate and

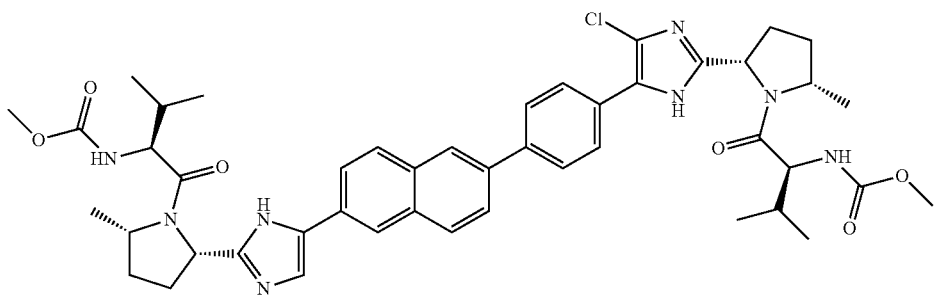

Methyl ((1S)-1-(((2S,5S)-2-(4-chloro-5-(4-(6-(2-((2S,5S)-1-((2S)-2-((methoxycarbonyl)amino)-3-methylbutanoyl)-5-methyl-2-pyrrolidinyl)-1H-imidazol-4-yl)-2-naphthyl)phenyl)-1H-imidazol-2-yl)-5-methyl-1-pyrrolidinyl)carbonyl)-2-methylpropyl) carbamate These two compounds were prepared in the reaction that prepared methyl ((1S)-1-(((2S,5S)-2-(4-chloro-5-(4-(6-(4-chloro-2-((2S,5S)-1-((2S)-2-((methoxycarbonyl)amino)-3-methylbutanoyl)-5-methyl-2-pyrrolidinyl)-1H-imidazol-5-yl)-2-naphthyl)phenyl)-1H-imidazol-2-yl)-5-methyl-1-pyrrolidinyl)carbonyl)-2-methylpropyl)carbamate (Example 87) and they were isolated as a mixture of mono-chloroimidazole regioisomers. The two regioisomers were separated by SCFC on a CHIRALCEL® OJ-H column (30×250 mm, 5 µm) using Solvents: 75% CO$_2$-25% EtOH/0.1% DEA. The absolute regiochemistry of the two mono-chloroimidazole regioisomers was not determined so each was arbitrarily assigned. Example 94: Methyl ((1S)-1-(((2S,5S)-2-(4-(4-(6-(4-chloro-2-((2S,5S)-1-((2S)-2-((methoxycarbonyl)amino)-3-methylbutanoyl)-5-methyl-2-pyrrolidinyl)-1H-imidazol-5-yl)-2-naphthyl)phenyl)-1H-imidazol-2-yl)-5-methyl-1-pyrrolidinyl)carbonyl)-2-methylpropyl)carbamate (18.6 mg) was isolated as a yellow solid. LC-MS retention time 3.756 min; m/z 851.62 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. Example 95: Methyl ((1S)-1-(((2S,5S)-2-(4-chloro-5-(4-(6-(2-((2S,5S)-1-((2S)-2-((methoxycarbonyl)amino)-3-methylbutanoyl)-5-methyl-2-pyrrolidinyl)-1H-imidazol-4-yl)-2-naphthyl)phenyl)-1H-imidazol-2-yl)-5-methyl-1-pyrrolidinyl)carbonyl)-2-methylpropyl)carbamate (24.1 mg) was isolated as a yellow solid. LC-MS retention time 3.770 min; m/z 851.64 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode.

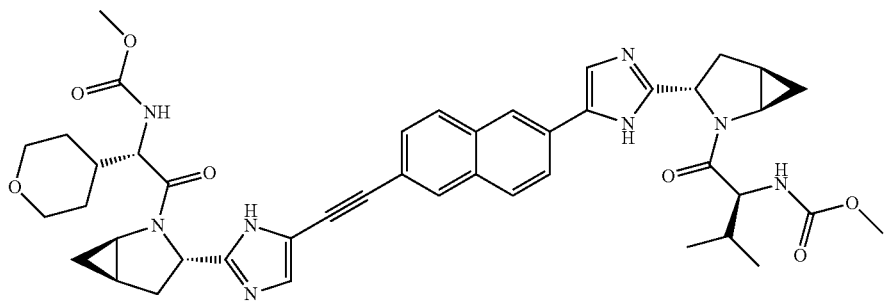 [SMILES: COC(=O)N[C@H](C(=O)N1[C@@H]2C[C@@H]2C[C@H]1c1ncc(-c2ccc3cc(C#Cc4cnc([C@@H]5C[C@H]6C[C@H]6N5C(=O)[C@@H](NC(=O)OC)C5CCOCC5)[nH]4)ccc3c2)[nH]1)C(C)C]

Methyl ((1S)-2-((1R,3S,5R)-3-(4-((6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)ethynyl)-1H-imidazol-2-yl)-2-azabicyclo[3.1.0]hex-2-yl)-2-oxo-1-(tetrahydro-2H-pyran-4-yl)ethyl)carbamate 4M HCl (0.370 mL, 1.48 mmol) in dioxane was added to a solution of (1R,3S,5R)-tert-butyl 3-(5-((6-(2-((1R,3S,5R)-2-((S)-2-(methoxycarbonylamino)-3-methylbutanoyl)-2-azabicyclo[3.1.0]hexan-3-yl)-1H-imidazol-5-yl)naphthalen-2-yl)ethynyl)-1H-imidazol-2-yl)-2-azabicyclo[3.1.0]hexane-2-carboxylate (Intermediate 150) (69 mg, 0.074 mmol) in dioxane (2 mL) and slurry was stirred for 1.5 h. The reaction mixture was then concentrated under a stream of nitrogen and the intermediate product was treated with (S)-2-(methoxycarbonylamino)-2-(tetrahydro-2H-pyran-4-yl)acetic acid (20.9 mg, 0.096 mmol), DMF (1.5 mL), DIPEA (0.078 mL, 0.44 mmol) and finally HATU (36.6 mg, 0.096 mmol). The reaction mixture was stirred at rt overnight, diluted with MeOH, filtered and purified by preparative HPLC (MeOH/water with 0.1% TFA) to yield a TFA salt of methyl ((1S)-2-((1R,3S,5R)-3-(4-((6-(2-((1R,3S,5R)-2-((2S)-2-((methoxycarbonyl)amino)-3-methylbutanoyl)-2-azabicyclo[3.1.0]hex-3-yl)-1H-imidazol-4-yl)-2-naphthyl)ethynyl)-1H-imidazol-2-yl)-2-azabicyclo[3.1.0]hex-2-yl)-2-oxo-1-(tetrahydro-2H-pyran-4-yl)ethyl)carbamate (35.3 mg) as a yellow solid. LC-MS retention time 2.726 min; m/z 803.74 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 8.27 (s, 1H), 8.18 (s, 1H), 8.06 (d, J=8.8 Hz, 1H), 7.98-8.02 (m, 2H), 7.88 (dd, J=8.7, 1.6 Hz, 1H), 7.74 (s, 1H), 7.67 (dd, J=8.5, 1.5 Hz, 1H), 5.15 (dd, J=9.3, 7.0 Hz, 1H), 5.09 (dd, J=9.0, 6.3 Hz, 1H), 4.59 (d, J=7.8 Hz, 1H), 4.56 (d, J=6.5 Hz, 1H), 3.91-4.00 (m, 2H), 3.74-3.84 (m, 2H), 3.67 (s, 6H), 3.34-3.45 (m, 2H), 2.70 (dd, J=13.6, 9.5 Hz, 1H), 2.61 (dd, J=13.8, 8.8 Hz, 1H), 2.40-2.54 (m, 2H), 2.14-2.23 (m, 1H), 2.01-2.13 (m, 3H), 1.56-1.64 (m, 1H), 1.38-1.55 (m, 3H), 1.05-1.14 (m, 2H), 1.01 (d, J=6.8 Hz, 3H), 0.92 (d, J=6.8 Hz, 3H), 0.82-0.92 (m, 2H).

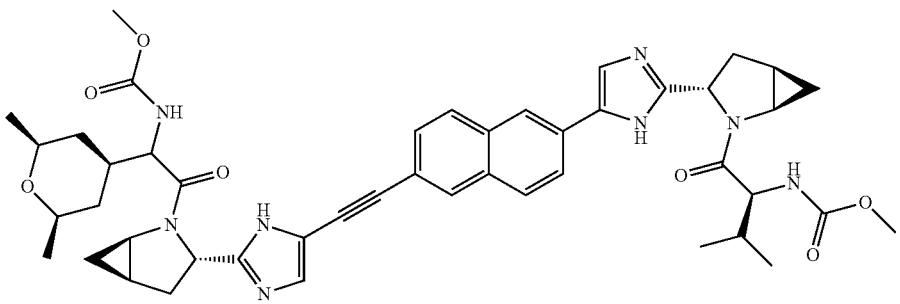

Methyl ((1S)-1-(((1R,3S,5R)-3-(4-(6-((2-((1R,3S,5R)-2-((2S)-2-((2R,4r,6S)-2,6-dimethyltetrahydro-2H-pyran-4-yl)-2-((methoxycarbonyl)amino)acetyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)carbonyl)-2-methylpropyl)carbamate 4M HCl (0.34 mL, 1.3 mmol) in dioxane was added to a solution of (1R,3S,5R)-tert-butyl 3-(5-((6-(2-((1R,3S,5R)-2-((S)-2-(methoxycarbonylamino)-3-methylbutanoyl)-2-azabicyclo[3.1.0]hexan-3-yl)-1H-imidazol-5-yl)naphthalen-2-yl)ethynyl)-1H-imidazol-2-yl)-2-azabicyclo[3.1.0]hexane-2-carboxylate (Intermediate 150) (62.7 mg, 0.067 mmol) in dioxane (2 mL) the slurry was stirred for 1.5 h. The reaction was then concentrated under a stream of nitrogen to dryness and then treated with 2-((2R,4r,6S)-2,6-dimethyltetrahydro-2H-pyran-4-yl)-2-(methoxycarbonylamino)acetic acid (Cap-179 stereoisomer 2) (21.45 mg, 0.087 mmol), DMF (1.5 mL), DIPEA (0.071 mL, 0.40 mmol) and finally HATU (33.3 mg, 0.087 mmol). The reaction mixture was stirred at rt overnight diluted with MeOH, filtered and purified by preparative HPLC (MeOH/water with 0.1% TFA) to yield a TFA salt of methyl ((1S)-1-(((1R,3S,5R)-3-(4-(6-((2-((1R,3S,5R)-2-((2S)-2-((2R,4r,6S)-2,6-dimethyltetrahydro-2H-pyran-4-yl)-2-((methoxycarbonyl)amino)acetyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)carbonyl)-2-methylpropyl)carbamate (28 mg) as a yellow solid. LC-MS retention time 2.898 min; m/z 831.80 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 8.27 (s, 1H), 8.17 (s, 1H), 8.05 (d, J=8.8 Hz, 1H), 7.98-8.02 (m, 2H), 7.88 (dd, J=8.5, 1.8 Hz, 1H), 7.74 (s, 1H), 7.66 (dd, J=8.5, 1.5 Hz, 1H), 5.15 (dd, J=9.2, 6.9 Hz, 1H), 5.10 (dd, J=9.0, 6.3 Hz, 1H), 4.56 (t, J=6.0 Hz, 2H), 3.73-3.85 (m, 2H), 3.67 (s, 6H), 3.43-3.54 (m, 2H), 2.70 (dd, J=13.7, 9.4 Hz, 1H), 2.61 (dd, J=13.6, 9.0 Hz, 1H), 2.40-2.54 (m, 2H), 2.01-2.23 (m, 4H), 1.55-1.64 (m, 1H), 1.46 (d, J=12.0 Hz, 1H), 1.17 (dd, J=6.0, 4.3 Hz, 6H), 1.04-1.13 (m, 3H), 1.01 (d, J=6.8 Hz, 3H), 0.96-1.03 (m, 1H), 0.92 (d, J=6.8 Hz, 3H), 0.88-0.93 (m, 1H), 0.82-0.87 (m, 1H).

1H-imidazol-4-yl)naphthalen-2-yl)ethynyl)-1H-imidazol-2-yl)-2-azabicyclo[3.1.0]hexane (Intermediate 154) (27 mg, 0.045 mmol) and (S)-2-(methoxycarbonylamino)-2-(tetrahydro-2H-pyran-4-yl)acetic acid (24.7 mg, 0.114 mmol) in DMF (1 mL) and DIPEA (0.056 mL, 0.32 mmol) and the reaction mixture was stirred at rt for 2 h. The reaction was concentrated under a stream of nitrogen, dissolved into MeOH, filtered and purified by preparative HPLC (MeOH/water with 0.1% TFA buffer) to yield a TFA salt of methyl ((1S)-2-((2S,5S)-2-(4-(6-((2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)ethynyl)-2-naphthyl)-1H-imidazol-2-yl)-5-methyl-1-pyrrolidinyl)-2-oxo-1-(tetrahydro-2H-pyran-4-yl)ethyl)carbamate (31.4 mg) as a yellow solid. LC-MS retention time 2.658 min; m/z 847.80 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. The $^1$H NMR presents as a −1:3.5 mixture of rotamers. The $^1$H NMR for the major rotamer is: $^1$H NMR (400 MHz, MeOD) δ ppm 8.29 (s, 1H), 8.18 (s, 1H),

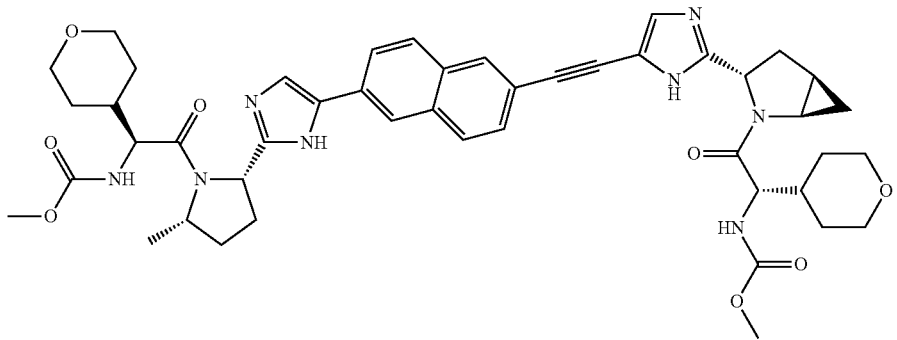 [SMILES: COC(=O)N[C@H](C(=O)N1[C@@H]2C[C@@H]2C[C@H]1c1ncc(C#Cc2ccc3cc(-c4cnc([C@@H]5CC[C@H](C)N5C(=O)[C@@H](NC(=O)OC)C5CCOCC5)[nH]4)ccc3c2)[nH]1)C1CCOCC1]

Methyl ((1S)-2-((2S,5S)-2-(4-(6-((2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)ethynyl)-2-naphthyl)-1H-imidazol-2-yl)-5-methyl-1-pyrrolidinyl)-2-oxo-1-(tetrahydro-2H-pyran-4-yl)ethyl)carbamate HATU (43.2 mg, 0.114 mmol) was added an HCl salt of (1R,3S,5R)-3-(4-((6-2-((2S,5S)-5-methylpyrrolidin-2-yl)-

8.06 (d, J=8.5 Hz, 1H), 8.01 (d, J=8.8 Hz, 1H), 7.99 (s, 1H), 7.89 (dd, J=8.7, 1.6 Hz, 1H), 7.74 (s, 1H), 7.67 (dd, J=8.4, 1.4 Hz, 1H), 5.19 (dd, J=10.5, 7.0 Hz, 1H), 5.09 (dd, J=8.9, 6.4 Hz, 1H), 4.59 (d, J=7.5 Hz, 1H), 4.22 (d, J=9.3 Hz, 1H), 3.86-4.00 (m, 4H), 3.72-3.82 (m, 2H), 3.67 (s, 6H), 3.23-3.45 (m, 4H), 2.50-2.70 (m, 2H), 2.24-2.50 (m, 3H), 1.90-2.13 (m, 4H), 1.70-1.85 (m, 1H), 1.57 (d, J=6.5 Hz, 3H), 1.30-1.64 (m, 6H), 1.23 (d, J=11.5 Hz, 1H), 1.04-1.12 (m, 1H), 0.85 (br. s., 1H).

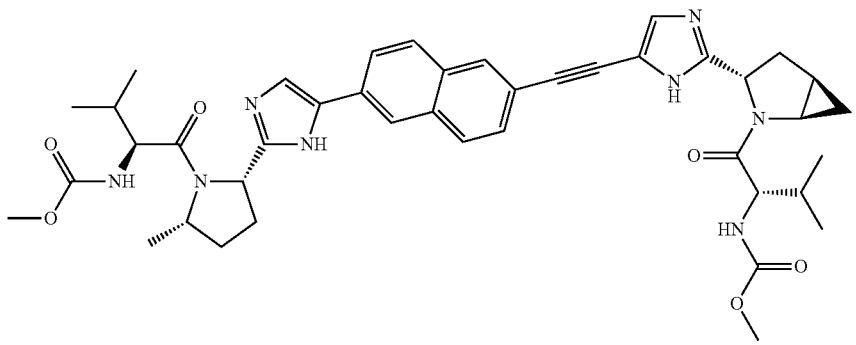 [SMILES: COC(=O)N[C@H](C(=O)N1[C@@H]2C[C@@H]2C[C@H]1c1ncc(C#Cc2ccc3cc(-c4cnc([C@@H]5CC[C@H](C)N5C(=O)[C@@H](NC(=O)OC)C(C)C)[nH]4)ccc3c2)[nH]1)C(C)C]

Methyl ((1S)-1-(((1R,3S,5R)-3-(4-((6-(2-((2S,5S)-1-((2S)-2-((methoxycarbonyl)amino)-3-methylbutanoyl)-5-methyl-2-pyrrolidinyl)-1H-imidazol-4-yl)-2-naphthyl)ethynyl)-1H-imidazol-2-yl)-2-azabicyclo[3.1.0]hex-2-yl)carbonyl)-2-methylpropyl)carbamate HATU (43.2 mg, 0.114 mmol) was added to a stirred solution of an HCl salt of (1R,3S,5R)-3-(4-((6-(2-((2S,5S)-5-methylpyrrolidin-2-yl)-1H-imidazol-4-yl)naphthalen-2-yl)ethynyl)-1H-imidazol-2-yl)-2-azabicyclo[3.1.0]hexane (Intermediate 154) (10.1 mg, 0.017 mmol) and (S)-2-(methoxycarbonylamino)-3-methylbutanoic acid (7.44 mg, 0.042 mmol) in DMF (0.5 mL) and DIPEA (0.021 mL, 0.119 mmol) and the reaction mixture was stirred at rt for 2 h. The reaction was concentrated, dissolved into MeOH, filtered and purified by preparative HPLC (MeOH/water with 0.1% TFA buffer) to yield a TFA salt of methyl ((1S)-1-(((1R,3S,5R)-3-(4-((6-(2-((2S,5S)-1-((2S)-2-((methoxycarbonyl)amino)-3-methylbutanoyl)-5-methyl-2-pyrrolidinyl)-1H-imidazol-4-yl)-2-naphthyl)ethynyl)-1H-imidazol-2-yl)-2-azabicyclo[3.1.0]hex-2-yl)carbonyl)-2-methylpropyl)carbamate (9.3 mg) as a yellow solid. LC-MS retention time 2.930 min; m/z 763.75 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR presents as a ~1:3 mixture of rotamers, the data for the major rotamer is: $^1$H NMR (400 MHz, MeOD) δ ppm 8.30 (s, 1H), 8.19 (s, 1H), 8.07 (d, J=8.8 Hz, 1H), 7.99-8.03 (m, 2H), 7.90 (dd, J=8.5, 1.5 Hz, 1H), 7.77 (s, 1H), 7.65-7.71 (m, 1H), 5.19 (dd, J=10.2, 6.9 Hz, 1H), 5.10 (dd, J=9.2, 6.4 Hz, 1H), 4.55 (d, J=6.5 Hz, 1H), 4.13 (d, J=8.8 Hz, 1H), 3.67 (s, 6H), 3.65-3.79 (m, 2H), 1.95-2.68 (m, 8H), 1.57 (d, J=6.5 Hz, 3H), 1.31 (d, J=6.3 Hz, 1H), 1.01 (d, J=7.0 Hz, 3H), 0.98 (d, J=7.0 Hz, 3H), 0.93 (d, J=6.8 Hz, 3H), 0.88 (d, J=6.8 Hz, 3H), 0.84-1.14 (m, 2H).

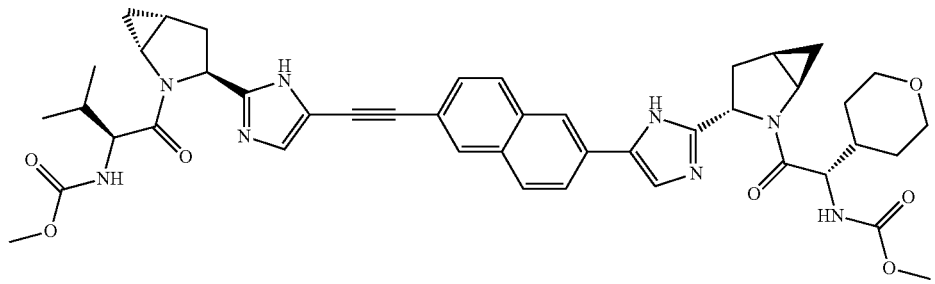

Methyl ((1S)-2-((1R,3S,5R)-3-(4-(6-((2-((1R,3S,5R)-2-((2S)-2-((methoxycarbonyl)amino)-3-methylbutanoyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)-2-oxo-1-(tetrahydro-2H-pyran-4-yl)ethyl)carbamate 4M HCl (0.32 mL, 1.3 mmol) in dioxane was added to mixture of a TFA salt of (1R,3S,5R)-tert-butyl 3-(5-(6-((2-((1R,3S,5R)-2-((S)-2-(methoxycarbonylamino)-3-methylbutanoyl)-2-azabicyclo[3.1.0]hexan-3-yl)-1H-imidazol-5-yl)ethynyl)naphthalen-2-yl)-1H-imidazol-2-yl)-2-azabicyclo[3.1.0]hexane-2-carboxylate (Intermediate 158) (60 mg, 0.064 mmol) in dioxane (0.5 mL) and the reaction was stirred vigorously for 4 h. The reaction was concentrated to dryness. Then (S)-2-(methoxycarbonylamino)-2-(tetrahydro-2H-pyran-4-yl)acetic acid (18.2 mg, 0.084 mmol), DMF (0.5 mL), DIPEA (0.067 mL, 0.39 mmol) and finally HATU (31.8 mg) were added to the crude material and the reaction was stirred at rt for 1 h. The reaction was partially concentrated with a stream on nitrogen, diluted with MeOH, filtered and purified preparative HPLC (MeOH/water with a TFA buffer) and then repurified preparative HPLC (MeOH/water with an ammonium acetate buffer). The material was purified a third time by preparative HPLC (MeOH/water with a TFA buffer) to yield a TFA salt of methyl ((1S)-2-((1R,3S,5R)-3-(4-(6-((2-((1R,3S,5R)-2-((2S)-2-((methoxycarbonyl)

amino)-3-methylbutanoyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)-2-oxo-1-(tetrahydro-2H-pyran-4-yl)ethyl)carbamate (27.7 mg) as a white solid. LC-MS retention time 3.291 min; m/z 803.67 (MH+). LC data was recorded on a Shimadzu LC-10AS liquid chromatograph equipped with a PHENOMENEX® Luna 3u C18 2.0× 50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 8.27 (s, 1H), 8.19 (s, 1H), 8.06 (d, J=8.8 Hz, 1H), 7.99-8.03 (m, 2H), 7.88 (dd, J=8.5, 1.8 Hz, 1H), 7.78 (s, 1H), 7.68 (dd, J=8.5, 1.5 Hz, 1H), 5.15 (dd, J=9.0, 7.0 Hz, 1H), 5.09 (dd, J=9.3, 6.5 Hz, 1H), 4.80 (d, 2H), 4.54 (d, J=6.5 Hz, 1H), 3.87-3.93 (m, 1H), 3.70-3.79 (m, 3H), 3.68 (s, 3H), 3.67 (s, 3H), 3.54-3.63 (m, 1H), 3.34-3.40 (m, 1H), 2.59-2.74 (m, 2H), 2.40-2.55 (m, 2H), 2.00-2.22 (m, 4H), 1.71-1.81 (m, 2H), 1.51-1.63 (m, 2H), 1.05-1.14 (m, 2H), 1.01 (d, J=6.8 Hz, 3H), 0.93 (d, J=6.8 Hz, 3H), 0.88 (br. s., 2H).

(60 mg, 0.064 mmol) in dioxane (0.5 mL) and the reaction was stirred vigorously for 4 h. The reaction was concentrated to dryness. Then (S)-2-(methoxycarbonylamino)-2-((S)-tetrahydro-2H-pyran-3-yl)acetic acid (Cap-177a) (18.2 mg, 0.084 mmol), DMF (0.5 mL), DIPEA (0.067 mL, 0.39 mmol) and finally HATU (32 mg, 0.084 mmol) was added to the crude material and the reaction was stirred at rt for 1 h. The reaction was partially concentrated, diluted with MeOH, filtered and purified by preparative HPLC (MeOH/water with a TFA buffer) and repurified in one injection by Prep HPLC (MeOH/water with an ammonium acetate buffer) to yield methyl ((1S)-2-((1R,3S,5R)-3-(4-(6-((2-((1R,3S,5R)-2-((2S)-2-((methoxycarbonyl)amino)-3-methylbutanoyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)-2-oxo-1-((3S)-tetrahydro-2H-pyran-3-yl)ethyl)carbamate (30.5 mg) as a white solid. LC-MS retention time 3.376 min; m/z 803.66 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10%

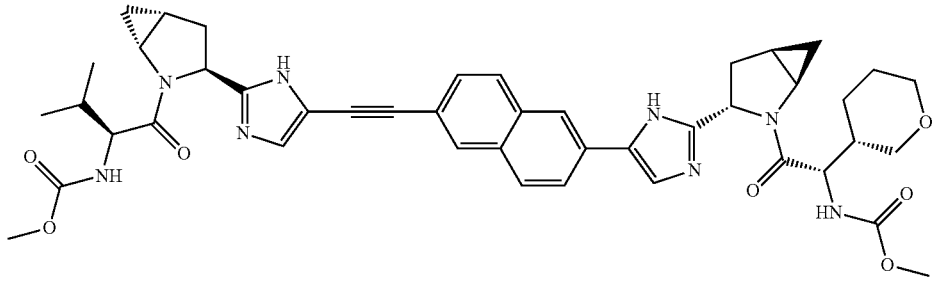

Methyl ((1S)-2-((1R,3S,5R)-3-(4-(6-((2-((1R,3S,5R)-2-((2S)-2-((methoxycarbonyl)amino)-3-methylbutanoyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)-2-oxo-1-((3S)-tetrahydro-2H-pyran-3-yl)ethyl)carbamate 4M HCl (0.3 mL, 1.3 mmol) in dioxane was added to mixture of a TFA salt of (1R,3S,5R)-tert-butyl 3-(5-(6-((2-((1R,3S,5R)-2-((S)-2-(methoxycarbonylamino)-3-methylbutanoyl)-2-azabicyclo[3.1.0]hexan-3-yl)-1H-imidazol-5-yl)ethynyl)naphthalen-2-yl)-1H-imidazol-2-yl)-2-azabicyclo[3.1.0]hexane-2-carboxylate (Intermediate 158)

MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 8.14 (s, 1H), 7.94 (s, 1H), 7.78-7.86 (m, 3H), 7.49 (dd, J=8.5, 1.5 Hz, 1H), 7.45 (s, 1H), 7.26 (s, 1H), 5.15 (ddd, J=12.9, 8.7, 4.5 Hz, 2H), 4.57 (d, J=6.8 Hz, 1H), 3.70-3.86 (m, 3H), 3.67 (br. s., 3H), 3.66 (br. s., 3H), 3.58-3.64 (m, 1H), 3.53 (t, J=8.3 Hz, 1H), 3.45 (dd, J=11.4, 8.2 Hz, 1H), 2.31-2.57 (m, 4H), 1.93-2.17 (m, 5H), 1.67-1.84 (m, 2H), 1.50-1.63 (m, 2H), 1.08-1.17 (m, 2H), 0.98 (d, J=6.8 Hz, 3H), 0.92 (d, J=6.8 Hz, 3H), 0.78 (br. s., 2H).

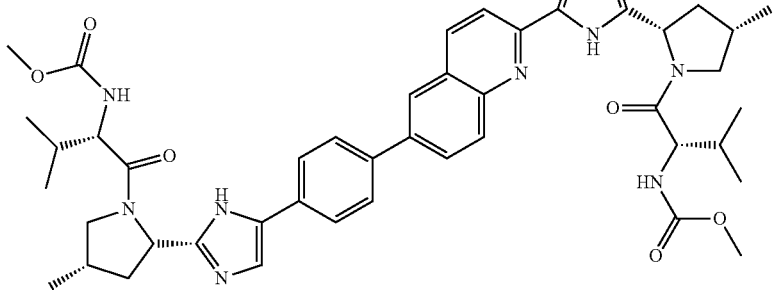

Methyl ((1S)-1-(((2S,4S)-2-(4-(6-(4-(2-((2S,4S)-1-((2S)-2-((methoxycarbonyl)amino)-3-methylbutanoyl)-4-methyl-2-pyrrolidinyl)-1H-imidazol-4-yl)phenyl)-2-quinolinyl)-1H-imidazol-2-yl)-4-methyl-1-pyrrolidinyl)carbonyl)-2-methylpropyl)carbamate HATU (20.99 mg, 0.055 mmol) was added to a solution of an HCl salt of 2-(2-((2S,4S)-4-methylpyrrolidin-2-yl)-1H-imidazol-5-yl)-6-(4-(2-((2S,4S)-4-methylpyrrolidin-2-yl)-1H-imidazol-5-yl)phenyl)quinoline (Intermediate 164) (16.5 mg, 0.024 mmol) and (S)-2-(methoxycarbonylamino)-3-methylbutanoic acid (9.7 mg, 0.055 mmol) in DMF (0.5 mL) and DIPEA (0.038 mL, 0.22 mmol) and the reaction mixture was stirred at rt for 16 h. The reaction was diluted with MeOH, filtered and purified by preparative HPLC ($H_2O$-MeOH with 0.1% TFA buffer) to yield a TFA salt of methyl ((1S)-1-(((2S,4S)-2-(4-(6-(4-(2-((2S,4S)-1-((2S)-2-((methoxycarbonyl)amino)-3-methylbutanoyl)-4-methyl-2-pyrrolidinyl)-1H-imidazol-4-yl)phenyl)-2-quinolinyl)-1H-imidazol-2-yl)-4-methyl-1-pyrrolidinyl)carbonyl)-2-methylpropyl)carbamate (8.3 mg, 6.94 µmol, 28.9% yield) as a yellow solid. LC-MS retention time 3.555 min; m/z 818.78 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1H$ NMR (400 MHz, MeOD) δ ppm 8.60 (d, J=8.5 Hz, 1H), 8.34 (d, J=1.8 Hz, 1H), 8.32 (s, 1H), 8.26-8.31 (m, 1H), 8.21-8.26 (m, 1H), 8.06 (d, J=8.5 Hz, 1H), 7.97-8.03 (m, 1H), 8.00 (d, J=8.5 Hz, 1H), 7.93 (s, 1H), 7.87-7.92 (m, 2H), 5.19-5.36 (m, 2H), 4.29-4.41 (m, 2H), 4.24 (t, J=6.9 Hz, 2H), 3.67 (s, 6H), 3.44 (q, J=11.0 Hz, 2H), 2.62-2.74 (m, 2H), 2.46-2.61 (m, 2H), 1.97-2.12 (m, 2H), 1.82-1.97 (m, 2H), 1.26 (dd, J=6.3, 3.3 Hz, 6H), 0.91-0.96 (m, 6H), 0.89 (dd, J=6.7, 5.1 Hz, 6H).

Methyl ((1S)-1-(((2S,5S)-2-(4-(6-(4-(2-((2S,5S)-1-((2S)-2-((methoxycarbonyl)amino)-3-methylbutanoyl)-5-methyl-2-pyrrolidinyl)-1H-imidazol-4-yl)phenyl)-2-quinolinyl)-1H-imidazol-2-yl)-5-methyl-1-pyrrolidinyl)carbonyl)-2-methylpropyl)carbamate HATU (15.74 mg, 0.041 mmol) was added to a solution of a crude HCl salt of 2-(2-((2S,5S)-5-methylpyrrolidin-2-yl)-1H-imidazol-5-yl)-6-(4-(2-((2S,5S)-5-methylpyrrolidin-2-yl)-1H-imidazol-5-yl)phenyl)quinoline (Intermediate 167) (12.35 mg, 0.018 mmol) and (S)-2-(methoxycarbonylamino)-3-methylbutanoic acid (7.25 mg, 0.041 mmol) in DMF (0.5 mL) and DIPEA (0.028 mL, 0.16 mmol) and the reaction mixture was stirred at rt for 16 h. The reaction was diluted with MeOH, filtered and purified by preparative HPLC ($H_2O$-MeOH with 0.1% TFA buffer) to yield a TFA salt of methyl ((1S)-1-(((2S,5S)-2-(4-(6-(4-(2-((2S,5S)-1-((2S)-2-((methoxycarbonyl)amino)-3-methylbutanoyl)-5-methyl-2-pyrrolidinyl)-1H-imidazol-4-yl)phenyl)-2-quinolinyl)-1H-imidazol-2-yl)-5-methyl-1-pyrrolidinyl)carbonyl)-2-methylpropyl)carbamate (3.9 mg) as a yellow solid. LC-MS retention time 3.616 min; m/z 818.73 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1H$ NMR (400 MHz, MeOD) δ ppm 8.68 (d, J=8.8 Hz, 1H), 8.39 (d, J=1.3 Hz, 1H), 8.30-8.35 (m, 2H), 8.26-8.31 (m, 1H), 8.16 (d, J=8.8 Hz, 1H), 7.99-8.06 (m, 3H), 7.89-7.94 (m, 2H), 5.14-5.31 (m, 2H), 4.14 (dd, J=8.8, 5.0 Hz, 2H), 3.68 (s, 6H), 2.47-2.59 (m, 2H), 2.23-2.43 (m, 4H), 1.95-2.10 (m, 4H), 1.56 (dd, J=6.7, 3.6 Hz, 6H), 1.01-1.07 (m, 2H), 0.99 (dd, J=6.7, 3.4 Hz, 6H), 0.89 (dd, J=6.8, 1.8 Hz, 6H).

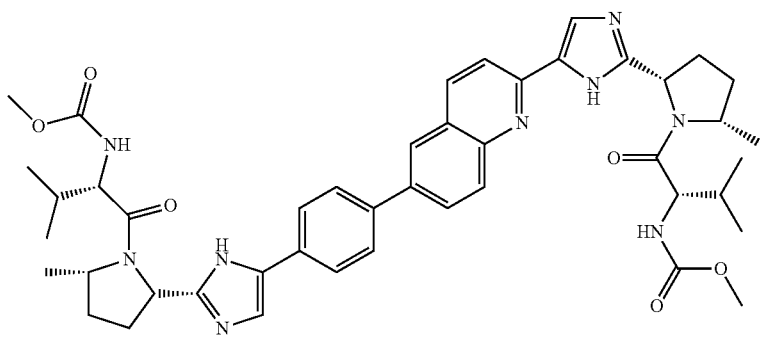

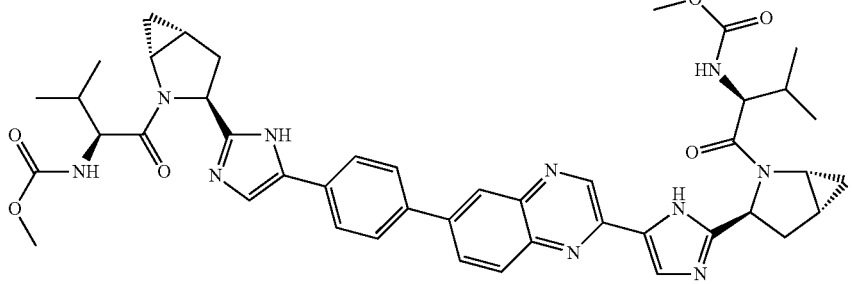

Methyl ((1S)-1-((((1R,3S,5R)-3-(4-(6-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-quinoxalinyl)-1H-imidazol-2-yl)-2-azabicyclo[3.1.0]hex-2-yl)carbonyl)-2-methylpropyl)carbamate HATU (50.7 mg, 0.133 mmol) was added to a solution of an HCl salt of methyl ((1S)-1-(((2S,4S)-2-(4-(6-(4-(2-((2S,4S)-1-((2S)-2-((methoxycarbonyl)amino)-3-methylbutanoyl)-4-methyl-2-pyrrolidinyl)-1H-imidazol-4-yl)phenyl)-2-quinolinyl)-1H-imidazol-2-yl)-4-methyl-1-pyrrolidinyl)carbonyl)-2-methylpropyl)carbamate (Intermediate 173) (41.7 mg, 0.058 mmol) and (S)-2-(methoxycarbonylamino)-3-methylbutanoic acid (23.4 mg, 0.133 mmol) in DMF (1 mL) and DIPEA (0.09 mL, 0.5 mmol) and the reaction mixture was stirred at rt for 16 h. The reaction was diluted with MeOH, filtered and purified by preparative HPLC (H₂O-MeOH with 0.1% TFA buffer) to yield a TFA salt of methyl ((1S)-1-(((1R,3S,5R)-3-(4-(6-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)-2-quinoxalinyl)-1H-imidazol-2-yl)-2-azabicyclo[3.1.0]hex-2-yl)carbonyl)-2-methylpropyl)carbamate (22.3 mg) as a yellow solid. LC-MS retention time 3.451 min; m/z 815.72 (MH+). LC data was recorded on a Shimadzu LC-10AS liquid chromatograph equipped with a PHENOMENEX® Luna 3u C18 2.0× 50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode. ¹H NMR (400 MHz, MeOD) δ ppm 9.41 (s, 1H), 8.43 (d, J=8.5 Hz, 1H), 8.41-8.47 (m, 1H), 8.28 (d, J=1.3 Hz, 2H), 8.03 (d, J=8.5 Hz, 1H), 8.00-8.07 (m, 1H), 7.87-7.95 (m, 3H), 5.10-5.26 (m, 2H), 4.57 (t, J=6.7 Hz, 2H), 3.76-3.89 (m, 2H), 3.68 (s, 6H), 2.70 (dd, J=13.7, 9.2 Hz, 2H), 2.44-2.56 (m, 2H), 2.14-2.26 (m, 2H), 2.04-2.14 (m, 2H), 1.07-1.16 (m, 2H), 1.02 (dd, J=6.8, 2.0 Hz, 6H), 0.93 (dd, J=6.8, 2.0 Hz, 6H), 0.83-0.99 (m, 2H).

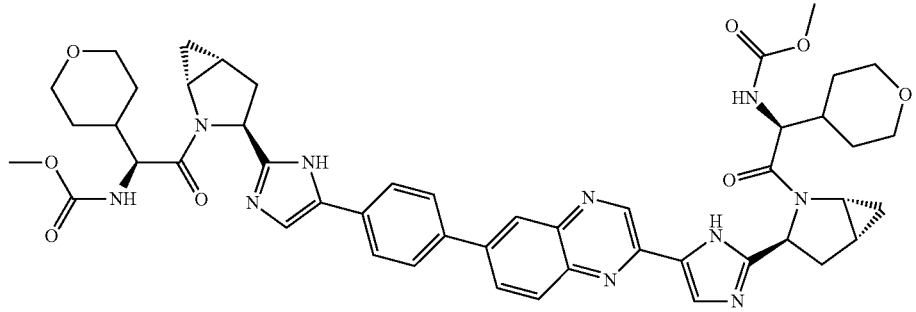 [SMILES: COC(=O)N[C@H](C(=O)N1[C@@H]2C[C@@H]2C[C@H]1c1ncc(-c2ccc(-c3ccc4nc(-c5cnc([C@@H]6C[C@H]7C[C@H]7N6C(=O)[C@@H](NC(=O)OC)C6CCOCC6)[nH]5)cnc4c3)cc2)[nH]1)C1CCOCC1]

Methyl ((1S)-2-((1R,3S,5R)-3-(4-(6-(4-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)phenyl)-2-quinoxalinyl)-1H-imidazol-2-yl)-2-azabicyclo[3.1.0]hex-2-yl)-2-oxo-1-(tetrahydro-2H-pyran-4-yl)ethyl)carbamate HATU (12.24 mg, 0.032 mmol) was added to a solution of an HCl salt of methyl ((1S)-1-(((2S,4S)-2-(4-(6-(4-(2-((2S,4S)-1-((2S)-2-((methoxycarbonyl)amino)-3-methylbutanoyl)-4-methyl-2-pyrrolidinyl)-1H-imidazol-4-yl)phenyl)-2-quinolinyl)-1H-imidazol-2-yl)-4-methyl-1-pyrrolidinyl)carbonyl)-2-methylpropyl)carbamate (Intermediate 173) (10.1 mg, 0.014 mmol) and (S)-2-(methoxycarbonylamino)-2-(tetrahydro-2H-pyran-4-yl)acetic acid (7.0 mg, 0.032 mmol) in DMF (0.5 mL) and DIPEA (0.022 mL, 0.13 mmol) and the reaction mixture was stirred at rt for 2 h. The reaction was diluted with MeOH, filtered and purified by preparative HPLC (H₂O-MeOH with 0.1% TFA buffer) to yield a TFA salt of methyl ((1S)-2-((1R,3S,5R)-3-(4-(6-(4-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)phenyl)-2-quinoxalinyl)-1H-imidazol-2-yl)-2-azabicyclo[3.1.0]hex-2-yl)-2-oxo-1-(tetrahydro-2H-pyran-4-yl)ethyl)carbamate (7.3 mg) as a yellow solid. LC-MS retention time 3.251 min; m/z 899.79 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 9.41 (s, 1H), 8.41-8.47 (m, 2H), 8.27-8.31 (m, 2H), 8.03 (d, J=8.5 Hz, 1H), 8.01-8.06 (m, 1H), 7.87-7.95 (m, 3H), 5.09-5.26 (m, 2H), 4.61 (t, J=7.2 Hz, 2H), 3.90-4.01 (m, 4H), 3.80-3.90 (m, 2H), 3.68 (s, 6H), 3.34-3.47 (m, 4H), 2.70 (dd, J=13.6, 9.3 Hz, 2H), 2.45-2.57 (m, 2H), 1.99-2.19 (m, 4H), 1.36-1.68 (m, 8H), 1.02-1.16 (m, 2H), 0.79-0.96 (m, 2H).

a stream of nitrogen, sealed and heated at 50° C. for 3 h. Additional N-chlorosuccinimide (5.0 mg) was added and the reaction vessel was flushed with nitrogen, sealed and heated at 50° C. for 3 h, then the reaction was cooled and concentrated under a stream on nitrogen. The remnants were dissolved into MeOH, filtered, and purified by preparative HPLC (MeOH/water with TFA buffer) to yield a TFA salt of methyl ((1S)-2-((1R,3S,5R)-3-(4-chloro-5-(6-((4-chloro-2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-5-yl)ethynyl)-2-naphthyl)-1H-imidazol-2-yl)-2-azabicyclo[3.1.0]hex-2-yl)-2-oxo-1-(tetrahydro-2H-pyran-4-yl)ethyl)carbamate (8.1 mg) as a yellow solid. LC-MS retention time 4.276 min; m/z 457.47 (½ MH+). LC data was recorded on a Shimadzu LC-10AS liquid chromatograph equipped with a PHENOMENEX® Luna 3u C18 2.0×50 mm column using a SPD-10AV UV-Vis detector at a

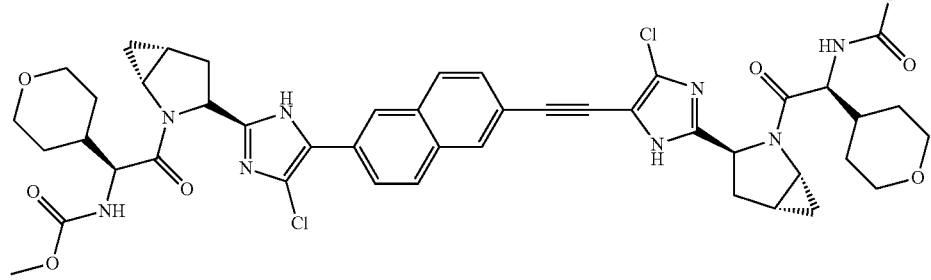

Methyl ((1S)-2-((1R,3S,5R)-3-(4-chloro-5-(6-((4-chloro-2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-5-yl)ethynyl)-2-naphthyl)-1H-imidazol-2-yl)-2-azabicyclo[3.1.0]hex-2-yl)-2-oxo-1-(tetrahydro-2H-pyran-4-yl)ethyl)carbamate N-Chlorosuccinimide (6.97 mg, 0.052 mmol) was added to a stirred solution of methyl ((1S)-2-((1R,3S,5R)-3-(4-(6-((2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)ethynyl)-2-naphthyl)-1H-imidazol-2-yl)-2-azabicyclo[3.1.0]hex-2-yl)-2-oxo-1-(tetrahydro-2H-pyran-4-yl)ethyl)carbamate (Example 82) (21.0 mg, 0.025 mmol) in DMF and then the reaction vessel was flushed with detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 8.18 (s, 1H), 8.07 (s, 1H), 7.98 (d, J=8.8 Hz, 1H), 7.93 (d, J=8.5 Hz, 1H), 7.88 (dd, J=8.8, 1.8 Hz, 1H), 7.59 (dd, J=8.5, 1.5 Hz, 1H), 5.05 (dd, J=8.5, 6.3 Hz, 1H), 4.99 (t, J=6.9 Hz, 1H), 4.62 (d, J=7.5 Hz, 2H), 3.91-3.98 (m, 4H), 3.74-3.81 (m, 1H), 3.68-3.72 (m, 1H), 3.67 (s, 6H), 3.34-3.45 (m, 4H), 2.45-2.56 (m, 2H), 2.39-2.44 (m, 2H), 1.96-2.11 (m, 4H), 1.37-1.66 (m, 8H), 1.05-1.14 (m, 2H), 0.74-0.84 (m, 2H).

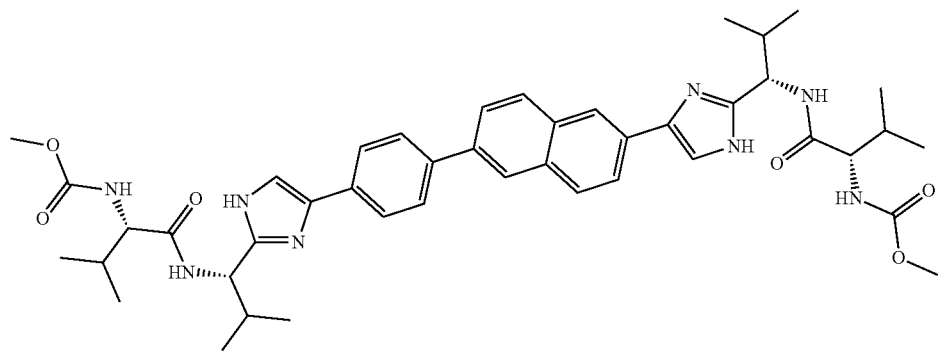

Methyl ((1S)-1-(((1S)-1-(4-(4-(6-(2-((1S)-1-(((2S)-2-((methoxycarbonyl)amino)-3-methylbutanoyl)amino)-2-methylpropyl)-1H-imidazol-4-yl)-2-naphthyl)phenyl)-1H-imidazol-2-yl)-2-methylpropyl)carbamoyl)-2-methylpropyl)carbamate HATU (77 mg, 0.20 mmol) was added to a stirred solution of an HCl salt of (S)-1-(5-(4-(6-(2-((S)-1-amino-2-methylpropyl)-1H-imidazol-4-yl)naphthalen-2-yl)phenyl)-1H-imidazol-2-yl)-2-methylpropan-1-amine (Intermediate 178) (57.4 mg, 0.092 mmol), (S)-2-(methoxycarbonylamino)-3-methylbutanoic acid (35.4 mg, 0.202 mmol) and DIPEA (0.096 mL, 0.55 mmol) in DCM (1.5 mL) and the reaction mixture was stirred at rt for 2 h. The crude reaction mixture was concentrated to dryness and purified by preparative HPLC (TFA buffer) to yield a TFA salt of methyl ((1S)-1-(((1S)-1-(4-(4-(6-(2-((1S)-1-(((2S)-2-((methoxycarbonyl)amino)-3-methylbutanoyl)amino)-2-methylpropyl)-1H-imidazol-4-yl)-2-naphthyl)phenyl)-1H-imidazol-2-yl)-2-methylpropyl)carbamoyl)-2-methylpropyl)carbamate (60.4 mg) as a white solid. LC-MS retention time 2.253 min; m/z 759.6 (MH−). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 5% acetonitrile/95% $H_2O$/10 mM ammonium acetate and Solvent B was 5% $H_2O$/95% acetonitrile/10 mM ammonium acetate. MS data was determined using a MICROMASS® Platform for LC in electrospray mode.

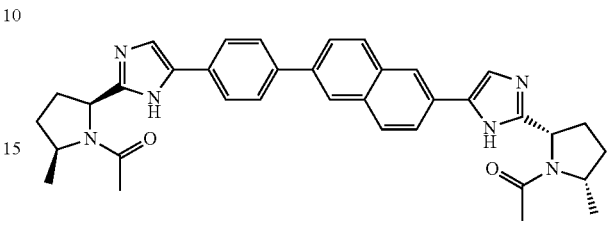

2-((2S,5S)-1-Acetyl-5-methyl-2-pyrrolidinyl)-4-(4-(6-(2-((2S,5S)-1-acetyl-5-methyl-2-pyrrolidinyl)-1H-imidazol-4-yl)-2-naphthyl)phenyl)-1H-imidazole HATU (63.2 mg, 0.166 mmol) was added to a solution of 2-((2S,5S)-5-methyl-2-pyrrolidinyl)-4-(4-(6-(2-((2S,5S)-5-methyl-2-pyrrolidinyl)-1H-imidazol-4-yl)-2-naphthyl)phenyl)-1H-imidazole (Intermediate 117) (contaminated with ammonium acetate) (38 mg, 0.076 mmol) and (S)-2-((2R,4r,6S)-2,6-dimethyltetrahydro-2H-pyran-4-yl)-2-(methoxycarbonylamino)acetic acid (40.8 mg, 0.166 mmol) in DMF (1.0 mL) and DIPEA (0.053 mL, 0.30 mmol) and the reaction was at rt overnight. The reaction mixture was diluted with MeOH,

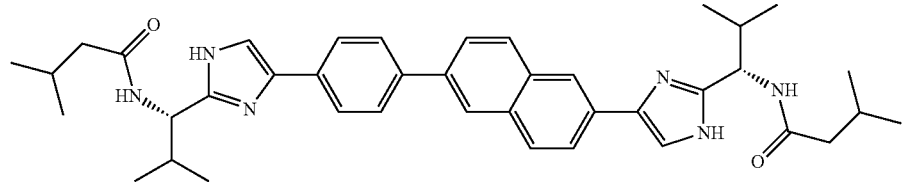 [SMILES: CC(C)CC(=O)N[C@H](c1nc(-c2ccc(-c3ccc4cc(-c5c[nH]c([C@@H](NC(=O)CC(C)C)C(C)C)n5)ccc4c3)cc2)c[nH]1)C(C)C]

3-Methyl-N-((1S)-2-methyl-1-(4-(4-(6-(2-((1S)-2-methyl-1-((3-methylbutanoyl)amino)propyl)-1H-imidazol-4-yl)-2-naphthyl)phenyl)-1H-imidazol-2-yl)propyl)butanamide HATU (119 mg, 0.313 mmol) was added to a stirred solution of an HCl salt of (S)-1-(5-(4-(6-(2-((S)-1-amino-2-methylpropyl)-1H-imidazol-4-yl)naphthalen-2-yl)phenyl)-1H-imidazol-2-yl)-2-methylpropan-1-amine (Intermediate 178) (89 mg, 0.142 mmol), 3-methylbutanoic acid (32 mg, 0.31 mmol) and DIPEA (0.149 mL, 0.855 mmol) in DCM (2 mL) and the reaction mixture was stirred at rt for 2 h. The crude reaction mixture was concentrated to dryness and purified twice by preparative HPLC (TFA buffer) to yield a TFA salt of 3-methyl-N-((1S)-2-methyl-1-(4-(4-(6-(2-((1S)-2-methyl-1-((3-methylbutanoyl)amino)propyl)-1H-imidazol-4-yl)-2-naphthyl)phenyl)-1H-imidazol-2-yl)propyl)butanamide (54.6 mg) as a beige solid. LC-MS retention time 2.375 min; m/z 645.6 (MH−). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 5% acetonitrile/95% $H_2O$/10 mM ammonium acetate and Solvent B was 5% $H_2O$/95% acetonitrile/10 mM ammonium acetate. MS data was determined using a MICROMASS® Platform for LC in electrospray mode.

filtered and purified by preparative HPLC (MeOH/water with a TFA buffer) to yield a TFA salt of 2-((2S,5S)-1-acetyl-5-methyl-2-pyrrolidinyl)-4-(4-(6-(2-((2S,5S)-1-acetyl-5-methyl-2-pyrrolidinyl)-1H-imidazol-4-yl)-2-naphthyl)phenyl)-1H-imidazole (20 mg) as a yellow solid. LC-MS retention time 3.123 min; m/z 587.62 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) ppm 8.30 (s, 1H), 8.27 (s, 1H), 8.13 (d, J=8.8 Hz, 1H), 8.09 (d, J=8.8 Hz, 1H), 7.93-8.01 (m, 4H), 7.84-7.91 (m, 4H), 5.25 (q, J=8.4 Hz, 2H), 4.31-4.40 (m, 2H), 2.53-2.66 (m, 2H), 2.28-2.40 (m, 4H), 2.25 (s, 3H), 2.25 (s, 3H), 1.88-1.97 (m, 2H), 1.47 (dd, J=6.5, 3.5 Hz, 6H), 1.14-1.19 (m, 1H).

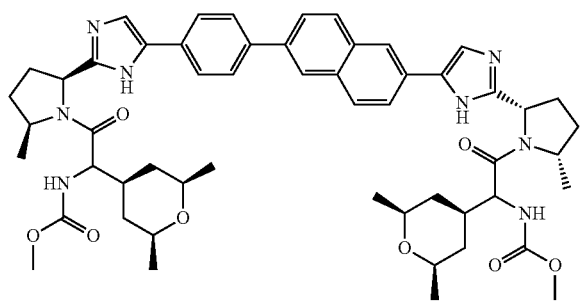 [SMILES: COC(=O)NC(C(=O)N1[C@@H](C)CC[C@H]1c1ncc(-c2ccc(-c3ccc4cc(-c5cnc([C@@H]6CC[C@H](C)N6C(=O)C(NC(=O)OC)[C@H]6C[C@@H](C)O[C@@H](C)C6)[nH]5)ccc4c3)cc2)[nH]1)[C@H]1C[C@@H](C)O[C@@H](C)C1]

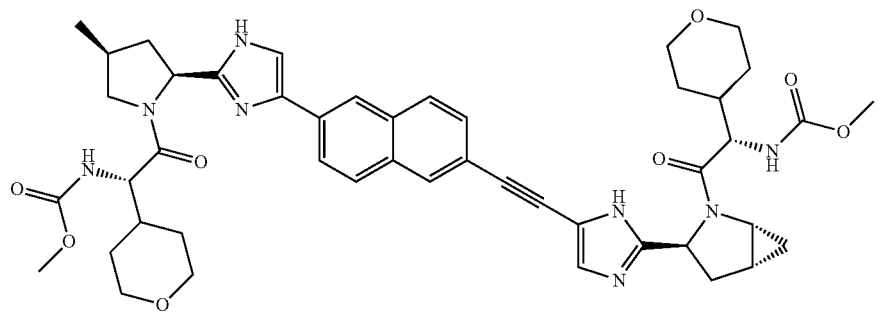 [SMILES: COC(=O)N[C@H](C(=O)N1C[C@@H](C)C[C@H]1c1nc(-c2ccc3cc(C#Cc4cnc([C@@H]5C[C@H]6C[C@H]6N5C(=O)[C@@H](NC(=O)OC)C5CCOCC5)[nH]4)ccc3c2)c[nH]1)C1CCOCC1]

Methyl (1-((2R,4r,6S)-2,6-dimethyltetrahydro-2H-pyran-4-yl)-2-((2S,5S)-2-(4-(4-(6-(2-((2S,5S)-1-(((2R,4r,6S)-2,6-dimethyltetrahydro-2H-pyran-4-yl)((methoxycarbonyl)amino)acetyl)-5-methyl-2-pyrrolidinyl)-1H-imidazol-4-yl)-2-naphthyl)phenyl)-1H-imidazol-2-yl)-5-methyl-1-pyrrolidinyl)-2-oxoethyl)carbamate HATU (61.9 mg, 0.163 mmol) was added to a solution of an HCl salt of 2-((2S,5S)-5-methyl-2-pyrrolidinyl)-4-(4-(6-(2-((2S,5S)-5-methyl-2-pyrrolidinyl)-1H-imidazol-4-yl)-2-naphthyl)phenyl)-1H-imidazole (Intermediate 117) (48 mg, 0.074 mmol) and 2-((2R,4r,6S)-2,6-dimethyltetrahydro-2H-pyran-4-yl)-2-(methoxycarbonylamino)acetic acid (Cap-179 stereoisomer 2) (39.9 mg, 0.163 mmol) in DMF (0.8 mL) and DIPEA (0.09 mL, 0.52 mmol) and the reaction was stirred rt for 2 h. The reaction was diluted with MeOH, filtered and purified in two injections by prep HPLC (MeOH/water with TFA buffer) to yield a TFA salt of methyl (1-((2R,4r,6S)-2,6-dimethyltetrahydro-2H-pyran-4-yl)-2-((2S,5S)-2-(4-(4-(6-(2-((2S,5S)-1-(((2R,4r,6S)-2,6-dimethyltetrahydro-2H-pyran-4-yl)((methoxycarbonyl)amino)acetyl)-5-methyl-2-pyrrolidinyl)-1H-imidazol-4-yl)-2-naphthyl)phenyl)-1H-imidazol-2-yl)-5-methyl-1-pyrrolidinyl)-2-oxoethyl)carbamate (55.5 mg) as a light yellow solid. LC-MS retention time 3.506 min; m/z 479.54 (½ MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. The $^1$H NMR presented as a complex mixture of rotamers.

Methyl ((1S)-2-((2S,4S)-2-(4-(6-((2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)ethynyl)-2-naphthyl)-1H-imidazol-2-yl)-4-methyl-1-pyrrolidinyl)-2-oxo-1-(tetrahydro-2H-pyran-4-yl)ethyl)carbamate HATU (23.99 mg, 0.063 mmol) was added to a solution of an HCl salt of (1R,3S,5R)-3-(4-((6-(2-((2S,4S)-4-methylpyrrolidin-2-yl)-1H-imidazol-4-yl)naphthalen-2-yl)ethynyl)-1H-imidazol-2-yl)-2-azabicyclo[3.1.0]hexane (Intermediate 175) (15 mg, 0.025 mmol) and (S)-2-(methoxycarbonylamino)-2-(tetrahydro-2H-pyran-4-yl)acetic acid (13.70 mg, 0.063 mmol) in DMF (0.4 mL) and DIPEA (0.03 mL, 0.2 mmol) and the reaction was stirred at rt for 1.5 h. The reaction was diluted with MeOH, filtered and purified in two injections by preparative HPLC (MeOH/water with TFA buffer) to a TFA salt of methyl ((1S)-2-((2S,4S)-2-(4-(6-((2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)ethynyl)-2-naphthyl)-1H-imidazol-2-yl)-4-methyl-1-pyrrolidinyl)-2-oxo-1-(tetrahydro-2H-pyran-4-yl)ethyl)carbamate (12.0 mg) as a yellow solid. LC-MS retention time 3.040 min; m/z 847.76 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 8.28 (s, 1H), 8.18 (s, 1H), 8.05 (d, J=8.8 Hz, 1H), 7.97-8.02 (m, 2H), 7.88 (dd, J=8.8, 1.8 Hz, 1H), 7.76 (s, 1H), 7.67 (dd, J=8.4, 1.4 Hz, 1H), 5.23 (dd, J=10.9, 6.9 Hz, 1H), 5.09 (dd, J=9.0, 6.5 Hz, 1H), 4.59 (d, J=7.8 Hz, 1H), 4.34-4.41 (m, 1H), 4.28 (d, J=8.0 Hz, 1H), 3.86-4.00 (m, 4H), 3.75-3.81 (m, 1H), 3.67 (s, 3H), 3.67 (s, 3H), 3.32-3.50 (m, 5H), 2.39-2.74 (m, 4H), 1.87-2.13 (m, 4H), 1.27-1.65 (m, 8H), 1.25 (d, J=6.3 Hz, 3H), 1.04-1.14 (m, 1H), 0.86 (br. s., 1H).

min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 8.28 (s, 1H), 8.18 (s, 1H), 8.05 (d, J=8.8 Hz, 1H), 7.98-8.03 (m, 2H), 7.88 (dd, J=8.7, 1.6 Hz, 1H), 7.76 (s, 1H), 7.67 (dd, J=8.5, 1.5 Hz, 1H), 5.24 (dd, J=10.9, 7.2 Hz, 1H), 5.10 (dd,

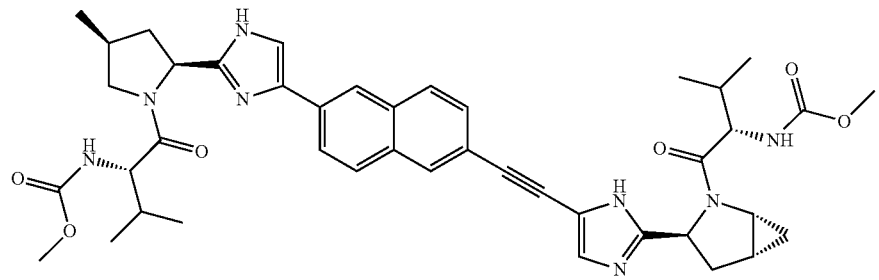 [SMILES: COC(=O)N[C@H](C(=O)N1C[C@@H](C)C[C@H]1c1nc(-c2ccc3cc(C#Cc4cnc([C@@H]5C[C@H]6C[C@H]6N5C(=O)[C@@H](NC(=O)OC)C(C)C)[nH]4)ccc3c2)c[nH]1)C(C)C]

Methyl ((1S)-1-(((2S,4S)-2-(4-(6-((2-((1R,3S,5R)-2-((2S)-2-((methoxycarbonyl)amino)-3-methylbutanoyl)-2-azabicyclo[3.1.0]hex-3-yl)-1H-imidazol-4-yl)ethynyl)-2-naphthyl)-1H-imidazol-2-yl)-4-methyl-1-pyrrolidinyl)carbonyl)-2-methylpropyl) carbamate HATU (60.8 mg, 0.160 mmol) was added to a solution of an HCl salt of (1R,3S,5R)-3-(4-((6-(2-((2S,4S)-4-methylpyrrolidin-2-yl)-1H-imidazol-4-yl)naphthalen-2-yl)ethynyl)-1H-imidazol-2-yl)-2-azabicyclo[3.1.0]hexane (Intermediate 175) (38 mg, 0.064 mmol) and (S)-2-(methoxycarbonylamino)-3-methylbutanoic acid (28.0 mg, 0.160 mmol) in DMF (0.7 mL) and DIPEA (0.08 mL, 0.4 mmol) and stirred at rt for 1.5 h. The reaction was diluted with MeOH, filtered and purified twice by preparative HPLC (MeOH/water with TFA buffer) to yield a TFA salt methyl ((1S)-1-(((2S,4S)-2-(4-(6-((2-((1R,3S,5R)-2-((2S)-2-((methoxycarbonyl)amino)-3-methylbutanoyl)-2-azabicyclo[3.1.0]hex-3-yl)-1H-imidazol-4-yl)ethynyl)-2-naphthyl)-1H-imidazol-2-yl)-4-methyl-1-pyrrolidinyl)carbonyl)-2-methylpropyl)carbamate (19.1 mg) as an off-white solid. LC-MS retention 3.288 time min; m/z 763.74 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1

J=9.0, 6.5 Hz, 1H), 4.55 (d, J=6.5 Hz, 1H), 4.30-4.37 (m, 1H), 4.23 (d, J=7.3 Hz, 1H), 3.72-3.79 (m, 1H), 3.67 (s, 3H), 3.66 (s, 3H), 3.43 (t, J=10.4 Hz, 1H), 2.49-2.74 (m, 3H), 2.44 (ddd, J=13.6, 6.7, 6.4 Hz, 1H), 2.11-2.22 (m, 1H), 1.98-2.11 (m, 2H), 1.89 (q, J=12.0 Hz, 1H), 1.25 (d, J=6.3 Hz, 3H), 1.06-1.15 (m, 1H), 1.00 (d, J=6.8 Hz, 3H), 0.95-0.98 (m, 1H), 0.94 (d, J=4.0 Hz, 3H), 0.92 (d, J=3.8 Hz, 3H), 0.88 (d, J=6.8 Hz, 3H).

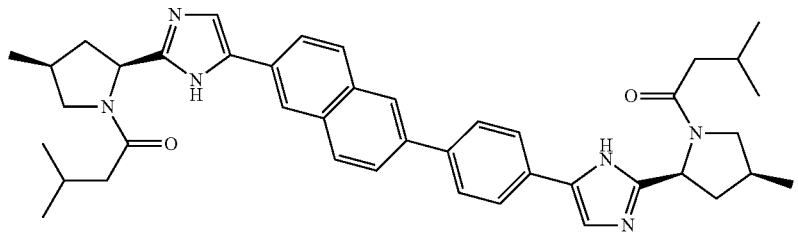

2-((2S,4S)-4-Methyl-1-(3-methylbutanoyl)-2-pyrrolidinyl)-4-(4-(6-(2-((2S,4S)-4-methyl-1-(3-methylbutanoyl)-2-pyrrolidinyl)-1H-imidazol-4-yl)-2-naphthyl)phenyl)-1H-imidazole HATU (76 mg, 0.200 mmol) was added to a solution of an HCl salt of 2-((2S,4S)-4-methylpyrrolidin-2-yl)-5-(4-(6-(2-((2S,4S)-4-methylpyrrolidin-2-yl)-1H-imidazol-5-yl)naphthalen-2-yl)phenyl)-1H-imidazole (Intermediate 196) (64.8 mg, 0.1 mmol), 3-methylbutanoic acid (22.5 mg, 0.220 mmol) and DIPEA (0.122 mL, 0.700 mmol) in DCM (2 mL) and the mixture was stirred rt overnight. The reaction mixture was evaporated to dryness and then purified by preparative HPLC to afford a TFA salt of 2-((2S,4S)-4-methyl-1-(3-methylbutanoyl)-2-pyrrolidinyl)-4-(4-(6-(2-((2S,4S)-4-methyl-1-(3-methylbutanoyl)-2-pyrrolidinyl)-1H-imidazol-4-yl)-2-naphthyl)phenyl)-1H-imidazole (61.7 mg) as an off-white solid. LC-MS retention time 1.853 min; m/z 671.64 (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% H₂O/ 0.1% trifluoroacetic acid and Solvent B was 10% H₂O/90% MeOH/0.1% trifluoroacetic acid. MS data was determined using a MICROMASS® Platform for LC in electrospray mode.

Hz, 1H), 8.00 (d, J=8.5 Hz, 1H), 7.97-8.04 (m, 1H), 7.89 (d, J=8.5 Hz, 1H), 7.85-7.95 (m, 2H), 5.17-5.33 (m, 2H), 4.32-4.45 (m, 2H), 4.28 (dd, J=8.2, 5.4 Hz, 2H), 3.83-3.98 (m, 4H), 3.67 (s, 6H), 3.22-3.54 (m, 6H), 2.63-2.75 (m, 2H), 2.46-2.61 (m, 2H), 1.83-2.04 (m, 4H), 1.52-1.64 (m, 2H), 1.30-1.53 (m, 6H), 1.26 (dd, J=6.3, 4.0 Hz, 6H).

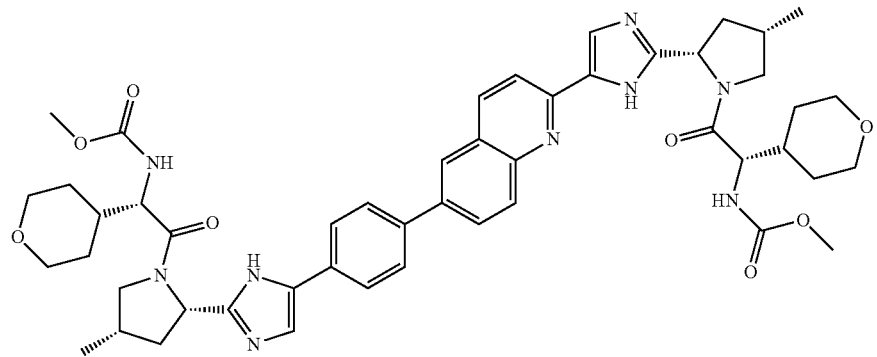 [SMILES: COC(=O)N[C@H](C(=O)N1C[C@@H](C)C[C@H]1c1ncc(-c2ccc(-c3ccc4nc(-c5cnc([C@@H]6C[C@H](C)CN6C(=O)[C@@H](NC(=O)OC)C6CCOCC6)[nH]5)ccc4c3)cc2)[nH]1)C1CCOCC1]

Methyl ((1S)-2-((2S,4S)-2-(4-(6-(4-(2-((2S,4S)-1-((2S)-2-((methoxycarbonyl)amino)-2-(tetrahydro-2H-pyran-4-yl)acetyl)-4-methyl-2-pyrrolidinyl)-1H-imidazol-4-yl)phenyl)-2-quinolinyl)-1H-imidazol-2-yl)-4-methyl-1-pyrrolidinyl)-2-oxo-1-(tetrahydro-2H-pyran-4-yl)ethyl)carbamate HATU (12.75 mg, 0.034 mmol) was added to a solution of 2-(2-((2S,4S)-4-methylpyrrolidin-2-yl)-1H-imidazol-4-yl)-6-(4-(2-((2S,4S)-4-methylpyrrolidin-2-yl)-1H-imidazol-5-yl)phenyl)quinoline (Intermediate 164) (10 mg, 0.015 mmol) and (S)-2-(methoxycarbonylamino)-2-(tetrahydro-2H-pyran-4-yl)acetic acid (7.28 mg, 0.034 mmol) in DMF (0.5 mL) and DIPEA (0.023 mL, 0.13 mmol) and the mixture was stirred at rt for 16 h. The reaction was concentrated and the residue was purified by preparative HPLC (H₂O-MeOH with 0.1% TFA buffer) to yield a TFA salt of methyl ((1S)-2-((2S, 4S)-2-(4-(6-(4-(2-((2S,4S)-1-((2S)-2-((methoxycarbonyl) amino)-2-(tetrahydro-2H-pyran-4-yl)acetyl)-4-methyl-2-pyrrolidinyl)-1H-imidazol-4-yl)phenyl)-2-quinolinyl)-1H-imidazol-2-yl)-4-methyl-1-pyrrolidinyl)-2-oxo-1-(tetrahydro-2H-pyran-4-yl)ethyl)carbamate (8.6 mg) as a yellow solid. LC-MS retention time 3.243 min; m/z 902.90 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/ 0.1% trifluoroacetic acid and Solvent B was 10% H₂O/90% MeOH/0.1% trifluoroacetic acid. MS data was determined using a MICROMASS® Platform for LC in electrospray mode. ¹H NMR (400 MHz, MeOD) δ ppm 8.61 (d, J=8.8 Hz, 1H), 8.35 (d, J=1.8 Hz, 1H), 8.22-8.33 (m, 3H), 8.07 (d, J=8.8

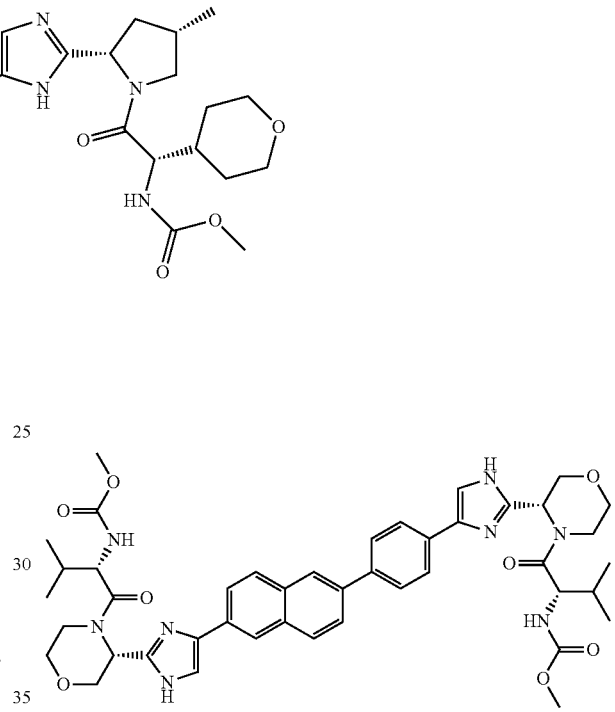

Methyl ((1S)-1-(((3R)-3-(4-(4-(6-(2-((3R)-4-((2S)-2-((methoxycarbonyl)amino)-3-methylbutanoyl)-3-morpholinyl)-1H-imidazol-4-yl)-2-naphthyl)phenyl)-1H-imidazol-2-yl)-4-morpholinyl)carbonyl)-2-methylpropyl)carbamate HATU (96 mg, 0.252 mmol) was added to a solution of an HCl salt of (R)-3-(5-(4-(6-(2-((R)-morpholin-3-yl)-1H-imidazol-4-yl)naphthalen-2-yl)phenyl)-1H-imidazol-2-yl)morpholine (Intermediate 181) (71.6 mg, 0.110 mmol) and (S)-2-(methoxycarbonylamino)-3-methylbutanoic acid (44.2 mg, 0.252 mmol) in DMF (1.0 mL) and DIPEA (0.13 mL, 0.77 mmol) and the reaction mixture was flushed with nitrogen, sealed and stirred at rt for 3 h. The reaction was concentrated under a stream of nitrogen overnight, diluted with MeOH (~5 mL), filtered and purified by preparative HPLC (MeOH/water with a TFA buffer) to yield a TFA salt of methyl ((1S)-1-((3R)-3-(4-(4-(6-(2-((3R)-4-((2S)-2-((methoxycarbonyl)amino)-3-methylbutanoyl)-3-morpholinyl)-1H-imidazol-4-yl)-2-naphthyl)phenyl)-1H-imidazol-2-yl)-4-morpholinyl)carbonyl)-2-methylpropyl)carbamate (75.5 mg) as a off-white solid LC-MS retention time 3.351 min; m/z 822.07 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR presents as a mixture of rotamers. $^1$H NMR (400 MHz, MeOD) δ ppm 8.47 (s, 0.5H), 8.33 (s, 0.5H), 8.27 (s, 1H), 7.85-8.17 (m, 10H), 5.95 (d, J=4.5 Hz, 2H), 4.71 (dd, J=12.5, 7.8 Hz, 1H), 4.35-4.58 (m, 4H), 3.94-4.20 (m, 5H), 3.79 (s, 3H), 3.68 (s, 3H), 3.53-3.78 (m, 3H), 2.76-2.91 (m, 1H), 2.12 (br. s., 2H), 1.05-1.19 (m, 6H), 0.81-1.00 (m, 6H).

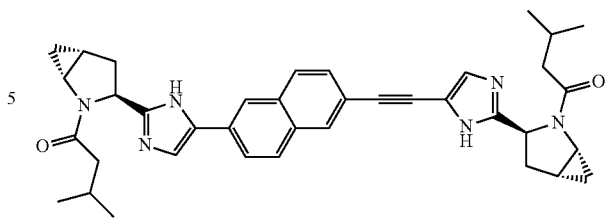

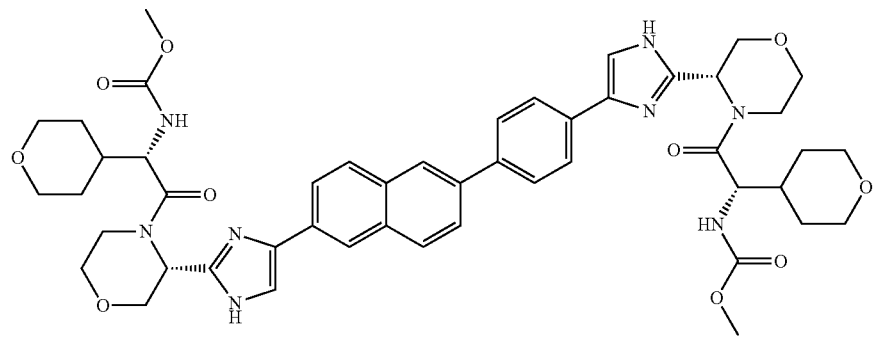 [SMILES: COC(=O)N[C@H](C(=O)N1CCOC[C@H]1c1nc(-c2ccc(-c3ccc4cc(-c5c[nH]c([C@@H]6COCCN6C(=O)[C@@H](NC(=O)OC)C6CCOCC6)n5)ccc4c3)cc2)c[nH]1)C1CCOCC1]

Methyl ((1S)-2-((3R)-3-(4-(4-(6-(2-((3R)-4-((2S)-2-((methoxycarbonyl)amino)-2-(tetrahydro-2H-pyran-4-yl)acetyl)-3-morpholinyl)-1H-imidazol-4-yl)-2-naphthyl)phenyl)-1H-imidazol-2-yl)-4-morpholinyl)-2-oxo-1-(tetrahydro-2H-pyran-4-yl)ethyl)carbamate HATU (88 mg, 0.231 mmol) was added to a solution of an HCl salt of (R)-3-(5-(4-(6-(2-((R)-morpholin-3-yl)-1H-imidazol-4-yl)naphthalen-2-yl)phenyl)-1H-imidazol-2-yl)morpholine (Intermediate 181) (65.5 mg, 0.100 mmol) and (S)-2-(methoxycarbonylamino)-2-(tetrahydro-2H-pyran-4-yl) acetic acid (50.2 mg, 0.231 mmol) in DMF (1.0 mL) and DIPEA (0.12 mL, 0.70 mmol) and the reaction mixture was flushed with nitrogen, sealed and stirred at rt for 3 h. The reaction was concentrated under a stream of nitrogen overnight, diluted with MeOH (~5 mL), filtered and purified by preparative HPLC (MeOH/water with a TFA buffer) to yield a TFA salt of methyl ((1S)-2-((3R)-3-(4-(4-(6-(2-((3R)-4-((2S)-2-((methoxycarbonyl)amino)-2-(tetrahydro-2H-pyran-4-yl)acetyl)-3-morpholinyl)-1H-imidazol-4-yl)-2-naphthyl)phenyl)-1H-imidazol-2-yl)-4-morpholinyl)-2-oxo-1-(tetrahydro-2H-pyran-4-yl)ethyl)carbamate (75 mg) as an off-white solid. LC-MS retention time 3.120 min; m/z 906.15 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode.

(1R,3S,5R)-2-(3-Methylbutanoyl)-3-(4-(6-((2-((1R,3S,5R)-2-(3-methylbutanoyl)-2-azabicyclo[3.1.0]hex-3-yl)-1H-imidazol-4-yl)ethynyl)-2-naphthyl)-1H-imidazol-2-yl)-2-azabicyclo[3.1.0]hexane HATU (74.8 mg, 0.197 mmol) was added to a stirred solution of an HCl salt of (1R,3S,5R)-3-(5-(6-((2-((1R,3S,5R)-2-azabicyclo[3.1.0]hexan-3-yl)-1H-imidazol-4-yl)ethynyl) naphthalen-2-yl)-1H-imidazol-2-yl)-2-azabicyclo[3.1.0] hexane (Intermediate 124) (64.7 mg, 0.098 mmol), 3-methylbutanoic acid (22.09 mg, 0.216 mmol) and DIPEA (0.103 mL, 0.590 mmol) in DCM (1.5 mL) and the reaction mixture was stirred at rt for 2-3 h. The reaction was concentrated to dryness and purified by preparative HPLC (TFA buffer) to yield a TFA salt of (1R,3S,5R)-2-(3-methylbutanoyl)-3-(4-(6-((2-((1R,3S,5R)-2-(3-methylbutanoyl)-2-azabicyclo[3.1.0]hex-3-yl)-1H-imidazol-4-yl)ethynyl)-2-naphthyl)-1H-imidazol-2-yl)-2-azabicyclo[3.1.0]hexane (51.5 mg) as a beige solidified foam. LC-MS retention time 1.775 min; m/z 615.41 (MH+). LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode.

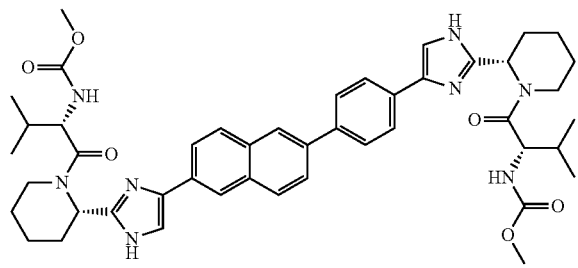 [SMILES: COC(=O)N[C@H](C(=O)N1CCCC[C@H]1c1nc(-c2ccc(-c3ccc4cc(-c5c[nH]c([C@@H]6CCCCN6C(=O)[C@@H](NC(=O)OC)C(C)C)n5)ccc4c3)cc2)c[nH]1)C(C)C]

0.1% trifluoroacetic acid and Solvent B was 10% H₂O/90% MeOH/0.1% trifluoroacetic acid. MS data was determined using a MICROMASS® Platform for LC in electrospray mode. ¹H NMR presents as a mixture of rotamers. ¹H NMR (400 MHz, MeOD) δ ppm 8.46 (s, 0.65H), 8.33 (br. s., 0.35H), 8.27 (s, 1H), 7.84-8.15 (m, 10H), 6.05 (br. s., 1.3H), 5.80-5.90 (m, 0.7H), 4.67-4.78 (m, 1.3H), 4.42-4.50 (m, 2H), 3.99-4.10 (m, 0.7H), 3.78 (br. s., 3.5H), 3.69 (br. s., 2.5H), 3.40-3.52 (m, 0.7H), 2.61-2.73 (m, 1.3H), 2.46-2.59 (m, 1.3H), 2.37 (br. s., 0.7H), 2.03-2.24 (m, 4H), 1.91-2.02 (m, 1.3H), 1.63-1.88 (m, 5.4H), 1.45-1.62 (m, 1.4H), 1.11 (t, J=6.8 Hz, 7.3H), 0.93-1.03 (m, 4.7H).

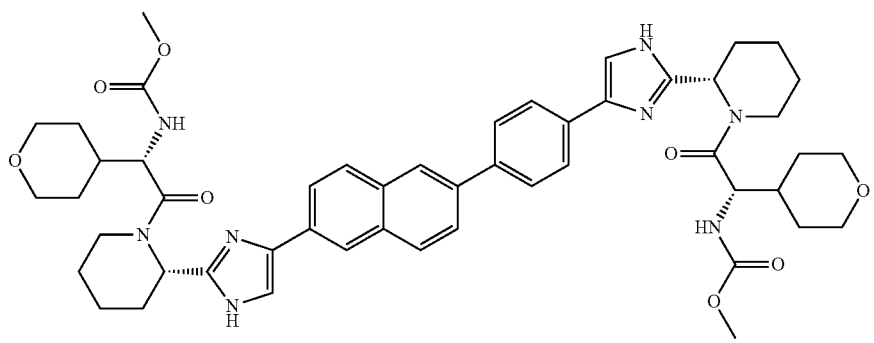 [SMILES: COC(=O)N[C@H](C(=O)N1CCCC[C@H]1c1nc(-c2ccc(-c3ccc4cc(-c5c[nH]c([C@@H]6CCCCN6C(=O)[C@@H](NC(=O)OC)C6CCOCC6)n5)ccc4c3)cc2)c[nH]1)C1CCOCC1]

Methyl ((1S)-1-(((2S)-2-(4-(4-(6-(2-((2S)-1-((2S)-2-((methoxycarbonyl)amino)-3-methylbutanoyl)-2-piperidinyl)-1H-imidazol-4-yl)-2-naphthyl)phenyl)-1H-imidazol-2-yl)-1-piperidinyl)carbonyl)-2-methylpropyl)carbamate HATU (93 mg, 0.245 mmol) was added to a solution of an HCl salt of (S)-2-(5-(4-(6-(2-((S)-piperidin-2-yl)-1H-imidazol-4-yl)naphthalen-2-yl)phenyl)-1H-imidazol-2-yl)piperidine (Intermediate 184) (69.0 mg, 0.106 mmol) and (S)-2-(methoxycarbonylamino)-3-methylbutanoic acid (42.9 mg, 0.245 mmol) in DMF (1.0 mL) and DIPEA (0.13 mL, 0.75 mmol) and the reaction was flushed with nitrogen, sealed and stirred at rt for 1 h. The reaction was concentrated under a stream of nitrogen overnight, diluted with MeOH (~5 mL), filtered and purified by preparative HPLC (MeOH/water with a TFA buffer) to yield a TFA salt of methyl ((1S)-1-(((2S)-2-(4-(4-(6-(2-((2S)-1-((2S)-2-((methoxycarbonyl)amino)-3-methylbutanoyl)-2-piperidinyl)-1H-imidazol-4-yl)-2-naphthyl)phenyl)-1H-imidazol-2-yl)-1-piperidinyl)carbonyl)-2-methylpropyl)carbamate (88.9 mg) as a light yellow solid. LC-MS retention time 3.530 min; m/z 818.08 (MH+). LC data was recorded on a Shimadzu LC-10AS liquid chromatograph equipped with a PHENOMENEX® Luna 3u C18 2.0× 50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/

Methyl ((1S)-2-((2S)-2-(4-(4-(6-(2-((2S)-1-((2S)-2-((methoxycarbonyl)amino)-2-(tetrahydro-2H-pyran-4-yl)acetyl)-2-piperidinyl)-1H-imidazol-4-yl)-2-naphthyl)phenyl)-1H-imidazol-2-yl)-1-piperidinyl)-2-oxo-1-(tetrahydro-2H-pyran-4-yl)ethyl)carbamate HATU (84 mg, 0.222 mmol) was added to a solution of an HCl salt of (S)-2-(5-(4-(6-(2-((S)-piperidin-2-yl)-1H-imidazol-4-yl)naphthalen-2-yl)phenyl)-1H-imidazol-2-yl)piperidine (Intermediate 184) (62.5 mg, 0.096 mmol) and (S)-2-(methoxycarbonylamino)-2-(tetrahydro-2H-pyran-4-yl) acetic acid (48.2 mg, 0.222 mmol) in DMF (1.0 mL) and DIPEA (0.12 mL, 0.68 mmol) and the reaction was flushed with nitrogen, sealed and stirred at rt for 1 h. The reaction was concentrated under a stream of nitrogen overnight, diluted with MeOH (~5 mL), filtered and purified by preparative HPLC (MeOH/water with a TFA buffer) to yield a TFA salt of methyl ((1S)-2-((2S)-2-(4-(4-(6-(2-((2S)-1-((2S)-2-((methoxycarbonyl)amino)-2-(tetrahydro-2H-pyran-4-yl)acetyl)-2-piperidinyl)-1H-imidazol-4-yl)-2-naphthyl)phenyl)-1H-imidazol-2-yl)-1-piperidinyl)-2-oxo-1-(tetrahydro-2H-pyran-4-yl)ethyl)carbamate (71.2 mg) as a light yellow solid. LC-MS retention time 3.348 min; m/z 902.10 (MH+). LC data was recorded on a Shimadzu LC-10AS liquid chromatograph equipped with a PHENOMENEX® Luna 3u C18 2.0× 50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/ 0.1% trifluoroacetic acid and Solvent B was 10% H₂O/90% MeOH/0.1% trifluoroacetic acid. MS data was determined using a MICROMASS® Platform for LC in electrospray mode. ¹H NMR presents as a mixture of rotamers. ¹H NMR (400 MHz, MeOD) δ ppm 8.45 (s, 0.6H), 8.32 (br. s., 0.4H), 8.27 (s, 1H), 8.02-8.15 (m, 4.4H), 7.85-8.02 (m, 5.6H), 6.08 (br. s., 1.2H), 5.90 (br. s., 0.8H), 4.70 (br. s., 1.2H), 4.45-4.59 (m, 2H), 3.90-4.10 (m, 4.8H), 3.77 (s, 3.6H), 3.69 (br. s., 2.4H), 3.36-3.50 (m, 5H), 2.35-2.73 (m, 3H), 1.36-2.22 (m, 20H).

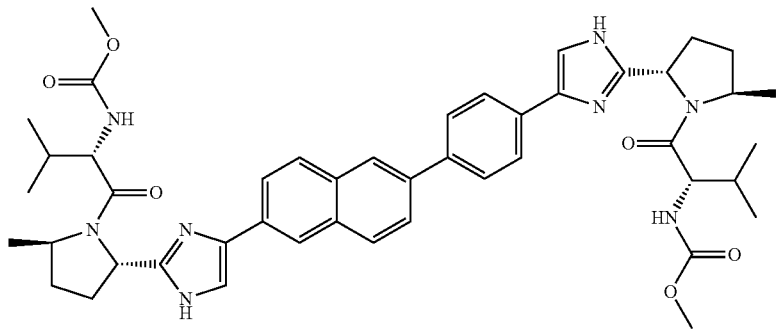

Methyl ((1S)-1-(((2S,5R)-2-(4-(4-(6-(2-((2S,5R)-1-((2S)-2-((methoxycarbonyl)amino)-3-methylbutanoyl)-5-methyl-2-pyrrolidinyl)-1H-imidazol-4-yl)-2-naphthyl)phenyl)-1H-imidazol-2-yl)-5-methyl-1-pyrrolidinyl)carbonyl)-2-methylpropyl)carbamate HATU (62.0 mg, 0.163 mmol) was added to a solution of an HCl salt of 2-((2S,5R)-5-methylpyrrolidin-2-yl)-5-(4-(6-(2-((2S,5R)-5-methylpyrrolidin-2-yl)-1H-imidazol-4-yl)naphthalen-2-yl)phenyl)-1H-imidazole (Intermediate 187) (46 mg, 0.071 mmol) and (S)-2-(methoxycarbonylamino)-3-methylbutanoic acid (28.6 mg, 0.163 mmol) DMF (0.7 mL) and DIPEA (0.09 mL, 0.5 mmol) and the reaction vessel was flushed with nitrogen, sealed and stirred at rt for 1 h. The reaction was concentrated under a stream of nitrogen overnight, diluted with MeOH (~3 mL), filtered and purified by preparative HPLC (MeOH/water with a TFA buffer) to yield a TFA salt of methyl ((1S)-1-(((2S,5R)-2-(4-(4-(6-(2-((2S,5R)-1-((2S)-2-((methoxycarbonyl)amino)-3-methylbutanoyl)-5-methyl-2-pyrrolidinyl)-1H-imidazol-4-yl)-2-naphthyl)phenyl)-1H-imidazol-2-yl)-5-methyl-1-pyrrolidinyl)carbonyl)-2-methylpropyl)carbamate (53.3 mg) as a light yellow solid. LC-MS retention time 3.255 min; m/z 818.08 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H₂O/0.1% trifluoroacetic acid and Solvent B was 10% H₂O/90% MeOH/0.1% trifluoroacetic acid. MS data was determined using a MICROMASS® Platform for LC in electrospray mode. ¹H NMR presents as a complex mixture of rotamers. ¹H NMR (400 MHz, MeOD) δ ppm 8.31 (s, 0.5H), 8.26-8.30 (m, 1.5H), 8.13 (d, J=8.8 Hz, 1H), 8.08 (d, J=8.5 Hz, 1H), 7.93-8.00 (m, 4H), 7.83-7.93 (m, 4H), 5.67 (t, J=7.8 Hz, 0.7H), 5.38-5.45 (m, 1.3H), 4.44-4.68 (m, 3.3H), 3.92 (dd, J=8.2, 4.4 Hz, 0.7H), 3.66 (s, 3.5H), 3.41 (s, 1H), 3.35 (s, 1.5H), 2.53-2.92 (m, 3.3H), 1.96-2.30 (m, 6H), 1.78-1.87 (m, 0.7H), 1.43-1.53 (m, 3.5H), 1.33 (dd, J=6.3, 2.5 Hz, 2.5H), 0.98-1.06 (m, 6H), 0.96 (d, J=6.8 Hz, 2.4H), 0.84 (d, J=6.8 Hz, 3.6H).

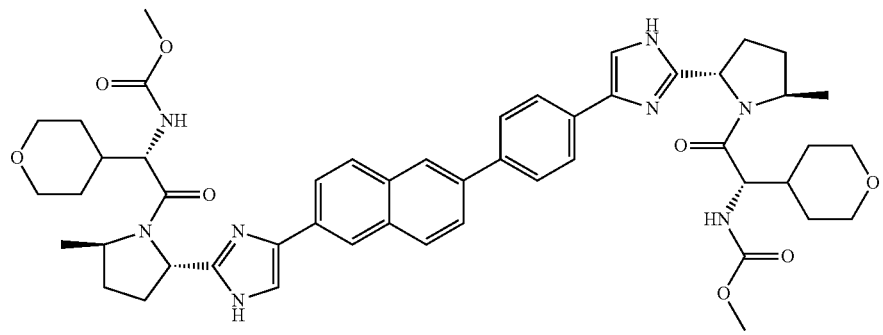 [SMILES: COC(=O)N[C@H](C(=O)N1[C@H](C)CC[C@H]1c1nc(-c2ccc(-c3ccc4cc(-c5c[nH]c([C@@H]6CC[C@@H](C)N6C(=O)[C@@H](NC(=O)OC)C6CCOCC6)n5)ccc4c3)cc2)c[nH]1)C1CCOCC1]

Methyl ((1S)-2-((2S,5R)-2-(4-(4-(6-(2-((2S,5R)-1-((2S)-2-((methoxycarbonyl)amino)-2-(tetrahydro-2H-pyran-4-yl)acetyl)-5-methyl-2-pyrrolidinyl)-1H-imidazol-4-yl)-2-naphthyl)phenyl)-1H-imidazol-2-yl)-5-methyl-1-pyrrolidinyl)-2-oxo-1-(tetrahydro-2H-pyran-4-yl)ethyl)carbamate HATU (55.8 mg, 0.147 mmol) was added to a solution of vial an HCl salt of 2-((2S,5R)-5-methylpyrrolidin-2-yl)-5-(4-(6-(2-((2S,5R)-5-methylpyrrolidin-2-yl)-1H-imidazol-4-yl)naphthalen-2-yl)phenyl)-1H-imidazole (Intermediate 187) (41.4 mg, 0.064 mmol) and (S)-2-(methoxycarbonylamino)-2-(tetrahydro-2H-pyran-4-yl)acetic acid (31.9 mg, 0.147 mmol) in DMF (0.7 mL) and DIPEA (0.08 mL, 0.4 mmol) and the reaction vessel was flushed with nitrogen, sealed and stirred at rt for 1 h. The reaction was concentrated under a stream of nitrogen overnight, diluted with MeOH (~3 mL), filtered and purified by preparative HPLC (MeOH/water with a TFA buffer) to yield a TFA salt of methyl ((1S)-2-((2S,5R)-2-(4-(4-(6-(2-((2S,5R)-1-((2S)-2-((methoxycarbonyl)amino)-2-(tetrahydro-2H-pyran-4-yl)acetyl)-5-methyl-2-pyrrolidinyl)-1H-imidazol-4-yl)-2-naphthyl)phenyl)-1H-imidazol-2-yl)-5-methyl-1-pyrrolidinyl)-2-oxo-1-(tetrahydro-2H-pyran-4-yl)ethyl)carbamate (27.6 mg) as a light yellow solid LC-MS retention time 3.135 min; m/z 902.15 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. Mixture of rotamers by $^1$H NMR. $^1$H NMR (400 MHz, MeOD) δ ppm 8.31 (s, 0.5H), 8.25-8.29 (m, 1.5H), 8.13 (d, J=8.8 Hz, 1H), 8.08 (dd, J=8.8, 2.5 Hz, 1H), 7.93-8.00 (m, 4H), 7.82-7.92 (m, 4H), 5.71 (t, J=7.9 Hz, 0.8H), 5.37-5.45 (m, 1.2H), 4.47-4.69 (m, 3H), 3.89-4.07 (m, 5H), 3.67 (s, 3H), 3.24-3.43 (m, 7H), 2.57-2.92 (m, 3H), 1.96-2.29 (m, 6H), 1.79-1.87 (m, 1H), 1.35-1.67 (m, 11H), 1.33 (dd, J=6.5, 2.5 Hz, 3H).

zol-4-yl)naphthalen-2-yl)phenyl)-1H-imidazole (Intermediate 189) (86 mg, 0.148 mmol), (S)-2-(methoxycarbonylamino)-3-methylbutanoic acid (47.1 mg, 0.269 mmol), and Hunig's base (0.234 mL, 1.34 mmol) in DMF (6 mL). The reaction was stirred 4 h at room temperature and purified by preparative HPLC (MeOH/water with 0.1% TFA) to afford a bis TFA salt of methyl ((1S)-1-(((2S)-2-(4-(6-(4-(2-((2S)-1-((2S)-2-((methoxycarbonyl)amino)-3-methylbutanoyl)-4-methylene-2-pyrrolidinyl)-1H-imidazol-4-yl)phenyl)-2-naphthyl)-1H-imidazol-2-yl)-4-methylene-1-pyrrolidinyl)carbonyl)-2-methylpropyl)carbamate (65 mg, 46%). LC-MS retention time 3.22 min; calcd. for $C_{46}H_{53}N_8O_6$: 813.40. Found m/z 813.7 $[M+H]^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeCN/95% water/10 mM $NH_4OAc$ and Solvent B was 95% MeCN/5% water/10 mM $NH_4OAc$. MS data was determined using a MICROMASS® Platform for LC in electrospray mode. $^1$H NMR (TFA salt, 500 MHz, MeOD) δ ppm 8.29 (s, 1H), 8.28 (s, 1H), 8.15 (d, J=8.9 Hz, 1H), 8.09 (d, J=8.9 Hz, 1H), 8.0-7.85 (m, 8H), 5.50-5.45 (m, 2H), 5.32 (s, 2H), 5.28 (s, 2H), 4.72 (d, J=11.6 Hz, 2H), 4.60 (dd, J=11.3, 3.4 Hz, 2H), 4.21 (dd, J=7.6, 2.8 Hz, 2H), 3.68 (s, 6H), 2.98-2.92 (m, 2H), 2.10-2.06 (m, 2H), 1.06-1.02 (m, 2H), 0.97-0.94 (m, 12H).

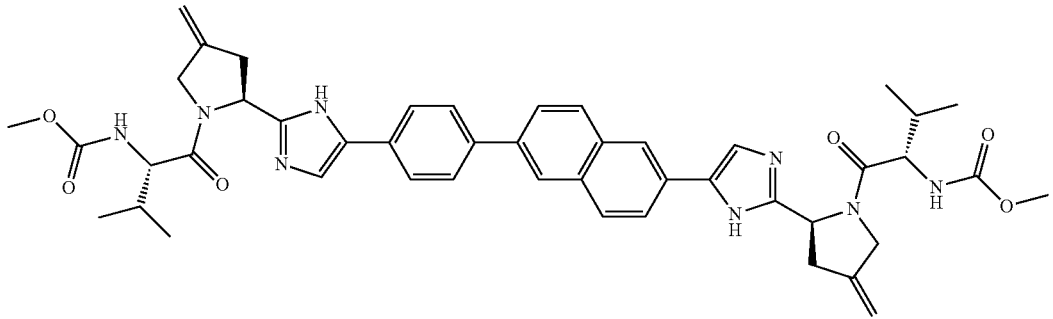

Methyl ((1S)-1-(((2S)-2-(4-(6-(4-(2-((2S)-1-((2S)-2-((methoxycarbonyl)amino)-3-methylbutanoyl)-4-methylene-2-pyrrolidinyl)-1H-imidazol-4-yl)phenyl)-2-naphthyl)-1H-imidazol-2-yl)-4-methylene-1-pyrrolidinyl)carbonyl)-2-methylpropyl)carbamate HATU (102 mg, 0.269 mmol) was added to a stirred solution of the tetra HCl salt of 2-((S)-4-methylenepyrrolidin-2-yl)-4-(4-(6-(2-((S)-4-methylenepyrrolidin-2-yl)-1H-imida-

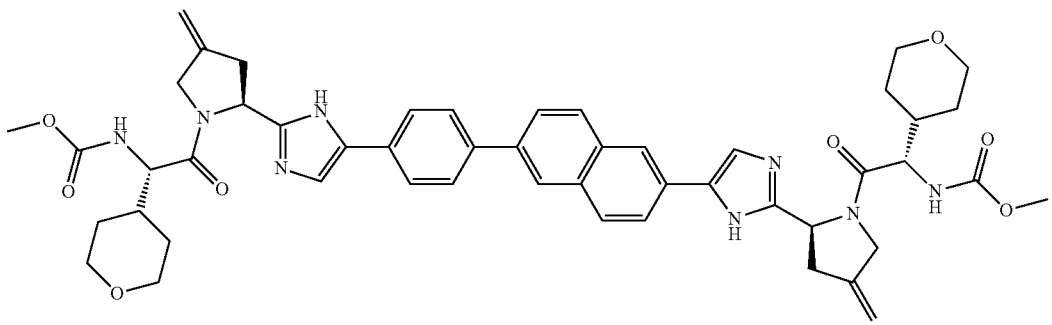

547

Methyl ((1S)-2-((2S)-2-(4-(4-(6-(2-((2S)-1-((2S)-2-((methoxycarbonyl)amino)-2-(tetrahydro-2H-pyran-4-yl)acetyl)-4-methylene-2-pyrrolidinyl)-1H-imidazol-4-yl)-2-naphthyl)phenyl)-1H-imidazol-2-yl)-4-methylene-1-pyrrolidinyl)-2-oxo-1-(tetrahydro-2H-pyran-4-yl)ethyl)carbamate HATU (102 mg, 0.269 mmol) was added to a stirred solution of the tetra HCl salt of 2-((S)-4-methylenepyrrolidin-2-yl)-4-(4-(6-(2-((S)-4-methylenepyrrolidin-2-yl)-1H-imidazol-4-yl)naphthalen-2-yl)phenyl)-1H-imidazole (Intermediate 189) (86 mg, 0.148 mmol), (S)-2-(methoxycarbonylamino)-2-(tetrahydro-2H-pyran-4-yl)acetic acid (58.4 mg, 0.269 mmol), and Hunig's base (0.234 mL, 1.34 mmol) in DMF (6 mL). The reaction was stirred 5 h at room temperature and purified by preparative HPLC (MeCN/water with 0.1% TFA) to afford a bis TFA salt of methyl ((1S)-2-((2S)-2-(4-(4-(6-(2-((2S)-1-((2S)-2-((methoxycarbonyl)amino)-2-(tetrahydro-2H-pyran-4-yl)acetyl)-4-methylene-2-pyrrolidinyl)-1H-imidazol-4-yl)-2-naphthyl)phenyl)-1H-imidazol-2-yl)-4-methylene-1-pyrrolidinyl)-2-oxo-1-(tetrahydro-2H-pyran-4-yl)ethyl)carbamate. LC-MS retention time 2.81 min; calcd. for $C_{50}H_{57}N_8O_8$: 897.43. Found m/z 897.41 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.29 (s, 2H), 8.4 (d, J=8.8 Hz, 1H), 8.09 (d, J=9.0 Hz, 1H), 8.01-7.85 (m, 8H), 5.50-5.44 (m, 2H), 5.32 (s, 2H), 5.28 (s, 2H), 4.75 (d, J=14.6 Hz, 2H), 4.63 (dd, J=13.3, 4.5 Hz, 2H), 4.27 (dd, J=8.3, 3.5 Hz, 2H), 3.99-3.91 (m, 4H) 3.69 (s, 6H), 3.41-3.37 (m 4H), 3.0-2.94 (m, 2H), 2.02-1.98 (m, 2H), 1.68-1.65 (m, 2H), 1.59-1.32 (m, 8H).

548

Methyl ((1S)-1-(((1S)-1-(4-(4-(6-(2-((1S)-1-(((2S)-2-((methoxycarbonyl)amino)-3-methylbutanoyl)amino)ethyl)-1H-imidazol-4-yl)-2-naphthyl)phenyl)-1H-imidazol-2-yl)ethyl)carbamoyl)-2-methylpropyl) carbamate HATU (149 mg, 0.393 mmol) was added to a stirred solution of the tetra HCl salt of (S)-1-(4-(4-(6-(2-((S)-1-aminoethyl)-1H-imidazol-4-yl)naphthalen-2-yl)phenyl)-1H-imidazol-2-yl)ethanamine (Intermediate 191) (111 mg, 0.148 mmol), (S)-2-(methoxycarbonylamino)-3-methylbutanoic acid (47.1 mg, 0.196 mmol), and Hunig's base (0.343 mL, 1.96 mmol) in DMF (8 mL). The reaction was stirred 4 h at room temperature and purified by preparative HPLC (MeCN/water with 0.1% TFA) to afford a bis TFA salt methyl ((1S)-1-(((1S)-1-(4-(4-(6-(2-((1S)-1-(((2S)-2-((methoxycarbonyl)amino)-3-methylbutanoyl)amino)ethyl)-1H-imidazol-4-yl)-2-naphthyl)phenyl)-1H-imidazol-2-yl)ethyl)carbamoyl)-2-methylpropyl)carbamate (91 mg, 47%). LC-MS retention time 2.96 min; calcd. for $C_{40}H_{49}N_8O_6$: 737.38. Found m/z 737.45 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.35 (s, 1H), 8.27 (s, 1H), 8.13 (d, J=8.9 Hz, 1H), 8.09 (d, J=8.9 Hz, 1H), 7.99-7.88 (m, 8H), 5.30-5.27 (m, 2H), 3.99-3.97 (m, 2H), 3.70 (s, 6H), 2.14 (br. s, 2H), 1.78-1.75 (m, 6H), 0.99-0.95 (m, 12H).

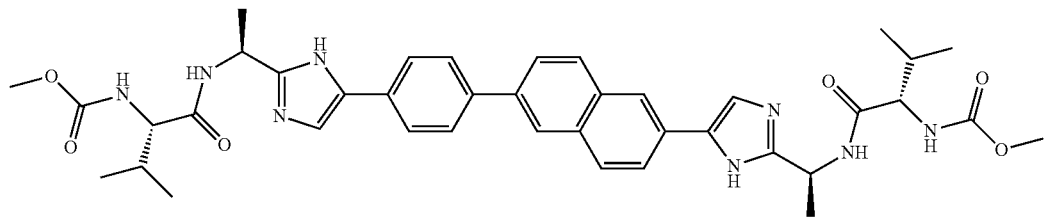

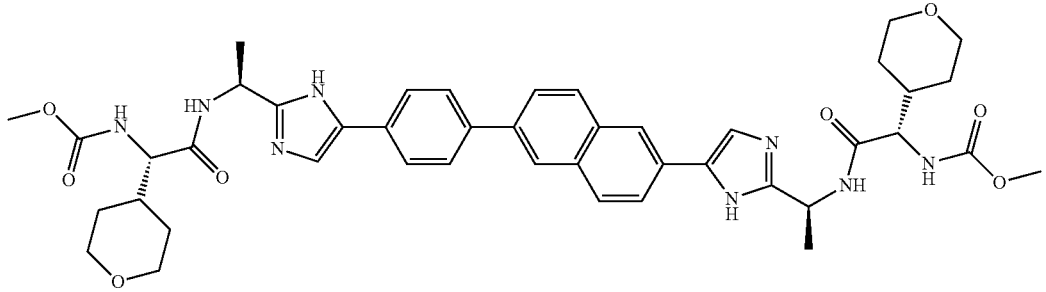

Methyl ((1S)-2-(((1S)-1-(4-(4-(6-(2-((1S)-1-(((2S)-2-((methoxycarbonyl)amino)-2-(tetrahydro-2H-pyran-4-yl)acetyl)amino)ethyl)-1H-imidazol-4-yl)-2-naphthyl)phenyl)-1H-imidazol-2-yl)ethyl)amino)-2-oxo-1-(tetrahydro-2H-pyran-4-yl)ethyl)carbamate HATU (149 mg, 0.393 mmol) was added to a stirred solution of the tetra HCl salt of (S)-1-(4-(4-(6-(2-((S)-1-Aminoethyl)-1H-imidazol-4-yl)naphthalen-2-yl)phenyl)-1H-imidazol-2-yl)ethanamine (Intermediate 191) (83 mg, 0.196 mmol), (S)-2-(methoxycarbonylamino)-2-(tetrahydro-2H-pyran-4-yl)acetic acid (85 mg, 0.393 mmol), and Hunig's base (0.343 mL, 1.96 mmol) in DMF (8 mL). The reaction was stirred 5 h at room temperature and purified by preparative HPLC (MeCN/water with 0.1% TFA) to afford a bis TFA salt of methyl ((1S)-2-(((1S)-1-(4-(4-(6-(2-((1S)-1-(((2S)-2-((methoxycarbonyl)amino)-2-(tetrahydro-2H-pyran-4-yl)acetyl)amino)ethyl)-1H-imidazol-4-yl)-2-naphthyl)phenyl)-1H-imidazol-2-yl)ethyl)amino)-2-oxo-1-(tetrahydro-2H-pyran-4-yl)ethyl)carbamate (89 mg, 42%). LC-MS retention time 2.64 min; calcd. for $C_{44}H_{53}N_8O_8$: 821.40. Found m/z 821.80 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% AcCN/95% water/10 mM NH$_4$OAc and Solvent B was 95% AcCN/5% water/10 mM NH$_4$OAc. MS data was determined using a MICROMASS® Platform for LC in electrospray mode. $^1$H NMR (TFA salt, 500 MHz, MeOD) δ ppm 8.34 (s, 1H), 8.2 (s, 1H), 8.13 (d, J=8.6 Hz, 1H), 8.09 (d, J=8.6 Hz, 1H), 7.99-7.87 (m, 8H), 5.29-5.26 (m, 2H), 4.02-4.00 (m, 2H), 3.98-3.93 (m, 4H) 3.71 (s, 6H), 3.41-3.37 (m 4H), 2.02 (br. s, 2H), 1.79-1.76 (m, 6H), 1.62 (d, J=13.0 Hz, 2H), 1.49-1.39 (m, 6H).

Methyl ((1S)-1-(((1S)-1-(4-(4-(6-(2-((1S)-1-(((2S)-2-((methoxycarbonyl)amino)-3-methylbutanoyl)(methyl)amino)ethyl)-1H-imidazol-4-yl)-2-naphthyl)phenyl)-1H-imidazol-2-yl)ethyl)(methyl)carbamoyl)-2-methylpropyl)carbamate HATU (84 mg, 0.222 mmol) was added to a stirred solution of the tetra HCl salt of (S)-N-Methyl-1-(4-(4-(6-(2-((S)-1-(methylamino)ethyl)-1H-imidazol-4-yl)naphthalen-2-yl)phenyl)-1H-imidazol-2-yl)ethanamine (Intermediate 193) (66 mg, 0.111 mmol), (S)-2-(methoxycarbonylamino)-3-methylbutanoic acid (38.9 mg, 0.222 mmol), and Hunig's base (0.194 mL, 1.11 mmol) in DMF (5 mL). The reaction was stirred 5 h at room temperature and purified by preparative HPLC (MeCN/water with 0.1% TFA) to afford a bis TFA salt of methyl ((1S)-1-(((1S)-1-(4-(4-(6-(2-((1S)-1-(((2S)-2-((methoxycarbonyl)amino)-3-methylbutanoyl)(methyl)amino)ethyl)-1H-imidazol-4-yl)-2-naphthyl)phenyl)-1H-imidazol-2-yl)ethyl)(methyl)carbamoyl)-2-methylpropyl)carbamate. LC-MS retention time 1.78 min; calcd. for $C_{42}H_{53}N_8O_6$: 765.41. Found m/z 765.41 [M+H]$^+$. LC data was recorded on a Shimadzu LC-10AS liquid chromatograph equipped a PHENOMENEX® Luna C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min and an analysis time of 3 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt; rotamers, 500 MHz, MeOD) δ ppm 8.44/8.34 (s, 1H), 8.27 (s, 1H), 8.13 (d, J=8.6 Hz, 1H), 8.10-7.88 (m, 9H), 6.17-6.14/5.33-5.30 (m, 2H), 4.64-4.6/4.41-4.39 (m, 2H), 3.84/3.66 (s, 3H), 3.83/3.59 (s, 3H), 3.37 (s, 6H), 2.10-2.05 (m, 2H), 1.90-1.87/1.85-1.82 (m, 6H), 1.15-0.90 (m, 12H).

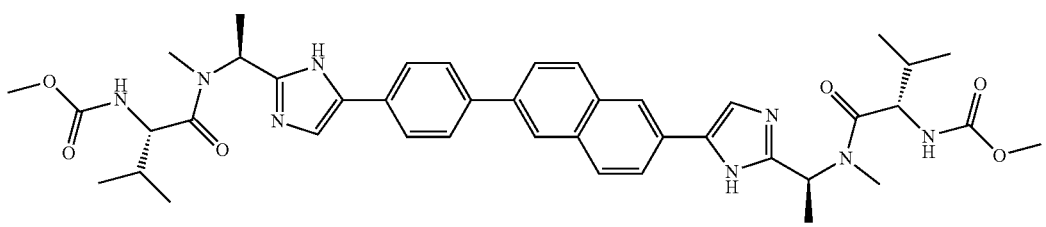

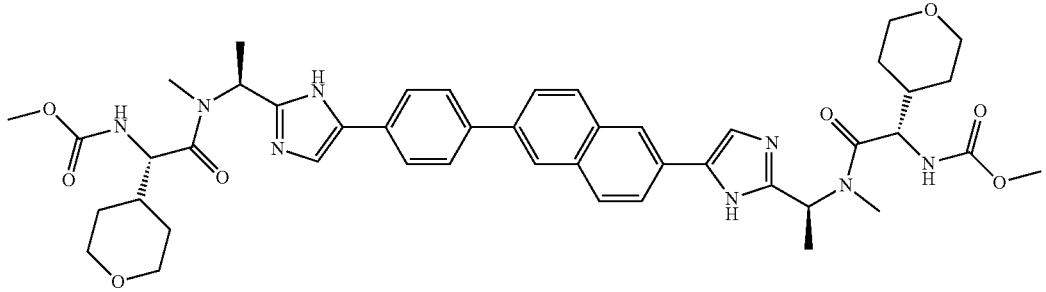

Methyl ((1S)-2-(((1S)-1-(4-(4-(6-(2-((1S)-1-(((2S)-2-((methoxycarbonyl)amino)-2-(tetrahydro-2H-pyran-4-yl)acetyl)(methyl)amino)ethyl)-1H-imidazol-4-yl)-2-naphthyl)phenyl)-1H-imidazol-2-yl)ethyl)(methyl)amino)-2-oxo-1-(tetrahydro-2H-pyran-4-yl)ethyl)carbamate HATU (84 mg, 0.222 mmol) was added to a stirred solution of the tetra HCl salt of (S)-N-Methyl-1-(4-(4-(6-(2-((S)-1-(methylamino)ethyl)-1H-imidazol-4-yl)naphthalen-2-yl)phenyl)-1H-imidazol-2-yl)ethanamine (Intermediate 193) (66 mg, 0.111 mmol), (S)-2-(methoxycarbonylamino)-2-(tetrahydro-2H-pyran-4-yl)acetic acid (48 mg, 0.222 mmol), and Hunig's base (0.194 mL, 1.11 mmol) in DMF (5 mL). The reaction was stirred 5 h at room temperature and purified by preparative HPLC (MeCN/water with 0.1% TFA) to afford a bis TFA salt of Methyl methyl ((1S)-2-(((1S)-1-(4-(4-(6-(2-(((1S)-1-(((2S)-2-((methoxycarbonyl)amino)-2-(tetrahydro-2H-pyran-4-yl)acetyl)(methyl)amino)ethyl)-1H-imidazol-4-yl)-2-naphthyl)phenyl)-1H-imidazol-2-yl)ethyl)(methyl)amino)-2-oxo-1-(tetrahydro-2H-pyran-4-yl)ethyl)carbamate. LC-MS retention time 1.58 min; calcd. for $C_{46}H_{57}N_8O_8$: 849.43. Found m/z 849.46 [M+H]$^+$. LC data was recorded on a Shimadzu LC-10AS liquid chromatograph equipped a PHENOMENEX® Luna C18 2.0×30 mm column using a SPD-10AV UV-Vis detector at a detector wave length of 220 nM. The elution conditions employed a flow rate of 1 mL/min, a gradient of 100% Solvent A/0% Solvent B to 0% Solvent A/100% Solvent B, a gradient time of 2 min, a hold time of 1 min and an analysis time of 3 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, rotamers 500 MHz, MeOD) δ ppm 8.45/8.34 (s, 1H), 8.28 (s, 1H), 8.14 (d, J=8.6 Hz, 1H), 8.09 (d, J=8.3 Hz, 1H), 8.06-7.88 (m, 8H), 6.21-6.18/5.38-5.34 (m, 2H), 4.73-4.70/4.47-4.45 (m, 2H), 4.02-3.94 (m, 4H) 3.84/3.63 (s, 3H), 3.83/3.60 (s, 3H), 3.46-3.38 (m 4H), 3.37/3.35 (s, 6H), 2.02 (br. s, 2H), 1.91-1.88/1.84-1.81 (m, 6H), 1.68 (d, J=13.0 Hz, 2H), 1.53-1.42 (m, 6H).

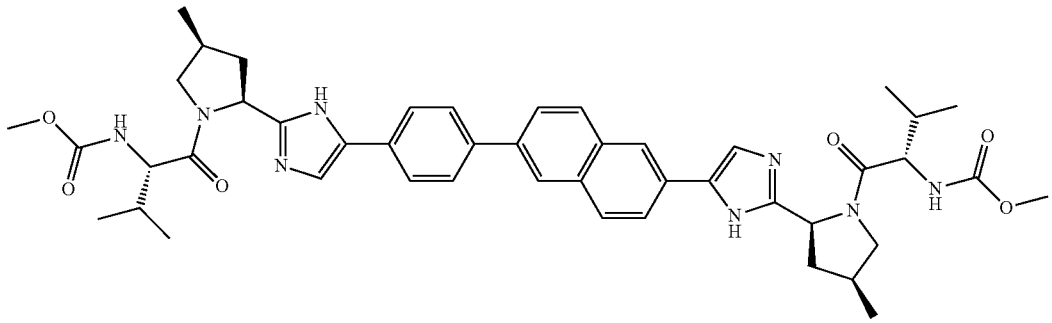

Methyl ((1S)-1-(((2S,4S)-2-(4-(4-(6-(2-((2S,4S)-1-((2S)-2-((methoxycarbonyl)amino)-3-methylbutanoyl)-4-methyl-2-pyrrolidinyl)-1H-imidazol-4-yl)-2-naphthyl)phenyl)-1H-imidazol-2-yl)-4-methyl-1-pyrrolidinyl)carbonyl)-2-methylpropyl)carbamate HATU (32 mg, 0.085 mmol) was added to a stirred solution of the tetra HCl salt of 2-((2S,4S)-4-methyl-2-pyrrolidinyl)-4-(4-(6-(2-((2S,4S)-4-methyl-2-pyrrolidinyl)-1H-imidazol-4-yl)-2-naphthyl)phenyl)-1H-imidazole (Intermediate 196) (25 mg, 0.039 mmol), (S)-2-(methoxycarbonylamino)-3-methylbutanoic acid (14.9 mg, 0.085 mmol), and Hunig's base (0.054 mL, 0.308 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of methyl ((1S)-1-(((2S,4S)-2-(4-(4-(6-(2-((2S,4S)-1-((2S)-2-((methoxycarbonyl)amino)-3-methylbutanoyl)-4-methyl-2-pyrrolidinyl)-1H-imidazol-4-yl)-2-naphthyl)phenyl)-1H-imidazol-2-yl)-4-methyl-1-pyrrolidinyl)carbonyl)-2-methylpropyl)carbamate (24.5 mg, 57.8%). LC-MS retention time 3.05 min; calcd. for $C_{46}H_{57}N_8O_6$: 817.44. Found m/z 817.36 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.29 (s, 1H), 8.27 (s, 1H), 8.13 (d, J=8.6 Hz, 1H), 8.08 (d, J=8.6 Hz, 1H), 7.99-7.85 (m, 8H), 5.27-5.22 (m, 2H), 4.37-4.33 (m, 2H), 4.25-4.23 (m, 2H), 3.68 (s, 6H), 3.47-3.41 (m, 2H), 2.72-2.68 (m 2H), 2.55 (br. s, 2H), 2.07-2.03 (m, 2H), 1.92-1.87 (m, 2H), 1.27-1.26 (m, 6H), 0.95-0.9 (m, 12H).

2-pyrrolidinyl)-1H-imidazol-4-yl)-2-naphthyl)phenyl)-1H-imidazol-2-yl)-4-methyl-1-pyrrolidinyl)-2-oxo-1-(tetrahydro-2H-pyran-4-yl)ethyl)carbamate. LC-MS retention time 2.84 min; calcd. for $C_{50}H_{61}N_8O_8$: 901.46. Found m/z 901.42 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1

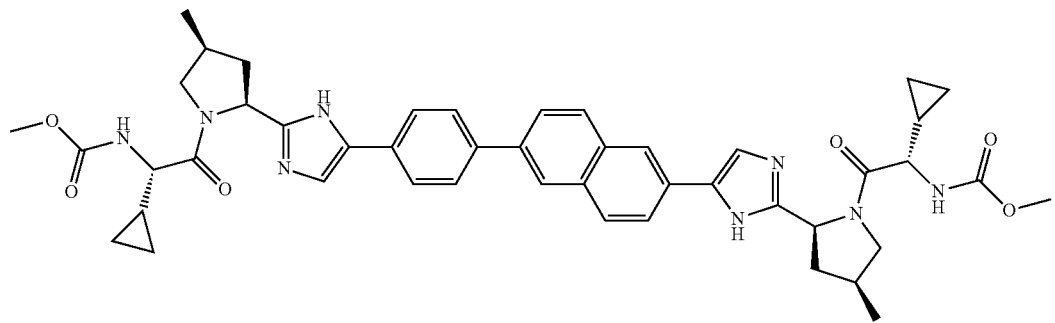

Methyl (2-((2S,4S)-2-(4-(4-(6-(2-((2S,4S)-1-(((methoxycarbonyl)amino)(tetrahydro-2H-pyran-4-yl)acetyl)-4-methyl-2-pyrrolidinyl)-1H-imidazol-4-yl)-2-naphthyl)phenyl)-1H-imidazol-2-yl)-4-methyl-1-pyrrolidinyl)-2-oxo-1-(tetrahydro-2H-pyran-4-yl)ethyl)carbamate HATU (64.5 mg, 0.170 mmol) was added to a stirred solution of the tetra HCl salt of 2-((2S,4S)-4-methyl-2-pyrrolidinyl)-4-(4-(6-(2-((2S,4S)-4-methyl-2-pyrrolidinyl)-1H-imidazol-4-yl)-2-naphthyl)phenyl)-1H-imidazole (Intermediate 196) (50 mg, 0.077 mmol), (S)-2-(methoxycarbonylamino)-2-(tetrahydro-2H-pyran-4-yl)acetic acid (36.8 mg, 0.170 mmol), and Hunig's base (0.11 mL, 0.617 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of methyl (2-((2S,4S)-2-(4-(4-(6-(2-((2S,4S)-1-(((methoxycarbonyl)amino)(tetrahydro-2H-pyran-4-yl)acetyl)-4-methylmin and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.29 (s, 1H), 8.28 (s, 1H), 8.14 (d, J=8.6 Hz, 1H), 8.09 (d, J=8.6 Hz, 1H), 8.00-7.85 (m, 8H), 5.25-5.21 (m, 2H), 4.42-4.39 (m, 2H), 4.30-4.27 (m, 2H), 3.96-3.92 (m, 4H), 3.68 (s, 6H), 3.49-3.35 (m 6H), 2.71-2.38 (m, 2H), 2.58-2.54 (m, 2H), 1.97-1.89 (m, 4H), 1.60 (d, J=13.0 Hz, 2H), 1.48-1.26 (m, 12H).

Methyl (1-cyclopropyl-2-((2S,4S)-2-(4-(4-(6-(2-((2S,4S)-1-(cyclopropyl((methoxycarbonyl)amino)acetyl)-4-methyl-2-pyrrolidinyl)-1H-imidazol-4-yl)-2-naphthyl)phenyl)-1H-imidazol-2-yl)-4-methyl-1-pyrrolidinyl)-2-oxoethyl)carbamate HATU (39 mg, 0.102 mmol) was added to a stirred solution of the tetra HCl salt of 2-((2S,4S)-4-methyl-2-pyrrolidinyl)-4-(4-(6-(2-((2S,4S)-4-methyl-2-pyrrolidinyl)-1H-imidazol-4-yl)-2-naphthyl)phenyl)-1H-imidazole (Intermediate 196) (30 mg, 0.085 mmol), (S)-2-cyclopropyl-2-(methoxycarbonylamino)acetic acid (17.62 mg, 0.102 mmol), and Hunig's base (0.065 mL, 0.37 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of methyl (1-cyclopropyl-2-((2S,4S)-2-(4-(4-(6-(2-((2S,4S)-1-(cyclopropyl((methoxycarbonyl)amino)acetyl)-4-methyl-2-pyrrolidinyl)-1H-imidazol-4-yl)-2-naphthyl)phenyl)-1H-imidazol-2-yl)-4-methyl-1-pyrrolidinyl)-2-oxoethyl)carbamate (24.5 mg, 57.8%). LC-MS retention time 3.08 min; calcd. for $C_{46}H_{53}N_8O_6$: 813.41. Found m/z 813.45 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.32 (s, 1H), 8.27 (s, 1H), 8.13 (d, J=8.6 Hz, 1H), 8.08 (d, J=8.6 Hz, 1H), 7.99-7.87 (m, 8H), 5.29-5.24 (m, 2H), 4.30 (br. s, 2H), 3.82-3.80 (m, 2H), 3.68 (s, 6H), 3.43-3.37 (m, 2H), 2.72-2.68 (m 2H), 2.55 (br. s, 2H), 1.91-1.86 (m, 2H), 1.25-1.24 (m, 6H), 1.11 (br. s, 2H), 0.60-0.58 (m, 4H), 0.53-0.51 (m, 2H), 0.04-0.38 (m, 2H).

4-(4-(6-(2-((2S,4S)-4-methyl-2-pyrrolidinyl)-1H-imidazol-4-yl)-2-naphthyl)phenyl)-1H-imidazole (Intermediate 196) (35 mg, 0.054 mmol), (S)-2-(methoxycarbonylamino)butanoic acid (19.14 mg, 0.119 mmol), and Hunig's base (0.075 mL, 0.432 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of methyl ((1S)-1-(((2S,4S)-2-(4-(4-(6-(2-((2S,4S)-1-((2S)-2-((methoxycarbonyl)amino)butanoyl)-4-methyl-2-pyrrolidinyl)-1H-imidazol-4-yl)-2-naphthyl)phenyl)-1H-imidazol-2-yl)-4-methyl-1-pyrrolidinyl)carbonyl)propyl)carbamate (36.4 mg, 61.7%). LC-MS retention time 2.91 min; calcd. for $C_{44}H_{53}N_8O_6$: 789.41. Found m/z 789.41 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1%

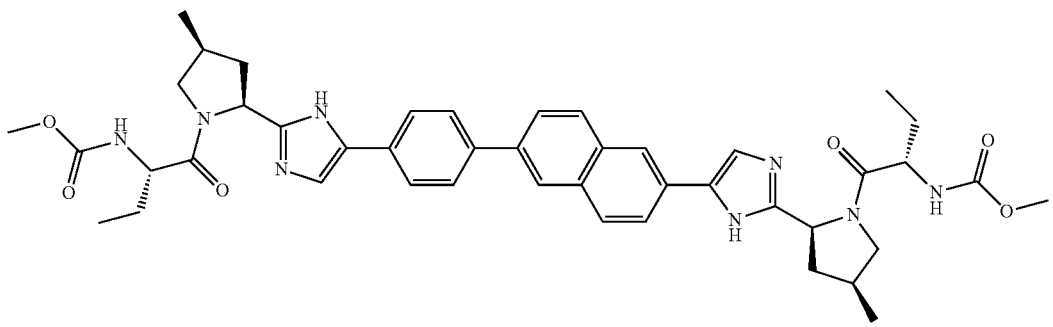

Methyl ((1S)-1-(((2S,4S)-2-(4-(4-(6-(2-((2S,4S)-1-((2S)-2-((methoxycarbonyl)amino)butanoyl)-4-methyl-2-pyrrolidinyl)-1H-imidazol-4-yl)-2-naphthyl)phenyl)-1H-imidazol-2-yl)-4-methyl-1-pyrrolidinyl)carbonyl)propyl)carbamate HATU (45 mg, 0.119 mmol) was added to a stirred solution of the tetra HCl salt of 2-((2S,4S)-4-methyl-2-pyrrolidinyl)-

TFA. MS data was determined using a MICROMASS® Platform for LC in electrospray mode. $^1$H NMR (TFA salt, 500 MHz, MeOD) δ ppm 8.30 (s, 1H), 8.28 (s, 1H), 8.14 (d, J=8.6 Hz, 1H), 8.09 (d, J=8.6 Hz, 1H), 8.00-7.86 (m, 8H), 5.27-5.22 (m, 2H), 4.37 (br. s, 2H), 4.24-4.23 (m, 2H), 3.67 (s, 6H), 3.44-3.39 (m, 2H), 2.72-2.68 (m 2H), 2.58 (br. s, 2H), 1.88-1.84 (m, 2H), 1.47-1.25 (m, 6H), 0.98-0.92 (m, 10H).

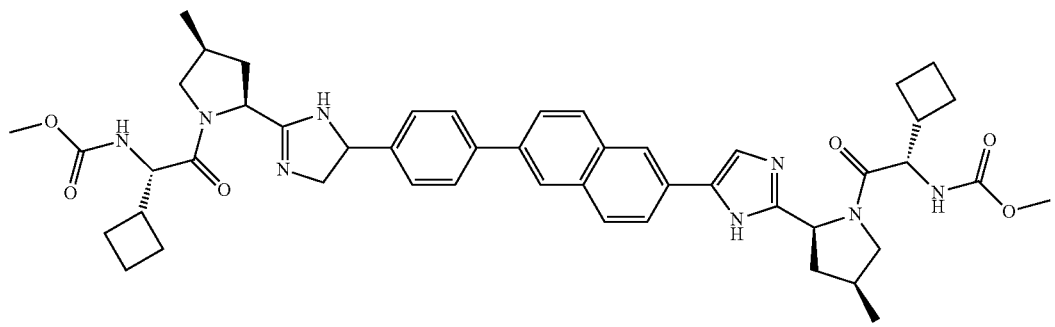

Methyl ((1S)-1-cyclobutyl-2-((2S,4S)-2-(4-(4-(6-(2-((2S,4S)-1-((2S)-2-cyclobutyl-2-((methoxycarbonyl)amino)acetyl)-4-methyl-2-pyrrolidinyl)-1H-imidazol-4-yl)-2-naphthyl)phenyl)-1H-imidazol-2-yl)-4-methyl-1-pyrrolidinyl)-2-oxoethyl)carbamate HATU (45 mg, 0.119 mmol) was added to a stirred solution of the tetra HCl salt of 2-((2S,4S)-4-methyl-2-pyrrolidinyl)-4-(4-(6-(2-((2S,4S)-4-methyl-2-pyrrolidinyl)-1H-imidazol-4-yl)-2-naphthyl)phenyl)-1H-imidazole (Intermediate 196) (35 mg, 0.054 mmol), (S)-2-cyclobutyl-2-(methoxycarbonylamino)acetic acid (22.23 mg, 0.119 mmol) (prepared in a similar manner as Cap-51 using commercially available (S)-2-(tert-butoxycarbonylamino)-2-cyclobutylacetic acid as a starting material) and Hunig's base (0.075 mL, 0.432 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of methyl ((1S)-1-cyclobutyl-2-((2S,4S)-2-(4-(4-(6-(2-((2S,4S)-1-((2S)-2-cyclobutyl-2-((methoxycarbonyl)amino)acetyl)-4-methyl-2-pyrrolidinyl)-1H-imidazol-4-yl)-2-naphthyl)phenyl)-1H-imidazol-2-yl)-4-methyl-1-pyrrolidinyl)-2-oxoethyl)carbamate (25.6 mg, 43.6%). LC-MS retention time 3.13 min; calcd. for $C_{48}H_{57}N_8O_6$: 841.44. Found m/z 841.48 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.30 (s, 1H), 8.28 (s, 1H), 8.14 (d, J=8.9 Hz, 1H), 8.09 (d, J=8.6 Hz, 1H), 8.00-7.86 (m, 8H), 5.26-5.21 (m, 2H), 4.41-4.37 (m, 4H), 3.68 (s, 6H), 3.48-3.43 (m, 2H), 2.71-2.66 (m 4H), 2.56 (br. s, 2H), 1.96-1.87 (m, 14H), 1.27-1.26 (m, 6H).

Methyl ((1S)-2-((2S,4S)-2-(4-(4-(6-(2-((2S,4S)-1-((2S)-2-((methoxycarbonyl)amino)-2-((2R,4S)-2-methyltetrahydro-2H-pyran-4-yl)acetyl)-4-methyl-2-pyrrolidinyl)-1H-imidazol-4-yl)-2-naphthyl)phenyl)-1H-imidazol-2-yl)-4-methyl-1-pyrrolidinyl)-1-((2S,4R)-2-methyltetrahydro-2H-pyran-4-yl)-2-oxoethyl)carbamate HATU (32 mg, 0.085 mmol) was added to a stirred solution of the tetra HCl salt of 2-((2S,4S)-4-methyl-2-pyrrolidinyl)-4-(4-(6-(2-((2S,4S)-4-methyl-2-pyrrolidinyl)-1H-imidazol-4-yl)-2-naphthyl)phenyl)-1H-imidazole (Intermediate 196) (25 mg, 0.039 mmol), 2-(methoxycarbonylamino)-2-((2R,4S)-2-methyltetrahydro-2H-pyran-4-yl)acetic acid (Cap-178, stereoisomer 1) (19.61 mg, 0.085 mmol) and Hunig's base (0.054 mL, 0.308 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of methyl ((1S)-2-((2S,4S)-2-(4-(4-(6-(2-((2S,4S)-1-((2S)-2-((methoxycarbonyl)amino)-2-((2R,4S)-2-methyltetrahydro-2H-pyran-4-yl)acetyl)-4-methyl-2-pyrrolidinyl)-1H-imidazol-4-yl)-2-naphthyl)phenyl)-1H-imidazol-2-yl)-4-methyl-1-pyrrolidinyl)-1-((2S,4R)-2-methyltetrahydro-2H-pyran-4-yl)-2-oxoethyl)carbamate (21.3 mg, 45.2%). LC-MS retention time 2.94 min; calcd. for $C_{52}H_{64}N_8O_8$: 929.49. Found m/z 929.64 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.32 (s, 1H), 8.28 (s, 1H), 8.15-8.12 (m, 1H), 8.09-8.06 (m, 1H), 8.02-7.94 (m, 5H), 7.90-7.86 (m, 3H), 5.28-5.23 (m, 2H), 4.50-4.48 (m, 2H), 4.44 (br. s, 2H), 3.95-3.91 (m, 2H), 3.71-3.68 (s, 10H), 3.46-3.41 (m, 2H), 2.72-2.67 (m, 2H), 2.55-2.52 (m, 2H), 2.19 (br. s, 2H), 1.97-1.92 (m, 2H), 1.60 (br. s, 2H), 1.48-1.46 (m, 2H), 1.39 (br. s, 2H), 1.30-1.26 (m, 8H), 1.14-1.10 (m, 6H).

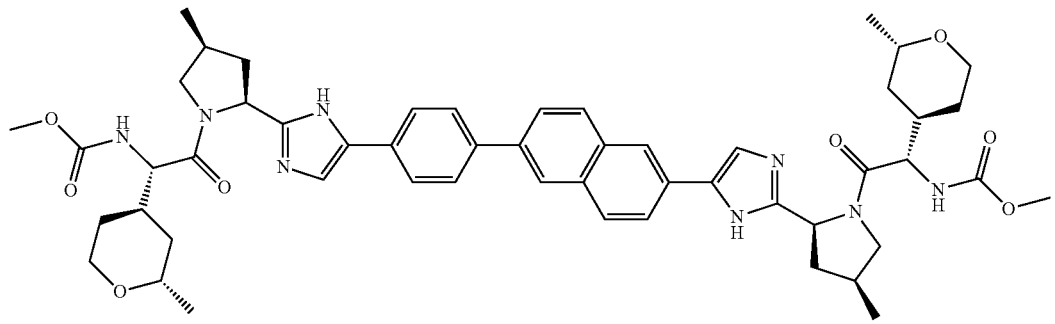

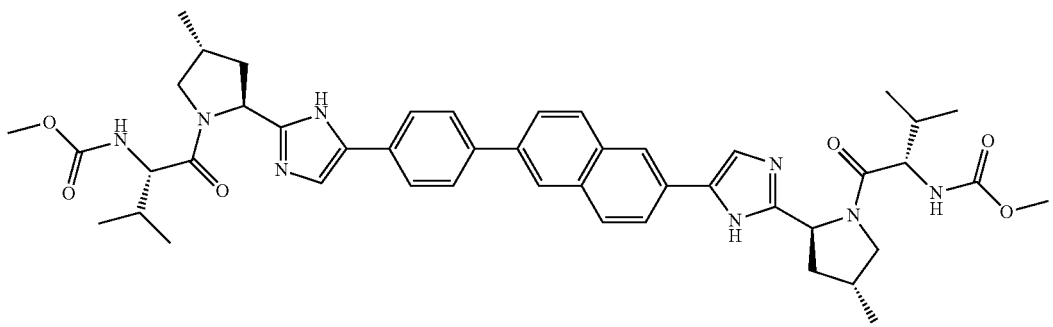

Methyl ((1S)-1-(((2S,4R)-2-(4-(4-(6-(2-((2S,4R)-1-((2S)-2-((methoxycarbonyl)amino)-3-methylbutanoyl)-4-methyl-2-pyrrolidinyl)-1H-imidazol-4-yl)-2-naphthyl)phenyl)-1H-imidazol-2-yl)-4-methyl-1-pyrrolidinyl)carbonyl)-2-methylpropyl)carbamate HATU (65 mg, 0.171 mmol) was added to a stirred solution of the tetra HCl salt of 2-((2S,4R)-4-methyl-2-pyrrolidinyl)-4-(4-(6-(2-((2S,4R)-4-methyl-2-pyrrolidinyl)-1H-imidazol-4-yl)-2-naphthyl)phenyl)-1H-imidazole (Intermediate 201) (50 mg, 0.077 mmol), (S)-2-(methoxycarbonylamino)-3-methylbutanoic acid (30 mg, 0.170 mmol), and Hunig's base (0.108 mL, 0.308 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of methyl ((1S)-1-(((2S,4R)-2-(4-(4-(6-(2-((2S,4R)-1-((2S)-2-((methoxycarbonyl)amino)-3-methylbutanoyl)-4-methyl-2-pyrrolidinyl)-1H-imidazol-4-yl)-2-naphthyl)phenyl)-1H-imidazol-2-yl)-4-methyl-1-pyrrolidinyl)carbonyl)-2-methylpropyl)carbamate (60.7 mg, 71%). LC-MS retention time 3.12 min; calcd. for $C_{46}H_{57}N_8O_6$: 817.44. Found m/z 817.46 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.30 (s, 1H), 8.28 (s, 1H), 8.14 (d, J=8.6 Hz, 1H), 8.09 (d, J=8.6 Hz, 1H), 8.00-7.86 (m, 8H), 5.43-5.38 (m, 2H), 4.26-4.24 (m, 2H), 4.09-4.05 (m, 2H), 3.69 (s, 6H), 3.64 (br. s, 2H), 2.76-2.73 (m 2H), 235-2.32 (m, 2H), 2.25-2.22 (m, 2H), 2.11-2.09 (m, 2H), 1.22-1.20 (m, 6H), 0.98-0.93 (m, 12H).

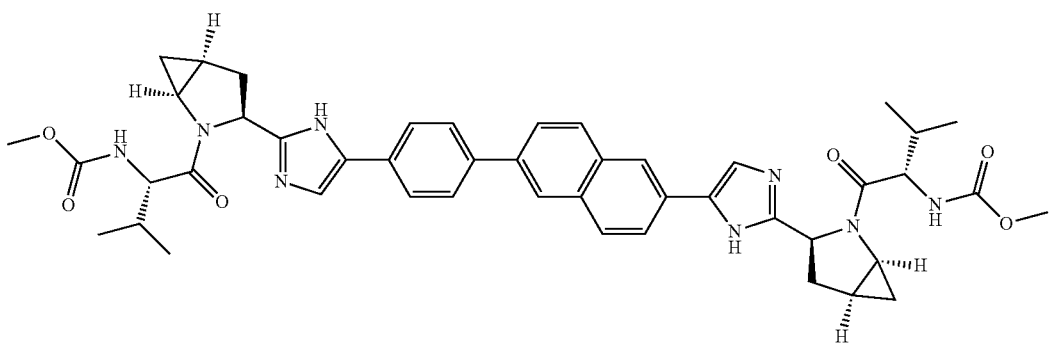

Methyl ((1S)-1-(((1S,3S,5S)-3-(4-(4-(6-(2-((1S,3S,5S)-2-((2S)-2-((methoxycarbonyl)amino)-3-methylbutanoyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)carbonyl)-2-methylpropyl)carbamate HATU (65 mg, 0.171 mmol) was added to a stirred solution of the tetra HCl salt of (1S,3S,5S)-3-(4-(4-(6-(2-((1S,3S,5S)-2-azabicyclo[3.1.0]hex-3-yl)-1H-imidazol-4-yl)-2-naphthyl)phenyl)-1H-imidazol-2-yl)-2-azabicyclo[3.1.0]hexane (Intermediate 203) (50 mg, 0.078 mmol), (S)-2-(methoxycarbonylamino)-3-methylbutanoic acid (30 mg, 0.111 mmol), and Hunig's base (0.108 mL, 0.621 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of methyl ((1S)-1-(((1S,3S,5S)-3-(4-(4-(6-(2-((1S,3S,5S)-2-((2S)-2-((methoxycarbonyl)amino)-3-methylbutanoyl)-2-azabicyclo[3.1.0]hex-3-yl)-1H-imidazol-4-yl)-2-naphthyl)phenyl)-1H-imidazol-2-yl)-2-azabicyclo[3.1.0]hex-2-yl)carbonyl)-2-methylpropyl)carbamate (54 mg, 63%). LC-MS retention time 3.15 min; calcd. for $C_{46}H_{53}N_8O_6$: 813.41. Found m/z 813.45 [M+H]$^+$. LC data was recorded on a Shimadzu LC-10AS liquid chromatograph equipped a PHENOM- ENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.33 (s, 1H), 8.26 (s, 1H), 8.12 (d, J=8.6 Hz, 1H), 8.07 (d, J=8.6 Hz, 1H), 7.98-7.86 (m, 8H), 5.80-5.74 (m, 2H), 4.36-4.34 (m, 2H), 4.02-3.99 (m, 2H), 3.73 (s, 6H), 2.99-2.95 (m, 2H), 2.28-2.25 (m 2H), 2.16 (br. s, 2H), 2.04 (br.s, 2H), 1.24-1.20 (m, 2H), 1.08 (br. s, 2H), 1.02-1.00 (m, 12H).

mg, 0.164 mmol), and Hunig's base (0.104 mL, 0.595 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of Methyl ((1S)-1-(((1S,3S,5S)-3-(4-(4-(6-(2-((1S,3S,5S)-2-((2S)-2-((methoxycarbonyl)amino)-3-methylbutanoyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hex-2-yl)carbonyl)-2-methylpropyl) carbamate (45 mg, 54%). LC-MS retention time 3.15 min; calcd. for $C_{48}H_{57}N_8O_6$: 841.44. Found m/z 841.50 [M+H]$^+$. LC data was recorded on a Shimadzu LC-10AS liquid chromatograph equipped a PHENOMENEX® C18 2.0×50 mm

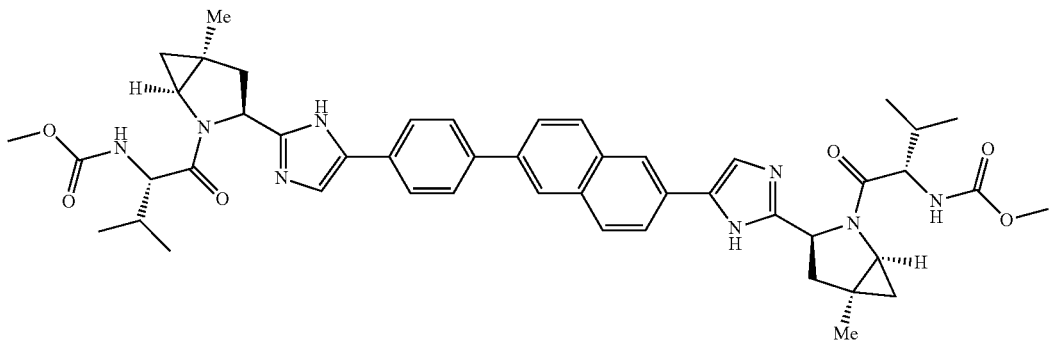

Methyl ((1S)-1-(((1S,3S,5S)-3-(4-(4-(6-(2-((1S,3S,5S)-2-((2S)-2-((methoxycarbonyl)amino)-3-methylbutanoyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hex-2-yl)carbonyl)-2-methylpropyl)carbamate HATU (62 mg, 0.164 mmol) was added to a stirred solution of the tetra HCl salt of (1S,3S,5S)-5-methyl-3-(4-(4-(6-(2-((1S,3S,5S)-5-methyl-2-azabicyclo[3.1.0]hex-3-yl)-1H-imidazol-4-yl)-2-naphthyl)phenyl)-1H-imidazol-2-yl)-2-azabicyclo[3.1.0]hexane (Intermediate 209) (50 mg, 0.074 mmol), (S)-2-(methoxycarbonylamino)-3-methylbutanoic acid (28.7 column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.33 (s, 1H), 8.25 (s, 1H), 8.11 (d, J=8.5 Hz, 1H), 8.06 (d, J=8.7 Hz, 1H), 7.97-7.85 (m, 8H), 5.82-5.75 (m, 2H), 4.31-4.28 (m, 2H), 3.73-3.71 (m, 8H), 2.75-2.69 (m, 2H), 2.44-2.37 (m 2H), 2.17-2.12 (m, 2H), 1.40 (s, 6H), 1.1-1.11 (m, 4H), 1.01-0.99 (m, 12H).

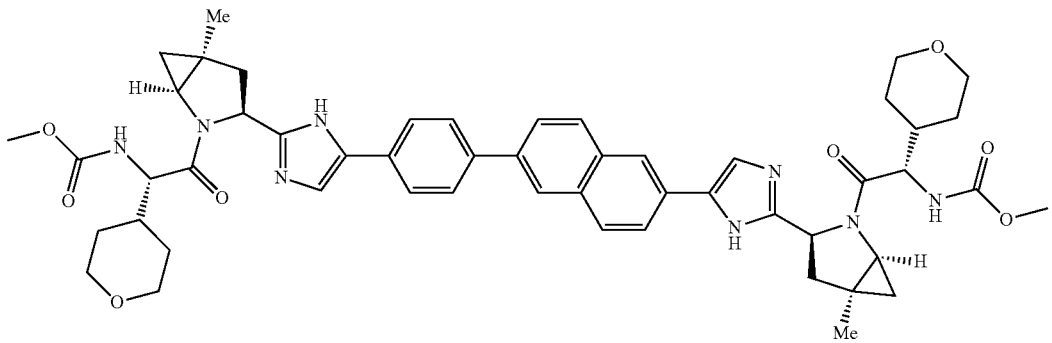

563

Methyl ((1S)-2-((1S,3S,5S)-3-(4-(4-(6-(2-((1S,3S,5S)-2-((2S)-2-((methoxycarbonyl)amino)-2-(tetrahydro-2H-pyran-4-yl)acetyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hex-2-yl)-2-oxo-1-(tetrahydro-2H-pyran-4-yl)ethyl)carbamate HATU (62 mg, 0.164 mmol) was added to a stirred solution of the tetra HCl salt of (1S,3S,5S)-5-methyl-3-(4-(4-(6-(2-((1S,3S,5S)-5-methyl-2-azabicyclo[3.1.0]hex-3-yl)-1H-imidazol-4-yl)-2-naphthyl)phenyl)-1H-imidazol-2-yl)-2-azabicyclo[3.1.0]hexane (Intermediate 209) (50 mg, 0.074 mmol), (S)-2-(methoxycarbonylamino)-2-(tetrahydro-2H-pyran-4-yl)acetic acid (35.5 mg, 0.164 mmol), and Hunig's base (0.104 mL, 0.595 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of methyl ((1S)-2-((1S,3S,5S)-3-(4-(4-(6-(2-((1S,3S,5S)-2-((2S)-2-((methoxycarbonyl)amino)-2-(tetrahydro-2H-pyran-4-yl)acetyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hex-2-yl)-2-oxo-1-(tetrahydro-2H-pyran-4-yl)ethyl)carbamate (46.3 mg, 51%). LC-MS retention time 3.15 min; calcd. for $C_{52}H_{61}N_8O_6$: 925.46. Found m/z 463.36 [M/2+H]$^+$. LC data was recorded on a Shimadzu LC-10AS liquid chromatograph equipped a PHENOMENEX® C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.31 (s, 1H), 8.25 (s, 1H), 8.10 (d, J=8.8 Hz, 1H), 8.06 (d, J=8.8 Hz, 1H), 7.97-7.85 (m, 8H), 5.80-5.74 (m, 2H), 4.36-4.35 (m, 2H), 3.99-3.95 (m, 4H), 3.76-3.74 (m, 8H), 3.43-3.35 (m, 4H), 2.75-2.68 (m, 2H), 2.44-2.37 (m 2H), 2.06-2.04 (m, 2H), 1.74 (app. d, J=13 Hz, 2H), 1.52-1.35 (m, 12H), 1.22-1.19 (m, 2H), 1.14-1.12 (m, 2H).

564

Methyl ((1S)-1-(((1R,3S,5R)-3-(4-(4-(6-(2-((1R,3S,5R)-2-((2S)-2-((methoxycarbonyl)amino)-3-methylbutanoyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hex-2-yl)carbonyl)-2-methylpropyl)carbamate HATU (31 mg, 0.082 mmol) was added to a stirred solution of the tetra HCl salt of (1R,3S,5R)-3-(4-(4-(6-(2-((1R,3S,5R)-2-(tert-butoxycarbonyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hexane-2-carboxylate (Intermediate 211) (25 mg, 0.037 mmol), (S)-2-(methoxycarbonylamino)-3-methylbutanoic acid (14 mg, 0.082 mmol), and Hunig's base (0.052 mL, 0.297 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of Methyl ((1S)-1-(((1R,3S,5R)-3-(4-(4-(6-(2-((1R,3S,5R)-2-((2S)-2-((methoxycarbonyl)amino)-3-methylbutanoyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hex-2-yl)carbonyl)-2-methylpropyl)carbamate (17 mg, 41%). LC-MS retention time 3.10 min; calcd. for $C_{48}H_{57}N_8O_6$: 841.44. Found m/z 841.542 [M+H]$^+$. LC data was recorded on a Shimadzu LC-10AS liquid chromatograph equipped a PHENOMENEX® C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.27 (s, 1H), 8.26 (s, 1H), 8.12 (d, J=8.5 Hz, 1H), 8.07 (d, J=8.7 Hz, 1H), 7.98-7.93 (m, 4H), 7.88-7.85 (m, 4H), 5.09-5.04 (m, 2H), 4.55-4.53 (m, 2H), 3.38 (s, 6H), 3.57 (br.s, 2H), 2.81-2.75 (m, 2H), 2.33-2.27 (m 2H), 2.22-2.16 (m, 2H), 1.44 (s, 3H), 1.43 (s, 3H), 1.05-0.93 (m, 16H).

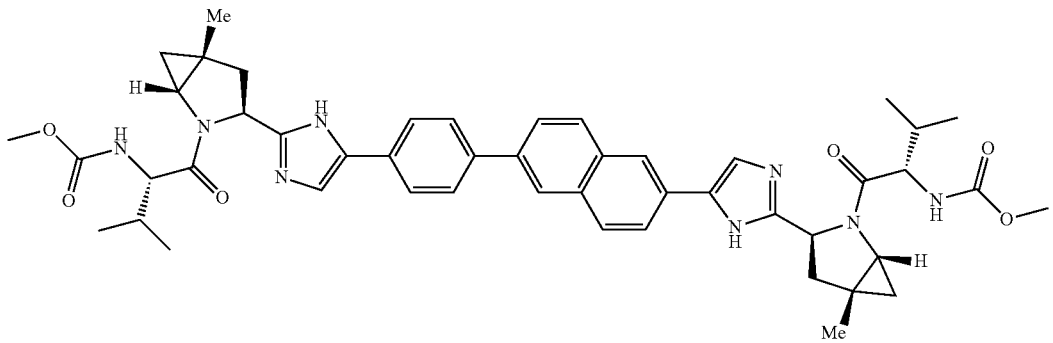

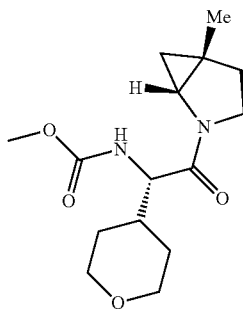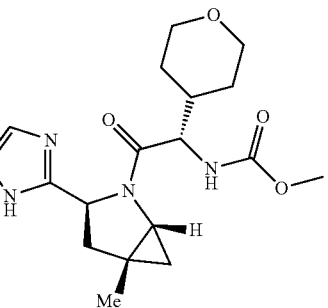

Methyl ((1S)-1-(((1R,3S,5R)-3-(4-(4-(6-(2-((1R,3S,5R)-2-((2S)-2-((methoxycarbonyl)amino)-3-methylbutanoyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hex-2-yl)carbonyl)-2-methylpropyl)carbamate HATU (34.8 mg, 0.092 mmol) was added to a stirred solution of the tetra HCl salt of (1R,3S,5R)-3-(4-(4-(6-(2-((1R,3S,5R)-2-(tert-butoxycarbonyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hexane-2-carboxylate (Intermediate 211) (28 mg, 0.042 mmol), (S)-2-(methoxycarbonylamino)-2-(tetrahydro-2H-pyran-4-yl)acetic acid (20 mg, 0.092 mmol), and Hunig's base (0.085 mL, 0.333 mmol) in DMF (2 mL). The reaction was stirred 1 h at room temperature and partially concentrated by purge of nitrogen gas. The residue was taken up in MeOH and purified by preparative HPLC (MeCN/water with 0.1% TFA) to afford a bis TFA salt of methyl ((1S)-1-(((1R,3S,5R)-3-(4-(4-(6-(2-((1R,3S,5R)-2-((2S)-2-((methoxycarbonyl)amino)-3-methylbutanoyl)-5-methyl-2-azabicyclo[3.1.0]hex-3-yl)-1H-imidazol-4-yl)-2-naphthyl)phenyl)-1H-imidazol-2-yl)-5-methyl-2-azabicyclo[3.1.0]hex-2-yl)carbonyl)-2-methylpropyl)carbamate (13 mg, 25%). LC-MS retention time 2.92 min; calcd. for $C_{52}H_{61}N_8O_6$: 925.46. Found m/z 92.53 [M+H]$^+$. LC data was recorded on a Shimadzu LC-10AS liquid chromatograph equipped a PHENOMENEX® C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.28 (s, 2H), 8.14 (d, J=8.8 Hz, 1H), 8.07 (d, J=8.6 Hz, 1H), 8.00-7.96 (m, 4H), 7.91-7.84 (m, 4H), 5.08-5.02 (m, 2H), 4.59-4.56 (m, 2H), 4.00-3.94 (m, 4H), 3.69 (s, 6H), 3.62 (br. s, 2H), 3.44-3.38 (m, 4H), 2.81-2.78 (m, 2H), 2.31-2.29 (m, 2H), 2.09 (br. s, 2H), 1.60-1.47 (m, 8H), 1.43 (s, 3H), 1.44 (s, 3H), 1.04 (br. s, 2H), 0.98-0.97 (m, 2H).

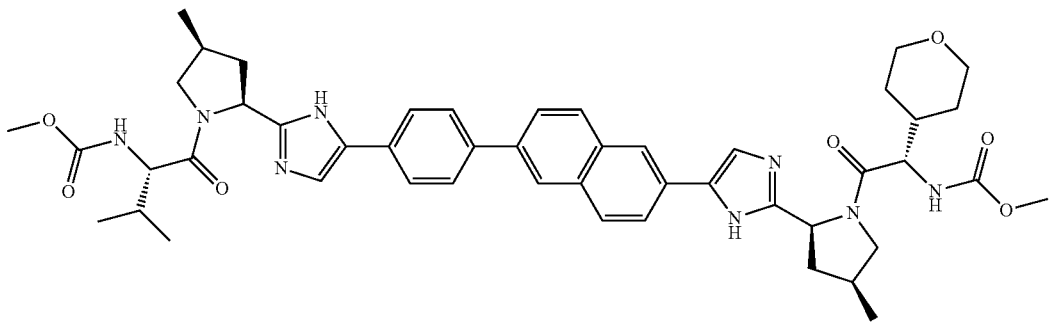

Methyl ((1S)-1-(((2S,4S)-2-(4-(4-(6-(2-((2S,4S)-1-((2S)-2-((methoxycarbonyl)amino)-2-(tetrahydro-2H-pyran-4-yl)acetyl)-4-methyl-2-pyrrolidinyl)-1H-imidazol-4-yl)-2-naphthyl)phenyl)-1H-imidazol-2-yl)-4-methyl-1-pyrrolidinyl)carbonyl)-2-methylpropyl)carbamate HATU (97 mg, 0.254 mmol) was added to a stirred solution of the tetra HCl salt of 2-((2S,4S)-4-methyl-2-pyrrolidinyl)-4-(4-(6-(2-((2S,4S)-4-methyl-2-pyrrolidinyl)-1H-imidazol-4-yl)-2-naphthyl)phenyl)-1H-imidazole (Intermediate 196) (150 mg, 0.231 mmol), (S)-2-(methoxycarbonylamino)-2-(tetrahydro-2H-pyran-4-yl)acetic acid (50 mg, 0.231 mmol), and Hunig's base (0.162 mL, 0.925 mmol) in DMF (1 mL). The reaction was stirred 1 h at room temperature before addition of (S)-2-(methoxycarbonylamino)-3-methylbutanoic acid (40.5 mg, 0.231 mmol) and add'l Hunig's base (0.162 mL, 0.925 mmol) and HATU (97 mg, 0.254 mmol). The mixture was stirred further at rt for 1 h and partially concentrated by purge of nitrogen gas. The residue was taken up in MeOH and purified by preparative HPLC (MeCN/water with 0.1% TFA). A second method of chromatography was applied to separate the isomers: SFC Diol-HL column, 20% methanol with 0.1% DEA; 4.6×250 mm, 5 μm Mobile Phase: 80% $CO_2$-20% methanol with 0.1% DEA; Temp: 35° C.; Pressure: 150 bar; Flow rate: 2 ml/min; UV monitored at 328 nm. The isolated sample was taken up in methanol (3 mL) and neat TFA (50 mL) was added at rt. The mixture was concentrated down to dryness and placed on high vacuum to afford a bis TFA salt of methyl ((1S)-1-(((2S,4S)-2-(4-(4-(6-(2-((2S,4S)-1-((2S)-2-((methoxycarbonyl)amino)-2-(tetrahydro-2H-pyran-4-yl)acetyl)-4-methyl-2-pyrrolidinyl)-1H-imidazol-4-yl)-2-naphthyl)phenyl)-1H-imidazol-2-yl)-4-methyl-1-pyrrolidinyl)carbonyl)-2-methylpropyl)carbamate (78.2 mg, 29.5% yield). LC-MS retention time 2.95 min; calcd. for $C_{48}H_{59}N_8O_7$: 859.45. Found m/z 859.50 [M-+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.30 (s, 1H), 8.28 (s, 1H), 8.15 (d, J=8.6 Hz, 1H), 8.09 (d, J=8.6 Hz, 1H), 8.01-7.85 (m, 8H), 5.26-5.22 (m, 2H), 4.42-4.36 (m, 2H), 4.30-4.27 (m, 1H), 4.24-4.23 (m, 1H), 3.95-3.91 (m, 2H), 3.68 (s, 6H), 3.47-3.36 (m 2H), 3.08-3.04 (m, 1H), 2.70 (br. s, 2H), 2.55 (br. s, 2H), 2.08-2.03 (m, 1H), 1.97-1.87 (m, 3H), 1.59 (d, J=13.0 Hz, 1H), 1.48-1.26 (m, 10H) 0.95-0.90 (m, 6H).

Found m/z 859.58 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.29 (s, 1H), 8.28 (s, 1H), 8.13 (d, J=8.6 Hz, 1H), 8.09 (d, J=8.6 Hz, 1H), 7.99-7.86 (m, 4H), 7.91-7.85 (m, 4H), 5.26-5.21 (m, 2H), 4.41-4.36 (m, 4H), 4.28 (d, J=8.24 Hz, 1H), 4.24 (d, J=7.32 Hz, 1H), 3.95-3.91 (m, 2H), 3.68 (s, 6H), 3.47-3.36 (m 2H), 2.73-2.66 (m, 2H), 2.59-2.53 (m, 2H), 2.07-2.03 (m, 1H), 1.97-1.87 (m, 3H), 1.59 (d, J=13.0 Hz, 1H), 1.51-1.25 (m, 11H) 0.95-0.90 (m, 6H).

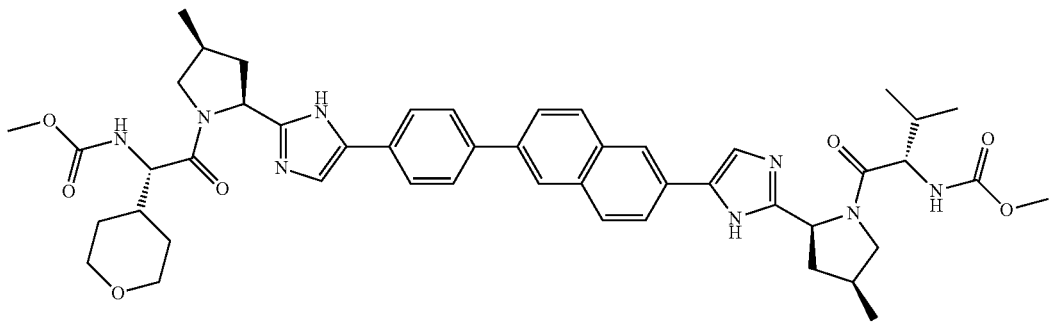

Methyl ((1S)-2-((2S,4S)-2-(4-(4-(6-(2-((2S,4S)-1-((2S)-2-((methoxycarbonyl)amino)-3-methylbutanoyl)-4-methyl-2-pyrrolidinyl)-1H-imidazol-4-yl)-2-naphthyl)phenyl)-1H-imidazol-2-yl)-4-methyl-1-pyrrolidinyl)-2-oxo-1-(tetrahydro-2H-pyran-4-yl)ethyl)carbamate The other isomer as reported in Example 140. LC-MS retention time 2.98 min; calcd. for $C_{48}H_{59}N_8O_7$: 859.45.

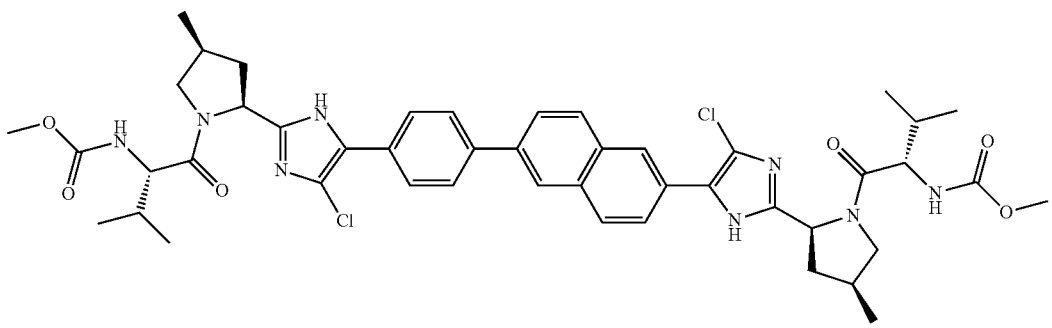

Methyl ((1S)-1-(((2S,4S)-2-(4-chloro-5-(6-(4-(4-chloro-2-((2S,4S)-1-((2S)-2-((methoxycarbonyl)amino)-3-methylbutanoyl)-4-methyl-2-pyrrolidinyl)-1H-imidazol-5-yl)phenyl)-2-naphthyl)-1H-imidazol-2-yl)-4-methyl-1-pyrrolidinyl)carbonyl)-2-methylpropyl)carbamate The NCS (18.0 mg, 0.135 mmol) was added to a nitrogen purged solution of Example 128 (55 mg, 0.067 mmol) in DMF (1 mL) and the reaction mixture was stirred for 18 h at 50° C. The solvent was removed by concentrate, and the crude product was taken up in CH2Cl2 and charged to a 4 g Thompson silica gel cartridge. Gradient elution was performed from 5-100% B over 1 L. A/B (A=CH$_2$Cl$_2$; B=10% MeOH/EtOAc). A sample of the purified product was taken up in MeOH and subject to preparative HPLC (MeCN/water with 0.1% TFA) to afford a bis TFA salt of methyl ((1S)-1-(((2S,4S)-2-(4-chloro-5-(6-(4-(4-chloro-2-((2S,4S)-1-((2S)-2-((methoxycarbonyl)amino)-3-methylbutanoyl)-4-methyl-2-pyrrolidinyl)-1H-imidazol-5-yl)phenyl)-2-naphthyl)-1H-imidazol-2-yl)-4-methyl-1-pyrrolidinyl)carbonyl)-2-methylpropyl) carbamate. LC-MS retention time 4.48 min; calcd. for C$_{46}$H$_{55}$Cl$_2$N$_8$O$_6$: 885.36. Found m/z 885.34 [M+H]$^+$. LC data was recorded on a Shimadzu LC-10AS liquid chromatograph equipped a PHENOMENEX® Luna C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.20 (s, 1H), 8.18 (s, 1H), 8.03 (d, J=8.6 Hz, 1H), 8.00 (d, J=8.6 Hz, 1H), 7.90-7.83 (m, 6H), 5.09-5.04 (m, 2H), 4.30-4.7 (m, 2H), 4.24-4.23 (m, 2H), 3.68 (s, 6H), 3.43-3.99 (m, 2H), 2.58-2.56 (m 2H), 2.43 (br. s, 2H), 2.05-2.04 (m, 2H), 1.93-1.87 (m, 2H), 1.24-1.22 (m, 6H), 0.97-0.91 (m, 12H).

Methyl ((1S)-1-(((2S,4S)-2-(4-(4-(6-(4-chloro-2-((2S,4S)-1-((2S)-2-((methoxycarbonyl)amino)-3-methylbutanoyl)-4-methyl-2-pyrrolidinyl)-1H-imidazol-5-yl)-2-naphthyl)phenyl)-1H-imidazol-2-yl)-4-methyl-1-pyrrolidinyl)carbonyl)-2-methylpropyl) carbamate HATU (34 mg, 0.090 mmol) was added to a stirred solution of an HCl salt of 4-chloro-2-((2S,4S)-4-methylpyrrolidin-2-yl)-5-(6-(4-(2-((2S,4S)-4-methylpyrrolidin-2-yl)-1H-imidazol-5-yl)phenyl)naphthalen-2-yl)-1H-imidazole (30.0 mg, 0.041 mmol), (S)-2-(methoxycarbonylamino)-3-methylbutanoic acid (15.7 mg, 0.090 mmol), and Hunig's base (0.057 mL, 0.33 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a TFA salt of methyl ((1S)-1-(((2S,4S)-2-(4-(4-(6-(4-chloro-2-((2S,4S)-1-((2S)-2-((methoxycarbonyl)amino)-3-methylbutanoyl)-4-methyl-2-pyrrolidinyl)-1H-imidazol-5-yl)-2-naphthyl)phenyl)-1H-imidazol-2-yl)-4-methyl-1-pyrrolidinyl)carbonyl)-2-methylpropyl)carbamate (24.5 mg) as an off-white solid. LC-MS retention time 3.77 min; calcd. for C$_{46}$H$_{56}$ClN$_8$O$_6$: 851.40. Found m/z 851.42 [M+H]. LC data was recorded on a Shimadzu LC-10AS liquid chromatograph equipped a PHENOMENEX® C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.23 (s, 1H), 8.22 (s, 1H), 8.06 (d, J=8.9 Hz, 1H), 8.02 (d, J=8.9 Hz, 1H), 7.98 (d, J=8.2 Hz, 2H), 7.93-7.89 (m, 3H), 7.85 (d, J=8.9 Hz, 2H), 5.26-5.22 (m, 1H), 5.07-5.04 (m, 1H), 4.36 (t, J=9.1 Hz 1H), 4.29-4.23 (m, 3H), 3.68 (s, 3H), 3.67 (s, 3H), 3.41 (dt, J=10.7, 4.3 Hz, 2H), 2.72-2.67 (m, 1H), 2.58-2.53 (m 2H), 2.45-2.40 (m, 1H), 2.06-2.02 (m, 2H), 1.91-1.83 (m, 2H), 1.26 (d, J=6.1 Hz, 3H), 1.22 (d, J=8.9 Hz, 3H), 0.97-0.91 (m, 12H).

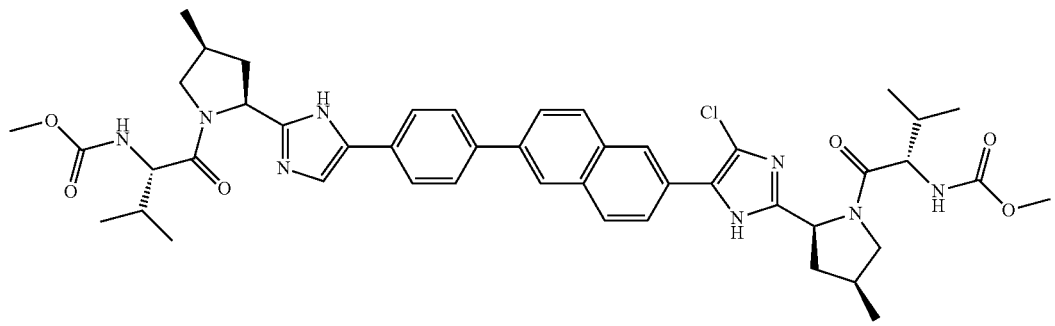

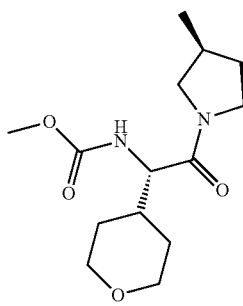
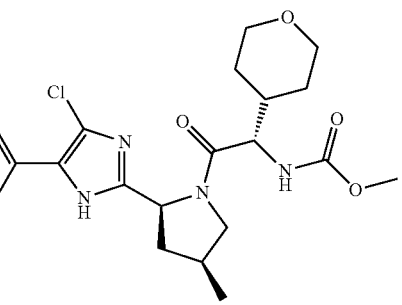

Methyl ((1S)-2-((2S,4S)-2-(4-(4-(6-(4-chloro-2-((2S,4S)-1-((2S)-2-((methoxycarbonyl)amino)-2-(tetrahydro-2H-pyran-4-yl)acetyl)-4-methyl-2-pyrrolidinyl)-1H-imidazol-5-yl)-2-naphthyl)phenyl)-1H-imidazol-2-yl)-4-methyl-1-pyrrolidinyl)-2-oxo-1-(tetrahydro-2H-pyran-4-yl)ethyl)carbamate HATU (51 mg, 0.134 mmol) was added to a stirred solution of an HCl salt of 4-chloro-2-((2S,4S)-4-methylpyrrolidin-2-yl)-5-(6-(4-(2-(((2S,4S)-4-methylpyrrolidin-2-yl)-1H-imidazol-5-yl)phenyl)naphthalen-2-yl)-1H-imidazole (32.7 mg, 0.061 mmol), (S)-2-(methoxycarbonylamino)-2-(tetrahydro-2H-pyran-4-yl)acetic acid (29.2 mg, 0.134 mmol), and Hunig's base (0.085 mL, 0.49 mmol) in DMF (1 mL). The reaction was stirred 1 h at room temperature and partially concentrated by purge of nitrogen gas. The residue was taken up in MeOH and purified by preparative HPLC (MeCN/water with 0.1% TFA) to afford a TFA salt of methyl ((1S)-2-((2S,4S)-2-(4-(4-(6-(4-chloro-2-((2S,4S)-1-((2S)-2-((methoxycarbonyl)amino)-2-(tetrahydro-2H-pyran-4-yl)acetyl)-4-methyl-2-pyrrolidinyl)-1H-imidazol-5-yl)-2-naphthyl)phenyl)-1H-imidazol-2-yl)-4-methyl-1-pyrrolidinyl)-2-oxo-1-(tetrahydro-2H-pyran-4-yl)ethyl)carbamate (22 mg) as a light yellow solid. LC-MS retention time 3.55 min; calcd. for $C_{50}H_{60}ClN_8O_8$: 935.42. Found m/z 935.52 [M+H]. LC data was recorded on a Shimadzu LC-10AS liquid chromatograph equipped a PHENOMENEX® C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.21 (s, 2H), 8.05 (d, J=8.9 Hz, 1H), 8.02 (d, J=8.9 Hz, 1H), 7.92 (d, J=8.6 Hz, 2H), 7.93-7.89 (m, 3H), 7.85 (d, J=8.2 Hz, 2H), 5.25-5.22 (m, 1H), 5.06-5.02 (m, 1H), 4.40 (t, J=8.9 Hz 1H), 4.31-4.27 (m, 3H), 3.95-3.92 (m, 4H), 3.68 (s, 3H), 3.67 (s, 3H), 3.46-3.36 (m, 6H), 2.72-2.67 (m, 1H), 2.57-2.52 (m 2H), 2.45-2.40 (m, 1H), 1.98-1.86 (m, 4H), 1.61-1.59 (m, 2H), 1.56-131. (m, 6H), 1.27 (d, J=6.4 Hz, 3H), 1.22 (d, J=6.4 Hz, 3H).

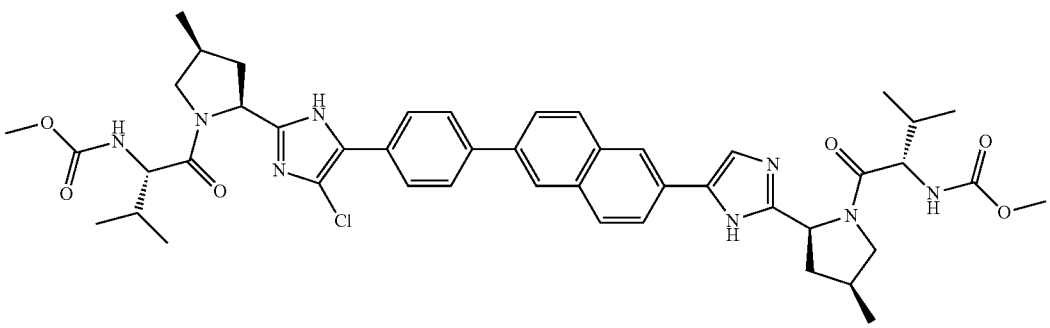

Methyl ((1S)-1-(((2S,4S)-2-(4-(6-(4-(4-chloro-2-((2S,4S)-1-((2S)-2-((methoxycarbonyl)amino)-3-methylbutanoyl)-4-methyl-2-pyrrolidinyl)-1H-imidazol-5-yl)phenyl)-2-naphthyl)-1H-imidazol-2-yl)-4-methyl-1-pyrrolidinyl)carbonyl)-2-methylpropyl) carbamate NCS (108 mg, 0.808 mmol) was added to a solution of a TFA salt of methyl ((1S)-1-(((2S,4S)-2-(4-(4-(6-(2-((2S,4S)-1-((2S)-2-((methoxycarbonyl)amino)-3-methylbutanoyl)-4-methyl-2-pyrrolidinyl)-1H-imidazol-4-yl)-2-naphthyl)phenyl)-1H-imidazol-2-yl)-4-methyl-1-pyrrolidinyl)carbonyl)-2-methylpropyl)carbamate (550 mg, 1.385 mmol) in dry DMF (10 mL) and the mixture was heated at 50° C. for 18 h. The solvent was removed by rotary evaporation under high vacuum and the residue was purified utilizing a Thompson 25 g silica gel cartridge (gradient elution 5%-100% B over 1 L; Solvent B=10% MeOH in ethyl acetate and Solvent A=dichloromethane).

The partially purified product was subjected to prep HPLC ($CH_3CN/H_2O/TFA$) on a Waters-Sunfire column (30×100 mm S5) 0-80% B over 35 min and the mono chloro adducts (116 mg, 20% as a 7:1 mixture favoring Example 145) were separated from dichloro adduct (see Example 142). The mono chloro adducts were further purified by chiral SFC chromatography; CHIRALCEL® OJ-H column (85% $CO_2$; 15%

EtOH with 0.1% DEA) to yield methyl ((1S)-1-(((2S,4S)-2-(4-(6-(4-(4-chloro-2-((2S,4S)-1-((2S)-2-((methoxycarbonyl)amino)-3-methylbutanoyl)-4-methyl-2-pyrrolidinyl)-1H-imidazol-5-yl)phenyl)-2-naphthyl)-1H-imidazol-2-yl)-4-methyl-1-pyrrolidinyl)carbonyl)-2-methylpropyl)carbamate (10 mg) as a yellowish residue. LC-MS retention time 3.75 min; calcd. for $C_{46}H_{56}ClN_8O_6$: 851.40. Found m/z 851.39 [M+H]. LC data was recorded on a Shimadzu LC-10AS liquid chromatograph equipped with a PHENOMENEX® Luna 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (TFA salt, 500 MHz, MeOD) δ ppm 8.20 (s, 1H), 8.15 (s, 1H), 8.01 (d, J=8.2 Hz, 1H), 7.98 (d, J=8.6 Hz, 1H), 7.90 (d, J=8.6 Hz, 1H), 7.86 (d, J=7.0 Hz, 1H), 7.83 (d, J=7.3 Hz, 2H), 7.79 (d, J=8.2 Hz, 2H), 7.44 (s, 1H), 5.14-5.10 (m, 1H), 5.06-5.02 (m, 1H), 4.27-4.22 (m, 4H), 3.67 (s, 6H), 3.46-3.47 (m, 2H), 2.57-2.51 (m, 2H), 2.45-2.39 (m 2H), 2.06-2.01 (m, 2H), 1.95-1.90 (m, 2H), 1.23-1.22 (m, 6H), 0.97-0.91 (m, 12H).

tereomer thereof. LC-MS retention time 2.86 min; calcd. for $C_{50}H_{61}N_8O_8$: 901.46. Found m/z 901.42 [M+H]. LC data was recorded on a Shimadzu LC-10AS liquid chromatograph equipped a PHENOMENEX® C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min and an analysis time of 5 min where Solvent A was 5% MeOH/95% water/0.1% TFA and Solvent B was 95% MeOH/5% water/0.1% TFA. MS data was determined using a MICROMASS® Platform for LC in electrospray mode. $^1$H NMR (TFA salt, 500 MHz, MeOD) δ ppm 8.34/8.29 (s, 1H), 8.27 (s, 1H), 8.13 (d, J=7.63 Hz, 1H), 8.08 (d, J=8.6 Hz, 1H), 7.99-7.95 (m, 4H), 7.92-7.87 (m, 4H), 5.29-5.21 (m, 2H), 4.38 (t, J=7.3 Hz, 1H), 4.31-4.28 (m, 2H), 4.16-4.13 (m, 1H), 3.99-3.91 (m, 4H), 3.68 (s, 3H), 3.65/3.61 (s, 3H), 3.56-3.36 (m, 6H), 2.76-2.62 (m, 2H), 2.56 (br. s, 2H), 2.00-1.83 (m, 4H), 1.71 (d, J=12.8 Hz, 1H), 1.31-131. (m, 7H), 1.26-1.2 (m, 6H).

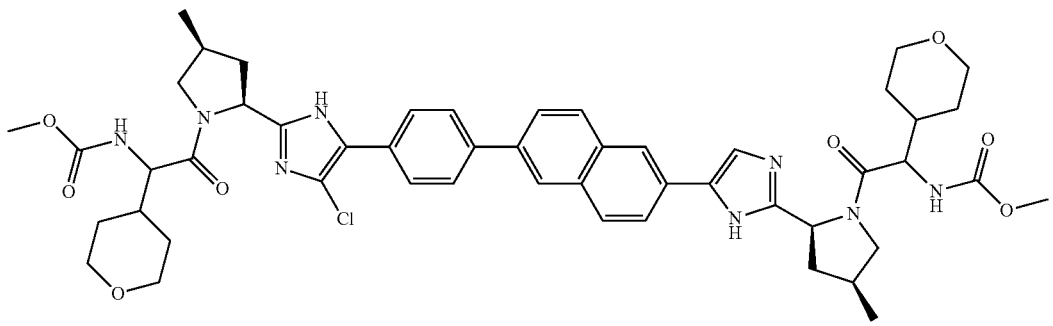

Methyl (2-((2S,4S)-2-(4-(4-(6-(2-((2S,4S)-1-(((methoxycarbonyl)amino)(tetrahydro-2H-pyran-4-yl)acetyl)-4-methyl-2-pyrrolidinyl)-1H-imidazol-4-yl)-2-naphthyl)phenyl)-1H-imidazol-2-yl)-4-methyl-1-pyrrolidinyl)-2-oxo-1-(tetrahydro-2H-pyran-4-yl)ethyl)carbamate Example 146 (22 mg, 13%) was obtained and isolated from the same reaction that produced Example 129 and as a diastereomer thereof.

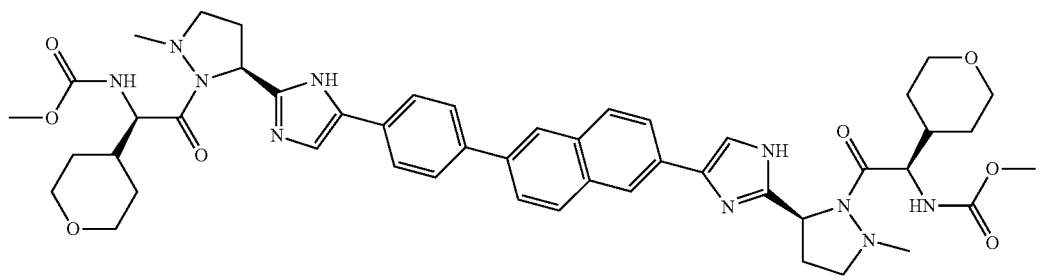

Methyl ((1S)-2-((5S)-5-(4-(4-(6-(2-((3S)-2-((2S)-2-((methoxycarbonyl)amino)-2-(tetrahydro-2H-pyran-4-yl)acetyl)-1-methyl-3-pyrazolidinyl)-1H-imidazol-4-yl)-2-naphthyl)phenyl)-1H-imidazol-2-yl)-2-methyl-1-pyrazolidinyl)-2-oxo-1-(tetrahydro-2H-pyran-4-yl)ethyl)carbamate (S)-tert-Butyl 5-(4-(4-(6-(2-((S)-2-(tert-butoxycarbonyl)-1-methylpyrazolidin-3-yl)-1H-imidazol-4-yl)naphthalen-2-yl)phenyl)-1H-imidazol-2-yl)-2-methylpyrazolidine-1-carboxylate (48.4 mg, 0.069 mmol) was dissolved into dioxane (1.2 mL) and then 4M HCl (0.687 mL, 2.75 mmol) in dioxane was added and the resulting slurry was stirred for 4 h. The reaction was concentrated and the residue and (S)-2-(methoxycarbonylamino)-2-(tetrahydro-2H-pyran-4-yl)acetic acid (37.3 mg, 0.172 mmol) were dissolved into DMF (1.0 mL) and DIPEA (0.072 mL, 0.41 mmol). The reaction mixture was treated with HATU (65 mg, 0.17 mmol) and the reaction was stirred at rt for 1 h. The reaction was concentrated to dryness with a stream of nitrogen, dissolved into MeOH, filtered and purified by prep HPLC (MeOH/water with TFA buffer) to yield methyl ((1S)-2-((5S)-5-(4-(4-(6-(2-((3S)-2-((2S)-2-((methoxycarbonyl)amino)-2-(tetrahydro-2H-pyran-4-yl)acetyl)-1-methyl-3-pyrazolidinyl)-1H-imidazol-4-yl)-2-naphthyl)phenyl)-1H-imidazol-2-yl)-2-methyl-1-pyrazolidinyl)-2-oxo-1-(tetrahydro-2H-pyran-4-yl)ethyl)carbamate (9.2 mg) as a yellow solid. LC-MS retention time 3.261 min; m/z 903.36 (MH+). LC data was recorded on a Shimadzu LC-10AS liquid chromatograph equipped with a PHENOMENEX® Luna 3u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% H$_2$O/0.1% trifluoroacetic acid and Solvent B was 10% H$_2$O/90% MeOH/0.1% trifluoroacetic acid. MS data was determined using a MICROMASS® Platform for LC in electrospray mode. $^1$H NMR (400 MHz, MeOD) δ ppm 8.32 (s, 1H), 8.27 (s, 1H), 8.13 (d, J=8.5 Hz, 1H), 8.09 (d, J=8.8 Hz, 1H), 7.94-8.00 (m, 4H), 7.85-7.93 (m, 4H), 5.47 (q, J=8.1 Hz, 2H), 3.93-4.01 (m, 4H), 3.66 (s, 6H), 3.34-3.49 (m, 6H), 3.20-3.34 (m, 4H), 2.77 (s, 3H), 2.77 (s, 3H), 2.65-2.96 (m, 4H), 2.08 (br. s., 2H), 1.38-1.73 (m, 8H).

amine (0.04 g, 0.061 mmol), (R)-2-(methoxycarbonylamino)-3-methylbutanoic acid (0.021 g, 0.123 mmol) and HATU (0.051 g, 0.135 mmol) in DMF was added DIPEA (0.064 mL, 0.368 mmol). The reaction mixture was stirred at rt for 1 h. The reaction mixture was purified by reverse phase HPLC to yield a TFA salt of methyl ((1R)-1-(((1S)-1-(4-(4-(6-(2-((1S)-1-(((2R)-2-((methoxycarbonyl)amino)-3-methylbutanoyl)amino)-2,2-dimethylpropyl)-1H-imidazol-4-yl)-2-naphthyl)phenyl)-1H-imidazol-2-yl)-2,2-dimethylpropyl)carbamoyl)-2-methylpropyl)carbamate (0.020 g) as a white solid. LC-MS (Cond. 1; shown below): [M+H]$^+$ 821.55, R$_t$=3.316 min; $^1$H NMR (400 MHz, MeOD) ppm 8.34 (1H, s), 8.27 (1H, d, J=1.25 Hz), 8.11 (2H, dd, J=15.94, 8.91 Hz), 7.84-8.02 (8H, m), 4.94 (2H, s), 4.07 (2H, dd, J=7.78, 3.76 Hz), 3.60 (6H, d, J=9.29 Hz), 1.94-2.14 (2H, m), 1.16 (18H, d, J=5.27 Hz), 0.95-1.07 (12H, m). Cond. 1: Column=PHENOMENEX®, 2.0×50 mm, 3 μm; Start % B=0; Final % B=100; Gradient time=4 min; Stop time=5 min; Flow Rate=0.8 mL/min; Wavelength=220 nm; Solvent A=0.1% TFA in 10% methanol/90% water; Solvent B=0.1% TFA in 90% methanol/10% water; Oven temp.=40° C.)

Example 149 and Example 150

Example 149 (a TFA salt of methyl ((1S)-1-(((1S)-1-(4-(4-(6-(2-((1S)-1-(((2S)-2-((methoxycarbonyl)amino)-3-methylbutanoyl)amino)-2,2-dimethylpropyl)-1H-imidazol-4-yl)-2-naphthyl)phenyl)-1H-imidazol-2-yl)-2,2-dimethylpropyl)carbamoyl)-2-methylpropyl)carbamate) and Example 150 (a TFA salt of N-((1S)-1-(4-(4-(6-(2-((1S)-2,2-dimethyl-1-((3-methylbutanoyl)amino)propyl)-1H-imidazol-4-yl)-2-naphthyl)phenyl)-1H-imidazol-2-yl)-2,2-dimethylpropyl)-3-methylbutanamide) were prepared from 2-bromo-1-(4-(6-(2-bromoacetyl)naphthalen-2-yl)phenyl)ethanone and the appropriate starting materials, obtained from commercial sources, by employing the procedures described for the synthesis of Example 148. Cond. 2: Column=Sunfire, C18, 3.0×150 mm, 3.5 μm; Start % B=0; Final % B=100; Gradient time=15 min; Stop time=18 min; Flow Rate=1 mL/min; Wavelength 1=220 nm; Wavelength 2=254 nm; Solvent A=0.1% TFA in 5% MeCN/95% water; Solvent B=0.1% TFA in 95% MeCN/5% water

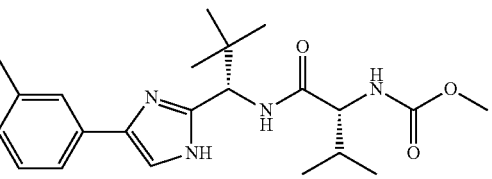

Methyl ((1R)-1-(((1S)-1-(4-(4-(6-(2-((1S)-1-(((2R)-2-((methoxycarbonyl)amino)-3-methylbutanoyl)amino)-2,2-dimethylpropyl)-1H-imidazol-4-yl)-2-naphthyl)phenyl)-1H-imidazol-2-yl)-2,2-dimethylpropyl)carbamoyl)-2-methylpropyl)carbamate To a mixture of an HCl salt of (S)-1-(5-(4-(6-(2-((S)-1-amino-2,2-dimethylpropyl)-1H-imidazol-5-yl)naphthalen-2-yl)phenyl)-1H-imidazol-2-yl)-2,2-dimethylpropan-1-

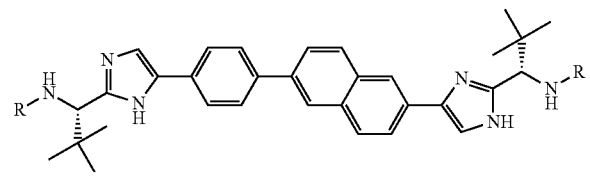

| Example | R | Analytical conditions |
|---|---|---|
| 149 | (structure with carbamate) | LC (Cond. 2): >95% homogeneity index. LC-MS (Cond. 1): [M + H]⁺ 821.55, Rt = 3.348 min. |
| 150 | (structure with isobutyl ketone) | LC (Cond. 2): >95% homogeneity index. LC-MS (Cond. 1): [M + H]⁺ 675.51, Rt = 3.488 min. |

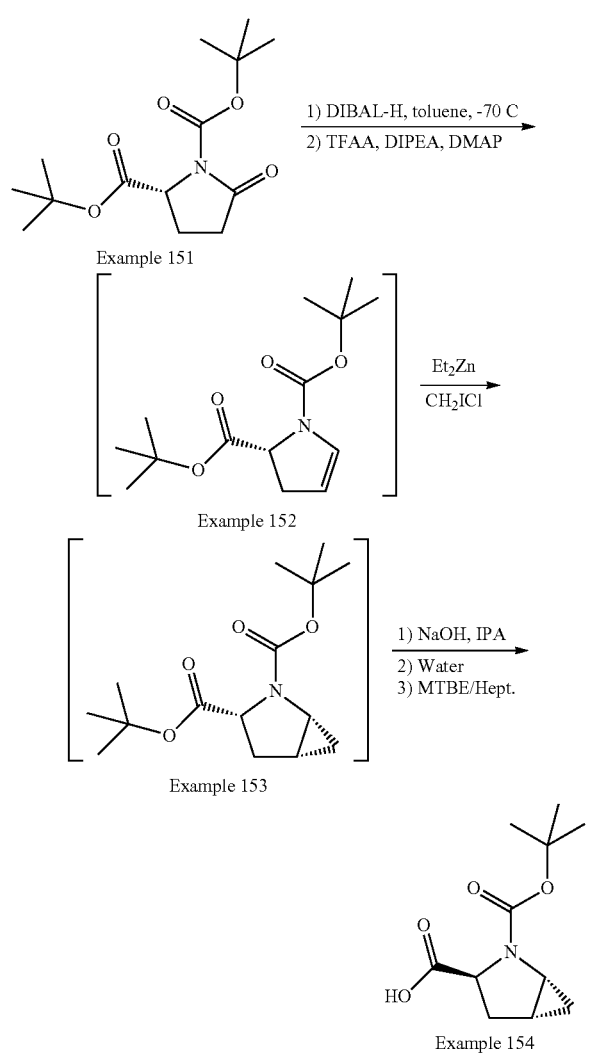

In a 500-mL reactor Example 151 (commercially available, 17.5 g, 1.00 equiv) was dissolved in THF (87.5 mL). The resulting solution was cooled to −75° C. and 1.5M DIBAL-H in toluene (61.3 mL, 1.5 equiv) was charged while maintaining the temperature below −70° C. The resulting solution was stirred at −70° C. for 1 hour. Trifluoroacetic acid (2.3 mL, 0.5 equiv) was charged over 10 minutes maintaining the internal temperature below −70° C. Triethylamine (51.3 mL, 6 equiv) was then charged over 15 minutes maintaining the internal temperature below −70° C. Trifluoroacetic anhydride (11.2 mL, 1.3 equiv) was charged over 10 minutes maintaining the internal temperature below −70° C. The reaction was then allowed to warm to room temperature over 90 minutes and quenched via inverse addition to a solution of 20 wt % aqueous citric acid monohydrate (96.6 g, 1.5 equiv) while maintaining a temperature below 15° C. The resulting mixture was stirred at room temperature for 2 hours then the lower aqueous layer was discarded. The product rich organic layer was washed twice with 70 mL saturated aqueous sodium bicarbonate. Solid sodium bicarbonate (1.7 g, 0.1 g/g Example 146) was charged and the solution was solvent exchanged into pure toluene under vacuum to provide Example 152 as a solution in 2 L/kg toluene.

A solution of Example 152 (16.5 g theoretical from Example 151) in 33 mL toluene was polish filtered into a 250 mL reactor. Trifluorotoluene (50 mL) and chloroiodomethane (43.2 g, 4.0 equiv) were then charged and the resulting solution cooled to −20° C. 1.1M Diethylzinc in toluene (111 mL, 2.0 equiv) was charged while maintaining the internal temperature <−8° C. The resulting solution was stirred at −15 to −20° C. for 14 hours. The reaction mixture was warmed to 0° C. then quenched via inverse addition to a solution of 20 wt % aqueous citric acid (135.7 g, 2.3 equiv). The reactor was rinsed with toluene (82 mL) and the rinse added to the quench solution. The resulting biphasic mixture was stirred for 20 minutes then the lower aqueous layer was split and discarded. The rich organic was washed twice with 60 mL 13 wt % aqueous NaCl followed by 60 mL saturated NaHCO₃. The resulting solution was solvent exchanged into pure IPA under vacuum to provide Example 153 as a solution in 10 L/kg IPA.

A 250 mL reactor was charged with a solution of Example 153 (147 mL, 14.7 g theoretical from Example 151) in IPA. The solution was warmed to 35° C. and solid sodium hydroxide (6.2 g, 3.0 equiv) was added. The resulting mixture was stirred at 35° C. overnight. Water (44 mL) was added and the organic solvents removed under vacuum. MTBE (145 ml) was added and the pH adjusted to 3.0 with 6N aqueous HCl. The aqueous layer was split and discarded. The product rich organic was washed with 60 mL water then azeotropically dried under vacuum via constant volume addition of MTBE. The solution was concentrated to 55 mL and stirred at 50° C. for 30 minutes. The solution was cooled to room temperature over 1 hour during which time a slurry formed. Heptane (90 mL) was charged over 90 min and the resulting slurry aged for 1 h. The solids were collected on a medium glass frit and washed with 22.5 mL 3:1 heptane:MTBE followed by 22.5 mL heptane. The tan solid was dried in a 50° C. vacuum oven to provide 5.48 g (46%) Example 154 with 94.9 LCAP purity.

The crude Example 154 was dissolved in 55 mL MTBE at 50° C. The resulting solution was concentrated to 20 mL and cooled to room temperature over 1 hour. Heptane (33 mL) was then added over 90 minutes. The resulting solids were collected on a medium glass frit, washed with heptane (15 mL), and dried in a 50° C. vacuum oven to provide 4.45 g (98.8 AP, 98.8% chiral purity, 37% from Example 151) of the desired product as a tan powder.

It is expected that the above reaction sequence (for the formation of Example 154) would be general enough to tolerate other functionality as well. For example, the tert-butoxycarbonyl group on the C2 carbon of Example 147 could potentially be replaced with an amide or another ester. Likewise, the tert-butoxycarbonyl protecting group on the nitrogen could be replaced by other protecting groups (such as other carbamates, amides, alkyl, aryl) or could be absent entirely (replaced with a hydrogen).

BIOLOGICAL ACTIVITY

An HCV Replicon assay was utilized in the present disclosure, and was prepared, conducted and validated as described in commonly owned PCT/US2006/022197 and in O'Boyle et al., *Antimicrob. Agents Chemother.*, 49(4):1346-1353 (April 2005). Assay methods incorporating luciferase reporters have also been used as described (Apath.com).

HCV-neo replicon cells and replicon cells containing resistance substitutions in the NS5A region were used to test the currently described family of compounds. The compounds were determined to have differing degrees of reduced inhibitory activity on cells containing mutations vs. the corresponding inhibitory potency against wild-type cells. Thus, the compounds of the present disclosure can be effective in inhibiting the function of the HCV NS5A protein and are understood to be as effective in combinations as previously described in application PCT/US2006/022197 and commonly owned WO 04/014852. It should be understood that the compounds of the present disclosure can inhibit multiple genotypes of HCV. Table 2 shows the $EC_{50}$ (Effective 50% inhibitory concentration) values of representative compounds of the present disclosure against the HCV 1b genotype. In one embodiment, compounds of the present disclosure are inhibitory versus 1a, 1b, 2a, 2b, 3a, 4a, and 5a genotypes. $EC_{50}$ values against HCV 1b are as follows: A=0.4 pM-10 pM; B=10.1 pM-1.00 nM; and C=1.01 nM-1 μM.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A.

TABLE 2

| Example Number (unless noted otherwise) | EC50 (μM) | Range |
| --- | --- | --- |
| Intermediate 52 | | C |
| Intermediate 70 | | C |
| Intermediate 114 | | C |
| 1 | | C |
| 2 | 2.18E−06 | A |
| 3 | | B |
| 4 | | C |
| 5 | | B |
| 6 | | A |
| 7 | | B |
| 8 | | B |
| 9 | | A |
| 10 | | A |
| 11 | 1.82E−05 | B |
| 12 | | C |
| 13 | | C |
| 14 | | C |
| 15 | | B |
| 16 | | A |
| 17 | | C |
| 18 | | A |
| 19 | | B |
| 20 | | A |
| 21 | | A |
| 22 | | B |
| 23 | 8.88E−04 | B |
| 24 | | B |
| 25A | | C |
| 25B | | C |
| 26 | | B |
| 27 | 4.77E−06 | A |
| 28 | | B |
| 29 | | A |
| 30 | | A |
| 31 | | B |
| 32 | | B |
| 33 | | A |
| 34 | | A |
| 35 | | A |
| 36 | | A |
| 37 | | A |
| 38 | 4.21E−05 | B |
| 39 | | B |
| 40 | | A |
| 41 | | A |
| 42 | | B |
| 43 | | A |
| 44 | | A |
| 45 | | B |
| 46 | 0.17 | C |
| 47 | | A |
| 48 | | B |
| 49 | | A |
| 50 | | B |
| 51 | | B |
| 52 | 5.90E−06 | A |
| 53 | 1.81E−03 | C |
| 54 | | A |
| 55 | | A |
| 56 | | A |
| 57 | | A |
| 58 | 8.49E−04 | B |
| 59 | | A |
| 60 | | A |
| 61 | | A |
| 62 | | A |
| 63 | | A |
| 64 | | A |
| 65 | 9.97E−07 | A |
| 66 | | A |
| 67 | | A |
| 68 | | A |
| 69 | | A |
| 70 | | A |
| 71 | 2.11E−06 | A |
| 72 | | A |
| 73 | | A |
| 74 | | |
| 75 | 1.23E−04 | C |
| 76 | | |
| 77 | | A |
| 78 | | A |
| 79 | | A |
| 80 | 1.08E−06 | A |
| 81 | | A |
| 82 | 4.22E−05 | B |
| 83 | | A |
| 84 | | A |
| 85 | | A |
| 86 | | A |
| 87 | | A |
| 88 | | A |
| 89 | | A |
| 90 | | A |
| 91 | | A |
| 92 | | A |
| 93 | 0.04 | C |
| 94 | | A |
| 95 | | A |
| 96 | | B |
| 97 | | A |
| 98 | | B |
| 99 | | A |
| 100 | | A |
| 101 | | A |
| 102 | | A |
| 103 | | A |
| 104 | 2.01E−06 | A |
| 105 | | A |
| 106 | | A |
| 107 | | A |
| 108 | | |
| 109 | 0.18 | C |
| 110 | | A |
| 111 | | A |
| 112 | | A |
| 113 | | |
| 114 | | B |

TABLE 2-continued

| Example Number (unless noted otherwise) | EC50 (μM) | Range |
|---|---|---|
| 115 | | A |
| 116 | | B |
| 117 | | |
| 118 | 3.74E−05 | B |
| 119 | | A |
| 120 | | A |
| 121 | | A |
| 122 | | A |
| 123 | | A |
| 124 | | B |
| 125 | 1.36E−04 | B |
| 126 | 6.54E−04 | B |
| 127 | | A |
| 128 | | A |
| 129 | | B |
| 130 | | A |
| 131 | | — |
| 132 | | A |
| 133 | | A |
| 134 | | A |
| 135 | | B |
| 136 | | A |
| 137 | | A |
| 138 | | A |
| 139 | | A |
| 140 | | A |
| 141 | | A |
| 142 | | A |
| 143 | 1.05E−06 | A |
| 144 | 1.77E−05 | B |
| 145 | | A |
| 146 | | A |
| 147 | | A |
| 148 | 8.43E−03 | C |
| 149 | | B |
| 150 | | C |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound which is

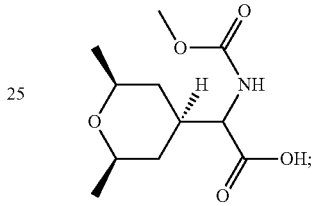

or a pharmaceutically acceptable salt thereof.

* * * * *